US010118945B2

(12) United States Patent
Oakley et al.

(10) Patent No.: US 10,118,945 B2
(45) Date of Patent: Nov. 6, 2018

(54) **DEREPLICATION STRAIN OF *ASPERGILLUS NIDULANS***

(71) Applicants: University of Kansas, Lawrence, KS (US); The University of Southern California, Los Angeles, CA (US)

(72) Inventors: Berl Oakley, Lawrence, KS (US); Manmeet Ahuja, Navi Mumba (IN); Ruth Entwistle, Lawrence, KS (US); Christine Oakley, Lawrence, KS (US); Yi-Ming Chiang, Temple City, CA (US); Clay Wang, San Marino, CA (US)

(73) Assignees: University of Kansas, Lawrence, KS (US); University of Southern California, Los Angeles, CA (US)

( * ) Notice: Subject to any disclaimer, the term of this patent is extended or adjusted under 35 U.S.C. 154(b) by 0 days.

(21) Appl. No.: 15/338,696

(22) Filed: Oct. 31, 2016

(65) Prior Publication Data

US 2017/0121719 A1    May 4, 2017

Related U.S. Application Data

(60) Provisional application No. 62/248,850, filed on Oct. 30, 2015.

(51) Int. Cl.

| | |
|---|---|
| *C12P 19/34* | (2006.01) |
| *C07H 21/02* | (2006.01) |
| *C12N 1/00* | (2006.01) |
| *G01N 33/50* | (2006.01) |
| *C07K 7/06* | (2006.01) |

(52) U.S. Cl.
CPC ..................................... *C07K 7/06* (2013.01)

(58) Field of Classification Search
CPC ....................................................... C07K 7/06
USPC ....... 435/91.1, 193, 254.3; 536/23.1; 702/20
See application file for complete search history.

(56) References Cited

U.S. PATENT DOCUMENTS

| | | | | |
|---|---|---|---|---|
| 2009/0119022 A1* | 5/2009 | Timberlake | .......... | C12Q 1/6895 |
| | | | | 702/20 |
| 2015/0310168 A1* | 10/2015 | Machida | ................. | G06F 19/18 |
| | | | | 702/19 |

OTHER PUBLICATIONS

Szewczyk et al., Identification and characterization of the asperthecin gene cluster of Aspergillus nidulans. Appl. Environ. Microbiol., 2008, vol. 74(24): 7607-7612 (Year: 2008).*

Chiang et al., An Efficient System for Heterologous Expression of Secondary Metabolite Genes in Aspergillus nidulans, Apr. 26, 2013, p. 7720-7731, vol. 135.

Takahashi, et al., Generation of Large Chromosomal Deletions in Kiji Molds *Aspergillus oryzae* and *Aspergillus sojae* via a Loop-Out Recombination, Applied and Environmental Microbiology, vol. 74, No. 24, pp. 7684-7693 Dec. 1, 2008.

Ahuja, et al., Illuminating the diversity of aromatic polyketide synthases in Aspergillus nidulans, Journal of the American Chemical Society, vol. 134, No. 19, pp. 8121-8221 May 1, 2012.

* cited by examiner

*Primary Examiner* — Ganapathirama Raghu
(74) *Attorney, Agent, or Firm* — Hodgson Russ LLP

(57) ABSTRACT

Modified fungal strains having deleted gene clusters are provided. The modified fungal strains include *A. nidulans*. The deleted gene clusters are selected from the group of gene clusters responsible for the biosynthesis of sterigmatocystin, emericellamides, asperfuranone, monodictyphenone, terrequinone, F9775A, F9775B, asperthecin, and both portions of the split cluster that makes austinol and dehydroaustinol. Methods for making compounds by culturing the fungus in a growth media and separating the compound from the fungus and/or separating the compound from the growth media are included, as are the compounds and compositions comprising them.

2 Claims, 76 Drawing Sheets

Specification includes a Sequence Listing.

Figure 3A

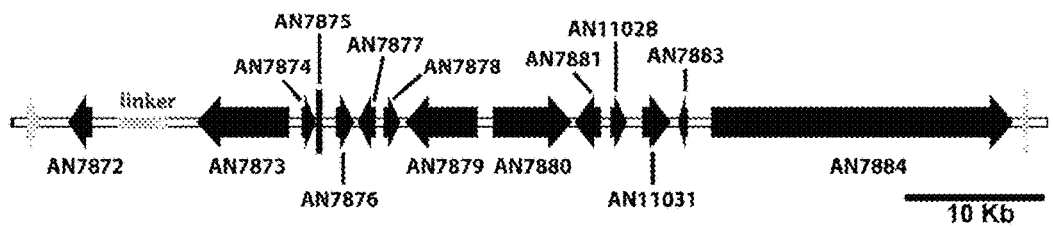

Figure 3B

| Gene | Predicted length gene/protein | Conserved domain/ Predicted function | Accession number of nearest BLAST hit (origin) | Protein coverage (%) | Similarity/ identity (%) |
|---|---|---|---|---|---|
| AN7872 atnN | 1876/571 | fungal specific transcription factor | KIA75995 (A. ustus) | 98 | 63/52 |
| AN7873 atnM | 6500/2111 | fatty acid synthase subunit beta | XP_002544941 (U. reesii 1704) | 93 | 65/49 |
| AN7874 atnL | 1011/306 | thioesterase-like superfamily | GAM42266 (T. cellulolyticus) | 88 | 60/46 |
| AN7875 atnK | 524/125 | hypothetical protein | none<sup>a</sup> | | |
| AN7876 atnJ | 1327/359 | amino acid aminotransferase | XP_001273101 (A. clavatus NRRL 1) | 99 | 76/61 |
| AN7877 atnI | 1305/383 | RTA1 superfamily | KIA75996 (A. ustus) | 88 | 83/70 |
| AN7878 atnH | 1237/396 | amino acid aminotransferase | XP_006962560 (T. reesei QM6a) | 93 | 74/58 |
| AN7879 atnG | 5099/1547 | ABC transporter | EPS26282 (P. oxalicum 114-2) | 91 | 61/42 |
| AN7880 atnF | 5577/1663 | fatty acid synthase subunit alpha | XP_001273102 (A. clavatus NRRL 1) | 98 | 69/54 |
| AN7881 atnE | 1845/518 | cytochrome P450 | XP_001273104 (A. clavatus NRRL 1) | 97 | 69/54 |
| AN11028 atnD | 1181/333 | short chain dehydrogenase | KIN00738 (O. maius Zn) | 95 | 66/47 |
| AN11031 atnC | 1985/508 | MFS transporter | XP_008086094 (G. lozoyensis ATCC 20868) | 92 | 57/38 |
| AN7883 atnB | 702/156 | YCII-related domain | KFY79913 (P. pannorum VKM F-103) | 81 | 50/65 |
| AN7884 atnA | 21390/7015 | NRPS | CEJ80515 (T. hemipterigena) | 94 | 34/52 |

Figure 5A

Sequence of the deletion of the Sterigmatocystin Cluster.

>ChrIV_A_nidulans_FGSC_A4 COORDS:ChrIV_A_nidulans_FGSC_A4:2737573-2789228W (51656 nucleotides) (SEQ ID NO:1)

```
ATTGTTTGGAAGGGTATGTCCTTTCTCGAGTTGCTTTCTCAGTATATCGACATCACCACC
AATAGATTTGAACCTATTGTACAGTTAGGCAGGTCGCAGAAAATCAAACAGAAACTTACC
AAACTGGGTCAATGTTCTCTAAGCACAGATGTGGCGACACGTCCGCTTGCTTTCCGCCCG
CTCTATCGAGCATCGTCCATCCCATCCCCAGATGTGCCCATGGATTAGCATCCGCGTAGG
AAATCTCAAAGTCCTCGTATCGCGGCCGCTCAATGACAGCTTGGTAGTGCAGAGAGGAGC
CGGGCCAGATGGCGTTTACTCGGCCGGTCTCGTTGTTCTTGTACCCTGGTGTTTGATCAG
TATATTCTAAGAAAGCTTAAGTAGGAGAAAGAAGAAAGAAAAAAAAAAGAATGGTGCTGC
ATTCACAAGTGCTAACGTACAGCTGCGACATTGATCACTCCAAACTGTGTGCTTCACCCA
CTCCTGTACATGCTCGTTGAAGCGGTCCGTAATCTGCTGGCGAGGCGCCCAGGCCCGGAT
ATTCTCGTTCTGCATCTTTTTGAGGAACTGAATCGCATATTCAGATACCGAATGCAGCGG
CGCCATCACACTACCGTTTTGAATCGGCCACGAGGGCCCAATGAAGGTGATGTAGTTGGG
CATATCTGGCACGGCCAGACCCAGGTATGCTTCGGGATTTGTCTTCCATTTATCTCGCAG
ATCGACGCCCCGTCGGCCGATGATGGGAAATTGCGGACGATATGTATTGTCGAATCCTGA
CGCACAGACGATGGTGTCGACCAATCGCTCAATCCCATCAGCGCCAACGATGCCATCTTC
AGTGCAGCTGGCTACGGCAGTGAAATGTACATCGACGTTCGCCTGCTGAATGGCGTGCAT
ATACGGGTCTCCTGGTGTGATGCGACGGCATCCGAAACCAAAAGTCGGCGTGAAGCCCTT
GGCCAGTCTATCATCTTTGATAATGCTCGCCATACGCTGTCGAAAGAAGGCCGATGCGCC
CTTCTGCGCCATAGAATCCCGGTAGAAGGCCCCCCACATGCCGTTTACTTCTGCCTCGAT
ACTCTTTGTATGCTCGACTAGTGCTGAAGGATTGGACCTGAATTGCGCGCGCTCGGCCTC
GCTGTAGATTTTGGTTGGCGCGCCGGTGTTTCCTGCAAGGACTCCAAACCACACACCCGT
CCGCACAAAGATATCGAGATGACCGACATGAGGTTGTATCCCAGCCACGGCCTGGATGGA
AGAAGCACCAGAGCCAATTACGGCGACGCGATCGCTGTTCCACTGCACCTCGCCATAGTC
GTCAGGCCAAGCTGCCGTGTGAATAACGCGGCCCTTGAAGCGATCGTGGAGTCCAGGCGT
ATCTGGCCACTGCAGCAATCAGATATGGACCAAAGAACCCAGCCTAGTCGCGCACCTTTG
GATTACTCAAGACCCCACATGCATTCAGCAGTATATGGCAATGGTCGTCGAACTCTTCCG
GTTCCTGTCCTGGCCGCTGTCGCCGGAGACGTACCTTCCACTGCCCTTCCTCTTCGTTCC
AGCAGGCTTTGATGACCTCTGTTCGGAACTGCATGTACTGTCGTAATTTGAAGGCTGCAC
AAACTTTGTCTAGATACTCCAGATATCCGACGCGTAGGAGAAGTAACGAGGCCAATCGG
GGTACTTGCAAGCCAAGTCAGATGGACTCTATGTATATCAACAGACAGGAATACAAACAA
GTGCAAACCGATACGTATACGCATGACTGGGAACATCACAGCCTGCATTAGGGTAACGAT
TTGTGAGCCAAGTGCCTGCGCGTAATTAGACTCATCCACATATGGGAGTGGGAGGAGGCA
TACCTCCAATATCATGATTCTTCTCGTACACCACATGTTCGATATTTGCGCATTGCTTCT
GGATTTGATACGCCATCAAAATTCCAGAAAAGCCAGCTCCAATGGTAATCACCCGCAGGC
GACGGTTGTTAGGGTCCATCCATGTTGTATGTTGCGGGATGCTATACCGTGACTCTTGAG
GCTCTGGGCCTTCGTGAACATAGTGCACAGTCATTGCGGGGGGTATTGTGTGCTGTATGG
TCTAAAACGGATATGAATCGCCTTTAGATATCCCAATGTTCATATAATGGACACATTATA
GTCAGGGTTCGGCCAGCGAGTCGGTTAATCGCATGCCGAGCATTGCATGACAGGTTGGCA
GAGCGGGGTCCATGGCTATAAGTGCGTGTCTTGACGGTTCAACAACTGCTCAACAGCATC
ATATCTGTACTCAGCAAGAACAATATGGCAGCCCTCCAGCACCTCAGCCTCCAAGTCTG
CTCGGCTACCACCGGGTTCTCTCGCCCTTGGCCGGAATCCGCGTCTCCCCGCTCTGCCTG
GGCACTATGCATTTCGGCGGGCAATGGACGCGGGCAATGGGCGATGTGACCAAAGAAACG
GCGTTTGCCCTCCTCGACCGGTTCTACGAAGCCGGCGGGAACTTCATCGACACGGCGAAT
TTCTACCAGGGTGAGGGCAGCGAGAAGTGGCTCGGGGAGTGGGTGGCATCGCGCGGGAAC
CGCGACGAGCTCGTCCTCGCGACCAAGTACACGATGTCCTACAGACTGACAGGGCCCGAG
AAGATCAAGTCTAATTTCCAGGGCAGCCACTCGAAGAGTCTCCGTCTGTCGGTCGAGGCT
AGTCTGGCTAAGCTCCGCACGGACTATATCGATCTGCTGTATGTGCATATGTGGGATTTC
TCTACGAGCGTCGAAGAGGTCATGCAGTCGCTGCACCATCTTGTTGCCGCAGGCAAGGTG
CTCAATATTGGGATCAGTGATGCCCCGGCGTGGGTTGTCGCCAAGTGCAATGAGTGTATG
CTCCTGAATGACCCTTATGTAATACCTCGCTGACCGAGCCAGACGCACGGTTTCACGGCC
TCACTCGCTTCTGTGTCTACCAAGGCCGCTGGGCATGTTCCTACCGCGACTTTGAGCGCG
AGATCCTTCCTATGTGCCAGTCTGAAGGGCTTGCGCTCGCACCCTGGGGTGCTCTCGGCC
```

Figure 5A (continued)

```
GCGGCCAGTACAAGTCGGCCGAAGAGTTCCAGCAAGAAGGGACGCGGAACATGGGCCCCC
AGGAAGAGAAGCACCGGCTGATGGGCGCAAAGCTGACCGAGGTTGGGGAGCGCAAAGGCG
TGGCCGCGGCTGCGATTGCGCTCGCATACCTGCTTCACAAGTCGCCGTACGTTTTCCCGG
TGATCGGGTGCCGGACGGTCGAGCAGCTGGAGGCGAATATTACGAGCCTCGGTGTAGAGC
TCAGTGATGAGGAAATCTACGAGATTGAAGACACGATCCCTTTTGATGTCGGCTTCCCCA
TGGCGTTCTTATTCGAATCGCCCCAGCAGAAGTACCGTAGTGATATGACGACCAGGCATA
TCTGGCAGGTTACCTGCAATGCCCGGATCGAGAGTGTGCCTAAGCCGAGAGTATGTATCT
CTCAACCTGAATTTATGATTTCGCTAATCGAATTTACCAGCCTATCGAGCCAAAGCAGGG
GTACAAGCAGATGGATCGGAAGTAGTTCTCGGTAGCATTAGCCAAGCATCGGGTCCCGAG
CGTTCAAGTATTTTATATATGAGCCTTGTTTCCTTCCTATGTCATGGTAGCCAGTATCCA
TAAGGTATAGGAATCAACCATGTCCTCCTCCGATAATTACCGTCTCGATGGAAAAGTCGC
TCTGGTAACTGGGGCTGGCCGCGGCATCGGAGCAGCCATCGCCGTAGCCCTCGGTCAGCG
CGGCGCGAAGGTCGTCGTCAACTACGCTAACTCCCGTGAGGCCGCAGAAAAGGTCGTCGA
CGAAATCAAGTCGAACGGCTCAGACGCCATTTCCATTCAAGCCGATGTCGGTGACCCTGA
TGCCGTCACCAAACTGATGGATCAGGCCGTTGAGCACTTCGGATACCTGGATATAGTCTC
ATCTAACGCGGGAATTGTCTCGTTCGGGCATGTCAAGGACGTTACGCCAGATGTATGCGT
CCCATCTCCTTACGAAAGTCCTGTAGAGCTCTGACCTCAGCAGGAATTCGACCGAGTATT
TCGGGTCAACACGCGCGGACAGTTTTTCGTCGCCCGCGAGGCGTATCGCCATCTGCGTGA
AGGCGGACGCATCATCCTCACAAGTTCCAACACAGCCAGCGTCAAAGGCGTCCCCAGGCA
CGCTGTGTACTCGGGCTCTAAGGGGGCGATTGACACCTTTGTGCGGTGCCTAGCCTATCGA
CTGCGGCGACAAGAAGATCACGGTCAACGCGGTCGCTCCCGGCGCCATCAAGACCGATAT
GTTTCTATCCGTGTCGCGAGAGTATATCCCCAATGGGGAGACTTTTACTGATGAGCAGGT
GGATGAGGTACGTTTGTCTTTGTGTCTAGTATCTACGGCGGCTGCTAACTGGACAGTGTG
CCGCGTGGCTGTCGCCGCTAAATCGGGTCGGATTACCGGTTGACGTGGCCCGGGTGGTCA
GCTTTCTAGCTTCAGATGCGGCCGAATGGATCAGTGGAAAGATTATTGGCGTTGATGGGG
GGGCCTTTAGATAAGTCACATCATATACTTGAACTATATAGGGTAGACATGCAATGTTCG
CTCCCCGCTCGCTTACCGATATCTGCCGATCATCGTCAGCAACCATTAGGTCACGAAAAA
AAGAGTATACTAAGAGTAAACATCCGTGCATGGTATGAACTTAGTTGGGTACACCGCAGT
TAGTCACACCGTACTTAAGTACACTCAGCGATTCACTTAGGCGGCTGAATCGGCATTTCA
TACTCTGCCAGCACCGGAGGCCCAGCAACATCAACAACAATAGGCAAAGCATGCACACGC
TCAAACCAGGTAGATAGGTTGCGGTGCTCATCCCTCCAGCGTTTATCAAGGAAAAACCGG
AATGCGCCCTGCACAATCCCGAGCACAAACAGATCAGCTAGGCTGAGGGTTTCCCCGACC
AAGTACTCTCGCCCACAAAGATGGTTGTCAAGAATCTTTAGCCGTGCTAAAGTGTCATCT
TTGCTTTGATATATGTTGTCAGCATTGAAGTTGGCTCGTCCGATGAGCGGGTTGAACCAG
CCCCCTAACGCTGGGAGGATTTCGGTGATCCCGAAGGCCATCCAGCGAATGATGGAGGCA
TATTCTTGTCCGGTAGTCCCAAGTAAAGTCGTATTTGAATCTTGAGATGTTACTATACCT
CTTAGTCAGGAATTGAATAGATGGAATTGCAGTAGCAGCATGGTACCATAGAGAGCAATA
GCAATAGATTCCGTCAATACGTAGCCGTCGGCCCCCACAAACGTAGGAATCTTGCCTAGA
GGGTTGAGCTGGAGATACTCTTCGGTAGCATCTTTGAATGAAGTGATGGTCTTGATTTTC
AGAGGCAAATTGTTCGCTTTTGCAATCGCAAGAATCGCCAGCGACCGCGGGTTGAACGGG
CGAGTGTACAGAGTGCCGAACGGCATTGCAGAAATATTCTCAATTCAGAGCTGATTCTCG
TATTGTATGCTTGTGGCAACCTGCTAAATACAAATACTGACAGCAAATCAACTATATGTC
AAGACCATGCCCTTCAGCTGTCCGCGTAACCCTAACTTCCCCCAGGACAACGGCCTTCAT
CTTTCCCCGATCCGTGAAACGGTCCTCGTCCGCCATAACTTCGGGGCTGCTCATGACGGG
GACAAACTCCTCGAAGGTGGCTTGGCTCGCAAATTGGACAACAGCAAATGCGTCGAAGGT
CAAATCGATCGAGTCGCCGGCCAGCGGGGTGACCGGTTGCTGCAGGTAGTGTCGGGTGTG
GCTGACTGGAAAGGCCCTCCCGCCGAGTCGTTGCAGCAGGGGGATATGTTCGGTCTCCCA
GTGGTTACGAAATTCGCTGGGTGTGAGGTCGCCGCGACGGGCTACAAGAATCAAGACAGT
GAACATGGTGGAGTGAAAGTGCTGTGTATGTTTGTCCACACTTGCTTCCAGAATCTCGCG
CAATACGCCTCTATATATGGCCTGTCCCTATCTCGGTCGCCGAACGAACTAAACAATTAT
TCAGAGAGACTCTTCTTACATTTTTGTCATTGTTGCCAAAGTCACTTCACTCATTGCTGT
CCTCCAACCATGTACACAACTATCATCACAGCGGTATGCGTGCTATTCGCTCTTCACCTC
CTGGACAGCTTCTATCAAGCCCGGCAGGAGGTATGGGCCCTCCAGCGGGCAAACCTAGTA
CGAGCCCTCTGACCCAATGATTGGCTAGAGGACGATTAACTGGTGATACAAGCCCATGCC
TTCTTTCAGCCTGCTGACCGGCCACTTTGGTGCCCTCAAACAAACCATCGATGGCATGCC
GCCCAACGCAACCCTGCATAGCATTATGCTGAAATTGTCGCAAAAGTTCCGCTCAGGGAT
GTTCTACATCAACATGTGGCCATTCAGCGGTACATGGCTAGTGGTCGCAACACCGTCTGG
CGCGGCCCAGATCCAGAGTCTGAATCTTTCGAAGCCGAACATCCTGCGAAGACCGCTGGA
GACTATCACCGGGGGCCCAAGCTTGATGAGTATGCATGGTGAAACATGGAAACGGTGGAG
GGCACTGTTTAATCCAGGCTTTAACCCCAACTACTTGATTGGGCTGGCGCCGCTGATCGC
```

Figure 5A (continued)

```
CGATGAGGTCGTTGTTTTTTGCGAGCAGCTACGGCAGAAGGCCAGAACAGGAACAGTTTT
CCAGCTTGAACCGCTCACTCTGAGGTTGACAGTTGATACGATTTGCTCTGTGACGTTGTA
TGTGGTTACTCCCGTTGGGCGATGGCCCTTTCTAACCCCTGACTTAGAGATTCACAGCTC
CACCACCAAACTCAGGACCACCCCCTTGCCTCAGCGCTGCAACGGCAGATCGAATGGGCC
TCGTTTGGAACTACCTTCAACCCCTTTAAGCGGTACCTGACCGTGCGGCCTCTGGTGATG
TGGTACAATAACCGCCTTATGAACCGCTTCATCGACCAAGAGGTTGACCGAGCGTACCGG
GAGCAGTCTGGCCGTCAGTCGAAATCCGTGATCTCCCTCGCCCTCAGAGATTACATGAAA
GAGAAAGATGGAAGTCTGGAAGACTTCAAACGACGTGTTGCGCCACAGTTACGGGTCTTT
CTCTTCGCAGGTAGAGATACAACGAGCAGTACACTGCTCTATGCATTCTACCTGCTTTCC
CGACATCCAGAGGCCCTAGCTAAGGTGCGCTTAGAGCACGACCAGGTCTTCGGCCCATAT
CATCAACAAGTACACGAGAAAATCCACCAAGATGCGAAACTCCTCAACCAACTCCCCTAC
ACAACAGCTGTCCTTAAAGAGACTCTGAGGCTCTTCCCTCCGTCTGCCTCCATGCGTGAA
GGCCGTCCCGGCGTTGAAATCACCGACGACAACGGCCAAGTATATCCCACTGCAGGGTGC
AACGTCTGGACGCTCACCGTGGCACTGCACCACAACAGTGCGCACTGGGCTGAAGCCGAG
TCATTTATCCCCGAACGGTGGCTCGTGGGATCTGACCATCCGCTGTACCCAGCCAAAGGC
GCATGGAGGGCCTTCGAGTTCGGCCCGCGGAGTTGTATCGGGCAGACGCTGGCAATGTTG
GAGCTGCGGGTTGCACTAGCGATGACGCTCCGCGAGTTTGATATTGCACCGGCGTATGAT
AAGTGGGATCACATTTATCCAAATGACGCCGTCAAGGAGTTCAATGGGCATCGGGCATAT
CAGGCAGAAAAGGGGGGAGGGGGTGCGCATCCGGCAGATGGGATGCCCTGTCTGGTTACA
TTTCGGGTGTAAAGTATATAGTAAAGAATTATTGAATACGTGAATAATGACATAACTGGA
CTTTCTCTAAGAAGACCTGCTGATGGTGTTAGTTTCGACATTCTCTTTTGTTTGTAGATG
TCTAACCCCATGGTTGCATGCTGATACAGGAGCCTCGATGGTAAGGAGACGACGAGAATC
TATACGAGGCGCCGAGAGGTAGATCAGGGTAATGCATCTGATACTTTGATATGCACTTCA
ATCTCCGTAAGAAAAAGTATCAGTTAACTCTAATCCATATTTACCAATCTTGCTGCAAC
ATTGCCCATCCCAGGCTTATCAGGAAACTCATCCCAGGCCCCCTCGACGCCGCACCAACG
CACCCATCTTACCATGACGCGAATGATCTCTTCGTCCTGGCGCATCTCTTCCCCTACCTT
CTTCCGAATGCTCTCCGGAACCTTATACTGCTCCGGTCCAAGCATCCTTTCTACAGAATC
AAGACCCATATGCGCAACTTTGATAAAATCCTCCTTCCGCAGTGGAAATTCCGGACGCGG
GTCAGGGAGGCCTTGGGCATGGAGGAGAGCCCGTGTCACCTTCGAAATATGGCCGTCGTC
GCCGTAGATCGACGCGCGATGCGCTAGCTCCATCCATCCATCAGCTGGTCGCTTGGGCGT
ATACCCGGTAATGCGGTCTGCGTAGAGGGTAGGACATCCACAGCCTGCATACGTCACAAG
ATCGCCCCAAACTTTAAAATGCAGGAGCCGAGCTTTATTCGACGGTGAGATCCAGTCTTG
CGCCAGGAAAGTCGTGTAGAAGATGGAGAGGGTGAGCGTATGCAACATGACAAAGTCCAA
TGCTTCGACTTTGCCAGGGCTCTGGGCTGCACCCACCATGTATGCGCAGGTGTGCACCAT
ATCTGTTGTCTGCTGTGCCAGCTCCTCTTCCGTGGGACTGACGCAGTACTGAGCGAGATA
CGGAATGAGCTTGTCACGGACCTTGGCCAGCAGCCCGTCACTGATTTTATTTATCGGATC
TGTCAGCTGCACTGCGTTGCGGATGACTGGGTCACTATGTAGTTCATCCATGATGTCTAG
CATCGACTTGAACGGCGCCTTCGAATGGGCAGTCTGCATCTCCTCGGTTGGGAACAAAAA
CGAATTGGGCCAGTCATCGTGCACGCAACCGGCTGCGAGTGCTTCTGCTATGAGCAGGGG
CTGATTGAACTCCAGCGCGCATCCGAGATGGATCATCGGGTGAAGAAAACCTGCCTCTCA
TTGAGCGAAAGATTACCACTCGAGGAGGTTACCTACCAGAGTGCATGCGGCCCAGGACAT
CATTGGAAATCTCATCATTCGCGAACAAATACTCGTTGATGACATCAGGCACGCCTCTCT
GCGCAATCTCGTCCTGGAAGTAGCGCAGAAAGCTGTCGTAGTAGCTGAGGTCGCCAATAC
ACTGCTTAAAGAAGGTGCGGTCTTTCAGCTGCACGACGACTGAGGCTGGACGGTACTGAA
CGAGTGACTGATACCCAATGTTGAGGTCATACATGGCCCGGATCTCCTCTGGGGTGGCTC
CCAGGGCAAACAGGGTGAGCAGGTGGTGGACGGTGTGATCTGTACAGGTTCAGGGTCTGC
ACTTTTCCAGATGATTCCACTTACTATGGAAGCCCACCGCATCAAAGAGGGTATGATAGC
GGGCATAGTTGATCATCAGCAACTCAGAGACGCGGTCTGCGCTCTGCTGCGTCAAGCCAT
CTACATGCGTGTTCCCGGGTGTCCCATCGGCCGACAGCTGGATGTTGTACGGACCGCTCT
GGGGCCTCGTTGGGCCTAGGGTTGTGGAGGTGAACATGGCTACTGCATGCCATTCTATTC
TGGATCACAATGTGCCAATATTTGTGATGTAATACTAGCCCCGAACCCCGAAGCACGGTG
AGGCTCGCTGAGCGAAGCCAAAATCTTACATTAAGTCCAGATCTTGGTGGTGCAAATACC
CTCACAGAACCAAACAATGCCTTCCTATGCGGTTCTGGGGGCTACGGGTAATACTGGACG
GGCGATCGTCCAGGTACTACTTGATCGAGCAGACACCGACACCAGAATTCACATCTGCGC
CTACTGTCGCTCCAAGGAAAAGCTCTTCCGTGTCTGTCCGGCGGCCGAGACTTCGAAAAG
CCTTTCAGTCTTTCAAGGACGGCTGGATGATGATAGCCTCATCGATGAATGTCTCAGGGG
CACCGATGCCGTGTTTCTGGTAGTCGCCATTGTCGACAACATGCCTGGCTGTACGGTGGC
CATGCAGACTGCCGAGGCGGTTGTAGCGTCTTTGCAACGGCTTCGCGCTACAGACCCTGC
AATACGTCTTCCGCGACTAGTGATTCTTTCGTCGGCCTCCCTGGAGCCCACGTTCTGCAA
CGATGTTCCCGCCCCGGTGCACTGGGTCCTCAAAACTGCCGTCTCCCATCTTTACCGCGA
CCTCGCCGCTGCCGAAGCATACCTCCGCGCCCAATCCGACTGGCTCTCGGCGACCTTTGT
```

Figure 5A (continued)

```
CAAGCCCGGGGGGCTTGTACACGACCAGGCCCGCGGTCACAAGGTCTGTCTCGACCGGGC
TCAAACCCCGCTCTCATTTCTCGACTTGGCTGCGGGCATGGTCGAGGTGGCCGACGCGGA
TGATGGCCGATACCATATGCGCAGTGTGAGTGTGGTGCCGGCGTCAAGGGTTGCAATATT
TCCATGGGACGGCGTTTACTATACGTTTACGGGCTTGCTGTTTCATTTTTGCCCGTGGAC
TTACCGGTTTCTTGGTGAATATAAGTTGCAGTCGAGAAAGGAGAGGGACAAGCAAGCTTA
GGCAGACTCCATATTTCACCGTTCTCCGTACTTATTACTTCCCATTTTCGGAGGTGAAAC
TATTTACTCTTGTCTGATCTATCTATGCATATTCTAAGCCGGTTCACCTCTCTGTAGCAT
CCATACATTTATCGCTGGTGTTGGTTGTTGACTGCACGTTTATCAATAATATGGACGCCA
TCTTCAAGCAAATCAAAGATGAGTACGCCCGTGCCGACGAGCATGGCAAGCGAGAGATTC
AAGGCTATATCCGCGAGTTGCAGGTTGGCTTCTATTCGGATTGGGATGTGGTGATGCGGT
TGAGCAGTGGTGTATGTTCCCTCCTTACTATCCACTTCAGCTACCGACAGTGTGTAGCCC
TTGCAAGTTGCACTTGCCAAAATCGCCATCGACCTGGACCTTTTCCGCACCCTCAAGGAG
AGTGAAGCTCCGCTATCTCTGGCACAGTTGGCAGAGAAGACGGGGCTTCCCCCAAGCTG
CTTGGTAAGTATGCAGCGTTGGCTATGTTGGATTGCCCTCACTAAGTCACAACAGGGCGC
ATTCTCCGCACGCAGGCTGCATTTGGCCTCATCAAGGAGACTGGGCCCCAGGAATACACT
TCGAGTGCATTCACTGATGTCTTTTCCAACCCCGATGCTGCTGGTGCCATTGCACAGCTG
TATGTCTCATTCCTCCACGTCAAAGGCACAGTAATAAATTTCTTCTCAGATTCGACATCT
CCGGCCCTTGCACTCAGCTTCTGCCCGACTACCTCGCGGAGACTGGGTATCAGGAGATCG
TCTCCAACAAAGAATGCCCCTTCCAAAAGGCGTTTCACACCAGCCAGACCCTATTTGAAT
GGATGCCCCAGCACCCAAAGCACATGAAGTCTCTCGGCCACTTAATGGCCCTTCAACGGC
CCACGGTCTGGGTTGACCACTTTCCTGTTCTCGAGCAGCTAGGCGAGTTCCCTAACCCAG
ACAAAACACTCATGGTCGATATCGGCGGCGGCTTCGGGCAGCAATCCAAAGCGCTCCGTT
CCAGATGCCCCAATGTTGAAGGCAAAATCATTGTCCAGGACATGCCTCAGACGCTAGCCA
GCGCTGAGCCAGCAGAAGGCGTAGAATTCTCCGAACACGATTTCTTCCAGCCGCAGCCCG
TAAAGGGGGCCAAATTCTACTATCTCCGCCACGTCCTTCACGACTGGCCCGACGAGCAGT
GTGTTCAAATCCTGCAGCAGGTCATTCCGGCTATGGCACCTGAGTCGCGCATTCTGATTG
ACGAAGTGGTAATCCCGGTGACCGGAGTGCCATGGCAGGCAGCGTTTATGGACTTGCTGA
TGATGGAGTCGTTTGCGAGTATCGAGCGCACGCGAGCAGAATGGGAGGCCTTAATGGACA
AGGCTGGGCTGAAGATTATCGAGGAGTATTACTATGATGGGAAGGAGCAGGCCATACTGG
TGGTTATACCGAAGTAAATTATTGTACTTCTACTTTAGGGTAGAATGGAGTCTCAAACCC
TCCGTGACAAATTTAACCAAGAAATTGAGAATATATATTTATACCTGCATAATTCCTGCA
CCTTCTCTATACATTCTATCCTAATCCTACATCAGGATGCCTTCGTACGCCCTTCTAGGA
GCCACCGGCGCTACTGGATCCAGTGTACTTCGCCATCTGCTTTACTCAGGCTCGTCCAGT
GACCTCACAGTGAATGTCCTGGTTCGCTCCAAGTCCAAACTGCTGGCTGCCTTTCCCAGC
CTCGACAAGCCTCGACCATCCGTGACGTCGTCCATCCCGACGATCCGCATTTTCGAAGGA
GACTCTACCAATCCCGATGTACTTTGCGCGGTTCTCCAAGACGCTAGCCTCGTGTTCATG
TGCGTCGCGCAGAACGGCAGTCCAATGGGGACAACCCTAGTGCAGAACACGGCCGCCGCG
CTGATTGAGGCCCGACGCCGACAGGCACAGCCACGCGGTGAGCTAACGGTCATCCAGCTT
CGGTCGGCGTCATTGAACCCCGTGCTTGCGGTTCAAGTGCCGCGATTTGTGCATCGCGTT
GTTTGCTTTTGCTTGGCTGCTGGCTATGCGGATCTCCGACGAGCATGTGTCCTCTATGAA
GCAGCGCGACAGAGGGCTGTTGCAATATGTGCTTGTAGACCCGCCGACTCTGCATGAT
GCGCGGGTACGCAGACAACTGGTTACAGGTTAATTGATACCACTGACATGAAGGACAAA
GAAAACCAGAGGCAGGCGATTTGTCTGAGCTATGCTGATCTAGGGGTTGCCATGTGTGAG
ATTGCCAGCCGTGCGGATGAGCTGCATGGACAAGGTGTAGGGGTGACCGCCACTGGCCCA
GTCAGGCAGACCTGGGCAGTGTTGGCTGGGTTCTTGCTAGAGGGAGGACTGGGACATCTG
GACTACAGATATGGCAGAGAAATGTTGTAGTCCTTGGGGTTTGTATTTTGTTGCTGCTT
GGGGGTCTGCTATATAGTATCAAAGCCTAGGTGGACAATATTACTGCTAGTCGCTCATTT
GGTCTCAATTTCCAGCAATAATATCAGCGGCAACCTTCTCTGCTAATGCATAGACAGTCG
CCATGGGCTGGCCGTCAATTGCAAACGGAAATGCAGACGCGTCGACAACTCTGAGTCCTT
TAACGCCCCTAACCCTTGCCTTTGAGTCGAGCACCGCAAGCGGATCATCCGGTTTTCCCA
TGGCACATGTGCCGACTCCCGCATAGTACGCGTCCGAAGTCTCGGCGATGTAGTTTAGGA
TCTCCTCGTCGGTCTGATACTCGAACCCCGGCAGCAGCTCGGGTCCGTCAATGACTTGCT
GCATCGTCTCTGAGGCGACAATCTCGCGGCATCGGCGAAACGCTGCCACAGCCATCTCCT
TGTCGCGCGGGTCGTCCAGCCACCGCGGGTCCACGACGGGGTTGTCGGCCGTGTTGGTGG
TGTTGATGGTGACGGTGCCCCGGCTAAACGTGGCCAGCAGCGCAGCCGACATACTGAAGT
AGTTCTTGCCGTCATACTGAGGCACAAATGTGTCATCCAGCGCAATATATGAGAAGGTCG
GCCAATCAGCCGGAAAGGCCTTGTCGATATCGGCAGCAGTCGCCTCGCTAAGGTTTCCTG
GCTGGTGCTTTTCGAAGGCAAAGTAGTCTTGCCCCGGGTTGGTGAGCAAGCCTGTGCGGA
AGTTGTTGTATTCGTAGATCGAGCGAGGAAGAGTCTCCTTGCTGCCCATCAACTGGCTGT
GGCTCTCGACTTTCACAGGGTTCGTGGGCCCAGGATGATGGTGTCCTGCATGTTCTGCC
CGACGCCAGGGAGATCAGACAGGACGGGAATGTCCAGCTTCTCGAGTGTCTCTCTAGGGC
```

Figure 5A (continued)

```
CAAGCCCAGAGACCATCAGCAGCTGAGGAGATCTCATTACTCCTGCCGACAGGATGACTT
CCTTCTTTGCGCCAATCTGCCACTCGAACCCGCCGGTATTGACAACGACGCCTGTCGCTC
GCTTCTCCTCGTCAAAGTCGATCTTCTTCACCAGAGTATGTGTAATCACATTCAGACTAT
TACTCGTCCGAAGGGCCGTCTGCAAGTACGAGGTAGACGCAGTATCCCGTCGACGAGTCT
TAGGATGAATAGTATGCGTGATGTATGAGCGGCCCAGCAGCTGGCCGTTGGAGAATCCCT
GGGCTTCAGGAAACCCCATCTTTTCGAGGGCCTTGTCTACCCACGACGAAATGGCGTTCG
TAAGGTACGGATACGCAACCTGGACGGGCCCCTCTTCTTCTGCAGTTGCTGCAAATGCTG
AGACGTCATTCGAGGCCGTTGCGTTGGCGGGCGAGGGTTCGTCAGTGGGCCTGAGAACT
GCACGCTTTTCTTGAAGAAAGGCAGCCAATTGTCCCAAGTGTAGCTGTCGTCGCCTACTC
GGTCAGCCCAGAGTTGATATGCGCCTTTTGAGCCCCTGTCTTTGTTAGCCTGTGATTATC
AGGATTTGAGGAGAGATACCGATGATATAACATGGCTCCACGTGCAGTCGAGCCACCAAG
GGTTTTGCCTTGCATGTAGAACATTTTTCGACCGGCCAGCCCCTGAAACTGTAAGCATCT
GAGCTATCTCGATTGTCGGGTAAGCATACTGGCTGGGCTTCGGTATATTGGTACCAGTCA
ACAGCGGGTTCTTGACATGGCCGTTGTCAAAAAAGTAGTTGAACAGGAACATTGGCACT
TCAGTGGCATTCCCTGCCTCAATTTCGTAGAATCCTCCGGCCTCAATAACCGCAACAGAG
TTGCTACCGTCCTCTGACAGCCGATGGGCCATTGCTAGGCCGGCTGTGCCGCCGCCAACA
ATCACATAGTCGAAGGTTTGGCCCGGCCACCCGTACCAGCCAAAGTGAGAGCTGAGGAGG
CCACGGCCTTGGATGCGGCCGTCCATTGCTGCTTCATGCTGCTCAGCGGCGGTGCCAAAA
AGGGTCTCCCATGGTGAGGAGAAGAAGGTCGTTTGACCGGCGAACATACCCACCACTGGG
AGGGCGGAGAGGACGAGGAGGGACCAGGCGGGCATAGTGACGATGGTCTGTCTGATGGTG
CTCGTCTGTAGCTTAGGCTCTCGCGAAGTTAATAAACCGGCCACCACGTACCAATACTTC
GGCACATGGCGGAGCCCTCACCGATCGCTTGCCGAGACCCATGTAGGCGTCGGTATAAGA
CGAGAAAAGAGACCTGGCAGATACCCCAAGCATAAGTTCATACTCCTGGAACTCTTCAA
AACCATGAGTAACGCTGGAGTGGAAGCCATAGCCGTTATCACCGGCACTTTCCTGTCCGG
TAATGCTGCCACGTCCCTTGCCGGCCGCCTAACTAATGCCACCAGGTGCAATGATGAGCG
TCTACCTCCTAGCGGTCCCGTCCCTCTTCGAAACAACAAGTAGTCCTGACCAGCTCGTCC
GCCACTGGAGCCGGATCTACCTCAACGGCGCACATAAAAGGCCCCATCATCTGCCTAAGCA
CAACCGCGTTGTACGGACTGGCGGCTGCGACTAAGTACTCGGCCGGCGAGGACTGGGGCG
TCTTCGCTGCCGCGGGCGCTATCACCATTAGCATGGTCCCATTTACGCTGACGGTGATGG
CGCCAACCAACAACGCGCTTTTCCGGCTAGAGGGGGAAGTCAAGAAGGGACATACCCCGG
TATGGTCAGATGCAGAGCGTCTAGTCCGCAGGTGGAACCGATTCAATGCAACTCGGGCCT
TTTGCCCATTAGTTGGGGCTGTTTTAGGGCTGTTGGGAGTTCTGAAGATTGTTTCGTTCT
AGCTGAATGTACATAGGGCTGCCCGGTGGCCGAGGACGGGTTATACTTGCTTGGAAATGA
GGCTGGTCAATCAACCTATGGCTGACTCTATCGTAAATCCGTCGCTCTCCGACATATCAG
AGGACCTAGAAAAGTCCCACAATAGTCCTTTTACGATGCCATGCTTAGGTCCATGGTCTA
GCAGGATGGCTTTCCTATCCCTTCCTATCCTAACAGCGCTCGGCGCAGTCGTTTACGTGC
TCTTCCAACTCGTGTACAACCTCTACTTCCACCCACTACGCGACTATCCCGGTCCTCTGC
TATGGCGAGCCAGCTCTCTTCCTTGGAAACTGACCCTCCTTCGCGGCACAATGCATCACG
ACCTGATGCGCCACCACCAGACGTACGGCGATACTGTGCGCATAAAGCCTGACGAGATTA
GCTACGCAAATGGCCAGGCCTGGCGCGACATCCACGCCCACGTACCTGGGCGCCCAGAAT
TCCTCAAAGACCCTGTCCGCCTGCCACTGGCTCCAAACGGGGTTATGAGCATTCTCGTCT
CTGACACTCGCAACCACGCCCGGTTCCGGAGTCTGTTCGGCACGCTTTTAGTGACAAGG
GGCTTCGCGCGCAGGAGCCCACGATTGCCCGCTATGCTGATTTACTGGTCGAAGTCCTCC
GCGAGGTTGCCGATACTGGCAAGTCAGTCGAGATGGTCCGTTATTTCAACATGGCGATCT
TTGACTCCATTGGCGCGCTCTCATTTGGGGAATCCTTCGACAGCCTCAGGAACCGCGAGC
TCCACCCGTGGGTAGACACGATCCACAAGAATCTCAAAAGTGTCGCCATCTCACACGTTC
TCCGCAGCATGGGCGTCGAGTTCCTGGCCCCTATCTAATGCCGGCCGAGCTGCGCGGCA
AGCGACAAGAGAACTACACATATGCCATAGAAAAACTCAAGAAACGTATGCAAAAGACGG
GTGATCAGGGCGACTTCTGGGACCGGGTAATCGTCAAAAGTGCCGACGGGAACCAATCAG
GAGATGGAATGAGCTATGGCGAGATGATCAACAACGCGGCGGTCATGGTGGTCGCCGGGT
CTGAGACGACCTCGTCGGCGCTATGCGGCTGCACGTATCTACTCTGCAAATTTGATAAGA
TGGACAAGGCTGTCGCCGAGGTTCGGGGCGCATTCGCGGCCGCCGACCAGATCGACCTGG
TCTCTGTCTCTCGGTTGCCGTACCTGACGGCCGTCATCGACGAAACCTTGCGCATGTACC
CCTCGGTCCCTGGACAGCCGCCCAGAGTGGTGCCAGAGGGCGGAGCAATAGTATGCGGAC
GGTTCGTTCCTGCTGAGGTGTGTATCATATAACCTAACCGTTTAGTTTCCTGATTGCCGT
GGCTAACAAGCAGCGGCCTCTAGACCCGCGTCGGTGTCAGCCACCTGGGCGCTTACTACG
CGCCATACAACTTCAGCCATGCGGACAAGTTCATTCCTGAGCGGCATCTGGCCGGTGCCA
AGTTAGAGGAGCCGTTCCGACACGACAACTATGCGGCGTACCAGCCGTGGTCTGTAGGAG
TGCGCAACTGCATTGGACGGAACCTGGCCTATGCAGAGGTCAGGCTGACGCTGGCTAAAC
TGCTGTGGCATTTTGATATAAGCCTGGACGAGGAGAGGACGGGGAACTTTTTGGACCAGA
```

Figure 5A (continued)

```
AGATCTGGTCAATTTGGGCGAAGAGGGAGCTGTATCTGGAAATTCGGACCAGGGAATTTT
AGCATGTAGGTAGGGTCTAAATGAGGCTGTGCTAGTTTTCACTAAGTCAGAACGAACTTG
ATACTTTATTACGTGTACCTTCCATTTCATCCATTTAGCGGCCGTTCTGCCGATATGATA
TAAGCTAAGAACATGTACCAGCTACCTATTCTCTTCAACCCGCCGTAACAGCTCTAGTAA
CGGCCGGCTCTGCGTTACCCCTTGTACCAATCGAATATATGGTGCGTCCAACGCAAAGGG
CTTCCCTGTTACATTGGGGATCCACCGTCCAACGAGCTCTTCCGGCTTGATATCAGACAC
CCGCAGATGGTGCCTCAGATATTGTCTGTAGCCATCAATATGTCCCCGTAGCATCTGCGA
GTGGAACGGAATATCAACCCCGGCAAGTGGAATGGTTGCACGGCCACGGGATAGTTCAGT
TTCATTCGTGACAGAGCAGCTGCTGGGGATATGGTGAGCAATGCATTCGCTCATGGTTTG
TGGGCTATTTGGCGATGTCGACCGGGATAGATCGTCGCACGCGTGGCTGAGTACCCAGAG
AGAGCGGACCTGTTCGCTATTAGGCCTGATAGGAAAACAGAAAATAGTATGACAGGGAGT
TTGAGCGAGAACATACATGGCCGGCACATACGTACTGCCGCGAATGCACGTTGTAGTTGA
CCACCTCCAGCAACACGCCAGTTGCCTGACTGACAAGTCGCACTAGCTCAATCAGTCGGT
CTTCGGTGAAGTCTACGAAATGTTAACTCAGAATGTCGCGCATGATCAGGGAAAAGAGAT
ACCTGATCGGATTCGCGATGGATCGGCAGCGACCATGCCATAGTCAGTACGCCCGTTAGC
GTTGCGCGGCAGGGTATTCTGCATTTTGAGCCCTCTATAGAGGATCAACGATAAAAGCGA
CTCAAAAGGCATGATAGTTGTACAGGCACCGAGGCTGCTATACTCTCCCAGCGAGTGTCC
AGCAAAGATGGCTTGTGTTTGGACGACGCCTTGCGCCTGTAAATGCGCATACTCGGCAAT
CTCCATGACGGCCAACGCGGGCTGGGCAAATTGTGTTGACATTAGGAGCCCAGAAGGATA
GTTGAATGTATATGATCGTGAGTCGCGAGTCAAGCCAGGCAGCATAGATGGATCAGAGTC
GGACATAGAAAGATAAATATCACGGATTTGCCGACCACGCCGACTGCCAAAGTTGACAGT
AAGGCTCGTAGGATTCTCACGGACTATGTGAAGGAGCGAAATGCCTGTAATCGGTATTAG
AGTTGCCCGTTCTGTCGAGCTCGGGTTGAGGAGGTAACGCACCATATTGGGATCTAAAGT
GCCGTTCTGCTCTGTCCCATACTGCTCGTGCAGCAGCATTCGTATCATACAAGGCCATCC
CCATTCCTCTCTCCTGCGTGCCCTGGCCGGTAAAGACGTATGTTGTCTGGGCCTGCTCGA
GTACCGCCTCTGCATTACTTGCTCACCCGTACTCTCCTTAAGCACTCTTACATGGA
CCACCATACACCCGTCCGCCATTGCAAAGTGTTGTATCTCCATTCGCAACCGGTCGTTTG
CCCGGACAAGTCCATCGAAGGAGGGCGCCCAGCTGCAGAAACGGGTCCGTTCATTGTCGC
CAATGATCCACTCCAGAATCCGCCGCACGGTGGCAGACAGGTGCAGCCCATGCACAACAG
GCTGACCCAGCCCGGCAAAACGAGAGAACAGAGGGCAAACGTGAATAGGATTTGTATCTC
CAGATACCATTGCATAACCCTCGCTTTGGGCAGGGGCAGTAAACGATATAGATGCAGCGT
CATCGCCAGTCCAGCCTGCCCGTGGGAGCGGCTGTCTCTGGACTCGGGGTGCACCGTGGC
GGTTCAGAAAATCCATGACTGGATTCGCTCCAAACCCCTCCTCCTCCATGTATACACGTC
CAATCCGGGTGCCGACCGAAGAGACACAGACAACTGAGGTATCAGAAGGGGCCAGTGAAA
CTGATCCAGAAACTTGCAGGGAAGCAGGTGCTCCTGCGGCGTCGAATACCGTTTGCGAAT
GCAGTTGGAATATCAATATCTTCCCAATAAGATCTGAGCAAGGTCCATCTAGCAAGAACC
ATTTTCGACTCATTAAGACTCTTAATTTTGTGTGGGAGTCAACACGTATGACCATATCTG
GCTCTTCAACGCAACGAAACTGCTGCTGGGATACGCTCTCCTCTGGCCGCCGCTGGATTA
TAAATGTCGTTTGGAGTCGAACCACCGGTTTTCCCTCTCTGAGGAGCTCTGCAGAAATCT
CAACTCGCTGGCCTATGGTGGTGATTGTGCGCTCGGTTATGCGCGACGAAGTTGTCACTG
TATCTCCCACATGCAACGGGCGGATGCCAGGCACGAAACGAGTTGAAGCAGACTGGTGGA
GGAGTCGAAGAGGGTCCGCATCAAGTGCTTCGAGCAGTATTGGCTTTGTGAGTGCAGTCC
AAGCTATAACGACAGCATAATCAATTGGCACAACTGGGCCCCGTGTCCCCAAGCTCGAC
AACGGGCCGGGCCAGCTTGACCGACAATAGCCAGGAACGTATTCACGTCCTCAGCTGTTA
TTGTCACTCGATCGCCAGTAAATTCTGAATTCAGACCGACAGAAGTTGGGCTAGGAAGGT
CTCGACCAATCCACAGGTCCGTGTACAGGCGCCTCACGCTGTCCAAGTAATCAGTCCGGT
GCATTTTGAGAATTAAAGGGCCCATGGTTCCTCCGAGCAATTCCATCTTAAACTCCAGCG
CGGGTCGTTTGCCCTTTGAGCGAGTTAGCAATGTCACTGATACCTTATTGCCGTCTAGAT
GTATCAGTCCCGAGTGCTGCACGTATCGCCCTGGGGTCTCCTTGCCGACGCAAGGAATGAT
ACAACGTGATTTCACGAAGGCAGCCATCCATATATTTTGCCTCAATGACGTCTCCAATAT
CTGGCTTGAAAGCGTCCCGAATCGGATTTGGAGCGCGATTTTGCCCAAAAACAACCTTTT
TTTGGCTGAGGGCAGCATAGCCCCAGGCGCACTCACCAACAAGGTGTTCGACTATTGCCT
CCGTCGATGGGAGGGTAGGTCCGACAAGATAATACCGGCACAGCGAGCCTTCCTGGCTTG
TTTCAATGCCAGGTAAGCGATTGCCTTTCTCATCGCGCTGGTTAGCCCAAGTGTAACCGT
TGTCAGAAGCTGCCTCCTTGAGCATCATTTTCAAATGCGCCTCAGTAATCCCATCAAGAA
TGTCTTTAACTGGCTCATCGCATACTCGCGAATGACGCACGGCTACAGGCCCTTGTATGA
TGCAAACACGTTGTGCATCCTGGTCCACCACAGCGTCTACATCTTCAGACTGCCATAGAG
AATCTTTCTTAAACCATGTCTGGAAATCTGCATCGAGCCGCGGAATAAAGGGCACCGGCT
TCTGACCTTGTCGGCGGAAAAGATTGATGAGAAGGCTTACATCTTCCGGATAAAGTATCT
GGTCGCCTTGCACGCCGTAGGCTGCGTCAAACGACGCTTCCAGCTCTATGGGAGTGTTGC
```

Figure 5A (continued)

```
AGGAAAGAAAGCGTAATTCAGCTTCTGAACCTGAGCCCAGGCGTCCTTGTGCAAGACGGA
GAAAGTCATGCACCAAGCTGAGGTAGGAAGAATCGATCCAGCGTGCCTGATGCTGCACAT
ATGTAAGCTGGCAGAGACGGCGTAAGACTTGCCTATAGCTCAGCTCCTCAATCTCTGTTG
GTTTACTGCTGTCTGTTTGCGCGAACCACGGCCGGGCAAAGTCGTTATTCAGTCTATTAA
TGATTTCAACACGATGTTGTTTTAATGCAGCTTTTAACCGTTTAGGGTCCCGAATTGAGA
AGAACCGGTCATCGAACTCCTTCCACAAACGCATTGCTCGAGTCGAAGCACATGGATTG
GTTGACCCATCTCTGAAGTGACCGAGATAACACCGCCAACTGCGTCATGTTCACATTTTG
CCCAAGCACCGTTGTCATTCCCATCATCCTTGACTCCGGGGCTTCGACTATAAGCTGCT
TTACAGCGAACGATGTCTTCGCCTCACGAGCCACCATCATGCGGCTCCCTAGGAGGATTC
CATCAAAGGGCATAGGCGCATAACCCAGTTTACAAGACCAAGAGCCATTCATGTATGGCC
AAGTGTCCTCAGCACCCCCGAATCCACTGCCAGCCACGAGAATGACGTTCTCGCAGTTCC
TGATACGGGCGTAACAGTCGAGAATCGGTAAATGGAAGTCCTCACAAGAATGGTGTCCCC
CTGCACGACCCCGGTCCATTGGATCCCAACGGGGAGTGTCGGATATTGCCTTGCGATGG
TAAGGACGCGGTCAATTGCATCAACAGACCCCGGTTTGAACCAAATATGTGAAATTGCCA
ACATGTCAATCCACTCCTTCACGACCTCGGGCGATGGGATCCCAGCGCCGACCGTTATCC
CATCAATTGGCAAGCCTTCTTCCATAATCAGGCGGCGCAACACCTGGATCTGCCAGGAAA
GTGCTTTGGGGGAAGCATAGATGACATTGCAGGTGATTGAGCGATGGGGAGGGATGGACC
TCGACAGCTGCCGGAGTGCTGTTTCTAGCGTTGCTCGGTTGTAATAGCCACCACAGGCAA
ATTCAACATGATAGTCCGCCTGAATGATAGCCGCTACAAGCTCAGGTGAGCATGTTGTTG
GCGTCATCCCTGCCACCATAACATGTGGTGTTCCTAGCAGCCGCGTCATTTTGGTTTCAA
TGGATGCATGAGCACTTCCCTCAGCTGCTTTCCGTAGCCGCGGGCGATATTTGCGACCCC
AGTCTTTACCAAGTGGGAGAGCAAAAGCAGACAGATTAAGCAACGATAGATTCGAAGCCA
TAGACTGGCCGGACAGATTAACGACGTTCATACCCGTTCCCTCCAAAACATCCTGCACCA
GGCTCCCAACAGCGCCAGGCCCAAATGAGAGCACATGGGTAGCATCGTTCATTGCCCAAC
ACAAAGCGGGCCAGTTAACTCGCTCAACAGTAACGGACTGTATGAGGGTCAAAAGAATAT
CGTGCGTGCCATAATCCTGCAGGTTCCGGAGAGATCCATTCGCCTGGCAGTAAACTGGTA
TAGCGAGATCGTTACCCCGCAAGCGAAGGCCGCCAATGGCATCAGTCACTCTTAGCTCGA
CTGATGACAGAAGAGAAGAGTGATAGGGAGCTGACACTGGAAGGAACTGGACATCGACGA
CGGACCGACGCAGGGGAAAGGGAACGCGGCTTTGGTCGAGCTCGGGCGATGCCTTGACGC
TACGAAGTGCTATGCATACTCCTCGCAGAGCATGTGGTGCTCCAGCCAGAACGAACTTGT
TGTGGCCATTTATAAGGGATATATAGAGCGAATCTCCACCTTGGTCGTTGAGCTTTCGCA
CCAGCCGCTCCAAATGATTAATGTCTAAGCCTGTCACACTCAGTAAATGTGACGGAGCGC
CTTCACCATTTTCCAGGCAGTCGATAACTTCATTTGCACACAGAATACTTCTTGGAGAAG
CATGGTGTGACTCCAGCCCGACCCAAAACGACAGTTGCAGGGCAAGGTCAGCCGCGCGGT
AGAAGGATGGCCATCCGTGGTCAGTGTGAGATATGGCGATTGCGGCGGCCACAAATACAC
CTTGAGAGTGTCCGATAGCTCCCTGGAGCTTTTGGCGGAGCTGACCAGGGTCCAGCTGGA
GGCTGTACGCAGTAATAGCATAGTGTAGGAGGCTCAGCAGAGTGTTGATTGGAAAGCTAT
AAGGAGACAGCGCCAAATCTTCCGGCAGTGGTGCGGATGCAGCAGCGTCGTTGAGCCAGG
CCTGTAATTGGAACCCGCGCCCAGCAAAAAATGACGATCGGTGTGGGATCGCTGCTAGTG
ATTCTAGACGGCGGGCAGAAGAGTCGAGCAAGTCCTGTATAGGGGCGCAGTCCGCGTAGG
CGTGCGAGAGATGGACTAACTCATCGAGTCCCGCCCAATTACTGGGCCCTTGCCCACCAA
AGCACGCATATAATCGTGATAGGCCAGCGTCGACAGCATCGAGAAACGGTGATGGAGTCA
TTCTCTTTACAGGTCGTCAAACTGTAGGCTAACAGATCAGAGCCATGGCTGGGAATGAGC
AAGTATATCGTGTAGCCGGGACCACCACCTATACGAGAGGGGAGAAACAAGTCAGCGCA
GGGTCGGCTTACGAGCAATCGGAGATCGGGCGTGGCGGTTCTCAAGTTTACATATCAGCT
GTTGTTCTTCAGTCTTTCCTGCAGAACTAGGCCATAACATGAATACAGCCATGGCGATAC
GAAACATGGAACAGACAATTGCCTACGAGCTACTGATTGAGCTTTTATCGTACGTTTCCT
TATAGGTGTTGAGCAAAAAACTGATCAGCAGCAGCCATCAGTTTGCGTTTCCGGTGCAAT
GGTAGGTCAATAGCGACTGCGATACACCACTAGGTACGCTGACGCGGCTTCGCGCACAGG
ATAGAAACGCAGAAAGCTATATTGCGAGACACTCGTCGCCTCGTCGAAATTGGTCCAGCC
AAGACGCTTATTGGAATGACCCAAAAGACTATACAGCAGGTCCCAAGACAGGGCTTAGAG
TTACTGGCCAGCACGCAGGACCTTGCCCAGCTCTGCTACATCTATGGCAGCCTGCCGAG
GGAGAGGATTCGACCGCCGACGAGTCCATTATTAATACGCCGCAGTGTAGCACAATTCCA
GAGGTAGCGGTAGAGCCGGAAGTTCAGCCAATACCGGACACGCCGCTGACCGCAATATTC
ATCATTAGGGCTCTGGTCGCCCGTAAGCTCCGCAGGTCGGAAACCGAGATTGACCCCAGT
CGCTCAATCAAAGAGCTGTGTGGCGGCAAGTCCACACTACAGAATGAACTGATTGGCGAG
CTGGGCAATGAGTTCCAGACCTCTCTCCCTGATCGCGCGGAGGACGTCTCCCTAGCGGAC
TTGGATGCTGCCCTGGGCGAGGTCTCGCTAGGACCCACGTCGGTTTCTCTTCTGCAGAGA
GTTTTCACGGCGAAGATGCCGGCCCGCATGACAGTGTCGAATGTGCGTGAGCGTTTGGCC
GAAATCTGGGGCCTTGGATTTCATCGACAAACTGCAGTCTTGGTGGCCGCACTTGCGGCT
GAGCCTCACTCCCGACTCACCTCCTTGGAGGCGGCATATCAGTATTGGGACGGTTTGACC
```

Figure 5A (continued)

```
GAGGCCTACGGGCAGTCATTGGGTCTTTTCTTGCGGAAAGCTATCTCACAGCAAGCTGCA
CGGAGTGACGACCAAGGCGCTCAAGCTATAGCCCCTGCAGACTCGCTCGGGTCTAAGGAT
CTTGCACGAAAGCAGTACGAGGCTCTTCGCGAGTACCTAGGGATACGGACCCCAACTACG
AAACAGGATGGTCTAGATCTTGCAGACCTACAGCAGAAGCTGGACTGCTGGACTGCCGAA
TTTTCGGACGACTTCCTCAGCCAGATTTCGCGTCGCTTCGACGCACGAAAGACGCGCTGG
TACCGCGACTGGTGGAACTCGGCGCGCCAGGAGCTTCTGACAATCTGCCAAAATAGTAAT
GTACAATGGACAGACAAAATGCGTGAGCACTTTGTCCAGCGCGCTGAGGAAGGCCTTGTT
GAGATTGCTCGGGCACATTCACTCGCGAAACCCCTTGTGCCGGACCTCATCCAGGCCATT
TCTCTCCCTCCTGTCGTCCGGCTAGGGCGTTTGGCGACCATGATGCCACGGACGGTGGTG
ACCCTTAAGGGGGAGATTCAATGCGAGGAACATGAACGGGAGCCTTCTTGCTTTGTGGAG
TTCTTCAGCAGCTGGATCCAGGCAAACAACATTCGATGCACCATACAATCTAATGGGGAA
GACCTCACATCAGTATTCATCAACAGTCTGGTACATGCCAGTCAACAAGGGGTTTCTTTT
GCCAACCACACATACCTTATAACAGGGGCGGGACCAGGATCGATCGGCCAACATATCGTC
CGTCGCTTGTTAACAGGTGGTGCCAGGGTCATTGTAACCACGAGCCGCGAGCCATTGCCT
GCCGCTGCCTTCTTCAAGGAGCTGTATAGTAAGTGTGGAAATCGCGGATCGCAGTTACAT
CTAGTGCCTTTCAATCAGGCCAGCGTTGTGGACTGTGAGCGTCTGATTGGCTACATTTAC
GATGACTTGGGGCTGGATCTAGATGCGATCCTCCCCTTTGCTGCCACAAGCCAGGTGGGA
GCTGAAATCGACGGACTGGATGCCAGTAATGAAGCAGCGTTTCGACTGATGCTGGTGAAT
GTACTACGTCTTGTAGGGTTCGTGGTATCTCAAAAAAGGCGTAGAGGTATTTCCTGCCGA
CCAACCCAAGTCGTGCTGCCTCTGTCTCCTAACCATGGCATCTTGGGTGGTGACGGTCTC
TACGCGGAGTCCAAACGCGGCTTGAGACATTAATACAGCGGTTCCATTCAGAGTCATGG
AAGGAAGAGCTCTCAATATGTGGCGTCAGCATCGGCTGGACCCGGTCAACGGGCTTGATG
GCGGCCAACGACCTTGTTGCTGAGACGGCAGAGAAACAAGGCCGCGTGCTGACATTCTCT
GTTGATGAGATGGGAGACCTCATCTCACTGTTATTAACTCCGCAGTTAGCCACCCGCTGC
GAAGATGCCCCTGTCATGGCGGACTTTTCTGGAAATCTCTCGTGTTGGCGCGATGCCTCT
GCTCAGCTTGCTGCTGCCCGTGCAAGCCTTCGTGAGCGCGCTGACACTGCCCGAGCTCTA
GCACAGGAGGACGAACGAGAATACCGTTGCCGACGCGCAGGAAGTACTCAAGAACCAGTG
GACCAAAGAGTCTCGCTCCATCTCGGGTTCCCATCACTCCCTGAGTATGACCCACTGCTA
CACCCAGATCTCGTGCCTGCTGATGCAGTGGTTGTTGTCGGCTTCGCTGAGCTGGGCCCA
TGGGGAAGCGCGCGGATTCGGTGGGAAATGGAGTCGCGCGGGTGTCTTTCTCCTGCAGGA
TACGTGGAGACGGCATGGCTAATGAATCTCATACGGCATGTTGACAACGTCAATTACGTC
GGATGGGTGGATGGGAAGATGGAAGCCCGTTGCAGATGCTGATATTCCAAAACGATAC
GGCGAGCGGATCCTATCGAATGCAGGCATACGTTCACTGCCATCTGACAATCGAGAGGTT
TTCCAGGAGATCGTGCTTGAACAAGACTTGCCGTCATTTGAGACTACACGGGAAAATGCC
GAAGCTCTGCAGCAACGGCACGGCGATATGGTGCAAGTCAGCACACTCAAAAACGGCTTG
TGTCTAGTTCAGCTACAGCACGGCGCAACAATCCGCGTTCCCAAATCCATCATGTCTCCT
CCAGGTGTTGCCGGCCAACTGCCGACAGGCTGGTCGCCAGAACGGTACGGGATTCCAGCG
GAAATCGTGCAGCAAGTTGACCCCGTTGCCCTTGTGCTGCTCTGCTGTGTAGCGGAGGCT
TTCTACAGTGCCGGCATTTCCGATCCAATGGAGATATTTGAGCACATTCATCTATCGGAA
CTGGGCAACTTTGTAGGCTCCTCAATGGGTGGGGTGGTGAACACCCGAGCGCTATATCAC
GACGTCTGCCTTGATAAGGATGTGCAATCCGACGCACTGCAGGAGACATATCTCAACACT
GCACCGGCGTGGGTGAATATGTTGTATCTGGGTGCAGCTGGTCCAATCAAGACTCCTGTA
GGCGCGTGTGCAACTGCTTTGGAATCAGTTGACTCCGCCGTAGAATCTATCAAAGCCGGT
CAGACAAAGATCTGCCTTGTCGGTGGCTATGACGACCTTCAGCCTGAGGAGTCAGCAGGC
TTTGCCCGCATGAAGGCTACGGTTTCTGTCAGAGATGAGCAGGCGCGCGGCCGCGAGCCC
GGCGAGATGTCGCGTCCTACAGCGGCCTCTCGCTCTGGGTTCGTGGAATCCCAAGGCTGC
GGTGTCCAGCTTCTTTGTCGCGGGGATGTGGCGTTAGCAATGGGTTTGCCTATTTACGGC
ATCATCGCTGGCACTGGCATGGCCTCAGACGGGATTGGTCGCTCCGTGCCTGCTCCCGGA
CAAGGCATCCTCACTTTTGCACAGGAAGATGCTCAGAACCCTGCCCCGATCCGGACAGCG
CTCGCGCGCTGGGGGTTAGGGATCGACGATATCACCGTGGCCTCACTGCATGCGACCTCG
ACACCAGCAAACGACACCAACGAACCTCTCGTGATTCAGCGGGAAATGACTCACCTTGGC
CGCACCTCCGGCCGTCCTCTGTGGGCGATCTGTCAAAAATTTGTGACCGGCCATCCAAAA
GCCCCCGCAGCAGCGTGGATGTTGAACGGGTGTCTCCAGGTGCTCGATACCGGTCTTGTG
CCGGGCAACCGAAACGCAGACGACGTCGATCCTGCTCTCCGATCGTTCAGTCATCTGTGT
TTCCCAATCCGTTCAATACAGACCGATGGCATCAAGGCATTCTTGCTGAATTCGTGCGGT
TTCGGACAGAAGGAGGCGCAGCTTGTGGGTGTTCATCCTCGATACTTTTGGGTCTACTC
TCAGAGCCAGAGTTCGAAGAATACAGAACCCGACGGCAACTTCGCATCGCAGGAGCTGAA
CGAGCCTATATCAGCGCGATGATGACAAATTCCATTGTCTGCGTGCAGTCACACCCTCCC
TTTGGTCCCGCAGAGATGCACTCCATCCTACTGGATCCTTCTGCTCGTATATGCCTGGAT
TCATCCACCAATTCCTACCGCGTCACAAAAGCGTCCACTCCAGTTTATACGGGCTTCCAG
```

Figure 5A (continued)

```
AGGCCTCACGACAAACGTGAAGATCCTCGTCCGTCAACGATCGGCGTCGATACCGTAACC
TTGAGCAGTTTCAATGCGCACGAGAACGCCATCTTCCTGCAGCGCAACTACACCGAGCGC
GAACGCCAGTCCCTGCAACTACAGAGCCATCGCAGCTTCCGGTCCGCAGTCGCGAGTGGC
TGGTGCGCCAAAGAAGCCGTTTTCAAATGCTTACAGACGGTATCCAAGGGCGCAGGGGCG
GCGATGAGCGAGATCGAGATTGTGCGCGTACAAGGGGCTCCGTCTGTGGTGGTAAGTTGC
CTTCTCTTCTTCTTGAAACGACGCTGACGCGCCCAGTTACACGGCGATGCACTTGCTGCA
GCGCAAAAGGCTGGTTTGGATAATATCCAGCTAAGTCTGAGCTATGGTGATGATTGTGTG
GTCGCGGTTGCTTTAGGTGTACGCAAGTGGTGTCTTTGGCCGTTGGCCTCTATCATCCGT
TAAGCAACGGCTCCAGACATGTCAGGTTCCTCATCCTGTTTTAAGATGAAGTATAATACT
TAGAAGATATTTAGATCCTCATCGCAATTCTATCTGGCTTTTTACGCCATGGTTGACGAG
AAATCGTAGGACAGCGTCAGACGTTCCTTCCTGGCGGGACATTGTTTCTCCGATCCGCCG
CCAAAATGATTACCTAATAGGGTCTTGTGATGTTTTAACTATGTGGAAAGAGCACACAGC
TCATCCGAGCTCCGCCAGAGCTCATATGAGCGTTACCCCTCAAAGCACGTGACGCCAAGG
CCATTAACAAGCAGAACGTCTCGAGCGAGCTACAAAAAAAATTACGGAAATACTTTGAAA
TTCAATAAGCTCGAGGCGGCCAGCAGCCACCTCACGGAGGTACCACTGGTACCACTTCTA
AAACCGGCATATTAGTAATTGGGCTGTAAAAAGCGAATTTAATGATAGAAGCCGCTGTG
CAAACAATTATTAAGTACTTTCTGAATAATTAACTTACGTTGTTAGAGAGAGGCCATC
ACGCAGCTTGTTTTGGTTGCTGGTAATCGGAAGCGAAGACCTGGCTCGAGACGAAATTTT
CCACAAGCTCGCTCGAGCGTCACATGGGCAAAAGGCCATTACATAAGCCATTTCGTCTCG
AGCGAGCCAAACCACAAACCACAAACCTGTACCCCGGCTGACCTGTAACCACATGTGGAA
GGGACGGACAATTATCAGTATTGGATGGCCAACGTGGCCGCCTATCCATACCTAGCTTAC
TAAATAATGACTAAGCGAGCTCGACCCCTAGGGGCAGGCGGTGCCATAGGACAGTATGCC
CCGACAAAGTATGATTCCTGAGTGCCACCTGACCTGTACCTGATGATTCCTAACTCTGAT
CGAGCCTTGACAGAACCGGAAGTTCTGTAAGAGTATTCATCCTGATATCTTTGAATTGGG
TAGTATCAGCTCCTGGTATGATAATATGTGCTTGATGACCCATAGTACTTAAAGAATGAT
ATCTAGACGACTGGCGCTAACCGTTCCCGCTGATGCCTAGATTAATATATATTTGCTGCG
CCTCACAATCAACCCACTGCCTTAGGGCCAAATGTATAACTATGGGTTCTGACAGACGCC
CGGCATTGCCTTACTCACAAACCCAGCATATTCCACTTAACAGATTTCCGAAGAAGAGTG
CCTGATGTTCCCTCAGTGCTGGTGACGGAAATAGCCACGAGAAATGCGGATAGCCAGGAT
ACTCATCGCACTTTACCGGGACTTCCAACGCGACTAGAGCGTCCCTCATCAGGCGGACGT
CGTCCCTCAGGGTGTCGGCGTCGCCAACGGCCATGTAGACTTTATTCAGTTTTCCAAGAC
CCGGATGCAGAAGACATGAAAGCCGGGGATCATCCGGTGGTGCGCCATAGCAATCGAAGA
ACGACCGCATCGCGGAGCCGGTGTTGATTGTCAACCGGTCATTCTCTTCATAGGATGTAT
ACTCTCCTCGGTCTCGATTGTCTGCGGACACGGAGTCAGGATGAACGGTTACCGGCGCGA
GAGCAACCACGCCTTGGACTCGGTCTCCTAGGCCGTCACTAACCAGGGTAAGTGCCGTAC
TGAACGCCATGTTTCCACCGGCCGAGGCACCGATGAAACAGATTGATTGCACGGGATACG
TTTCCAGGACCGATCTCGCAACAGTTAGACAATCGTCAAGCGCCATCGGGAATCGGAATT
CGGGGGCTAGACGGTATCCCACGCTGAAGATTCTCGTGCGGGCCAGTTTACAGAGAGTGC
GGACGAAGCCGTCCTCCTCGTCAATGCTGCCCATGACCCATCCGCCGGCGTGGAAGTAGA
GGGCCAGCGGTGGGTCAGCTACATCCGGCGGCGTGTAGATGCGTGTGGGGACGCCGCCGA
GGATCTTGTCCTCTGCCTGAACGCTCAGGTCTGGAAGAGGAAAGTCGTAGCGGCTCATCA
GCTTGCCGACTATCGTCTTCCATCCCTGCATGAGCCTCTCGTACGGCCCGTCAAGAGCCG
GCGAAAAGCCAAGCTCTTCTATGAACTGGTACAGTCAATTTTACGCATCAGGTGCTTGGA
GGACTGTTCGTACCTGCTGCCATGGCTCTGATAGCTTGGAATCCATTGTTGAAGCGATCT
GTTGTCTGCTACGGACTTTCATCGCGAGGTTCGATTTGTCTTATGTTGAATGTCGGTCAC
CGAGCTACAATGTTCTTAATTGGATCTTCATCCGTCTGGTAAATGTCCACCATAACGTAT
GGCGTTATTGTATCTGATCCGTCTGCAGCCCACTTAGCTACCCCCTGAGTCCTCAGTAT
GCCGGTATATCACGTCGGTATGCATACCCTAGGCGACAATGAACACTGAGACTGATCTAT
CCACCGACAGCCCTATTCAAACTCAAACCAGACGCCGACCCTAACCGTATCTGTTTATGG
CAGGAGCTCGCGCACGCAATGGTCGGCAAGGTACCTGGCCTACTGGATCTGCAAGCTGGG
CCTCCCCTCGACTTCACGGCTCGACTGGCGAAAGGGTTTGATATGGGTGTAGTCGTGCTG
CTAGACTATGTGGAGTCTCTCGCTACCATGTTTACGCATCCGAGCCATGACCAGTAAGTG
TTCAGAATGAATGGCCTTCCGTGTTTATCATCGTTGATGTACGACAGAGTTCACGAATTG
TACCAGGAGGTTTGCGAGGACGGGAGTACTGTTGGTTACGATATTGAATTCTAGAGGGCT
AGGTTGCAGCATATCCTCTAGAACTGTTCTACTCCGAACTAGTGCAGGCATAACCGTGGG
AATGTGTATATAATCAGACATCGAACCCAGCATCCCGCCGCCGCTGCATAATAGGCCTCA
ACTGATTCCCACCCCCATCCGTCCTCCAAATCATCTTTCAGGTCAAAAGTACCCTCCGGCT
GTACTGCCAAGGCACGTCCTGTAGAGCCACTTAGTATTATCCCAGCCAAGCCAATAAGAT
AGAAGAGAAAATAGGAGTAAAATGTACCATGTATCTCTGGGCTTGCAACACAATAAGTCG
CGGCATCAACGCATGCGTCAATAGACGTAAACGTGAGTACCTTGGCCCATATCGACTCCAC
```

Figure 5A (continued)

```
GCGCTGCCATCGCATGCTTGATTGGGGCAATGAGCGGAGAATCGAAGAACCACGGCGCAA
GCAGATTGCAGCGAACGCCCAACTGCTTGGTCTGAGAACGCGTGCTGCGAAACAGCCCGC
GGACGCCGAACTTGCTGGCCGGGTACGTGGACGCCTTGGGGCTGTCCATATATGCTGCGA
TGGAGGCGCAGAAGAGAAGGCATTTGTTGCTGGGCAACTCGGGGTCAGTTCCCGTGCCTG
GTATACGCAGGTAATACAGCCCCAGCCAGGAAGTGAAGTAACTTCCCACCAGATTCACCT
CGATATTGCGGACACTGGAGCTCGGCCGGGGAGGATCGACCTCTAGGCTGGGAACACCCG
CGGCAAGGACGTGATCTATCTGGTTTCCGGGGGCGAGAGCCGTTCCGGCAAAGCAGGCGA
CTATATCCAGGGCGCCGCTGGGTGAGAAGCGAAGGGCGCTCTTAAAGGCGGCCACTTGAC
TCTCCCAGCTCGTGACATCGCAGTAGACATAGTGAAAACAGTGCGCGAGTCCAGGCTGGA
CTGGGCTCGTTGGCGGTTGGATGTCGGCGATGGTGATATAGACCCCGGCCTCTGCCCATT
TCCGCGCTGTGGCCAGCCCTAGGCCTGAAGCGCCGCCGGTGATGAATGCGGATTTGCCGT
TGAGGCTAGTCAGGTCGCAAGTGAGATCGAGGGGCTCCATATTGAGTCCGGGTGAGTAGC
TATGGGTTATCTTTTGCGCGCATTGGGTTGGTGGTCATTCATTTATAGCCCTCGGGGTAT
AGAGTTCGGAGTCTCAGAATCTGAACAAGGTCGTAGTGCTCAGGAAGAAAGATACTAAAA
TCGCCGTCTTCGCCTTCGTGGGTTTCTAAATAGCTCCAAACAGCCAAAATCCAACATTAT
TCGGCATGATTCTGCCTCTGATATTGGTCTTGTATCTGCTCTCTACGGCGGCTTACCGTC
TATGGCTGCATCCGCTGCGCAACTACCCTGGCCCGTGCTGGTGGGCTGTTTGGCGAGTTC
CATATCTGAAGGGCACCATTCGAGGGACGATTGTCAGAGATATCCAGCGATTGCATAACC
AGTATGGTCCCGTTGTACGAATCGCGCCAGATGAACTTTCCTACATCACGCCAGAGGCAG
CAAAACCAATCTACACGTCCAGTCCCGAATTCCCCAAAGACCCAATGCATCTCCCTCCGT
TTCATAATGGCGCCCTGGCATTCTCGCTGCCGACTACGCCCACCATCGGCGATATCGAC
GGCTTCTTGCCTCTGCCTTCTCTGAAAAGGGACTTCGCGCACAGCAGGGCATGATTCAGA
GCCATATTGATCGACTAATGACTCGTCTCCAGGGGAATTGCTCGTCGGGCTCGCTGGACA
TGACCGTCTGGTTCAACTGGGCGACCTTCGATATCATCGGCGATCTCGCTTTCGGGGAGC
CGTTCGGCTGTCTCGAGAGAATGGAGACTAACCCATGGATTGCCTCAATTCAGGGCAACG
TCAAATCCATCCCGATCCTAAACGCTCGGTACGTCGGTACCGTCTGGACAGGCTCATTGAGT
TCCTCGCGCCTCCCAGGCTACTGGAGATGCGACGGCGTAATGCGCAGTTCACAGCAGAAA
AGGTCGATCGCCGACTGAAGCATGCAACGACCACGCGCGGCGACCTGTGGGACTCGGTGC
TGGCCGACCCTCCAGATGGTGAGCCTCCGATGTCGCGCGCCGAGATGGTCAGCAATGCCA
GCGCAATCGTTCTTGCGGGGAGCGAGACGTCGGCAACCACTCTGAGCGGGTGTCTTTGGC
TGCTTCTCACGAACCCTGAGTATCTGCAGCAGCTCACTGAGCGTATCCGCGCTCGGTTCA
GCACGGCCACAGTCATTGATGCACAGACGGTGACGCAGATCCAGGGGCTCCAGGCGGTCC
TTGACGAGTCGCTACGCCTATATCCTGCAGTGCCAATGCAAAGCAACCGTATTGTTCCAC
CACCGGGCGCCCGTCTTGCAGGCAGCTGGGTTCCGGGAGGGGTAAGTCTGCAGCCACTCA
TCCTGCCCTTTTCCTTCTTTTCTCTTTCAGCCGATGGGCCTCTCGCTGACCGATTGATTA
CAGACCTCGGTCGCCGTCCAACAGTTTGCTGCCTGTCGCTCCCCCACCAACTTTCACCGT
CCAGACGAGTTTATTCCCGAGCGGTGGAAAAGGAAGGTGAGTTCATCAATGATCGGCGG
GAGGCCTCGCAGCCATTTAGCATTGGTCCCCGCAATTGCATCGGACGCCAGTTGGCTCTT
GCCGAGATGCGGCTGATCCTGGTCCACCTCTTATGGCACTTTGATATAGAACTGGACCGG
CGGCGCATGGAAAATATGGACTGGATGGCGGTGCAGGGGATCTGGATCCTGTGGGACAAG
AAACCGCTGTGGGTTGTGTTGAAGAACAGAAGTACGTAGGCACCAAAGTCTTTGCAGCGC
TAGTATGGATGCTAGTACTGCCACTGTACAGCTTATTGCTTTACTAAGAAATTAAAGTAG
TAATGCCCGGCAAAAGACTGTGGTAGTATTATTCACGTAAGAAAGAAGATCATAATAAGA
TAAACTAGCACAAATAAAGCTAGAGGTTCTTCCAGACCCTAGAGTTAGGCCTTCACATGC
GGAAAGCTGGCCCTGATCTGTCTGCCCTACTGCCATTCCAGCTATAAGAATTATAATTCT
TACAGCCCTTCTATGCTTAATGGCTCTAATATGTTGTGTAACCCACTGTATCTGCCTTAA
GTATTTACAGCTTAGAAATATCCTTTGATAACTGGATTATTCGCCATCTTTCAATTAGTC
AAGTTTAGCTTTCAAGTACAGAGCAGGATTATGGGCATGGTGTGTACCTTCTGGCTATGT
TCTGCGTTGTATAAATGTTTGATCTAAGAATATCGGGTATATTAGCTGTTTTAATCTGGG
CCCAATAAGAAAGGATATATACTTGAAATCGTTTAGATAAGGTATTGGCATTCAAGGACT
GCAGGCAGGAAGGGCGCATACAGTTCGAAGGCAGATTAAAAGCAGGCATATTTGCGGAA
ATGTACTTTTCAGCCTCTTTAAACTAGTTTGATCTGTTAGTAGCAGTCTGGAAGCTTTAA
AAATAGAAAATGGCTATGTTAATGTTTGCTCTGGAAGATCAATCTCAACCAATAACCTAG
TTGTCTAATAGCCGGTAATTATATCATATGATATGGCATCAAATATTACTAGCGCGGCAA
AAAATCCTGGTGCACACCCTCACAATGACAAACCTTTTACAGCGTCGTGGACTTGCAGTA
GGGCTTCTCGGCAGCCAAGACAGGAAAATGCACACTAAAGCTAATCCAGTGTCCACCAAT
CACTTGCTGCCGTTTAGCTTTTTATCAGCTGCAGTCATGCTATAATGTTGGGCGTCAAAG
CGTAGTCCATGATGCGGTACCCCTCCGACGTGGCATTCCTTAGTGCTTTCTAGCAGACGG
TTCGTATCGCACCTCTAGCCCAATTGCAGCACTGGCTGTTGTGTGTATCTCGCGTGTCAC
CACTAAACAGCCCCCTGAGTCCCTGATGCCGGTAACAATCTCGACGATCTCTGTCTTGGT
```

Figure 5A (continued)

```
AGGCTGCCGCTCATTAGACAACTGCAGGAGCGACATGTCGCGCAGTCGCACCATGGATTC
CGTCTCCTGATTGACTGTTCCAGGCGACGGCAGGACTAAGGCCGCTATCATCAGGCGGGA
AGTGGGCTGAGTGCGGAGAACCTGGAGATGGGCCTGCAGCTCCATCACAGTTTGGCTCCG
CAATTTCGTCCAAGGTAGCATGGGTGAGGGGGACGGGATGCGGACGATGTAGACCGCTGG
ACCTAAGACCGTCTGGGGGGCGCCGGCCCCCGCGAATGCACCGAGACACGATTACTGAT
GGACGGTGGCAGCTGGTATGTCACCCAGGATGGCTCAGAGCCCGTTATCGGCCCGACTG
GCCGTTACCAGGCGAGCTTGTCTGGATAACTAACTGGGCGGCAGGACCCAGGGCAGCAAT
CATGCCGATGGTGCTGGTGGACGGGGGATGGATCTGGATGCTGTCAGCGGGATGATCTGG
ATCGACGATATGGTAAGCTGACATCCACGATGGTGGCCGGCCCAATGGCACCCCAGTCTA
CCAAGCGAAGCACCTCATCAACGGCCAAAGGCTCATCAAGAATCCCTCGAGCAAGATAGG
CTGCAAACTGGCGTTGCACCTTGGGTTGTGCAGGATCAGGTCTATCTTCCAATCCCGTTG
CCCTACTCTCTGATCGAGCAATCAGCGACGGAGAGAGGCCACGATCATAAGGGTCCGGCT
GGCACGTTGAGCGTGGCATCTTCAGTGCCGCCGGAACCGCAACCTGGGCCAGGAAAAGCG
CTGCGTCTAGCAGCTCTGGCTCCGTGACAAAGGAGGCTGATAGTGGGGTATGCGCAACGT
GCCCGCTAGGTCTCTCGCTGAGGAATCCTGCAGTCACCATCAGGCGTACGACTCGCTGCA
GCTGGTCCACAGGGACATTGCTGATATCCGCGACCTCCTCGAAAGCCACCTCTCCGTCCA
GGGGAATGCAGGCCAACACTTGAAACTCGCATAGCCATTGTAGATTGGCCAGGAGTTGCG
TCTTTACTTTGTTAGCACCGGTCATTCTTCCGGGACTGGAAGCAGGACGATCCCAAGGGG
GGAACACAAAGACTTGCCTGAAGCGCGAACTGTTGCAAAAAGCCAGCTGGCTGAGTCGCC
ATTACTAAAAAGTCTGTACAGCAAAGACAAAGATATGCGGTGGGAAAGGGAGAGCAGCGT
CTCGAATAGGAAAGCCCACTGCTTGCGGGCCCTAGGTCGAAGCCTTGATATAGCCCAGCG
GCTGCCGACTCCTAGACCCCGACAGGGCAGCTTGCGGTGCTCAGCCTTCGCTTAGGATAA
GTAATGGATCAAGCTAATGGGGTTATCGTATGGCTCATGCAGTCAACCAGTTCTAGCCCG
CAGTATCCCCTCTCTGGAGTCGTATCTCCTCATGGCGAATCTCCAGGCTAAGTTTGCAAC
CCTTGAAACCCATAGCCAGTAAAGTTGAATTGTTATTTCTTGTGTCAGTCGGTAGATATC
GAGCCCTGTAATCCCTGCGGGAATATTGACCCCAAGTACAGCTTACACAGTACAGCTTAC
TCCCCATCTTCTCTTCACTGATATATATCATCCAGATCTCGCGGTTCAATCCGCAATGCG
GGCCTGTATCATATGCAAATATCATGGAGCCCCAGCGATCAGCCAGCAATCCACACCCA
CGGCCCCGGGGGAACGCAAGGGACACGCAAACTGCGCGAGAGTTGCATCTCGTGCTCCA
GATCCAAGGTCAAGTGCAATAAGGAGAAGCCCACATGCAGTCGATGCGTCCGCCGTGGTC
TGCCTTGCGAGTATATGGTTTCCAGGCGCACTGGACGCACTCGCGTCATTGGTGTTGAGC
AGCCAAAGACAGCACCATCACCAACAACACCGACGAATACGACAGCAGCTACTACAGCAA
CGAAGGCAGGACCACCAGTTACAACAGACAGTGCTGTTCATACACCTGTCATTACTACGG
CGCCCTCTCCCAAGCCGGTGCAGATCCAGTCTCCTCCAGCCGAACCAGATCTCTGGGGCG
CCATCCTGTCTCCAATACTTCCACCTCCACCGACCTATCGTCACTCCTCTCGGTGAATA
CAAATTTCAGTCAGCTCTTCGCCTCGCTTTCTCCTTCGCTTCTTGAGGGTATGGATGGCA
TGGATGCCGAAATGCACGCGCCGGAGCTGGGCGCATTGTCGGTCGCCGACCCATCGTCCT
CCATGATGCAGGGGTTAGAGGCCCCTAACGCTGCCCAACCACCGTCTTCGAACACCACAA
GCCACTCCTACTGCCTGTCCATCTGCCTGGATACTCTCATGCGGCTCTTTCCGAATGCTG
GCGCTAACTGCGAGCGACCCGGGCACGAGAGCAACCCCGGCAAACTGTTCACTATCGAGT
CCGTTATTGAGGACAACAAACAAATCTTGGACACAGCGCAGACAATCCTGGCTTGCCGCT
GCGCCGAGGATGAGTACGTGGTCACTCTCGTCTCACTTATTGTCTTCAAGGTTCTTGGAT
GGTACGTCGCCGCGGCTCGGGATAGGTCGTCGGACCCGGGGCGCGAAGAAGACTTCAACT
GGTCGACTGCCCAAGACAGTCGTAGAGGTTCGGTCTCTTCCTTTGAGGAGCAGGTGCTGC
ATCTTCCCACCGTCGTCGGCAGTTATTGCATTGATGGCCATCATCAGAGCCGCATGGCAG
CCCAGCTGGTGCTGAGCGAGCTATACCGCGTCCAACGACTGGTGACTCAGGTAAGCCGTC
GCCTAGAATCTATTCGCCGCCGCTCCTCGAGCAGCTCGAGCTCTGCCTCTAGTAATACAA
CGGACTCTGACGGCGGGATGTCGACCCCCTTGTCGTCGACCACCCTGGTCCATCTAGAAG
ACGATTTGCGCAAGCGCCTGCGTGCCGTCTCAAGCGAAACGATCAGCATCCTCCGCCACG
CCTGAGGTTGAATAATCTGGAATGATATTTATGCGATCAAAGTTCATTATGACGAGTGTT
GGGTGAATGGTATGCGACTCTAGGGTTCCCTGCCGAATGTCCAGCTTATTTGATACAGTG
GTGGACACCGAGAAGCATTCAACGAGGAGCATTCATTCTACATTCCGGGCGTTCATTACA
GCCAGTAGTATAACTACACTACATTTGAATTATTCATAGAGTTAGGCGAGCACGTTGAGG
TGCAAGAAGCAGCGATAATGAGTTCATGATATACTGATTTTAACAGGATTCAGCACATGG
TAGCCAAGTAACAAAGGTAGTCACCAAGTAAACTACCAGGGCACGTCTGAGCCGTCCGAA
AATAGAATAAAGCGCCCAGACGTTGTATTCTTGTCGGCCTCGGTCATCTGTCCTCACAGG
ATTAGTTCGATGCAGAATTAGCGAAACGGAAACATACCCTGGCACAGATACCAGCCACGC
TTTCCTCTATCGTCGTGGGGCCTCTTTGCGCCCGAACAACCTGGCAGCCTGGGCGCCCA
TATCTGACTGGATGTGTCTACCGGCCCGATCTCGTCAGCCAAGATGAAGTGCGCTTCAGA
CAGTCATAATCGAATCCGGGCATTCTCACCCAGGGTCGACAATGTACGCAACAAGCCACT
```

Figure 5A (continued)

```
TATTCTCAAAGTGGATCTTGCGCACCAGATAGCAGGCGGCCAGCTTTGAAAGTGCATAAT
TTGTGAGCGGTGCCCGCGCACAGCTCTCCATCTCGGTAATCGTGCTAATCGGGGCCCCGA
CGCAGATGAACTGCGGCGATTTGGCGGCCTGGAGAAGGACCCTAGTCGCCTGGAACAGTA
GCAGGGCCGCGTATGCGTTAATCTGCATGTGAGTCTCCAGATACTCGAGAGGCATGGTCG
AGGCTGGACCGTAGTTGGCCGCAATAGCTGCGTTCGCGATCACTACATCGAGATGCGTAA
TGCCGTAATCGCGCTGGAGAATGCTGACCGCGTCGGCGGGATCGGACTTCGATCCACTGT
CCAGTTGGACTGCGATCAGCGAGGAGTTCTCGCCTCTTGGGAGCGCATCCAAGGCCCCCG
CCTGCGAAGTGCGATTGCGGAGACCGGCGATGACGATGCTGTTGGGGCGAAGGAGAAATG
CCTGCACGAGCCCCCTCCCGAGGCCTGCAGTTGGTGTTTAGATCTGTGTTAAATCTGTTT
CAGGAATGCAGGCGAACGTACCCCTGCTGGCACCGGTCACTAGGTAGACCGTCTTGCGGT
CGGACGAAGGAACTTCTGGTACAGAAACGGCTGCAGATGGCATGGCGGCAGTACAGAACT
GAGCTGAGAAGACTACAGTATATGGATTTGCGGAAGATGGTGACCGTCTTATATTTCTCG
CCGGGCGTACAAGTAGCCTCATCGGCCATTATAGGGAAGGATCGGGGATTTGACCAAGTG
CCGAAGCACGATCATATTTTGTTTGGTTGCTTTTGTAGATATGCTTCCATATCTCCATAT
CTCCTTATTTCCCGATTCTCAATGGCCTATAACCCAATAACCCAATAATCAAATAAACCA
TCAACCATGCAAAAGGGCATCTGGCCGATGCGCAGGCGAACCCTTACCCGATTCAACTCG
ACACTAGTCGTCTAGTCAAAGAGGCCCAGAAAAGCCGCCCCGAGGGCCGTCATCATTGGC
GCATACGACCAATGGCCCCATTCTCCCTTTCCCCAGCTATAGCAGATCGCGCCGTCGGCA
AACGCGACCAGACTGCCGGCCACGAGGGTCCAGCCCGTCGACTTGCGGGTCCCGAACGCG
TTGGCAATGTAGAACGAAAAGCCCCAGAAGATGTCGCGGACCCCGTACACGTAACTCAGG
CCCTCGACGAGCCGTCTTTCGGCGGGCGAAGCGGGCAGCTCCCACTCAAAGAAAGAGAGC
GCGTGCGCAGGGCGAAGGAGCGCGTTGACGCCGAATCCAATGGCGATGAGCGCAAACGCA
TTGGCGCCGATGCTGAGGGCCGGGTGCTGAGAGACGGGCATTTTGAAGTATTGTTTAACG
GATTGGTGGCTTCTGTCAGTGTTAGTATTGATGTCAAGATTCAGTGCAGCGCAGCTCCAG
TGCAGTCGAGAGTAATTTTAGTGCCAGTGCCAGTGCAGTGTTGATGGATGTCAATAGAAC
AAAATCAAAGTCAGCTTCTTACCTCGTAAATCAATCCAGATTGATGGTTAAGCAGTATTG
CGACGAGAGAGAGATGAAGAATGTGCAGTGAGAGAAGACGAGATTTAAGGCGAGGGGTCG
GGAGTTAGGCACGGAGATAGCAGTTCTTTGTCTTGGCCTCTGCCTTGTCTCACACTCATT
TCCACACAATAAATGTCGCTTGTAGCTAGCCTCGTCTCGTTGGCCATCAGGTCTGTTGGT
TGGTTGGCCTCTGGTCGACCGTCTGTCAGTCGTCTGGCCAGTCGTCTGGTCGGTGGTCTT
GCAGCGCGTACTAGTCATCTCAGCTCTCAGCATCTCACCATCCAGGGCCGTCCCTCTGCC
ACTCCCAGGGCTGAGATCACAGGTACCAGATCAAGTTCTATTCATAGCGCAATCCTTCTC
AGTGAACCCGTGCCCGGCGCTAGGATGTCCGCCCAGGGCACAGTTCTCAAGGGCCAGGAA
GCAGCCGCAGCTCGCATTCGCACAGTCCCCATTCGTCAGCTGCCTCGTGGCAGTACCGTA
AAGCCATCGTGAGACCATTTTGGACCCTGCAGAGAACGCCACCTTGCTTCCTAGTTCTAA
TTTCGTCGCGTGGCCCCCATGCGGTCTCATCCTCGAACTCTCTCGACACCTGTCGCAGTC
ATTCCGCGCCGCTCGCGCTGGGTTAACGGGCCATAGACAATAGCCAGTGGCCGCTTAGAA
TCGGGCTGAAGGGCTTCACAGCCCCTTCGCACGCGAAGGGGCAATACGAGCCGACCAGTT
CGTGATGCGGTTGAGCGGGAGATGCCCGCTAGATCGTGCTGTTCATACCATGGATAAGAA
TAGAGCATCAGCAGTAGAATGGCTATATAAACCACTTGGTCTTCGCCGGGATGTCCTTGC
TCGACCAGCAATCTCAATATCTTCTGTCTTACCAAGAAACTTGCGCGACAAGAACTCTCG
CGACACAACTTTCGCTATACAATGTTGCTCAAGAGCATCCAGAACATTGTCTGTGGCCTC
GTGCCAACGTTCTTCCTGTTTGGCTCTGCAGCTGCCGAGCTGGACTTTGAACAGTGGCAT
CCAGCGGGACTGGGAGACTTGCGCTGCGGCTGCCCGGCCATGAACAGTCTTGCCAACCAC
GGGTTCATCAACCATAACGGCAGCAACATCACGGTCAACGAGGTCATCCCGTTGATGCAA
GAGGTCTTTCATCTCAGTGAAGAGCTCGCCACGATTGTCACGGGCCTCGCCGTCCTCTCG
GCGGACGACCCTGCCTCGGGTATTTTCAACCTTGATATGCTGAACCGCCACAACATTTTC
GAGCACGACGCCTCACTGACCCGCAAGGATTTCTACCTGGGCGGCGACGGACATACTATT
GACCAGCCCACGCTGGACGAGTTCCTCAGCTACTTCGACGGCAAAGAATGGATCGACCTC
AACGACGCCGCAGCAGCCCGCTATGCGCGCGTCCTCGACTCCCGCGAGAAGAACCCGAGC
TTCCTCTACCAGGACCAGCAGCTCATTACTTCGTACGGCGAGACGATCAAGTACTTCCGA
ACCATGGTCGACCCGCGCTCAAACAAGACATCCGCCGAGTTCGTCAGGATCTTGTTCACC
GAGGAGCGGCTGCCCGTCAGGGAAGGGTGGCAGCGCCCGCGAGAAGAGATCAGTGGGTTC
TCGCTGGCCAGCGATGTCGTTCAGCTGGCGCTGCGCACCCAGAGAAGTTCATTGGCATG
CCGTTCGACCAGCGTCCGTTTGCAGAGCAGGCCTTTGACCCGCTGCCATGGCAGCGGCCT
CCCATCTGGACTCCCCCGAACTACCCGGGTTTCAGTAAGAGGCATTTCTCTGAGCTTGTC
GGGAGGTTTGCGAAGAAGGCCCTTCCGTTTCGTGCTTGATAGACATCTATCTTTCTGAGG
CTTTGGTCACTGCCTTCGCTCGGCGTTGCAGCGCAAAACTATATACACGCACATATATAT
TTCTCTTTCGTTTGTCTATAGTACTAGAATTGGTCTTGTTTGTACAAACATAATTAATCA
TTGGCATCTATCAATTCAAAGTACCAGCTCTAAACTGCTCTACCAATCCAGGTAATAATG
```

Figure 5A (continued)

```
ATCCCTTATAGTATGATCTTACTTAATGCTGGCATGTTGCTGGCGTGAGAATAAAGTGCG
GCAGAGGATTCAGTAGTGGATCCACTGCGTGGTCTAAACAGGCCGGTGCGAGTTTAACAT
CTGCCTGAGATCTACTAGTGGCTACGAGAACAGCAGGAAGAAACACAAGTCAAGAAAGGG
CTTGGGATTGGAAAAATATCACTATCCAGAGCGCATGACTAAACTGACAAGGGTGAGTAT
TTTTAATGGAAATTCGGAACGCCAAGGTCAATGTTAACCGCGATCGCTAAACTGGGCTTA
GCGTAGGGTGTTTGACACGTGACTAACTAGCACTGTGGAAAGGGACGGACAATTGTCATT
ATTGGTGGCCAACGTTGCCGCCTATCTATACCTAGCTTACTAAATAATGACTAAGCGAGC
TCGACCCCTAGGGCAGGTGACGCGACTTGAAACTCATCATCGTCTTTATGGTCGCGTGAC
AGTCATGACTAATGTTGCTTATATAACCAATTTGTATCGCGCGACTAAAAATCAGGTCTA
ACCGAGCTGCAATCTGGGCGGTGCCATAGAACAGTATGCCCCGACAAACATCGCGCATCG
CGTCGGCTCTATCCGAAGCGAGTTAGAAAATTGTTGGTGCGTCTGGCATGGTACGCCAGA
CTCTCCACGACAGCGTCTCGTTCCATCAATCGGCGTCTATGTCAGTGTAATGGCGCATCG
ACGATCGCGGGGAACGCCCGCTATGAAACTGTCTACCACGTGCATGCTCTCGTCCGTCAC
CGATCGTCCTAATCGCGCCCAACACATTCGCGAAAAACATGGCCGCAGCCAGACGCAT
CTCCATACGGCCGAGATGAATACCTAGGCACTGGCGTGCCCCGTACCCGAACGGGTTGAA
AGCCAGCTTGGCTTGGTCAGTGATTCTCGAGTTGGATAGCCAGCGCGTATGATCGAACCT
AGCCGCTCTGTATCAACACTGCCATCCGCATTTTTTTGTTGATTCGCTTCCACTGGGCT
TCCACTTACGTGTCTGCATCATCCCAGATACTCGGATTGCGCTGAAGACTCCAGTTCTGC
GTAGCAACTATGGTGTCGTCGGGAATGAAATACCCCCAATTGTCACACCCCGGATGGT
GGACTGCGAGGCATGCATCCTGGAGCCGCCCCGTATAGCCGTAGACTTTCGTCGATGACC
GCATTCAGGATGGGCAACCGCTCGCAGGCTTCGTCGGTCAGTTCACCTTCAAGAGTGGCG
ACCTCGGCCTCGACTTGCTTTTGGACTTCTGGTCGACTCAGCACACACCAGAGAAGGAAC
GTCAGAGAGATTGCCGTCGGGTCGGAGCCCGCCAGTAGTAGAGCCCGGCGTCAGTTATG
ATATCTGTATCAGTCAAGTTTCCGGCCTCTAGGGCCTTATTGAATAGATTTCTCGGTTCG
GCCTGGGCCTTCTTTGCCTCTCGCGCTCGGGAGACCACGTCGCCTCCCGCAGCGAACATT
CTCTCCTGAGAATAGAATATATCCTGGAGAGGTGGGATGAACCAAGCCAACGCACGGCCA
AGATAGTAGCCAGGGGGAGCGAAGTGCTTGAGCAGATGCGCAAGGTCTCCCATCCGCCGT
TCTAGCATAAGAACGAAGGGTTCCTTGACACCTTTGGCGACGATGCCTGCGCCACCGCCG
AACGTAAGCTGGCAGACTATTTCGTTGGCCATGAGAGTCCACCACCCCATGATCTCGGCC
TCGCCCTTTACGGCGTCGCATTTGATCTTCTCCACGGTCAGCTTGATGATATCCCGGACC
TTTGGCTCCCACTCGTTTCGTAAGCTCTGCAGCGTGAAACCCCGGGCGTAAAGTTTACGA
CGCGCCGCATGGAGTTTTGGATCCCGAAAGTTGAAGATATTGTCTACCGGCCCTGGTGAT
AGAAGCTCATAGAAGGGAGCTTTCATGAAGCCAGATCCCATGCGGTGGATCTCGCGTCCT
GCCACAGGATCTGCCACGTCGATTTCTTGAGGTCCGATACGGACGATGGGCCCATACTTC
TGGTGCAAGCTATGGACGTAGTGGATTCGATTGTTGGCAAAGACGGACCACGACAGGCGC
AGCCCTGTCAACGACGCATACCAGGGACCTGGAATATGTTTCAATGGAGTGAAGTAAGCT
ATGCGAATGGCCTGGGATACATCAGCGCCAGTTGCCTCCGGGCCGGACGAAATACCTTGA
TTATGCTAAGTAGTATGAAGAAGCTGCCGACATAACTGAGCATGGAGAGCCATTTCATGC
TCAGAAGGGCCGCATAGAAGTCTTTACTGTCCGAAGTCATTGGACTCGCAATCAGAGGGG
GACAATCTGCATCATGAATTCCCCTTCTGTTGGAACGCCTGATATAGTACGCTTGTGCGG
TTGACCCCAGTGTATCGGCACTCAACCGGTCATCTATTCTTGACTCGGTGAAGAGAGAC
TGCAATCGGCAGATGCTCGGGTATCGCTAAAGAATACTCTGTCCTCTTCCCAGTAAACCC
CGGTACAGTCAGCGACGGATCACGGTCAGCGAGGCCATGACCGACTCGGCAGCTCCTTGA
TTGACACCTTGCACATGTAAGATAAAATAGGCAATCTGAATCTCACCGTTAGCTTAGAAT
CATGGAACTGCAGACCATACTATTTTCGCAATAAACGGCTCCAGGATGGCCAGTCACGCT
GAGCCAACCAGGCTCTTCCTTTTTGGGGACCAGACCTATGACTTCGTTGCAGATTTGCGA
GATCTTCTCAATATTCGCAACAATCCAATTCTAGTGGCCTTTCTCGAACAATCGCACCAT
GTTATACGTGCCCAGATGATCCGCGAGCTGCCACCAAAAGAGCACAAGCAAGCTCGGACT
GCGTCCTTAGCAGAGTTACTGCAGAAATATGTCGATCGAAAGCTGCCGTCTGCTTTCCAG
ACTGCCCTCTCCTGCGTTACTCAGATAGGGCTATTTATGCGTCAATTTGATGACCCGCGT
GTTCTTTACCCACACGCTAACGACAGCTACGTCTTGGGAGTCTGCACAGGATCTCTTGCG
GCAGCCGCCATTAGCTGCAGTACTTCTTTATCTGAGCTTTTACCAATTGCTGTCCAGACC
GTCCTCGTCGCCTTTCGCCTTGGCCTTTGGGCAGAGAAAGTGCGCGATAACCTTGAAATA
TCCGAAACCAACCAAACACAGCCCTGGTCGGCAGTGTGTCATGTTCCACCGGAGGAGGTG
GCCATTGCCATTGACAGGTTCAGTCATAAAAGGTCCGTAGCCCTGTATACCGTGCTCAA
AGGTCTTGCTAACCCATTGTCCACCTGAACAGGCGCTATCGAACACGCGCAGACCCTGGA
TTACTGCAACATCAGCCAAAACTACGACAGTTAGCGCAAGCCCTGATATCTTGAGCCAGT
TGGCTAGTCAAGCACCCTTCACGAATAGCAAACTGTGGAGGGAGATTCCAATCTACGTTC
CTGCGCATAACAACCATTTGTTCTCCTCAAGGGATGTCGACGACATCCTGGCGACCACGA
ATGAGAACCCCTGGTCCACCTTCGGCGCCCAAATACCGTTCCTGTCCTCCGTCACTGGAA
```

Figure 5A (continued)

```
AGTTGGCTTGGGTCCGAAACTACCGTGACCTCCTACATCTGGCCCTCTCGCAATGCCTTA
TCGAACCTATACGATGGGACGTCGTCGAGGCAGAAGTGCCGCGGCTCCTCAAAGACCGTG
ATGGTCTCGATACGCTGACAATTGTAGCCTTCACAACCGTGCTTTCTAAAAGTTTGTCCA
ATGCTCTGGTTACCGAAGGAATAAAGCCAGCAGAACCTCCGACCTCTATAAATAAGACCC
CGGAGCGATATAGCCACCGTCCAGGGTCTGACAGAGGCAAACTGGCGATTGTGTCTATGT
CTGGTCGATTTCCCGAGGCCCCTTCTACCGATTCATTCTGGGATCTGCTTTACAAAGGCC
TTGACGTTTGTAAAGAGGTCCCCTTGCGTCGATGGGATGTAAAGACCCATGTTGATCCGA
GCGGCAAAGCGCGCAACAAAGGGGCCACACGTTGGGGTTGCTGGCTTGACTTTGCTGGTG
AATTCGACCCACGCTTCTTTAGCATCTCGCCCAAGGAGGCGCCGCAAATGGATCCGGCCC
AGAGGATGGCATTAATGTCAACTTACGAAGCCATGGAGCGAGGAGGCATTGTGCCAGACA
CGACACCGTCAACTCAACGTAACCGCATCGGAGTTTTCCACGGCGTTACCAGTAATGACT
GGATGGAAACGAATACCGCGCAAAATATAGACACCTACTTTATCACGGGCGGAAACAGGG
GGTTCATTCCTGGTCGGATCAATTTCTGCTTTGAATTTTCAGGGCCCAGTTATAGTAATG
ACACTGCATGTTCCTCCAGTCTGGCAGCTATTCATCTCGCATGTAATTCCCTGTGGCGTG
GTGACTGCGATACTGCGGTGGCTGGAGGCACGAATATGATTTTTACCCCTGATGGACATA
CTGGCCTGGATAAGGGGTTTTTCCTTTCTCGAACAGGCAACTGCAAGGCTTTTGACGATG
CAGCAGATGGCTATTGCCGTGCGGAAGGAGTCGGTACCGTCTTCATCAAACGTCTTGAGG
ATGCATTAGCAGAAAATGATCCTATTCTGGCCACTATCCTCGACATCAAAACAAACCACT
CGGCCATGTCGGACTCAATGACACGGCCGTTTAAGCCTGCGCAGATTGACAACATGTCGG
CTTTATTGAGTACAGCCGGAATCAGCCCGCTTGACCTTAGCTATATCGAAATGCACGGTA
CCGGGACGCAGGTGGGTGACGCCGTCGAAATGGAGTCGGTTCTGAGTCTCTTTGCTCCGG
ACGAGACATTTCGACCCCGAGATAAACCGTTGTACGTGGGATCTGCCAAAGCGAACATTG
GCCATGGAGAAGGAGTTTCCGGCGTCACCAGTCTCATCAAGGTCCTACTGATGATGAAAA
ACGACACCATTCCTCCTCACTGTGGCATTAAACCGGGAAGCCGAATCAACCGGAACTATC
CAGACCTTCCAGCTCGCAATGTGCATATTGCTTTTGAGCCAAAACCGTGGCCTCGGACAG
ATACACCTCGACGTGTGCTCATCAACAACTTTAGTGCCGCTGGAGGGAACACCGCTGTCC
TGGTTGAGGACGCTCCTGTTCGTGATCCCGTAACTGCATCAGATCCCCGAACTAGCCACA
TTGTTACTGTTTCTGGCCACGTTGGGAAGTCCCTCAAGCTGAACTTGGAGAAATTGCGGG
ATCATTTGGTGAAGCGGCCGGAAATCAATCCTTCGGAGCTCTCATATACGACCACTGCCC
GGCGATGGCACCACCCTCATCGGGTGAGTATAACAGGAGCTAACACTATGGAAATCTTGC
GCAATGTAGAAAGCGCTATAGCAAGAGGGCATGGAGTCAACCGCCCCGCAACTAAGCCGA
AAATTGTCATTGCTTGTAGTGGGCAAGGCTCCCAGTACACAAGGGATGGCTGGCAGCTAT
ACAACAGTTATCCGACTTTCCGGTCTGACCTAGAGCGATTTGATCAATTGGCTAGGAGCT
ATGGGTTTCCCAGTTTCCTTGAGGTCTACACCTCCAAGCCAGTCGGCGACAGCATGGAAG
ATCTCCTCCCCGTTATTGTCCAATTGGCTTTGGTGAGTCTTGAAATGGCTTTGGGAAACC
TTCTGGGCTCCTTCGGTCTGAAACCAAGTGCAGTCATTGGCCATAGTCTTGGCGAATACG
CGGCATTATACATCAGCGGCGTTCTTTCAGCTGCCGATACATTGTACTTGGTTGGGATGA
GAGCGAAGCTGCTTCAAGAACGCTGTCAGCGAGGCACCCACGCGATGCTCGCCGTTCGAG
CATCACCGGTCACGCTGTGTGAAGTATTGGCCGAATCCAACTGTGAAGTAGCCTGTCATA
ATGGCCCTAACGACACTGTTTTGAGTGGACCACTTAAGGAGGTTATGAACCTTCAGAATT
CCCTGTCTGCGACAGGTATCAAAGGTACTTTACTGAAGCTGCCATTTGCCTTCCATTCTG
CTCAGGTTCAGCCTATTCTAGAAGAGTTCAAGAACGTGGCCCGTGGTGTGACCTTCCACA
AGCCACAGATACCAGTATTGTCTCCTCTTTTGGTTAAGGTGATCGATGAAAAGGGCACCG
TGGATCCAGTTTACCTCGCCCGCCATTGCCGGGAGCCAGTCAAGATGGTGTCAGTCCTTG
AACATGCTCGCGATCAGCATATCATCACAGATCGCACAATTGTCATTGACGTTGGACCCA
AGGCATTAATGGCTGGAATGATAAAGACGACACTTGATAAGGACACCAGTTCGGCTCTGC
CAACTCTGGGACCCAGTCTAGACGTTTGGAAGAGCCTGACTAATATCTTGGGTACGTTGT
ATTCACGAGGGTTGGATATTAATTGGGTTGCGTATCACGAGCCGTTTGGATCTGCGAAGA
AAGTCATCGAACTCCCTTCTTACGGCTGGGACCTGAAAGATTACTTCATCCCATACAAGG
GTGAATGGTGTTTACACCGCCATGAAATTCGTTGCAGCTGCGCGACTCCAGGGAAGGAGA
CTGCAACGAGCGACTACCAGCTTCCTTCAGATGAGCAGGTCGCAGCTAAGAGGCCTTCAA
AACAAGATGAAAGCAAGGAAGCATATCCCGAGATAGTGGCCACTACAACAGTGCACCGTG
TAGTGGAAGAGAAGACTGAGCCACTTGGGGCTACTCTGGTAGTAGAGACCGATATCTCTC
GCCCAGACGTGAACCAGATTGCTCAAGGTCACCTGGTGGATGGAATACCACTGTGTACCC
CGTCAGTATATGCAGATATCGCCCTTCATGTTGGGAGGTATTCCATGAACCGCCTTCGAG
CAAGTCACCCCGGCGCCATGGACGGTGTTGTCGACGTTGCCGACATGGTAATCGACAAGG
CCCTTATTCCTCATGGCAAATCGCCACAGCTGCTTCGGACGACGCTGACTATGACATGGC
CGCCGAAGGCTGCAGCTACCACACGTTCCGCGAAAATCAAGTTTGCTACCTACTTCGCCG
ATGGCAAGCTTGATACTGAGCACGCGACTTGCACTGTTCGCTTCACAAGCGAGGCGCAGC
TCAAGTCATTACAGAAAAAGTACCCGAATATCAGGAACGAATAAAGAAATTAGGAGAGG
```

Figure 5A (continued)

```
GCCTTCGCCAGGGCCAGTTCATTCGATATACGACCAAGAGCGGATACAAGTTGATGAGCA
GCATGGCCAGTTTCCATCGTGACTACAAGCTCCTGAACCATCTGATCCTGAACGAGGCGG
ACAATGAAGCGGTCTCGACAATGGATTTCTCCGCAGCCAAGAGCGAGGGCACATTCGCTG
CGCACCCGGCATATGTTGATGCCATTACTCAGGTTGGCGGCTTTGCTATGAATGCCAACG
ACAATACGGATATCCAACAGGAAGTTTTCGTAAACCATGGATGGGACTCGTTCCAGGTTT
ACCAGCCGCTCGTCAAGGGCAAGACTTATGAAGTGTATGTGCGGATGACAGAGGACGAGA
AAGGAGATCTTGTTCATGGCGATACCATTGTGCTGTATGGCGATGCTGTTGTTGCATTCT
TTAAAGGGCTTTCGGTAAGTCTGTCTCACTTATAGGAGACCCAGCTAACGTCGTGGTAGC
TCCGCCGTGTCCCCCGAAGAGGCCTTCGAATGGTTCTGCAGCAGGCGTCCGACAAGGCAG
CTCGTCTACATGGGAATCAACAAGCCGTCAAAACCCAGGCACCACAGCGTGCAGCTCTTA
AACAAAAACCCCAGTCGTCACCAACACAGCCGCATGCATCAAAGGTGGCTTACTCAAGAT
CAGCAACCTCGCCAACGGCTGGAAAACCAGTGGTGGCTGCGAGAGACCTATCGCGAGAAG
GAGATGATAAATTCAAGGCCGTTTTGAGCGTTATATCTGAGGAGAGTGGTGTTGCGTTGG
GAGAACTCACAGCTGATACCAATTTTGCTGACATCGGGATAGACTCTCTTAGCTCTATGG
TCATTGGTAGCAGACTACGTGAGGACCTTGGCCTTGAACTTGGAGCCGAATTCTCCTTGT
TTATCGACTGCCCGACTGTCAGATCCCTCAAAACGCTTCTCTCTGGATCAGCGGTAAGTG
TGAATAACGACAAGGATGAGCTGGAGCCTGGTCAAGAAGCAGAGACGGCGGCGCCAGAGC
AACTAGACTTACGCATTGGGGACGCCGCGCCCAGCAAAGTTAGAGATGCCAACATCGAGC
CACTCGATCTTGGGGATGAGCTGTTCCGGAACGTGCTCAGAATCGTTTCGGAAGAGAGCG
GAGTGGCGCTCGATGAGTTGAGCGCTGAGACTGTCTTTGCTGACATCGGCATCGATTCGC
TGAGCTCCATGGTGATAACGAGCCGCTTCCGTGAAGACCTTGGGATGTCTCTGGACTCGT
CGTTCAACCTATTTGAGGAAGTACCAACAGTTGCACGCCTACAAGAGTTCTTTGGCACCA
CAAGCGGAAGCACGACCGGTTCGTCAGGCTCGGGCAGCTCTGAGGACGAGACCGATAGCA
TCCCATCGACTCCGGAGGAATACACTACCGCAGATACCCGGGTCCCTGAATGCCGTCCAA
CCACTTCGGTAGTTCTTCAGGGTCTTCCCCAGATGGCCAAACAGATCCTGTTCATGCTCC
CCGACGGCGGCGGATCGGCATCTTCGTACCTCACAATCCCGCGTCTCCATGCCGACGTAG
CCATCGTCGGGCTGAACTGCCCCTACGCGCGAGACCCCGAAAACATGAACTGCACT
```

Figure 5B

Sequence of the deletion of the Terrequinone cluster

>ChrV_A_nidulans_FGSC_A4 COORDS:ChrV_A_nidulans_FGSC_A4:735650-745504W
(9855 nucleotides) (SEQ ID NO:2)

```
ATATATAAAATATACACAAGCTCCCTCACCCGCTAGGGAAAAGGCACAAGGGAAGGGCTC
TCACTACAGGCCCCGCTCCCTCAGTACATTCTTCAATGTCCCTGCAAAAGCCTCAACATA
CTCCCGATTCAACATGGTGTAATGTGCTCCTTGCACATCGTGGAAACGCACGTCCTCCCG
CACAAACTCCTTCCAGGCACTTAACCTCCCCTCCACCCAGTCGATTCGGTCCTTTGCAAC
ATGGCTCAAAGGGTCCGCCACAAACACATCCATACACTTGACTGATCCCGAGGGTTCATA
GTCCACCGCCAGACTCTGCATATTAGATGCTAGACCTACCCAGAGAAGATAGTACTCCTC
TGAAAGGCCGAGCTCGTCCCACCGTGCGGCATCGCAGTGCTGGCGCAGGTACCGGATGGC
GTCCAGACGGCGGTTTGCCCGATTAAACTCCTGCAGAGTAGGTTTATGCGTATACGCTGC
CAGCTCGGTCATCAGACCGACGAAGTAGAATAGATGGATCACGCACTCCTCCCAGACGAG
CTCACGCATGCGGAACTTGATATGCGGCGGAAGATTCCAGCTCCCGCAGTAGCGGACCTC
ATCGCCGTCCTGTTCGAGAAGCTTGCTGACTTCAAATGCCACCATCCCGCCAAACGAGTA
CCCCGCTATTGCGTAGGGCCCGTGGGGCTGGCGTTCTTTAATTGCGTCGCGGTAGGTTGT
GAACAATTCCTCCAGTGAGGTGAAGGGGGTTTCGGGCAAGCCGGCCGCCGCGTTGAAGCC
TTTTGCGCGGAAGGCGTAAACGGGTCGGTCTGTAATGTGATGGGCCAGGTTCACGAAGAC
TAGGACCTCACCGACGCCCGGGTGTACCAGCCATAGAGGACTCTTGGTCCCGTGCGGTTG
CAGGGTCACGACGGGGTCGTAGACGTGCGTGGAAGACTGATCCTGTGAGCGAGGCGCGGC
CCCTGTTGCGAGGGCGACGGCTAGCCCCTGGCTGTCGAGTCTTTGAGGATGTCTGTTAG
GCGGAGGGGCTGAGAAGGCTGTAGGCACTTATTGATGCGGTGGATGATAGCGACTAGATC
CATCGACGTGGCGCCTATTGAGAGGATTGAATCGTTGACGCCAAAGCTGTCATCATCAGA
CCGGATCTCCAGCTGTTCCTTGATAATATCCAGAATTACTGCTTCATCCGGCGTCTCTGG
GCTCGCACGGGTCTTTTGCTGGTAGCGTCTTATAGCCTCGTCGTTGATCTGCTGCTGCGT
AGCGAACTGGCCTTCTTCCAGAGCCGTCTTCAGTTTTGCGCGCGACAGTTTTCCCAGCGT
GCTCTTTGGCATATCCTGCGGACGCAGCGGCACTACGCGCGGCCGGGACCGCGTGTGCAT
GGCCACGACACGGATGATGCTGCTTTGCGTGCTGAACCTGGCTTCGTCATCGCTCTCCAC
ATAAGATGGAAGGTAGAGCACAACCACGACCTCGGTATCCATGGTTGCATCGCGGCTGCT
GAACGTGCAGAAGTAACTAGGTGTTGCGCCTGGGATCTGCGCCTGCTCGAGAGCAGCATC
CAGTTCGTACGGGAGGTATTTGACTCCATTGATGTTGATCATCTCCTTCGTGCGCCCGTC
GAGGTGCAGATTGCCGTTGCTGTCAATGAACGCCAGATCCCCGTCCGGAACCATCCATC
GCTGGTGAACGCCTCTGCTGTGGCGGCAGGATTATTGTAGTAACCTTTAAAGACAACTTC
CCCGGTTACTTCGAGGCTGCCGCGCTCACCGGGGCTGCCTCTTCGCTCGGAGTGTCAAG
CCGTGTCACCCGCATTCGCACTCCAGGCATCGGTTTCCCGAGACAGGCGAACTCATGGCG
CTGGGCGTGATCATAGCTTGGGCAGTGCGAGTTGAAGATACATCCGGCCACGGTTTCGGT
CATACCGAAGGAGGGCTTGAAAACGTTGTCGGGAGCCCCGTACCGGCTGAGGAGGGATTG
GAGTGCAATACAAACCTCTGTGACGTTCGCCTCACCACCGGTATCAATATAGAGCGTCTC
AAGGTTGAGGCCGGGGTCCAGGATATACTCTGGACTCCCCGACTCCAGCTGTCGCCGCAA
CTTGGCGCAGAGGAAGTTCGGCATGAACGTGCGCGAGACGCGGTGTCTGCTTATCAGGTT
AAGAAGCTGAGCCGGGTTGATGAGAAGATCCGGAGCAGGGACTTGAATCTGTGATATGCC
GGACACGATGGCGAAGATATGGCAGTGGACTAGATTGGCGACGTGGTCCATGTGCACCCA
GGAGAGGAACGGGCTGCGGGGGAAGCGGAGGCTGGCCGCGGTGGACTTGCCCCTGAAGGC
CGCAAGGAGCTGTTGATGGGTCAGAGGGACAGCTTTTGCGTTGCCGCTGCTCCCGGAGGT
CAGCATGAGGGCAAGCATATCGGTCGAAGACGGGGTTAGGGCAGGCAGAGGTGCGTCAGC
AACGTCCGCAATTTCGGGAGCTGCGAGGATCTCATCCACTGTTCGAGCTTTGATCCGGTC
ATCCGCTGTCTGCTCTTCAAAGGGGCCAAGAGGGCAGGCCGGGTCAGACAGACCGGTGA
ATTGAGCGTCTCGGACAGATGACGCAGATGCCTCTCTATCTGCCGGGTTCTGGCTGAA
CATCCCAGGCCCGGTGAGGGCAGGTATGCCCCCAGCCAGAAGGACAGACCAGTACCATAC
GATGCTGTCCAGTGCGGACTCAAAGTGAACGAGGACAATGGACTTGGGGCTACATAGCTT
CTGCTGCAACAGTCTGGTGGCATTCGCCTCTGCCTGATGCAGCAGATCTTTGTAGGAGAC
TGTCTGTGGAGGTGATGAGGTGCTGATGCTGTTTGGGTGGTATACTATAATGCCCTCATC
GGTATGAGCAGCAGCATGTCGAAGAGCGTCCACGATGTTGCCAAACGGGTACTTGGCTGC
CCTGAGCGGTGCGATCTCGGTCTTGCTTGGTGCCATCTTGTTACAGTCTAAGAGGAGGTC
CTAGCCTGGCCAGAAGGGTCTCAATGAGTGAGTTATGAGTAAGTTGGGTGAGCCACTGTG
CCTGTTTCTCCGCACTCAAGACACTTTAAGTATGCAGCCTGCCCTAATACGAGATATTCC
CGTCCTCGCGGGGTAAGTCCAAATCAGGCCCGTGTTGCACAATGACGATACTATTATTAT
```

Figure 5B (continued)

```
TACTCGTTCATATTACACGCTGACGGGATACGAGGTTGCATTCCGCCACACGAGATACCA
ATTCAAGGTCACAAAAGGACAAGCTGCAGCCGGGCCTGGACCATGGGGCGTATATATGAT
GACAGTAGAGTACTCTGAAATTCCTTGCAAACAGTCCTTTCTTTTGCGCAGAAACTGTCT
TCATCATGGCTACAGAATACTGGTCCCGTCATCTACGCTCAGTGCTGGCTCCGCTGTTCG
CTGCAGCTGGCACATACTCTCCTGAAGATCAGGAGTCCCATCTGGCCTTCATTGACGAGC
ACATTGCGCCCAACCTGGGCCCTCTCCCTTGGGAGCCCCATGGACCCTACAGCACTCCTT
CCTCCCTCGTGGGCTCCCCCTTCGACCCCAGCATCAACATCGTCTCATCCGGAAAGGCCA
AGGTCCGTTTCGACTTTGACGTGATCAGTCCACCTGATCGAACAGGCCCAGACCCCTTTG
CAGAGGGATCCGCCAGGGAGATCCTCCACCGTCTCGCCGACCTTGTCGGCGCAGACACAC
AGTGGATGGGCTACCTCATGGATGCTCTCTACCTGACCCCCGCGGAGGCTGAGGTTGCGA
AAACGAAGTTGCCTCCAGGTGTTGCTATCCCGCCCAGCTCAGTGGGCTTCGACTTCGACG
GCCCCGAGCGGACGCTGAAGTTCTACATCCCCAGTGTGCGGAAAGCGCTAGCAACGGGGC
AGGATGTGTCCGAACTCATGCTAAAGACTCTACGTGGATTACAGCCACTTGGGTCTGAGC
TAGTGCCAGCGATGGACCTGATTGCTTCGTAAGCTCTAACTTCACATCTCTAGATTATTC
TGTATTAGCGCGATGCAAGCTGACTGAACCAGGTATCTCTCAACCCGCACCAACGACGCC
ATGCTCCCGCTCGTCGGGATTGACTGCCTCGATCCAAGGACACATAAGAACGCTCGGGTC
AAATGCTACCTGCACACGAGCAGCAACAGCTTCGCAGTCGTCCGCGACGTCCTCACGCTG
GGAGGCCGTCTCAGCGACGACACCTCGCTCAAGCGAGTCGAGACACTCAAATCGGTCTGG
CCTTTGCTGATCAACGAGCTAGAAGGTCCACAGAGCGACGCGGCCACCATGGACGAATCC
TGGTCCAAGCCAGAGCGGCTCAACCGGACAGGGTACTCGGGGATCCAGTACACGATTGAG
ATTACCCCCGGTCAGGCAATCCCCGACACGAAGATCTACGTCCCGTTATTCCAGTACACG
GACAGCTCTGAGGTCGCTGAGCGGAACTTTGAGAGCGCGCTAAAGAAGCTGGGGAATGAG
TGGGGGCTGAGTGGCAAGTATAGGAGCGTCATGCAGGAAATCTTGTGAGTCATTTCTTCT
ATTTCATTTATCTATTTTTATTGTTATACGATCCCTTCTGACGGCCGCAAAGCAAGGAT
GTAGAGAACTATGGCCAGACGTACGCATCTTTCTCCTACACGGAGGGAAAGGGCGTCTAT
ACGACCTCGTATGTTGCTATGCCTATTAAGGATGAGGGAGGGGGTAGCCTCGCTGGAGAT
TTCGGTTTCAGGAACTAGATCAAGTACTCGGTGCTGTAGCGCTCAATCAGATACTAGTCT
AATCAAATCATTGGCTGTCGTTGATTCGGAGTGTAGGAACTATTTCTTAGTAGACATCTT
CCTCTCACTACCCAAGACCTCCGCCAAAACCTAGCACCCAAATGAGCGCGGAGCATCCGG
CTGTCCCCACATTGACATCAGATGCCAAGCATCGAGCAAAGTAAAGAAAGGTCTCGACC
AGATCTCTGCCTCATTCCTTTTGAGTGGGATTTCGTCAGCTGCATGCCCAGAAAGCTAGG
GCTGCTTAGTACGGGACGGGCCAGCTGCACCTGCAGCTTGGCTTCGTATCCCAGAATAGC
CAACATTTATCCGGAGACTCGCACATTGTATCCCCTTGTGGCGATTCGAGATTTTGAGCT
TCTTTCTATCAGGGTCTAATTCTTACTGCATAATGCGGGGTTGATTGTCGTACGTACTAA
GGTCAACATGCACACGGCCTACCTGCAACCTTTCAGCCTACAAGATGTAACCCAAGAAAA
CCCAGAGTATAAAAAAGCGCAAATAATATAGGCTGACCTCGACTCCATCTCATTCTTCAG
CCTACCATCTTGCTATTTAGGTTAACTCCGCATCGCAGAGAAACGACTCACCCAGAACGG
AAACGACTATGCATGCCGCTCTCGTCCCAACCTGGTCCTCCCCCTGTCCCATCTATACCG
AGATTCCAGACCCGGGGCCTCCGCCACCAGAACAGCTCCAACTGAAAGTCTTGGCCGTTG
GGATTCCCCGCGTTGTACGGCTCCGTGCTCGAGGGATCCACCCGACTGCCAAGTCAGCCA
GTCTCCCGTACGACCCCAGCATTGACGGCGTAGGGATTGACGAACAAACCGGCATTATGT
ACTACATTCTTCCGCTCTCGGCGTCTTGTCTTGCGGAGAAAGTGAATGTGGACCGGGACA
ATCTGGTCCCGCTCCAGCCCGGGGCACCTAAACCTCAACCTCGAAATGGACCTGAAAATG
GATATGGAATTGCACTTGGCGATGCTGCTGACCATAGAGCTGAGACGCTGGACCCCATCG
CAATTGCGGGGCTCGTGAATCCCGTGTCGAGTAGCTGGATGGCGTTGAGAACAAGGGTGG
ATGGCGAAATTACGGGGAAAACGGTCCTGGTTCTGGGGGCAACGAGTAAGAGTGGGCGAG
CCGCAGTGCTCGTTGCAAGGTTTCTGGGAGCAAATAAAGTGATTGGAGTGGCGAGGAGAG
AGGAAGGGCTAAGAAGTGTGGAAGGGTTGGATGGCTGGGTTACCTCGGGGGATATGCTTC
CTGGGGAGACCGGGGTTAGGTTTGCTCTACCGGACTGGGTTGGGCCAGTGCATATCGTCC
TGGATTACGTTGGAGGCAGCGTTGCCGCGGGAGTCCTGGGCAGTGCTGAGATTGAAGAGG
GTAGAGAGTTGCAATACGTGCAGGTTGGGAACCTCGCGCTTGAGCTGGGCACGGGAGAGA
AGCATATGTTTGAAACCTTACCAGGCCACCTGATCAGCCGGAAGCCCATCTGCATCCGCG
GATCAGGGATGGGAAGTTTCAGTAGGAGGGATCTGGTCCGAGAGATGCCTGGCTTGGTGG
CATTTCTTGCACGAATGAAGGCGCCGTTTGGGATTGCGAGCGCGCCGATGTGCGAGGTGG
CGTCGGTTTGGCAGGATGAGGATACGAAGGGAAGCCGAGTGGTGATTGTACCTTGAACGA
CACTTGTACGAACTGGGGCGGTTTGTCATGACACATTCAACACGGACTGACAGTTACAAT
CATGGTAGTAGTAGCCTGAGATCCCGAATACGAAGCCATTCCTGTGGTTCATCGCCTTCT
ATGCTATATAGAGGCTTTTAATTTTGCTGGTGTCTAGTATCAAACCCACTACTGTAGACC
ATCGTGCTACTGAATATCGTACCAACATCACCATGGGCTCAATAGGGGCCAATAATGCTG
TGGCGGACCCAACTCCTCTTTTCTCGTCACGGGTGCAGAAATGGGAGCCCGGTGCAAGTA
```

Figure 5B (continued)

```
AGCCACGTTGGCCATGACAGCGCAATTCCAAGCTGACCAGATCTTCAGTCCGGAGCCTAC
TCCCTCTCGAAGCCCTTCCTGGCATGATCTCCCTCGTGGCAGGAAAACCCAGTCCCGAGA
CGTTCCCCATTGCTGAGATCGCCATCTCACTCAAGGATACTCCAGCCGGGACAGGTAGGA
TCGTGGTTGATGGGGACGAGCTCAACCAGGCTCTTCAATATGGTCTTCCTCGAGGAAATG
CCCAGCTAATCCAGGTTTGCTCTGTCCCTTAGTCTCCATATTTCCTACTGATCATTGTTG
TTCAGTGGTTCGAAAGTCTTCAGAGGAGCGTCCACGGCCTCGATGAGAACGGAGGCTGGT
CGTGCTGCATTGGCACATGGAAGTCAGGAGCTCATTCATCGCGTCATCCAGGTCTTCACT
GATCCTGGGGACCCAGTTCTTCTCGAAACGTGGGTCTCACTCCCTTTGTATGCATTCCCG
GACGCAGGCGCCGCTGACTGAAGCCATAGACCAGCATATCCGTATGATTTCCTCCAGGAA
TTTTCAGAGTGGACATTTTAGCACCTTGCTGACAGGGACCACAGAGGCGTCGCCGGGTTC
CTTCGCGCAGACGGACAGGAGCTTATCCCGGTCTACTCTGACGCCCAGGGCCTCAATCCG
GCCAGCCTGGAGCAGGCATTGTCGGAGTGGCCCGGAGACTCGCCGCGCCCCAAAGTCCTC
TATACAACCCCGACTGGGTCGAACCCAACCGGTCAATCCTGCACCGAGAGCCGCAAGGCC
GAGATGTAATTACTCCTCTGCCCAGCCACTGCTCCAGACCTGAGACTGACAGTTCCATCC
CGACACCTATAGTCTCCGTCTGGCAAAGCGATTCAATTTTATCATCCTCGAAGACGACGC
ATACTATTATCTCAACTACGGAGACGACAAACAGAGAGCGCGGAGCTATCTCGCCCTCGA
AAGAGACGTCAATGGAGAGTCAGGCCGCGTCGTGCGTTTCGACTCGCTCAGCAAGATCGT
CAGTCCCGGCATGCGTCTGGGGATCCTCACAGCACAAGCAGCGGTTGTTGACAAGGTGGT
GCGGATCACTGAAAATATAAAGTATGTTTATCCTTCTCTCTTCTCCTGTCCTGTTCTGGC
TGCTTCAAATGACTCGCTCACTGAATCCCAGCCTTCAACCCTCCTCCACAACTCAACTTC
TAGCCCTCTCTCTACTCCGCCACTGGGGTCAAGCTGGCTTCCTGAAACACTGTGCAGAAG
CCGCCGAGGTCTATCGACGTCGCCGAGACGTCTTTGTTTCTGCGGCGGAGCGGCATCTCC
AGGGTCGAGCTACATGGGTGGTTCCAACGGCCGGCATGTTTGTCTGGCTGGAACTTAAGT
TGCCACCGGAAATGGATAGCTTCGAGCTTCTGAAGAGCCAGGGAATGAAGAATGGGGTTC
TTGCTATTCCTGGTGTTGCCTTCATGCCTGGGAACGAGCAAACGTGCTATATCCGGGTGA
GCTTCAGTCTAGTTCCTGAGAGAGATATGGATGAGGCGTGTAGGCGGATCGCGGGTCTAG
TTGATCGATGTGCTTGCCATTCCTAAGCTTATTATACTTTTGTTCGATGGTTCTAATACT
ATTTTCCCGGTCAAAAGATCTTCGCCATGAATTTGGTTCACTCGCTATCTGTAATCACGT
CGGATCCAGGTGCAGCTGGCTTCTGCCCATACACAACATATCTATTCGCTCGACTCAGCA
TATAAGACCTCGTAGGACAGTCATGAAAGGGATGGTAGACTTACACCGGCCAGTAACCA
TGCACACCCTCATTCATCAGCTCCTCCTTTACGTTCCCCAAGAACGTCTTTGCATCATCC
ATCTCCCATCCAAGTACTTTTACCAACAAAGCCACCGAAAACTCTTCAAAGCGCTGCAAC
ACATTGTACAGATTCCAAAGACCCAAGGTCTTACCCTTTTCATCCGCAGGCCACGGGTTC
GTGGGCCAATTATACGCAACGGTGTGGCAATTCACGAATCCGGCCTCGCGCATCCACGTC
TCATATTTGGCAGGATTGTCCACGGGACGGTTCATCTTCTTTGAGGCCTCTATAAGAAGA
CGGCCCCATTGGGAGAGCGGGTTGTTCTCTGATAGGGTTCCGTCGTCGCTTGTGACGGGG
TTACTGAGTTCTTGCATCTCCAGCCAGCCGCCGGGAGTGAGGGAGCTTTTTGCCAGTGAG
ACCGGGCTCAGCACGATTAAGCGAATGGTACTTGCCTGAACGCCTGCTTGAAGAGTCGGG
GCTCGTCTAGGCGCCGGTGATGCTGGCGGCAATGGACAAAGTCGAACTGGCGGGTGTATG
TCCATGGTTCGTTGGCGTCGCTTGCGTCTGGAATAACACTGAGACCTAGAGGTATTTAC
TTGTGGGACTAGGATCGTTGGCCACGATATACGCAGAAGGATTCTGTTCAGCTGCTACCG
GTTAGGGGATATCTAGTGTATATAGACCGAGAATGCTGCAGCCTACCAAAAGCATGGACC
CATGTTGAGTCTCCTGTTGCTATATCGAGCACAGATTGCACTGGTGACGGTAGGGAGAT
AACTGAAGTTTCCCATCTAGGGTTAGATGGAAGAGCTGGTGCTGGAGTGCTTGGTGGTGT
CAGTCTGGTACGCCTTGAAGTTTCTATGCAACCACTCTATCTTATCCACGTAGACGGACG
ATGGACTAAGCTTACCAAGTCGCTCTGTCTGTGAGACAGGTTTCGCGTCAGCATTGCGTT
CATAGTCAGGGATCATAAACACTGCCTGATACGGACCTCGATATCCCGTTCTGTAAGGGG
CTCAATTAGCTTAGACTGGTAACGTATACATCTAAATCTTCATACCTCCATTATTGGTTT
TCTGAAACAGTCCATTCCTCGCTTGTCCACTGTTGTCCAGGTACTTTTGTACGGACTCGG
CGACCGCATTGGCAAGGTCGTTCCTGGGTCAGTTAGATATTGCTGTAAAATATGTCTACT
AGTGTCAAGGACGTACATGTTTGCGTACGGGCGGTTAACCATGGCGACGGATTGTTAATA
AGATTCTTGGTACCT
```

Figure 5C

Sequence of the deletion of the F9775 cluster

>ChrII_A_nidulans_FGSC_A4 COORDS:ChrII_A_nidulans_FGSC_A4:201024-225673W (24650 nucleotides) (SEQ ID NO:3)

```
AGCAAGATGGCAGCCCCTGGAGATATCACAGTGAAAACCCTTAAAGGGTCGTGGACATTG
GTATACTTGCTCCTGGCTTCCCCAACTGGCATATTACAGAATGCTGACGCTAAGTAGGAC
AAGTCCGTTTCTGATAGCATGGACGGTATCCTCAGGCTGGTAGGAGCGACCAGAACGCAC
CAGAATTATCGACTGACATGGTCTTCTAGCAAGGCGTGGGCTGGCTCACACGCAAAGGGA
TCAGCGCTGCAAGCATAACATTGCAATTCACCTCGGGCGTCGAGCCATCTCCATCTTCGG
GCGAACCCACGGTACATCTTACAATGCGCCAAACGCTGACCGGCGGAATCGGAGCTTCGA
CTGAAGAGCGCATCACGGACTGGGTCGAGAGAGAACGAAGCAACCACATCTACGGCGACG
TGCTCTCGCGCAGCCGGCTGATCGCTGGTGTTCGGGAGGACGGTTCTGTGCGACCAGATC
TGGATCTACAATCGAAGCCTTCCAATGACGCGATCAAGGAGGAGGTCCAGAAATTCTTGC
GTGGAGCAGTGGGTCCCACGGATACCGATGACCTTACAGATTTGTTTATCCACGACTTTG
GACGCAATGAAAAGTCCGGCTGGACAGCAGAGCAGGTATGGGCACTGAAATTCAAACGGC
AACCTCGACGGGTACTAACGATAGTCTCTCTGCAGATTTGGAGCATTGAAACTATTAACT
CTGAGAAATGTCTCGTTCGCCGTGTTGCGGTCGTGCAGGAAGAAGGGTATGAAGTGGCCC
GCCTGGTATATAAGTTCAATGGGCTCTAAATCCATTACTTCGCCTCGTGTGGTGAACTAC
CTTACTGTATATCCCGCCTGGCGCGCATGTTTCCTGTGGATACTCTACGAATCCTTTAC
GCTGCATTAAGCTTGAAATAGCAATTATTTGAAATATGGAAATTGAGCACAACCTAATAC
ATAAAGGCCTTTTATAGTTTGCCAGCTCGATATTCCAGTCTTCAAAGTCATTTAGCTTTT
TTATTGCTCTTGAATTCTGTAATATATGGTTCTTAATCTCCGCTGGTCCGGATTAACCTG
CTAGCAATCTCACGCCGCCCTATCTGGCCACTGGCAGCTCTACAACAGCCGCAGGGCGTA
GGTGCTGAAGAAGACCACGCGTCATGATATGATCAGTGTACCGTAAACAACTAAAACCGA
CTTAACTCCATACCGCAAAACATATGGAGTTCAAGGAATGGTTCAGGTCTCAGACAAGT
TCATAGAAGCTAATAATGCGGCCAGATCCCCCTCGACGCAATCTCGGCAAGGTGCCCATC
AAGATCCGCAAAATAAATGCTCTTTCCACCGCGTTCCCAGTTCGTGCAGCTGATAATCGG
AACCCCCTTTTTCTGGAGGTATGCTTCCCACTTCGCTACATCTTCGGTACTCTGGACGGC
GACACAGAAGTGCTGCTTCAGGCTGTCAATGTCGCCATCGCCCTCTTTGGCTGCGTTGAG
CTTCGCGACGATCTGCGCGCTGGGTCCATGGCCAGGAATGACGCCGCTGGGAGTAGTAAT
ATCTGCGTCTGTTTGGCCCAGTTGGAAGAGGAGGAGAGTTGTATTGCCTAGGGAGAAGCA
GGCACTGCGGTGCTAGGAAGGGTATCAGCCTCACCTTAACAGTTGCCCAACATTGTTGGT
GAAAAGGGATCGTACCGATTGCATGAACGGCTTAATGTTCAGCACATCCTCATAAAATTT
CCTTGAAGCATGGATATCGCGCACGTAGAGGCATGTCTCGAGGACGTGGGTGAGGGGAGG
TGGGTTGTTTTCAGTGGCCATGATCCGATCCTGTACAGGAACGTATCTAGTTCAATGTTC
AAAGAGAGTTCTATATCCTATCTCGTAAGGACTAAACAAATATGGATTGAGCACAGTTGT
GGATCAAGATACAGTGAGCCAGCTTCTACGGAGCCCGTCGAATCCATTTATGTCTAATTG
ATTGAAAATTATTGGGTTTTCGGCTCGCATCTCTGGCCTGAGGCAGGCTCTCACTTCAGG
ATGACGCTCACATAGTTGCGCGTGACCCATAAATACGGACTGCCGGAGATCTACCTTACT
AAGCACATTAGCACCTCGGCCGAGTGCTTAACCACTGCTTAACCTGGTTGTAACTGCCCA
AATAATTTGTTAACATTTCCTTCAATGAGGCTCTTTTTAAGAGTCTCGAAAAGCTACAAA
CTGTTTTTATATCATGGATAGGGCATCAGATCTCAATTATATTCGTTTGTCGCAGACGAT
GGTCACATGATCAAGATCGACGCTAGCAGCTCTTAGAGTGCGGGGTCTTAGCTCGGCGTG
GCTTACTCTGAATTCCGCGAACATGGCTCAGAGCGCGGAACGGATAAACATTTTAAACAT
CCGAAATAAAGTTCTGACTAATATACTGGCTGTCACATCAACATCTTCGCTTCGCTTCAG
AGTCTGTCCCAGATTACGAAGCACATTCATGAAAACGCCTAACTACGCTCCTAAACAGGT
CTTAGAAAGCCTAATCGTTGAGTACGATTATCTTTTCTATTAAGTTGTTTCAATTTTAGT
TATTTTATACGAGCCTATTCACTAGTAACAATACTTGTAACAATACTTGCTTCTGATGAA
TTCTCTCTCATAAGGCTTTATCCTACAATTATTAGAGAGCTTTCTCTACTATAGCTTC
AGGTGCTTATGGGCTGATTTCATAGTCTCATCACGTATACTAGTGAAGAATGTCAGAATG
CAAGATGCCAGAATTGTCTGAAATATCTACCGTTAGTTCTCGTACTTGTTAAAGATGGAT
CTAAACTAGGAAGTTGGTGAACACACCCGAACTTACCAGCCTTGATTGTAGACTCCCGCA
ACAGCTTCAGAGCCCAACCAAAGCCACAATATAGAAGATATGTCGTTACGCGTAAATCAC
TCAGGGGAACGCATTTCCGGATTTCTGCACGAACGATATCTATCTGCTGCGCTTGACAAG
AAAAACTCCAGTTGCTCTGGGTGGTATTACTAATTCCACCACTGGCTAATGGTTGCTGTT
TAGAATAGGAGGAAACGACGCTAAACTTCTGTGTGGACGCTCGCGTCGGCGTCAAGTTAG
TGGCTTTGGTGGACAAGTCGCTCGTAAAGCCTGGGTTTAGATGCCGTGATGTCTATCATG
```

Figure 5C (continued)

```
ATATTCATTGTAAGAAGGAGGTAAAAGAGATCTATGATAGGGAGAGGCTTGTAAACAAAG
TCTTATAGACAGGGAACTCCCAGGTACAGCATCATCTCAACCGTTCACTGGGGAGTTGAT
ACATACGAGTACGGCGAATGAGAGAAGCCTACATACCTAAATTGCTATGATTTGCTAATA
GGCCAGTTTTAGTGCAATTACAATAGTTTAGACTCCGTCAGTGGATAGCCTGCGGGAAAG
AGATGGACCTCTAGGCCGCCAGCTGTGATGTCGGGAGCATCGCACGAAATCAACCAAATA
CGTGTACCAAAGGGCGCTGTGACGATATATACCACCGAAGCTCTCGATAAGGATCTGTGA
TGCGTTCGGAGGAGTCTCTCGTTGTCTTCTGACTGTCTGCTCTAATCCAGCGCGGAAG
GTTGTCCTCTCACCACTGCCCCATTCCAATGACTCGGCTCCTATTCATGTTAGTGGTACA
GATGGTATAGGGGGCTCGCCCCTTATCTTGGTTGATGTACTTTGTATTAGACGGTACTCC
CATTCACGCTTCTCTGGCTCCGGGCGGCGGTGCGAATCTTGCCGCGTCATTGACAGCCAG
GTACTGATATAGGGTATGGCTGCTCCTAAAATGTTCGGTATCCATATGGTATAAGCATTC
CTGGTCTTGAGAGTGCCCGGCATGGCCAAGGTGAAACCTATGCGAAAGAGCCTTCCGGGG
AACAATCCCAGGAAGATGTCACTACTGCACAATCAAACTTTCACAAGCAAATATAGACCC
CTACGGTTTATAGCTGACGATTCTGTATCTATTACTGTATCATGCTGGGGGTTATGGAAG
TACAGTCCTTTGTGCTGCCATTCCGTAGCTCTTGTATGGTCTATAGGGTTGCTTTCTTTT
TAAACAGCAATGAAAGTTACTGAGCTAATCCTCGACTATGAGTGACAACAAAAGCCCAAG
TCAGCCATGAAATATCTTTCTGCCTTATCAACAACCAATACACTATGCTGAGCCAGTA
AAAATGCAGGAATAGACGGCTTCCTCCTACCGGTCATTAACCCCTCGACTACCCTTGCCC
CTGCTTCGCCCACGGCCACCACTCCATCATTCAGCAAGCAAAGGTTCCCTTGCTCACAGT
CCCCTGGCAATCAATACGCTCCATGTTGATGCCATCTAACATGTCATAATTGTCTATAAT
TCTAACATGTGTTCTCCAAGGCAGAACATCCCGAAGAAAGTACGTCTGGACAAACAAAAA
CACATCTCCGTTGCATACCCGGGGATATACACTAGTATCTTGCTACGCGTCTGGGGAAAA
TGGTGGTTCTACCGTGAAATGATCCCAGGGACACGTTGGTAGTTCATATTTGAAAATATT
ACTACGCAAAGGCTAATTTGCCTACGGTTCTAGTTTTAAAATAATAGATCATTATATATC
TACTACGTGATTATATTTTCTGTCTCGAGAGGCTTCAGTGATTACTCGTCCGTCTGGCAT
AACGTTGATGCCAGTCTTTAGCGCTAATGTCATATTGGTATTTAACGCGTGGAAGGACTT
GTTGAATTCAATAAGACGACACTTCCTCAGTGAGCCCACCGCTTCTTCATTTTATGTTTT
GGTAACGTTTACTGGCCCAGGGACTAATTAGACGTTCTAATCCAGTCTATTAGTACATAT
CGAGCCCTCTCTACAACACACAACACCTTTCTCTTCTCTCTCTCTCTCTCTTTTTTTT
TTATAATTTTTTTTTTTTGAGGTTGTCTTTATATATTGATTCCTGCCAGTTGTTTGGTA
AATTCGAATGACATGGCAGACCTAAAAAATACAATAGTCGCGGCGGCATTTCCTTCGACG
GGCTATAATTATTTGTTTCAGATTGTTTCGAAGTATATACATTCTAAGACGCTGACCCAC
AATCAAGTAACAAGACGGCATGGGTAGCTCCACCTTTCCTTTCCCAAGCACCCTCACTTC
AGGGTGAGGAGCCCTGGCCGATATGGCAGAAGGTCGTAGCCGGGGTTGAGGCTGGGATCT
CGGCCCTGATAGAGGAGCTGCAGGTTGCAAGGGTCGATGCTCATTGTCTGATCCGGGGTA
CTGCGCACAAGATCGCCATGGCTGATATCGTCCGTCCAGGTGGCACCGCTGTTGGCTTTG
CCAGCAAAAGGTGCGCTCTCAGTGGCCGCCTGCGGTGTCCATGAGCCACCAAGGCTGTCG
GCAGTGAATGACCGGAAATAGCGCCCTGTGCCCGATCGCTTCGACAATCATTAGGTAT
GTGTCTTTGCTTTGACCTGAGACCGTGTACACCTGGACAGCTTCGAACAAGTTGTTTCTT
TCATCTGACAGGATAATCTCGGACTCGGTACCGAAATCGCCGGGGAATTGGTCGATGGGC
ATACTGGCGCGATAGATGCGGCCGTTGTCTCCCGCGAAAAAGAGGTACATTGTTGTACTG
TCGCCGATGACTGTCTGGTCAATGACCCCGGTGTCTGAGTCTGAAATTGACCCGGAAAAG
AGCGGTTGGGGTGATGACCAACCATTGGCATCGGTTGGATCACTCGACGTCAGGTAGGAA
AATGCAGTAGGGCCCCATTGGTACGCGAGGATCCAGACATCCTTGGGCTCGAAGTAGAAT
AGCGTGGGCGCGACAGTCGACTGAGTCATTGCGTTCTGGCTCGCCGTGGCCATGTCGGAC
CAGTTCGAGAAGAGGCCGAAATTCATGGAGCCCCAGCTCGTGCCCGTATCATGATAAGTT
GCGTACACAAGATACTGCCCATTGTACGGGACCGCAGTGAAGTCCTTGAGTGATGCCCAT
CCGTCCTTGGGTTCAGCGAGCGGGCCAGTCGACGTCCAGCTGTACGTTGACGGGAGACCG
CACTGCGCCAGGACCCTTGGAGCAGACCAAAGGAGGGCTGCGAATGTGGGCCAGGTACTG
AGGTTTCTCATTGTAGCGCGTTGGTTCTAGGAGTCAAGATGAGATGCAGGAAGAGTTCGT
ATAAATTGTTGGTCTCAGCTGAAATGCCTGAATACCGTCAACCTTAAATAGGCTGTATGC
AACGGATTGCCCTTTTCTGCCACGGGCTTGTCCCCACGAAGGGGTCATTTGTTTCACC
CTGTGGGGATCCGAGACAATCACTCAGTACTGCTCCACCGACGCAAAGCACTGATTCGT
TTTCTGGACCTTGAATCTCCAAGCCCGCCGACGCAAAGAAAGGGTGCTTTGACACGCCAA
GCAAAGATCGGCCTTTGGGGAATCTTTTGGGTCGCAACCCTGATTATCCGGTTAAAGTCA
ACAATCTTCTCCCTCAATAATTACCCGGACGAATGCTGAAAGGCGTCATTTTCGAGGGCG
GATCCACTGTTTCTTACTGTGCTGGTTGTTGATGTCGTGGACGTCAGGCCGGTCCCCCAA
CTATGTCGCATGCGCGCAAGCTGGTGAGTATGTTACTGTGGTATGTTCTATTGTGATATG
TCTTTGGAGACGTGCACATTATACCTGTTGTTTTCATATAAACTCTAAAAGCATCAAGGT
CTATACATCTATAAGTGACAATCTATTCCACCGCCCGAGTCACAGTTTCAATAACAATAT
```

Figure 5C (continued)

```
CACCAACCTCACTTGCATAGGGCGGGCACATCATGGAGAAGTGATCTGAAGGCCAAGTTA
GTAAGTTACCATAGATGGGGGCCAGTATAGTTCCAACGTACCTCCATTGACGGTATAGAC
AGCGATATGGTCTCCAAGTAAATCCTCCCACCCATTCGTCCCAAACTGCTGTCGGCGCCC
ATAGAACCAGGAGTTGAAATAGCGCTCAAACTCATCCAGGTTCATCTCGTACATACTCTT
GCCGATATCCAAGCCAGGTCGACCCATGGAGGCAATTGGGGCATCCGGCCGATTATCGAG
ACCCAGTAAGGCCCAGACAACGGCGACTTGCTTTGGCTGGCGGTCCGATGGGAACGCCGG
TGCATCGTAGCGGGAGAGGGCCCGGCAAGTTGCCATGAGATGGGCACGCTCCTTGACTGA
GAGGTCTTCAGGGAGGTCGCGTGCGCGGTTAATGCCCTCAAAGGTACCGAGCTTGTCGAC
AAAATCGGTCGTTACGATAGAGGTCGGAATGAGCGAGGGTGCGCGCATGTCGAGGATGAT
AAGGGCCTGGATGGTTTCACCCTCGCGTGTCAGACGGTGGGCAACCTCGTAGGCATACAT
AGAGCCCGCGGACCAACCGCCGATGAGGTAGGGTCCATGAGGCTGGATGCGCCGGATTGT
GCGCAGGAAAATGGTGGCCATCTCCTCAATGGAGAGGTCGAAGAGCTCCGGCTGCTCGAG
GAAGGGGGACTCGAGGGCGTAAATCCGCCGGCCCTTGGGGAGGGCTTTCAGGTGGATGTA
GGACTCAACGGTCCCAGAACCATCCGTCGTCAGGAAGAGAGGGGCTTCGCGGGAGCGAGA
CTGACCCCTTTAGTAGACTGCACGCGAGACGGCGGCATCCAGTTTGTGCTGGCGGCTGGA
GTCGATCGTGGTCTCTTTCGCTGGGTTCGTCGATGTCTGGGCAGGGGCACTCTCCTCCTC
TGCGTCATCATCCAGAGCTTCCTGGGCGGCGCCCACTGTAGGGTTGGCGCTGAAGAACGC
AGCAGGGAGTTCGATCCCCGTCTTGGCGTGAAAGGCAGCGGTGATTTTGATGCTGAGCAT
CGAGTCCATACCCACCGAGTCAAAGGTCGTCGACGGCGTGAGATCACTGGCTTCCAATCC
CAGCGCTTGAGCCACGAGAGAGAGCAGGTGCTGGCTTGGTGCCGGGCCTTGCTTCCGGGC
TTGGGTCTGTTCTGGGCTAGGGTCGGCTTGGTGATGTCCTCCTCCAGGTCATCCAGTGC
TGAGCCTCCCAGCTCGGCTTCGGCGTCAGCCGGAGTAGGGAAGTTGGTGAAGAAGGCTGC
CGGCAGCTCTACGGCCGTAGTGCGCTGGAAGTTAGCCAGGATGGAGATGGCCATCTGCGA
ATCGACCCCGAACTCGGTAAAGGTGGTGCCGGGTGAGCTCTTCATCTCCGCCACACTGAC
CCCAGTCTGCTCAGCTACGGCCTGCAGCAATTCTGTGCCCAAGTCGACCATATCTGACAC
GCTGCTAGGTGTTGGTGACCTCGACATTGGGGTGTTCGAGCCGGAAGAGCTGCTGGGGCT
GGGCGATGGAGCGAGCTGCCGGGCACGCTTTGCCATAGACTTGGCCGGCGCAGCAGCCAC
CGGCTTGGTGGAGCGGCCGCGGGTGGCACCAGTGAGCAGGGCAAAGAAGTCTCGCTCTAG
CTTCTTGAAGCAGATGTCCGAGCAGACTGCAACAAGGCGGTCCTGGCTATCGGTGGTATA
GACGTCGCACAGACTTGTGCCAGCCTTCTGATCCTGCTCGCGGATCGTCGCGTAGACGTG
GTACGGGCCAGGCGAAGAGAGATCGCCCACGATCCGCAACGAGCCAATGTGGTTGGCAAT
GTGGACTTCATTCTTCGGTCGGCGGACGTCTGCGTTGAGCAGGAAGCCGGCAACATGGAC
CAAAGCATCCACGGCGAAGGGCTGCTGGTGAAGGTACCCAGGTCAGCGGTGGGCGTCAG
TTGGAGAGTGACAGCAGCGTCGTGGAAATCAGCGGCTATCACTGCTTCTTGGACTGCGTG
ATATGGCGCCGAGTAGTCAACGATCTCTGAGAAGACCTTGTAGAAGAGCGCCGTGTCCAT
GGCATGGACTTCGCGAGGCCGGACGGAGCGGTTGAGGGTCTGCACGCGCGCCCTTACCAG
CGACTGGATGCGAGACCAGTCCCTTCGAACGGCCGAATCGGGCTGGCCTAGACGCATCGT
CGCCGAGCCGTACCCAACTGCTCCTTTCGAGGTTTGGCCCTTGAAGTGCACAGACACGGC
ATTGGACTTGATGTCGAGGACCGCCTCGACCCAGACCTGCGGCAGGACTTCTATATCCTC
GCGGAGCACCAGCGGGCTGTGCATCTCTAAACTGCTCAGCTCGTAGGTGTTCAGTGCAGC
ACCAGCGCCGTTCTCCTGCTCTAGAAAAACTGCCGCGGTGTAGGCCATGTCGATGAAGAT
ACTGGCTGGGCAGATGGCCGACTCATCGACGACATGGCCACAGATGGCCTTGGCCAGCTT
GGGATCGGAGAGGTCTACTGTAAATGTCCCCAAAATCTTCCCCTCCTCTCGCTGCAACTT
CTCAACTGCATGAAGTGTGGTAGATGCCAGCCTCGAGAGCCCGGTAGTGGATGGTGTGGC
CGACGCGGCGCTCACAGCCGCAGCAGGGGTTTTGTATGAATGCCAAAAGGTCTTGAGGTC
GAATGCATACGTGGGAGATCACTGATCAAGCGAACAGTGTCAAGATGGTCCTTGTGGAA
CTCACTCCAGGCCACCGGGAGCTGCGCACTGTGGCTGCAGCAAGAGTCGAGGAGACCGA
TTGCCAATCATCGCCGCCGCGACGGAGGCTGGGCAGGCGTTAATTTTGGCCGACTGCAG
GCAGGTAGCCATCAGACTGATGCAGATAGGATGGGCCCGATCTCGACGGCAAATGAGCG
GTCTGGTATGAGTCCCTCTGTCTCGCAAGCGCGCACAGCGTCAAGGAAGGCCACTGGCTC
CCGCGTGTGACGGCGCAGGTAGTTGGCATCGAAAACGCCCTGCTCGCCGGGCCTGACAAT
GCGTCCGAGGACGGTGCTCGCCACAGGAAGGGTCGGAGCGTGGAAAAGGGACCTGGGCTGC
ACTGGCCTCGAGCTCGTCCAACAGGACATCCATCTGGCGAGTATGGAAAGCATGCTGCAC
TCGCAGACGTGTGGTCGACACCTTGCCATCCGACTTTAGGTATTCGTCGAGGGCCTGGAT
GGCGGCGACAGGGCCCCTACCACGGTGCTGGATGGGCCGTTGACACAGCAAACCTCGCA
TCCAGTGGTGGCCGCTGAATCACGGATGCGATACTGCACAGTGCGCATCGGCAGTCCAAC
AGCCAGCATTGCTGCTTCGGATGGCGGACACCGAGTGAAGATGAGCGTGGCGCGTCTGAA
GGCCAGGGCCAGAGCATCGCTGGCAGACAGCACCCCGGCCACACAGAGCGCTGCATACTC
TCCCAGGCTGTGGCCGATCAGCACCGTCGGTCGGATGCCCAGCGACCGCCAGTACCGAGC
GAGAGCGATCTCGAGGGCGACAGTCGCAACCTGCATGTCCACTTCGGTGACGGTAGCGCC
```

Figure 5C (continued)

```
TTCGGCGCCGCTACCGCGGATGGCGTTGAGGAACTTCGTCGGCAGCCCCTGCACCTCGCA
GATCGACTGCAGAGAGTCCAAGAGGCGACGGAAGGTGGGCGACGTGCTATACAGAGCACC
CCCCATGCCCAAGCTCTGTGCGCCTTGGCCTGTGAAGGTAAAGACGACTGCGGGTGGCGG
CGCGGATTCCACCTTGTCTGCTAATGGCTTCTCGAGCTGCCGCACAAGGTCGCTAGTAGA
TGAGGCCACATACGCCTCACGGTGGACGTTGTGTATCCGGCGTGCGGTCGTCGTGTAGGC
GAGGTCGGCGAGGTTGGTGTCTGGGTGCGCAGAGAGATACGCATGAAGGCGCTTCCGATT
GGCCTCATGGGCCGTTGCGGTGCGTCCCGAGGTGACAACGACGTGGTGTGTTCGAAGACC
AGGCCCAGAAGCTGGGGCTGGCAGGGCAAACGCCGGGGGATCTTGTAGCAGCATGCTGAC
ATTGCCTCCGGCAGCGTCGAAGTTGTTAACGAAGATATACCGGGGCTCGGCGCCGTTCCG
GGTCCAAGACTGTCCATTTGCTAGCTGGATTTGTTTCCCGATCAACGGTTCAAGATATGG
GTTCATTTTGATGGGCTGGTTCGGCTGCGCTGGAATCTTGTCGTGCTGCAGGATGAGAAT
TGCCTTCATCAGGGAGATGATACCCGCAGCGGCCTCACTGTGTCCGATATTCGCCTTTAG
GGCGCCCACAATCAGCGGTTTCTCGCGCTGGTTCCCGTTTGACGGCGCAAAGACGCTCTG
AACGGCATGTGTCTCAACACGGTCCCCAGCCTGGGTCCCAGTTCCATGCATCTCGACGAC
GTCCACTTGCTCCGGCCTGACGGCCGCCTGGCGCATCACTCGGCGATAGAGAGCCCCCTG
GGCCTTCTCGCCTGGGTAGGTGATGGAGCCAGCGCCCGCATTGCAGTTGCGAGATGCACC
GGCGATTACTGCGATGACGTTGTCCTTGGACCGGACAGCATCAGCCAGACGCTTGAGAAT
TACTACACCCACGCCCTCACCACGGCAGTAGCCGTCCGCGCTGTCTGAGTACGTCTTGCA
AGCGCCGGTAGGCGACAGGAAACCCCCTGGCTCAGTCCTGCAAACCATTCCGGCGCGGT
CAGCAGCGTACCACCGCCGACAACGGCGGCGTCGTACTTGCCTGCCGTCAGAGCGTCCCG
CGCAAGGCACAGTGCTGTCGCGCTGGATGAGCAGCCTGTGTCGATGCTGTAGAAGCCACC
GGCCCACTGGAAAAAGTGGGATAGTCGGCCAGGCGCAAAACCACGGTTGACACCGGGGAG
ATAGTGGGTGTCTATCCCCTGCTGGTCGTTGATGCTCTTCCAGTCGTCGATTGTCTGGCC
AAAGTAGGTTGCAATGCGAGGCGGCGCCTGCTCGCTGTCACCGGGTGCGGCGGGGGTTGG
AGGTGAGTAGCCCGCCATCTCCAGGGCTTCGTACGTGGTCATGAGGAGCATGCGCTGCAC
GGGATCCATCTGCATCGCCTCGCGAGGAGAGATGTTGAAGAGTCGGTGGTCAAAGTCGCC
GGGGTTCTTCAGGAAGCAACCATAGCGCGCCAGGAGCGCGTTGTGCTTTGCGCGAGTAGG
GTCATAGAAGTCATCGACATTGAACCGGCTCTCGGGGATGACCTGATGGGTTGTAGTTGC
CGTCTCCAGCAGCCGCCAGAACTCGTCAAGAGTGTCGCTGTTAGGGAAGCGTCCGGACAT
GCCAACGACGGCAATGGCGTCGGCTGGGATGCTGTCGAGGTCGTTTCCATACGGCCTCGG
CGTAGGACTAAGCTGCCCAAGCTCCACCGCGAGGCCATTCTTCTCCAGGAGACTCTGGAT
TCCCGACGTCTCAGTTGAGGCGCCGATGGCAGTGAGGACGATGTCTGTGATATTGGCCCT
ATGCAGGTCATGAATAAGGGCAGTGACGGCCTGATGAACGTCGATGGGCTTGTTAGCGAC
TTCCTCCACAGCAAGCTTCCAAAGCTCTGTGGCCTGTTGTGACGAAGAAGCCGCAATCAT
AGTCGCGCTGATAGGGGGCAGATGAGCCCCATGCAGCGGCACCTGGGCCAGTGCTGAGGC
AGGGCTGGTGATCGTTGCATGGGCGAGTTCCGGTCTCTTCGCCAGGGCGTCCAAGGTGGA
CGGTGGTCCAAAGACGACCGTGCTTTCTGTCATGACCTCCCCGATATATGCTTGGTTTAT
CGGTCTGAGTGAGGCGTTGATCCTATCCAGTGCCTGTTCCAGGTCTGCAATGGTGGTGGC
GCTGGAGATCACTTGCGCCCATGGGCCATTCGAGTCTTCGATGTCTTTTCCCCTCCGCTG
GAGTTCTACCCCCAGACGAAAGGCCACCGAGACAGCCTCCAGGCCCAAGTTGACTATCCC
ATCCGCTGACGTGGCGGCTGCAGCTACACCAGCGGCCACCAGCCCGGCGCCGAATCCCAT
GGGAATTGCCCTTGCCCCTGCATGTCCGGATAAGATCGCTGGATCATCTTCGGCGAGGCT
ATTGGAATACTAACGTCAGAAAGAGACTTCAGGAATTTCCGGGTCAAGAAGACGTACACA
AGCAGCTGGCCGATCTGGACGGTGGTCAGAAGTACCAGGTCAGCGACAATGCTACCCCGG
GTCTGGGTGGTCTGCCGCTCAGCGAGCTCCACTAAGTCCTCAAAGGAACCGATATCGGCA
CGCTCGAGTCCATCAAGAGATGCTGTCCAGTGCTGTACGACGTTTGATGCCGCAGCCAAA
AGGCTCTGGAGTCTGCGGCGTGACTTAGAGCGCACGTTTAAGTCGTGCACGGCATCAAAG
GTGACCCGCTCCTGCGGGAAAAAAGAACGTGATTTGGAGCCATGGTGACTTAAAGAGAA
GATAATTAGATATTGAGATGGGAAATATGTCTATGATATTATAGCGGCACTGCTGTTCT
ATTGCCGTGAAGAGTCAAGCTCCGTGATAACTCAAGCTCAACTCCAAAGCAGGTGCAATG
GGATGTTTTATATAGCCTCGCCTTGTCAAGTAATCCGCCTCCCAAATCCTTTTTCTTCTG
GCTCACTTAATCATGGCTGGAAGCTGAAGCCGGGCAATCCTTCAGCTGCGTTGTAGCCTG
CCCCCTTAGGCAAGCCGGGCAAGAGGCATAGCCATGCTCCTCTGGGTACTATTCTTGTCC
GTACGAGGGTCCAGAGTGCCAGGGTACGCAGTTTACGAAAGAATGTTTCGGTAGTGGAGT
GTACGCGACTCTGGTCCGTGAGTATCTGTTGAGTATACACATCTGATAGAGCCCCAATCT
GGCCGTTGATGTCAGCCCAGAAGCGACATCAGCGTTACAACGATAGTACATCGTAAGACC
ACACTTCTGCAAGCTTATCCTTGGGCAAGTTTCAGTGCGATACGAAGAACAAAAGAAAT
TTTCCGGGTCAGATCATCTTGTGGGCGAATCATCAGCCCTATGACGGCATACGCCTCCGC
TGCAGCTTATACTCTGGTCCAGATGTGAATCATCATAGATACTCTGCTCCTACAGTAATT
CAGACCGCATTTCATTCATTTGCAGCCTCGATACTCAGCAATGTTTGAAGAGGTACTGCG
```

Figure 5C (continued)

```
GTCGAGCCCGCTGATAAGGACTCCAAAGGCCTACTCCCATAAACCTACCGGCCCACCATA
ACCCTGTCAAATCGTCTCATTCCTAAACATGGCTACTGAGATTGCCGAGATCACCAATCT
TCTGAAACGCGAGCGCTACTACCGGGACACTGCTCAGTGGGAGCTGTGCCGGGACGCCTA
TCATCCCGACGCGAGCATGACCTACATTGACGTTTCCTGGTACGCACAACCAGCCCAGAC
AACAGCCGGCTGCACGCTGACTACGAACAGGTTCCAGGGAAATATCGACGAGTTTCTGGA
ACGCTCAGCCAGGGTGCATCAAGGTCGAGTCAACGTGATCCACTCCTCCTTTGATCCGGT
CGACGTCCAAGTCCGCGGCCGCCGAGCCACCAGCGCGGCATTTTGTCTCATCACCAGCTC
CATCACGCTAGACGGGGTTGAATATGAGCTGGCCTCGTATATGCGGCTTCTCTCCCGATT
ACAGAAACTTTCAGACGCCGGTCCGTGGCGAATCCTCCGGCTAGAAGCAATCTATGTCCG
CGACCGACTGGTATGCTCCTTTCCCGGCCGAGACGCTGCGGCGCCGCTGGTGATACCGGA
GAAGGCTTTAGCGTATCCCACGCCCTACCGCTGTATGGCCTTTGTCATGCTACATCGAGG
GCTCGAGCCTCGCGTTGACCTTCCAAACGAGGATGATCAAGATAGCGTCCGGCGAGTGGT
GGAGGGCAATGTGGCATTTCTTAGTGGTGCCGAGGATATAGTTGAAGGCACAGTAGCATA
GGCAGGCGTTGATTATGTCCATTCGACAGTGCTATCTTTATCTCTCCCATTTTCCAA
ATATAGACTCAATCCCGGGAACCGTACTGCAATAGGCCAATTCCTACTGGTTTATCACTG
CTCCTTCTTCATATGCACCTTAAGCAAGTCCTCCGCGTTGCGGTAGGCCACCATCTCCAA
CTGCTCTTCGGTCAACAGGCCACTGCCCTCGAGTTCCTTGAACCACTCCAGTCCCCGCTC
GTTGGATTCGAAGGGGTAGTCAACGCTGTACATGATGCGCTCCACTTTTGTGTTGTGGAG
GATGCACTTCAGAGGCGCGAGACTCCAACTCCCAGATGTAGTAATCCAGATATTCTCATC
CCAGACCTGCCGGAGCGGTCGGTCTCGAGGGCCCCATCCGCCCCAGCGAGTACTCATGTC
ACTGGCTCGTTCGAGCATATAGGGAAGCATCTCACCCATGTGGCCCACGATGATCTTCAG
CCTTGGGAAGCGATCAAACACCCCCGCAGCGAACAGCTTCAGCACGTGGAGGCCAACATC
GGGATGCCAACCCCAGCCCGGGCCGCCCAGGCTGATGCCGACGGGGACTGGGTAGGAGCC
CATGAAGTTCTCGGCCATGCGGGCCGAGGGCCAGGTAGGGTGCAGGTAGATGGGCACATC
GAGCTCGCACGCCTTGGCCCAGAGAACATCGTAGTCGTGACCGTCGAAATGCTTTCCGTC
CGCATGGTTGTCAATCAACGCACCGACGAACCCTAGTTCAGAAACAGACCGGTCTAGCTC
CGCCGCCGACGCAGTTGGGTCTGCAACGGGCAGGACTGCGAAGGCAGCGAAGCGCTGGGG
ATCGCTGATCTGGGCAATCTCGGCCGCAAGCTCATCGTTGCCTGCTCTGCAGGCTTCGGC
ACTGGGTCCACCTATCGATCTATGCAGTCAGCTCGCGTGGCTTTTGTGCTATTCTGGGTT
ACATTAGGTCTTACTGACCCGGAGTAAAAGCATGGGAGACCACCTGCAGCGAGATGTTCC
CACGGTTCATTGCCTCGAGTCGCCCATCTCCGAGGCTTCGCAGCTGGTCGGCGAGACCAG
GCACGCCTTGCAGGGTTCGCTGGAAGGTCTCGCCAATCGAGTTGAAGATGGCGGTCGAGT
AGTAGTGTTCTTCGAGGGCGAGGAGTGGCGGAGTCATTCTTGCCAGTAGAATGCTAAGTT
GATCTGGATTTTCTCTTTGTTGGGACACCTTAAGGCAGACCGGCCATTCATACTCTCCCT
ATATATTTTCCCCATAGAGGCTCCAGTCTAAATGCTGACGTGGATCGATAAAATATTCC
CGTATACGCCGGGTATTAGGGCACAGCAGCTGGAGCAGCCAGGGACCGCCCAATACGAG
GCACAAGGTCGTCTGAGACATCATCCGCCCCTTTGTTTCTTGACGCATAGTTCGTGTTTG
AACGGTGGTCTGATTGCCGAGGGAAAGAATTGCAGGGCATATAAAATGGGCTCCGTCTTT
TCTTCTGGGTAGCTACGGTTAACCATCAATTACACTAGGGATAACCATGTTGGCCTTCAA
CCCGCTTGTCACAGCGCTTGCCGCTCTCATTTTCCTCTTCTGTCAAGCAAATGCCAATCC
GCCGCTTATGCAGAGGCTCGTCCATGAGTACCAATGGAAGACCAAGCAGGGCCTACCTAG
GCAAGGTGCTTGCACCCCCATAACCTTGCGGTTCGCAGAGAGTGGTATGTATACGTCCA
TGCGGCGCTCTCCCCCTTCCGCGACTTCTATTTGCTGACCGGTTTGCCAGGAGCACCCTG
GATGTCGAGACCCGGCTTGAATACATCGAAGCGGTCAAATGCCTGGCCCGCTTACCCTCC
ATCATTGATCCTGAGCTGGCTCCAGGTGCGCGGTCCCGGTTCGATGACTTCCAGGCCACC
CACATCCGCCACACCAGGACCATCCACGCTACAGGGTCCTTCTTCGCCTGGCACCGCCAT
TTCGTCTACCTGTATGAAAAGGCGCTGCGCGAGGAATGCGGATACACGGGGTACCAGCCC
TACTGGGAATGGTCCCACTGGGCTAATCTCCCATCACGGCCAACCCCCTCTATGACGGC
TCCAACGCGTCTCTTTCAGGAACGGAGTGTATATTCCCAACCGCAACGGCACCCTCCAG
CTTTTCCCAATTCCCAACCCGTCTCCCGATACCGCTATCTATACTCCTCCCGGAACCGGC
GGTGGATATATCTACGACGGCCCCCTTGTCGACTGGGAGCTTCACCTCGGGCCCGTCCTC
TATTCGTACGATAACGGCCAATACATCCCTCCAAACCCACGTCCGGACGGATTGGGATAC
AACCCACGTCCCCTAATCAGAGACTTCAATAACACCCTCCTCCAGCAAGGCGCCTCCTGG
GACATCATCCTCAACATGCTCGTCAACGTGACCGACATGCATGAATTCCATCCTTTATTC
TTCCAAGGCCCGCCATCTGGCCGGTCATATCTTCATATCGGGCGTCGACAATGATATTTC
ACTTCGCCTGGGGATCCGCTATTCTGGTTCCACCACGCCCCAGGTCGACCGCATCTGGACC
ATCTGGCAGGCCTTGGACCTGGAGACGAGGGAGTATGCCCTGGACGGCACGCTAACGCTA
CTGAACTGTAAGAACCTACCTTTCCGCCGGATTTTAGCAGGCGAGCTGACAGTCTGCGAT
GATAGTACCGCCCAGCCGTAACGCAACTCTAAACGACACGATGGTATTCGACTTCAGCCC
CGAGATTACAATCGGGACCGCCATGAGCCCTACCAAGAACGAATATTGCTATATATATGA
```

Figure 5C (continued)

```
GTAATCGTGAGACGTAATTGGCGAATGGGGACACTCCACGGATGAGTGGCTCTCTTGGCT
GGTACCGGCTTGGACCCCGAGTATGCGGCTGCTGCATGCAGTTTGTTCGAGGAGAAAACG
TAGTCAGTGCCTAGTCGGTGCCCGGTCGGAATCGCACGGTCTCGCGATATTGCCTGATTG
TATAATTATAGAAGCTTTGATTAGAAGATATGCATATCTAAATTTAATTCTTCTTGTCTT
GACTGAGCACAGCCAGCTTAGGTTATGTATGATATCACTGCAGGCTAGTATGTATGCTTC
TATCAGATGCAAGGATATCCTAGCAGAAAGCGCCCGGCCAGCTAGCCAGATTATCAAAT
CTTCAGGCCGTGCTTTGGCAAAGGGCTGTAGCGAAACCGCATGTGTCTGGTAATCATTAG
TCTAGGCCGCAATAGTAAGCGCAACAAGCCGCTGCACATTTCCGTCATCGTCCTCCGGCA
GTCGCTCAGCGATCCGTAGTAAGATCGTCATGGCCAACCCCTTGACTAGCCAGCATCCGC
AGCGCTCGGTTCGATTGACCATCAGTGCTGCCCAATGGGCGACCACCACGAGAGATGCTG
GATAGTGGCGTGCCACCAGCTCCTTGAAACGAAGCGGCACTCGCGTCCACCAGGTCGCCA
TCCCCCACCACGCTGGTCCAACTTCCTCCGACGCAAAGCTCGTGTCACAGCACTCACCCA
TAGCTGCGAGGGCTGACAGGAGGACAAGAACGTCCTGAATATTCTCCGGTCTCCCAAAGG
TATCGGCCATGCGAGCTGGTAGGTCATGAAGACGGTTCCGGATCTCCGCAAGGACGCTGT
TTCCGGCCTCTGAGGTGTTCCATCTGAGAATTCGTGTCGCGTAGGCCGACGTTTCAGCTT
CGTGTGGTGCGGCCGCGGGAACAGTACTCGTGAATGGTGCTGATGATGGACTGGAGGTGCT
CTGGTACGCCCGGCTCTGGCATGATGCGTTGATCGCAGGGGGATTCAGCCAATGCCCAAT
GTGCACAACGTAGCAAACACTCAATCTCGGTCGCTACCTCTCGCAGACCCTCACCAGATG
TGTCGGCCAGTTCTCTCCATCCCGTTCGAAACTCGAGGGAGAATTCAGCCGCTCGTTTGC
GGTGCTGTTGGCCAGCCGCCGCATTGTCCGGGAATGCGGCCAAGTGACAGGCAGCGAGCG
CCAGCAGACCGCACATCAACCATCTCTGCTGGAGCGCTTGAGGGACTGCCTTTTCTTTCC
AGTATTGAGCCCCCGACTGCATATCCTGCGGACATGGTAATGTCAGGCTCGTTGCCGACA
TGAAATGGTGAAAGTAGGACAGGGTTTCAAGGTCCACGTTGACAGAGGGAGCGGAAGGGC
CGGGAGAAGTTGTGACCGTCGTTGACTGCCGACCACCGTTGTCGTCTTCCTGCTCTTCCA
AATCGACATCCCCTTCTTCCTCGTCATTCTCGCTCTCGTTTTCCTCATCGTCCTCATCCT
CTGTCGTGGGAGTCACCTCAAAGTAGCGGATCTTAGTCCCCGAAAGAAAGTCTGTAGCT
TGGCTGGACGCGCGAGTGACGCATCCGCAATACCATGGCTCTCTCCAATGGCCCTTCA
TGCGCTTCAGACTCGCACAGAGATTAGCGCAACCCGGGGCTGTACAGCGGTACCCGCGA
TGACCGGCAGCCCGTCGATCGGGGGTGACTCCGGAGGCGGCAGCAACACATCGTCAGGCT
CGAGAAGATCGAGCTCATTAATCATAGCGACCAGCTGCTGGCGGTCGGCACGGTAGATCT
TATGGCGCAGCAGGTGGCTCTGCAGCGCGCTCTTCTGGATCGCATACCGGCACTCGTGGC
AGATCAGAACCCCGTAGCGACCGTCGTACTCGAGGATCTTCCGGGGTCCAAATCTCACTG
GGGGCATCTTGTCGTGCAAGAGACATGATGAGCTCCAGAGGAAGGAGTGCGATTGAGGTC
GGAGGGAGGGAGGTTGCTCACAGACGAGAGGCTTTACACGACTCGAGCAGGATTGAGTGA
AATGAGAAGAATGCCAAGCCGAACAGGCAACGACAGTACCATACAGTACCGTACCGTACC
GTCCTGTTTATAAGCATAGCTGACTAAGAGTAGAACCACACCTGCTGTTCTTATTCTTGC
AAGCGGCTTGCAATAAGCGAGAGAGAACGGCAGGTGCCGTTCTCTTCTATGTACTGGGAT
ACTCTGGACTCACCCTCGTCACCTTGTCCCCTCGTCCTCATCTCTTCTGTACTGCTACAG
AATCGCACCTGCCATTTGGTTGATTGTTAAAAATCCTTGACAGCCTCAAGATGTATATAT
TGCCACCGTTTCACCATCATTGCCCTGATGGTTTCCCATTCCATGCCCATTGTCCAGTCT
CGTCTCTGTCCATCTTCAAACAGCAATCTCTACTCAGTCTCTTCATACTCACTCCATAAC
ACATAATCTCATAAAACAAGATGGCAACCAACCAAGCCGCGTGGCTCACCAAGGCAGGCA
ATGACCTCGAAGTCGGTGATGCCCCGTCCCTACGGCTGGCCCAGGCGAGATTGTGGTTA
AGAACGCCGCGGTGGCCATCAACCCACTCGACACCCATATGCAGGACGTCGGCGTCTTTG
TCCAGCAGTGGCCCACCATCTTTGGCTGCGACGTCGCCGGTACAGTGCATGAGACGGGTC
CAGACGTCGAGCGGTTCAAGAAGGGGACCGGGTTATTGGGTAAGTTCATGGCCATTGAC
TTGTCGTTTGGCTCGTGACTGACTCTGATATTGTAGTCACGCCATCAATCTGGTCACCGG
GCGGCCTCAGGATGGTGCCTATGCTCTCTACACCGTCGTCCCCGCCAACAAGGCGGCTAT
CCTGCCGGACGCTATCTCCTTCACCGACGGAGTCGTCGCTCCCTTCGCGGTCGAGGCGGC
CGTTTGCGTCCTCTCCCTGAAAGAGCCCGGTGTGGCCATGCCCGGCGTCTCCACGCCGGC
ATTAGCCCTGCCGTATCCCTCTCTTGACGATCCCGTCAAGCCGTTGGGCAAAGTCCTGGT
CATCTGGGGCGGCTCTTCGTCCGTTGGGTCCATGACGACCCAGATTGCCACCGCCGCTGG
TATTCAGGTTATTGCCATTTCTGGTGCTCACAACTTTGAGTTAAGCAAGCGCTGTGGCGC
TACCGAAGTCTTTGATCACAAGGATCCCGAGGTCGTTGACAAGGTTGTTGCTGCCGTGCA
GAAATCCGGCCAGGAGTTTGTGGGAATCTTTGACGCCGTCGCTACACCTGACACCTACAC
CAGCGATCTGGTCATCCTCGAGAAACTTGGAGGAGGCCATCTGGCTGCGGTTCATCCTCC
GCCCGCAGAAGTCCCGAGCAACGTCAAGGCCGGCATGATCTTCGCGGTCAACGATATTGC
AACCCCGGTATGGAATGACTTTGTCACCCCTGCTCTCGAGAGCGGGAAGATCCAGTGCTT
GCCTCCGCCAACAATCGTCGGGAAGGGTCTTGAGGCGATCAACGAAGGGTTGAAGAGGTG
CAAGGCGGGCGTGAGCGCGACCAAGCTGGTTGTGGAGTTGTAATTGCGTGCCGGCTGCAA
CATATTAGAAAAGAATATTGTGTACAAGTTCAAGATAGCATACAATGAACGATTGGTCCT
```

Figure 5C (continued)

```
TTTCTTTATTTTTCTTTATTTTTCTTTCGTCACTCTCTAGCACCAAACAATGATGATGTC
CCGCATGCTGAAATTGCGCGATTTCTAGTTTGAAAATCCTGTAAGTGACGAAGTAGAATA
TTTCGGCTTCCCCAGGGGATACGGCAAAGAAATTAGGCTGCCTTTTGCATTGTTCGATCT
TCGTTGGATTTCTTAGCCCACAAAGCTCCACGCTGAACTCGTATTGCCTTAGCGTTCGT
GATATCAAAACGCCCCTCCTAGTAATATGGTTGGATAAACAGCTATTATTGGCTTCACTT
GGGTCGAGAGACTCGTTGTCGTGACTCGCAGGTCGTATGCTGAGTGGCGGCTCACTGCTG
ATATGGAACATACCAGGCTGAAACTGGTATAAGCTCAGTGGTACATTCCACACCTGTTA
TTTTAATAGTTTCTTTACCCTTTCTTTCAATGGCTGTGCCCATCAGACGCTAGACTGTCC
CAAGCGGCGTCCATGTTACTGTTTAAACATCCTTGGATGTCGGTCTTTCTACTCGCACGG
CTCTGAACAACCAGGCTTACATAGCAGCAACTCCTCAAAGCTGGCACTCAATACTTGAAG
TGAGGAAGTCGGTTTGCGATGGTTATGGGTAGCTTGCATTGGATTCAGGGTTTCATCACG
GACATATTATCTTCTCCGCAGGTGACTGTCATGAAGCTTTGGGTGGCCTCGCAGATTGTC
ATGTCTAGCAAATGAAGCGAATGCTTATTGAGAACTCTAGCTGGGAATTGCCGTGACACT
AAAACAAGAGTGACTCCGAAGATAGTGACTGATACTGTACAGGTAGTTCAATTACAAAGT
CTATCAGTCAGATTTTTGCCTTGACGCCTTGACGTTTTGTTTCACGCCTTAGTCTTGACA
ACAAAAGAGCCATGCGTTCTGAGATCCCTGGAGCTGGCGCCCACCCAAGCCTCGTACGTA
CCAGGAGCAACTGCCCACTTTTGGTGCTGGACATCCCAGTAGGAGATGTCACGGCGGCGG
AGCTCGAAGGTCACCTTGGTCGACTGACCCTTCTTGATGTAGACATTGTGGAAACCACGC
AGCTGGCGCACTGGCTGCTTCGCGACGTCCGGGTACGAGATGTAGAGCTGAGGCACCTCG
GCCCCATCAAGAGAGCCGGCGTTGCGGATGGTCACGGTCACCTTGGCGACTGTATCCCAC
AGATCTTCATAGCCACCGACCGCGAGCTGACCTGTAGGGTAGGTGGAGAGGGCAGAGGGG
CCCTGGATGTGGAGGTTTGAGTAGGCGAAGTCGGTGTAGGAAAGGCCGTAGCCGAACTCG
TAGCGAGGAGTAACGTTATAGGCGTCAAAATAGCGGTAGTCGATATAGTTACCCTCGGTG
AAGTTGCACTGCGCTGTGTAGCAGATATCCACATTGTAGTCGGATTCGGTCTTCGCGATG
GTGTAGGTGAGGCGGCCGCTGGGGTTGACATCGCCGTAAAGGACATCGACAATGGAATTG
CCTGATTCCTGACCCAGCAGACTGCCGTACAGCACGGCCGTGACATTTTCGTGCTCAATC
CAACTGTCCAGGATTCTGGCGCCAACTGTGTTGATTACGACCACGGTGTTGTCACAGTTG
TCTGCAACCTCGTTAATGAGATTGTCCTGATCGGTGTTGCGCAGCTCCGTGCGATCAGCA
CCCTCGCCAGCTAATGCGTTGATAAAAACTAGGCAGACATCCATGTTCTCGGAGTATGCA
CTGACGGAGGGCGTGACAGAGGTGCTGGATGAGCCCTGCATGACCAACGCAGAGCCAGTG
GAGGAGGAGTAGGTGTCGTTGGCAATCCAGCGCAGCATGGTGCCGTCCTGGCTCGCCTTG
ATGTTGAGAGCGTTTTCGGGCGTGATCAGGTATGGCAGAGAAGCCTGTCCAGATCCCGAG
TCCGTCGCGATATGGCCGTCGTACGTAGGTCCAGAACCCTCGACACTGAACTGCATGTTA
GGGCCAGCCACCGCCGCACGGGCGTGCGAGCCAAAGATGGCCATCTTGTGAGGCTTGTAG
AGGGGCAGGGTATTGTTCTTGTTTTTCAGCAATACCATCGACTTAGAACCATGAGAACGG
ATCAGCTTGGCGTGGTTGGCGCGGACATCGACATAGTCATCTTGCGCGGCAGTAGAGGGC
TGGGTTCCGTTATCGAGGTTGACGTAGTAGTAGCCCATCAGGTTGCGAATAGCCATGTCG
TTCAGACGAGCTTCGGTGATGTTGTTGCTCTCAAGGTACCCTTCAATCGTTGATTCACTC
CAGAGGCTGGACGAACCGTAATCAAGTCCATTAGCAGCAGAAGCAAGGGCATCCTGCTGG
CCGTTCGTATCAGGCCAGACCATACCGGGGAAACCAAGCTCGGTCTTGAGAATGTCTAGA
AGGAGGGAGGAGCTTTGGCATGAGAGCGTGCCGTTGACTTTGGTCATGGCGCACATCACA
CCACCAAGGCCGGAATGGACCGCGTCGTAGAAGGACCAGAGGTATGTCTCGTGGAGGGTC
TTGTCATCGGCGTTGGATGAGTAGGGAGCGCCGGAGGACGACGAGGACGAGAAAGCACTG
CTACCAGCCATTCCACCACCCATTCCAGAGCCGCCGGGGGTCGAAGTGGACGATGGAATG
GCTCCCGCAGAGCTTGTAGGAGACATGCCCCAGGGACACTAGAGCTAAACTCAGCGCCT
CTCCCCATGCCGCCACCACCAGGAGCACCACCGCCACCTCCCATGCCGCCGGTCCGGTTG
GTCTCCTGCTCGTTAAGGATAAAGTGCTAAACCGCATTAGATAGGCAGTAATTTGTCGGT
CAGGTGAAATGCTTACCTTAGCCCCGGCGATAACTCCCACGTCCGCATAGGCCCTAGTTT
CCAACCCGGTTGCAATACCATTCAGATACGGATCAGGTCCAAAGCTTTCCACCAGTCGGC
CGCCCCATGGAGTACGGCCAAGAGGCTGCGAGGTCGGACCGGCAACCATCTGGATTCCCT
TGCCGTAGAACTCAGCCGCAATGGCCCTGCCCTGCTCGTACATGGCCTCCTTGTCCCAAG
TCATGGCCAAGGCGGAGGACAGACTAAACGCCGAGACATAATAGTAGGCTTGCGCGCCCA
TGTCACCGTCGAGAATGTCGAGAGCCGTAAATGTCTCGCCATTGGTAGTGGTCACACTGC
TGCCGGTGATGAGCTTGATCTTCTCGGTGGTGTTGAGCTTGGCAACAAATTGCGAGGCTT
TCTCGTGTGCGGATTTCCAGTCACCGAGAGACACTGTCAAGAGTCAGCCACTGGCAAAGA
ACTGGTCCCTAGTGCAGAGAGGATACCTTTGCCGCTGGACAGAAGGCCGGCTTCAAAATT
GCTGGCGGCGGCCAGCGCGGTGCCGAGCAGAAAGGAAAGAACTGATAACG
```

Figure 5D

Sequence of the deletion of the Monodictyphenone cluster

>ChrVIII_A_nidulans_FGSC_A4 COORDS:ChrVIII_A_nidulans_FGSC_A4:4435825-4460326W (24502 nucleotides) (SEQ ID NO:4)

```
AATTGAACTCTTGTCGATGCATAGATTGACTGCTATCGATAGACCTGTAAAGAGTAGAGA
GTAGAGTCACTCTTGGCTTGTTGATCGTACTAGATGGCCAAGACCCATATACAGCACTGC
GTATATCTAATCAATCAGACGACTGCACTTTGAAGTCCTTCCAAGCCCCGTCCATGCCTG
CCATAACCACCCACCGATTTTGCATGTTCGTCTCAATCGTCGTCTCATACGCCATCCTCG
CAATCCTCAACCACATATCCCCCTTGACCATAAACTCCTCTCCATCCTCAAACTGCCCGC
AAACCTCCTGCCCGTTCTTCAGCGCTCGCACAAACTTCGCCACATGCCCATCATCATGCT
GCTCATTAACAATCGCAAACAATTCCTTCCAGGACATAGTCCCCGTTCTCTCCCCCCTGT
AGGTTCTCACAAATTCGAAATCAAGCTCGGGTACACCGCAGAGAGCATACCACATCAGAT
CCAGCCGGCCCTTCCACTCGACTAACCTTACTCTATCCCGCATGGAAATCCAGTCCTGAC
GCCCGAGAATAGAGAAGAAGATACTGCTTGTTACGCAGTGCATGAAGAAAAGTCAATCT
TTGGCTCATACCCGTCCTTCGTCCTCTGCGACGCACCAGCCAAGTAAGCACAGAGGTTTA
GCATCTCGGCAGTCTTTCTCGCGAGCGTTTCCTCGGTGACTTTAAACCGCGACGCAATGT
CTATTATTTCATCAGCTGCATTGACGAGAATAGACTTTCTCATCTTCATCGTCCCAATGA
GGCCCTGGACGCGTCCGGCTTCGACAAGTTTGGGTGTGTCCCTGATTTTCTGTAAAAGGT
TCACGAGAGTCTCTCCCTCTTCGTTTCGCCCAGCAGCTCGCTTTTCGGCCGTGAGGAAAA
AGTAATCGGTCCCAAAAGAGTCGTGCGCGGCCGCCTGCGCCAATGCCTCAGCGATGATCC
CCGGCTGTTCGAACTCGACTCCAAGCCCGAGATGAATAATTGAGTGAAAGGCGCCGTCGT
ACATAAGCGGAGGATCTTCTCAGCAATGGGCGAGCGCGAGAAGACGTACTCTATCACGA
CGTCCTTCCATGAGTCTCGTCGGTCGATCTCCGCTTCGAAGAAACGTAGGAAGTTTGTAT
ACTGGTCAATCTGTGTAATTTGGGACTCGAAGTAGGAGTTGTCAGATAACCTTTCCACGA
TAGAAGGGACGAGAGGCGGCATGGCGCGCTGAGTAGGGAGGTCATCGTCGTAGGCGGTTT
GGAGTTGCTCTGGGGTTGCACCCAGCACTAGCCGAGTGAGAAGGTTATGGACCAGGTGGT
TGTGGCCGTTTAGATTCGGAAAAAGATGTGCAGCGTGTCGTGGTTCTTTTGTAGGAGGT
GATTTGTCAGAGTGAGAGTCTGGGAGGGGGAGTTTGGGCGTAGATGTTCTGGCCGAGTT
TGGTTGAGAGAATATTGATCGAAGAGGACATTTTTGACGCCGTATTCGTGCTTTCTTGTT
GACTTGGTATGGTAGATGGTTGGGTTTTGCTGACTGGTTTAATGTCCTGAGCCCAAAGAT
ATATACTGCACAGCTAGCTTCGGATAACGAGACCTCGAAGCCCGATGACCGAGCAGCCAT
ATTCACATATTGTCGACTGGACTGGTTCTCTATATCTAGCAAATGGCAAAGGTACGCCGA
GCGTGACTAGTACGAATGAGTGACTGAGGCCTTAACCTCGATCAGGGCTACGTTTTGCGG
TGTTGGGAATCCATAAAATTGACCCATCTAATAACCAAAACGTCCTCCTAGAGACCCAAT
ATTACATACCCCAGGCTACAATCCCAGGCCATTAGGAAGGCCCCGTTGTTGGCAGAAATC
GATGCAACCCCGGGAAGAAATGCCTGAGCAAGCCAACAATGATACATTTCGGAGTTCCAG
GCGGGAACCTCGCCTTGCCCCCCGTATTAACCACAGAGACGTTCCTCCCATCATACCTCC
CATCTGTATCATTTGCCGCCTCAAGCATGGCAGCCGCCAGATCCAGGTACGAGATGAACG
ACTCCTGCTCGTCAAAGTCGAGTTTGTGACCACGCTGAATGTCGACGCTCAAGCCGGCAG
GCTTGATGAAAATGCTTGTGACCCAGGACTCGTTCGCTCGCAGCATCTCCTCTGCCTTGA
TCAGGTCGGCGTAGACGTTACTCGCAGCTGTTTTCATAATCGGTAAGAACCACGAGGGCA
TTTTGCGGCTTAGGTGCGGATCTATCGTCGCGGAGGAGAGAAGGACCAGTTTCGGCACAA
CTGCATTCGGTTCCGCTGTACGAATCTGCTTGAGTGCCTCGAGAACCGTCTGCACCGAGT
CCTGACTCAGTCGGCAACCGGGAATATTGTCGTTTGAAGTGACGGTCAAGAAGACCGCAC
GTGTGTTGCGTATGCATGCGGTGATGAGGGATAAGTCGGTGATGGAGCCTTCAAAGATAG
TCACATTTTTCGTGTCGTTGAGTTCGGGCAAGAGGTTTAAGAGTTTGGGCTTGTTTCGAC
AGTAGGCGTTTATGTGCATTTCTGAAGATGGTGGCGAGAGCAGATTCTGGATCAGAGCCG
TGCCAGTATTGCCGGTTGCGCCCAGAACGGCGTAAGTGGCCAGAGGCATTTCGATTGATG
ATATTCAGAATTTAGTATTTCGTAACCAATACGGTGCCGTGAGGATTATGGTTGATGGTG
GTTGGGTGTTTATAAAGCACTCGTATAGAGCTATGGCAGTCGGGTACCGTAGCCTAAA
CCGTCGTTTTCAGACTTCAATGTCTCAAATATCTCAAGATACGAACTATACCGTGCTAGA
TGCTGGATATCAAGATCTGCAGTGCAACCTCAACCCCCGGCCCCGAAATCTCGGAGTTC
ATCGAGCGTATCGCAGTCGCAGACCCCGGGTTCCGGTTCGACGGAGTAGATATAATCAC
CGACAGCCCATACCCACCCGCATTATCATTTCCAAACAGACCAGACCGCACAAATGTCAT
TCGGAACACTCTACACCCATAACGTATGTTCTTACACCTCAGGGCCCAGAATTAGAATTG
GGGGTTTAGCTAACCTTGAATCTTGCAGCCAACGCCTCGCTCGACGACCCTCATCGCTCT
AGCAAAGCTCCACAACCTCGACGTCAAAATCATACACGCAGAAAAGAAGAATAAAGAGGC
```

Figure 5D (continued)

```
ATTTGAGGAGCTTTGCAGATATAATCCACTCGGGCAAGTCCCTACTTTTGTAGGCGCAGA
CGGGTTCGTGCTGAGTGAATGTATTCCATTGACTCTTTACTGTACTCAGCCCCGACACTC
CCTGGTTAATGAAAGAGGACTGAAAAGTCCTGCTGAGCAGTTGCATCCCAGAGTCAGGAC
CCGATAACAAAATCCCTCCTAGGCAATGACGAACGCTCCTCGCTCAGGATCCTCCAATGG
ATGTCTTTTGCAAACTCCGACCTCTTTCCAGCAGTCGGCGGCGTCTTCCTCCCACGCATT
GGGCAACGGCAAATAATCCAGCAAGATGACGGGGACTCACTGCGTGCGATGCTGCAGCGG
TGCAAGTACCTAGATGAGCATCTGAAGCGCAGCAGATATCTTGTGGGGAAAGTATAACG
ATTGCGGATTTTTTCGCCGCGAGTCTGCTCATGGGAGCGTTTGCGGCGTTTAGGAGATCC
ATGCAGGAGAGGTTTGGAGCACTGTGCAGCTGGTATGATGGGGTCCTTGAGATTGGCTGG
TTTAAGAAGGTTGCGGGAGGTGTCCCGGATTTGGGACTTGAGTTAGAGATTCCAGAGGAT
ATAAAATGGTAATGATTAGAATGTCTAATGGGACAACCCGAGTCGGCTAGTTGGAGCCAT
GTCTTGACGTCTTGAGTGATCTGATGTACGATTTCGGTGGCGTTAAGAATAGCATATTGA
GACGCCCTCAGCACACAATCCATCTATAGGTAGGGTTCTATCTACTGGTAGGCTCAGTCT
GCAAATAGGCCAGCATAGCCCCCTCCACATCCCACGAGCAATCTTATGCGTCCCATTAA
CCGGAAACCTTTCCAGTCCCAACTGGTGCAGATAAATTACTCCGTTCAACGCATTGCTCT
TCCCAAGTGCCCGCACAACATGTCTTCTGATCTGGGCTTCTTTCTTGCCGGTATATCGTG
CCAGGACAGCAAAGGGGCCGCCAGCATTTACCACACATGTCTGGTATGCTTGTTTAGATC
TCAGATCTGAGGCAAATGTGGTGGAGGTATGGGGGAAGAATAAAGAAAGAAAACATACCT
GAACAGAAGTATATTTCTCAAGGCAACTCTCAATCGGGGCAGGCATCACTTTCCCATTAA
TCATATCCTTCATCCGGCCAAGGATAAAAACAACGCCCTGCTTGTCCATCAAGCCCACAT
CACCTGTTTTGAACCATCTTCGCCCATCCTCGTCGTGAAACGACTGGGCTGAAACTCCAC
CCAGATACCCCGGGATAATACTTGGGCAGGAGACATGGAGCTCGCCCAGCTCTCCTCTTG
CCACTGTCGCGTTTGCGCCACGGATCCTGACAGCAGCGCCTCGTGCAACGGATCCAACAG
GACTCATCTCACCATAGAACGGAATATCTCTGGGCCTGTTGAAAGGCCAAACAAACGCCC
CTCCACCCTCCGTCATCCCGTGATTCACGACAACTCTCGCTTTCGGAAACAATCGCGTAC
ATATCTCAAGTGCGCCTCTTGTCACCGCATCGCCACCGATTTGAACTGTCCTGACAGAAT
CAGCTGCGCCATTTCTACCCTTCAACTCGTCTGCAACTGGATGAACCATCGCCGGCGTGA
GCACCACGAAACTAACCGCGTGCCTTTTTACCGCATGCACCAAATCGCCCGCATTGAAGC
CATTCCCCGTCATGACTACTGTCCCACCTTCCCTCCATGTCTGGAGTGTCTGTGCAATGG
CAATGCCCCGACACGGATGCGCTTGTTGCAGTGCCCGCGTGCAGTTCTCTGCGTTGACCA
GCCACGACTGGGATTGGAGAACGTAGCTCATTCCCGAAATATGCAACGGGCACCCTTTAG
GGACCCCGGATGTTCCTGACGTATAGAGGATGGAGTATGTACGGGCTGCGTTGGAAGAGT
CCCAGCGAGCAGAAGATAGAAGAGACTCGGTTTCAGAAGCTGAAAGAGCTGGTGTCAGAG
ATAGGGACAGAAGGGATCTCCAGGCTGAGTCTGGTTGACTTCCCGCAAGCTCGGATAGAG
TGATCTTGAGGATATCCGGGTCAAGCGGTAGATTCCGCAACGCGACATCGATCACATCCG
CGCCTTTTACGTCTTGCACAACAATAACCCTTGGATTGATAGTCTTTAGCATTCTGCGTA
ACTCATCATGCTGCTCAACGTTAAGCAGTTCCTCATCGAGACAGACAATCGTCACGCGGA
GAACAACCGCAGTCCAAAGCAGAAGACAGAACTCGGCGCCGTTGGGGATGAGCAAGAGCA
TTCTCGTGCTTGGCTGGGCATTTCTCGCCAGCAGCCCCGCCGCAATCCGTAACGCAGCGT
GGTGGAGTTGTGTATATGTCCAGGCGAGGCATGTCCCCGGTTCTCTCTCGACCGCATCAT
AGTTTGGCGCACCGCCATTTTCAGTCCCACTTCCTGTCTGAACAAGCGCAGAGAAATGAC
ACGGTTGTTGATGGGTACTCTGAATAGCAAAACCCTGTGGATTCTGATGGAGGCCACGCT
CAATGTGTGTAAAGACCGAAGGGTCAACGGGTAGGTGCCCACCATCGATTTCTGCTGGGA
GGAAAGGCCTGAAGCACGAGCGTGAAACCGACATTCTGTTTGATAGGTGCTTGAATACTC
CACTGTAGACTCTGGTCACTGCTTTGACTGTTTCAAAATACGAGCCGTGGTGACTGGACA
TGCAGCGTCAGCGTCAGCGTCGTGCTATCCGAGCTCGGGTTTCAGTGGAACTGTCGGGGT
CCGGTGTGCATCTGGAACTCAGTAATCAGATAAATAAAGAAGACGACCAAGAAAAACAAA
AGTAATCAAGTAATAGTTGTCATATCAACAAACAGATACGGTTGATGTCCCGAAGCGACT
CTAGGTAACTAACTGCTCCCTGACCGTAAGCCTTAGGACAGAAACCATTACCCAGACCAA
AGAAACCCTGTTATTTGAACGAATAGCCAGAAAATGATAAAAAATTGTCAAACACAGAT
TCCCACCCCCAGCACTGCCGCCATCAGTGGAAATAAACTCCTGACCAGGTGCATCCATTT
CCAACGCACCAGGAGCTCCCTGACCCCTTCCAAAGTAGCCATCTCAACACCAATTCCGAC
ACTAACATTACCAAGGCCATGACTCTGACTTGAATTCGCACCTTTCAAGCCACTTCGGTT
GGCACCCTGCTCGAAAAATTGGCTGTGGTCCCGATTCCCAGCCTCCAGCCCAAAGAGCAT
CCCGTTCGTGGAACTCATCACAATCCACGTGAATGGAACCATGACGATCGTCAGAAACCC
GACAAGCAGCTTTGCGCCACGGCTGCTCCCTTGCCCCCTGATAAGCAGCGATGTAGAA
GTATAGAATAGCCGTGGCGATCGAGATCGTAGGCAAGGAAATGTGCCCGTAGTGGTAGGT
GCGGACCCATTGGTGCAGGAGTTGGGGTGGATGGGTAGATGTCTCGAGGAGAACAGGGAC
CGTGATTGTGCTGAGAGTTATCATTGCTCCTTTCATTCGAGAATGAGGGTATGAGTTATC
TTTCCGCAAAGGGGGTTGGAAAGGTGAAGGGAGATACCAGAGAGAAAAGAGCCCGTGACG
```

Figure 5D (continued)

```
ATGGCGGTGTTCTTGAGGGTTGTGAGGGAGGCCATGATTAGGCTGTACTTAATGTTGGCA
GAAAGATTACTGGAAGCGCTGATATGCAGAATAAAGCTGTTTGTTTGACTGAACCCTGCT
AGGCTGTGAGCAATTTTAAATCTACTCTTCCCTGTTGAGGCTGACCGGCAGCTCGGTGAT
GGTTGATCTCGCTGTCCGATGGAACGCACTGCGTTGTTGGAATGAACCCCGGACTGGAAG
TAACACACTTGCATTGAATATCGAATGTGGCATATGGACTCAGTATACCATGCTGCATAG
CGAGTAGCTACCTACTTCTTCGGGCCTGGAAATCCCTCAAACCCTTCTGTGACAACGCCC
CGATCAATAAACTGCGTGATCCAGCCGATCGTCATCCTGCATGCGTTAGTGATTAGCCCT
CATTTCCTTTATCTTGATTATCATTCCATCCAGCTGATTGACCTTCGCCAGAAGGGATGG
GACGGGACGGCATAGGATTAAGGACGTACTTGCTTCTCTTCGTATCCGCGAAATTCTCAT
GGTCCCCTACAAGATGTTCCTTATACCAGGGGTCATCCTTGATTTTCTTGTAGTCCTCGA
AGTTGCGAAATACCACTTGGCTAAAGCAGTCGTAGTCGGCAATATTCGCCATTTGCGGGT
CCATGATCTCGTACATCAGTTCGCGCGTTTCGGTGGGGTTGTGGATCTTGCTTCTGTCAG
GACATTTCTGACAGAGTACGGTATATGTCTTCAAGGAAAGATATGGTTGCGGTGGTGGAT
GCACGTACGACAGTCCATCTCAAAATACCATACTTGATCATCAGATCCTTTGTCAACGGT
GCAGAGTGCTCAATCATGTGTTTGCGGTAAGCTTCCTCACTCATGCCTTGTTTGCGGTAG
CCGAGGATAGTGAGGCAGAGGAGACGATCCTCGGAGGTGGTGGAGTTTGTTGCTGGGGGA
TTGGGAGTGGACATTTTCTTTGAATTGATGCGGGTGAATTCTGAGCTGGTCGATGTGGTT
GATGAGTGAGGATGGGCGAGTGGAGGCTCCCTATATAATGCAAAATGACCCGAGACGAGA
TCCGGACAGCGGCGGGAAATTAAGCACAGATCGGGTCATTAAGCTGTTATCTACGACGAT
AGATCACATCGAGGCTTACTTCGTCGCGTCAAGGATAGTGAAATATGCATAGACCAGTGT
TTTCATCTGTACCTATATACCATAACTCTAACAACCGAAAGCAACAGCGCAGCCCTTTCA
CTACCGGTTAACATACTGCCTAATTATAGTACTCTAATAGCCAGCTTCGCAGATCGCCGA
TGGTAGGATACTCCAGGAACAAACTACCAGTCACCGTGACCCCAGCTCCTCCCGAAACT
TCTCTGCTATCACCAGGCTCATCAAGCTGTCAACCCCGAGGTTGGCAAACGAGGCATCGT
CCGTGAGATCCGAAAGCTCCAGCGCAGCTTCTTTGGCAATAAGCACAAGAGCTTTGGCTG
CTACGCTGTCGCTCTCACCAGCGGCGGCTGGTGCAGCTGCAGGTGTAGGGCCAGGAGCAG
GGGCCGGAGCAGGGGCTGGAGTAACTGACGCCGGTGCTGCAGGAGACTGGGCAACTGGTG
CAGCTGCAGTAGCCGGGGTAGCGACTGGAACAGGCTCGGGTTTGGTTCTGGGGGCTGGCG
TACTCGAAGCGGCGGCATGCGAAATGGCTCCTGCCTCTTCCGGTGCCGTGAAGAACCTAT
TAAGCAGGATGCGTGGATACCGCCGGAACTGGATTCCACCACACATCCCAATGATCGCCC
CGTCTTGCATAATGTATACATCGCCGAGGTAAACAGTAGGATCCTCTTCGGTCTGAATCA
TCTTGACGTATGACCGGTATTTGGCACCTGCTACAAGCGGTTTGGCGAATCGCAGAGACT
TCCATCCCGGAGTCACGCAGTAGTTGGCCTTGGTATCAATAGCGTCGGACACATTCATCA
CGAACCCAGCGAGATGCGCGACGCTGTCGATAAAGTAAGGCGGAATAGTCCAGGTGCCAC
TCTTCTCCGTGGACAGCGTGATATCGGCGAATGCTTCCAGCTCATGCAGAACCACAGACT
GCATACCGCGGTACTTCTGCGCGTAGTCCACGAGGTTGTTGGCAAAGAGCAGGTAAGCCA
TATTGCGGGTAAAGCGGTTGGCAATGCCATCTTCCGCAAGTCGCTCCAAAGCCTCAATCC
TACCCTGAACCAGATGCGTGCTTGGTATCCAAGACTTGAGCCACAGAGCCGCATCGTCGT
ATAATATCGAGGCACTTGCAAAAGGCTCATCCGCTGTGTTGTCATTGAGGACGTTCTGCC
AGATGAGCTCAGCAACCCCCGAATTGATATCTGTGGTTGAAATGGTGACTCGGATATACT
GCGGCTTTTTGGTGTTTTTCTGCGCAACAAGTCCCCTCAACACTACAAGATTGGCCATGT
TCATATCAGGCGCCTTGCCACCTTTGACCAGGTTCTTGTACAGATACCCTCCCAGAGTAA
AACCAATGTCGCCGTGTATAGACTATAAAATGTCAGATTATAATGGGGCGCTGAGTGGA
ATACTTACCGAAGTTACCACACCGCATCCGTTCATCTTATGTCCATGTGCAGCATCCAAA
AAATCTGGCTGCATCATATCGGACTGCATCACCACTTTACCCGCCGAGCCGTTGAAGCTC
TCCTCGATAATCTGCTGAACAGTGGACGTCCTCAGCCCGGATGGTACGGAGGCCAATTGC
CCTGTTTGCTGTGCCTTGAGTGACTTTTCGGCATCGTAAAAGGTGTTCCCTTTTGTCAAT
GCCCAGTCGCCGTTGTACTGGATCCAGTACGTCTTGTCGTTCCAGGCGTATGTAGGAAGG
TCTAACAGCCTCAGCCCTTTTTCGAACGGGCGTTGGTATTCGTTCCATTCGATTGGCACA
CCAGCACAGTGCAAGGCAGTAAGACTATTACATAAAGTCACCCAGTTGTCCTCACCTCTC
TTCATTGAGGCGACCGTCTCATTGACAGCTGGGAGAGTGGCATTCACAAAGCCCATGCAA
ACGGGATGCGGCCCAATTTCCACCCAAACAGTCTCTTCATCAACCGTCGAGAAAGTCTGT
GCCATCTCAAGTGCGGATAAGAAGTTTACTGTCTCTCGTGTGGCACGGCGCATGTATTTA
GCGGTAATGGTCTTGTCATCAAAAATGACTTTGCCCAACAGGGGAGATATCACGGGCATA
TTAGGCGCACGAAACAATACTCCATCCTTTGCAGCTTCTTCAAAGTCATCAAGGATAGCC
TCTGTTTGTGAGGAGTGAAATGCAAATGCGACGTCAAGGCTGGTGCATCGATAGCCTACT
GATTGTAGGATTTCAGACACAACCTCAACCTGCGCCTGCCTCGAGTACGGTTTCT
TTTGGTCCGTTGATGCATGCAACTTCATAGTTCGTGCCCTCTAAGGCTTTCTCGATATCA
GCCAAAGGAGCACGCACCGCCAGCATTTTGTGGCTGCCGATCTGACACTTTTCCTCCAGG
AGCTGCGCACGACGGCCAACCAAGAAAAGAGCATCGCTAGCGGAAAGCACGCCCGCCACA
```

Figure 5D (continued)

```
TGGAAAGCCGCATATTCGCCAAGACTATGACCGACAACAGCGTTGGGCTTGACCCCAAGT
GAAATCCAATACTTGGCAAGAGCAATCTCCACTGACACAAGTGCTAGCTGCGTGACAACC
GGCGAGTGAGCGTAGTCTTTCTCGTGGCTGCCATCCACTGCCGGAATAAAGCTAGGAAAA
CCTTGCCCTTGTGCCAAAGCGTCTAGATGAAGAAGTTGAGATCGAAAGTATGGAGAGTGA
TGGAACAACTCTAAGTTCATTGACTTGTACGATGCACCTTGACCTGTAAAGGCGAAGGCA
ACCTGGGGCGGCCCGGTGGCGGGAATGGGCTTGTGCGCTTCAACTTTATCTATGTAAGAC
AGAAGCTTCTTCTTCACTTGAGCTATATCAGTAGCAGCAACTGAAGCTCGGTGGTTGTGG
TGGTAACGTCGGGCAGTCGTTGTGTAAGACAGGCTAGCCAAGGAGGTATCCGGATTTGCG
TCGAGATAGGCGACAAGGCGCTCAAGGTTTTTCTTGAAAGAGATTTTGCTCTTTGCCGAG
ACATTGACAACATGAGCTGTCCGCGGGTCAACATAGTCTGTCTCCCTGAGCGGTGGCTCT
TCGAGGCAAACGGTGGTATTTCCACCAGCTGCACTAAAGTTATTCACTACAGCATAGCGC
TTTTTACCTTTCACTCGCGGCCATGGCACCTTCTGGTACGGAATGTGCAAGTTCCGCTTG
TCCAAGTCTTTTGGGAATAAAGGGTTGAGGCTGTTTTAATGCCAACATGCGGCGGGATG
GCGTTTTTTGGTACATTAGCAAGACCTTGAGGAGGGCAGTCACTCCAGCAACGGCCTCT
CCATGTCCAACATTGGCCTTCACAGCACCGATATGGAGTGGTTGTTGGGCGCTTCGTCGC
TTAGTGATCGGAGCGAAAATGTCAGTTATTGAAGTTATTTCAACTGAATCACCGGCCTGG
GTACCAGTGCCGTGCATTTCGACAAGCTGACATCCAGCGGGTCAATACCAGCGGAGCTC
ATGACTTGCCGGTACAAATAAGCCTGAGCACCAGCGTGCGGATGAGTGATTGAAATAGCT
TCAGCCGAATGATTCGTTGCTGCAGCACGAATGATCCCGATGATATTGTCGTTGTCTGCC
TCAGCATCTTCAAGGCGCTTCATCACGATTGAGCCTATACCGTCTGCGCGGCAATATCCA
TCGGCGTTAACATCCCATGTCTTACAGGCCCCCGGAGTCTTCGAAAGGAAGTGGCCATGG
CTGAGACCAGCGAAAGCGTCGGAATTTGTGAGAACATTCATTCCACCGGCGACGACCATG
TCAGTATCACCGTTCCACAAAGAGGTACAAGCAGCCTAACAACGTTAGTTTTTCTATAAT
TCAAGTGAAACCTCCATACCTGAATTGTGGCCAAACTTGACGAGCATGCAGTGTCGCAGC
TGAAACTGGGACCGGAAAATTTGAAAAAGTAGTTTATGCGCCCCGGTCCAAAGGCACGAC
AACCGCCAGGGATGAAGTAAGTGCTAATTTCCTGAGCTGTATTGACCTCACGATAATCAT
CGCTAGCTTGACCATAGAATGTCCCAATGCGATGAAGGTTAGTGGCTGGTGTGCGATTAG
CTACGTAACCCGCCCTCTCTAGTGCCTCATATGCGGTGACAATCGCAAGACGCTGCATTG
GATCGGTTTGCTGTGCTTCCCTGGGCGACATATTGAAGAACGGTGCATCAAACAAGCCAG
GCTCATCAATAAAGCATCCGTACGGTGTATGGCTCGTGTTGACCCTTTTCCCTTTCGGAT
CATAATGAGTCTCGACGTCAAATCTATCAGCAGGAATTTTTCTAGCTACGTCAAGCCCTT
GCTCGAGCAGTTCCCAAAACTTTTCCGTATCAGTTGCTCCGCCAGGCATGCGGCATGACA
TGCCAATGATCGCAATTTTTGACTGTGCAGTTCCTCGCGGGATTTCCATATCAGATTTCT
GAAGAATCCACGGAATCAACTCCTCGGTTGACGTTTCGAATCCTTGCAGTTTAGAGCCAA
GAGCAGTCCGCAGATCGTTGATTGGCACCGAAATGCGGAAGACCAAAACATCACAGCTAG
TTGCTGATGTTGCGTATGCCTGGTCAACAACGCCTTGGACGACATTATCCCATAGGATGG
GCTGTGTGAGAAGTTCCAAGACTAGCTGCTCAAACAATCCTTTGGCCGTAGAAGCCGTAA
ATGGTCGGCCAGTTGAAGTCTGATAGACAGGAATTGCCGGCGAGTAAAGTGCATTTATGG
AGTCCATAGATCTCGTGGATATGATCTCACGTGCATGTTGTTCGTTGTAGAGGTGTTTGG
CATGGCACAGACCGCTGTACACAGGAAGGCTCACTACCCTGTGTCGCCTGAAGAATTCGG
ATAGGCGCAAAACACGCCTGATCCGTGACGGTGGACCACTAATTGTGACCGACCCCTCGT
TCCAGGCACTGATAAATATCTTGCTAGGTTGGGGTGTTTTCTATCAAGATGTTGGTAAGC
TTTAACGCGTTACCACGGTATGGCAGCTTACCTCTCTTGCGTGGATAGCGTCCAACTCAG
CTTGGACTTCTTCAACCTTGGCGCCGGGAACAACAGAAGCCCAGGTGTCTGGGGAGCCGG
ACGTATCGCGAGGCTCGAGGTTCTGCGAGATCTCATCCACTAACGTTCCGAGACGGAAAG
AAACTCGCACTACCTCGGCACCAATAACTGGGACGTCGGCCAATGCAGAGCATAAAGCAA
CAGCAGCGGTTGACAAAAGCCCAAGACCCAGGCCAGCCAGGTACGTGGACACGGCATGTA
GGTCAAATCGTTCGGAAGCATTCTCATAGTAACTACAACAGTCAGCAGCCTCTTTGAAGT
AAAGTCGTGGTACATGCCCTATCAGAGTCGCTATCTCTAGCACGCAGAGAAGAACACCCT
CCAAGGATCCGCCAAGAGGACCCTTCCGAAGTTCGGGGTAGTCGGCAAGGTTCAAGACTG
TTTCAAAGGCAGGAACAAGAGCCTTTACAGCCGTCGGTAACTGCCGCACTTCTTCACGGA
CAGCGAGTGTAGCTTCATGGATAAACCTAGCGAGGAGGGGATATCGTCTATCTTTGCTGT
GGTTGTACAGACGGCGGAAGAGGCCTTGGAGATCATCCTTCGGGAGTTCGTTGCTAAAGT
AAAGGAGCTTCATCTTGGAGTACTCCGGCAGTGAGCCTGATTGAGGAGTATATACGGGCA
TTCTGAGGCGATGGAACCACCAAGAGAAGGTGGAAAACAACAAAAAAAAAAAAGACAGGA
AAATGCAGACTCGGCCTGAGATAATAAGGAGAGCAGTCTGCAAAATTGGAATCAAGTGCA
AGACAGATTTTTGTTGCACCAGGTCAGCTTTATTGTGATCAATAAAGACTGCTATCAGGC
TGCCAAGTGACAAGCGTCAGATCGGCCAATTTGACCGGGGCGGCATTCGGCGATGAGTAC
TCTGGACTCGTACTCGTACTCGGAATACTAGATCCCCGGTCGGAGTCCAGTCGATTTGCG
GCTGACGGGGCTATTATTAGCAATGCCGATAGTATGGAAGTGTTGTAATGTTTATTTCGC
```

Figure 5D (continued)

```
CCAGTTCAGCTTGATATGTCCCAGATGATTCCAGCTTTTTTCCACTGCTCTCAATAAGGT
GCAAAAGCATCGGCTAGACTTGGGGTTGTGCATTTTCTAACCAGACACAATGGCTCAGCC
GCAGCAGCATAAAGGCGGGTACAAACAAATCAACAAAGCTCTCAACATATGTGCGTTTGA
GGATTACCTTTCCGCCCAGCTAAAGCACTTGCCGCAACTTGCGGATGTAGAGCAGCTCAG
TCCTCGAGTTATCCGTGTCCTGGGGCAGAACGCTGGGAAGGTAAATGCCCCGAATCGGCC
TCTTTTCTAGCTAACGAATTCTGCGCAGTTCACTTTGCAGGGGACAAACACATATATTGT
CGGCACCGGACCGCAAAGACTCATCATCGATACCGGCCAGGGAATTCCGGAATGGGCAGA
CATCCTCGATGCTACCCTCAAAGAACGCTCGATCTCCTTGTCGCACGTGTTCCTCTCGCA
CTGGCATGGTGATCATACCGGAGGAGTTCCGGATCTCCTTCGTCTTTACCCTAATCTTGC
CGGCGCCATATACAAGAACTCCCCTGGCAGCGACCAACAGCCAATTGACGACGGCCAAGT
CTTTCGTGTCGAGGGCGCTACTATTCGAGCAGTGCATGGCCCAGGGCACTCGCATGACCA
TATGTGCTTCATCCTCGAGGAGGAAAATGCCATGTTCACCGGAGACAACGTTCTTGGCCA
CGGCACCAGTGCAGTTGAAGAGCTAGGTGTTTATATGGAGACTCTTCGAAAGCTGAATTC
ACACCATTGTGCGGTTGGCTACCCCGCCCATGGCGACGTGATCACCAACCTTCCCGCGAA
GATTGCTGGTGAACTAGCGCAGAAAATGAGACGAGAGAAGCAGGTCCTTTTGACACTGGA
CAGGATCAACAAGGAGTCCAGACGCACGGGACAAGGTAAGAAGGCTAGCTGTTACGGTTA
AAGAGCTAGTGGTGCTGGTGCATGGAGATGGAATCGACGAGGAGGTTCGCAAGATGGCAT
TGGAGCCGTTTATCGACGAAGTGTTACGCAAACTGGCAGAGGATGGCAAGGTAGCATTCG
AAATGCGAGGAGGTGTAAAACGATGGTTTGGAGTAGGAGTGCTTTAGTTAAGCGAGGCAT
TGGATGGAGTGAGGTTGGGATGCCAAGCCTGAAGCTTTCACTTTCTTTCATACTCCACCT
TCGCTCTCCAACAACACATTAAACGGATTTCTACGATTGCCGACAACCTGTTCACTAGAT
TTATCAAACGATTTTGCTGCTGCCTAGATTGTCACTCTAAGATTATCAACTAAACGCAGA
TTACAGTCTACTTCAGTCCTCTGTTGACGCGCGTCTTTGTCCTTGGCGTGGATTCATCGA
CGTACGGTAATACACATCTAACCGTCAACTGCTCGCAGTCTCGACTCTACTATTCACCAT
ATACACTGTATTGATGACCAAGCTGATCGGTTCGTGTCAACAGATAGACCGTGAGCGTCC
AATTGCGCGTTGTAGCCGAAGTAGATAAGACGATGGCTAGGCCGTCTCTACTTCAGATAT
GCGCCGTTGACAGGGGAACTGCTTTCTGCGACACGAGGCAACAGACAAATTCCATAAACC
CATTCTTGACGGGCTATACCACCCCGAACTCTGCCAAAGTGACGAGTGACGACAAAATAA
GGTCGAATTTAGCATGCCCGCTAAGCTGGACTAAGACCGGTTGCGAATAGCGTGCCGATA
GTTGCGGGTGGATCTGCAGTGCAGTACTAGCCGATTGGGTTATACTATGGATAGTTTCCG
ATCAGCTCAACGGCACTGAGCAAGCCACGCGAGATACCTTCCGACCCTCTCTTTTGCGGA
TTCCAAACATTCCCGTTGGCTTTTTGAAAGTTTCCTATCCGGTTTCCCGTTGATGAAGCG
GTCATCTTCGAATCGCCTTTTGCGATGACAACTGCTAATGACCGGACAGCGGCGGTGATG
TCGGTCACCGGGAACGACGTGGGGCCGGTTAACCTGGGTCCGAAAGTCTCCACATCTAT
TCCGTTACCCGTAAGCGTACATCTGTACTCGTCTCCAAGTAGGTACGAGTAGGGCGCCT
GGCTTGGTTAATGCTTGATTTATAGTTTCGTTGAGATGGAGTTATCGGTCGAATGGGATT
AACTGCGATGAGCAAAGTCCTTCTCCTCCGTTAAATCCGAGACCTGACTCCGGCAAATGC
ATGATAAAATCGGTTGTTGCTAGCACTATAGTGCATATGAATGGATTGCGGCTCCCAGGC
CACTCTGGCTGATCACCATCACTGTCGGGGACAGCAAGACTTGACCCGCCCGAAACAAAA
GGATCATGAGCATTGCCAGGGGCTGTTTCCGGATCCCACTCTGGGCATCAGCTCAGGCC
CCGGATGGAGTTTAGAGACTCCAATGGTATCCAACTGTAAGCTGACATCCAGCAGCTGGC
CTGGTGCTATCAAAGCCAATGAACCAAGCGGTGGCCATGCGAGCATGGAGTCGAATCCTT
CCTGCAGATGCTCTCTTACTTTAAGCCTGGGCCCCCTCATTTTCCCACGCTGTAATCCCC
CGATTGATATCGCCTCACTCCCACTATGACATCTTCAGAGGGTCCAGGTATCCCCGCTAT
CAAAACTCCGCCAGTCAAGCTGCGAGGAAGCTGTCACGCATGTGCCCTGTCCAAATTGAA
GTGCAGTCAAGATAAACCTACTTGCTCACGATGCGTCAAAAGAGGTACAGCATGTCAGTA
TCTCGCCAGCAAGCGCGCAGGTCGCAAACAAGGCAGTAAAACAGGCAGCTTCAAGTCATT
CTACAATATGAAGACAGACTATTCCACGTCTATCAACAAAGATGATGATCGGAGGGAGCT
CATGGAGGTGTCGACAGAGCTCATGCAATACGCTCTTCAGCAGGACCGAAGCCTCGAAGT
ATACCGAAGAAATCAATATCACCAGCGCACACCAAGCTATCCAGAGAGTATACCAAGTCT
TCTCTCATCAACCGGCCCCGGAACCTCAGCTACAAGCCCTCTTACCTTGGGGCCCCCTGA
CTACGACGGTTATCTTGCTTCGCCTATATCTCTATCGCTTCTCGATGTGCCTGACATGGA
TTACTTCCTGGAGCTGATATGAGCGCGAATGTCATGGATGGTTTTCCTGATCCTCCGTC
ATTCTTCCCATCTGGAGAACCGATACCAACGCTCAAGAGAATATCTTGAAGACCAGTTT
CGCGGATTCTCCCGTTCCGGCAAATTCGCCTTCAGTTCCTCCTACACCAGATGTAACCAG
TGTTGGGACACCACGGCAATGTTTCTGTTTCCCACGTGCACTGACACTGCTGCGCGAACT
CTTTCCAAACCCTTCACTATCATGCGTGACTCCCTCAAGTGAAAGTGGCAGTGCAAGTCC
TCCTACAGTTCAACAAGTCATCACTAAAAATGAGCAGACTTTACGAGATATTACTGAGAT
CATAGAGTGCTCCTGCTCGGAAGACGGCTACACCATCACAATCATAACTCTTGCTGCCTT
CAAAGTACTAGCCTGGTATAGCGCCGTAGCGCATATCTCCCTATATCTGAAGACAGCCA
AGCATTAGAAGAGATCGACAGGACACCGGCTGTTGTCAGGGGCTACAATATCGATGGTGA
```

Figure 5D (continued)

```
AGATCAAGGCCGCATGGCCGCACAGCTAGTTCTCAGCGAACTGCATCGCGTTCAACGATT
AGTGGGCAATCTCTATCAGCGACTGAAAGACCAAGTCTCAGGCGGGAAGCCTGCTAGGTT
GAGTACCACTGGGGTCAATGACAGCAATCATTACTCTCTCCCTTTTCATCTGCTGGAAAG
GCTGGCGGTTGATCTCGGAGCTCAACTTCGGAGCCTGTCAAGTGAGATTGTCGACCGATT
GCGGAGGGGTTGATTGTCAAACATTATCGTACCGGAATCCATATACCCTGTTCCATTGCG
TTTCGTGCGCGCGTTGTATTTGCAACTTAGTTGTTACAATAAGACCTAGCATATGAGTGG
TCGGAGTCTTTTTCCCGTGCTTATCAGTGCCGTAATAGTATCCATATTATGACCAGCGTA
TAGAGGGGTAATTTGGATTAAGGCTATTAAGTTCCCAATTGGACTGGGCAGTCCCGTTCA
AGAACTAAATTTATATCCCCGAGCATATCAGCTCTCCTAGTTGGAATCCAAATGTGTTAT
GTCAGCGTCTGTGACTTTCAATGGCTCTATCCGCTGCGATCTTCTAGTCTAGATATTAAC
TAGTTGTACTAGAAAGTATCGAGCACAATAGCCAAGCTTCAGTGACAGTTTCTATCATCT
AGTGCTCCCTCAATCAACACAGGTAGCCCTAGACCACCGGCTCGGTGCTTCAATGACCCT
ACCCAACGCACTACCTACTCGGCCCAGGTCCCCAAACACCACCAGCACTGAGAGTCACAA
TGACCCATTTCCCCGTCAACATCGCCAGTGACAAGCAGGAATTTGATCCAGAGCGCTGGG
CAAAGACGCCTACTACCGAAAGCAGTGTTAACGGCGAGAATGGCACTGCTCCTACCTCTG
GTCTTCCATCTCGGCACCCCTCGACCGGAATCTCCGTCCTCATTGTCGGTGCTGGAATGG
GTGGACTGATGACGGCGTTAGAATGCTGGAGAAAGGGCCATGATGTTGCGGGAATTCTAG
AACGGAGTGAGGGACCTGTGTATTCAGGTATTTTGTTGATACGTCTCGTGTATTCCCCCA
GAGCATGAGAAACCGAGTAGTTAACTCTATACTTTCTCGAGATAGGAGATATCATTGTCA
TGCAGCCTTCTGCCGTATCTATAATCCGGCACTGGCCCGACATGCTCCATGATATGAAAG
CGGAGCAAGTCCACGCCGTCGTTAGCTACGAAACTCATGATGGACGGCACATTTACGGCC
CAACCGTCCCTCGTTCAATGACCCCGAGCACCTGGAAACACGCAAAGGTCCATTTGTTG
CCCCCGCTCAGGTTCGCCGGAAATTCTACCGCATGCTCCTGCGCCAGGTCGCAAGGTGCG
GGCTCCGCGTTGAATATGGAAAGACGGTGAAGAGCTATTTTGAAGATGAAAAGGATGGCA
AGGGCGGCGTTATAATCGCAACAACAGGAGAAGCAGAGGTCAGAGTGGCTGATATCGTCG
TTGCAGCGGACGGCCTCAAATCTCCTTCAGAGATATTGATAGCCGGTCAGCATGTTCCTC
CAAGATCAAGCGGGCTGAGTATCTATCGCACTGCATTTCCGAAAGATTTAGCAATGCAGA
ATGAGCTCGTACGGAAGCGATGGAGCGATAGTCCACCCATCTGGGAATACTGGCTTGGAC
CGGGCATGTATCTTGGTGTCTTCGTCGGCGACGATATTATCTCCTTCGGATTCACGCCCC
GTGATGACATCGTTGAAGGCACAGCCACTGAATCATGGGAGCCTGATACAGATCCCGAGA
CTGTGGCGCAGGCTATGCTCTCCGGTGCAGGAGACTGGGATCCCGCTGTGCTAGCGCTCA
TTCGAAGCGCGCCGAAAGGCGCAATTGTTCATTGGCCTCTCCTCTGGCGGGACCTTCGCC
GCGAGTGGACCTCACCTGCCGGACGGGTAGTGCAAGTCGGCGACAGCGCGCACAGCTTCA
TTCCTACCTCAGGAAACGGAGGCTCGCAGGCCTTGGAAGACGCAATCACGCTTGCAACAT
GCCTCCAATTAGCCGGAAGCTCGCAGCGTGCATATCTTGGGACCAAGATCTACAATCTTC
TCCGGTATGAGCGGGTCTCTTGTGCACAAAAAATGTCGTTCGTGAATTCTCAGCTGAAGA
CGGGCACGGACTGGGATGCGATCTGGAAGGATCCGGCGAAGATCAGGACAAGGTTTCCTA
AGTGGATCTTTCAGCATGATCCGGAGGCGTATGCATATGAAAAGTTCGGCGAGGCGTTTG
CGCATTTACTTGATGGGAGAGAGTTTGTGAATACGAACTATCCTCCGGGCCATGAGTTTA
GGGCTTGGACGGTGGAGGAGGTTTGGAGGAATATTGCAGATGGGAAGAGAGTGGAGGATT
TGTTGGATGGTGATTGGTCTTAGTTACCTTTTCTCCAAAGATTTAGAATATATATTGATT
TGGATATCATCAGTCGCAATGTGATTGAGCTTAAAGCTGGCGCTCAAGGCTAGATTCATA
AATGGTTTGATATTCGTATTTCCCAGAAAATCTAAGTAGGGCGACCTAGCTAGCAGTTCA
TCCTTGATTAAGAGACAATGATTCTGATCTACTGATATCAAAGTCATTCTTCTCAACCAT
GGATACTTAACGAGTGCTACTCAGCAATAATGGTAACTCTTATATTCTCTTGGTCGGGCC
AAATTGATCACATATTCACAGCTCGTGTTGCAACACGCTCATGCCCATCCTCAAGGCAGA
AGTAATAGTATTATATGCAGGTAAAACATCGCTGTCCGTACTCGCATAATGCATCTAAGT
CACCGAAACCTCTCTCTTATCCCCTGCGCCCAAGTTACATATCCCGATCGAGACTCGGGC
ACCGTACCCTTGCACACCATGTGCTTACGAACTTAGGGCTCTAATCATCCGTTTCTAAGA
AACCTGAGCGCAAGATACATAAGGTAGGTAGGAAAGCACCAATGTCTCCAGCAATCCAAC
GTCTCTCCCTCGTGTCCTCCCACCTCAATTCCAACGTCAGCGCGCTCCCAAAAATGACCG
CAACCACGCACGCCCATACCGCCTCGAAGGCAAAGTTGCCCTTGTGACTGGCTCCGGCC
GGGGAATCGGCGCAGCAATGGCCCTTGAACTAGGACGACTCGGTGCAAAGGTCGTGGTGA
ATTACGCTAACTCCCGTGAACCCGCTGAGAAATTAGTCCAGGAGATTAAAGAGCTGGGTA
CCGATGCGATCGCGCTGCAAGCCAACATCCGCAACGTGAGCGAGATTGTGAGGGTCATGG
ATGATGCAGTGGCGCATTTTGGGGGCCTGGATATTGTTTGTAGTAATGCGGGGGTTGTTA
GTTTTGGGCATCTGGGCGAGGTCACAGAGGTATGAACCCGCTTTTCATTCGACTCCTGGT
TGAGGTATTGACGATTTTTCATAGGAGGAATTCGACCGGGTCTTCAGTCTGAACACCCGC
GCCCAGTTCTTCGTTGCGCGTGAAGCTTACCGCCACCTCAACACCCACGGCCGCATAATC
CTCATGTCCTCCAACACTGCTAAAGAGTTCAGCGTCCCCCGGCACTCCGTGTACTCTGGC
TCCAAGGGCGCAATTGAGTCCTTTGTGCGTGTGATGGCTAAAGACTGCGGCGACAAGCAG
```

Figure 5D (continued)

```
ATTACCGTCAATGCTGTCGCCCCGGGGGAACGGTGACGGACATGTTTTACGACGTGGCG
CAGCATTATATTCCAAACGGCGAAAAACACAGCGCGGAAGAGCTGCAAAAAATGGCGGCA
ACGGTATCGCCGTTGAAGCGGAATGGGTTTCCAGTGGATATTGCAAAGGTTGTCGGTTTT
CTGGCGAGTAGAGAAGCGGAGTGGGTGAACGGAAGATCATTACCGTCGACGGAGGCGCT
GCTTAGTTCTGCTAGATTTAGTAGCTAAGTCGTAGCCAGAACAATAAAATGGCACATTGC
GTTGATGATCTAGGCTGCATTGAAATGGGTTCCACTCAAATATAGGTACCGGACACCGAA
GGTCGGGGACCAAGTAAAACCCGCCTTCATACGGTACTTAGCAAGTCACCGACCTGAAGT
ACCCTTGCATGGTCTTCCCGTCCTAGACACTGTCTTGTGAGTTGGGATCGACTTAAAATA
TTGCTTTTGAGTCTACCTTTTCTCCGTTTGTCCCATCTTGTAGAGAAACAGGGACGGCAC
AATGACGCTGCAGCCAACATTTGAAGGTAGGACCCCTGAACAGTGTTTGAATGTGCATAC
TGATAGCCATCCAGACATTACGGGCTGTCAAGCTGCCTGTTCGAATGGGCAGAGAGCTA
CGACAGCAAAGACTGGATCGCTTAAAACAATGCATCGCCCCTTTCCTTCGCGTCAGCTT
CCCAGTCTCGTCCTATATAATCAGTGCTGACGGTACCAGATCGATTACAGAGCCTTCTTG
GACAAGCTCTGGGAGAAGATGCCGGCCGAAGAATTCGTGGCTATGGTCTCTCATCCCCAC
TTCTTGGGTAACCCACTCCTCAAAACGCAGCACTTTGTGGGAACAATGAAATGGGAGAAG
GTCGACGACTCGAAAATAGTTGGGTATCATCAGATGAGAGTCGCCCATCAGAAACACCTT
GATTCTCAGATGAAAGAAGTCGTTGCAAAAGGTCACGGTCATGGCTCAGCGACGGTGACG
TACCGCAAGATCAATGGCGAGTGGAAGTTTGCCGGAATTGAACCGAATATACGATGGACT
GAGTTTGGTGGAGAGGGGATCTTTGGACCCCTGAGAAGGAAGAGAACGGAGTCGCTGCA
GACGACCAAGTGATGAACTCGAATGGTTCGAGTGAGGTAGAGGAGAGGAATGGTCATGTG
GTGAACAAAGCGGTTGAGGTCAGGTCCGTCTGATCATGTGTTAGACGGCTGGTATATCCA
TAAACTATATAATATCGCCTACAACCTATCGGGTAATTAGTTCCATATATCTTGGTACTG
AGGAAAGGTAGTTTCTGCGTCGGAATCGCCTCTTGCTCCCATCGGGGTTTGTGTAAGGC
CGTTATTCGTGTTGCTTCACTGTTCGCGGTCATGTTCGGCTGCATATGCATTCTTCTGCT
GTGTTGCCTGAAATATCCCGAGTGAGGTTCAGGCTCTATCGGTTGTGCTTATATAGCTCA
GAACCTTTCCTGATGTGATTCTACTAATATATACTGCCCACCAATATATGGTGTCAAGGG
ACTTCCAGGACATGATGTCTAGTCTATCCGACCTTGAAACCCACGCCAGTGAGCTCACAA
GCGCTGTCAAGACGATCATCTCGCAATGCCCTCGCCAAAATGCCGCCTCTCGCAGCAGAA
CTCAACCCCTCATCACCTCTAGCGCTTCCAAGGAAGCGCATCGAGCCCAACAATCGATCT
TATCAACCATTTCTGGCCTCCAGAAGCTCCTCACCAGCCCAACCGACTTCCTCCACCACC
TCGCCGTTCAGAACCAGCTGCTTGCCTGCCTACAATGGCTCGGAGAGTTCCAAGTCCTCG
CTTGCATTCCCCTCACCGGCACCGTTCCCATAAAAGATGTCGCTGAGCTGGCCGGTGTCC
CAGAGACTCATCTCTCACGTATTATCCGGATGACAGCCACCGCTGGCTTCCTGGATGAGC
CAGACCCCGGTCAAGTCGCTCACAGCGCGCTCTCCGCTCCTTTCGTCACCAAACCGTCTT
ATCTTGACGCTGTGATGTTTTGGCTGGCACCATTGCCCCTTCTGCTTTGCAGATGCCTA
CTGCAACGCAGCGATTTGGCGCGAGTTTGCGTCCAACGAGACCGCGTACAACCTAGCTT
TAAATAACCCAGCGACATTCGCCAGTACGTCTGAGCAACGGCCAAAGCTTCAACGCCAGT
GGCCTGCTTTTCTTCAGTATGGGACCAGTGATACCGACGATCGAGTGACGGATCTGTTGT
CGAGGCTGGACCATTTTCGAAGAGGAAGTATATCTGTCGTTGAGGTACTTCATCCAATCC
ATCTTCATTTTGAGATCATCCATACGATTGTCTAACCAATTGCCCAAATTATAGGTCAGC
GCCCGCTCCCTCGACCGCGCAACAACCCTTGCAAACCTCTACCCATCCATCAACATCACA
GTCCAAATCGCATCCCCAGCAGGCCCAACTGCCTGGTCACCAGCACACCCCAATCCCATC
CGCCCCCAACTCCCGGCGGTAGCCACAAACACGACGACCTTCGCGCACTCACTGCAAGC
ACGGCCAGTACAACACCGGCCTCTAGCCACAACCACACCCATACGCATACCACCAATAGC
ATACCCCAGGCCTCCAACATAACGATCCAACACCGGCTTCCAACAGCACCGCAACCCATT
ACCTCAGCAAATCTCTACATCCTACACCTCCCCTCTCCCTCACCAACAGTTCCTTTCGCC
TCCCTTGCAACGCACATCCTCGCAGAACTCCGCTCACATCTCGACATCCTCCGCTCAAAC
CCATCGGCGACCCTGATTCTCACCCCGCGGCCCTTGCCTGAACCCTCAGCTGTGCATAGC
GAGGTCGAAGCAAGCGCGCGACTGCGCGACTTGACGCTGATGCAGTTGGCAAATGAGCGT
GAGATTGAGCTGGCGGAGTGGATTAATCTGCTGAGCAATGTCAGTGATAGTATGGGCCGG
TTGGTGGTGGTGAATAAGATTCAGTCCAGAGAAAGCACGGTAGTTTTGTTGGAGATTCGG
TACCAGGCCTATAACAGGTGACGGTTGGAAATTTTTTTTGAGTTTGTGAGATGTTCAGG
ATGGTCCATCTATTTCATGCATCTATCAGGTCCTAAGACTGATTCCGCAACTGCCCGGAT
GGAACGGTTTGGAACGAGCGGA
```

Figure 5E

Sequence of the deletion of the Emericellamide cluster

>ChrVII_A_nidulans_FGSC_A4 COORDS:ChrVII_A_nidulans_FGSC_A4:4288463-4326127W (37665 nucleotides) (SEQ ID NO:5)

```
ACAGACTAAGGCCTCGGTCAACAACTTCATCAACAGTTACTTCATGACCTCTCTTCTGGA
GTTCAAAGGCAACAAGACTGGCATCAACCAGATCGCCTTCAAACTTTGGAGCTTCATTCA
CTCCTTGAGCATTTAGCTCAGACACACAATCAACAGTAGGTAGCTCAGCATCCAGAGCCC
CGTTCATAAACGCATCAACAGTCTCGCACAGTTGACTGAGTAGCTTCTCCGCAACCTCGA
CAGTAACCCCATCTTCGAGGTAAGCCATGGCAATCTCAACATAGTCTGTACTAGCAGTCG
ATGTAACCGACACATCAGAGACATCACCCGCACCTTCAGTCTTCGCAACAGAGACATTGT
ATTTCCCATCATCAAGGTCAAGCGTCCACTCGGATGCTTGGTCCAGATGGTTCAGGAGCG
AGGTGAAGACTGTACCAACTGGCATATCCGTACAGTTGCGCATCAAGTCGCGGAATCCGA
GGGATTCGTGCGGCAGGCGGGAAACAAGCTGTTGCTGCACAGATCTGAGGAGGTCATGTG
TGGTCCAGGCTGGGTGGATAGTAGCGCGCACAGGAACGAGATTTGCGCAGCATCCGGCTG
CTCTTTCGGCAATGGGTCGCCGTTGCGGCCTGAGACGACCTCCCCAAAGAGTACGTCTG
GGTTCCCTACGTGTTGGCCTAGGGTCAGAGCCCACGCCGATCGCACGATCGTTGAGAGAG
TGATGCCTGCTGGAAGGGTTTTGAAACTAACACGGCGAGAATCGTGGTAGACCTGTCTAG
ATGGTAGACGTCTGGGTTGCGAGGATGAGCTGGATGGCCGGCATTGTACAGCCTTTGAGGA
GCGAGCGCCAGTACTCACGACTAGACCAGGTGTCCTGGTTCGCGAGGCTGGAAATATACT
GGGGGAAGCCAACGTACTCCGTGGTGGACTGGCGCTGGTAGATCTCTCTCAATGAGTTGA
CAAAGTACGATAATGATATCGCATCGTACTCGGCGTGGCTTAGTCGGAAAAGGACGCGAT
GCCGGTTGGCGACGGGAGAGCAGATGATGGCAAACTCAAGGAAGGGGTAACCCAGTTGGG
GTGGTCGATGCATGTCATGCGCGATGAACTCTTTGGTGAATTCTTCGATAGACTGATCTG
TCTGATAGTGGGTTACAGCAGGGGCGTAATCTCGAAGAACAACCTGAAGGAGTTGATTTT
TGTACACGACATAAGCCGTTCGAAGGATATCGTGCTTCTTGACTACCTCCAAGCAAGACG
CTCTCCATCGGGCAAAATTAGGGCTGCCAATTCCATCAATACTAACGTACGCCATTAGGT
CACGAGAGGGTCGCAACGATGTGGCAATCGAAAGAGACTGGAGGTCCGTGGTAGGCGCAA
CGTCAATTATCTCGCTGGGTACTGAGAGGAGAGGCTTGATGGAGTCGCGGATGGCATAAT
CATCAGTCATTGTAGAGAACGGGCAATATGCTGGCTTTGTCACAGTTGTTTTTCGATCTA
TCAGTGTGGCCATGTCGGATAGTATTGGATGACGGAAGACATCCGCCACCTTCAACGAAA
TATGAGCGTCCTCACGGGCGCTGGCAACAAGTCGCATAGCCGAGATAGAGTCTCCACCAG
AGCGGAAAAAGTCGTCTTTTGCGCCTATGGAAGAGGCAGGAACCTTGAGGACCGTCGCCC
ATAGACTTTGCAAAAGGCGTTCGGTGACAGTAGCGGGCTCTGCCTTAATATCATCCACCA
GGAAATACTGCGACCATGACCCGCAACTGTAATCATTTCCCACGTTGCTCGACGATTGA
GTTTGCCGGAATCTGTAAGTGGTAGTTTGGCGAATGGCAGGTATAGTTGGGGGACCATGT
ACGAAGGTACAACAGTAAGGAGGTTGCGGCGGAGTTCGCCAAATGCTTCGCGAAGTTCGT
CGGACAGTGATAGCAAGCCGGACGATTCAACAGAGCTTGATGGCACTTCCATCGCAACAG
CCAGGAGGGGCTCATCCTCTTCGTAAATAGGTTTAAACAGGCCTGCCACAACTTCACGTA
CATCTGGGAGTTTGTTCTTCACCCAGAACTCAATTTCTCCAATCTCAACACGTTGCCCAT
GAATCTTGACTTGGGTATCCCGTCTACCAATGTAAATGAAAGAGCCGTCCAACTTCTGCT
GAACAAGATCTCCAGTCCTGTAGAATCTTCTCCCGGAAACGGGGCCTAGATCGTATTGCT
GTAGCCAGGCTGGGTCGGTCACAAACGCCTCGGCAGTTTTCTTCGCATCCCCAAGATATT
CCCGAGCTAACAGAGGTCCTTCGATAAGCAGCTCGCCGACCATGCCAACGGGAAGCAGAT
TGTGGTAATTGGACGGATCAACGACGAACAGGTTACTATGTGCCAAGGGAAGCCGATAT
TGGGTGCTTGAACTGGGTCCCTAATGCGCTGGCTGAAAGTCGTCAGGATGCTTGACTCTG
CAGGCCCATACGCGTTGTGAAGTTCGACGTGACTGGAGCTCCATGGCTCAGCAACTTCAG
GGCGAAGAGCTTCGCCCACAAGTAGCAATCTTCTGAGAGAAGGCACCTGTTCAGGTTTGA
GAAGACTAGCAACTGTAGGTGTGAGGATGGCGAAGTTGACAGCAGCCTCCTCCATTGCCT
CCGCGAGGCGACTGACACGATCATCTTCTGAAATAACGCATACACAGCCACCAAAGGAAA
GAGTCGTGAATATCTCGGCGATACTGATATCGAAGTTCAAGGCGGAGAACTGTATCGCTC
GAGTGTCGGGGCTTGCGTAGAGTGAGCCGTGGCCTTGTACCATGCTCGAAACAATGGCAC
CGTGTTGAAGCACCACGGCTTTGCTGGTCCCTGTCGAACCAGAAGTGAAAATGATAAAGG
CGGAGTCTGTAGCTTGTACAACTGGGTGAGGGTTGTCGGAATCAGGAAGCTGCGTGAAAA
AGTCTTGATCGACCTTTAGAACAGGACCAGTGACAAGACCTTGGAGGCGTCCAGGGTCTT
GTGAGGTCAAGATGACTCGAGTACCGATGCTCTGCACCAAAGCCTGCATACGCTGCTTGG
GATGCTGATGATTGACTGGCACTATTGTTCCTCCTGCTTTTAGTACGGCCAAGTAGGTGA
CCACCACCCATTTGGTTTTTTCGAAAATAGTAGCGACCGGCACTTGGGGACCTACGCCTA
GACCTTCAAGATGGTAGGCAAGTCGGGTGGCAAGACGATGGAGTTCTCGGTATGTCAAAT
```

Figure 5E (continued)

```
GTCCGTCGAAGGCATGGACAGCCTGCGCATCGGGGCAAGAAAGTAGTTGGTGATGAACGA
GATCGTGGATACAGCCATCAGCCATGGTCATTCTTTCATCGAAATGGTTCCATTTCTGGA
TCCGACCCAGGTCCTCCGGCGTCATGAAGATAACGTCGCTTACCAGGACCTCGCATGTCG
CTTCATTTGCAGCGCTCTGGAGCTGTCCAAATACGTGGGTAAAGCGTTCCAAGATCGTTG
TTGCCTTCTCCACAGAGAGGACAGCAGGGTCGAATTGAAGTTGCAAATCAACAGCACTGT
CAGTATCGGTCATGTTAGTGCTGCACTCTATTACAAGAGGATAATTGTGGAATCCATATG
TCTCAAACGGCACAGGCGTAAGTCCTTGGAAGCCGGAGTTTGCCTGGTCGAGACGGTCAA
CTGCGGGCTGGACGACAAAAAGATGCTGGAAGTTGAGAGGCAACGACGTCATCCGGCTAA
TGTTGTGAAGACCAGCATGCTCAAACGGTAGCATTTCTGTGGCTTGTTGCTGGATTGAGG
CCAAGTACGCCGAGAGGCTCTGGGCAGGGTCAACAGAAACGCGAATAGGCACAGTGGTAA
TGGTAGGCCCCAAGACGTCCAGAATCCCATCCACTGGAGCAGTGCGACCTGAAAGCGCTG
TTGGGAAGCCTACGATTTGGCTTCCAGTTTCCTGGGACAGGATTAGTGCCCATGTAGCTC
TCAGGAGCGTGGAGAGAGTAAAGTCATTGCTGTTATTGGCGGGAATGCGGCAACTTTGAA
TTCTGAGCTTCCTGGGAGAACCGTTCTTCGGAGACCCGGGGAAGCTAGGGCCTATGCCAC
CCTCGAGTTGAGACTTCCAGTAGTCGCGGGTCTCCTCGGCAGAGTTTGACTGCAGATACT
GCACAAAGCGAGTGAATGGATGGAAAGACGGCGCGGGATTATTGGAGTAGAGTGCAAAAG
CAGCCTCCATCAACTTTCGGGCTGTCCATCCGTCATACGTGCTATGTGGGCAGTCCAAA
CGAAGAATCGCGCCTGTCTGCTGGTTACAACTGCCAAACGCACCAACGGATCTCCGAAGC
CCATGGGCTTTGCAGAGTCCTCTGCGATATAAGACGGCAGCTCGGACAGGACGTTATTCC
ATGTTATTTGCTGCTGAAGAACCACTTGCATTCCACCAGCCTTGGGATCTTGTATAATGC
GAGTACGTAAAATTGGATTAAGTTCAACCAACGTTCTCCAAGCTTGGCAAAAGCGAGACT
CATCGATGGTGTCTTCCAAACGGAAGACCCACCGACTGATATATGCCTGAGGGTGTTGAG
CTGTGATTGCCATGAGACCTTGCTGCAAAGGTGTGCACGGGTAAGCATCTTCAATGACGT
CGACTTCAACTTTGCACTGCGAGGCAATCTCCTGGAGACGTGCCTGTCTCTCATGTTGAG
GGTAGGGCAACAGCAAAAACGGTGGCACATCGTTGTCATATTGACAGTTCTCAGTGGATT
CTGAATTAGCAATTGTATTGGCCATGTCCGAGAGAACGGGATGCTTGAATACGTCACTGA
CAGATAACAGGATAGGAGGCTGTGCGGTTCGAGCTAAAGCGACTAGGCGCATAGCAGTGA
CCGAGTCACCACCAACGCGGAAGAAATGAGCGTTGGCGCCGAATTCTTTTGAGGTGTTGA
GAGCGGCTACCCAGACTCTGGCCAAACGGCGTTCGGTCTCAGTCGAAAGCGCGACATTGC
CACCATCAGCCAGGCTGTACTGTGCAAGCTGCTCCTCTTTTAGGCCCCCTATCAAGGTTC
GAAGTGCTCTTCTGTCTAGCTTACCAGAGGCTGTATTTGGCATGTTCTTGATGGGAATGT
ACTTCGAGGGTACCATGTATGAGGGTAATGCTTTGAGAAGGGCCGCCTGCAGCTGTAGGA
ATGATTCTCTGAGCTGATGGTTGACGTCCAGGAAGACACATTCGTTGCTGGAACGATCCT
TGCGCAACTCGATAGCAGCCACTAAGGCTACGTCGCCTGTGCTTGCACCAATAACGTCAA
CAGCGACAGTTTGGGTGTCGAAGTGTTGCCGAAGCCAGTACTCAATCTCACCGACCTCGA
CACGTTGACCGCGTATCTTGATCTGACCATCCGCTCGGCCGACAAACATGATTGAACCAT
CAGTCGGATCTTGCCTGACCAGATCACCAGTCTTGTAGATTCGCTTTCCAGCCCAGGAAT
GGAAGCCGTATTTAGAAACAAAGGCAGGATCCGTGATGAAGGATTGTGAAGTTCGCTCGG
TGTCATTTAGATAGCCACGTGCAACTAGCGGCCCTGAGATGAGAAGCTCACCAACTACGC
CCAATGGAACGAGACGGTTGTGATCTTGTGTGTCAACCACCCAGATAGCGCCAGCAAGGG
CCGTGCCAACACTAGAAGCTTGCTCTTTCTCAATAATCGGGCCGTTGGTAGTCGCAAGAA
TGGTAGATTCTGCTGGTCCATACCCATTAAAGAGGGTGACATGACTTGCCCAGGTTTCGA
CGGCGCTGTGTGGAACAACTTCTCCGGCTAAAACTAAGGTCGACAGCGTCGGTACTGTCC
GAGGGTCAATAAGACTGGCGACTGTGGGCGTGAGGACTGCAAAGTTCACGGCCATAGCCT
CCATCTTTGTAGTAAGACTGTTGGTATCAACACGATCTTCCTCCGAGACGACGCAGACAC
AACCGCCGAAGCGAAGAGTAGACAGGATATCGAGAAGGCTGAGGTCGAAAACATAAGCGG
AGTATTGTAATGCTCTAGTATTTGGACCCATTTGAAGTTTTGGCCCATGGCTTTCTATAC
TTGTGCAGATTGTCCCATGTGTGAGGACAACACCCTTGGGTGTACCGGTTGAACCTGAGG
TGTATATGACCACAGCCGCACTTTCAGATGTCAGACTACTCTCGCTGGGGGATGACAAG
GGTTGGGTAGTGTTGCTATAAATCCACCATCAATAGTTAGGACGTTGGCAGAGGTAATAT
CCCTGAGTTTGGAGGCATGTTTGTCCATGGTCAGAACAACTGGGGCTGTGATCTCGTTCA
GGATATGCTGCAGACGCTGGACAGGCATCTGAACCCCAAGAGGCACAATTACACCACCAG
ATTTGAGAACAGCGATCATGGACACAATGGTCCACATGGACTTATCAAAACAAAGCCCCA
CCATCACTTCCTCACGCACCCCTAAGTTTCGTAAGTGATGAGCAAGCCGGTCGGACATGC
CTGTAAGCTCAGCGTAAGTCAGCTCCCCGTCCCAGCCGCACACTGCCTGGGCCCCTGGCT
GAGAAAGAGCCTGCTCATGAATCTTGTCGTGTATACTGCCGGGAACAGTCTCTCCGACGG
TTGAGTTCCAGATATGAAGCACTTCAACGTCACCAGTTGGTATCACATCAATCTCATCGA
TGTTTGCGTCGGGGTTTGCGGCAATAGAAGATAATGCGCGGCCGAAGCTACCCAACAGGC
GTCGGGCTGACGGTTCGTCGATAAAAGTGGTGGCGTATTCAAGGTCTAGTGATAGACTTT
TATCGTCACTCACAATTTTAACCTGTACATCATATTCGGTAGGATCTTCGCCGGCGAGGC
```

Figure 5E (continued)

```
TTTCAATCACCAGACTTCGCTTTTCGTGAGTATCCATCATCGGCTTGGGCTTGTAGATCA
TGGTTGTATTGAAGAGGCCGCGCTCAGATAGATGAAGAGCGTGCTGGATATCGCTAAGAG
AGGTTCGCTGGTGATTGAAGGCATCTAAGAAATTGTGCTGAACCTGCTTCGCGGCTTCAG
CCACGGTAGTGCCGGGGTGTGCGAGTTGAACTCTAGACACCATTAAGTTAATCATGGGCC
CGCACATCTCGTGTATCCCGTCGATTGGAGCATCCCTGCCATTTGAAATATAGCCAAAGC
TGACATCGCGGGAACCAAGATACCGAGATAAAACCGTGGCCCAGGCGAGCTGTGTGATGT
TTGCAATCGTAACTCCATGCGTGTCTCTGAAATCTTGCAGAGGTTTTATGTTATCTACTT
CGAGAGAAACCGTTCTCAAGGAGCGCTTTCCGGAGTCTAGATTAGAAGAGGCAGGAAGGC
ATGACGGCTCTGCACCAGCAAGGTGATTCGTCCAGTAGTTCAGGGAGTCGAAAGCGAAGG
TCTGTTGCAGGAACGAGACATAGATGCCATATGATGGAGCAGGCGAGTCTGGAAGCATAT
TATCATATGCCAGAATGAGATCATTGAGAATTAGATCCATGGATGAGGCGTCCATTAGAA
CGTGGTTGACATCAACCTGGGCGTAAACTTGCCCTGTAGAAGCTTGGGCTAGGGTGAGCT
GGTAAGGCGGCTGCCCGGGGCGTACTCCGGACGTTCGAGTCCTTCGAATTGAGCAAGGA
AATCATCACTACTGCAAGACTGCAGCACTGGTATTGTTGGAGTGTATCTTTTGAGTACAA
CTTGATAGAAGAGTTCCCGTCCCGATGGACTAGGGACAAAGAATGTACGTAGAATAGCAT
GTCGCTGCACAACCAACTGCCACGCGCGTAGGAGTCGGTTCATGTCGACCGGTGAAGAAT
CAGCGGCACGAATCTCTCCGGCCTGGCGCACTTGATATGTTGTGTGGTCCTTGATCTGGC
TCATCAAGATGCCTTGTTGGATAGGGGAGCAATAGTAAATGCTCTCAATTGCAGAAAGGT
TCTCGACGCCGGTCCGCGGAAGCACGTCGGTCTCAAGCTTAGACAAGTCGCTGGCGTTGA
TATCAAAGGCCGTTGGTGCGCTTGTAGCGGCTGGAGCTTGATCGATTGAAGAGGTAGAGA
GCTGAGTGTCAGTGTTGGGACTCGTGGTCTTAATCACAGCCTTCTTCGCCAGTTGAGAGA
TTGATTCGCATTGCAGCACATCGCGAACAGTAACATAGATGGAATATTGGCTGCGACACT
TTGACACGACTTGCATAGCAGTAACTGAGTCACCACCCACAGCCAAGAACGGGCGACTCA
TAGGGACCTTTCCAATCGAAGCGTGGAGTACATCGGCCCAGACAGCTTGGATGTTTTTTT
CTTCGGATGTGCTTGGAGTTGTCGTACCCTCCGTGTAGCTTTGCGTGAGGATTTTAAAAT
GTTCCACCTCCATGGTCTCCAGCCATTGCGTGAGTCGGCGACGATCAATCTTGTCGGAAC
TGTTGTGCGGCATTGCTGCAAGTGATATCCAGGAGTTGGGAACCATATACTCGGGAATAC
AAGAGTGTAGGTGATCACGGACGGATGAAGCTTGCTGCAGGGCATGGGGAAGCTGGTCGA
GGGGCGTGGTTTGGATTCCCTCATCTGCGTCAGAAGAAATGAATCCATGCAATGTCAATA
TCCCAACGAGCTGCAACTGGGCTGGGCCACAGTGAGGGTAAACTATCACATTCTCTACCA
CAGAAGGATGCTCGGTGACATGGTGCTCAATTTCCCCGATTTCGACTCGTTGGCCGCGAA
TTTTGACTTGACCATCGCGTCGTCCGACATAGATAAGTGATCCGTCTTCCATCTGACGTA
CCAGATCACCAGTGCGATACATGCGCCGCTCGCGGCGCTGTGAACAATGGTCGTGTTCAG
AGTACCGGGAGATCCAGGCAGGATTGCAAATAAATGCATTGGCTGTCTTAATAGGGTCGT
TCAAGTAGCCTCGAGCGAGTAGAGGACCCTCGATCAGAAGCTCACCCACTGCCCCAAGAG
GTAGAAGTCGGTTGTAGTTGTTCTCATCCACCACCCAGAGGCCACCTGCTATCGCACGGC
CGATATTCGGCACATCCGCTTTATTGGCAACCTCATTGCAGGTGGCGGCGATACTACATT
CCGCGGGGCCGTAGGCATTGAATACACGAACACCATTTAGCCAGGGTTCCAGGTATTCTG
GTTGCACCGCTTCACCACCTACCACTAAGGTCTTGAGGCCCGGCACGTCAGACGGCTTGA
TGGTATGTATAACACGTGGAGGAAGGAACGAGTAGTTAACTCCCATACGATTCATTGCAT
CGGCCATGTTATTTACTCGCTCTCTTTCTGATGGCATGCAAACACAGCCGCCGAATTGCA
GCGTTGATATAATGTCATGGAGCGAGATGTCGAACGTAAAGTGGGCGAAATTGAAGGCGC
GGGTCTCTGAGTTCATGCCGAACTTCTTGCCATGTGCCTGCATGCTGGTTGACATAGCGC
CATGCTCAACGACGACACCCTTGGGGTTTCCAGTCGACCCGGAAGTGAAGATGACGAACG
CAGCATTGGAAGGTGTAACGGTTGAGATGGGCTGCGTGACAGGGCTTGGGAGCGACTGGA
TCAGATCATCGCCTATAGTTATTACATTAGGCACTAAACCTTCAAGCGCCGAGGCAAAGC
CCTCAGAGGCGAGGATCGTTGTAATGCCAGTCTGTTGCAAGATGTTTTGCACACGCTGAA
TGGGATCAGCTCGAATAGGGACAACCGCGCCCCAGCCTTCAAAACAGCGAGGTTTGCGA
CCAAAGCCCATTTTGATTTTTCAAAACAAAGAGCAACCATGGTCTCTGGTATTACCCCAA
GCGTAGTGAGGTATAGAGCTAGCTTGTTTGCTAGGCGGTCTAGCTCTTCACGCGTAAGAT
CACCATCCCAAGCACATACCGCAGGGGCATAAGGGTTGGTTGAAACATGCTGAGAAACTA
GTTCATGAACCAAAGCTTGCTTGACCGGGGAATACCTTGGTTGAACTGGAAGAGTCGTC
TGGCCTCGTCCTTGCTCAATAAATCAAGATACTTTAGTTGCGTTTGATCTCTGCCGTTAG
TAACAAGCTGAGTGACAATGTGACTAAAGCGGCTGAGCAGATCATTCGTCTGGGAAGCTG
AAATCATTCTTTCATCAAAGTGCGCCTCAATCGTAACTGGGATATCGGATATATCACTAG
TAACGCACTCGACGGTAAGGGCATAACCGTCGAGGTTGAGCTCTGGAACATGACCATGCT
CGTACGCTAGGAGCTTACCATGTACAGAACTCTCACGTTCTTGCGCTGGTTGCACGGCGA
AAAGATGTGGAAGATCGATCTGGCCAACGAAGCGGCGAATGTTCTGCAAGCCTGTGTGCT
CGAACGGTATCATGTCGACGCTTTGCTTGTGAACCATGGTGAGATATTGATTGATCGTTT
GTTCCGGGTTGATATGCACATGAACTGGGACAGTTGTAATTGTTGGTGCCGCCATGTCCA
```

Figure 5E (continued)

```
GAATGCCGGGAACTGGCGCAGAGCGCCCAGAGAGTGCAACTCCAAACAAGACATCATTGC
CACCGTAGGCGGAGATTGCCAGTGCCCAAGCAGCCCTTAGAGAAGAAGCTAGCGTATTGG
GCCCTCCAACTGGGCGAATTTCGACGCTCGAGCTCAACTTCTGAGTAGGCTGTGGCCGGT
ACGAAAGCTTGTGAAGAGAGGGAACGGTGCCCCAACTTTTCTCTTGATCTGAGACTGCC
AGAACGACTTAGCGGCCTTTAGATCTTGTTGACCTATGTACGAGATGAATCTTGAGAATG
CAGGAGTTGGAGCGAGCTCTTTTCCATCATAGAGGAGTGCCACCGCGTCAAACAGCTTTC
TTAAACTGTACCCGTCGTATACACTGTGGTGAGCTGTGAGTACGAAGTATCGCTTGTTGC
CGCTGTAAATTAAGGCTTGTCGCACCAAGGGCTGGCCGTAACCGAAAGATTGTTGTAGGT
CTTTATCCAAGTACTGCTTGAGGTTCAGGTCTCCACCCCACGCGACAGACTCACGGACTA
CCACTTGAAGTCCACCTGACTGACTGGGCGCAATGCGCGTACGCAGGATTGGTGCCTTTT
GGGTCAGTGATGACCATGCCCGTTTAAATGCGTTAGTATCAACAGCTTCTTGGATTCGGA
AAACCCAGCGGCCAATATAAGACCCTGGTTGCTGAGTGGTGATAGCCATGAGACCTTCTT
GGAGGGGTGTACATGGATACACATCCTCAATATCGTGGACTGCAACATCACATAACTTTG
CAACACGGAGAAGTTCCCTCTCACTGACAGAAGCCTCTGTCTGTTGGGCTTCCTTCCAAA
GCCCAAACCGAGGAATATCCTGTACGTCCCGGCGGCGCCCATCTGAGCTTCAAGATGAG
CGGCCATCTCCTGCAACTTAGGATACCGGAAGACGTCGGCAACGCTTATCGGGATGTCTT
TGGCATTTGCCAGGGAAACGAGGCGCATCGCGGTGAATGAGTCGCCCCGCAGTGAAGGA
AGTGGTCTTGGACACCTACATGGTCCTGGTCTACGTTAAGCACAGTGGCCCATAGCGACT
GTAACTTCTTCTCCATAAAGGTGGATGGTGCAACACTCAAACTGGTTGAAAGGGAGTACT
GGAAGAGGACATCACCCGGCAGGTTCTCCAGCATCTGCTTGATCGTCGACGGTCGAGTT
TGCTAGACGTTGTCTGAGGGAGGTGCACTACCGGAACGAAAAGCCGTGGCACCATGTACG
AGGGTAGGACCTCTAGTAGAGAGGCATGAAGCTGAGAAAATGCATCTCGCAGGTGAGGGG
CGTTGGGGAGGAATATTTCGTGAAATGGGCGGATAACAAATGCCTCTGAAGGAAATCAT
CGCTGAGTTCCATCGCAACAGAAATCATTATGTTGGGGGAATTGCCACCAGGGGTGATAA
GGCTTGCCACAAGACTCTTCACAGCTGGCAATAACTTCTTAACGCGGTACTCAATCTCCC
CTATTTCAACGCGCTGGCCACGGACCTTAACCTGGGAGTCCTTTCGAGCTTGGTAGATCA
AGTCGCCGTTTGGAGACTGACGAACGAGATCGCCGGTGTTATAGAATCGATGACCTTCAA
GTCTGATTGCCTTCGCCCACTTAGGGTTCGTGACAAAAGCTGCCTTCGTCTTCTTCGGAT
CGTTGTGATACCCGCGAGCCAGTAACGGGCCTTCAACCCAGAGTTCGCCGACAGCGCCAA
TGGGACAAATGGATTCGCCGTTGGCAATTACCCAGACGCTCCCCACAAGCGGTCGGCCGA
TGTTGAGTGCCTGTTTCTTTTGGACGAGAGCTGCACTGCAGGTCGTGTAAATCGAGCACT
CACTCGGACCATATCCGTTCAAAACCTTGACTCTTCCCGCTGCCTTGGCGTGCTCCTCAA
TCATGGCCTCCCTGACGGCCTCTCCCCGAGAATTAGTGTGGTAAGACACTTGATGTTCG
CAATATCCAGCAAGCTAGCCACAGTTGGAGTAACCTGTGCGTGAGTAGCACCATAAGCCT
CAATAACGCCCTGAAGGTTGTTCATGCGCTCCTCTTCTGATATGACACAGACGCACCCCC
CATGCGACATAGTGCCCCAGATATCACTAATGCTGGCATCGAACGTGTAGGCAGCGAATT
GGAGTGAACGAGTACTGGGAGACATTTCGTAAATCTTGCCATGAGCGCGGAAGCTGGAAC
ATAGAGAAAGATGGGTTAAAATGACACCTTTTGGCATACCGGTACTGCCACTTGTGTAGA
TAATGAAGGCAGCGTTGTTGGGGGTAACATTCGTACTTGGAGGCTGGGGTTGTGAAGAAA
GGGCAGAAAATAGTGTCTCGTCCATGTGCAGAATATGCGGACAAGGTTCCTGAACTGAG
ATGAATACTGATGCGACGTCAGCATCACCTTTGCGTTTATATCTTTGAGGACGAGTTCCA
GGCGCTGCGTTGGGTGCTTTGGATTGATTGACACAACGACGCCAGCTGCCTTGAGGACAC
TGAGCTGAGCAATGATGGCGAATTTAGATTTATCCAGACACAGCGCTACCATTACTTCGG
GACCAATTCCCAAGGTCACTAGGTGGTGAGCCAGCGCATTGCTCATCTCGTCCAGTTGTT
GGTATGTTAAGTCGCCATCCCAGGCACAGACGGCTGTTGCGTTAGGTCGGAGTAGCCGCT
GTTCATTGAATAAGTCATGGATAAGACAATATCCATCAACGGCAGGAATCTTGTCATTCC
AAGCACGGACTTGCAGGATATCCTTCGGCGTTACGGTGTTTAGCTGTCCGACATGGGTAT
CTCCGTTAGTAACGAGGGATTGGATTCCCTGCCGGACACAGCCGAGCAACCTGTTCGCGC
TATCGTAGGAAAGAAAATCTGGCGAGTACTGCAGAGAAGCGGATATCTTTTCTGGCGATG
CGAACACACTGACCGTCACATCATACTCTGTGGGATCCTCACCGGTGATCTGCTCTAGCG
CGAGACTGAGCTGATGTTTTTCTGCTGAAACAATATGGCGATAGGAAAGCGCTGTGTTGA
ACAAGCTTCTGCCCTGGAGCTGAAGGGCGTGCCAAATCTCAACCAAGGGTGCTCTCTGGT
AGTTGAAGCTCTCAAAGAAGTTCTCTTGTATTTGCTTGAGTGTGTTCTGAGCACTGGCCT
CCATGTCTAGTTTGATATGAGTGACCATCATGTTAATTAGGGGCCTACCATGGTCTCAA
CATCTTTGACAGGGACGTCGCGACCACTTGATAGATAGCCAAAGGACACATTAGGCGAGC
CGGTGTACTGGGCTAAAACCATGGCCCAGACGAGCTGGAACACGTTGGCAATTGTGACAC
CATAGGTTTCGGTGAAGCTATGTAGCTTTTCAATGCAGTTGATGTCAATTGATACTGTTT
GCATGGGCCTCCTTGGTGTGGAGTCATCAGCAGTAGCTGGCTGCATTCCATCCTCTGTCA
TGCCTCGAAGGTAGCATGGCTCTGCGTCAGCAAGGCGCTTGGCCCAGTAATCCAACGCCT
GATCCGCGGGTATCTTCTGCAGATGCGAAATATATTCGCTATAAGCAGCGCCGATGGTGT
```

Figure 5E (continued)

```
CAGGCGCCAGCTTGCCATCATATGCCTGGGCAAGCTCGGCCTGTATGATCATGAGAGATG
AGGCGTCTACGAGTGCGTGGCTGATAATGATATTGCCGAACGTCCGGTTGGAAGAGGTCG
AATAAATCGTAAGCTTATGACCGATGCGCTTGTCAATATGTCGTTCATCTAGAGTAGCTT
TGACGGCAAGGTTTCTGAAAAGATCGTCGTCTGTGCACTCGACATGCTCAGCTTCGGCCT
TGCACGACTTGAGGACCACCTGATCAAACAAACGCTCGCTTGATCCGGATGCCGAACGGA
CGAATCGTGTTCGAAGCATGGGGTGGCGGTTTATCAAGACCTGCCAGGCAGCAAGAAGAC
GAGTATGGTCAAGTTTGCCAGAGGAAGTGGTCGGTATGATCTCAAAAGATTGCTGGATAT
AATATTCGGATGGTGATTTCACTTGGCTGATAAGTATGCCTTGTTGGATTGGAGAACATG
GGTAGATGTCTTCAACATCAGAGCAGTTCAAGCCGGCGTCAGGCAAAATTTCATCTTGAA
GAACCCTGAGGCTCTCAGATGTTAAATGCAGCAGTGGGAAATCAGTCACAGTTAGAGTCG
GCGACGCTCCTGACAACTCAGTACCAAGGGCACTGATGGCATTGGCATAGGAGTCAGCCC
AATCCCGGATCTTCTCCTGGTACTTCATGTTGCGATTGAACTTGAAGCGAATACGCAACT
TATCGGGGTACGCAATGACGTTGACATTAAACACACATCCACGACGGGTACTCTTGCCAA
CTGGAGATGTCCCAGGTCCAGTGAGATCTACTGTCTCGAAAATAGTTTCGCTTGCGAGTC
CTTCGGAATATTGAAAGAGCACTTCAACCCATCGGTCAGTGAAAGCTTGTTGACCGTCCG
ATAGAACCCTTCCGAAGGCGCTGCGTCTTGCGTCCTTAGTCTGTCTTACAATATCCAAGC
CGTTGTGTGGCTCATCGAGAAAGATGTGTATAGGTGTCATACATTCGAAGTTGCCAACTG
TGTTTGAGAAGTCAAGTCCACTATCACCTACGTTTCGGCCATCGTTAATTTCAAAAACGG
CTGGGAGTCGGCGATTTGGGAAAGTTTTCTGGAAGGACTTCAACAGTGCAGCAAGAAGAA
TCTCCACACGTTCTGTACGTAAGGCTCTGTTTGCGTCCCTAAAGTATGCATTCGTGTCGT
GGCTGTTGAAGATCACTTCTTCGACCGTTTCGTCCTCGTAGGTATTGCCATCGTTCAAGC
CCCAGTACTTAAAGTCAGCAGGTGGCAGATCAGATCTGAAAACTATTCCCTCAAGGTTCT
GGCTCCGTTGGGCTTGTAGTTTGATCCAGGTCTGGAATGATAGCGGGTTAGAAGTTGGAA
ACTGCTGTCCTTCCAGAAGCACACTTATATCTCGGCGAATGATGTCCCAGGACACTTCGT
CGACTACCAGGCGATGGGCTGTCATGAATAGAAGATCTGTATTTCGAGCGTCTTCCACTT
GGATATACTCAACGAAGAATACGGGACCTTGCTCTAGGTCTAAACTGCCCTGAGCCTCCA
CAATAAGGGCCTCCGCCTCCTCGCTGGTAGATACAGTGTAATGCCTCAACGCAAACGGTT
GATCACCATCACTGTGTAGACTCTGTTGCCACCCAGCGACGTTATGACGCTGAAATCTGG
AACGTAAAATAGGATGTCTGTCGACAAGCGCACCCACGGCTTGAGCTAGTTCTGAATATT
CAAAAAGTTTGCGAGGTACCAAGCAGATATTGGAATTGTATCTGTGGGCACCACTGGACT
TCAGAGGCAACTCAGGATCGGCAATGGACTCGAAATACCACTTCTGCATAGGCGACAGAA
GAGATTGGTGGCCTTCCGTCTTCTCATCCTTTACTTCTGCGGTTTGCGCCAACTGAGCCA
CGGACTTGCTTTCAAGCACATCTCGCACCGCTACCGTAATCCCCCGCACCCGCAGCCAGG
ACACGACATGCATGGCAGTGATGGAGTCTCCCCCAACACTTAGGAATGACTTGTGCTCTA
TAGGAATTTGAGTAGGCGGCAAACGCAACACATCGGCCCATGCTTGTTGGACTTGGCGTT
CTAGAAGCGTTTCGGGCTCTCGACTCTCAGAGCCAGCGTCAGAAGACTTGGTGAGAGCTT
CCAGGAACGCTGTATCAATAGCCTCAAGCCACACCCCAATTTTTTGCGGTCCAATTTTG
ATGAGTCGTTTTGTGGCATCATGCTTTCCAAAGGAATCCAGATCTTTGGGACCATATGCT
CAGGAACATGATTTGAGAGCTCTTCCGATGCAGCAGCCAGTTGACTTTTTGTGTGAGAAA
GTTTTCCACTTGGTATAGGTATTATGTCTTGTCCTGGACGTTTTCCGCAAAAGAAATCGC
GCAAGGTGAGAAGGCCGACCAATCGATCTTTGCAGGGTCCTTGTTTAGGGTAGATTATCG
CTGCATCGAGAACTGCGTCTTGTTGTAGGAGGTGGTGCTCGATCTCACCAACCTCAACCC
GTTGTCCCCTCACTTTAATCTGTGTATCACGGCGGCCAATGTACGTGATGGAACCATCTG
GGTTCTGCTGTACGAGGTCTCCAGTCCGGTAGAGGCGTCGGCCGGATCCAAACCCGTTCT
TTATCATCCATGCCGCGTCTACGACGAACGCTGCTGCGGTTTTCTCGGGAGAGTTGAGAT
ACCCACGAGCTTGCAATGGCCCTTCAATGAGTAATTCTCCTGGTGCTCCGATTGGGACAA
GGCGATTGTAGTCATTGGGGTCAACAACCCAAAGAGCCCCGCAAACGCCCAGCCGATGT
TTAGTGCATTGCAACCAGGTGTCAATCGGTTGATACTGGCTTGCATCGAACATTCTGACG
GCCCATACGCGTTGTAGACCTCTACGTGACCAATCCATTGATCTACGACCGCTTGCTTGA
CGGCTTCCCCGAGTAGGACCAACTTCTTCAGGGTTGGCACATCTTGCGGGAATATCGTTC
CAGCCACCGTTGAAGTTAGCCCCGCACAATTAACCTGATATTTCACCATTTCCGGTGCTA
GATTGCTGATACGATCCTCTTCTGAGAGAATGATCAGGCAGCCGCCGTAGTGCCACGTGG
TATATATCTTGAATGGAAATATCAAAGGTATATGCCGAAAACTGCACTGTGCGAGTAT
CTGGACTAAGCTTGAATCTAGCACCCATATGCTCAAGACTCGTACAGAGACTTGCATGAG
GGAGCACAACACCCTTCGGAACACCAGTGGATCCACTGGTATAGATGATAAAGGCGGCGT
TATCGACTGTTGCAAGGCAGGGACCATTTCGGAAGGTGGTAGTTCGGCCATGAACGCTT
CATCAATGACCACTGTATGGGTCACGAGGTCCATGAAGCGGGAGGCAAATTTCCCTGACG
TTAGGATGATTGTGGCTTGTAGGTCCTTTAGGATTAGCCTGGTTCTCGATGCTGGTTGTG
TCGTTCCAAGAGGAACAACGCATCCACCAGCCTTGAGGATCGCTAGTTGTGATATCACTG
CCCATTTCGATTTTTCGAAGCAGATTGGGATCTTAGTCTCGGGCTGCACGCCTAAGCGAA
TGAGGTAGGATGCCAGCTGGTTAGCCGTGTCGTCCAGCTGCTGATATGTTAAGTCGCCGT
```

Figure 5E (continued)

```
CCCAGCCCTGAACAGCCCAAGCATCGGGTCGGCGGAGTCGCTGTTCATACACTTTGTCGT
GGATACGATAGTCTGCCTTTGGTGGGATCTCCTTGGCCCATTCACGAAGCTGATTGATTT
CTTGAGTGGTACTAATATCAATCTCTCCCAGCACGGCATCTTCTTCTTTGACGATGTTCA
GGAGCGCCTGCCGGAAGGATTGTGCCACACTCTCCACCGTGCGCTGGCCAATCCGTGAGT
TCCAGTAATCAATCATTACTTCCAATCCCTCATGCCCTACTTGGATGTTTATGGACATGT
CATACTTGCGCACTTGTTAGCGTCGAATGGACTGTAAGGGATATAATCACTACTTACTTC
ATTGGGGTTGGCAGCATCAACAAGCTCAAAAGCAAGCCCAGATCCCGCTAATTCAGTTGC
AGCTTTTCGTTGGCATGACATTAATGTGTTGCTCTTGAAACGGGCAAAGTCCCCAGATTG
CGCATCATCCAAGGCTAAGTAGTACTGATGTGAGAGGCTTTCCACGAAGTCGTTCCTAGC
TTTCACCAAAGCCTGCGGAACTGTTGCAGTAGGCGGCAGCTTGATGCGACAGACCACTGC
GTTTAGGAAGGCTCCAACCGTATTGTTGATTCCTTTAAGAGGAACATCCCGCCCCGACGT
TGCATACGAGAAACACACATCTTCCAACCCGGTGTAGGACCTGAGCACTAGTGCCCATGC
TACCTGGCAAATATTAGCAGGCGTGATGTTGAACTTACCACAGAATTCCCCTAGGACATC
AGAGCCCAGCTGAATGTTTGATCTGACGGTACGAAGGTCTTCGCGACTCAACTGGTCTCC
GTACAATGGGAAATGGGATGGCTGGGCTCCTGCAAGGTAGTTGGACCAGTAAGTCATGGA
TTCTTGCATAGGCAGCCGTGATTGGTAGTTGACAAAGTCTTGGTAGGCCATGACACGACT
GGCCAGCTTCTGTTTGCTATAGAGTTGAAAAAGGTCCCGCATCAGGACCAGAGCGGAAAG
CCCATCAACAACGGCGTGTGACATATCAAGACGGAGGTAGACAGAGGATGGTGAGATTCT
GCAAAATGTCACTTGATGAGTTTGGCCGTAGCTCTTGAAAGTTACTGGACGGCGACACGC
GAGACGGCGAGCTGCCTCTTCACCCTCGTTCTCTAAGAAAGTGATGGAGCTAATGCCCTG
CTTCATTACCACCTGGTCGAAGTGCCCTTGGCGATTTGGGCTTTCAATGAACACGGTCCG
AAGAGCTGGATGGCGTGCCACGAGGCGAACCCAGGCGTCTCGAAGACGCCGCAGTCTAG
TTCGACATTCAGATCCTCGGAGCTCAATTTAATTACAAAGGAACACTGGTACAGATCGGG
GTAAACAGCTTGAGCCACCAAGAAGGCTTCCTGTCGCGGCCCACAGGGGAATACTGCTTC
CACGTCGCGGAAAGGGTCGCCCGTTACAGCCTTGAGCCGAGATGAAACAAGGTTGTCCAG
CTCTGAGTATGTCAGTTTGAGGAAAGGAAAGTCGCTTAGTGTTCCTTGCACTTCGCTCAT
CTCACACTCAGCAATCAGTTCCTTCAGGGCAGCGCGAAACAAGCCAGCAAGCTGACCTAG
TTTTTCCCGCCCTAGCTCTGCAGACCTGGACCGAAGACGAAGCTTTAGCTGCTGTTGCTC
CAAGAAAGGTTCAACAAATGCTAGGCACCCGTGAGGAAGTATGGAGAAGTCATCCTGGTG
GAAAAGCTCATGGAGGGTATCAGCTATTGGCGCTGTCGTTCTCCCAGTTGCCCCATATG
TAACAGAACATATCGACTGCGATCCTCGACTCCTGATATGCGAGAGACATTAAGAAGCC
CATCCGTGTATCCTTGACTTTCCGTAGGAATCCAAGTCCACCGTCCTCTTCTGCTCTTTC
CACGGACCGGCGGATGATATTGTCGAAGCACCCTACTGTAGCTGACAGCTTAGGACCGCC
ACTGTGCCTGCCGTTTGAGATTATACCAAAGCTCAACGTCTCCTCCGACCTGGTTACTCC
TTTAAGTGCGATATGTAGTGCGGCAACGATAAAATCCTCTGGCTGAGTGCGAAGCACAGA
GTGGATGCTTTCATCCTCCAGCTTCGCCAGACCAGCTGCATCTGTTTCCAGGATAACCAC
ATCAGCCAACTCGATTTTGCCATCATTTTGGTGTCTATTGTGTTGTCTTTCATTTGTGTT
CCGCTCATCGTTTGTGCTTTCGACCGGCGTCGAGCGTCTGAATGTAAAGTCGCTTAGGTT
GTGAGTGGAAGCCCAGGAGTCAAACGAAGTCTCTGGATACCCGCGAGCAAGCGGCTTTCC
GAGTACTGCATGGTCCAAATCGCGCTGAAGGATATCCCAAGACGAGACATCGATGATGGC
CCGGTGAAAGTCGAGCCGAAGATAGCGGGCGAGGCACGTGCCGTGGTCACGGTCTTTTTG
CACAAATACCGTGGCGGCGAAGAGTCCATCCTCTCTCTTCCCGTCCGCTTCCCAGCCCAC
GGTCAGGTATCCCTGCTCTGCTTGCGTTGAGATCGTCGGAATCTCGATTCTTCGATGGGC
GAAGGCGTCGATCGTATCATTGTATGTGAGTCCCAAGTCATTATTTTCAAGTGTTGTAAA
GTTCGCTCGGAGGATGGGGTGGTGGCTGACGAGCAATTTCAGTGCCGCATAAAGCGTCGA
TTCTGCGATTCCACCTTCTAACTTGAAAACTTTGGCATCCCAAGCCTTCGTCGAGGCATA
CAACTTCTGTGCCTCTGTTAATGGCTTCGTCCGTATCTCGGCAGGCTGCGCAGGCCCGTC
CAGCACCGGGCCTGAGCTGAGCTTCCCTGGCGCGCTGCTCCCCTCTGCTAGTTTTACAGA
CTGGCATAACTCTCGGATACTCGTCGCTTGGAGCATATCGTTGATGGTGATTGTATACCC
CGCCTCCCCGCAGCGCGCCATCAGCTTGATTGCGAGCAAAGAGTCCCCTCCTTGCGCGAT
GAAGGACTTGTCCAACTTGATCTTTCCCACCGGGCGGCGCAGCACCTCTGCGCAAATCTC
CCTGATGTCCTTCTCAACAACCTCATTATTCGTAACTGTTCGGTTTGGCGAACCGGCTGT
CGCAAACGTACTTTGCTCCATTGCAAACGATTATTATGATTATGATTAGAGGCCGCTATC
AAAGGCGAAGAAGAAAGTTACTGCCGTTCCAAGCTGGTCTCAGTCTCCGCAAGATAAAG
CCAGCAACAACGTGATTATCGCAGAACGATATATCCAGGAGTATTACTGAGCTGAGTCAA
AGTATGAAAGCCGTGAGCGGTACATACGCTTTGGACCTACGCGAAGACAGCTGATCAACA
ATGCCGCTACTCCAGACCACCGTATACTCCAATTCGCCGAAGTTCTAGCTCCGTATCCTT
CGTCCTTATCCACCAAAGTGTCGATCACGCTGTTCCACACCTCTCGAACGAGATCTGTGC
CTTCGGCCCACTTGACCTTCCTCGTCTTGGCACGACATTTCTGGTATCCGCAGCAAAGCG
GGCCGGGTTTGGAAAAGTTGGAATTAAGAGGAACCTTAAAGGAAGCTGATGCCGCTTTCA
TGATCCAAGTACCCGTACGTATTGAACCTTTCAGGCAATATCCACGAATTCGATCCGGAG
```

Figure 5E (continued)

```
TCTGAACTGAATAAAGAAAATGCTCGTGACGTATCATTTTCCCAGCGCAGGGAGCAGGAA
ACCATGTTCCTCGTGAGGTTCATAGGAGTCAAGTGGGATTCGATAGTCGGAAACCTTCAC
CTCCCGACCATCTACATACTTGCTTTTCCCTTAGGAAAATCGGGTATGACTACAGCGGCT
TCATCATCACTATGTCAAAAGCAAAGCACACTCTGGCTTACATCGATTTTGTTTTTTACA
TCGACATTGTTCGCAATCATACTCAAGGTATACTTAACGTACGATTGGTGGATATATTCC
ATTGGTGCTCAACAACAACCACAAGAAGCATTGAATCCAATCATGCTGATCATGAGAGAC
GCCCTCCGATACTGGTTCGCACGCGAGCGATCCCGCGAGCTAGTACATTAAGCTCGGGAC
AGCCCTTGACCATTCAATCATTTTCGCTCTGATATTCAAGAGTTTTCTCAGTCTGAACCG
GACTGATGGAAACCGATCTAATCGGCGGACGTGCCCCTGATGCAATAATGACTTTTGCTT
TTGCTTCTTATCCAGGTCTATTTTATGTATCTTACGTATTAGTTTTTATCCTTTTTTATT
TGCGTTTTCCTTTTTTGTCTTTTTTTTTTTTTTCAAACCGAGAAGGACGGGACGCCT
AGATCATTTGGCAGGTACCAGAACCACATTATTCATGATGCGACGAGTCCAATATTGTCG
GAGCAGCGACGATCAACAAGGCAGGGCTGGCAAAGATCAGGATCCCGACTTTAAGCCTGC
TAGCTGCTGGTGGCGGGAGAGGCAGAGCTGCAAGTTCCAGAAGCGAGATACTCCGAGGG
CTTGTTTACTTTTTTTCCCCGATTGCGTCAACTCCTGCACAAGAACAAGCCGGACCAATG
GTCTATTCCCACGCATGGCCGTGGCACTATCGACCCTAAATGCAGTGGCTCTAATGGTGT
GCCGACGTGTCCAAAGTACAGATCCCTGGGCCTCAGGTACCCAGTCGCGAATCTGAGCCT
CGTTCGCAAGCTTGTATTGATCGTCGAATCCAAGACATACTGGTTCCACTGAGCTGCTAT
CCGGTCGCTAGCACCCCCAAACGCCACCAGTATTCAAATATATTTTCTCATCGGACACTG
CACGGTAAATTACAGCGCTGTGGGCCAGATTGATGGGGAAGTCTTCTGCCATGCTGAGTC
TATGATTCAACTCAGCTGAGCCATGTTTGGTGTCGCGTTGACTTGGCTCGCCGCGATTGT
TGGCAGCTTCGTATCCGAATGCTACTCCTAGATCACTGTAATCAGCTCGAGAGTCAGA
CGCAGTCTGCGTGCCTGTCCCAGTCACAGTGTTCCGCTGCAACACTTCTCCTGTGCCTCC
GTGCCGCTTCGCCGAGTTTCTTGGTCTTGCTCTCTCGTACCTTCTCCTGGATGTTTCTAC
GTTCACCACTTGCATTCTCAAACGCTGGTAAATCACCTCTAGATCATTCTGTCGAAATCT
AGCCTTGAAACGCGACACTCGGTTTCTTTCTGTTCGCGCTGAGCTTTGCGTCAATAATGG
CGACCTTCGACAACCCATTTTATAGTTTTCCCACCTCGCCTTTCACAGAAACATTCTGGA
CGAGTTGGAACTTGGATGATTTCCCCGTTTTACCCCAGAATGACGAATTGAAGACAGATG
CAAGCTGGCAGTCTGCCATCTCGATGCCGGATTATTCTTGTCTGCCCCTCAATAACTTCT
CAAGCTTGGTCCCTACTGGCGATTCAATCTATATCCCACAAATTCCAGATAGCCAATTTG
ATCCCCCAGGTTGGGTACCGCCAGCCGACACTTTTGGGGCTCCAGTGTTACCAGCGGCTT
CCACAGCTTTTCCATGCGCCCATAATTTCACAACCGACTGCAATCCGTTCCAAGACTCGT
CGCACCCGCCGTCCGGCGTATCAACCCCAACCGATCGCTCCTCTCCATCTGAGTCTAGCA
GCAGCCGTCCCTCGCCCACGCCCTCTGCCGTTACCAGGACCAAGCCTAACCGCGACATAA
AAGGCCCTATCCGATGCTGGGAGCACAGCTGCGGCGGTCGGGCTTTCTCTTCTCTTGGAA
ACTATGAGCGACACCTACGCGAGAAAAGTGGACGAGCTAAGAGCTTTACCTGCGAGCAGT
GCGGCCAGCGCTTCACCCGATCGACTGCGAAGAACAAACACATAAAGCACGGCCGGTGCC
GAGCGCAACAGGCCTGATAAACTACCAACCAAGGACATCATCACTTACACTTTATACCCG
ATTTCTTTTGCGAATGCACATATATACATATATTGAGCTGGGATTTGGAGCGACGGCAAA
AATTTTTCTTTTACCCTTGGAATGAGATAGGAGTTGATACAGCACGCAAGCGCTGTGGCT
GGCATGGACTGGCAGGATACTAATTGGACCACAAGCATCTGTAGGGTATTCCACCTAAAT
AAGTAAATATGTAAATAATGCAACCTGTTGCGATATTGTTGCTGCGATTTGGTACAGTTT
AATTTAAGGGGCTCGACTAAATTAAGCTTACTTCAGCGGTGCGAACATGGTTCGGATAGC
CGATGCTAGTTCCGATCTCATGAACGCCCTAAAGGTGACGCTATTTAAACTACCCTTATT
GCAACAGATAATTTTCTCCAGATAGGAGAGGCAGAGCTATATAGATCTAAAGCATATAGG
ATACCAGTAGCATTGAAGGTGATTACTTCAGACATGGGCACGTTCGATTCGAAAGTGCGC
TCAATGATATTAAGATCGTCCAATTTCCCCATAGCGTGAATATAAGGTCGCTGACTGCTG
ATAACAGATATCCTGGAGAAAGAAATAGCACCCTTGATTTATTAGGCTCTAACACTCTAC
GAAGAATAGCAAGCTTGCTAAGATGTTCTTGATTTCAAGACTCCACAAACTGATGTACTA
TATTGAGGATTCGAGGTATGGAGCTGTGCTATGCTAGTACCTGGTCAGTCACTTATGCGC
TTTTCCTATAACCTACCGCAGCCGAATCCATCATTTTGAAAGAACACATGTGTGAGCATC
CAAGAGATAAACATTAATATCTAAGAATAGTAGTTATATATAAACGCGTAGACACATTAG
AGGTAGCACAGGATATATCCCGAAGAATATTGTCGCAAATTAGTCTGTCACAAAGTGTAT
CAAGAGAACACAAAATGTGGTTAGATTTAACCATCTTGATCAATTAATCAATGAAAAAAA
GACATATTGAGTTAATATGAGCAAGATTAGAGCTTGACAACCCTCGACTCCTTCGCCACA
ATTGCCGCCAGTTGCGAGATGCTCCCTGTCCCGCGAATAACCATAAGCTGGACATTCGCA
TGCAAGTACGCCCCGATCCAGTTTCGCAATTCAACAGCAACAAGCGAGTCGACGCCGTAA
CTGTCAAGACTCTGCGCAGGTGAAAGCATCTCCACAGGCGTGACTATAAGCTTGCTTAGC
TGGTTGAGAATCGCGTTTGTGACGATATGGACAGCTTCGTCGAGTTGTGTTGCCGCTGAT
AGGAGAGTGATTGCGTCGAGAGCCTCACCGGCGCTCTTCTGCTTACTGCCGTTGTGCTTG
ACGAGTTGAGAAAAGCGACGGTCCGTCATGAGGAAATCGCGTCCGTTCTCGGATTCGTCG
```

Figure 5E (continued)

```
TCGGAGGCGATGAGCCCGATTGATGCAACGCAGGTGCTTGGGTTGGCACCGCGAGCGTTC
AAGATGGCGTGGTTCAGAACGATGAGGACGTCAGACACACCGATTGACCCGAGCCCGTTG
CGGCGGAGGGCCTCTGCGACTTCCGGGTTCTCCGAGACATATCCGACGTCGCGGATGGGG
CCGATATTGATGGAGAATGCGGGCTCGCCTTGCTGTACCATGTGGCGGACAAACGTGTCC
TGGAAGCTGCACGCCGCGCTGTAATTTGACTGGCCGTAGTTGCCGCGCACAGCGACGATA
GAAGACATCATGACGAAGAAGTCAAGCGATTTAAATGTTGTGTGCAGATTCTGCGATCCG
CGAACCTTGGAGGCGAGAGCAGTGCGCCAGTCGTCTTCTGTCATGTTGTCGAAGAGAGTG
TCGCGGAGGACCATGGCCGAATTGATAACTCCGCGCACAGGCGGTAATTCTGAGCGCTTC
AGCTCTTGAGCCAACGCAACCACGGCGTCAGCGCAGACGACGTCACAAGGTGGTGCAATC
AGATTTACTCCGCGGCCACGGATGTTACTGATGAATGTGCGGCTGTCTGCATCCTTTGCA
CCCGAGCGTGAGAGGGCGACAATGTGCTTTGCGCCATGATCAGCTAACCAGGTGGTAAGC
CAGCGTCCTAGACCACCCAAGCCACCGACAACTATGTACGATGCATCTTCGTGAAGCCTG
GCCTGCTTTGGCATAGACGGGACAGCCTAGACAGATGAGCAAGTTATATTCACGTGTAGG
AAGTATTTGGGACTTACCGGTACTTCTTGGTTCTCTTCCACCGTGAGGACAATCTTCCCA
GTATGCTTGCCAGCCTGGATTTGACGGAAGGCGATCTCAATATCAGAAATCGGCATTGTG
GTCAGAGTCACTGGTCGAATAGAACCAGATGCTGCAAGATCCGCAATGTCATGGAGCAAC
CTTCTCGCCAAGGGTTTCCTTTGCTCAATAATAGCCGTCAAGTCAACATAAGAAAAAGTG
ATGTTGCGTAGGAGGAACTCCATTGGCATCAAAGCATCATCCATTAGATCCTTACGCCCA
ATCTCAACGAAACGACCGAAGGAGGCCATCAAATTGCATGATTCGCGGAACATTTCGCCG
CTCAGAGAGTTCAGAACAACATCCACACCATAACCGCCTGTGGATTTCATGATCTCCCCG
TAGAAAGCTGTCGTACGGCTCGAGAAGATATGGTCGTAGGGAACACCGTATTTAGCGTGA
AGAAGATCGCGCTTTGCCTCGCTTCCAACTGTGGCGAAGACCTCGGCTCCGAGATGCTGG
GCAAGCATGATCGCGGCTTGTCCAACAGCACCTGCGGCGGAATGGATAAGAATCTTCTCA
CCCTTGGACAGGGAGCCCTTATCAACAAGTCCATAGTAGACCGTAGCCCAAACAATCGGA
AGCGATGCGCCCTCTGCGAAGGACAGAGAGTCGGGTATGACCTGACAGCAGTCTCCGTGA
ACAAGAGGATAGTTGGTGTAGGAGCGGGAATAAAGTGCGCAGACCCGATCTCCGGGCTTG
AAGCGGTGCTTCATGTTTTCGCCCACTTCGACGACGACACCGCTGCAGTCGTTTCTCATC
TCCGTGATGCCCTCAAGCTGCCAGCAGCGGATAAGAACATCTTTGAAGTTGATACTAGCT
CCACGTAGTTCGAAGCGAACATCATCAGGTCCGAGAGGTGGGCATTCAATATCGTCCTTC
CAGCGAATGGTCTCAAGTAGACCCGGAACTCCTAGCTCAGCAGTCAAAATTCTGCCCGTA
CTGACGAATGGAACCGGTTCTGAAGCTGCTTGTCGACTAGTCAAATCCACATCTCTACTG
ATATCAGGTCTGTATGCGTAGCGTGATACAAACAGCTGCCCATCCTTTTCCGTGAACTCA
TTCTCAACTTCACTACTGAGACAGTCAAGGTCAAAGCTCGAACTGTTAAGGATTATCGGG
AGAACTTCTTTAAGTTTGCTCATGACTGGCACGTTGGGAGTCTGGATGTCCAATACAACC
TGGCGCAGATTTGGATATTCCAGACGCATTGTTCGGGCGAAGCCAGCCCACAAGCCGGTT
TCTGCATGAGAAGAATCCGCCATGGTGCAGTTGCTGACCAAGAGCACGGCCCGCGATTTC
AAGATCCAGTTTTTGAAAGAATTCCAGACATTCACATCTGGTTCAGCGCATAACAGCTTG
GCAATTTCTGGAAGCAAGATGGCAACTCCCCATGCTGACATGGATGAGTAATGGGCAAT
AGAGCTACCGACGTCTGACAGGCCTGCTGAATCTCTTGCGCCTGCTCTTCTGTGGCGTTG
GATGCATTTGAATCTGTGAGGAGATGGATCGGAAGCGATTCATTCCTCCTCGGGAAAGGC
GCAGTAGATATGAAGACGCTGAGACTGCCGCCATTTTCATGGGGGTAATCAACAAAGGCC
TTTTCAATATGAGCAAAGCCAGCCTTTTCCAATCGCTGACACCACTCAGAGTCCGTAAGA
AGGGGGAGCGCGTGCGACCTTCATCATAGCCAAGCCACCAACCTTCAAATAGGCCAAAA
ACTATGTTAAAATAAAGGGTATAACGAGAGATCTCCATTAGCATAAACTTGCCTCCGGGC
TTCAACAAGGGTCTGATGTTGCGGAGGGTCTCATCAATCCGCGGCGTCGCGTGGATGACG
TTGCATGCGACGATGAGGTCGTATGCGCCTTCCTCAAATCCCTGCTCTTGGGCATTGCGC
CCCGCATCCAAGACGCGAAACTCGACCACGTTGGCAAGATCACCTAGCCGCTCCTTAGCA
GGCTCGAAGAAGCCGGGTGAGATATCTGTGAAATCATAACGCTGGATAAATCGGCCGCTG
CAATCGTTCAGGGCCTTCAGAATCGGCAGTGTGGCTGAACCAGTACCGGCGCCAATCTCA
AGAACCTTCAGTTGCGGGTTGAAACGACCTAGCTCGTGACAATACGCGCTCATCTGCGGG
TATAGTCTTGATGAGCACCATTCAGTATAGACACGGGACAACAAGTTGTTTTTCGTCAAT
AATGACAACGCAGACGTCTTGCCCTTGAGGATATCCACTAGATGCGGTCCCAGAATAGCT
ATTGCCTCACCGATAACTCCAAGGTCTTCGGGTTTGTTCTCGAGTAGTATATTGTCGTAA
GTTTCGTCTGCAAGAGTACCCATCCACTGGAAATAGCGCTGGAGATGGGTTTCCTGAATG
TCATTCAGCGAGATTTCACGTATAGCGTTTTGCGCAAAGTGGATGGTTATTGCATCCAGG
GCACGGTTGGTCTCCATTAGAGAGCCTAACTCAATTGTAGCCCTGCAGACCTGATCTCGA
TGTTCTGTTGTCCAAGCATCAACATATGGAACAAGCGTCTGAGTGTGGCACGCCTCCCTT
TTCGAGACTCCTGCTGCAACGTCACCTCCCAAGCTAGTGACACGGATACCCTGCGCGACA
ACAGCCATTTGGTTAATCTCATCCTTGGTGTGAAGGTCAAAGACTAATGGCTCATTCCGG
CGAATCGTGGAGCAAGTCAAATAGCTCCCTGGAGCCACATGACGATTCGCAACCCAAAGC
```

Figure 5E (continued)

```
TGTTTTATGAAGGTGGGCACGTATGCGGATGAGCGGCCATCTTCCAAGTAGATCACAGTA
GACAGACCGTGGAAGAGGGCAGAGTCAAGCACGGCCGGGTGGAGCAAATCCTCCATTCCG
CCTGATGGCATCTCGTACTCGGGAACGCGAGCAGTGGCAACGCACGAATGCTTGCTGCTA
CGAATTTGGTGCAAGTTGTTGAAAGGGTGCTGCCAATCAAGGCCGTTTCGTTTGCCAACG
GCATAGAACTTTTGTGGTATGGTGCCATGAGTGCACTCTGAGTCGATACGAGAAATATCA
GCAGGCGTGAATATACTCCTGAAACCTTCAACAGAGTCAACCTCTGCCTGGACGAGACCG
CGACAGTGCTCCGTCCATTTCTGGTCGGGTGTCACGGTGAAGATACGGAACTCGTTCCAG
ATACCTGATGACTCGCGAGCGGTTCTCGCTTGTGGACGCAGAGATAGCGAGATCTCGACT
TCGGCGTTCTCATCAGGTAGCACGAGGCCTTTCCCAAAGCTAACATCACGGAGACGAATA
AATTGAATTGTAGAAGCTGGATTGGCTGTGTGCATATGCTGGCGAATGGCCTGGATTGCC
ATTGTGATATAACCTGCCGCAGGGAATGTGATGAGCCCTTGTATAATGTGGTTACGGAGC
CAAGGGGTTTCCTTGAGGCTGACGAACCGCCGCCAGCGGGGCTCTAGTTTGTTAACATCT
GCAGAAAGGGTTCCAAGGAGTTCATGCGGGAGATGTTCTCGGTGTCTATAGTCCCTAGAC
AGGCGGGTTTCGTGCCAAAAGCTACGGTCATGGTCGAAGGAGTAAGGCGGCAAATCAGCC
AGTGGCTGGATGTCGCTATCCTTGGAATCCTTGTTGAGATCACAGAGACGAACCGAGCCG
TTCTTGATGGCCAAAAATCCCAGGCATCGGAGAAGAGCGGTTTCTGCGTCATCGCCACGC
TTCAACGTGTTGGTGTAGGAGGCTTGGCCATGGGGCCCTGGAATTGTCTTGAGGATCTGG
TTCACTGGACCACTGAGTTGAGAATGTGGGCCAACCTCGATGAGCGTGTCAATGGGCAAA
CCATTGTAGTCCTGCTCACACATGGTTCGTAGTGCCTGCGAGAAGAGGACTGGACTGACC
AGGTTCTGCGCCCAGTATCCACCGTCAAGAACAGTCGATTCGTCCAGCTCCTTGCTTGTG
ACGGAACTAAACATGCGGATAGATGAACTAACGGGCTTGGCTTTCAGACCCTTGAGCGCT
GCAATGTACTTGTCCTCTATTAATTTCATTTGGTGAGAGTGATAGGCAGCACCGTGGGTA
ATCAGCTTGCGATTGAAAAGCCCTTCCGTATCCAAAACCTCCTTTATACGGTCAATAGCC
GCTACGTCACCTGATACAGTGACACTGGATGGGCTATTGAAGCAAGCAATGCGCATGCGT
CCAACATCAGTACCTAGCTTGTTGATATGCTGCTCGGCAATATCGGGCGGTGCACCAACG
GCTATCATAGCTCCTGGGGATTGGTTCTCAGCAAGGAGTTCACTGGCCAGCTTCCCACGG
TAGTATGATACACTTATGGCATCTCTGAAGGAAAGAGCGCCTGCAGCATATGCTGCCCCG
ATTTCGCCGCTAGAATGGCCTAGTACAGCCGAAGGCGATACCCCAAATTCGTTCAGAAGG
TCGACCAGGGCCAGTTGGATAGCCGTGCACATTGGCTGAGAGAAAGCTGGCTCGTTCACC
CGAGAGTCCGCTTTGGGCCGGCAGAGTTCGCTGAGAAGATCCCACGTACAGCCCAGCCTT
GACAGCTGTTGACGTGCACGCTCAAGAGAGCGAACGAAAGAGGGATAGCTTTTGAGTAGA
TCGCGGCCCATCTCGGCATATTGCGCGCCCTGACCGCTAAATATAAGGGCAATGCGATGT
TGCCCGAATTTCTCTCGTCTAGTAATAGTAGAATGTGAGGCAGTGATTAGCTGTTTGATT
AATTCGTCAAGTTCTGATGCGACAAAAATGACGCGATAAGCATGAATAGACTGTTTAGCT
AGGGTATGGGCTAGACGAGCGAGCAGGGCATCAGGGTTAATGGAGTTTCGGTGATTGACG
ACAAGATACCTAGCCAGCCTGGCACACACCCTCTGGCAAGCTTTTTCGCTTGCGCCGCTC
ACCATGAAGACTCGCGGTTTCTCGGAGTGATACGATAACTGCAGGTGTCTGCTTAAAGAC
AACCGCCCAAATGCAGAGATGGCCTCATGAGCTGCATCTATAATTACGTGGGCATTTGTC
CCGCCATATCCAAAACTATTCGCCGTTAGTACATTTTGAGTAGTTAACTCTGAATCGCTA
GCATACCTATTAAGAGAGATGCGACGCAGTGTTTGCCTCTCAAGTTTTGTGGGGATCTGG
TAGAGTCAGTGTTGTCATGTTTTCGACAGAATTCTTACGTACTCGTAAATTCCACTCCTC
CAGATGGATGTCAGGGTTCGTTGTCTCATAGTTCACCTGAGGCGGAATCATACCGTTCTC
AAGCATAAGAACGGACTTGATCAGCCCAGCGAGACCGGCGGCACTTTCCGTGTGGCCAAT
ATTTCCCTTGATGGATCCAATGGGCAGAGGCCGGGAAGGCGACCTCCTTTGCGTTAGGGC
CGCTGCAATAGCGCTCGTCTCGATTGGATCGCCAACCTTGGTTCCGGTGCCATGGGCTTC
CACATAGTCAGCATACAAATCCAGCTTTGCCTGTCTGTAGGCCCTTATGATGGCTTCTTT
CTGGGCAACAGCGCTCGGCACACTGATACCAGGTGTCCGGCCGTCCTGGTTCAGGACAGA
GTTTCTAATAACAGCCCGAACAGGGTCACCATCTCGCAGGGCAACTGATAATGGTTTGAG
AACAACACCCGTGACACCTTCACCTCGTCCATATCCATTAGCACGAGCATCAAATGGAAA
AGATCGACCGTCTTTAGAAAACATTTTAAGCCGGCTCTGGTAGTGAAAGCGTTGTGGGTC
AAGAAGTAGGTTAACGCCTCCAACAAAGCACTGCGTGGTTTCCCGGTTCCGCAAGCTGAG
GACCGCTTGATGTAACGCCACTAAACTTGACGAACATCCAGTATCCACTGTGAAGCTGGG
CCCGCGCAAATTGAAGACATATGAGACCCGATTGCTTGTGATTGCAGGCCCGGTGCCTGT
CACAAGGTATAGAGGTGGTCTCTCAATATCACGAGTAGCTATCTCGTGGTAATCCGAAGC
CCACTGACCGACGTATACACCGGTATTGGATCCCCACAATGCATCCATCGTGATACCGGC
GTTTTCAAAGGCTTCGTAGGCTACTTCGAGCATCAGGCGTTGCTGGGATCCATTGCCTA
ATTGCAGAGGCGAAGCGTTAGAATCGCATTCGATCGCTAATTTGAGACAAAGGCCTGCGC
CATGCATATTTTATACATACCTGTGCCTCGACAGGGTTGATCCCGAAAAATGTAGCATCA
AACTTTGATATATCTTCTCGAATGAAGTGTCCTCCTGTGGCATTTGTCTGAAAGAAATG
AATCAATTTAGCACATACTCTTCTTGAACCATCAAGCGCCGCTTACTGTTCCAGACCTGG
```

Figure 5E (continued)

```
TCCCTGTCGGGTCTTGGAAGGCCTTCATGTTGAACCGTGTCCCAGGCCCTGGTGTCCATC
CCGAGCGACCAGATTTCAGCATATCCCAAAGCCCAGAAACGTCTGTTGCGCTTCCTGATA
GTCGACATCCTATACCAATAACTGCGATTGGCTCCAGTGAGCCGGGGCCAGCCCTTGTGC
TGCGCTCATCAGATGTATTGCTATCATTGTCGCTGAGTATAGACCACGGCGAGGAAGAAA
GCCTCTCACTGTCTGACTCGCTATCAGCGATCTCAACACGGGACCTGGATGCAGGACTCA
TGGCTGTAGAAATTAGGAGGTACGGCTAATCGTTGACCGTCTGAATAGCATGGGGTATCG
TGATCAAGATACGGGATGTTTGAAGAAAGATACAAGGCCAGCGTTAAGTACAGCACGCAA
TACCAGGGAACGAATCCTCGGTTCTAATCCGTCATGTCAGGTCCACCCAGGGCATGCCCA
GAAATCGAGTTACCATTTTCATTACGTGCCATGATCGGGGTCGTTGCTAGGGCTTTTCCA
CCAAGGGAACTATTCTCCCTCCACGGAATCACTGACGGACAGATTATCTCGGTGGCGAAA
CTTTCATTTCCTGCAGCGCCCGAAGTATGCTATATCCGAGATACCCTTGGACGTGTTCGT
TGCAGAGTGGTCATGGGGAATCACGGGCCAATCACTACCGAAGAGAACAGGGTTAGCCCA
CTATGACGAGACGAAGGAAATAAAAGGAAGGTAGGTTACTCCGTAACTCCAGAAGAGTCA
AGACAGATCTGCGATGCCCAGGCCATAGGACCGGCCGAACTACTTGCAGACGATCGACCC
GCCATTTGACGCGAAGGAATCACAGATCGACAGGCCTAATCTAGGCGAAGGAAAGCAGAG
TGGGCTCTGCTGCCATGCGATCCTATTCCCAAGAATGGTTGAGCGCTAAGCTGCTGGATC
TGCATTGATACTCGGTTACGTAGGATGTTGTCAGTATGTGACTGTAGGGTGTAGTGGAG
AGAAGAGGAACCTGAGAGGAACCTGGGAGAATCGATATTTGGCGATTAGGCTTGGCGTTG
CATTAGGCCGGAACAGTGCGTCGCGTTATGTCCTGCTCCAAGCTTCGCGCTCCATATATG
CTCTTGTTTACCTATACAACTCTTTTTTGCAATGCAAAGAACCCGGTCAATCAAGCATC
TATACAAGCTCTATCTTGACTTTGGGACTGTGACCAAATCTCAGGGTTTTACTCACAATG
GAAGAAACAAACGTCAAGCTCAGCGTACCTCTAAGCGAGGACGTGATCAAGCTCTCGGCT
CTAGATCAACAGATAATGCGATTCTATGCAAAGGCCGTCTTTATCTTTGAGCGCGATTCC
TCAAAAACCTCGATTGACATTGTTCACCACCTGAAGCAAGGCCTCGCCGTGACCTTGAGC
GAGATACCTGACCTCGCCGCGACCATTGCTCCAGTCCCGAATTCTCACCGCAAGGACCTG
GAGCTACGCATCGGGCCCAATTCGGGCGTCCCTTTCAAGGTCGTGGATCAAACAAAGCAG
GAATCTTGGGTATATGGCACCTACCCTGATCTGGCTGCGAAACACTTCCCCACCAGTGAT
ATTCCTCACGATATCCTCTTCATCCCACAGCCGCAACCAAGCGCGGACGGACTGCCTGCT
GCGTTTCTGCAGGTCAATATTATTGATGGCGGAGTTATCATCGCGATCTCATGGCACCAT
TCAGTATGTGATGCGAGAGGCATCAGTATCCTGATCGATGCCTGGGCCAGGCATACAGCG
ACGTCGCTAGCAAACGGCAAACCCGATCTGCCTGCGACACCAGCAGAGGGCAGCCGTGAT
CGGTGGCGATTAGATCACGGCCTGCGAGAGGTTACTATTGACCAACTTCCCGAATACACG
ATTGATAGCTCTGCCCGCGAAGACCCAAGCGGTTCCTACCTGCTCGACCGCGAAAACCCC
GTCACAGTACCTTATTCTGTAAGCACCTGGTATTTCAGCGCATCATCGCTCAAAGCCCTC
CGCGATGCTCTCGCACAAGTCGAAAACGACGAATCCACCCAGTTCACTAAAGTCGAGGCC
GTCTCAGCCCTCGTTTGGAAACACATGAGCATCGCGCGCCAACTGGACAGATCCAACCCG
GACGGTTCCTCGCTCTTCACCACACGCCTGGACTTCCGCGCAAGAACAAAGCCACCCTTT
CCTGATACCTTCATTGGAAACATCAACGAGCCCACAGCCCGCGTACGCTTGCCCATAGCT
GAGATCTGCCGCGCCTCCACCCCAGAATCCCTGACGACCCTAGCTGAAGCTGTGCGCGCC
GCCACCGAAAACACTACCGAGCAAAGCATGCGCACGCTCATCGGTCTAGTCAACGACGCG
CCTGCGGTCACCGATGTTGCTTGGAAATATAACTACTTTCCCGGCCCTGACCTGGGTGTA
ACTGATATCTCGAATATCGATGCCATGAAGAAGAACTGGGGCGCTGGCTTGGGAACCCCA
ACTTGTGTTAGGTCTTATTCTAGAGAAACGGGTCTACTTTACCTGTTTCCGCAGGATGAT
GATGGAGGCTTTGAAATTCAGGTTCAGTGTGAGGTGGAGGCTGTGGAGAGACTGAAGGCT
GATGAGACTTTCACAAGATATTGTGAGTTCAAGAGGGCTTCCGCGTATAATGCGTGAATT
GGTACAACTGTAAAGATAGGCTCTTTTTTATATTTTCTTTCGATATTTATTTTTTATTT
CGGACTTTGATATACATTTTATCGTTAGTAAATTATGAGCTTTAATTGAAACTAATGTTG
AGTAATCAAAATATATATATTCTTACTGCATGTTGCGAGCATAGGGCATTGACCTTAGGA
AATGGACCTGTATGTGCATCAAAGCGACCCTGCAAACATCACTTGGAGGTAGATAACCTA
GTCCACTAGCAAACAGGTAAGTCCATATCGTGCTCTCATCTACTTGACATATACTCTTAG
CACTATGTAAACTACGAACAGTGAACAACCGCTATCGGCGGAGATTCTGAGCTAGCCGAA
GTTAACCAGTTCAGCATTCCACTAGGCTACGCTGGCTCCATAAAAGCTGTACCATAGAGC
ACGACAGGCAGTCCTTAGATATAATCTTTATCATTCATTTAGTGAGCATGTATCTACCCA
ATTAAGATTAAAAAGTATAGATATTCCTCCTACGGGATGGGTTTAGTTCATGGCCTTCAA
ATCCTTCTTCAACACTTTCCCACTCTCACTCTTTGGCAACTTCTCCAGGAACACAATTCG
ATCGTGAAGCCAGTGCGATTCATGCAGCTTTCCCTGCACAAATTCGTCAATCTCGTCAGC
CAGATCATCCTCGTCCAGATCTTCCATCACGGTCTTCGAGCGCACGATGTACGCTTTCGC
ACGCTCGCCAGAGAGCTCGTCCGGAACGCCGATAACAGCTGCATCGATTACGGCTGGGTG
CGAAAGAAGGACGGACTCGATGTCCCGTGGGAGGACTTGTTCGCCCTGTTTTGTATTCAT
TAAGTTGACCTTGCTCATATATTTAAAATTCCATTCAAGAAACGACGTACCTTGACTTTG
```

Figure 5E (continued)

```
ATCATATCCTTGATGCGTTCGAGAATGAACAGGTGAGCGTGTCCGTTAGGCGATTTGCGA
AAAACACCGATGTCTCCGGACTTAAGCCACCCCTTTTCGTCGAAGGTGTTCTTGTTGGAC
TCGTCGTCGCCGACGTACCCGAGGAAACAACTGGGGGAGTTGAAGTGGACTTCGCCGGGC
TCGTCGAGGCCCTCTGCGTCTGTACCGTCGGGCTTGACGAGTCGGATCTCGAAACTTGGA
AGGAGGGAACCAGAGGAGCCGTGCCAGACATCGTGTGGGCTTGTGAGAGTTGCTACCACA
CCGGTTTCGGTGAGGCCTATTTGTCTCATATTAGCCGTTAGCTAGCGCTAGGGTTATTGA
CAATACCGTATGCATGGTTGATTTTCCACGTGGGTCGCAGTTTATTCAGTTTCGCGGCGA
TACTACGATCGAGTGCTGCAGCACCAGTGACGGTCGCTTGGACGGATGAGAGGTCGTGGA
GGTCAAGAAGGAAGGGGTTCGCTGCTAATGCCGCAAGGATTGGGGGAACCTGCGCAATTA
GTTTGGCTTGCATTCCTAGGCCTGAGAATACAAACCACGTATAGTCTTTCGACGCGGAAA
CGCTCAATTGTCTTGAGCATCAACTGCATATCGAACCGGGGCAGATAACGTAGGTGTCT
CCGCGGTAGACCATGATGTGCCCAATGTTCAGTCCATATCCATGGGTCAACGGAATCGCG
CCGAATGCGATCTCGTTACGGCCATTCTTAGCATAGCTCTCGTGCATGCACACTTGCATG
ACATTGGCAATGAAGTTGTAGTGTGTGATTTTGGCCAGTTTCTACAATTGCCCGTCAGCC
ATCATCTCCATTCCCGAGAAGAGCCACCGACCTGCTTCCCTGATGTTCCACTGGTAGCGC
AGTAGTATGCGACCTGTATTTTGCGCGGCCTTTCTCCCACTGTAATGGTGGAAGTCGCT
GCAACTTCTCACCCTCAGCAATCAGTTGATCTACCGACTTGAACTGGTCAATCGGCTCGG
GATTCTGAAGATACGCTTCGGGTAATGCCGTGGTATAGATCTTGTCTCCGGGAATAGACA
GCTCCCTGGCAGCTTCCAAAGTGTTTGCAACAAGAGACTGACAGGTGAATATGACTCTAC
ATTTTGCTCTTTTCATGTGCGCTACGACCTCGGGGACGATACTAAACGGATGGAGCGGGA
GACAGATCCCATTGAGACGATGGACGGCCAGCAGAGAGCAAAAAAGTCAAGCTATTTTT
TTTTCTTCATCAGCTTATAGCAAAGGAAGAGCAATGCAAACGAGTGTCACCGACCGTATT
CCAGCTGTAGATACCGACAACTTTATCCTCCGGCTCCCCCTCGTTCGGCGACCATCCCAG
CTCTTGCGCAAGTGACCGCGACAAGAACTCTACTCGATCAACCAGTACCTTAGTCGAGTA
TGACTTTCCGGTAATTGCGCAGACAAACGGAGGCCGTCCGCCGCATTGCGGGGGAAGACT
GGTGTTTCCTTCCAACGCAAACTGGCCTACAGGAATAGAGTCTGGGATTTCGCAGGGGAT
CCGTGGCACCCAGGAGGGAGAAGAGAAGACCATAATGATAGAATGTAAACAAGGGACTTT
GACAAAGAACGTAGAAGTTAACTCTCTCGATGGCTGCCGTGGTGTTCTAGAATGAGAACC
GCCCTGAGATGATCAACACTATCGCCGACCGGTGCGTTCAGTGAGAATTCATTGATTGCC
GAACGGTTCCATAGCCGAAGGAAGCCAGCTTGAAGCTAGCTCTGGCTCCGCGATACGTCA
CATCTGACTAGATTGAAAGAGTATGAGTTGGAGCTGTGATCTGCA
```

Figure 5F

Sequence of the deletion of Dehydroaustinol of the Austinol/Dehydroaustinol cluster

>ChrVIII_A_nidulans_FGSC_A4 COORDS:ChrVIII_A_nidulans_FGSC_A4:54064-88319W (34256 nucleotides) (SEQ ID NO:6)

```
TCTTGACCCGACGGCTCGCTTTCCTAATACTTAAGTTTGTTGATATTGCTTAAGAGACGA
CGCGATAACTCGAGTTATGGTATTGAGAGCTACAGATCGGATACCTTGACCCGGAAGGGC
CGATGCCTAACAGCTCCACAGCGGCATTCCTCATAACGGCAGCAAGAATCAAGTCTGCGT
ATACGAGCATGATCGAGGACATGTGTACATGTGACCGTCAAGTATGATTCTTCAAAAACG
ACATTCGCCCTCCAAAATACACTAAGCGCTGGAGATCAAGCCAAGATGCTCCCCAATATC
CTTCCCATCGTTACCCCAAAAGTGCACCGTATCAACATCACAATGCTGGGTTGAACTGCG
GAACCCAAACATCGCCTGCGTGCGCGGCGACAACTCTGTAGCAATTTGCATCGGAATCCA
CAACGGAAACGCCTGCACAGGGCGTAGTTCTCGGCGGATCGTGGAAAACGCCAGCGCGCG
GCGCTGGTCCGAAAGCGTCGCATTGTGGCCGGCTCCGTGAATCACCTTGCCACTCATCAT
ATAGCAATCACCAGGTTGCATTATGGCAGGCACAGAATCGATCTTGCCGTACTGCGGACA
ATCGGTCGCGTTGATCAGCGTGAGCTCCGGCCAACGGTTGCTGCCCGGGACGAGACGGGT
GGCGCCGTTCTCTACGGTGAAAGGAGTTACGGCGCAGAAGAAGTTGACGAGGCACTCGGG
AGCATCTGGGCCCATGGAGTTCCACCACGGGTAGAGCTCCTGGTCGCGGTGGAGGCGCTG
CGCGGGGGCGCCCGGTTGCACTTCGATGACCATTGTGTCGTTGAAGTGGTAGCCCATGCC
CTCGCCGGGCTTGCTAAAGACGCGCTGGAGGAGTTCGTGCATGAGGTCATTCTCAAGGAT
CTCGTGGCGAAATGTCGGGCTTGTGGTGACGAGCTTACTGAACCGCTTCACGCGGTCGTT
GCTGTTGCCGTCGTTTGTAACCTGGACTTGGATCTTCTCCATAGCGGGCTGGATCTCCTG
GCTGAAGCGGGCCATTTGATCCGGCGGGACGAACCCCTCGATGATAACGCAACCATCTTC
CTTGAAGGCCGCGTAAATCTCGTCGGCGGGGCTGTGGCAGGAAATTTCTGGAGACGGGA
TGGAGTAGCTGAGCCCATTTTCAGTGTTACTTATTTCCGTTTTATACTCGAAATGAGGAT
CAAGAAAGCGCGGGATGGAGATTTTAGTGGTAGAAGGCGAAGGATGATTTAAGAATCACT
GGGAGGCATAAAAGTATGCACAAAGATTGAAAAGCGGCTTCGGTGTCCGATATGCAAGGG
TAACAGCCCCTACCTTCCAAGTATAACAAGAACGAGAAGAAGCTAGGGAAGGGCTAAGCA
ATGTAGCACAGGATTTATGGTGAGCAATATCAGAGCTCAGCACATAGCAAGTAAGGAATT
GTCCACGACACCAACCGGCAGCCTACGTAATCACTAATGCCAGCAGATATATCAGTGTAC
CAAAGGCCCAGCATCACTATGACCCCAATCTCTGTTATCCTCGTCACTGATAATAAGCTG
TAAGTTTTCATTAAGTCCTAAGAGCCACATGATTGCCCTACTGACAGGACAAGGCCCAAA
ACCATGTCCACCACACGAGAAAAGCTCCTCAGAACAACCTCCAGATTTGTCTCAACGTTC
GGGTCCTTTTGACATAGAGGAAATTCTCTCCATTCGCACGCCAACATGCCTTTACCACCAG
TGCTGCCCCAGCTTCAACAAAAATGTCGTAACGAACGAGGAAACCCGTGCGAACTTCCCG
CAGTTCATCGCTACTTTCAAACGATTTGACTTTTCCATCATCGAGCCAGACCATACCCTT
GTCGATGAGGCTGCTAGGAGAGTGATGATCCGCGCTAAGGCTTCCGCAGAAAGCATTGTT
GGAGCCTATGAGAATGAGTACATCTTTATTCTGAAGATGACGGACGACTGTAGGTTTATC
GAGGAGATCTACGAGTTCTACGATACCATAAGGCTGAAGGATCTCCAATACCGGTTAGAA
GCGAAGCATATCTCTTACGGGGATGCTGCGCCCTTTAAAACGAGGGATACTCAGTTATGA
GAGAGCCCATTATCTGGAAAGGGGCTCATAATCACCGGCAGATGGTCAGATTAGGGTTAC
TTTACGAAGTTCTTGGAGAGATGGATAGGTAAAGCGAACATCAGAACCTTATGTTGGATG
CATTTGGCAGGATGACTTCATTCCTACTGCGCGATGACCACTGTACTCATCCTCTTACCC
TCCTAGCTCGACTGGCTTACTTTGAGCAAAATAACAGGGTGCACCAATTATCTGTTGAGG
TCGCGTACATAGATCGCGGGAATGAATGCGCGGTATCGAGAAAGGTCACCGCGCTATGAT
AATCTGGCCGACACGGCGGGATAAATCTCTTTCTTGAATCTTGACTTATAGATGTCGCTT
CATTCCCCTGTAATTGTAGGCAAAGAATACTAGAGAGGAGAGCAAGCAAACAGGATTG
AATTGGGATGATACTTCCGCAAGGAGTTCAAATGCTATGGACGAACACAGACCGCCACTT
ATGCCTCGGTGTTTGGAATTCTGGAGGACTGAAGATGGAAGAATCCGTGCTGCATGCCTC
TAGATTCGGCGACGGCTCCTTGCGTGTTCGCGTCTTTTGACTCTGATCCACAGCGAGCG
CGTGGCTAAGAGTTGTATGCCCATCCCAGGACAATATCGGGCCAGACTTCAAGACCAGAA
TCATGAAGGCAGCAGCCTGCAATTATTGCTGCATGGAGCGAGTTGAGCGCACGCCACGTC
CGCGTCCACGCAAACCTACAACTGATCAGCAACGGCATGGATAGCGTGATGCGCATAGGT
ATCTTACCAGAAGATCTATTTGACACAGTACTCAAAAAGCCGCGATCGTCTCCACTATGG
TGAAAGCATCGTATTTTATTATTATAATCATTATTTGTTCGCGTCAACAAGCGTCCTGCG
AAGCACCCCAATAATTTTCCAACAACCCAATAGCGGACAGAAGACAGCTAAGAATAATAA
AAGAAACGACTAGAGGTCAATTTCAGATCACTATCTCCTCCTTCCTTCGGCGGACACAGA
TCCTAGCATCGGGATTCGTGGCTAAGAAGATCCCCGACTTGCTGGGTGCAACCGCGCCAT
```

Figure 5F (continued)

```
TATCAGGAAGTTTAATGTCGTATTTCATAAGCATATGGGACAAGACAATCTTCAGCTCGT
TGGCGGCAAAGAATCTTCCAGGGCACGCGTGTCGACCAAGGCCAAAGCCTAGATGTTCTG
GGGAAGCCGAAACCAGGTAGGCGGAACTATCGCCCTTTTCACGCCGAGTGGTAAAACGGT
CAGGAACGAAATCATCAGGGTCGGGGTAGATATTGGAGTCTCGCATGGCCACGTTGGCGA
TAAAGACTGTTGAGCCTTTGGGGATTATTGTTCCGTCTGAGAGTGTGATCTCGCGCGAGG
CGTATCGCCCCATCGTTACTGTATGCATGGCCAGGTTAGAAAAGGAGGGGATCAACTTGT
GAAAAGAGGGTGATAGAGGAAGCTTACCAGTTGAGGCTGGCTTTAAACGTTGAGACTCTT
TCAGCACACTGTCCATCAGTTTAAGGTTGTTCAAAGCGATCTTATCCCACCCCTCTCCCT
GTAGCGAGGATATGATTTCTTTCCGAAGCTCCCTGACCAGAACTTTCCAATCTGGTCTCA
TGCAGAGGTCAAGGAGGACCTGCCCCAGGAGGTCACTGGAGGTATGGAAAGAGCCGATGG
CAAGGAGCATTTGGGATAATATAGGATCATAGGGTTGACCTGTACTGCGAGACGTCTCGT
CGAGCCATTCTATCGCGTCGTTATACTCCCTTCGATCACCCTGGCTCTGGGCATGGCGCC
GTTGCTCAAGGACTGGGACAAGAAGCGCACGTGCATCACGGATATATCGACGAAGCTGGC
GGCACGATGGTTTTAGACGGGCGATGAGGGGTCGAAGTATCTGAGGCCAGAGGTTGAGCT
CTTCGGCTGCTGCAAAAGCCTCGGTGTTGTATGATGTTAGGATGCGTATCCAATCCGGGT
TGCGCCCGAGGTCATCGCCAACGAAGACGAGAGAAGAGAGCCGCGACAGAATAAACAGAG
CCGTCTCATGCGGGCTCACCTCCACCCAGTCTAGTGCGAGGTATCAGTAGAGGTTGTGTG
ACAAAAGCGGGCGGACTACTGATGGACTAGATACCTGGTGCATCTTTCCATTGGGATTGT
AGAAGAAGGGGAGTCTCGCTAGTGAAGCGGCGTCAATTTTGCTAAGAGATTTGGTATA
TCAATATGGTTCATCCGAAGGCGAGAAGCAATGAGGTGACGCTATTCTAGGACGAACACT
TACTCAGCTGCCGGGTCAGTCTCGTCCTCACAGACTCAGAGATGACATCACTGGTTCCCA
GTTGTGCAAACACCTCGAATCCATTAATATGGGAATTGAACTCGTCTCCAGCGATTGGGC
CGGGGTTCAAGTCAGGATGCTCCGCGATCTCATGTGCATACGATGGAGCAAGTACGATGT
TGACTCCATCTGGGGCTGCGATCCGAAAGGCACTCGCCTATCTCTGGGCTCAGCGGTTAC
TACTATTTGGAGGATAGATGAGTACCTTGGAAAGCCCATCTGCAACTAATCTCGGTAGCT
CTGTGGTAAATGTCTTCCGTGAGCGATACCCTCGTAGTATACCGATGCGCCCCTTTCCGG
GATTGATCAATGGCAAATCAGATTTTTTCCGAAGAGGATGAAAAGAATGATTGTAACCG
AGAAGAGTAGTAGGAGCCAGGGGAGCCCGCAAGTAACCAGAAAGCCGTTAGGAAATCTAA
GGCTGTTTGGAATCCCAGGCTCATGAGATGAACGAAAGAAATGTGTCCGCAACTCTGGAT
TTCCCATTGCCATTGTAGCTCTAGAATTTTGACGGGGGACGAAGAAAGGATTGTTAGATA
GACGATCACAAATTCAGTGCAGATATTAATATAGTCTTGCACTTGAAACTCGTGTAAACA
GTGATTGAATATGTCTTGTTCGCATTCCCGCTGTGTATGAATTAAGTTACGAGCCGTACC
TTTTTAGTTACGACAATTCCATTACTAGGAATATATCTCTGGCCCTCCTAGGAATCACAT
ACTTCAGTATTACAAGCATGACTGTGAAATGCAGGGATTGCACTACCAGGAAAAACAACA
TATGCTCACGTCGTAGCGTGCCTCTCATGGCATTGATTCTTCCCAATGAGGTGTGGCTTC
CCATCCATGCCTCAATGCTGATCACTTTTGTGCAGCGAAGCAGGGGCTAATATTAATCAC
TAAATACGGTGTGGTTGGTCAACCTATACGGAGGGATCAGAACATAGTTGCCTTCGTATC
ACCGTACATCAGCCTACACTCTTCTTGCCTTATCCAACCGAGGCGGCAGACCGCAGCCCG
AGGTATTTCTCATTGTACTGGGTTCCATCATCTGTGAGCCATTCCCAAACACAACCGATC
TAATTCCTCGCCGAGAAATGCGCCTCAATTTTCTTCCCCCATGCATCCCTCGTCGCCGAA
TCTGCAAACTGGAAAAAGTCCTCCACCATTGTTCCTTCCTCATTAATCTGCAGAATGTAG
ACGTACTCGGTCTCAAATCGACCAACCAGGGAGTCCCCCTTCCCCTCAATATGCAGTACA
ACCTTCCTCGCAGGCTCGTCGATGACTGGCTCCGCACCGTCCTTGACGCGTAGCTGGAAA
TTGTAGAAAAATCCTTTAGCCCTTGGAAGTCCGCCTTGCTTTCTTCTTTGGTTTGCAAA
GCTGGTTTGCCGAGGCTGGATGGAAAAGAGCGGAGGGTGCAACTGGGTGACATGAACGAT
AGGACTGATTCGACGTCGAGTTTGGCGAACTGACCCACAAAGTTTAAAGCCGTGCATAAG
AGCTCATCGCGTGTAGGAGGCATTCTTTCGGTGATGAGTTGAGGTGATGGATCGAGTAGG
GTAGAGCAAAGACAGATGGGTTGGTCAGTACGGTGGAAATAGTTGTGCAACCGCTTATTT
AACAACTGCTGCCCCATACAAACTTACTGGGCCTTCTGTTGTCATTGTATTAGAGGTCAT
CCCAAGATTGCCGACGATCATGCCCTTGCTTGGTTCCCGGCAAGGAGGAAGTTCGGGAAG
GTCGTCTGACAAAATTTGACAAAGGATATTTGTCTGTTTGCCCGCAGTTCAATTATGCGC
AGCTTTTCTGCTCGGTGGAATAAACAAACATACCATGACCATTGTGCTGGCATTAAGGCC
ACTGTAAGGGCTCGTATGACCCCAAGTACGCCGCTGGCAAGATACATACTTGTGCGTGCA
CTTTCATAGCCAGAAACTCCAGACTTGCGGATAGAAAACTCTAAAGGAAATCCCATGCAC
TACGAGCAATCCGTTGATTTTGAGTCTAACCGACATGGTCGACAAGATCAGCGTAATTGA
GTTGAAACGCGTGAGTTTTGATAGAGAAGCATTCTATGAGAGTGGTGTTTTAGTATACC
TATCCTGTTCGAAATACATAATCCAATCTAGTCCCAGCGGATCTGATTGAAAGTAAGGAG
GGACTTTCTCTGGTTGACAGGCCGCATAATGTGGCATAAGCCAGGTGTCGGGCATAGCA
GTATCCGATGCCGCCTGCCCTTCGGGTGGTGCCCGTTTAGTCATTATTTAGTAAGCTAGA
TTTATAGATCGGCGGCCACGTAGGCCATCCAATAATGTCAATGGTCCTTCACCGGGCGTA
```

Figure 5F (continued)

```
CACGATGAGTCACATGACATTTCCTTATAAAAATTTGTCGGCTATTGAGGTGGTTGCTAG
CGTCGATTTTTAATCATGTGATTGATATCTGTAATGAGCAACTGTATTGAAGGTCTTAAT
TTCCTAACTACAATCTGTATAGGCTATTTATGTCTTTTCAAAGGCTTCAAAAGAATGTTC
TCGATATCGGTAGATAGTTCAGGTTGTATAGGCAGATGTGCCTGTCATATAGGCAATATG
ATGTATCAAATGAGCGGACGAGCGAGGTGCTGTATGTTGATTAGTAAGGAGAGGCTATCT
CCGGTCGACAAAATTCAATACAATTATACTTCACGATAATGAGGCATACATACACCTCGC
CGGTGAAATCCTGGAATCAACATCTCACAAGAATTGCTCAAGCTCCGACAGGTGTGCTGC
TACACGTCAGCCTTGCAGTCGCATGGGCCTAGAACCTTGCTTTTCCTTGCTCCAATAGT
GCCCAACGTAGAGCCGGCTCATTCTTGAAGCAATACATCGTACTCTCGTCCAGCGTTATC
CGCACATTCCAGGGCGCGGAACCTGCCACATCCGAGCTATTTGCGCACAAGGGGAGAATT
ATACAGGACCCATTTACCCACGGTATTCCGGTTTCGAAGGCCTGGATTTCCCCTAGCTCC
GCTCCAAATTGTAGCTCGTATGTCTTGATGTGTCTCAAGCTTGAGACGATAGCGCAAGCC
GGGAGGATGTTCACAGCCTTCTGTTCCTCGTGGGCGTTCAGAAAGGAACTTAGCGAGTCG
ATGTAGGATTCGCCGAATCTCGCTAGTTTGGCCCGGATTGTATAAGCCGTCTTTGCGATG
GCGAGGAAGAATGACGTGTTCAAACCGGTGGGTACTTCTCGGACTGCCCGATGGAAGTCT
GGAGAGGCGTGTCGTTGAGAACTGACCTCGAAACGTAGCGGGATAGCAGCGTTCCCCATG
TAGTCATGGGGGAGAGGAGGTTCAACGAACTTGCGCAGGTCTACAGCCATAAGGCACTCA
GAGACACTTGGCTTCGCATGGAGCTTCTCATCTCTGTACGGGTGCTTGGCGGCATGCCGT
GCCTGAGCTATCGATTCGCAGATGAGCGCCGTGAGTACATCGTTGATCGAAAGAAACCTT
ACATCTCCTTGACCTGTGACCGATTTCTGATTCTCATGTAACTTTTCAAGTATAGAGGTA
CAAGCAATCCTCAGCTGTTGGAGTTTTTCAGCGCAAAAGACAAAGCATTCATCCTTCAAT
GGTGGGGGTGCTGCAACCGGTCTGTGAGAGATATTTTCAGAGAATTCAGATGGCGAAGGC
GCATCTACACGAGCACGGTTATTTTTTTTCAGCCGCGAACTCAGAGCCAACAATGGGCTT
CGCACTCGTGCCTGCGTGGAAGGGATTCCCAATCTCCCGTCCATTCCTATTTTGTCCTGG
TTGCGACACGATTCGGCCAGAAGTTTTACTATCACCGCGGCTCCGAGAGCATCGAATACT
GCATGATTGAACGCCAGCGTCAGGATAAGGCCGTCATTGACCAAGTTAATCTGGAAACGA
ATGACAGGTGTTGGTCGATTAGGAGTTGGGTATGCGGCGAGTGGATTGAAGAGACCATTA
AGCGGAAGACTCGATGGTACGTTAAATGGAGACTGTTCTAGTTTCTTGACCGGCAGGGCA
CAATTGGAATGGCGCTTTACCTGGACCAGTGGAACTTGATCTTCAGACTTGGCCCTGGGT
GGTCGGACTATAAGGACATTGTTCGCGTCAGGAACTGGGGCAGGAAACGCGATCTCCCCG
TTCAAAAACGGCACCTTTTCAAGAAGGACATCGATAGCGTTATGGATGGTTTGAAGGGCA
GAAGCTTCATTCCGCACCCGATACGATATGTTATAGAAGAAAAAAACTTGGCCATTCGCC
TGATCGATAGGGGTCAATGAGAAGGCTTCGAAATCAGGGGAGGGTGGCATTTGATGGGCG
ATCAAATAGGGATTTATTTTCAACAAATCTTGATGGTCGGAGGATGGGTGTCCAAGTTGG
TCGGGTTGACTGATAGACAGACTATGTAAGAGAACCTCGTCCCGAACCTAGTTCAAGGAA
GAGTTCCTGTCCAACTTTCACACATTCCTCCGTAGCTGCAGCTATGCCCAATGAGTTGCA
AAACACGAAAGTTGAGGAATGATTATTTTCAACATCTCTGCCCTCGGTCCTCCCAAGCCC
ATGCTTCAAGTATGTAGGGGCAGCGGTCCACGTAGCACGAGTGGTAAAGGCCAGCTTGGA
CAGAAAATCGCCTTGTTACTTGGCGAGTCTGTATAGAACATACTCGACACATCTTAGTTC
GTCGGACGAGAGCTTGTTGAAACATCACGCGCGACCATGTTGCGACTTCCCATCGATAGC
GCAATGCACCCCTTCTCAACTCTACCTAACCATGAACTCGGCCTCTATATCATGTGGATG
ATGTCTGCTGTCTTTGTGATATTTAAGCTGCTGGCACCAGCTAAATGCGATATCCCAACC
GTGAACGGACGCAGGCGGTTTGAGATAGGACAGTACCAGGCAAGGCGGCGCTTTTCTGTC
GATGGACGGGGCATTATCTTGAATGGGCTTCAGATGGTCAGTTGTTACGTGTGTAATTGT
TTGATTCTGGGTTGGAGACTAAAATAAACCGCAGGCGCGTGTATTTCGCGTGGTTTCTCA
AAAAGGGCCCAAGATAATCCTTGGGCCCGAATATGCCAATGAGGTTAAAAGCCATCCGGC
CTGCAATGCGGATGTCTTTATAGCAAAGGAGTTCCACGCTCACGTATCAGGCTTTGAGGT
CTTGCGGCCACAGCAAGTAATGAAAGATGCTATCCGGCTTAGACTGACCAGGTCCATCGG
TAAGAGCCAGCTGTCTATAAGGGTTACTAGCTTACGTTTTTTGGCCTTCAAGGGGCCTTG
ATGAAACCCATCTCTGCTGAAACTGCACTGATTCTCGAATCACAATGGGGGAATAGTAAT
TGTACGTGACCATGCAGTCTTGCAAGGTGCCACACTAATCTGGTGTTCCCAGGTTGGCAT
GAGTTAGATCTAAATTTCACCATAGCCTCGCTTGTCTCTCGAGTGTCGGCAGTCATGTTC
GTCGGCGAGGAACTCGGCCGTGATCAGAAATGGCTTAGCATTGTCACCAACTACAGCTCT
GATATGTTCGTGGCGGATCTAGATCTTTGCAAGTGGCCAGAGGCTCTGCGTCCCATTGCT
ACGTATTTCCTGCCTTCTTGCGGTAAACTACGACGCCATATCCGAGAAGCGGCACTAATG
CTCTACCCCATACTTTCAGAGGGATACTCTGCGCATCAAAACAAGCAGAACTTTCTAGAT
TGGCTTGAAGAAATTGCAGGTGATCGGAAATACAACCCCGTGCTGGCACAGCTTTCCCTC
GCTGCAGCGGCAATTGATACTACATCCGACCTCATAATTAAGACTCTGACTGATATCTGT
CGTTTCCGCGATTCGCAGAAACTCCAAGAAGATCTTCGGGAGGAGATGGTCAGGGTTCTG
CGGGCAGATGGATGGGAGAAGTCTGCCATGTACAACCTTAAACTTTTGGACAGCGTCCTG
```

Figure 5F (continued)

```
AAGGAAACACAGCGTGTCAAACCTGTCGTTGTTTGTAGGTGTCGTTGCTTCATTTATGAA
TCATGTTGAGCTAACCCTAATGTCACCGCAACACAGTCGGTATGGGTCGCTACGTTACTG
AACAGATAACATTACATGACGGAACTGTGATCTCAAAGGCGAGACAATTAACGTCGTCA
ATACACGAATATGGGACCCAGCTGTCTATCCCAACCCGCTAGAATGGGACCCCTATAGAT
TTGTACGTCGTCGCGACTCGGGCGATCACGCAGCACATCTCGTTTCGCCCACACCAGATC
ACATGGGGTTCGGACTGGGAAAGCATTCATGCCCAGGCCGATTCTTTGCAGCCACGAAAA
TCAAAATCATACTATGTCATATTCTGTTAAAGTATGATGTGAAAATCCCTGATGAGGAAA
TTTCTACAGTGATTTCTTCGGGAAACTTTCTATTTCCCGACTCAACTTTGAGGATCTCAG
TCAGGCGAAGGCAAGACAACTTGACTATCTGGGACTAAACACCCTTCCCTCATAGCAGCT
GTCTGTAATTGGAATGATTTGATCATAGACTTTGGAATCTTGCTAAGACTTATTTTGGAA
AGGCGTGCAGACAATATCAGTGTTTCTCTCCGAGCACAATACATTTCATAATTGCCCATT
TATCATCAATTCCTAGATTATTGAGCCTCCTCGAGGCGTCCCTGGAACTGGCGAAAACGG
GCTGTGTCCAAGAACTGAAAGATCTCATCCACCAGAGCTCCCTCCTCATTCATAGCCATT
ATAAACATTGCTTCGTTCTCGTAGGGTCCAACCGTCGTTTCACACCTGATTTTCACCTTC
ACGACAACTTGTCTTGACACCTCATCAACAACCGTAATGTTGTCGTCCACAATGCTGGCA
TTGACTGATCGAAACACTCCTCGCGATAACATCATATGTCTCGTGTGTTCCTCCATACTC
TGAGTAAACTTGCAGGTCGGTGCAACTCCATGAGTAAGGCAGGTTGGTGTGCGAACGGTC
TTCATAGCACTTGGATCGAACTCGTTGTACGCGGCAATGTATTTCGAAACAGTTGCAAGC
AGTCTTTCTCGGATTGACATGGCTCTAATGTAAAATTAACTGCTGGTGGACTGATGATGC
TTTTTTAGACTGAAATGTTAACCTGACAATAGTCGATTGATTTCTGGCCGATCAAAACCT
AACAGTGGACATGTGCGTGCTGTCTCTGTAGGTATATCCGTAAAAGTGCAGAATCCTACC
TCCTTGGGTTTCTCTAGCCCCTTGCTCTTCCGGCATTTTGTCCCTTACAGCGCAAAAGGG
GCTTGAGATGGCAAATTCGTTCCATTTAACTTGAGCCCATCACAATATCTTCGAGGCTAC
ATCGTAAAGTGTTCGATTCGCGAGCCACTGAAGGGTTAAGCTATACCTTTCCCTTGTCAA
GTCGGACGAGTCACACGGCGAAGTATTCAATATAGCAGACACAGACATGCCTGGGTCGTG
GAGTGCCAAGTGGCCCTCTATCTGCAGATACTTTGGGCTTGAAGCCAGCGAAACTGTTGA
CGATCAGTGGACAAATATAGACAGCAGGTGGCACGCGAACCAAGTGGCTTACGAAAGAAT
GTACACCGAGTACGGACTGCAGAAGCAGTTGGTTTCACCAACAGCTTGGTCGTTGGTGAA
ATAGGTCATACGTTGTTCTACCAGAATCGGGAACTCTGCCTCGATAAGACTCGGGGACT
GGGCTTTACCGAGGATCATCCCGTCGGATTTAGCTATTTCCAGGTTTTCGAAGACTTCGA
GAGGATGAAGATTATCCTGGCTAAAATTGTTTTGGCCTCGCTGCCGCGACGTTTTATATC
AGTGCTAAATTGATTTCGCTAGAGCACATGAAGAGACTCGACGACCGCTATACCGACCGT
TGTTGATACTGTGAGACCGGCTTCCAGCAGATGACATGTATTTAGACGCCAGACAGATCC
TATTTTTACCGATTATTGAGGCATTTTGCAACTGCGCCGGGTTGATTGATTTGGCGCGCG
GCTGTGCTGGGGTTTTAATTCTGTCAGGTTAACGTGACATATTATTACCGCTAGTTATGT
ATTAACCCTATAAATGGTAAAATAAACGTATCCGTATCAATTCGAGTCACCTAGCCCTAA
CTGGTCACTGCGCTTGACATTTTGATATGCAGCTATCACGATGGCTAGTATACGCGCCAT
AGTACACATTCCTCGCCATAAGGACTTGTGAAAGGGTTACAACACATAGTAAGCTCTACT
ATAGATGATATAAGAAGTAATTATCAAGCTTTAAGCTTGATAGTTTATTCATGGCCGAGA
GCGTTCATTTTGCCGCCACGTATTCAGGCAAGCAATATTATATATATTTGCCGTATATGT
CTGCGGTGAGTGTGCTGGAAAATAAGTTTGAATTAGCGGATGGCGTCAAGCGTCAGCTGT
ACCTTTCTAGTTCGCACCAATCACCAGCACTTGATAAAACGACCGCTAGTGCCTGGTTCA
TGTGTCCGGCGAACATAATTACTGCGTGAATTAACATGGCGCTGGCCGCTTCCGTGTAAT
GGTCTCATTCTCAAAGGCCAGGAATTAGATCTGGATCTCCGGCTGTCGCCGTCTTACTAG
CACCTTTGCGGTCATGTTTGCGTTGATTGCTGCCGCAAACTCCCACACGTGCTGCCCAGT
CTCCCCATTGGCCGGTTTAATATCATACTTCATCAACACGTGGCAAAGAGATATCTTCAG
CACCGCTGCGGCGAAGAACCGTCCTGGACAGGCGCGGCCTCCATAGCCGAATCCCAGGTG
ATCGGAGGTAGGTGATGTAAACTGTGCTGTATTCTCCTGCCCTGGAGCCTGTCGGAGTCT
GTAAAACCGATACGGGTCAAAGTGCGCGGCGTCAGGATACTTGTCCTCATCCCACATTGT
GTGTCCAGATATGCGGATAGACTGGCCTTTCTGAATGATGAGGCCGTCTTTCAACGTTAC
GTCAGCGACGGCGACCCTGCCAACTGCTGTCTGATAGTTAGGGTGTGTCCGAACCAGGAG
AAGGGATTTGGCATACCAAACAGGATTGGATCTACCCGTTGAACTTCCTTAAAGGCACTG
TCCATGAGTTTCAAGTGGTACAGCGCCGTTTTGCTCCACCCATGAGTCTCGTAGACTTGG
ATGACCTCTTTACGAAGGTCGCTGACGAGCTGAGGATCCTCAGAAAGGCGCAGGAGGATC
TTAACCAGATGGTCGCAGAGGCCATGCATGGACGCAAAGGCAATCCGCAGGTTAAGTATG
AGCTCGTCATATTCTTCCCCGTGCGAGGCTTCTTTGAACCATTCAAAGAAGTTTAGCGGT
TCTTCGCCTGTTGATGCCTGCAGAGCCGTTCTCCTGCGCATGTCACGGCTCATGAGCTCT
CGGCCAGATTTCATGATGCGGTAGAGCTCCAGGCACTCAGGTAGAAACTTGGCCACAATC
CGTCGTAGCATCACAGGCCACGCGGAGAGTGCCGCCGATGCCATACCCAGAGCCATTTCC
ATCTTTACCACAAACTCGGGCCACGCCTCGTCCAGGCAGTACACAGAAGATGTACCCTGG
```

Figure 5F (continued)

```
GCTATGGTACGCTCGACCACCGACCCAAGAACTATTTCCTGCCAGCCTGGGGATTATTAG
ATAGACGGGTCAGCCACACTTTCGCGCATGTCGACGGAAGTCATGGTTTACCTGATTCAC
TAGGCCATCTATCGCTAATTGCTTCACCGATATCTGATGCGAGCGGCTGGATCAGTTTGC
CTGGAAAAGCTTGTTAGTTTGGTTGTGCTTCACGTATCGTAGCTCCTCTTACCAAGCGAC
TGCGCGAGCTGTGTTCGCACAGACTCTATCAAAATGCGATCTTCAACCGGCTGTGACCGG
CATAGCTCAAAGCCCGGAAGATGACCGTGATGCATCTGACCAAGAATTCAGAAATCCGAT
TTCTTCCCACAGGCGGGTGTTCCATTGACTACCTACCTTTGCAGTGAACGGGAATACCTT
CAGCGAAGGGTGATTGCGGAACTGGTCCGCATATTCAGGAGACGCAAACAATTCCACCCC
TACATCCGTACGCATTGCGAAGACATTTTTGTACTAGTGTCACTGGATGAGCATACGACG
CCGTTTCATTCTTGTTCAATTTCTGCGTGCGAACTTACAGAATCAAAGCCGGATTTTATG
AGCCGCCGGGCATCGCGACGAAAGCGATTCACTGCTGTCACCTGAAGAAAGTCGAATGGG
CCCCCATCGTTCAAAAGAGGGAGATTGTTGGGACGCCATTGCTGGGTGTTGTAGAGCAAA
TATAAAACAGCGGAGACTACCACGAAACCGGCGATCAAAGGTTGGCCCAGCGGGGTGAGA
CTAATAGTTTCCTGAAGCATGGTGTAGTGTATCTAAAGTAAGTTTTTGAGAGCCGGACGA
GCCGCGAGTATATGGTTATTTAGCCATAGTGCTGCTGGATTGGCGCTTATGTGGCATGCG
TGTCGGCAAGGGGCCGAAGTCGGTCAGGGATATTCATAGGCCTCAGAATCCCCTTACCTG
GAAGGCTGCAATACAGCGCGGCTTCCGATCCTGAGACTCTCATATGTCGGGTGGGTGGTG
AGGACAAGCTCGCATAAAGGCGAACGGACTCTTCTAATAGGTTTTACTGTAGTGCTACTA
ATGAAAAAACCGAACAGACTGTATCGGGTGATTTACCTCCATGTTATCCTATTGGTTTTG
GATATGTGCAAACTGTTATTGATATAATACGAACTAAAGGGGTGGAAAGTCGTTAGATAA
CATTACGAGACAATTATGCTAATAGACAGTGGGCCCCAGCTACGATTATTTACTCAGTGG
CCCTTTTGCCTTGTAGCGGTTTTGCTGTCTTCAACTTCAGTCCATCCTCTAAGCACCCGA
CTGATGTGTATTTAACCCAACCGTACTGAGCACTACTGGTCTAACAGTCCTCCAGCCAAC
CATCTTCTGTGAAAGCGGGGCATGGTTCCAGAGTAACCGGGCTCTCAAGAGCAACTAGC
TAACATCTTGTGAAGAAAATTAGTAGCATTCGTCTTGTATTCGGTGCCTGATTCGTATGC
TTCCCACCAGCGTGCAGCAGCCGCTGAGGGATTACCAGCATGTCCCCAGCGTTTAGCTCT
GCTTGCACGGCCTGGTCCTCCGATGGTGTTCAACAGCCTCCCATTTTGGCTGCTGAGAAT
GACCCGCGTTGCACCGTTGGCAACAGTGGCGTCCGTCATGGAGACAAGGAGCGTCACTAT
CAGGGATGGTGATGTGGCAGGTTGGTACTGAAGGACGGGATAGAGCAATGTGTCCCGGTG
AAAGCCTTGTGCTGGGCTTTGTGGTTTTGTGGTTCGTAAGTTCCCAGTGGTCAGCCAGTA
GTCTCCCACGTCGCGGAAGACGGCCTTGCATGTTGTGAGTACTGCCGAGTTGTTCAGTAT
GTCGTCCCGGTAGGGTGGCGAGCCCGAGGAGGAAATTTTCTTTCCTTCAGAACGGGTTAT
CATCAAGCCAAACAGGTTGGTTGGAGCTTTCGACTTCGTTTTGGAGGCGCTAGGTCACAT
CAAGAGACCGGATGCATCTAATTAACAACACCATCGTCGTCGACCGCTTTTGACAATGTT
TCTAGATTGGTGTCAGAAGCAAACCGTTGTAACTGCGTTTGGGAATGATAGTCATGATGC
GGACACAGAGAAGCAGGGATGATACTGTGACAGGGCAGTATAGCGTAGTTGAGAGCTAAA
TGAACCAGGTAGATACACGCCTCGCGGAGGCGAGCAGTGGCCGGACGTACTATAAATATA
TGCTCTAGCGAGACGGCTACAAGGCAACATTTCATGTAGATGGTCGTCCTGGTTATCTAC
AACAACTAACATACGAATCCTATATCACGACAACTGTTCCTCTCACTGTTATCACTGCCA
TAACATATATTGAACGTCACTTTGCAAGCAACGCATGGGGTCAACTTGAGGCGTGGTCCT
CATCTGACCGCAGCCTAGCCCGTCAATAATCCCACATGATGGGCTACTATCCTGTAGCTG
CGTGAACCGTTCGAGAAGTAAGGGATGCGGGGGTTGTCCTGCGCAACCACGTATTCACCG
GAAGAGTCAGTTTCCGAGCATTTCTTGTCACTCAAGGGGGGCCTTGTTGGCTAGATCATG
TAAGAGCAACGCCTAAGTACCCCCATGCCTTAAGCCAGCTTCATCAGCATTGGCGTGAAT
TGATCGCACACGAGCTTCCAATCGCCTTAAGCTTGCTCTCCGGAGTATTCGCCTTTGAGC
ATTGAATACATCACCTGACCTAGTAGGAGGGTTTAGAATCCCTTGCTAGTCCCCGCACTT
CCTCACGGTTCTCCAGAAGCCCTTAATGATTGTAGTACGGCGGTTGTGTGAGGTTTCATA
ATACTAGCTGCCTCTAGCACTGCTAATTTTTCTTTTATCTGTCCTCTGGCAACTTTCTTG
GACGAGTGCTCAGGTATCAAAATGGCGGGACTGACAGGTCAACCCATCCGCAATTATTGC
GATGTCCGGGTGATTTCCCCCAGAACCTATGGTCAGTACTTGTGAATAAACAGAGTAAA
GGAAGCAAGGTGCCACCGGACCGGTTAATGTCAATGCGTTCTATCACCCTTCTGGCTCG
CAGGCCGGCACCGTGAATAGAAATGGGGCCATTTCATGAAGCGGCACCCTGCTACTTTTC
GCGCCGTGTTTTTCTGTGCTTTCAAAGCAGGCTCGAGCAATGGATCTGCAGAGCCGTAAT
GCTGAAATGTGCATTCTAGGCGTTTGAAAACGGTCAGTCGAGTGCTACCACAGAAGCTGA
CTACTTTCTCTAGCCAGTATGATAATAGACGATTTTGCAGGGACACGGACGGCATGTTAC
GTCCCCAGCTCCGCCGACTTCAGGGAGCTTCTGGGGCAGGACGAGTTGCAGCCGAGATAC
AAATTTACGGTGTTCGGAGGAGGGATGCTCGCAAACCGTATCTCGTGGTTCTTTGACCTC
CAACCAACCATTTTAACGGTTGATACTGCGTGCTCTTCGTCTGTCGTCGCGCTTCGTTTG
GGCTGCCAGAGCATCCGCACAGGAGATGCTGATATGGTGCGCATTCCTCAACGTGTACAG
CGAGATTACTTCTATTACCCTGCTTACATGCAAAATAACACTCCAGGTGTTAGTCGGTG
GCGCCGATGCGAATTTGTACCGCAGGTGATGACCAGTTAGGGTTTGCTCGGTTTTCTCAG
```

Figure 5F (continued)

```
CTCGGACGGCCGCTGCAAAGGCCTCTGAGGAGCAAACAGACGGATACGCCAGGGGTGAAG
GAACTGGGTTTGTCCTTCTTAGGCCCCTTGATGCAGCACTCTCCGATGGAAATGCATTAC
GCGCCGTTATCCGGACCCCGGCATCACCGCTTTCCTCAGCAGAGGAGCAAGAGCGATTGA
TTCGAAGTGTCTATGACCAAGTCTGTCTCGATCTCGTTGAGACGCCTTTTGGGAAGCGCA
TGGAATCAGGTACACGAAAGGCGATTTGACCGGCGCTTCGTCACTGGCTCGCGCCTTTAG
CCACAGGCGGCTGCCGCAAGATTTGCTCTATATTGGAAGCGTCAAAACGAACATAGTGCA
CCTTCGGGTTGCGGTGGTGTTTCCCAGATATCAAGACAGTTCTGGCCCTGGAGAACGGTA
TTATTCCACCAAATATATAACTTAAACAGCTATGTCCAGACGCACCTCTTGGCAGATGGC
GCCTAAAAGTGCTGGCTGAACCGGTCTCCTAGCCAGAGGGTGAAAGCGCAGAGCAAATAT
CAACCCCTTTGGGTATGGCGGCACAAACCCGCACTGTATTATGAAGACTCTAGAAGAGTA
CACGGGTCGCAAGGTGCAGCAATGGCTGGAGCCTTGGGTCAGGAGCCAAGGTGCAACAAT
GAGGCCAAGTCTAGAGAAGAAGAAGCGCCAGTTTTGATTTCTTGCTTCTCCCGTGATACG
GGCGGTATCTCTCGCCTGGCCGTTCAATACGCACAGTATCTTGAAACGAAGATCAAGTGC
CATAGATCGCAACAGTCTCTCAGCCTCAGATTCATTGACGGAGCGGGCTTTCTGTCGCAG
AGCTCGGTGCGCGCTGCAGATAAGGTCTCCAAATTTCAACTTTCTGCGCGCCTACCTTGC
CACCGAGGCTCGACTTGATATCTCCGTGTTGGAGCTGATGCGTAGTATACCGGTGAGAGA
ACTTGCTCGAGACGTGGCCCTGCGGTCAGGATACCTTAGTCGCTATACTTTAGACCAGAG
CTATGTAGCTACGTAGCTATCAACTGCGGAGTGAGGCAGGCGCCCTGAAAATGCGATATT
AGGAGCCAAAGGGCGCTATCGGTGTAGTAACGACAACGACTACTTCTAAGGGTCAAACAC
TTCCACTACAATATCTGTGTGGCTAGATCCATTCCCATAAAGCAAGGGGATGTTGCCTAA
TCATACCCCGATTATACCGCTGTTACGATATATATACATAGGGCAGAACCAACAATTCCT
CCACTTCCGTCGACCTTACACTGTCCCCCACAGCAACAAAGTAAGATCATATCTCTATT
TTTCCAATCAATCCTGACCATCGTAAATAGTCCATGAACACCACGCGCCACAGGCTCCTT
GCCACCGCGTCGCGGTTTGTCGAGACACTCGAGAGCTTAGACGTGGATGCAATGCTCGCT
ATACGATCTTCAACATGTCTTCATCATATGTGCTGCCCCAGCTTCAGAAACTACAGCATC
ACGAATGATCAGACCCGTGAAGCGTTTCCCCAGTGGAAAGCTACGATTACCAAGTATAAA
TTTGGTGTCCTGGATGACAGCCAAATTCTGGTCGACGAGCAAGCGAGAAAGGTCATGATT
CACGCCGAAACCGCCGCAGAGACAACGGTCGGTGACTACAACAATGAATATGTGTTTATT
CTTCGAATGGCAGAGGATTGCAACACGGTGGATGAAATCTGGGAGTTTTATGATACCATT
CGTCTACAGGACCTTCGTCACAGGCTGGAGGCAGCCATGTGCCAATTGGCGTTGACGCT
CCTGCTCCCTTTACCACCACTGCCTCACCTGCGGCCCTCTAATAGCCTGTATATCCTAGT
AAGACTCTTATTAGTGTATTTAATTATGGCTAGTCAATCAAATCACAGCGCTGCAAGGAG
ACAATCGTCCCTTACATTTTCACATTCCATCTCTGGGACACTCACTATACCCGCCTTGAC
CACCAGGGTATTCCTAGCCACTAATTGTCCCTGTTCGATCTTCAAACAACCTCGTATTCT
TATCATTGCTATATCTTAATGCTATGACAGGTACACGAATCCTCGAGCTGTTCGGCCCGG
CGCCAGAACCCCCCTCCGAGTTAGGCCGCTACCGAATCCTTTCACCCACGGCGGGCATAC
GTGTTTCTCCCCTCCAGCTCGGTGCACTATCTATCGGAGACGCATGGAGCACCGACCTTG
GCTCAATGGATAAGGACTCGGCGATGGAATTGCTAGATGCCTACGCCGCTGCGGGGGGGA
ACTTCATTGACACAGCAAACGCGTACCAGAATGAACAGTCGGAAATGTGGATTGGAGAAT
GGATGGCCAGCCGCGGCAATCGGGACAAGATGGTGATTGCCACCAAATTCGGGACCGACT
ACCGCGCCCATGAACTGGGCAAAGGGCTCGCAGTGAACTATTCGGGGAACCACAAGCGCA
GCCTACACATGAGCGTTCGCGACTCCCTGCAGAAATTGCGAACAAGCTGGATTGATATCC
TCTACCTGCACACGTGGGACTATACCACCTCTATCCCGGAGCTCATGGATTCACTACATC
ATCTTGTCCAGCGCGGAGATGTCCTCTACCTGGGAATTTGCAATACGCCAGCTTGGGTTG
TTAGTGCAGCAAACACTTATGCCCAGCAGCAGGGGAAGACCCAGTTCTCTGTCTACCAGG
GTCGTTGGAATCCGCTGCGGCGTGAGCTCGAGCGTGATATTCTACCCATGGCCCGGCACT
TTGGAATGGCCGTGACGGTGTATGACGCCCTTGGTAGTGGTAAGTTTCAATCACGGGATA
TGCTCGCACGCCGCAAGGATCAGGGGGAGGGGCTCAGAGCTATATATGGTGGGCAGCAAA
CCGCGCTGGAGGAGGCAATGAGCAAGGCGCTGGGAGTTGTTGCCGCGCAGCATGGGATTG
AATCAGTTACAGCTGTTGCCCTGGCGTACTTGCTGGCAAAGGCCCCATATGTCTTTCCGA
TTATCGGCGGACGCAAGATCCAGCACTTGCATGACAACATCGAGGCGCTCTCACTCCGGC
TCAGCCAGGAGGAGATCGAGTATTTAGAAAGCGTGGGAGATTTTGACCCGGGTTTTCCGT
ATGATATGGCTGGGGTCGATCCAGCTGATACTGGAATAGCTACTCCGATTGTGGCTCAGG
CAGCGCCGATGGCGTTTGTCCAGAGATCGAAGGCTATAGGGTACGCTGAATCTAGCAAGG
GAAGTCAGATGTTCGGCTGAGTTAGTAGCCTGTAGCGGAGTATCAATGTTATGGAAACAC
AATTCAGGAACCAACTTAGACAGCTTGCAATATGGATGAATATGATTCGTCTCCATACAC
GTCACAAAGACCTGTACAGTATGTTGCAACAGTGTCGCTGTAAGACGCATAATATGAATG
GCACCTGCGGTAGTCAGTTAGGAGAAAAGACTGGCTTTGATTTGGCCGGCTTTGGAATG
ATACAAGGATTGGCTGTTAATCTGCACGAAGGGGAGCTGGAATCTGATCTTTGATAATAT
ATTGTCTCTATAGGACTGTCCTGTTGCTCAATACACCGGAGCCTGGCATCGATAGTCTGC
CCAATGTGTACCGTGTTTACCGCGAGCTTCTTAACATACTAGAGAGCGGCCACAAGAACG
```

Figure 5F (continued)

```
ATGACATGTTTCGTATCTGTTCTTTTGCCAACACTTCCCCGTAGCAAGCCCGATCGTTAC
ATATACTATACTAAATACGTCTAAGCGGGTGCGAGCATCAACACTGAGTCGCTTCTCTCA
GCCAGGATGCAATCACTGTTGTTATTCCCTTGCAAGCAAAGCGGGTATGTGGATACAACT
AAGGATCTTGCTAGGGATCTGCTCTGTAAGGTGGAATGCTGATATTTGCGTTATCTGTGC
GGGTAACATGTCTGCCGGCACCGGACGATTGAAAAAAATGTCTTCATGCTCTGTGACAGG
GCCACTAGGTCTCGCAAGTATCGGCTGGGGGTGCTTTGGCATACTCCTTACGGCGCAGAT
CATAGTGAAGGTGACAGCGACGGTGAGGATAGTTCTTATGTGGAGTTTATTGAAGGCAGG
GCAACTCCTGATCTTGCATATTCTTGCACCAACAGTACCCTACAAGTCCCGAGTTGAGCC
AAATGGTTGGGTCCTCAGAGGCCACCAGTCAGGGTAAAGCGATCGACGCTCAACCGGCTC
TTATTGCTCCGTTTCCACACATGCAAGGGCTAATCGAATGACTTAGCGTCAAGGGTATG
CCAGCTTAGACCCTAGGCCCGGCCCGAAATTCAGTAGTAATAAGAGTTGACTTGGGTCGG
CACATTCCAGACCGACTCATGTGTGACACGAGACAAGCTTACTGGCCCTGCAGGCAAGGG
GCCAGGACTAGATCAGAACTGAACATCCACCACGCAAAGTCGCCCGCGATGGGCACATTT
GAGATGCCTCTGGATATGACAAAACGGCTGGAATTATACTGCCGTCGTATTATATAGACG
TTTTCCTCAAGTAATGAGAGGCTGCTCACGTAGGGCAGCAAAGGGAGTCGGTTCACCAAT
ACCAGAAAGGGGAATCCTTTCCTAAGAATGCAACGAATTCCAGGAGCATATGTACGACAT
GCCCACTCAATGCATGCTGTGGCAAGGTAGTGATTATGCCATTGAGCTCCAGGCCAATCA
GCATGGAAGGGAAATCACTTCAGAATGAACAGCCGTGAGCGCTCTTGTTAGTGAGAGCAG
GCCTCGTCTACAGGCGTTCCGTGAAGCGTTGTGAGAACTAGGAATACTTTCGAGTTTGGC
AGCTCGTTCTGCTTCCTTCAACCGTTTCGGACGAGTACCAACAATTCGCCGTTGCTGCGT
ACACCCTACGTCCCTCGTTACCATAGTTCCCTCTATCTCCAACCTATGGGTCGCAGAGCC
CATCTTTGCAACCTCTACGTCCTGTGACTGTGTTCTTTCGGCCGGTATACCCAGAGGTAA
CCGAGCCGAGTTCATATATCCGACAAACCCTTTCCGATAAAGCATCTCCAGGGTGGCTCA
ACGAGACCATACAGGGGCTGCCATCTGTCTGGCAGGGTATCGTGCGGCAATGGTCAGCTC
TCAAGATTTCAGGTGAGTCTCCGGCCCAGCCAGCTGCTCAATACCTACTCCGCGGGTCATC
TAGCCCCGTTACGAAGCCACTGAACTTGCTGCTTGTTCCCGTGACGGTGTTGCGGCATAT
TGTGGAATTCCAAAAGCTCAAAGAGAAGAGTAAGAACCTTGAGATTAGAGAGGTCTAAGC
GTTCTGCGTCGGGCTGTTTGCTGCTATTACAGCATGCTGGGAGCACGAAATCCCCAGAGT
TGACAGCACTGTTCTCCGGGTGGTTATCAGTATCAGGGCACTCGGAGCTCAACGGGTCCC
CTTCTGAGCTTATGGGCGTGTAATGGAAGATGAAATGTGGGTACAGACATCTTGGGGAGG
CCCTTCAGCGGTAGAAGGTGTGATTTTGACCGTGTCAAACGTCTAGTGGCGGCTGACGAG
ATAAAACAGGATATATTGCGTGCATGACCAAGACAAACGCGCCACAGTTACAGTCCCTAC
TGAAAACTACGTGTCCTTGACACAGGAACTTGTGAGCCACAGTATGTCAGTCAACAGCGT
CCTTCTACGTGGAAGGTTCCATACCTCTGATCATACCCCTGCCACGAATCAGTTGCTCGC
ATCTGTGCAAAGGATCGATTTCAACTGCCAATCAAGAAAAGTCTACATCTACCACCGAGG
TCTAATGTATATGGCTTGCGAGTTTCGAGCAATCTGCTGATTGCAGTTGCGGTCGAGTCC
ATTTTGGCCAAGCGGGCCAACTGGTTGCTCACGGGGCCGAAGCTCTCAAGAGCGAGGGGC
CGCAAAATGAAAAACACGCCATGATCATCAGAGCAGGACAGATCTTTCTTAGCCAGTGTT
GAGCACATCTGAGACCAGATGGCGCCCAACGACACTTCACTTCATCGGTCAAGCCACACC
ATGAATATACACTCCACCACGCAAAGTAACGGTACCGTTTTTTTTGGGACTTTCGACCC
AGGCTCTCGTCGCGCCAATTGCCCGTTACTGGATTCGCGTGTCGGATCCCCAGGCAGCAT
GTTGCGCTCTAGTCCAACTTTGGAATATCCTTTTCTAATCTCCTACTTTTTATTTTTTA
TTTTTATATTTTTATTTATTTATTTTATTTTATTTTTTTTGCTATAGCTAGAATACTA
TGTTGTGAAATTGTCTCGTTAGCTTATTCGATGCCTAGAGGCGCTATCCGCAAGTCTGCC
TGCGATTTGAACCAGAAACGTCAATACCTTGTACGGACAATGGTATTGCCAAAATTAGTG
CTGTTATGTCTGTTGGCAAAAGCCAGCACTGTGCAGACGAACTTATTATATGCCAATATC
TCGTCGAGTGCAAGCGACGAATGACCGGGCGCAGCCAGATGGAAGTGAAGGCTGGAGATG
CTGAAATTTGTACCAGCAACCATTGACTGCTTTGGGGTGAACGAATTCAATCCCGGATGG
TGATCATCCGCCGAGACAGGAACACGATGCGTGCGAACGCAGTAGGCCTGGCACTCTGAG
AGTGGGTTGCCCGTCTTGGAGGCTCACCGGGTTCAGGACTCTGGTGTAACTTGTGAGAAC
GGCATCGTAGGCCTCTGCCCGGCCAATCTCTCTTGGTAGACCGGCTGGTTTCAGCACGGC
GCCAACTTCGATAGTGGTATAAAGAGCTTCCGTAAACCTTGTCTAAAATCTCAACAAGGC
TTTTATATTATCCAGCTCAGACATATTAGACACATTTTCGCCCAGTGAAAGCACCAAAAC
ATCTCGATGAAGCAATCTACAGTTGCGCTCCTTGGAGTCGGCATGCTGGGCGGCGCCGCT
GCTTTGCCCGCAGGACAGCTTGCCAACGGCCCTCAGGACGGTAAGTGAGGTGATGATCAT
TACAACCCCTGCTTCAATACATGCACATCATCATCCTCCTCCAGCACTAGCCAGAAGCC
GTATTGGTAGTGATAAATTGAACCCAGCAGCCTCCATGCATAACCTCCAGGCGCGCCAAG
TTGCCGGGACCAATGAGCAAGGCATCGTGCCACCGGTCACCGATTACGTGTTTGGCTCTC
CTCCAGTTATACCTTATCCTACTTGGGCATGTTTGCTCCGGGAACCGAGTTCAATGCTG
ATGCATTCGCCGCTGCGTTCCTTGAAGTTGGCGGTCTGCCATCGTCAACTTCAACTACGG
TTTCTGAGGCTTCTGTGACTCCAGCAGCCAGTCCCATCCCTGCGGTGGCCACTGCTGGAA
```

Figure 5F (continued)

```
CCTCAATCTCGACTCCAGCGGCTTCTGCAGCGACCTCTGCTGTTTCAAGGGCTACTCCTG
CCTAGGCCGTGACACAACTCGCCGGTTGGGTACGGTCTACTCCTGCCACCAGGGACACGG
CTCGAGAGAGTACGAGTGGGAAGGTCATTGTACGGAAACATTCCACTTTTATAATTGTGC
TTTGTTTCGGCGTCTTTGTCGTTTTTGGCGTTCGCATGGGGTAGGGTTTTGGTTACACGG
CCATTCCTTTCAGTAAAGCCAGCCATCAATGTGAACCAAATTAGTATTTTTGCAAGGAAA
AACGATCTCCGTCCAATAATAGGTTTCAGCGTCTGCATTTTGCATAGCTCTGGGTGTCTG
GGACATTCTTCCTTACGTCGCTTGACAGGTGGATACGTTCAGTTATGGGTTTGATAAGCC
CCTTCATGATCTTGCCGGATCCTGCTCGCATTTCCTAGAAGCCCTGGATCTTACCGAAT
TTGTAGAAATTCCGCCAGTCAATACAAGCCATAAAAGAAGCCTGACCACGGTTATGAACG
ATCGCATGCGCGTCCAGCCGTCGCCGGCACAGTTAGCTCTAGGGAGCGGTGTCTCATTGT
AAGTGAAGGCGTTGAAGCTCTTCTGCGGTCGCTGCTGCCAGCCCGCTCCCTGACTCGCAA
TCTCCTCCTTCTACTATGCCGGGTCGGTGAGGCGATTACTGCGTTCATTGACGGCGGCG
GGAGTCCGTGGAATACGACCAGCGAGCGGCTGTACCGCGCCAGGTGGTTGATGATCTGGA
CAGCGCTGGCGCCTTTGCCCGAGTATTCCAACGCGCTTGTCAGCCAACCCAGTGAGCTTT
GAAATCTCTAATGGCTCGCCTGTGAACTGGCAGTCCCAAGCGTGCGGTGTGGAAGAGCCT
CCTCTTGTACTTGGTGATATCCGGGTAGCTGGGGACACGAGGACTTGCAAAAGAGCCCGA
GGAGAGGAGGACAATGTCTTGAACTGCTTCTCTCTGCCTTGTTTGTATCTGATACATTTT
CAAGCAGCTGGTCAGCTACGTACCAGATCTTCTTGTCCTCGTCCCACGCCAAACCTCGCA
CAATGGTGCGGAACATGGCCCGGGCCTCTAGTCCCCAATGCTTGCAATACGCTCGGCATG
TTCGCGAATCTAGGTGCCACTGGCGTACCTGTGTCGTGGCATGTATCCTGTCTCCTCTAG
GAGCGGCATATAAATATAACTCTCCGTGTTGCACATCAACCCGGGTACCGATTCCAGTAC
CACGTCCCTTAGAACCCTGCGGCTGTATCTGCAATGGCGATATTACTCGCCTTGAACTGG
CCGGTCTGGAGCAGGTGCACGGCGAATAGGAGGCCGCCAAAACCTCCGTTAAAACCTCCG
CCAACAATCAGGACCCTGTGGCGGCCCTAAAAGAGTATATGGGTTTGCAGGAAGAGCAAA
TGTGGCGATTCTCCTGCTGGCTCTGGGCAGCTTGCTCAGGCTCACGGCTGTGACAAAGAA
AAGGGCGTTGAACTCCAGCCGCAGAATATTGCCCATAAACATTGCCCATATTCTATTGCT
GAATGAGCATAGGAGGGGGTCAGTTGCGCAGTCATTCCTGTTGATAACGCGTGGTCGACT
ATTAGGTGATAGGCAAGGCACTGCGACCTAGGGATGCTGGAAATCAATCATTATTCTTT
CCCACACACTCAGTTGTAGCAAAGAATCGACGGATGATGGTAAGACGAGAGCGCCAAATT
TCCTGCAATCTTACATATTCACCAGGACCAATAATCGTTCGGAAGATGTTATGGGTGTAC
CGCTGTGGTATGCATTATTTACTCCTCACTTGCAGTGATTAGCAAAGGGCATCAATAGCT
AGTTGCGCAAACATTCCCTGCATAATGCCACGGATAATAAATGACTGCCATGTAGCACGA
CCGTGGTCTTAGGCTTATAGCTTTGTTCATAATTAACTGAGGATACCGTGTTATCGCATG
CTGAAGCAGCACTCATCGCAGTTCAGGACACACCACAACACGCACAACCATGTCTCAACT
AACAATCTCCAAGATCATTGAGGAACCCTTCAGCGCACTCTCCCTCTCCGAAATGCTCAA
GATCCTCGCCGCGCTTGGTTGGTCGACAAACTATCTCGCCATGGTCTACCGCACGCAAGC
TGACAAACTCCCCGCCATCGCCGTCCTCCCCCTATGCTGCGATATCGCCTGGGAGTTTAC
CTACGCGTGGATATATCCACAGGCCAGCGGCCACTGGCAGGGCGTCGTGCGCGTGTGGTT
TTTCCTGCACACGGCCGTCCTGGCCGCGACCCTGCGCTACGCCCCGAATGACTGGGCGGG
CACGCCATTGGGTGAAAGCCGAGGACGACTGGTGCTGTTGTATGCGGCGGTGATTGCCGC
GTTTGCGGCCGGCCAGCTATGCCTGGCTTTGGAAATGGGCGGCGCGCTGGGCTTTCATTG
GGGTGGCGCGCTGTGCCAGTTTCTCTCGAGCTCGGCCGCCGTTGGGCAGCTGCTTACCCG
TGGGCATACGAGGGGAGCCAGTTTGCTTATTTGGTAAGTTCCATGAATTTACGGTTCGCG
TTGCTACTAACAATGATCAAAGGGGGCTCGTGCGATATCCACCGCCGGCGGGTTTGTA
AAACTCTGCATCCGCTTCCAGCACCAGGTCGATGGGGCGCCATGGCTTGACAGTCCAATG
TGCTGGTTTTATATAGGGATCGTGCTCTCATTGGATGCGTCGTATCCGGTGCTGTACCAA
TTGACCAGAAGGCATGAAGAAGCCAGTGGGGGTGGGAAATCAGGAAAAGTGAAGAATTGG
TGATTGCGCTATATCTGTTGTATCGAAGGCCTGCTTTGGAGATTAACTGGCGTACAAGAC
AAAGAAAAACCAAGGATCACTGGAAGGTAGTGTACTTGCAAGTTATACATGGCTTGGGTT
ACGACAGGGCCATGTCAAACGAGATGTCTTATTTCCAGCGCAAAACAAGTACCTGCAAGG
TTCCTGTTGATAACTTGATTCTATTTGTTGTGAATGCTCAGAGGGGAAAGGCCAGAAGGA
AACTGTATCAAGTACACGAACGTAGCCTACTAAGAATCGGACGCCATATGACGATCGATT
CTCTGCCTTGTTGACGATAGATCTCTTCCTCCTCCCTGTATTCTTCATCCTGTCGTCCTT
TCTTTCCCCCCACTATACCTTCTAGAACTACGCGATGTATAGTCAAGCCACCAGAGATAA
CGTGGCCTTGTATTCCTATATCATTATTGATAACGTGTATTCTGGCACTCTGAATGCCAA
TGTGCCACCTAAAATGGAGATCATTACATATTGTACAAGATGGATATGCAAGAGCATAGA
AAACAATACCAGCAACGAAAAGCCACGAGACAAGTCTCAAAGTCCATATAGCCCTTGTT
CAAGCATGCGCCATGGGCGGGATTCTCGATCCCTTGACGGACAGGCACTTGATCGGCAGC
ACCCCAAACAGTGCTAGGGTGCATAGCGCAGTGCCGGCATAAAACACCTGTGTAATTGCT
AGACTGTATGCTTCCAGAGTTTGAGGGAGGTACTCGGGCTCAATTGCATTGCGTATCTCC
```

Figure 5F (continued)

```
CTCGGAGAAACATCAGCCACCCTCGCCGTATCCACTCCTGGAAGCGCCGCATTCAGGTTA
TGCACAAGGCGACTCTGGAAGACACTTTGGGCCACAAAGTTAAATAACGCGCCCGAAAGA
GACTGAGTAAATGTGATGATGGCGGAGCCCGTCGAGACGTCGTCGGTAGGGAGAGCAGTC
TGTACAGCGACAAGGGGGAGCGCCATGCCGGATCCGATGCCGACGCCCAATAACAGCTGG
TATGTGATCCAGGCAGCCGGTCCGGAAAAGACGTGCAGTGTCGTGAGCAGTCCCGCGCCA
ATAGATCCGACCACCGGTGCCATGTACATAAACGGCACGTAGTAGCCAACCCGGCTGACG
CCCCAGCCAGAGAGCATCGAACATACAACTACGCCGAGGATCATGGGAAGATTCATCACC
CCCGAGCGCGTTGCGGAGACAGATTTGATGGCCTGGAACCAAATGGGGAGCTGGCAAGCA
CATATCCATGTTAGCATCCGGATTCAGTAGCAAGGGGGTGTTCTCACATAATACGTAAAG
ACCGTGAAGGAGCCGTAAATGCAAACCGAAAAGGCTATTGCACCCCAGACACTGCGATTC
CGGACTATTCGTGGCGGAATCGTAGCCCTCTCGCCCTGCCACAGTTGCACAGCAGTAAAG
GTCAACGCCAGAGAGCCCGCCATGACCAAAAGCACGATGATGCGCCAGTTGCTCCAGGCG
TATTTTGCCCCACCCCATTGAAGTACGAGCAACATGCACATGACGGCGGGAAGGATGAGA
ATAATACCGAGGGGATCAAGATCAAGCAACTGCGCCCAGGGGGTTTTCTTTACTGTAGCC
TTTTCGCGGACCCGCGGCCTGACGAACAGAACAATGATAAACGCTGTCAACCCTCCAATG
GGCAAATTGATATAGAAGCACCAGCGCCAGCTGACGTAGTCGGTGAATACGCCACCAAGA
AGGGGACCCACGACGCTAGCGATACCGTACAGACCGCTAATAAGGGCGATAAACAGTGGC
ACTTGATGGAGCGGCATGATTTCGTGGACAATAAGCATGGAGCCGAGGAATACCCCTGCG
CCACCAACGCCGGCAATGGCGCGGCCGATGATGAGGGCAAGGGAACTGGGTGCGGCGCCG
CAGACTAGTGAGCCGGCTTCAAACAAAAATAGCGTTGTCAGGTATACCCATTTCACTCTG
TACAAGCTGTAGATCTTGCCGTAGACGAGGCTGAAGCTGCTTATCGTCAGGTTGTATGCA
CTCACGTACCAGGCCATGTCGTGTAGCGAGTTGAATTCAGCAGTGATCTTGGGGATTGCA
GTTGATAGCACTGTGCTGTCCTGGACATTGATCTGTTAGAGTACATCCTTGATGCGGAGA
ATGTGGTTGGTTCCAGGACGTACTAGGGACATGCAGAACACCGCCAGTGATAATCCAATG
AGAACAGCGGCGAGTTTCCAGCCTGATACAGTACCAGAGCCACTTGTGCCGTCGTCGACC
CGGTCATTTGAACCATGTTGGAGCTCGGCCACCGTGGGCGCATCTCCCTCGTTCGGCGCT
GGCGTTGGATGGGCACCCCCTGCATTGTTATCACCGGATGCTTCGCTTAGGCCCTGAGTA
GCACTTTGCTCGAGGTGCTCCTGCGATTTCGTCTCCTCAATGGGTTGGGCGTCGTCCGGG
CTCGCAAGTCTGGTGGTTGACTCGGTGGGCGGTTGCTGAAGACGCCGAAGGCGAAACTTA
GTGTGGCGCTTGCTTCTGCTGCCTGTGACGCCTGTCATTCGGCCAAGCAGGCTGGACTGC
ATCTTTGGTCAAGGGCGATTGGCTGAAAGATGAGGCAAATACGGAACGCTGAGACCTCG
GGAGTTATCCGTGCCTTTGTCAGTCCCAAATTTGAAGCTTTGAAGAAATCATCGCGGTTG
GAGGACGTCTTATTCGAAGCGAGTGTTTGATCATCGCATGTAACCACAGGGAGAATTCTC
ATTTGGGCCTCAGAAATAATCCCTTGCTGCGGATAGCTGCGGCATCCGAGGCATTTCAGT
AAGATTTATGTATTTTACGACATTAAACGGGCTCATGTGGCAGGTGCCTAAGCAGGGGAT
ACGCATTCTTACCGATTGAGAATGACTGCAATTGCCATCCCCAGTGATAGTCTCAGCAAT
TGTGCACTCGTCAAGCTTTGTGTAATTCAAGTGTCTAACATGGAATAGCAATAAAAAAAT
CCCAGCCAGCATGGTTTCCATCCGACATAGCACATTCCAGCCTGTTCTGACCTAAGGAAA
AATTGGCGTGACAAATACGCTAGAGTAGACTAGATAACATAACATTGAAGCCAAAACTGG
TAGCGAAATCACCAGCCAAGGGAGGGTCGGTGCGCCAACCTCTGGGCTCCCGGCGTAGTC
GCTCCATCCAGGGCCCGTCCTCTTCGGGGTGGGCAGGAAATCCACCTGAGGGGCACCTGC
AATGGCTTGCGACGTTCTCTCAAGCACCTGCTGCCTGAAGCGAGGAAAGATGTAGCGGCC
AACAAAGGCCTTGAGCGCGTCGTCCCTCGTGTGCAGCCTGGCGCCAAAGTACGCACGTTG
GTATGTGCTTTTCACGCGCTCGTACCTCAGCGAGGCGTATTCTTGGAGCACGGCGTCTAT
TGTGCAACTCGTGGCCGACGAGTCGGAAGTCGATAGTCTTTGTAGCAGAGATGCGAGCAC
TCCTGCGTCTTCTGCTGCGGTATTGGCACCTTGCCCGATATTGGGCGTCATCTACACTGG
TTAATCACATCCTGCTGTCCGTCTGTTGATACATCAAGCCACTCACCTTGTGGATGCTAT
CACCGAGCAGGACTACGCGCTTGAATCTCCAGGTCTCCAGCAGGCCCTCTTCCAGCGCAG
TCATGGAGACCGACGTCTTGTTCCCCAGAGATCTCTCACGCATATATCCCCCCAGACCG
GTACATTAGCATACTCGGCACAAATCTTGGCCGCATCGCTGGCTGAAAAGCGCGGAGTAA
ATGGGTAGATAAACCTCTTCTGTAACTTGATGAGGATAAACCAAAAAACACGGCCATCCT
TACCATGGAAGGTGATCACACAGAGCCCATTCGAGTAAGAGTTAACATGCTCCCACTCT
CCAGGCCGGAGATAGGGCTCGAAATTCCAAAAACACATGCATATTCGACAGTGAATGCTG
CAATCTCATGATTAACGTCTGCAACAATGAGGAGATATTGCAAAGCACACCTTGTCGATC
TCGCCGACCAACAAGATCCTTGGCCTGGCGCCACATCTCGGCACGCACTGCACTGTGTAT
CCCATCCGCACCAACGACCAAATCCCCTTTGTATACGGCCCCATCGGCTGTGAGCACCTG
GGCTTCTCGTTCGGTTTGTCGAATCTCAGTCACCTTCTTGTTGACGTGAATGTTGGACTT
GGCCGGGTAGCGGTTGTAGAGAATCTCCAGGACTTTCTGGCGATCGAGAGATATAATCGG
ATATCCAAACCTACAATTCCCGTCGGTATCAAGTTCAAACAGTGTTTAGAAGCAACAAAC
CTTTCTTGGACTTGCCTCGGCAGCTCACTGCTAAAGGAGACCCCATCTGGAAATCGCACC
```

Figure 5F (continued)

CTCATTTTGTGTATTGGCACCGTGCACTTTTCCAGGTCTGCATAGACGCCCAGCTGGTCA
AAGATTCGGCCTCCATTGGGCCAGATGCCTAGGAACGCTCCCTCTTGCGGGCTGATCTCA
GCGCGCTTTTCGAGTACTATATGATCGATATTTGCGTTCGCTAAACAGTGTGCCAACGTC
AGGCCAGCGACAGACCCTCCGACTATTATCACACGAAGATCAGTCTTGCGCGTAGGTGTA
TCGCTCATTGTGGCTCATCGGTGTGGTGCAACTACTCTTCTCCATCAGCTAACTACGGTC
TATTAATTATAGTAACTAGGATAATTGAGCCTAGCCCGCTGAGCAGCTATGAGAGCCGTC
CACATTGGTTCTTATGCTGCTTGCACAACTCATAACATAAGGATCCCTTGCGAGACGCTC
TCTGCTTCATTGGCTAGCAGCAAGCTATGGGTCCAAATAATACAAGCACCCACCCTTGCC
GAGAAGTTGGTTTCACCCTTGCTATGTGCATCAACGATGATAGAAGTTGTCACACAACGG
ATGCTCTTTCAGGCTCTCCGGGCATGATGGCCCTCAGGCTTTCCAATGGAGAGAAAGATC
TCCTGCTAATGGCATTCTGAAGACCTAGATGCATGATTGCCGGAACCCTTGTCAGTGGTA
TCTCCCCTTACTGGGTAGGCTTTCGAGAGATATCCCCGTTATTTCCGAGTCGGCGGAATA
CTGGGCCATATTGAAGAGGCCGCCTGCTTCCCGGCGCTATATCGCCCAAGGCCTTGATGT
TCCTTTAACACCCCAGGGCGCGCTCAATCCTCTTGATTTCCTCCTCCTCTCTCCACCGCC
CAAACCTTTTGTGAAAGAAAAAAAATGGCCGTCATCTCAGAATTGAAGAGACATCATCC
CAAGACAGGACTGCTCAGATATCTCCCTACCGGCGTTGTTCCATACGGAGAGCTGGTGCG
CATCCACCGCGCCCTAGGTTATTACCTCAACACATCTCCCTACGTAGTTGGAATCGCATA
CACTGCCGCAACTGCCGAAACAAAACTGCCCCTCGACCTACTCTTGGATCGCCTCCTCCT
GCTCACGCTCTGGTCTCTTATCCTTCGCAGCGCTGGCTGCGCCTGGAATGATCTCGTCGA
TGTCGACATTGACCGACAGATTTCGCGCACACAAAGCCGCCCCTCCCCGTGGCGCCAT
TTCGCTCTCCGCAGCAACCATCTTCACAGCATGTCTCTTCGTCCTAGGTTGTTCGCTTTT
ACTCTTTCTTCCGCGAGAATGCCTATTCGACGCCGGCATTAAAGTCTTCTTCGCGCTGCT
TTACCCTTTCGGGAAGCGCTTCACCGATCACCCTCAGCTCATCCTCATTAACATCGCCTG
GGCAATTCCCATGGCCATGCACAGCCTAGGTATGGAGCCTTCGAGCCAGATCCTCTCAAT
GCTCTGCATGTGCGTTTTCTTCTCGGCCGTGATTGTCATGATCGACCTGGTTTATTCGCG
TCAGGACACAGAGGAGGATCTCAAAGTCGGCGTGAAGAGCATGGCCGTGCGATACCGAAA
TTGTGTAGAAACGATGGCCTATTCGCTTTTTGCCATCAGTTCCCTGGCACTACTGTTTGG
AGGCGTGCTTGGTGGGCTTCGAGTACCGTTTGTGCTTTTTTCTGTGGGTGGGCACATTGT
GGGCTTTTGGAGGTTCCTGCGAGCATCGCTGCAGGCTGGACCGGCAGGGGTGGAGTCGCG
TGCCAAATCATCCTGCTTGATAGCGAGTGTGTTTGGGTGCTGGGGTTAGGTATCGAGTA
TGCTGTGCGTGTTTAGCTTTGCTTTTCGGGGTGTTGGTTGACCACACGCGCGTAAACGAC
GCCAAATTGGTCGTGGCTCATACGAATTTGCATATTTTCCAGATAACCGGCTCAATGCTA
TATGGATGGCCTACAGGAAATGGTCAAAGAAAAGGATAACCCCACTGATAAGAAGAAGCA
TCCTCATTGAGAGATCCAGAAACGCTTCCAAGTCAGCCCTACACGGTAGTGCGCATCTAG
ATCGCTGGGAAGGTTGGCGTAAGATCGTTACTGGGGCGATACCAATGCTGCCTGCC

Figure 5G

Sequence of the deletion of the Asperfuranone cluster

>ChrVIII_A_nidulans_FGSC_A4 COORDS:ChrVIII_A_nidulans_FGSC_A4:1721557-1754434W (32878 nucleotides) (SEQ ID NO:7)

```
TCAGCTATAGATGCGATCCGCGCCTCAAGCGCATTTCAAGCCCTCCCTCTTCAATACGTT
TGCGATACCTTAGAGAAACAAATCAACATCCATCAACTGGCACAGATTCATCTACCAACT
CAACGTGATTACCCGTCCAGCTTTGACCTAAACCTCCATAATCCCCATCCACAAGGCACC
ATGGGCAGCACATCTTCCGAGCCCACATACGACAGTGAGCCCATCGCGATTATTGGCCTT
TCGTGCAAGTTCGCTGGGTCCGCAGACAGCCCCGAGAAACTATGGGAGATGCTTGCGGAA
GGGCGGAATGCATGGTCAGAGATCCCTGAGTCGCGGTTTAACCACAAGGCCGTGTATCAT
CCTGATAGTGAGAAGCTGGGGACGGTACGTCTTTCCTTCTAGACTTGAGTTTCAGTGGTG
AAGTGGATGGGAAGCAAGAACCTGGCCAGACTAACGCGGAATCTTCGCAGACGCATGTCA
AAGGGGCACATTTTCTCGAGCAAGATGTCGGGCTCTTCGACGCGGCATTCTTCAATTATT
CGGCGGAGACAGCTGCTGTACGGTCCCTATGAACGATTTCAGGATGAATGGCCAGGCTAA
CTGAGCATGATGTACGGATAGACCCTCGATCCGCAATTCCGCTTCCAGCTCGAGTCCGTC
TATGAGGCTCTTGAAAATGGTACCACCCTCCCCCAACAGCCCTTGCGCAAGGCTGAACA
GAGAGTACAGCTGGCCTGACGATTCCATCCATCGCCGGCACCAACACCTCCGTCTACGCC
GGCGTCTTCACGCATGACTACCACGAAGGTCTGATTCGCGACGAAGACAAACTGCCCCGG
TTCCTCCCCATCGGAACCCTCTCCGCCATGTCCTCGAACCGCATCAGCCACTTCTTCGAC
CTCAAAGGAGCAAGCGTGACTGTAGACACCGGCTGCTCGACGGCCCTGGTGGCCCTGCAC
CAGGCCGTCCTCGGCCTGCGCACGCGCGAAGCAGACATGAGCATCGTCTCTGGATGCAAC
ATCATGCTGTCGCCGGATATGTTCAAGGTGTTTTCAAGTTTGGGAATGCTAAGCCCTGAT
GGGAAGAGCTACGCCTTTGACTCAAGGGCGAATGGATACGGACGGGGCGAGGGCGTAGCG
ACGATTATCGTGAAGCGACTCGCGGATGCGCTGAGGGACGGGGATCCCGTGCGCGGCGTG
ATCCGCGAGAGCTATCTGAATCAGGATGGAAAAACAGAGACTATCACCTCGCCGTCACAG
GAAGCGCAGGAGGCACTGATCAAAGAATGTTATCGGCGCGCGGGGCTGTCGCCGTCGGAT
ACACAGTACTTCGAAGCGCATGGGACAGGCACCCCCACTGGAGATCCGATTGAGGCGCGC
TCAATCGCGTCAGTATTTGGAAAGAATCGAGAGCAGCCGTTGCGGATTGGCTCTGTCAAG
ACGAATATCGGGCATACTGAGGCGGCCAGTGGTCTTGCCGGGCTGATCAAGGTCGTGCTG
GCCATGGAGAAGGGGTTCATCCCGCCCAGCGTAAACTTTGAGAAGCCGAATCCGAAGCTG
AAGCTGGATGAATGGAGGCTAAAGGTGGCAGATACTTTGGAAAAGTGGCCTGCACCGGCG
GAGCGGCCATGGAGGGCGAGCGTGAACAACTTTGGGTATGGGGGTACGAACAGCCATGTC
ATTGTGGAAGGGGTGCCGAAGAGATTATACACACCGGCAAATGGAAATGAGACCGGCCAG
ATAAAGCATGAGACAGAGAGCAAAGTGCTCCTCTTCTCTGGCCGCGACGAACAAGCCTGC
CAGCGCATGGTTGCCAGCACGAAGGAGTACCTGAAGAAGCGCAGGGAGCAGGATCCTCCC
ATGACACCTGAACAAGTCAAGACCCTCATGCAAAATCTCGCCTGGACATTAACGCAGCAC
CGCACTCGCTTCTCCTGGGTCTCCGCACACGCGGTCAAGTACTCGACCTCCCTGGACACC
GTCATTGACGCCCTCGAGTCTCCGCCGCCGGCCTCAAGACCCGTTCGCATCCCTGACTCT
CCATTCCGTATTGGCATGGTCTTCACGGGGCAAGGTGCGCAGTGGCACGCCATGGGCCGC
GAGCTGATCGCCGCGTACCCGGTATTCAAGGCAACCCTAGACGAAGCGGAACAGTATTTG
CGCCAACTGGGGGCCGGCTGGTCCCTCATCGAAGAGCTGATGAAGGATGCAGCCACGACA
AGAGTCAACGACACCGGCCTCAGCATCCCTATCTGTGTCGCCGTGCAGATCGCTCTCGTC
CGCCTGCTCAAGGCATGGGGGATCACTGCCTCGGCCGTGACATCCCACTCGTCCGGTGAG
ATCGCCGCCGCGTATACGGTTGGCGCTCTCTCGCTGCGCCAGGCCATGGCCGCCGCCTAC
TACCGCGCTGCCATGGCAGCAGACAAGACGCTGAAGAGCGCAGAGGGGCCCAAGGCGCA
ATGGTTGCCGTGGGTGTTGACAAGGCTGCCGCGCAGGCATACCTGGACCGCGTTGAGAAA
TCGGCAGGCCGCGCTGTGGTGGCATGCATCAACAGCCCCAGCAGCATCACCATTGCCGGC
GACGAGGCAGCCGTCGTCGCGGTCGAGAAGTTGGCCACTGAGGAGGGCGTCTTTGCGCGC
CGACTCAGGGTCGAGACGGGATATCACTCGCACCATATGGAGCCAATTGCGAGCCCGTAC
CGGGAGGCGCTTCGCCGCGCATTGGCCGCAGAAGATGCTGAGTCTGGTACCAAGGACCAG
ACTGATGTCCCGGGCTTTGCGGATGCCACTAAACCGGGCAGCCTAGACCACACCGTCTTC
TCCTCCCCCGTCACGGGCGGCCGTGTCACAGATGCCAAAGTCCTCTCTGACCCGGAGCAC
TGGGTCCGCAGTCTGCTCCAGCCAGTGCGGTTCGTCGAGGCCTTCACTGATATGGTGCTT
GGCTCCACAGATAGCAGCAATATTGACCTGATCCTCGAGGTCGGGCCGCATACAGCCCTT
GGCGGACCGATCAAGGAGATCCTTGCCCTGCCTGACTTCAGCAGCAGGAATGTCAGCCTC
CCCTACATGGGCTGCCTCGTTCGTAAAGAAGATGCGCGCGACTGCATGCTCACTGCTGCC
TTAAACCTTTTCTCCAAGGGCCACAGTATCGACCTGCTCAGACTCAGCTTCTCGTCTGGC
ATCCCAGAGTTGCAAGTCCTGACCGACCTCCCCTCATACCCGTGGAACCACAGCATCAGA
```

Figure 5G (continued)

```
CACTGGTCTGAGTCTCGCCGCAATGCCGCGTACCGTAAGCGCAGCCAGGAGCCGCATGAG
CTGCTGGGCGTGCTGGAACCGGGCACGAACCCGGACGCTGCCTCGTGGAGGCATATCATC
AAGCTCTCCGAGGCGCCGTGGCTGCGCGACCACGTTGTCCAGGGGAACATCCTCTACCCC
GGTGCAGGATTCGTGTGTCTCGCCATTGAGGCAATCAAGATGCAGTCTGCCATGAGCGGG
ACGAATGATGTGACCGGTTTCAGGCTGCGCGATGTCGAGATCCATCAGGCGCTCGTGATT
GCGGACAGTGCAGACGGCGTCGAAGTGCAGACGACCCTCCGGTCCGTAGGAGGCAAGGTC
ATCGGCGCCAGAGGCTGGAAGCAGTTTGAGATCTGGTCGGTCAGCGCAGACAGCGAGTGG
ACAGAGCACGCGAGGGGTCTAATCACCGTCGACACTGAGACCAAGGCATCCACGCTCGTG
GCAAGCACTCTCGATGAATCCGGCTACACGCGCCGCATCGACCCGCAAGACATGTTTGCT
AGCCTGCGCGAAAGGGGCTCAACCACGGGCCCATGTTCCAGAATACGCTGAGAATCCTG
CAGGACGGAAGGGCCAAGGAGCCGCAGTGCGTCGTCGATATCAAGATCGCCGACGTATCG
AGCAGCAAGGACAGCGGCCGGATGAGTCTTCTGCACCCGACGACGCTCGACTCAATCGTT
CTCTCCTCATACGCCGCAGTACCCAGCTCGGATCCGTCCAACGACGACAGCGCGCGCGTT
CCCCGGTCCATCCGCAGCCTGTGGGTGTCGAGCATGATCAGCAGCGCCCCGGGCCATACG
TTCACCTGTAATGTGAAGATGCCGCATCACGATGCGCAGAGTTACGAAGCGAACGTGACA
GTCGTGGACGAGGCCGGAGCCAGAGCTGAGAGCATGGTCGAGATGCAGGGTCTTGTCTGC
CAGTCTCTCGGCCGCAGCGCACCAGCAGAGGACCGAGAACCCTGGACGAAGGAGCTATGC
GCGAACGTCGAATGGGCGCCTGATCTCTCCCTCTCTCGGCCTTCCGGGCTCGTCAGAC
GCCATCGACAGGCGCCTCAACACCCTCCGCGACCAGAATCCAGACGAGAGGAGCATCGAA
GTGCAGACGGTCCTGCGCCGCGTCTGCGTCTACTTCAGCCACGATGCCCTTTCCTCCCTG
ACAGAAAACGACGTGGCAAATCTCGCATTCCACCATGTCAAGTTCTACAAGTGGATGCAG
GATACCGTCAACCTGGCACTCGCGCGCCGCTGGAGTGCCGACAGCGACACCTGGATTCAT
GACAGTCCCGCCGTACGGGAAAAGTACATTTCCCTTGCTGGGTCGCAGACGGTGGACGGA
GAGCTGATCTGCCAGCTAGGCCCATTGCTGCTGCCGGTCCTTCGCGGGAACGAGCGCCG
CTGGAGGTTATGATGGAGGGACGCCTGCTGTACAAGTACTACGCCAACGCATACCGGCTG
GAGCCCGCCTTCGAGCAGCTCAAGTCATTGCTGGGCGCGATCCTGCATAAGAACCCTCGT
GCCAGGGTTCTCGAGATCGGAGCCGGCACCGGCGCTGCCACACGACACGCGCTCAAGACC
CTAGGGACTGATGAGGATGGCGGTCCTCGCTGCGAGAGCTGGCACTTTACTGACATCTCC
TCCGGGTTCTTCGAGGCAGCCCGCGCTGAATTCGCCACCTGGGGCGGCCTGCTGGAGTTT
AATAAGCTGGATATCGAGCAGGACCCCGAAGCGCAGGGGTTCAAGCTCGGTTCTTACGAT
GTCGTGGTCGCCTGCCAGGTTCTGCACGCCACGAAGAGCATGCACCGGACTATGACCAAT
GTCCGGTCCCTGATGAAACCCGGCGGCACGCTGCTCCTTATGGAGACGACACAGGACCAG
ATTGACTTGCAGTTCATCTTTGGTCTCCTGCCGGGTTGGTGGCTGAGCGAAGAGCCTGAG
CGCCACGCGAGCCCCAGCCTGAGCATTGACATGTGGGATCGGGTGCTCAAGGGGGCCGGC
TTTACGGGAGTCGAGATTGACCTGAGAGATGTGAACGTTGATGCTGAGAGTGATCTGTAC
GGCATCAGCAATATCATGAGCACGGCTGTCGGCACGGCGGGTTCGAGCCCTGAGAAGGTG
GATGCCGCCCAGGTGGTGATCGTGACGGGCAACAAGACGGGCTTTCAGGACGATTGGGTC
AGGGGACTGCAGGCAGCCATTGCTCAGGACTCCGGTAGCGATGCCCTTCCAGAGATTATA
TCCCTCGAGTCTCCCTCGCTCGGGGCAGAGGCCTTCCAGTCCCGGCTGGTCGTCTTCGTC
GGCGAGCTTGACAGACCCGTTCTGGCGTCTCTTGACTCCACAGAGCTCGAGGGAATCAAG
ACCATGGCCCTCGCCTGCAAAGGTCTTCTCTGGGTCACCCGCGGCGGCGGTTGAGTGT
ACGGACCCCGACTCTGCGCTTGCATCTGGGTTCGTCCGCGTTCTGCGCACCGAGTATCTC
GGCCGGCGCTTCTTGACTCTCGACCTGGACCCAGCAGCCCATTCGCCTGCGTCTGATATC
TCAGTCATTGTGCACCTCCTCTCCTCGCGCCTACAGCCGGCCGTTGAGACAGCGGCCCCG
GCCGACAGCGAGTTCGCTCTGCGAGACGGCCTCCTCCTTGTGCCGCGCCTTTACAAAGAC
GTTGTCTGGAATGCACTGCTGGAGCCTGAGGTCCCCGACTGGGCCTCTCCAGAGAGTATT
CCCGAAGGCCCCCTTCTTCCAAGCCAAGCGGCCGCTTAAACTCGAGGTTGGGATCCCTGG
TCTGCTCGATACACTCGCCTTCGGCGACGACCCCGACGCGCTGGACGCCGCCGGGCCCAT
GCCCGACGAGATGGTCGAGATAGAGCCTCGCGCTTATGGCCTCAACTTCCGCGACGTCAT
GGTGGCCATGGGCCAGCTCAAAGAGCGCGTCATGGGTCTAGAGTGCGCAGGCGTCATCAC
GCGCGTCGGCGCTGAAGCTGCGGCGCAAGGCTTCGCCGTGGGTGACCGGGTCATGGCCCT
GCTGCTGGGCCCGTTCAGCTCTCGTGCACGGGTGAGCTGGCACGGAGTCGCCAGTATGCC
CGCGGGGATGGGGTTTGCAGATGCTGCCTCTATCCCGATGATCTTCACCACGGCGTACGT
CGCTCTCGTGCAAGCAGCGCGACTGTCGCAGGGGCAGACAGTGCTTATTCACGCCGCTGC
AGGAGGTGTAGGGCAAGCAGCCGTGATACTGGCCAAGGAATATCTCGGAGCAGAAGTCTT
TGCAACCGTGGGCTCGCAGGAGAAGCGAGACCTACTGATCAAGGAGTACGGAATCCCCGA
CGACCACATCTTCAACTCTCGCGACAGTTCCTTTGCACCGGCTGCCCTGGCCGCAACAGC
CGGACGGGGCGTGGACTGCGTCCTTAACTCGCTAGGTGGCGCCCTCCTCCAAGCCAGCTA
ATCGAGGTTCTCGCGCCCTTTGGCCACTTTGTCGAGATCGGCAAGCGCGATCTCGAGCAG
AACAGCCTGCTCGAGATGGCCACCTTCACGCGCGCTGTCTCCTTCACTTCGCTCGACATG
```

Figure 5G (continued)

```
ATGACCCTCCTCCGCCAGCGCGGCGACGAGGCGCACCGCGTCCTGAGCGAGCTCGCCCGG
CTGGCCGGCCAGGGGATCGTCAAGCCCGTCCACCCTGTGTCCGTATACCCAATGCGCCAG
GTTGACAAGGCCTTCCGTCTGCTGCAGACGGGGAAGCATCTCGGCAAGCTGGTACTGTCC
ACCGAGCCTGACGAAGAGGTTAGAGTTCTTCCCCGGCCGGCCACGCCCAAATTGCGCGCC
GATGCATCTTACCTCCTTGTCGGCGGCGTGGGAGGTCTCGGCCGCTCCCTCGCCAGCTGG
ATGGTCGAACACGGCGCAAAACACCTTATCCTCCTCTCGCGGAGTGCAGGCAAGCAGGAC
AGCAGCGCATTCGTTAATGGCCTACGGGACGCAGGATGCCGCGTCGCCGCAATCTCCTGC
GACGTCGCCGACAGGGCCGACCTCGACCGCGCGATCGCGGCCGCCTCAGAGTTGGGGTTC
CCGCATGTCCGCGGCGTCATCCAGGGCGCGATGGTCTTGCAAGACTCGATCATTGAGCAG
ATGAGCATTGCAGACTGGAATGCGGCAATCAAGCCCAAGGTTGCCGGGACACGCAACCTC
CATGACCGCTTCTCCCAGCGCAACAGCCTCGACTTCTTCGTCATGCTCTCTTCCCTATCC
GCGATCCTGGGTTGGCCAGTCAGGCCTCCTACGCGGCTGGCGGAACGTACCAGGATGCG
CTGGCGCGCTGGCGCTGCTCCAAGGGTCTGCCTGCCGTATCCCTCGATATGGGCGTAATC
AAAGATGTCGGCTACGTCGCCGAGTCGCGGTCAGTCTCAGACCGGCTGCGCAAAGTTGGC
CAGTCCCTCCGCCTCTCTGAAGAGTCGATCCTCCAGACCCTGGCAACGGCGGTCTTGCAC
CCATTCGGCCGGCCCCAGCTCCTCCTGGGCCTGAACTCCGGCCCAGGCAGCCACTGGGAC
CCTTCCAGCGACAGCCAGATGGGGCGTGACGCCCGCTTCGCACCTCTCCGCTACCGTAAG
CCCGCATCTACGAAGTCCGCTCAGACATCTTCCAGCGGCGACGGCGAAGAGCCCCTTTCA
TCCAAGCTCAAGTCAGCCGATTCCCCCGATGCGGCGGCGAACTATGTCGGGGGTGCAATT
GCCACCAAGCTCGCAGACATCTTCATGGTCCCTGTGGCCGATATCGATCTGACCAAGCCG
CCAAGTGCGTACGGGGTCGACTCGTTGGTTGCTGTCGAGCTGAGGAATATGCTGGTGCTC
CAGGCGGCGTGATGTGAGTATCTTTAGTATCCTGCAGAGTGTGAGCCTTGCGGCGCTG
GCGGGGATGGTGGTCGAAAAGAGTGCGCATTTCGAGGGAAGTGCCACGGGAACTGTCGTT
GTTGCTTGAGCTGCATCGGTCATGTTGTTCTTCTATAGAGTTGAAGCAAGGTTTGTAGTT
TGCTCTGGGTGTCTGGAGTTGTCTGGAGTTGTCTGGAGTTTTGTTATGATGTTGATGGGT
ACTTCTTCATACTAGCATTTTGGCATGTTATAAGAACATATTATCAGTTAAATGTCTTTC
AATTTAATCAATTTGTTTTTAGAATGATGTTGTCTGCCTGGCTATGTATCTAGATCCTAT
ACAAGCTCTATCGACTCGACCTAACTACTACGACTTGAAAGTCAAGCGAGAAGTGATGAT
ATGAACCCATATGTCAGACCCGCTAAATTTATTAGTGATAACAACTATATTACTCAGAGC
TTTTCTTTCTAGAGTATGTTAGAATTGCCCTTTCTGGCTCAGTGGGAAGCTCGAGACCTA
GTCCTTAGTCACGTGCTGCTACATCATGTAAATATAAGCCCTACATGGCTGTCTTGTGCA
TGAGGCTAACACCATTATCTGTCACTGGTCCTTTTATTTGGTTCTTTTCTTTACTTTCTC
GGGCGGGGGGAAAGCCGCTAACACTGTCTATCGCTTGGACAGAAACTCACCAGTTTGTT
CGCAATCCTGAAGCGTATGGGAAGCTTACAGTTAAGGAGTAGCTCGAGTCTGGACCCTGT
TTTCGACTTGTACCTTTGATTTGGATGACTGGTTAACCTCAGCTTATGTATGATGTGCTC
TCATGGTGTCAATATCTGGTAGTCTGATTCTGAGCAATTTGATAGTATCTGATGGCTGGC
GAGTAAGGCCAGGGCGATGACTGGTATAAAGTCAGCCCTAAAACTTCCATCCGAGATGTA
AAACCATCGATTCCCCTCCAAGATCTCCTGACGAGACTAAACAAAGATCAAGTGGCCTTG
TAGTAACTCTAGCAAGCAGCGACAAAATGCCTCAACACGAGATGACCAAGTCAGACTCGG
AACGAATCCAGTCCTCGCAGGTAAGAGCATCAGGACATTTGCTAATACCATTCCGCCCCG
CTAATCTGCTTGAATGCACACAGGCTAAAAGCGGAGGGGACATGTCTCTTGGAGGATTCG
CCTCGCGCGCCCTGTCTGCCGGGACTGCTGGGTCAATTCCCAGTCCTCGGCCACTGCTTC
CGGCCACGCGGACTCGGGTGCCGGATCTGCAGGCGGATCTCATTCGGCCGCACCTGGCGG
TGATGCGGGGCAGGGAAGAAGATAAAAGTACCCTGTTGTCTTTGGGGCGTTGAGGTATAA
TGGCATCGTGGTAGACCGACTGGGCTTTTTTTTTGATATAGTTGATCCTGAAGCGGAGG
ACAGTTGGTAGGATAAATGAAAGATACTGAACCATGCCCGGATTTTGTGCTCAAGGACCT
AAAACTGAGAAGCTGAATCTGTTCTTGTCTGGGAGAAGGCCTGCCAGCTGCATCCGAGTA
TCTATCTTGCCAGGACCAAACCGGGTCTGGGCTCAGTTCTTCTAACTTCTTAGTGGAGTT
TTGCAGTGTAGATTCCTTTGCACTATCTGGTATCCTAGTAGCAGCCTACCAGGAAATAAG
AGATAAATAAAGTCTTAATTGGCATTATTATGTTTCTCAGAACTATATATCTCGGAACAA
AGCTGAGCAGACAGAAGTTTACCCTCACATATGGACAAATTGCGTGCTCAGGCATAAGTC
GGAAACAGCCTTAGCCAGGTCAACACTTGTAGCCTTCGCTAGACGACGCCCCAGCTTTTC
ATAATGGCCGGCCTGGAGGGAGATACGGCTATCCACCCTAGAACCTCGGAATAGGTGTCC
CCTTCCCAAAGACCCCCTTGGGATCCCACTTTCTCTTGAGATACGACAGCTTTGGCAGAT
TCTCCTTGCTCCACCAGCCTCCGCCCTCATCACCAAATGCATAATTGACGTAGATAT
GTGGCTGGTCAGCAGGAAACCCGCTGGTGGCATGGAGCTTTTCGCGCAGTGAGACCAGCA
GCTCGTTCGTTGGAGCCTCCAGTTCCGGATTCAAGAATATATTCTCGTGCAGCCAAAACA
TCTTCGTGTCGCGCCAGGGATACACGGCCGTGTGCGCAGGCGTTTTGAGCGTGTTGTTGT
TCGCGTATCGCTGGAACAGACTCTGCCCCAGATACCCCGGGTACTGCTCGTAGAACGCGG
TCATGTCGTCGAACACCTCCTGCATGGTGGCCGCGTCTGTTCGGCCTAGTCCTACGGTAC
```

Figure 5G (continued)

```
CGCCGGAGACGTAGGCTCCCGTCTGGCAGGGTCCGTCGAGGCCAGCGTACAGCTCGACAA
GAGTGACGTTCGATACGTTCCGGCTGATCGGGCCGAGCGCCTCGGCGTGCTCCCAGTGGT
CGACGAAAGTGGCCCAGGGGGCGAAGTGCTTGATGTCCACGGTCAAGAGGGTCTCGTTGA
TGGTGCGGTCGTACCCGATCGAGAGCTGCACTCCAGTTCAGGAGGGAGGACATTATCGA
GGACAGAGAGGTACTCGAAGACGCCGAGACTCTTGGATGAGTTATACACAAACGTGCCGA
TCACGGCGTCGCCGTTGTTCGGCTGGTCGAACATCTTGAATGTGGCGGCGGTGATGATGC
CGAAGTTTGCACCGGCGCCGCGGATAGCCCAGAGGAGATCGCTATTGCAGGTCTCATTCG
CAGTGATCAGCTCGCCCGTCGCAGTGATAATGCGGACAGAGACGAGTGCGTCCACGCCGA
GGCCGAAGAGCCCTGTTTCGTACCCAATTCCGCCGCCGATAGTGGCGCCAATAACCCCGA
CGCAGGGAGAGTTGCCGCGGGCTGTCTCTATTAGACGGCATGCTTAAGAAGGAGAAGGAG
AGAATGAGGGGGCATACGGATGGCCTTGCCCGCTTTATAGAGCGGCTCAGTGATATCTCC
CAGCTTTGCGCCCGCACCAACGGTGACGGTGTTGGACTCCAGATCGATGTCCACGTTGTT
AAAGTTGGCCAGGTTGATATCAAGCCCTTTGACGGTGCCGTAAATCAGACTAGTGCCGTG
GCCACCGCTGGTGGCCATGAAGCTGACATTGTTCGCGACGGCGATGCGGACCTGCCTCGT
CAGTACACTATTTCCTTAAGAAGCAACACTACAAAGGCAAACAGAGAACAAGAGGCATAA
GAAGAAGAAGAAGAAGGGGGTATACAATCTCCTGTAAATCCTCCTCGGTCTGCGGCT
TGATCGCGCCTGTCCAGGTCGGAGGCCTCCATTCGGACCATCTGGGTGATACGACCTCGT
CAAAATCCGCGTCGCCAACCTCGGCGATCTCTGTTTCAGGCGAGACGTATGGGCCGAAAA
GAGATTCGAGGTCGATGCTTGCCGCGCGCCGCAGCGACTAGTGTTATTGACTGAAGCA
GAAACCGCATCCTGGTGTGATTGGGCTGATTAGGACAGGCCGGATGGGTGTGCAAGATAG
GAGGAGAGGACTGGTACGGCGAATGAGCTTTAATAGCCGGTCAGAGATTGCGCGTGGCTG
CGCCCAGATCCAGCAGCTCCAGCCATACTCCAGCATACTCCGGCCAGCCGGGGCATATG
GCGTGGTCACTGGAGCTGGTTAGGATCAACTGCTGGTTAAGGCTTACTGTGTTGCCATGC
TTACGGTGCACCGAGAGGGAAGGTTGGAGTTAACGGAGTTGTAACTCCGGGGATCCAATT
AGGGCTTACAGTCTGCAAATCCATGCAAAGTCCGCTGCGCCCTGACACAGCAAGGAACA
GTGTAGAGTCCGATTGGATAGCGGAGTTGAGGTGACTGGCTGGTTCCTGTTAGCCCCTGC
ATCGACCTGCAATGTATTGCATCAAATTAGGGCTAGCCTCTAACTCCGTTAGACTATCCG
CAACGCCTGTCACACACGTGGCTAGGCAGCAGATGATATACTTTTGAAAGCAGTACTCTA
AATTTGTGGGTATATGGTGTGGCTATGCTGGATCGTCGTCTAAGGCCCATTGTTACCAG
CACTATTTAAGTTGTCGACAAGATCTAGTCACATACTACCAGCGAGTGCATGCAGGGCCG
CAGGATATAGACCGGACTCAGCATTGAGCCATGTCTTTACGTACCACTGTAGTTAGCCAC
TGAGTGATAGACACATTGCAGCTTCTCTAGACTGATCAGTAATGACGATCTCGCTTGATA
CTGTCTGCTTATGCAGTATTTATATAGTATAGTGTAGACTACGGACAGATTGCATCTATT
CCGTGAGGAAAGGGTCTTCAAGCATCTATAAGGAATAAAAACTCGCTGTCACTGTACATG
CTCTAGCTACCTAAAAGAGATATTGCAGGTGCATTGATAAAGGACTATGCAGAGAGCTAG
ATCTCATGTTTCTACTCAAGTTACAGGGCATGGCCTAGCCTAATATGCAGTTGTCCTATA
TGTGAGCTAGCTGGAGCCGATGGGAAGTGTGTTTGATGAAACTGATTGGAATAATATGGA
ATTGTAAGCAAAGTAACAACAGTCTAGATACAATGAATCATTCCCAACACCAGAATACGC
CAGACTAAAACCAGAGTTAGCGAAACAAAGAATATCTGTAAGCTCAAGCAATCAGGCGAG
GTAGCCCATATCCTTCCAAGCCTGCACATACAACCTCGCAAGCTCCGTGCCAACAGGCCC
AACCCCCGCCATAGTGGTCGAGTGCTCCTTCGCCTTGCTTGTGTCAAGCACCAGGCCGCC
ACAGCTCATGCGCTCGAAATGGTCGTCGAGGAAATCCACCAGCCGCGCCGCCGGATTCTC
CGTCTCCATCGGCAGCGGAGACCGCCGCACCCTTGAGATCCACGTCTTGAATGGGATGAT
ATTCGATGCGGGAATATCGAGTGCTGACGCAAGCACATGGTTCATGGCTTGCCAGTTCTG
ACCGACAGGATTGTCCATATGGTACACTGGGTATGCCTCGTCGCCTCGTGAGGTGAGATG
GAGCAGGTCCACAACACCAGCAGCGCAGTAATCCACAGGAATCCACTGCATCTGGCCCTG
CAGGTCCGGCCAAGCACGCAGCGACTGCGAAGACTTGACTAAGAAAGCAAAGTGCTCGAC
CGGGTTCCAGAAACCGCTCGTCGACGAGCCCGAGATCTGGCCGGGCCGCACGACCATCGC
CCGGAAGAGACCGGGATGCCGGTGAAGGGTCTCATCAACCATGCGCTCACAAATCCATTT
CGCCTCGCCATATCCGGACGGCAGTGCTGCAGATAGCGGGACGCGGTCCTCGCTCACGCG
GGACTGCCCGCAGAATCCGACGACGCCGATGGAGGAGATGAATTGGAAGCCCACGCGGCT
GGAACCATTGAAGGGCCGTTCTGCAATGTCACGGGCAAGATCAAGAAGATTCCGCATTGC
CTGTAGCTGGGGCTCGAATGCGGACACTGGCCGTGTCCCGCTCATGGGCCAGGCGTTGTG
GATGATATCCGTCGCGTTCTCGAGGAGCCAGCCGTACTCAAGCGGCGGGAGGCCCAGCTG
TGGCTTAGAAGTGTCTGTCTCTAAAACGCGGAGCTTTGCCCGTGCGCCGGGGACAGGGT
GATGCCGCGGGCTGTTAGGGCTGCCTGTTGGCGCTTCTCTGGGGTGGTGCTGCTGCTGCG
ACGGTTGAGGCACACCACCGTCGCAACCGACGGTGTCTCGGCGAGTCTCTGAACGATATG
TGAGCCTAGGCTGCCAGTCGCACCAGTGACGATGACGACGGCCTCGTGCGCTCTGCGTCC
TGGTGCTGCGTGCGGCGCCTGTGTTTTGCCAGACTCCTTCTCGGCCCGGCTCGCTAAAGC
ACGGAGTTTGGGCGTCTCCCAGCCAGCCGTGTACTTTGCAACTAGGCTCTCTGCTGTCGC
```

Figure 5G (continued)

```
TGTGCGCGCCTCAACATTCTCCCGGTTCAACTCGGGGATGAGGGTCTGCACGGGCCCTGG
CTTGGGCAGACGGGCTCCCTGAGCCCCGACGCGAGCGCGATAATGACTTTCTGGAAGGT
ATTTTCAGGCAGGTTGCCGTCTGTCCAGTCGACGTGGCCAAACCCGGCCCTGTGCAGCTC
ACTCTCCCAGTGCTCGGCCGGTACGACGGCGTGGTGCCGCCCGTCATCGAACAGCCACCA
CCCCTCGAGCAGGCCGAAAACAAGATCGACAAAGGGGACCACCTCGGTCATTTCCAGCAT
CATCAAAAACCCATCGGGGCGGAGTGCCTGATGGATGTTGGACAGCGAGACCCCGAGATT
GTGCGTGGCATGGATGGCATTGCTGGCGAGCACCAGATGCTGGTTCCTGAGCTCGTCGGC
CGGGGGCTTCTCGATATCGTGCACGGCGAAACGCATAAACGGGTATTGCTTGCTGAACCG
GCGACGGGCGTTGGCGACCATGCTGGGGGAAATGTCTGTGAAAGTGTATTCAATGGGCAG
GGCGCCCGATTCAGCCAGGGTCGCCAGGAACGGCGCCATGATGAGCGTGGTGCCTCCTGT
GCCGGCGCCCATCTCGAGAACCTTGAGCGTCTCTCCGGTGCGGCCAATCCGCTCAGCGAG
GAGGTTCGTGACTTCACGCATCTGTGCGTAACTCATGCAGTTGAAGGTATGCTCGCAGTA
CATGGCCGCGGTCAGCTCTCTTCCCTCAGGGCTGCCAAACAGCACGCGGATGCCGTCCGT
CGAGCCGCTCAAGACGCCCGCCAGCTGCTGCCCGGCGTAGTAGGCTAGTCTGTTGGGGAC
TGCAAACCCGGGGTCTGATGCCAGGACTTCCTGCAGGATCACCTGGCTGGTCTTGCGCGG
GGCCGTGATGTGCGTGCCGTGTAATCTGGCCGCTGGCCGGGTCGATGTTGATAAGGCGTGC
GTCACGCTCAAGGAATTCGTAGACCCATTGCATGAGGCGGCCATGCTGAGGGAGGAAGGC
GACGCGGGCGAGGGGCTGGCCTGGTGATGCCGTGCGAAGGGGGCATCCGAGTTCATCCAT
CGCCTCGACGACGAGGGCAGTACAGAGTCTGTTGCTTCCAGAGAGCATGACGCCCTCGGT
CTTGTCGACTCCGTACTCCTTCATGAGGGTGTCGGTCTGCATCTTGACCTGCCCAAAGGA
GGCTAGAATGTCGGAAGAGGATAGGGCAAGCCGAGACTCGACGGGAGGTGCAATCGCTGC
GAGCCCAGCAGACTTGTGAATGGCCACTGCCTTGAGAGGCAAAGGCTGCTCCTCTTCGCC
AGTGGGCGTGAGGATGCCCGTGTCTGAGCTTTCGGAGCCGGCGTCGTCGCTCTCAGAGGC
AGACTCGCTGGACGAGTTGTCGCTCTTCTCTTCGTCTTCGTCATCTTCTGCCTCCGCAGG
ACCTGCGTTTGGACCAAAGAGCGCATTCGAGACGCACTGCACGAACTTGCGTAAACTGGT
TGCTTCCATCTGCTCGTTCTGGTCGAGAGTGCACTTGAACGCGGCCTCGACCTCCTTGCC
CAGTTCCATGCCCATCAGACTATCGATGCCAAAGTCCGCCATCTCGGCGTCCAGCTCGAG
CTCGCTGGCATCAATGCCAGAGACTGTAGCCACAAGGTTGCGCACTTCCTCGGTAATATC
TCGCCAACCAGAGGGCTTGCTGGACTTGGATTTGGCCTTCGTAACGGGCTTCTTCTCTTT
CTTCTCTTTCTTCGAGGTCTTGCTGGCCTTTACCTTCGCCCCAGGTTCAGAGCTAGCTCT
TACCTCAGGAGCAGTCTTTAGAGCAGCCTGGAAGGCTGCCGCTGGTGTTGGTCCTGGCAC
CAGCGCTTTCGTTCTCAGGACCGAGTCGTCCTTGGTCATCCGTGCGAGCATCATGCTCAT
CGACGCCTTTGCGACACGCATATACTGCACGCCCAGCATGATCTCCACGAGCTGGCCGCT
TACCGCATCAAATACAAACAGGTCCGTCATGATCGCTTTGTCGCCTTGTCTTGAATGGCG
GGCATAAACATGCCAGACGTCCGCATCCTCTCGGCGGTGCTCTAGGCGAGCGCATGCT
CAGCTCGCAGCCCGTCGCGATGAACATGTCGCTGCTCGGCAGGTCCGTCATCAAGTTTAC
CCAGACACCGCCGACCTGGCTGAAACTGTCGCTGAGCGGGACATCGAGCCATGTATCCCC
GCGACTGGATCTGGGGAGTTGCACACGGCCTGCGCACTCAGTTCCCTTGCCGACGACATA
CTTGACCCCGCGGTAGACCTCGCCGTAGTCGACGATCGAGCTGAATGCACGGTAGACATT
GCGGCCCTGCAGGACCTCGACACCTTCGTCGGTGTCCTGATCGAGGCTTAGACGGAGAAG
ATCGGTGCATTGCTTGTGTGAGACGAGCCGCTCAAAGTTGGCGAACTCGCGGACGTGCGC
TTGGTCAGAAGAGGAGCGCATTTCGACCGTGGCTTCGGCGTGAATTTCTGGTGTTTTCTT
GGTCGCGTCATCATCAAGGCTGAAGATCCTGACCGTCCAGTTTGTCCGTCTCTTGTTTGT
CGCCGTCAAATCGAGGTATACGACCCGGCTGGGATCCTTGCAGATAGGGCTGTGGTTGAT
CATCTCTCGGACAACGGGCTGCACCCCATCTTGCCTCCACCCTGGCTCGAGACTGAAGAG
GGCCTCGATAACGATGTCGCACTCGAGCGTCCCCGGGCAAATGGGCGCAGTCTGTGCGAT
GACGTGACTGAGCACGTAGCGGTTGTACTTGTCCGCGGAGGTATTAACCCGGAATCGGGC
CTGCCTTGTCTCGTCGTCTTGATAGCCGACGAACTCCCACACCGGCAGCGTCCGGGGGTC
CTGCGGCGTGCCGGCCTGCTGACCCTGCAGCCCTGCCCCAGCGAGGGAGCCGCCGTTGGC
AGCGATCAAGGCGAGAGCGGCTTCCTTAACTTTCTCAACGGGGGACTTCATCGGGAGCCA
GTGGCGGGAAGAAGTATCGAACTGGTATGGGGTAGGAGGAGGTGGGCATACTCAGCGGT
CTGGACAGCATCATGCGCCCAGAAGGTAACGCGGAGACCCTGCTTCCAGAGCGCGGTTGT
GGTATCGGCGAGAGAGTCTAGGGCTGTCTCGTTGGTGATGCTGACAGCCTGGAAGTAGTG
GCTCTCTGACGACGCCTGGCCCTGAGCAATGGCCCGGCCGGCCATGACGGTGATGGTCGA
GCTAGAGCCGGCTTCGAGGAAGATCGCCTGCGGGTGTCTCTTTGCGAGACGCTGCACTGC
GTGGTTGAAGAAGACGGGTTGGCGCATGTGCTGCGAGACGAAGGAGGCATCTGTCGCTCT
GGCAGAGGCCACCTCAGTGGCTCGCTCGACGGGGATGAGGGGCTGTTGAAGGTCAGCGT
CTTGCCGATAGAGTCCAGCCCGTCACTGATCTTGTCAACGAGCGAGGAGTGGAAGGCGTT
CGTGACATTGAGACGCTTGCCCTTGATCGAGCCGAATTCGGGCCGCGAGATCGTCTGCTG
GACCTGATCGACAGCACTGGTGGACCCAGCAATCGTGAAGCTGCGCGGGCCATTATAGCA
GGCGATACTCGCAGAGCCATCAGACCCTGAAGCTCCGTTGGCCTCGGACAGTAGCTGGTG
```

Figure 5G (continued)

```
GACTAGTCCCTCATCGCCTTCCAGAGCCATCATGGCGCCCCGGTCAGCGCCCCAGCTGTC
CCGGACGAGCTTCGCACGCGCCGCAACCAAACGGACGGTCTCATCCAGGCTCAGGGTCCC
GGCAACGCATAGGGCCGTGATCTCTCCAAAGCTGTGGCCCACTAGGGCCTGGACCTTGCC
GTTGAGGCCGCAGTCTATCCAGGTCTGAGCGCAGCGCGTACTGCATCGCAAAGAGCATCGT
CTGAAGCTTAACGGTATCTTCAATGGGCTCGCGGCTGAATATATCGGGCGCGGCGTAGAT
ACTGACCAGCCCCTGCGCCTTAACAACAGTATCCACCGCATCTAGATGCTTGCGAAAGAG
GGCAACTGCGTCAAAGAGGCCCCGATCCAGCCCGACAAAGCGCGAGATCTGGCCGCCGAA
GCAGAGGATGACGGGTCGTTCGGCCTTGACGGGGCAATGCCCACACTCGCGGCGGCATC
CTTGCTGCTCGGAGCCGCGGCAACGGCCTGTTCGATCTTCTCGTGGAGTTCGGCCAGCGA
GCGGGCATTGAAGATGAATCCCTGAGGCAGACCGCGGTTGGATTGCGACTGAGGTTGAA
GGAGATGTCCGCCAGGGTCGGCTCTTCGGCGCGCGAGCGCAACCAGGGCCCGAGTTTGGC
ACAATACGCCGTTATTGCTCGAGTATCGAGCCCAGGAATCCAAAAGGGGTAGCGTGCTCC
TGCAACAGCGTGGCTTCTCGAGTGAGGGCCTCGGAGATCGGGCTGGGTGACGATCATGCT
TGCATTCGACCCGCAAGCGCCGTAGTTGTTCAGCAAGGCCGTCTTCCTCTCCTCCTCCCA
GGCCCGTAGTCTTGTCACAACCTCGATATTGTCGTCCGCCTTGACGGGGATCTTCTTGTT
CATCGTCTTGAAACTCGCTTGCGGGGGGATGAACCCCTCGCGCATCATCATGATTATCTT
GACGAGCGCAATCGCCCCGGACGCGCCCTCTGTATGCCCAATATGGCCTTTGACAGACCC
AATTGGCAGCTTCTTCTTGCGGCTTGGTCCACCCAGTGCAGCAAGGATGCTCTCGTACTC
TGCAGGATCGCCGACGGGCGTTCCGGTGCCGTGGGCCTCGACCAGCGAGACGTCGTTAGC
AGTGACCTTGGCCTGGCGCATGACGTCCTTGAACAGGTGCGACAGGGACGGCGAGTTCGG
GACGAACAGGGGCGTGCAGTTCTCGTTTTGGTACACGGCGCTCGCGGCAATGGTTGCAAT
AACCTGGTTCCCATCGCGGAGGGCATCAGACAGACGCTTGAGGTAGACGAATGCAGCGCC
CTCAGCGCGGCAGTATCCATCAGCATCGTCGTCAAAGGGCTTGCACTGGCCAGTAGGAGA
CACAAAGCTGCCCGCCGCGAGGTTCTGGAACCAGTTCATGTTTGTGACCGTATTGGACCC
GCCTGCAAGCGCAGCCGTGCACTCTCCAGAGAGCAGGTTCCTGCAGGCTGTATGGATAGC
CACCGCCGAGGAGGAACACGCCGTATCAAAGGTCATACAGGGGCCCGTCCACCCGAAATG
GTGGCTGACTCGGCCGGTAATGAAACTCTTGAGTGCACCAGTCGCCGTGAACGCGTTCGG
GTCGTAGCACGAGATGTTATGCTCGTAGTCGACACCGCATGAACCCAAGTAGACACCAAC
ATGCATCTTGTCACGCCCGTCCGGGGTATACCCGTTATGGTCTTCGACAAAGTACCCAGA
CTGCTCAACAGCCTGATACGCAGCCTGCAGGACGATGCGACTCTGCGGATCCATCGCTGC
CGACTCCCGCGGCGAGCGCTTGAAGAATTTGTGGTCAAAGGCATCGCCGTCGCGGAAGAA
GCACCCGTAGAATTTGCGCTTCGGGTCGGCATCTGCGTTCTCGCGGAAGAGCATGTCGTG
CATGAGTCTGTCCCGGGTGATGGGGATATGCTGCGACTGGCCCGTCTTGAGCATGGCGAC
GAACTCATCTAGATCGTCGGCTCCGGCGGTCTTGACGGACATGCCGACGATGGCGATGGG
CTCAGACTGGGGCGAGACGGGCATGACTGGCTCGACGCGGGTGGTCTGCTGCTGCTGCAG
TTGCAGGACCGGTTGAAGCTGGGGTTGTGGGGAGGTGATGATTGCGGTGTAAGCCAGAA
TGAAGGCTTCTCAGGGTCTTTGGGAAGGTCTTCGTAAAAGACCTGTCTTCCTCCGAGAGT
TCTCATCAGAGTTGGAGGGACACATCTCTCCAGGCCAAAGGTGACCACGTAAGGGTCTGG
GAGGGCATCCGCCACGGCCGAGAAGGTGTCAAACCACCGGCATTGCTGCACCAGGATCGA
CCGCACCACCATCTCAGTCATGTTCCCTGAGCCAGAAACCGGAATGCCCGATCCCTGGTT
GTCGTAAGTCTGCAGAGCGAGCTTCGACACCTCTGCATACTGCAGCCCAGGCAGAGAGGC
GCACAGCTCCACCAGGGCATTCGTATGTTGTTTCCGATCAGCATTGGGGCTATGGATCTG
GCCCTTGATTCCAACCTCGGCCACCGTGACTCCTGCAGCTCTGAGGCGCTTCATGAGCAG
TGGCGCAATTGTCTCTGAGGCCGTCACCGTTGCCCGCGCCTGGTCATACCGGACAGCAAC
ATACGCGTCGTTTGACAGATCCCCAATGATTCGGTTCATCTCGTCCTCCTGTTTCTGGCC
GCGCCAGGCGACGGCGTAGGACGCTGAACTGCCCTTGCCGGATGCCTTGTCCCATACTTC
TTGCGCGTCGATGAGAGCGCCGATGAGCATCGCCAGCCGGACGGCGACGGCTCCGTATTC
CTCGAACCCGGCCTGGTTTCTGGCGCTAGCCACTGAAAGCGCAGCGAGCAGGCCAGCGCA
GAAGCCCAGGATGACCGTCGGCCTGCTGCCGGACTGTGTCTGCTGCACCAGCTCCGCCTG
CAGATCTACGGCTGGGGCACTGCCGTCCCTGATCATCTCCAGATGCCGCCAGTACTGCGT
CAGCTGGATTAACACCACTAACGGGCCAACCAAGATGCTCGGCAGAGACTCGTCGTCAGA
AACCGAGAGCCCGGCCGTGTCGAGGCTGTGCCGAAGCCATCTGTCCAGTTCAGACAAGGA
GGTCGGCCCGTCGATATCGCGGGCTATATCAGGCATCTTGGCTGCCAAGGCATCCCAGTA
TGTTGGTAGGTCGGCGATTGTGCGCAAAATCCAGTCGCGTTGTGGCGATTGTGAGAGTGG
ACGAACGAGCTTGTCCATGGATGCCTTTGTGAATGTACCGACATGCGGGCCAAATAGGAA
GACTGTTGAGGCCTCGTGGCCTGACCCAGAGGCGCTTGCTCGGGTCATTGCGGGAGGGTA
GGAGGGTAGGAGGGTAGCTAGGTAGTTGATAGTGCTAAGTGCTCTGCCGGGTCAACTGTG
AATGAATGAGGTGTAGTTGAGACACTTGAGGTTGACTTTCCAGGCGAGCGAGCGGGTCAA
GAGAGCAGAGAGAATATGATAGACTGGGTGTCTGTAGTAGATAGACAAGATGTATGTCTG
TCCCTTGGGGAAGTAGGGCTAATACTTCTACCTTAGCACATGTTGCGGGAAGCCACGCAC
TGAGGAAACACTGACATCGTTGGGCACTCTGATTGGAGCCGGAGATTAAGGTAAGATGG
```

Figure 5G (continued)

```
AATCCTTCTGGCTGCAGCGCTGTAAGCCCTAAGCCTGGTGGCGCTTCTGGCGGACTTTTC
GGACTACAGGACTCCATCCAAGACTCCAGATCGAGACTCAGCTTCGCTAGTCCGGAAGTC
CGCTGGCTGATGCTTGTCTCAGCTTTTCGTCTCAGCTTTGTCGTCTTCTGTAGAGCCTTT
AGGGAAACCCCAACTCAGCATATGGATGCAGGGCTGGTTGGGCTGATTGGGCGTTGTCTG
GACTTGTATCTGGGTATGGCTGCCGTCTGGGGATCAAAGGTAAATGGGGCAGAAATTGCC
TGTTGAAATAGTTATTGCGGAGGCCAATGCAATATCCCAAGAATTTCCCAAAATGCAAGC
TACTATAGATGCTACATAGCCAGATAGAGGTTGATAATGCCACATTTTCAATATATACAC
ATACGTTTGTGTGTATAAGTACATAACACGACTACAGTGGCTGATATATATGCAGTGGAC
GCCTTTAGACATGTTTCCATTTATGATTATAGAGCGATCCTCAGGCAAGTGGTTATACTA
GACCTTCACTACAGCACGCTCATACGCTTCTCTCGCCTGGTCGACCATGCCCTGCACATC
GAAATCCCAAATCACCCTGCTCCTCCTCTCCCATTCAGCCTTACACTTTACCCCGTCACC
CCCAATGTCTTCATACCGCCATTCGTAGAGATCTCCCATCTCCCTTGAGCTCTTCACAAG
CCACTGGCTACGCTCAATCCTCACATCGCTGTAAGTCTTCAGGGCAAGCTCAATATTAGA
CTTCTTCTCCTTGAACGCGGAGCCGTTCTGGACCTTCTCAAGCAACTCAGCGAGAACAAG
CGCGTCCTCAACGCCCATACAGGCCCCAGCCCCGTGGAACGGACTGGACGCGTGCGCGGC
ATCACCGGCCAGCGCCACCCGGCCAGCGGCATAGTAAGGAAGCGGGTGGTCCGCCTGATC
GAAGATGCGTACTTGCCTTAGCTGTTCCGGAAGAGGCTGGCAAGTTCCTTGATATGCGG
GCCCAGTTCTCGACCGCCGAGAGTATCTCCTCCTTCGAGCTGGGCACTGTCATGGTGTG
GCCGTGAGTCCACTCGTTCGAGTCGTGCGTGAAGAGGAAAACATTATAGATCTGGGCGTT
GTTTACCTAGGCACAATCAGCGCCTTCTTGCAGAATAGATGCGGCATGCTAGGCCTGGAG
GTAAGGTAGGGTACCGGAAAAGAGACAATGTGCGCGTCCGGCCCGCAATGTGCGATCTGG
ACATGCGCCTTTTCGGTCCCCAGCGCATCAATTGCTGCTGGCATAGGCACGAGAGCGCGG
TAGACAGCTTTGCGAGAGTACCTGGCGTTTGCAGCAGGGTGTTCTGCGCCGAGGAGGACT
CTGCGGGCCGTGGAGTGGACGCCATCGCATGCGATCACTTCACCCACCGCATTAGCATTA
TGAAACGTCCAATACCCAGCTCAGGGAAGAAAACCAACCAATATCTGCCTCCTCCACCTC
CCCGTCCTCGAACCTCAGCACCACTTTCTGGTCCCCACCATCCTCATATGCCACCAGCCT
CTTGCCAAACCTCACAACCCTCTCGGGCAGCAACCGCGCCATCTCCGCATGAAAAACACC
CCTCAAGCAAGCCCAGTACGCCATATTCTTCTCCTCGATCTCAAACAGCACGCTCTTCTC
TGGATCCTGTGCCTCCTCTTTGCTTTTCGGGTGGAATCCGTCCCAGTACCGCACTTTATC
ATGCGGATTGCGCTGCGCAACTTTGGAGAGAGCGGATAGAATTGCGGGATCAAGGCGCTG
CATGCACTCGCGGGCGATTCCGGTGAAGGCAAATGCGGCCCCAATGTCGGGCCAAGCTGA
GGCGCGCTCGTAGATTGTCACCTTGCCGATGTTGCGGTGGAGAAGCCCCAGGGCTGTCAT
AAGGCCGATGATGCCGCCGCCTATGATGGCGATGGAGAGGGGTTCCTGTTCCTGCTCGTG
GTCTGCCATCCTGTTTAGAGTGGCCAGAAGGTGTGTGTTATCTGCAGGATGCCGGTAC
CAGTAGGGCTGTATGTAAATACGGCTGCAGTAGTTTCAAGTTCTGCTTCGATCAAGCGTT
AGACCTAGGATTGAGCGCGGCTCTGGCAATGGCGGCTTTTCTCATGGTATAGCATGGCAT
AGCCTGAGGATATAGGTACTCCATACCGAGGTACGAGTACATCTATACTAAGAATAGTGA
CTCCCAGCTTGCCTATCCCCTGCTTATCCCGGAGTTTGCATCTCCGCCAGGAAGCACGCG
GACTGAGGCGGAGTAATTAACAGAAGGCATGGCAATGCTTACTGCGTGGGGCTTAAAACC
TGACCTGACCTGGCCTGGCCTGGCCTGATCTGATGTGAAACTGGTTCTCCTTCTCTATCT
CCCTCTGTCAGATTGATCGTCAAAACCTAACCCTAAGTCAAATTTAAACGCCACGCACCG
GATACTCTCAACTCTGAATACGGCCTTGATCAGCCAATCACAGAAGATTGCGAGCTGACA
GTTCGTATTGATTACTTTAAAGCCTGGCATAGACGATCTGCCATTGATTTGCAATTCTCC
GGCCCAGTTGCATAATGCCGGCGCTCGATATCGCCTCGGCCCCGGCCGCAGTCTATCAAC
AGCAACTCCATCTCCCACGCATCCTCTGCCTCCACGGTGGCGGCACCAACGCCCGAATTT
TTACCGCGCAATGCCGCGCTCTGCAAGACAGCTGACAGACAGCTATCGTCTCGTTTTTG
CCGACGCGCCATTTCTCTCGTCCGCCGGGCCGGATGTGACGTCTGTCTATGGCGAATGGG
GCCCGTTTAGGAGCTGGGTTCCTGTTCCTGCGGGCGTGGATATCAGTGCATGGGCCGCTG
CCGGTGCCGCTAGTAGGATCGATATCGACGTGGAGGCGATCGATGAGTGCATCGCAGCTG
CCATAGCGCAGGATGACCGGGCCGGCGCGACAGGGGATTGGGTCGGCCTGCTGGGGTTCA
GTCAGGGGCGAGGGTCGCTGCCAGTCTGTTGTACCGGCAGCAGAAACAGCAGCGCATGG
GTCTGACCAGTTGGAGTAGGGGTAGGGATCGCAAGCGAGGTGCGACCTCTAGCACCAATT
ATCGCTTCGCTGTCTTATTTGCCGGCCGCGGACCGCTCCTGGACCTAGGCTTTGGGTCTG
GCTCTTTAGCCGGCTCGAGTGCTGCTTCTTCGTCTGCGTCTGCGTCTGTATCTGGATCTG
AATCTGCGGGTGAAGAGGAAGAGGACGGGCACCTCTTAAGCATCCCAACCATACACGTCC
ACGGGCTGCGAGATCCAGGCCTCGAGATGCACCGGGATCTAGTCCGGTCTTGCCGGCCCT
CGTCTGTGAGGATTGTCGAGTGGGAAGGCGCCCACCGGATGCCAATAACGACGAAAGATG
TGGGAGCGGTAGTAGCGGAGCTTCGACACTTGGCGATAAGCCGGAAATATGAAAGCTTGA
GATGTTGAATTCAGCCTATTGAGATTACAGCCACGGAAGTAATCCTGTAAGGATCAGGAT
GCAACTCCATGCAAGGCGCTAAGGATCAGGATCCTTTTCTTCAGGATTGTGGCAACGGCG
CCAGCGGCCAGCGGGCGCTATCGCGTCGGTGGTGATGGCGTTATTTGGATTTCGGAGGAT
```

Figure 5G (continued)

```
AGAATCCGGTCAGCCTAATCAAGCCAACTCCGTCGGACTTCGGCGGGACTGTCCGGTCAG
TTAGAGCTAGAGAAGGAAGGAGGTAGAGTCCCAGATAGACAAAAGACTTGGCTGCTATAT
ATCTTATTATTCAATCCTCAATCCCGCTAGCTGTCAATAGAATGATCCTCAGCCGCACTT
GAAGTCTTGTCTACATCCCGAATCCAGGCGCAATGGCTGAGACGGATTCCTCCCACACCC
GTGGGCCCGTAGACTCAATCCAGAAGAACGACGCCTCAAGCGACGATGCCGAGGCAGAGA
CCAAGATCCAGTATCCCTCGGGCTGGAGGGTCACGATGATCCTGACTTCGGTGACATTGG
CGTACTTTCTTTTCTTTCTTGACCTAGCCGTGCTGTCGACCGCGACTCCTGCCATTACCT
CGCAGTTTGACTCGTTAGTCGATGTTGGATGGTGCGTTATGTCCCCTACTGCGCTCTTCC
CTAGGTACATATGTGCTGGATGCTAAAACCCACCTTGCCGGCAGGTATGGAGGCGCCTAC
CAGCTTGGAAGCGCAGCGTTCCAGCCCCTGACGGGCAAAATCTACAGCCAGTTCTCGATC
AAGGTAGTTCTCCCTCAACCATTTGACGCAGTTGGAGGCTTGGGTGCTCATGAATAGCAG
TGGACATTCCTTGTCTTCTTCATTGTCTTTGAACTCGGCTCTGTCCTGTGCGCCGCAGCA
CGCAACTCGCCCATGTTCATCGTTGGTCGGGTCATTGCAGGCGTAGGGTCGGCCGGCATG
TCCAACGGCGCCGTAACCACAATCTCCGCGGTCCTGCCAACGCAGAAACAGGCGCTCTTC
ATGGGCCTGAACATGGGTATGGGCCAGCTCGGTCTTGCGACGGGACCGATTATCGGAGGC
GCGTTCACAACGAACGTTTCGTGGCGGTGGTGTTCGTCCCCTGCTCCCTCCTTTCAAAT
CCCACCTACTAGGCGACCATGCAGAGAAGATGCACCAGCTGATGACGACGCAGGCTTCTA
CATCAACCTCCCCCTCGGCGCCGTTGTCGGCGGCTTCCTCCTCTTCAACACGATCCCCGA
GCCGAAACCAAAGGCCCCTCCGTTGCAGATCCTCGGCACCGCAATCAGGTCCCTCGATCT
GCCGGGATTCATGCTAATCTGCCCTGCCGTGGTTATGTTCCTCCTGGGTCTGCAATTCGG
GGGCAATGAGCACCCCTGGGACAGCTCCGTCGTGATCGGCCTCATTGTCGGAGGAGGTGC
CACCTTCGGTGTCTTCCTCGTGCACCAGTGGTGGCGTGGCGATGAGGCAATGGTCCCGTT
TGCCCTCTTGAAGCACAAGGTTATCTGGTCTGCGGCCATGACCATGTTCTTCTCCCTGTC
CAGTGTGCTCGTCGCGGACTTCTATATCGCGATATACTTCCAGGCTATCCGGGACGACTC
GCCACTCATGAGTGGTGTGCACATGTTGCCCATCACCCTAGGTCTGGTCTTGTTTACTGT
TGTTTCAGGGGCGCTGAGTATGGTCTTTTCTCCTGCGTGCTTGAACAATGGCTAACCGTC
CAGTCTCCGTACTGGGCTACTACCTGCCCTTCCTTCTTGCAGGCGGCGCCATCTCCGCCG
TCGGCTACGGCCTCCTCTCGACGCTGAGCCCGACCACCTCTGTCGCGAAATGGGTGGGAT
ACCAGATCCTCTACGGCGTAGCCAGTGGCTGCACCACCGCCGCTGTATGTCTTCAGTTTT
ACATACCCCCGGAACCCTTTTGCCTTCACCTTTACCAGGTAGAATGCCGCTGACAAGGCCG
AATGCAGCCCTACGTCGCAATCCAGAACCTCGTTCCCGCGCCCCAAATCCCGCAAGCAAT
GGCAATTATCATCTTTTGGCAGAACATTGGCGCCGCCATATCTCTCATTGCGGCAAACGC
CATCTTCTCCAACTCCCTCCGCGACCAGCTAGCCCAGCGCGCGAGTCAGATCACCGTCTC
CCCGGGCGCGATTGTTGCGGCCGGTGTCCGGTCCATCCGGGACCTCGTCTCCGGCTCTGC
GCTTGCGGCTGTTCTGGAGGCGTATGCGGAGGCCATCGACAGGGTCATGTACTTGGGCAT
CGCGGTTAGCGTGATGGTTATTGTGTTCTCGCCTGGTCTAGGGTGGAAAGATATTCGGAA
GACAAAGATCTGCAAGCTCTAACTAGCGATGGAGCGCAGGGTGAAGCGACGGAGAAGGA
GACTGTTCCGGTTGCCCTGGGTTAAGGCATCGTCTACAAGCAGATGCTAGGCACACATTT
CTTTCTGCCGCTAAAAATTGGGTAATGCAGAGCCACCTCGCTTTTTTTTTTCGAACATT
TTCCATCTTGTGGTATTTCTGGGTTCATTTCGCTCCATATAACGAAGATTGGCCTTGGTA
CGGGCTAGGGTTCGCGGGTGGGATAGTTATAGAATGAGAAATAATACTTTTATATGTAAC
AATTTCAACTTCTCAAGATGAATATACCATTCGGATAGAGCAGCTTCTGAGTATCGACAG
ACTTAGGTAGGCTTATGGGTATGCTCTGTTGAATATCTTGTAGATGTGACAGGCAATAGA
TTGTTAGATTATAGCCTACAATCCACAGCTCAGCTCAGCACGAGTTTGATTTTTTCATTA
TAATTGGAATAAGCACTGAGCTCAGAATGAAACCAATAGATTACTAGGGCTATGCGTAGA
CGTTGAACGGGATCCATCACCAAGCGCAGTATTAGGGCACCTTTTGTCGTGGGTATATAG
CAACTAAACACATTCTCTTCGGTCCGTGTTCGGCCCTCTTCGGCCTCCATTAGCCAGTCAA
AATAAACAGTAACCAGCTACAAAGTGACAACAAGCTTCTTTCCCGAAACCCCCTTTCGCT
GGATATCCAGCGCCTCCTGGATCTTCTCGAGCCCCTTTCCGACAACGAGCGGCGGCGGTG
CAGGCACAAACTGCCCTCTCTCGAGCGCTTGGGGCAGAAAGTCCATGTAAACCCGGCTGA
CCACACTGTCCGGGTCCACCAGCCCGTCAACAAGGATAAACTTGGCGATGACGCCTGTGC
GGCGCTGCCGGATGCTCGATTTCACCATTCCTCCCAGCATCCCAATGAGGTAAGTCCCCT
TGCCGACGAAGGTGGTTAGCTTCTCAGGCGGGATGATCTCACCGGCGACGGCGATGAACT
TTCTCGTCAGCGCAGGATCATGCTTGCGCATCACGAGGGTGCAGGCTTCCACCGCACCGG
CGCCAATGGTATATGCGCCGACGAGCTCTCTGCCCTTGAGGGCGGATAAGAGATCCTTGG
CCAGGAACTTGCTCCGGTAGTCAAAGACGTGGCTCGCCCCGAGCCCCTTGACATAGTCGA
AGTTCTTGGGCGACGAGGTCGAAAGGACCTCGTAGCCTGCTGCGACAGCGAGCTGGATCG
CATTGCTGCCAACGCTGCTGGCGCCGCCCGTGATGATCACCGCGCGCGGGACCCCGACC
TGCCCCGCTGCACCTCTCCCCTGCCCTTTTCCGCAAGCTGCGGCATATCGAGGGCCAGAT
AGTCCTTGTGGAAGAGACCAAATGCGGCCGTACCCAGCCCGAGTCCGAGCACAGATGCCT
```

Figure 5G (continued)

```
GCGCATCGCTGATCCCAGCGGGCACCGGCGTGAGCATATGCACTCGCAGGACGGTATACA
GCTGGAACCCACCCTCGGCCGGGTCGTTCACCTCTTTCGCAATCGCCGTCGCGCTTCCAC
AGACGCGGTCGCCCACGGCGAACCGGGTGACGCCCGGTCCGACCTCGACGACCTCGCCCG
CAACATCAGTCCCAAAGATGAACGGGTAGTGGATATACCCGGCCAGCGCGGGCCCGATGA
ACTGCAAGACCCAGTCGAACGGGTTGATAGCTACGGCGCCGTTCTTGACGACCACCTGGC
CAGGGCCAGGGCGCGTGTAGGGGCGTCGCCGACTTTGAAGGGGATCACCTTTTTGGCGG
GGATCCACGCGGCGCGGTTTTGGGTTTGGGGGTCCCGTTGCCGTTGGTAGCCGGCGCTG
CTGCGGTTGCTGCGGTTGTATCTTGAGTTGCCATAACGAGGTCCAGGTGACGGTAACGTG
GTTCAGTGCAGTTCCAATGTATGGTAGCGTTGTAAGCTGACACGGCGACGGCTGCGAGAG
GGGTTGGGGGGACGGAACCAGCTGAAACAGGACTGGCGAAAGAAAGCTGCTGTGTTATAT
GTAGGCAGAGCTAAAGAACCTTGTGGAGCGACAGAACCAAAGTCAGTCTGGGCCATGGGC
TATCTTCCATAATTTTGGGAGCTCGAGGTCCGGATTGCCCGTTAATACTCCGCCAGACTA
GGGCAAGATAGGGCTACGCGGAGTTTTAGGTGGACGGATTTCAACCCTCCGAAGTCCGCT
CGAACTTTTGTCGACGAGATTAAGCCACTAGCCTAAAGGAATCAGACCTTTAATTCCTCA
GGCCGAGTCGGGATCATTGAAGGCGAGAATGAGGTGAGGTTGTCAGCCACATCGTCAGCT
CAATCCTTTAGACCACGTTCTTATCTCGCGGCCGTTCTCCAATCGACGGGCCCGCTGGCC
CCCAGCGTGCAGATTACACCGTCTCGCTCCGACTGCAGGATCTGGCGTCTTCCATGCGCG
GACGTTTCGGACGGCGATGACTGTCTGAGTGGTTGGCAGGGATGCACCCCTACCTACCCC
TGATCGAAGCTAATGGTAATGCAGAATACGAGGTTGGTTAGACTAAGCGCTTCTGCAGCT
GCAGCGCATGGAAGCTGTTCTGTCTGGTGGAGAGACTAAGCAGTGCTCTGTGCTCCTCTG
TGCTGCTCTGCATTGCACTGCACTGTACTGCATTGTACTGCATTGCTGTTCTGCACGGAT
CATTCATCCATCTACCATGGATCCACTACTAACCTCGCTTACTCTAGTCGATCTGGTCAA
GACGACCAAGACCTCGGAGAATTAGATGGCCAACCAAGGATAGATGCGAGATCAACTGAT
CCACCGCTGGCAAACTTAGTTGTGAATGTCGCGAACGCAAATACCACGGAGATGGCATGC
AGCCGCACCCGAAATGGAATGCTGTAGGCCTAATCAAGCTCATCGATTCTCGCCCCCAAA
TCTGGGCTGCGCGGTCCTGCAGGTGAGACGGATCCTGGAGGCTCCATGCTGGCTGGCTCT
GCCTCCTCGTGGACGAGGGTACGATGGCAGCCAGTCTGCTGGCGTGCTGGCGCCGCTGGT
AGCACGGCCACGAGCCTATTGATTGCACGGGCAAACGTTCGTAACTCGCTCGTAACCTAT
AATTACGATAGCTAACCACATCCTGGTTCTCTCTCATAAGAATGAATGGCATTCCCGCCT
TGATCCGTCAGCATTGTCAACCCGGATAGACCAGTGCCTCGTCATTCAACATCACAGATC
CAGAGACTACAAAGACCAGCAATCATGGCGTGTCCCACCAGACGAGGACGACAGCAGCCC
GGCTTTGCATGCGAGGAGTGTCGCCGCCGCAAAGCGCGCTGTGATCGCGTGCGTCCGAAA
TGCGGGTTCTGCACTGAGAATGAGCTGCAGTGTGTGTTCGTTGACAAGAGGCAGCAGAGG
GGTCCGATCAAAGGGCAGATCACCTCGATGCAGTCGCAGCTGGGTAGGTGTTTGTCTTGT
CTCATTGTATCTCGTCTCGTCTGCGCTTTTGTGATTATGGGCTGCCATGTTTCCGGTCC
GGACACAGGCATCTGCAAGGCCCGCCGCTGTGCTCCCCGATCTGCAGGGACCAATGCAG
CTGGTTCTGGAGCTTGTGCTGTGCTGCTTCCCTGTCTTTCCACATGGTCGAGTCGAGCGA
GCTAGCTAACATGGGATGCCTCATGCTTTCAGCAACGCTTCGATGGCAGCTTGATCGATA
CCTGCGACATCGACCTCCCCCGTCCATAACCATGGCCGGCGAGCTCGATGAGCCACCAGC
GGATATCCAGACGATGCTGGATGACTTTGATGTACAGGTCGCCGCGCTGAAGCAGGATGC
CACGGCAACCACCACAATGTCGACGTCGACAGCTCTCATGCCTGCCCCAGCCATCTCATC
TAAAGATGCTGCTCCTGCTGGTGCTGGTTTATCGTGGCCTGACCCAACCTGGCTGGATCG
CCAGTGGCAGGATGTCAGCAGTACCAGCCTCGTCCCTCCATCAGACCTGACAGTCTCGTC
GGCCACTACCCTAACCGACCCTCTCAGCTTCGACCTTTTGAACGAGACTCCTCCTCCTCC
TTCTACGACGACAACAACGTCGACGACGAGGCGAGACTCATGTACTAAGGTCATGTTAAC
TGACCTCATCCGGGCTGAATTGTACACTACCTAACTGATTTGTCTACCATGACACCTGAC
TGACAATGTGCAGAGACCAACTCTACTTCGACCGGGTCCACGCCTTCTGCCCCATCATCC
ACCGGCGACGGTACTTTGCGCGGGTCGCCCGAGATAGCCATACCCCAGCACAGGCATGTC
TGCAGTTCGCCATGCGAACGCTCGCAGCGGCAATGTCTGCTCACTGCCATCTTAGCGAGC
ATCTCTATGCCGAGACCAAGGCCCTCTTGGAGACGCACAGCCAGACGCCCGCCACACCGC
GAGACAAGGTCCCGCTCGAGCACATCCAGGCCTGGCTGTTGTTAAGCCACTACGAGCTGC
TGCGGATCGGCGTGCACCAGGCTATGCTCACGGCTGGCCGGGCCTTTCGTCTCGTGCAGA
TGGCACGACTGTCAGAGCTGGATGCCGGGTCAGATCGACAGCTCTCGCCGCCGTCTTCGT
CGCCGCCGTCTTCGCTAACCCTATCTCCTTCGGGGGAGAATGCTGAGAACTTCGTCGACG
CCGAAGAAGGCCGGCGGACGTTCTGGCTTGCTTATTGCTTTGATCGTTTGCTTTGCTTGC
AGAATGAGTGGCCGTTAACGTTACAAGAAGAGATGGTACGTCGCGCTTCTTTTATTCTAT
TTACCTCAGAATTTATATTCAGTTATTTTTTATTCTAACCCTGCTAGATATTAACCCGCC
TCCCCTCCCTCGAACACAACTACCAGAACAATCTCCCCGCACGCACGCCCTTTCTCACTG
AAGCCATGGCCCAGACCGGGCAGAGCACAATGTCCCCGTTTGCCGAATGCATTATCATGG
CCACCCTTCACGGCCGATGTATGACGCACCGCCGCTTCTACGCAAACAGCAACTCGACTG
```

Figure 5G (continued)

```
CGTCCGGCTCCGAGTTCGAGTCTGGCGCCGCGACGCGAGACTTCTGTATCCGCCAGAATT
GGCTGTCGAATGCAGTGGACCGGCGAGTCCAGATGCTACAGCAGGTCTCCTCGCCCGCTG
TTGACAGCGACCCGATGCTGCTCTTCACGCAGACGCTCGGCTACCGCGCGACCATGCACC
TGAGCGATACCGTCCAGCAAGTCTCCTGGCGGGCTCTCGCCAGCTCGCCCGTTGACCAGC
AGCTACTGAGCCCGGGCGCGACGATGTCGCTGTCGGCCGCCGCGTACCACCAGATGGCCA
GCCACGCAGCCGGCGAGATCGTCCGCCTGGCGAAGGCCGTCCCCTCGCTGAGTCCGTTCA
AGGCGCACCCGTTCCTACCCGATACGTTGGCGTGCGCCGCCACGTTCCTCTCGACGGGCA
GTCCCGATCCCACGGGCGGCGAGGGGGTGCAGCATCTGCTACGAGTGTTAAGCGAGCTGC
GCGATACACACAGCCTGGCGCGGGATTATTTGCAGGGGTTGTCGGTGCAGACGCAGGACG
AAGATCATAGACAGGATACGAGGTGGTATTGTACATAGAGACTGATTAGCTGGCCGATAG
CAATGCCGCCAATAAAACTGATAGAGATGCGGCACGATCCGACAGTTAGTCTTGGGGC
```

Figure 5H

Sequence of the deletion of the Asperthecin cluster

>ChrI_A_nidulans_FGSC_A4 COORDS:ChrI_A_nidulans_FGSC_A4:1540648-1549188W
(8541 nucleotides) (SEQ ID NO:8)

```
TACTCAATACAACCCTACCCACCAACCCGGCACCTACCGCCTCACCGTGTGTCCCAACAC
CAGCACCACCACTACTGTGCACAGTCAACGAACAATGACACTCCCAGTCCTCATCATCGG
TGCCGGCCTCTCAGGTCTCACAACCGCGCGTCTTCTCACAAACGCCCACATTCCCTGCAT
CGTCTTCGAAGCCTCCCCTCCCTCCCGCACTCAAGGCTACGCCATCTCCCTCCGCGACTG
GGGCTTCAACGCCCTCCTCAGGGCCCTGGGAAACCTCCCCCTATCCAGCCTCACCCGGGC
CGTCGCACCTGATCGCCACATTGGCGGCTGGGCTGGCTTGACCAGTCATGGCGGAATAA
CCAGACCGGGGAGATAATCATGATGCCACCCAAAGAGTCAAAAGAGAAACCGACCATACT
GCGCGCTAATCGCAATGCGCTTAGGCAGTGGATTGCGGATGCAGGTGTGGGGAAGACGA
GGAGATTGATGTCAGGTATGGACATCGGCTTGTCGGCGTGCAGCTGTTGAGAGAGGGTGG
AGATGGAAATGTGGTAACAGCCGAGTTCGCAAACGGCGCCACATACACCGGTTCCCTTCT
GATCGCTGCGGACGGGGTACACTCCACAGTACGGACACTGATCCTTCCCGCTGTGAAGCC
GGAGATTTTACCCGTCCTCGTCTACCATGGCGACTTCAAGCTCAGTCGCGAGGAATACGA
GTGTGTGATCCGGCCGCATGCAGGCGAGTCCACGATCGTCGCGGGCGTGGGCGACGGGTT
TAACACGCCGCTGACTGTCTGCGACGTCAACGACAGTGCACATGGACTGGACGTA
CTCGCGGCCCAGCATTGGTGACAACGACCCTCTGTATAATCCCAATATTACGTCGGAGGA
AGCTAAAGTCATTCCCGAGGCTTTGATCGAGGAAATCAATGCGAAAAAGCTGGGAGAACC
ATGGTCGCTGTTCCTGAATGGGGAGGCGATGCGCAGGCATCGGGTGTTCAATTGGCTGAC
GCGATGTGTTTCGATGGAAAGGAGTGACGTGAATTCCTGTACGGGCAAAGGGGTCGTCTT
CGTCGGAGACTCGTGGCATGCCATGCCAATCTTTGGAGGCGAGGGTGGAAACCATGCAAT
ATTCGATGGGATTGAGTTGGCGAAGATGTTGGAAGTGGCTTGGGGACGTTCCAAGGAGGA
TGTGCAGGCAGCGATCGGGAAGTACTATGACAAGTCTTGGAGACGGTGTAATGATGCTGT
GCGAAGGTCAAAGCAGAGGTTCTATCAGCTTCATCGACCTATTAGCGAGTGGATTGAGAT
TGCGGAGAAGCAGAAGATGCGTGCGTAATTTGCTCGTTCATTAATTAGGGTTTGATCTTG
GTACAGTAGGGACAGAATCCTTTTCTCGGTACAAAAGAAGAATTCAATCTTCAGCGTAAA
TAAGAGCAAAGCAATCTAAATAGTTTACTACATGGCGAACAACATCTAATCAGTTAATTC
GGCCGGCGCGACCTGACGTACCATCGCCTTTTTGCAGCACTCCCCGGCTCAAACCCGACT
TTTCGATCCTCAGCTAGCTTCCACAGAACCTGGCTCAAGAACGGCGCAAGAGCTTTCTCA
ACCTCGTCTGTAATCTCCCCATACATTGCTAGGATGATTTCGTGTAGCGTCAAGCCACCC
CGCCCCCGCCCCTGCCCAGCTGCTCGGCTCTCCTCGAGTATCGCGTAAACCTGCTGCACG
CGGAACTCTCTGTGCTTGATGTACTCTCGCATTTTATCCGGAAGGTCATCGATCACTGCC
CCGTGCGCTGGGTAGCCCAATGGAAGGTTCAGGTTAGCCATCGTGTACCATGCTATTCATG
TATTGTCCCAAGTCTTCCACCACCGAGTATCCATGGCCGAGCACATTGTCGCCTGTGAAG
AGGGCGTTCTCTTCTTCAAAGAGAAAGCACATATGGTCGGCAGCGTGGCCGGGGGTATGA
ACGGCGCGGAGAGTGGCGCCTTCAACGCGAAAGACCTGGCCGTCGAGAATATCCTTTTGT
CCGGCATCGGGTCGGTTTTTGTATATGCGAGAGGATAGCGCTGGATTGTACGCTATCAGG
TCCGGCACACCACCTGTATGATCGCCATGCCAGTGTGTAAGGAGTACATAGGAGATGTCT
ATATCCCTCTCTTCGAGGACTTTGGCGATATCACGGATCCACGAGGGCATTCCCTGGAGC
AGACAGGGAGTGTGAGCCACGTCGCCCTCCATGCAAGGTCGGTAAACAGTCACGACGTAC
CTGACCAGTATCAACTAGGATACGGGATCTGCCTGTTCCAACGAGATATGTATTTGTCCC
CTGCAGTCTCATTGGTCCAGCATTTCCGCCCAAAACTCGGATGACCCGTTCAGTGATATC
CGTCACCACAGGCAGAGTAGGGATAGTGTTTTCTCTGCCGGAAAGGTACTCATTCCAGAA
GTCCTGGGCAAATGGTATTCTGAAGGCCATGTTGGTGACTGAAGCGCCATGGGGATGCCG
AGCGAAGGAATGTGCGTCGAGTCTGTAATATCGGCAGAGGTTCTGCTCTTCGGCCCTATC
GCCCTATGACGGGATTTTAATCGGGCATATTTTATGATCCACAGTAGTATAGAAATAAGA
CCCGAACGAGATAAAATGCAGGTCCGGGCCAGCTCATGCCGGAGGCTCGAGCAGTCATTT
CTCCAAAAGTCCCCGTATGGCATTTTACACAGGGTCCCATCACAGGATGGTAATTCCATC
GCAATTTGCGAAACTTCCCGTGCGGGCATTTTGCCCTCATTGAACAATAGCATCAAAACC
CCGGGTGTATCAGTCGATTCTGTGTGCAATGATTGCTTGGGAACGCTCTGCTCTGATTT
GAACGTAATGAGCGCTTGAGCTCGACCAGCAGAGAAGTAACAATGAAAGACAATGCAT
AGCACAACCCTAATCTTCTTTGGAAATGAGTTTCCCAACGATGATCTCAAAGGGCTGTTC
CGCTGCCTGCTGCGGCTTAGCAAGGACCGCAGGTTTCGTCAACTGGCTGCCTTTCTCGAG
GAGTCGACTTTGGTCCTCAAGAAAGAAGTCGCTGCACTTCCACAGCCCTGAGGGATCTC
GTACCGCATTTTCACACGGTATTGCCCCTCGCGGAGCTTGGTGACTTTCGTCAAGGTCCT
CTAGGGGCTGCTATGGAGAGTGCACTCTTGACTGTGCTGGAACTTGGCATGTTCATAGGG
```

Figure 5H (continued)

```
TAAAATACCCGTTGTTTAGTTGCGGACAAAGAGAGCTGATAGAAACCATTAGGCATTATG
AAGCTGAAGGCCGTGACTGGAATTTGCTTGAGCACAACACCACCCTTGCTGGCTTGAGTA
TCGGCCTTTTAGCTGCTGCTGGTGTGGCCCTATCCACCAACTTAGCAGAGGTCGCCCAGA
ATGGAGCAGAGTGCGTTCGCGTGTCTTTTCGACTAGGAGTATACGTCAGCGAGATCTCGC
GGAAACTCGAGGCGCCTCAAGCAGACGGTACATTACTGAGCTGGGCTCATGTTGTTACCG
GAGAGACAAAGTCCGCCATCCAAGACGAGCTGTCAAAATACAACTCAGAATCAGGCACGC
CAGAGCTTCTTAAAGTCTTCATTAGCGCTGCCGATAAGACTTCCGTCAGTGTAAGCGGGC
CGCCATCACGCATGAAAGCCTGCTTCAGCAGTTCGCACCTCTTGCGGTATTCCAAGTCTT
TCGCCCTCCCAGTATACGACGGTCTATGCCATGCGTCGCATCTGTATAACGAGGACTCGA
TCAACACAGTTATCAACAGTGCAGAGTCAGTCATTCCTGTCTCTCGTCCGGTGCAGCTTT
CGCTTCATTCTTCCAATACTGGCCAGCCTTTCCCAGCGGCTACAGCTCACGAGCTGTTCC
AAGCCATCGGCAAGGAGCTGCTGACTGGTACCATCTACCTTGACAACATCATTGACGGAA
TCATAAAACGCATTGAAGGGTTCAACCCGAGTGATCTTCAAGTCGAGACTTTTCGCACGT
CAATAGTGTTTAAGAGCGTACGAGCGGCTCTTGAGGGTGAGTTCCCTGACTTGGAGATCA
AGATAACCGACTTGATCCCTTGGGCTTTCAGAGACTATGGTCCTCGTCTGCCGCGTTCTT
TCGCCCATTCGAAGCTGGCTGTTGTCGGTATGGCCTGTCGTATGCCGGGTGGTGGCAATG
ATACCGAGCTTTTCTGGGAGATTCTGGAGCAGGGACGTGACGTTCACACAACAGTGCCGG
CAGATCGTTTCGACTTGTCGACTCATTACGATCCTAGTGGCAAAACAGATAATGCTGCAA
CGACTCCCTACGGTAACTTTGTTGATAAACCGGGATTGTTCGATGCTGGGTTTTTCAACA
TGTCGCCGAAAGAGGTACGTCGCCCCATCCAGACCGGAACTCGATGCAAAAATACAGGTA
TGCTGACAGATGCAGGCTGAACAAACAGACCCTATGCAGCGACTGGCGCTCGTCACTGCA
TATGAAGCTCTGGAGATGGCCGGTGTAGTCCCCGGTCGAACTGCATCGTCGAACCCCAAA
CGCATTGGTACTTACTACGGGCAGGCGAGTGACGACTGGCGAGAACTGAATGCCTCGCAG
AACATTGGCACATACGCAGTGACGGGTGGTGTACGTGCCTTTGGCAACGGGCGCATCAAC
TACTATTTCAAGTTTCCTGGGCCCTCATTCAACGTCGACACGGCCTGTTCTAGCGGGCTG
GCTGCCGTCCAGGTCGCATGCTCGGCTCTTTGGGCGGGGGAGGCGGATACAGTTCTTGCT
GGGGGCCTGAATATCATCACCGACCCCGACAACTATGCAGGTTTGGGGTGTGGTCACTTC
CTCTCCAAAACAGGGCAGTGCAAGGTTTGGGACGAAACTGCGGACGGCTACTGTCGTGCT
GATGGGATCGGCTCCGTCGTCATCAAACGTTTGGAGGATGCTGAGGCAGATAACGATAAT
ATCATCGCCGTCGTACTCTCTGCAGCTACGAATCACTCAGCCGAGGCTATCTCGATCACC
CATCCCCACGCAGGGAATCAGAAAGACAATTACCGCCAGGTTATCGATATGGCTGCCGTT
AACCCGTTGGATGTGAGCTATATTGAGCTTCATGGAACAGGGACCCAGGCCGGTGACGCC
GTGGAGTCTGAATCTGTGCTCGATGTATTCGCGCCTCGATCGCCGCCACGACGTCCCGAT
CAGTTGTTACAGCTGGGTGCGGTCAAAAGCAATATCGGGCACGGTGAAGCGGCAGCAGGT
ATTGCGTCGTTTCTGAAAGTGCTGTTAATGTACCAGAAGAACATGATCCCCGCGCACATT
GGTATTCATACAGTTATTAACCCGACTATTCCCAAAGATCTTGAACAGCGTCGGGTCCGG
TTGACTCAGACGAACACGCCTTGGCCGCGTCTACCGGGTAAGAAACGGATTGCAATGGTC
AACTCCTTTGGAGCTCATGGTGGAAACACGACTGTTCTGTTGGAGGATGCGCCTGAGCGT
AACAAGGATGTTGCCCGAGAGAACCGCTCGACTCATACCGTCGTCATATCGGCCAAATCT
AAGAAGTCTCTCCAAGCCAATATTGCAAACCTAGCGCTGCATCTGGAGGAGAATCCTGAC
ATCGATCTGGGCGATTTGTCATACACAACCTGCGCACGTCGCATCCATTACACTCTGCGC
GTTGGCTTCGCGGTCTCGAGCATCGCCGGGCTAAAGGAAGCCCTACGCAAGGCTGGCGAG
AAAGAGGCTCTTGCTGAGGTCCGTCCAACACCAGGGGACGTTCCTCCGGTCGTTTTCGCC
TTCACCGGCCAGGGAGCCTTCTACCAGGGCATTGCCCGGGAGCTATTCGAGTCATTCTCT
TACTTCCGTGACGAAGTATTGCAACTTGACCACATTGTCCAACGGCTTGGTTTCCAGTCC
ATTGTGCCCGTGATTGACGGAAGTATTGGCGAGAATCCATCAGCAACCGTGTCGCAGCTT
AGCATTGTCGTGATCGAGATTGCGCTTGCGCATCTCTGGACTCTACTGCTCGGCATGCAA
CCTAGCGCCGTCATCGGCCACACGTTAGGCGAGGTATGCCGCGCTGGTCGTTGCGGGCGTC
CTATCTACCGGACGGTATCTTCCTCGCCGGGCGACGTGCCCAGTTGATTGAAAAGTGT
TGTACAGCTGGCAGCCACGCGATGTTGTCGGTTCGTGCATCAGTATCGGAGATCAGCAAG
CTTCTAGGCAATGCCAAGTACGAGATATCCTGCCAGAATACTCTCAACGATACAGTTATT
GGCGGCACCAAGGCAAATCTGGACGCTGCCCGTCAAGTTCTCGAGTCTAGCAGCATTAAG
TGTGTGCCGGTAGACGTGCCCTTTGCATTTCACACCGAGCAGGTCGACCCAGTACTAGAC
CAACTAACCCGAGTCGCTGAGACTGTGCACTTCAAGGCCCCCAGTATTCCAATCATATCG
CCATTGTTGAGAAGCGTGGTGTTTGACGGCAAGACTATCAATTCCAGTTACTTGATTAGA
GCCACACGCGAGCCCGTCCACTTTGCTGGTGCCATAGAGGCTGCGCAGGATCTCGGCATG
GTGAATGATAAAACAGTATGGGTCGATGTTGGACCGCATCCTATTTGCGCTAGCTTTGTG
CGCAGTTTGATCCCCAAGGCGCGTGTCGCTTCGTCATGCCGGAGAAATGAGGACAACTAT
GCAACGATGGCGAAGAACCTTGTAGCTCTGCACCTGGCTGGTTGCACTCCTGTCTGGGAC
GAGTATTTCCGGGCTAATGAAAAGGCGTACAACCTGCTTACTCTGCCCAAATACGCCTGG
```

Figure 5H (continued)

```
AACGATGTCAACTACTGGATCCAATATATCGGCACATGGACGTTGGATAAGGCTCATCTG
AAGTATACTGGAACAAATGGACCACCGCAGGTTAAGCCGTCGTCTTCGGCATTGCGCACA
TCTCTGATCCACGAAATCATCGAAGAGACCATTGGCGAAGAAACGGCCACGCTCAAAACC
GTCTCTGACTTGCAACACCCGGAATTCCTCGAGGCTGTTCATGGTCATCGGATGAATAAT
TGTGGCGTAGCAACATCAGTAGGTTCAGCTGTTTTATCCTTTTAGTTAAGTAAACTAACG
ATAGCCCTCAGTCAATCTGGACCGACATGTCGTTGACGGTTGGCGAATATCTGTATAACA
AACTAGCACCCGGATCAAAGGTACACATGAATGTGGGCGAGCTTGAGGTCTTGCACGCAA
CTGTGGCCAATCCTGCCAAAAACTGCACCCAGAACCTGTACCTTGACGCCCATCTAGACT
TACGCACGCAGAAGATGTCACTTGCCTGGTTTAATGTCGATCCTGCAACTGGGAGCAAGG
CAGCCGAATCTTATGCTACTGGATCTGTGCGTTTCGAGGCTGATGCGGAGAAGTGGAAGT
CTGAATGGGAGCGTCTGACACACTTGGTGCTCGGCCGAATCGAGACATTAGAGAGCATGG
CCAAGGACGGACAAGCAAGCCAGTTGTCCAAGGCGTTATCCTATGCCCTATTCAAGAACG
TGGTTGATTACGCTGACCATTATCGCGGCATGGAACGGGTGGTAATGCACGACTATGAAG
CGTTCTGCGATATCAAGCTCACGCCAGAACGCCGAGGTATGTTCCATACGCCGCCGCACT
GGATCGATAGTGTTTCCCATCTTGCTGGTCTTATCATGAACGGGAGCGATGCCTCCAACA
CCCGCGATTACTTCTTCGTCACACCAGGCTATGAGAGTTTCCGTTTGCTGGCAAAACTGG
ACCCTGACGTCAAGTATCAGAGCTATGTGCGCATGTTCCCACTGCCAGAGGCCAACATGT
ACGGAGGCGATTTGTACATTTTGCAGGATAATCAGATCATTGGCATGGTTGGTCATTTCA
AGTTCAGACGAGTACCACGCCTGCTCATGGATCGATTCTTTTCGGCTGAAGCAGCCTCAA
AACAATCAGTGGCGGCTTCTGCGTCTTCTGCGCCTAAGACTGCAACCAAACATGCCCCGC
TGCCGGCCTCCAAACCGGCCCAAGCACCAGCTGAACCAACACCCTCGTCGCTTCCCACAG
TTCAAGCACAGAATACCAGCCCCCCTCAACAAGTAACGCCGTCGAAACCCGCAATGAACG
GCGTGAAAACGCCTGAAGAGGAGAAGCCCGGCAAAGCAGATGCCGAAGGTCCGAACGGAA
CGACCTCTCAACCAGAAGCGACCGGCGTAGTTGGCCAATGCCTGCAATTGATCGCTAACG
AGACAGGACAAAGCGTGAATGAGTTGACACCGGATGCCACTTTTGTGCAGCTAGGAGTTG
ACTCGCTCATGTCACTTGTGCTCTCAGAGAAATTCCGGGCCGAGCTTGGTTTGGAGGTCA
AGAGCTCGCTTTTCCTAGAGTGCCCGACAGTTGGAGATATGATGGACTGGTTAGAGCAGT
ACTGTTAGAGAAAGATGCTTGGAAATCAGTATAGCTTTCTGTAGTTTCAATGAAGAATGA
GTATTAGAATGATCTCCATAC
```

Figure 5I

Sequence of the deletion of the Austinol of Austinol/Dehydroaustinol cluster

>ChrV_A_nidulans_FGSC_A4 COORDS:ChrV_A_nidulans_FGSC_A4:298019-318185W
(20167 nucleotides) (SEQ ID NO:9)

```
AAAGTCCTAAACCTCTTGTACTTTCTCCTGGAATGGTGTTGTCCGTATACTTGGGTGCCA
CCAACAACCAACAACAGCTATGACTGTGAGCCCTACCACAGACGCTATGGGCACCTCTGA
AGAAACACGATCCAAACAAACCAAAGGGTCAAACGACGATATTTTGAGCGCGAAGATAGC
TGGAAGAGTTGCTCGCCCCGTTTATCACTGCACAAGCGCACGGCTCCATGACCTAGCCTA
CGACCCATGGCCCATTACCACCATCGATACCCACGGTCTCAGTTCACTGAAGGCTCCATC
AACGCACACCCGGATCTTGATTATTGGCGCAGGATTCGGCGGCCTCCTCTTTGCGGTGCG
CCTCCTCCAAGCCGGATTCTCCCGTGACGATCTCCTCCTCGTGGATTCGGCGGGTGGGTT
TGGCGGGACGTGGTACTGGAATCGCTATCCCGGCCTAATGTGCGATATAGAGAGTTACAT
CTACATGCCCCTACTTGAAGAGACGGGCCACATGCCCAGCCGGAAGTATGTACCCGGTGA
AGAGTTGCGTACCCACGCGGAGGGGATAGCGGCAAAATGGGAGCTGGAGCAGCGGGCGCT
ATTCCGTACAACTATCAGAACTCTCGAGTGGGATGAAGGTGGGAATCAATGGATTGCTCA
CGCTGAGCAGTTAGGTGTATTTACAGACGCAAAACAGGGGGGAAATGGTGGTGGTGGACC
TTTAACATTTACCGCAACTTTTGCCATCATTGCGAGTGGGACACTCAGCAAGCCCAAGGT
CCCCAATTTACATGGTGTCGATGACTTCCAAGGACATATCTTCCATACTGCCCGATGGGA
TTACGACTATACCGGCGGTTCGCCGGCTAACCCTGCCATGCACCGGTTACAAGGGAAACG
GGTAGGAGTAATTGGGACTGGCTCAACGGCTGTTCAGGTGATTCCACAGCTTGCTCGCTG
GTCCAAGGAATTAATCGTATTTCAACGGACACCGGCTGCCGTGGGCTTGCAGAAAAATCA
GGTTACTGATCCCGTGTGGTGGAAGGGCAACATTCTGAAGGCTGGGTCGGGATGGCAGAG
GAAACGATCGGAGAATTTCAACGCGTTCATTTCCATCTCGAACCCACCCTGCATGGAGAA
TCTAGTAAATGATGGTTGGACGAGTTCGCCATCATTCTCTGCCGCAATCGGTGGAGCACT
GAACATGCAGCCGGATTTCCTGGACCTAGTCAAAGCTATTGATCGACCTAGGCTGGAAGC
TGCCCAGGACCATATCAGATCAACTGTTCGGGATGATACCACCGCAGAGGCCCTTATCAA
TTTAAACCACGGATGGTGCAAGAGACCCTGCTTCCACCAGGGATATTTTGAGACATACAA
TCTGCCGCATGTGAGGCTGATCAAAACCGACGCCGCCGGCGTTACAGGGCTAAGTCCAAA
GGGAATATTGGTTGGGGACACCCTCTACGAAGTTGATTTGGTTGTTTTAGCTACAGGCTA
CGATCTGGGCAGCTTGTGTCCGGCCGATGGGCGCAAATCCAGGTTCTAGGCTCAGAGGG
AGTGGCCATGAAGGAGAAATGGGCTGGCGGTCCTACAACGCTGCATGGGGTAATGACTCG
TGGATTTCCAAATCTTTTTTTCCCCGGTACCTCGCAGGCTGGTGTTACCGCGAACCAATC
TTATATGTTCGATCGTGCCGCAGAACATGTGGCCTATATCATTCAGAACTCCACACTGGA
GGCAGGAGGCTATATTGACAAGATCCGTATCGAGCCCACGGCGGAAGGAGAAAAGCACTG
GACGACGCAGTCAGTCGCACGGATAAGTGCATTCGCAGCCACAACAGCGTGTGGCACTGG
GGATTATACAATTTCGAACCGTTACAGAAGCAGCGATGTTGACACGATGGCAAGGCATAT
GCCGTGGGGAGAAGGTATGGCAAGTTATGTGAAAATTCTAGAGGCCTGGAGAGAAAGTGG
GACTATGGAAGGTTTGGATATCAGGTACCACTCATCTGAGGGTTCCAGGTAGGAGTTATC
AGCACGGGCGAGGAGAAGGGGGCTATTGCTCTAAAAATATTCTCTGTATGCCCGAGTTCC
ATGTTTAGCAGACTCATTAAGTCGACAAGTAATCTAGCGCATTCATTGTGTACATCTCTC
CAGCATTTCACTCTTCTGGGGGGTAGTCTAACACTTTCAATGAATAGTAGATTCACCTTG
GTTAGCACAGGAATTGGATAGACTCGGTCGTATTAGCATAGTGGTGAGGTTACTAAGAAC
AACTTTCAATGCTTTCATATAATTGATACTTTCTAGTAAAGGTTTTGTATTGAACGAGGC
AGGACCACAAAGCAAGTAAGGGATTGATTTCACCTCATTCTCATATATTGGCAATGATGA
GTGAGAGGAACAGGAAATAGACCTACGTAGACGTAATCTTATAGTAATAACGTTTGAGG
AGTGTTCACTTTTATTAGGATTACTATTTCCGAACAACAGCGCGCCTTTTTGTTTGCACA
CCTGACTACTTCAATCTGTATCAAGCACAGTGTGAGAACATGTAAATCGCCTCTGTTTCC
TTTGCGCCCACAGCAGTGAGCTACCTGTAATGACAGGTAGCTAATCGCCCTTCGCCTCCT
TCCCATCCCTACCACTTTCAGTACGACGGAAATGGAAAAACACGGTAGGGTATATCGCGT
CGAGAGTTAGGGTAATCCCAATATAAAACCAGCATAACGGGCTATCGAGCCAAGGGTCGC
CGCCATGCTCCAATAATGATCGTCAGTTTTATGAACCTACTGGCCATTGCTATAGTGCGG
AAAAAGCAGTTTCTTGGGTGAGTAGGAAGGAGGCATGAAGGGAATCCAGAGGACAAAAG
CGCGAGTCTACTTACCAGGTATTCAGTGACGCCCTGGAGTACTGCCGCGAGAGACCAAC
TGACAGAGAGATCCAAGACTTGCCATAGTCTGGCACAACGCGCCGCTCCAATGGAAGCCC
AGATCTGGGCCAATTCCATGGGCCAATGCTAGATGACCTGCCATGTACCCAACTGTTACC
GCTACATAGGCCAAGCCAGCATGTCGCTTCATCAACGGAACGTGGGCCCAATCAGCCGGT
GCGTGTCTTGCAATGATGAATAACATGACACAATGCATCACGAACCAAGCACAAATGCCA
```

Figure 5I (continued)

```
CCAGCCCAATGCGAGCTGGATATTGGGTAGATGAAAGCATAGACAGATTCCCATCCGACA
TCGCAGCAGATAGACATGAACGAGCTGCTGAGTAATTGGTCATTCAGTGTCGTCCTCATG
GTGCTAACGCAGCTCAGCGACCAGCAAATGAATTGTATTAGCCGCAGTACAATTTCATAG
GCTCTGGGGTCCGCGAGTATAGAGTATTCTGGAAGTCTCCATTACGGAGAACATGGTGAG
CAAATGAATATAGAATAAGTGCAAAAGGTAGACTATTTGGAACAAAGCCTTGCACAGCTT
CGCTTTCGTAGTTGATGCGTCGAAAGTTAAATTCTTATTTCACAAGTTGACTAATTTTGA
AACAGTACAATCAGAAGCTCTCAGATGCTACTGCGCTAGAATGTCCCAAGGGGCTAGGCG
TGTTCGGACTAGGAGACGAGACATATCTGAGTCCAGTGATAGGACACGTTAAGACCGGTG
TGCTGTGTAGGTAGGCTCAGGGGCAGATTCACTTCCCTTGCTTTGCAAGCCTCGCTGGTT
ATTTCTAGACGTGGCCGTAGCTTGCGCTGAGGGTTCTGGTTCCTTGCGGCGCAACACTAT
TATGGCTTCGATATTCCAACCGTCCACGTCTATGCATTAAGCTCCAAAATGAACCGCACG
ATTAATAGATAATCTGACAATATATGTTGGGAGACGGCCCGGTCTATTATGGCAACTATC
AGGGCTCTCTGAGCAGTGTACTGGAAGAAGGAAGAGCGCGTTATCTGCGTTTCAGGTTGG
ACTCTCGATGCGATGAGACGAGGCCCTAAAAGAGCTGCAGTTTCTGATTCCTCCGCATCG
TCCTATCTAGGGAGTTCGGACTGGGTTATTAGTCATTCACATGCAGCTCAGATTGCCTTT
TACGAGATAAGGGGAGATGTCCGATAGTGATAGCGAGCTCCTGCAAGCTCTCTATAGGAT
TCTCAATCCTACGATCGAGCAAAGTGCTGCAGGACTTTCCAATGCGCTATGATAGACATT
AAGCAATCATATATGAAATGGCACAGCCAATATGCAAACCAAGAGACCTGCTGCTATTCA
TCCTACACTTTCGAACTGCAATCGCGTGTTTGTAGCTTATGCAACAGATTATGCTCGTGG
CTGTTACCGCATGGTATGGCTTCTCGCTCTAATTGCAGCCAAACGATCTTCACATATAGT
TAGCTCACAATTCGCGGAGGCTTTTCACAACTGGCAGGCTGGTCAGCACCCTGTCAGGTT
CACGAGAGAGCGGGCAAGGAGGTTTCGGAATGACCAATCTGCCTTATTGTGCTACGCTCA
AGGCTCCTGAAGTCACCAGTTGCTAATGCCGGACATCTATTGGTACTTCGCTCATAGATG
TTAGAACCGTCGGTCATAGCGCATGATCACCATGTACAGCATTCGGGGTAGAGCATGGAT
CAGGAGCAACTTTTCGCCATCAGCAGGGAAAGATTCGCCTCCACCACGCATTCATCACCA
ACCGACATTCATAGAAAGGGGTGACTGCAACAACGAAGGAGTTAGATCGCGATGCCGAGT
CTGGCCAAGGATGTCGCAGGCAAGGAGCTCGGAGATACCAGTCATGCAAGGAGGACACGG
GTGCAACCTTAAGGCTCGTTCCGGGCCCGGCACCGAATTGTGTGCATAATCTGGGGCCTC
ACTGATGTGATATGTTCCAATATGGGTCAGAAGCTCGCATCTTCTCACTCGTTGGCAAGG
GCTGCAAGGGAGAAGGAGAACCACGCATCCATCATTTTCTCCTTACGATGAAGCGGCAGG
AGTCTAACTGGGAAGCTTAGCCCGCTGATCGCAGAATGTATGCATCGAATAAGACGTATC
CGTCTTCTAGGGCGCTCCCTTGCCTCGTTGAGAAGGTCGAGGCACAACACGTTGACGGGG
CGATTAGAGTAAGGATCACAACGCTGGAGCAGAGTACGCGTCGTAAACCATCCCGAGCAG
ATTATCTATACTTTTGTGAAGCCTTTGAGCTTTTAACACCTTGAGGTCGTTCTCAGTAC
GGATTTGCCAGTATGACTATTACACCCAACATTCTAGAAGACTGGCGTCAAGCCAAAGCC
GCCGCTGTTGAAGCCAAATACGAAGCGGAACGCGAGATCCAACTTCGAGCTCACGGAAAC
GTGAAAGACATTGAAATCACCCGCGAGTCAGCCTTTGAACACTTTGCAACAGATCCCTGG
GCCCAGCATGTGGGGGTAGACATAGAAGCTCAGCGCGAGCGGTTGCTAGCGGAACCTGGA
AGCCGCAAGATCCTAATCATCGGGGCCGGGTTTGGAGGTCTACTGTTTGCCGTGCGTTTG
ATCCAGACTGGGCGATTTACCGCTGAGGATATTACCATGATCGACAGTGCCGCGGGCTTC
GGTGGCACCTGGTATTGGAATCGATACCCCGGACTGATGTGCGATACTGAGAGCTATATC
TACATGCCCCTTTTGGAGGAAACTGGGTACATGCCCCGGAACAAGTATGCGTCGGGCAAC
GAGATTAGGGAGCACGCGGAGCGGATTGCACAAACGTACGGGCTGGCAACTCGAGCCATG
TTCAGGACCGTAGTCGAAAAGCTGGATTGGAACGAGGCGGAAAAGTCTGGACAGTAGCT
GGTTCTATGCTGGGCATTGCAAATAACGGGCAAAGGGATAATATGATGTCTTTTCAGATG
GTTTCACAATTTACGATCATGGCCTCGGGTTCATTCGCCAGTCCGAGAGTCCCGGATTAT
CCTAACATATTCGACTACAAAGGCAAATTGTTCCACACAGCTCGATGGGACTACAACTAC
ACGGGAGGCTCCGTGGAAAACCCGAAGATGCTGGGGTTAGCCGACAAGACGGTTGCCATC
ATTGGAACAGGGGCCAGTGCAGTCCAGATTGTGCCGCAGCTGGCAAAATATAGCAACAAA
CTCATAGTATTTCAACGGACCCCAGCTGCAGTAGACGCCCGCAACAATTGTCCCACAGAC
CCGGTGTGGTGGGAAACCGAGACGCAGGCCGAGGGCACTGGATGGCAGAAGCGCCGCCAG
GAGAACTTCAACGCTTTCACCTGCAACGAGAAACCCCTTCCATCAGTGAACAAAGTGGAT
GATGGCTGGACTCGAATGCCGTCCTTCAGCATCCTGATTGGCGGCCCGCAGGGACTGGAT
CCCGACTACGTCGACCGGATGCGCGCGGTCGATATGAATAGACAAGAGAAGATCCGCGCG
CGTGCACACAATATTGTACAGTCAGAAGGTTCAGCCGATCTCCTGACGCCCTGGTATCCT
GGGTGGTGCAAGCGGCCATGCTTCCATGGAACTATCTTTCTGCATTCAACCTGCCCAGC
GTGGAGCTAGTCGACATTCGCCATAATGGAATCTCCACTTCACAGCCAATGGCCTGGTC
GCAAACGATATTGAATATGAGCTAGACGTCATCATCCTGAGCACGGGGTACACTGTCCCT
GTCACGCGTGCAAGCCCGTCTTCGCGCGCAAACATTGCCGTCTCCGGCCGCAACGGGACC
ACCATGGAGGCCAAATGGGCGAATGGCCTCGCAACCCTGCATGGGGTCATGACCCGCGAC
```

Figure 5I (continued)

```
CTGCCAAATCTCTTTTTCGCGGGAACCTCGCAGGCTGGTGCCTGTGTCAATCTGGTCTAC
GCACTGGACCAGAACGCCACCCATGTAGCTTATATACTTGCCAATGCGTTTGACAGACGC
CCCAGCGACAGCGCGAGGGTTATCATTGAGCCGACACCCGGGTCAGAAGAGGCCTGGGCG
ATGCAGGTGCTGCAGCGGGCAGCTGGATTCCGCGGCATCGCTGGCTGCACGCCTGGATAT
CTCAATGGCTACGGGATGGATGCCTCGTCATTAAGTCCGGAGCAGCAAATCAACGCGGCC
CGTCTAGCTGCATGGGGAGAAGGAATCGCGAGCTACGTGAGATACCTGGAGGCATGGAGA
GCGAAGGGAGACTTGAATGGGATTGAGTTGACTTTTTTTGCGAAGTTTTGAAGCAAAAAG
GGAACCTTGTGACTGAATTATGCGAGTATCAATAGTCACTTGGAATAAGCGTGAAATATA
ACTCACGCATACGCAGTAAAAGCTACCCAAAATGAACCCCGAGTTCCATCATGAGAAAA
CAAAAACAAGAAAACTGAAAACTGAATAAGTGCTTCTGGGATTAGTTCTCTAACTTTCAC
ATGTTGCCCAATTTCAAAGAAAAGCAAAATGTCGTCTAGTACCAGGCCATCAACTATTTT
ACCCCACTAGATATTCCAGGAACGAAATGGGTCACCAATAGTGCACTTATCACCACTGTC
GAATTGCGCACAGCCCGATAACAATACGAAGAGAGCCTCAATTCGCCTTCAGAGTTCCT
GCACTCAAACAAGGCATTCCGGGGATCCGTTAATGCAGCGGCATTGATGGGTGGAAACGG
GGATAAATGGGCTTCAATTGACCCGCGAAGTTCCTTGATAGAATAGCCTTTAAGAGACAC
GTAGAATTAACATATATGTCCTGCGTATAGGATGACATGTGTTACTGACCATGGATTTTC
CCCAGCGTCGAACCACAGTAATACATGGATTGTTTGCAATTCCCTGAGAGTGCGATGGTT
GCGGGCAGCAAACTGCTCAAGACGGCAATTTCTAGGATGAGTTTCATCTTCCTGTCGAGA
TTATCTGGGTAGGTTCCTCCTGGAGGTTGTTATAACGTCAAAGGCAGAATGGACATGGAA
CGCACGGCCCCTGCGTGCAGCTTCTACAATGCGTCAGCGGCATGCTATGGCCAGCAACGC
CGGGTTCTCTAAGGAGGGAACTATACGCAAGGAATGTATTAATAAAGACAAGCTCGACTA
CACTGTAACCAGAAACAAAAGCGGTAGAAAATAAATGAATTCGCCGCAAGTGGAATCCG
TAATGTTGGCCCAAATAACATTCCCATTAATTCCCCAACACTATCCGATAACAGCACTAC
AAGCAAAGTTAGGGCACATCACTCCCTCACATTTCAAAAGCCACGATCGAAAGTCACTC
AGTAAATACTTCCGTATTCCCTGTAGGAGTTGAGGCTCGAGATTTCCCCATGCCCGGTGC
ACCATCACTCAATCTAGGGCGCTGCCGTGGGAGAAGGTACAGCGGCTGCTGTAGCCGCCT
GAGGTGCATCAATGTGTTCTATCGTGGCGTCAATCATCTCGGCCTTGTCAGGATTATCGG
CCGGGCGGTCGTCTTTGGGTGTTGACTGAGGAGCATCCGCTTTTGCATTTTCTGGCCCGT
CTTCCAAATCTTCGCCTTTAGTAAGGGGTGTGGCACAGGAGTGCAGGCATTGTGCGAAA
TGCCTCCTTGGGTAGTAGTGCTTGGGTTCAAGCTACTACCAAAGAAGTTGGGGAATCCAC
CAGAACCTAGGAATCCACTAAAGCCTGGGAATCCACTGAAGCCAGAGGAGCCACCGAAAC
CAGGGAAACCACCAAAGCCAGGGAAACCACCGAAGCCAGGGGAACTGGCTGCAGCAGGTC
CTGCCGTGATTGATCCCGTTGGTGCTCCGCCACCACCTCCAGGCATGCTGTGAGACCCGT
CGAAGCCACCGAAGCCCGGAATCCATAGAAACCAGAATTGCCGTATGTGCCAGAGGAGG
GTGCAGTGCCCAGAACACCGGGCCAGCCACCCATGAAGCCTGGATAGCCGGCCATGCTTG
GGAAGACTGCAGTGCCTGGGTTGCTGGAACATGTAGTGGGCGCATCTAAATTAGGCGCTT
GGTCTTCAGTCATATGGTTAGCTTAGCGGTAAGTAATTGGTTGTTCTGCTCATTCTCACC
CTCGGTTGCCTGGGGTGTGGGCAAGGCCATTCCATGGCTAAGCATACTAAGCAGCGCAAT
GGTGGAGGATTTCATTTTGAGCTCAAGGACTTGGTAAATCTTGAAATAACAACGATGCTG
GTTTGGATAATGGCACAATTCGAAGCTGAAACGCTTCTTTTACCACTTTATATATACGCT
GGAGAGCAACTAAGATAGACAGGCTGGCGAAAACAGCCACCAGAAGCCGCCGTTTGCGAG
ACTATGGAGGCGGTGCTTTACTTTGAGGAGAGCTCGCATCCGGGCTCACAGAACATGCTC
GGAATGCCCTATGATTTTGCGGACGGTGGAGACAGGATGCTGCTCTTACAATGATATAAA
TCTAACTCCTACGGTCAGTCAGAAGAAACTACTGTACGCAATCGGCTTCCCTACAGCAGA
TTGAGTACGTTTGCGGTGGTTATATTCTCCCCATCAATACATGGCTATACGAAGCCAGCC
ATGCAGATTGCAACCAGTAAGATGGCTGCTGGATGCTGCAAACGATTCACATTACCCCGA
TTAAAGCAGATGAGATACATTGCTAGATCACCATTACTCGATTTAGTAAAGAAGAGTAAA
TCACCTATGCTAGGGGCGCTATTTTGACTACAATACTTGCACTAGCATGAATACAAATAG
AAACCTCTAGCGGTTTGTGGAGCTCCTTCAGTAGAAGACAGAGCCAGATGTCGGACAAAA
CCCAGCTTCAGGCACGATGGGCCATTTGCCTTGTAATATGGCGGACATCAACGATACTCT
TGAACATACGCTATCGAAGCTTGAGCAAGCCAAAATTCATATAACTATCTCACTGAGATA
TGTAGCGTAGTAGACATAAAAAAAACCCGTTTGATCACAAATCATGACATAGCTATGTTA
ATCTGTGCCTTATATAATGGCTTAAGATTTGCGAGAAGATAATTTCCATTACCACAACGA
GGATAGGCACTAAATACTAATTATAAGCAACGTGTCTTCGCAGGAACTCGTACCCGTCC
ACGACAGCCTGGAACGCATGCTGATTGCCAGCAAAATTGGCCTCTAGGTCAAACAAATGT
AGCCCATCACGCACGATACGCAAGTCAGAGTCCACGCCACAAGCCTGCATCTTATCATGT
GTCCGTTGCGCCTGTTGTACGGGAATCAAATCATCCAGAGTACCATGAATCAAGAAGGTA
GGGGCTCTGTACGACCCCGCAGAGATCTGGGAGAACGGGCAGACTTTCTGAACCTCGCTT
AGAATTGGTTCGGGTAGGACGACTTCATAATCCTGCCCAGACTCAGCAGCTCGGGCCCTG
TAGTTGCACCCGTAGAACAGTACTGGTAACGTTTGGCCGGTCCAGTTCATGTAAAGCGCG
```

Figure 5I (continued)

```
ATCCTGCTACGTGGATCACTTGGTGCCATCCAACCCCCCAGAGCTCGCTTGCTGGGTGGA
GGGTTGTACCCGGAAATAGGCGCATCCTGCAGCGCATCCAAAGGATTACCTGTCTGGATG
TCAGATGTAGAGACGTCGACTCTATACGGGAAGTTCGGTTTGCTCCAGAACGGGTCAGTG
TAATCCGTAGGGCTGTAGAAGGAGAGAATTGCCTCAGGGGCCGAAACGCCGCGCGCAGGT
GCTGTCCATGCCAGCGTCATAGCTAGGTGACCACCAGTCGACCAGCCTACGGCAACGACA
TTGTTTCCGTCTGGAAGAATGTCACGGCGCTGAAGCTGTAGTTGAGGTAATTGTTCCGC
GCCCAGGCCAAAGCATCACAGGCATCTTGCATGGGCCGTCTAGGAGTGATACCTCCGGG
CAAAGTCGGTAATCAATACTGACGGGCAAGAACCCCATGTCAAACAGCATTCTGACTTGT
TCATGGTGTATTTCCTTGCGCGAGAGCATTATGTGGCCGCCGCCGTGGATGAGTAGGGCT
ATGTGCTCAAGTTAGCTCCTGAGTACCATTGAGCCAATTGCAGTTATATAACCTACCGAT
TGGTCTTTTTGCTCCGCTACGATCCGTCTTTTCCGGATAGTAGATATCCGCAAACAACTC
CAATCCGTCCCTTGTGTTGTAGAGAACCGTTTGCTCCTGCACAGTGTTGCAGTCGGCTTC
GCATTCATCGTCACCTTCCAGGGCATAGAAAGGTTGAGTAGACGACGCAACGATAAGACG
CAGAATATCCGACTCGGCAGAGTCGTTGTCTGTCCAATCTACCCAGTTGAATCCAGCTTG
CCGTAGGTTGTGGTCCCAGAGACGCTCGTGAGCCAAAGCATGCGAACGACCATCGTTAAA
CAGCCACCAGCCCTCGAGAAGACCAAAGACGAGGTCAAACCAGAACAAATTCCTCGTCAA
CTCAATCAGGCACAAAATGCCTTCGGGGCGTAGCAACCTCCGAATGTTTGTGCAGGAAGT
GATCAAATTCCGGGTGGCGTGGATACAGTTTGTGGATATTATGATATCGTACTGTCCCTG
TAACTCAGGTGAAGGATCATTCTCAATATCGAGCGTTGTATAGCGCATGAAATCGTAAGC
CTTGAATCGCTTGCGAGCCAAGGTGACCAGGGAAGAGGAGATATCTGTGAATGTGTACTG
GAATCGGAGGCCAGGTACTGCTGCCAGTTCTTGAACGAGGTAATTGGTCGTTCCTCCTGT
GCCAGCGCCAATTTCCAAAACCTTGATCTCCCTTTGGGTACCTAGGTTAAAAAGGAGGTC
TTTGAGATATTGTGCCAACTGTATCGTGGCTGACTTGAACATGGCGCATTGGAGTATAC
GTCTGTCATCAATGCACGGGCTTCTGCATTCTGGAACAGGAGGGACAAAGGGTCTGCTTT
TCCACTAAGACACTCTGCTAGTCGCGAGCCGGTAGTGTGTAGTAGTTTGTGCTCCGAGGC
ATGCTGAGCGTGTTTGTTGAGTATCTTCTTGTAGAGAATTAGGGACGGAACGGTGCCAAC
GGGCTGTTGGCTTCGAATTATCTCTGATTCTCTTCGCTCGATGAGATCGGAGTATTCGAG
CACAGCGACCAGCTGATTCATGACCTTGCCATGTTGGGGAAGGATTTTGACAGGTGGAAC
TACCTGACCGGGTGTGAGCGATGCTAGGTCGGCACCCAATGCGTGAAATGCCTCCACCAC
ATAGCTAGTGACAAGCTCCATCTGTTGAGGGAAGACGGTGTCGCAGAAGCCTGCGAACCG
TGTCTTGCGGCTGAATTCGGCACTCGTGCGTGTGGTAGCAAAGAGTTTACTAGCTTTATC
GACAAATGCCGTCGGTGATGTATCACATACTGGCGCAAGATCCACCGAGATACTCTTTGG
CTCTCGGTCTGTGATTGTGATTTCGGTCTCGACGGCCCCCTGACTGTGAGTTTTGATGCG
GACAACCGAGTGTCCCGGGAAGATACGTTGTACCAATCCGCCAACATCCGGGATTTGTGT
AAGCTCAGCGTTGGATATAGCCACTCCAAACCGTTTATTAATTTCGGTTAAGACTTCAGT
GCTCATAAGCGAGTCGACACCGATATCGCCGAGGGCAGCAGCTGCTGAGAGTTCGTCGGC
AGAGATTCCCAGTAGTTCACCGAGCATGGTCTGCACAGCTAGAAGATCACCATCGCTACT
CGAAACGTGAGCCACTGGGGTAGAGGAGAGAGCTGTCGCCTCAGCAGCAACATTAATGGA
GACCTGCTCTGCCTCCGTTGGCCTGGCAGTATGATTACTCAGACGGTTTAGGGTTCGCTT
TAACGATTGAATGGACACACCCGTGAAGGTAGCGGACAGCATGCAGACAGCAAGCGCCCC
TGTAGTATGGTCTAGTACAAAGACATCGCATACTATTTTCTTTTTTGACTCCGGCTCGTA
GTTGGAATACACAGCCCAGGGAACCGTAGCTGCTGTGTCCCGTCGCACAAAGGATTCACC
GATCAATACATCCCCTACCGAACTACACACGAAAACCTCATCATCATGCGTTTCAGAAAG
ACAGTTAACGTGGATGCCGGCTACCTGAATGAAGTTGTCTATCAGAATCGGGTCGCAAGG
ATTGCACTTGGTCGGCGAGGAAGGCAGGATGACTCGGCCAGTGGCTTCGTGCCCTACAGC
GTAAACTTCTTCAACGCCGCGGTAATAGTCTGCGTAGTTGACGGCCCTGGCAAATGCTTG
GTAGACTGTTGAGCGCTTAAGCCCACTGGAAGAAGGAGACGTAGCAATGGAGTTCCAGCT
AGCAAGATTCAGTAGACGTTGTAAGGAGCTTAAGCGAGCGCATATCCCGGTGTTGCTACC
GGCAGCTTGTAACGATACTCTGCCTGTAGCATGTGTCACCGCGTCCTGCAAACCGTCACG
CGTGGACAGCACAAATGACCACTGTCCATGGCTCTCATCCTGCTGCGTCAGCTGCAGGAG
AACCGCACCGGGCATCCCGAGGACAAGGGGCGAGCAAATGTTAAGGCTCTCGATGTGATA
CATTGTTGGCTTTGTCGCTGTTGATGAGACAAGTAATGCTGCCTGAACGACAAGTTCAAA
ATAGAGAGAGGCAGGGCATAAATTCTGGTTGGCGACTGCATGGCCGGCGGTGCACATTCG
GAAGACGTTGTCCTTGTTGTTGATGGTAAAGAGAGCTTCTTTACCATCTTGTCTCAGCAG
CCGCACGAGACTCGCTTCTTGTACATTTTCTTGATCCGGTACCTGCGGAGGCGAACGGAA
GGCGTCAGGGTTATACTCAATCCAATGGCTGGTTTTCGCGAATTGGTATGGGGCAGGTT
GATCCACCTGTACCCGGTCTCCGAAGGATGGAACGGCCAGAATTGAACCGGCACAGCTTT
TGACCAAAGTGTACAGGTCACCTTTGCGAGATTTGCCTGGGCTTGGGCACCGGAAAGATC
AGTCGGAAGGTATACATGGCTTTTGAGCGGCCGTGACGCTTCCACGACACGACGCACCAT
ATTAATGACTGGTGAAGCTGTTCCTGCCTCGAGCCAAACACATGGGCCATCGACACGCGA
```

Figure 5I (continued)

```
AAGAGTCCGTTCCACGGCATCATGAAAAAACACCGGCTTGCGTGAGTGTTGCACAATCTT
GTCACCTGTGACCCATAACCAGTCATCCTCCTGTTCGGCACATGCCTCGACAGGAATATC
CAGCTGTCTAAAGGTGAGCGTATTGGCTACCTCGCTCAATCCTGGCAGAATTGCGTCCAC
GAGACGAGAGTGAAACGCATGAGTATTCTTCAATCTCTTCAGTTCAACATGCATTCCCTT
CTCGGTGGCGATGATTTCGATGCGGCGAATGGACTCCTCATCGCCGGCAACAACAAAGTT
ATCAGGTCCATTCAGGCATGCAAGGTCTGCGTGACCTGATGCAGCGTCTAGCAGAGCTTG
GACCTTCTCTTTGCTCGCTCTCAAAGAAAGCATCACTCCAGTATGCGGTCCCCAATGTTT
CTGGATCAGCTGGGCGCGAGTTGCGACAAGTCGCATTCCATCAATGAGCGATAAGCCACC
AGCAACGCATAGGGCAGTTAATTGCCCAAAGCTATGACCGATCATTCGGGTGACCTGCAG
TCCAGAATCAAGCCATGCCTTTGCAGTGGCGTATTGAATGGAAAACAATACGCAATGGAG
GTTCACAATATCTTTGTTAGGGAAAGGGCTCACAATAGCCGGGAATAGGCTAGGGAGATC
TAACGCGTTGCAAGCGTTTTCACATTCATCCTGATGATCAGATCAGCACGAGGCCTTACG
CGTATCCAGAATGAAAAGATAGACTAACCACGTGGAAGCGCAGGAGCTCGCAACTCTCA
AATAAATTTCTTGAGATGCTCGCTGTATCTCCGGTCTGTCCGCCGAAACAAATAATCACA
GGATGAAAGGACTGGGACCGTCTTTCGACCTGCGTATGAGCGGAGGCGATAGATCCTAAG
CGTGTCATAAGCTCTGAAGGCTCCCCAGCGGCGGCTGGAAATGTGACAAAGTGCTCCATA
TCTCGGTTCTGCTTCCGTGCCAAATTGTATGCGATATGCTGCACGGTGTTAGTACCTGAC
TGTGCTACCTCACGGATGGTGCTCTGAAGAGCTTCACAGTACGAGCGAAGGGACTCTTCG
GTTCGAGCAGAGACGTAAAAAGGAACATGCGAGGGCAGGGTCTCCCGATGGGCACTGTTT
GAGGTAGCAGGTGTTGACGCAGGTTCTCGTAGAACGATAGCAGCATTGCTACCGGCCGCC
CCATAATTAGTCACCATAGCCACGCGTTTTTCAGCTTCCCAGTCAATTGATTGAGTAGGG
ATTTCTATATGATTCCTCTCGTTTAATGTAATTCTGGGATTCAGGCGACGAAAGTTAGCT
TGTTTGGGGATTCTGCGCTTCTGTATCATCAGGATCGTCTTCAGCATGCCCGCAACACCA
GAAGACGTCTCAGTATGCCCAATATTGTCCTTGATCGACCCAACATAAAGCTTTGTGGCC
CTATTAGGCCCGGAGAATGTTTTCCGGATACTTTCAAACTCAATTGGGTCTCCGACTTGG
GTGCCTGTCAATATGTTAACGATATCTACAGATGGTTAATGATAACAGGTAGTGGGTTAC
AGACCAGTGCCATGTGCTTCAACATAGCCAACAACGTCTGGAGTAAGTCCAGAAAGCGAC
AAGGCTTTCAAATATAAGCTTCTTTGCGAGTTTGAATCCGGGACAGTTATCGGCGAGCAG
TTTGCTCCCTGATTGACGGATGTTCCAGTAATCACGGCGTGAATGGGATCGCCATCGCGA
AGAGCTGCTTCCAGGGGCCGCAGCACAAGCAGCCCAGCACCTTCACCACGACAGTATCCA
TTGGCATCTGCATCGAATGCCTTAGATGCCCCGGTTGGCGACAGAAACGATGCCCCAGCC
AGGTTTTGGGACCATCGGGGATCTGTCATTATATTCACTCCGCCGGCTACAGCGATAGCG
CAATCATTCGTTCGAATGGCCTAGGTCAAGGTACACTTTATTAGCATAATTGTAATAGTG
TTTGTTTGGCTAGGGAACGCACTTACCTGGCACGCGAGGTGAATAGCAACAGCAGCTGAT
GAGCACGCCGTGTCAACCGTGACAGAGGGGCCACTCCAACCAAAGTAATGGCTGATGCGG
CCACTGTTAAAAGCCTGGAGTGTACCAGTTGCTGAGAAGGCAGTGGCATTACGAGATCCA
ACGTTTTCACTATAGTCGTCGCAACCGACTCCAACGTAGCAGCCGATGTCGTCAGGAAGC
TTCGAGCGGCGCAGCCCACAGTAACCAGCGGATTCCATAGCTTCATACGCAACTTGCAGT
AGTACTCTTTGCTGTGGATCCATTGACTCGGCCTCCCGCGCGGATATCCCGAAGAATCGA
TGATCAAAGGCATCTGGGCGCGCGAGGTAATTTCCAAAGAATGGCCCTTTTGGCTCTCTC
TGCAGACTGCCACTTTTAAGCCGACTGTTGGGCATTGGACTGACGGTGCACTGGCCCAGA
TCTAAGATTCTCCACAGTTCTTCCACGGAATCGGCTTGGGGATATCGGCATGCCATCCCA
GTAACCGCGATAGGCACTGCGGTGGTCTCGGGGCCGTGACATTTACCCCGACATCAAGT
GCAGTGGCGGACTGCATCTTGCGTCTGCCATTTATGTGCTCGCCTTTGTTGAACTCAACA
ATGTTCAACATACGACATCTAGCGTGTCGCGGTACGAATTGGCCTGCACCTATGGGGATA
ATGCTTCTAGCATCCGATTGCCCCATGTTGTCTAGAGTAGCGGTGACGGTGATCTTCCAA
TTTGCTTGCGTTGTCAAGATCGACTCGACTGCAACAGTGAAAAGCGAGTCAGCTTCGCAC
ACTCTCCCGTTGATATTGGATCTCGGCAGACTGCGCTTGTGACACTTCGATGGCAGGCAA
AGTCGGCTATTCCGCTCACAAGATTGCAAAATATCCTCCACAGCTTGAGTGTGGTTCGAG
TGATGGAATCGGCCTCTAAGTGTCGTAGTCTTCACCGAGAGCCCATGTTTCTCCAGCTCC
TTTGCGAAGGAAACGGACTGAGAGTCCCAAACGGTGACCGTTACAGCGTTTTCATCAGTC
ACGCATGAAATGTATGCCTGTCGCGTTCATTAACAAGAAGAAAGAAGAATATAAGCAAG
GAACAAGCAGCACTGACACCTTGATAACGAGTTAAGACTTCCGTCAGAAGCTTATGCTCC
TGAGCAGTTCTCCACCTGACGGCGATTGACCTTGCAGGCTGTTCACAAAGCTCGTCCAAG
TCCACTGCAGCCCAATGTAGACGGCGAGACGCAAGACGGTGCTCACAACTTTGCCGAAT
TCATCCTCGTTGTCCGACCAGCATGCAGCTGCGATGGCTGCCAGGAATCCGACGCAGAAT
CCCTGGATATCGCAGACGTCGTAGTTCTTGTCTTCTTTCAGCTCGAGGAAATCGACTAAA
TGTCGCAAGACTGTGGCTGGTACTAGCAAGAAATTCATCGGCTCGGCCATATCAGGCCGT
AGCGTTCCACCCCGAGAAACGCTGAAAGCTGACGGAGACGTGCGTCCCATGAAGCTTC
TCGGCTGCTGGCCAGAGCCTCAGGATATCGTGCCAGACGGAAGGTAAATCTCGGATTGCG
TCGTGAAGCCAGTTTGCATTCCGCTGATTCGAAAGATATCTGCGTATGTGCCCAGCTGGC
```

Figure 5I (continued)

```
AGTTCAACCTCCGGATATTTCGGTCCGAAAAGGACCGAAACCTGCTGCAAAGTATTATCA
TCAAGGGACCCCATCTTTCGAAATAAAGTGATCTTGACTAAAAGGAATGAGACACAGTCG
CTTAACAAAGTGTGCTTATGAAAGAACCAAGAACCAACGGCGTTGAAGCAGTTGCTCAAA
TGACTAGTCCCCGACTCTTAGAACTTGACCGAGAATTTCAAGGGATATAGGCGGAGCCCA
TTGAAGGAACCCTCTAATCTCAGCGGACGGTCTACTTGAAGCTCAAGAGGGGTTACTGCA
GCAGCGCCTGCACTACCGCCCATAGCGGTCCAAGAATCCCCAACCTATTCCTGCCAGCTG
CAAGTGAGGAATTTTGTCGAGATCTCGTCAATAAAGACTCAGAAGACGATATCCTGACAT
ATTGTTCTCAAAACAACGCCTGTATAGGGCAAAGTGCGCATAGCGACAGTCCGCCCGTGT
CGCACGAAAGGGCGCCTGCTATTTCAGCGTCGATCAACAGCCTTCTTTAGGCCAGATTTC
GACTTCTGCAGGAGCCACTGTCTGGTTACATACGACCAATTCGGTCCAATTGCCAGATAG
CTCGTTATGTATATAAGCTAGGGCAAAGGATCCACACCACTTTGGACCGAACCGCCCGAA
AGCTAGACCAGAAGAATGTTGGCTTCTCAGTCAATATGCGGCCCCCTTGCTCCAGGCTCG
AGCCAAGTGGGCACGCAAGGCTTAGTTTGCATTTGCATTGTCCCAAGTGAGGAACCAGAT
CGGACTCAGATCAAAGACATAACCCAAAGGACGGCATTTTGTACAACCCTAAAAAGCGTT
GATCGACATATAAAAACAGCCTCCTTTGCTGATTGCCAACCACAGCTCGTGCTTGGATCC
GTCTTTCCACTACTTGAGGAATGAACGGGCGTATCCATCATGCATAACACATCTACGTTC
CTTGTAGATTATGCCCGAGTAATTCCGATCGCAGCCCTTCATGCTCAACGTGGAATCATC
TCGTTGACTCCGGACTGTCTAGCTGCACCGCCATTCCGTTCGTGGCTCGTAACAGTAGCT
GGCAAGGTATGGCAGCTCTGCAGCGTAGTATCACATACATATTTCACATAATATGATACT
CTGGCGCAAGCGATTTCCTTACTGTTCTTAAACTCTTCTTATCTTTCCGTACGTGTCCAT
CACTCTACAATTTTGGTGCTGCGGGGTCTCTCCGTGATGAGTGCTCTTAATTCCATACTA
GGCCATCTATCTCTGCTATTCAAGTTTATTGCTCGTTATTGTCATCTTCATTTTTACTAA
CTATCCACTCATTATAGCAAGCACAAGCCGTTCTCAAGATTGAACGATGATAGCAATGCA
ACCCGAAACCCAACTAAAAACCGCCCTTAAGAACGGGTTTGACCCGAACATCCTCTACAA
AGACCCTTTAACAATCGTAAAGGAGCCTATGTGTACTATTCTCGAGAAGCACAGCAAGAT
CCCAGTGGACAAAGTCGTCAGTCATGTCAACAAGGTGGTGAGTAAATCAGCCAGCCCTTT
CAAATCTGCTAGTCTGACTTCCTTTCGCCAGAGAGATCGCGCTTTTGCCGTGGTTAGTAC
TCTGTATCCCTATGCACTCCCCAATCTGACCCAATGAAAGTTTCCTTATGCATGCATTGG
GCAATTCTCCTTTGTCGAGCTGAGCATCGCCGCATCGCCGTACTATCCCGAGATGCTCGA
GCGCGTGAAGAATGGCCACAAACTTCTGGACCTAGGCTGCGCATTTGGACAGGAGCTCCG
TCAGCTGGTGAGTTCCTTGTTTCATTCCAGCGATGCCTTCTACCCCACCATCTGTCCTGA
CTGATGTCCCCAGATATATGACGGTGCTCCTGGTGAAAGTTTGTACGGCTCAGATATCCA
GCAAGAGTTTCTAAACCTCGGCTACGAACTCTTCCTGGACCGTGCAACGCTCCCTGAGTC
CCATCTTATCGCTTCCAACATCCTAGACAGACAGTCTCCTCTCTTCACCCACCTCACCGG
AAAGCTCAACATCGTCTACATTTCGCTTTTCCTCCACGTATTTGACTTCGAACAGCAGAT
AACTGTGGCAGGAAACGTGTTGGATCTTCTCGCTGCCGAGCCTGGCTCACTCATCGTATG
CCGGGTTACCGCCTGTCGTGACCAAGGCGTGCTTAACGCAACAGCGGAACGTATGCCGTA
CTACTACCATGACCGGGCGAGCTGGGAACAGCTCTGGGAGGTTGTGCAGAAAAGGACTGG
TGTAAAGCTTTGTGTAGATACCTGGGAACAGCCCGATGAGTTGGTCAAGAAGCATCCCTT
GCCAGGGATATATATTTTGGGGTCTGCGATCCGGCGAGTTTAGCCCACCCGCCGCCTTTT
CGGTCCGAGCTGTTTATCTACAAAGGTTTAGTGTGACAGTCTCCAAAAGTCCACAGAGTA
TACTACAAAGATAAATTTATGAATTATCTGACTTTGGTTGTTAAGGAGCTTGAGTAAAAT
GGCTGAT
```

DEREPLICATION STRAIN OF *ASPERGILLUS NIDULANS*

CROSS REFERENCE TO RELATED APPLICATIONS

This application claims priority to U.S. provisional patent application No. 62/248,850, filed Oct. 30, 2015, the disclosure of which is incorporated herein by reference.

STATEMENT REGARDING FEDERALLY SPONSORED RESEARCH

This invention was made with government support under contract no. NIH Grant No. GM084077 awarded by the National Institutes of Health. The government has certain rights in the invention.

FIELD

The present invention relates generally to modified fungi, and in particular to modified *Aspergillus nidulans*, methods of using the modified strains for production of compounds, such as pharmaceutically useful compounds, and compounds made by the modified fungus.

SUMMARY

To reduce the secondary metabolite background in *Aspergillus nidulans* and minimize the rediscovery of compounds and pathway intermediates, we have created a "genetic dereplication" strain in which we have deleted eight of the most highly expressed secondary metabolite gene clusters (more than 244,000 base pairs deleted in total). This strain has allowed us to discover a novel compound that we designate aspercryptin and to propose a biosynthetic pathway for the compound. Interestingly, aspercryptin is formed from compounds produced by two separate gene clusters, one of which makes the well-known product cichorine. This raises the possibility that fungi use differential regulation of expression of secondary metabolite gene clusters to increase the diversity of metabolites they produce. In this disclosure the modified strain has reduced secondary metabolite background, facilitating production of other secondary metabolites and eliminating a number of toxic compounds normally produced by *Aspergillus nidulans*.

BRIEF DESCRIPTION OF FIGURES

FIG. 3A. Schematic representation of the AN7884 (atn) cluster. Each arrow indicates the direction of transcription and relative sizes of the open reading frames (ORFs). This cluster spanned contig 134 and 135. The linker represents the connection between contig 134 and 135.

FIG. 3B. The deduced function of each ORF and the amino acid sequence coverage and similarity/identity, as compared with the BLAST search of the NCBI nonredundent protein database. Genetic symbols we are assigning to members of the aspercryptin cluster are below the AspGD gene numbers in column 1. The nearest hit to AN7875 only has 40% of protein coverage and was considered to be irrelevant.

FIG. 5A-5I. Sequences of deleted gene clusters. FIG. 5A: Sequence of the deletion of the Sterigmatocystin Cluster (SEQ ID NO:1); FIG. 5B: Sequence of the deletion of the Terrequinone cluster (SEQ ID NO:2); FIG. 5C: Sequence of the deletion of the F9775 cluster (SEQ ID NO:3); FIG. 5D: Sequence of the deletion of the Monodictyphenone cluster (SEQ ID NO:4); FIG. 5E: Sequence of the deletion of the Emericellamide cluster (SEQ ID NO:5); FIG. 5F: Sequence of the deletion of the Dehydroaustinol of the Austinol/Dehydroaustinol cluster (SEQ ID NO:6); FIG. 5G: Sequence of the deletion of the Asperfuranone cluster (SEQ ID NO:7); FIG. 5H: Sequence of the deletion of the Asperthecin cluster (SEQ ID NO:8); FIG. 5I Sequence of the deletion of the Austinol of Austinol/Dehydroaustinol cluster (SEQ ID NO:9).

DETAILED DESCRIPTION

The present disclosure includes the fungi described herein, cultures of the fungi, spores of the fungi, culture systems comprising the fungi, culture media in which the fungi is grown, including such culture media but from which some or all of the fungi have been separated, and isolated and/or purified components of the fungal culture media and/or the fungi. Methods of making compounds with the modified fungi of this disclosure are included, including end products and intermediate compounds that would not be formed without the modifications to the strain that are described herein. The disclosure includes modified *A. nidulans* wherein combinations of genes and gene clustered as disclosed herein are deleted. In embodiments, secondary metabolism gene clusters are deleted. In embodiments, deleted secondary gene clusters that are deleted in an *A. nidulans* strain are selected from the gene clusters responsible for the biosynthesis of sterigmatocystin, the emericellamides, asperfuranone, monodictyphenone, terrequinone, F9775A, F9775B, asperthecin, both portions of the split cluster that makes austinol and dehydroaustinol, and combinations thereof. In embodiments, some or all of these gene clusters are deleted. In embodiments, these are the only gene clusters deleted. The disclosure includes use of such as strain to synthesize a number of compounds, each of which is encompassed by this disclosure. In one aspect the disclosure includes the compound termed aspercryptin given as structure (8). A non-limiting depiction of an aspercryptin synthesis pathway which is included in this disclosure is provided in FIG. 4 and its structure is provided as (8). Aspercryptin and methods of making it are included in this disclosure. Isolated and/or purified aspercryptin is included, as are pharmaceutical formulations comprising it.

In more detail, genetic and molecular genetic approaches that up-regulate secondary metabolite (SM) production are dramatically facilitating the discovery of new fungal natural products,[1] but these approaches often result in the production of a large number of compounds, including pathway intermediates, and, consequently, complex metabolite profiles. We have thus devised a strategy we call "genetic dereplication" whereby we simplify the discovery of novel compounds by eliminating the major known SM biosynthetic pathways in *A. nidulans*, reducing the complexity of SM profiles such that novel compounds are more easily detected. Elimination of highly expressed biosynthetic pathways might also reserve pools of SM precursors such as acetyl-CoA and malonyl-CoA for pathways expressed at low levels.

Example 1

Figure 1:
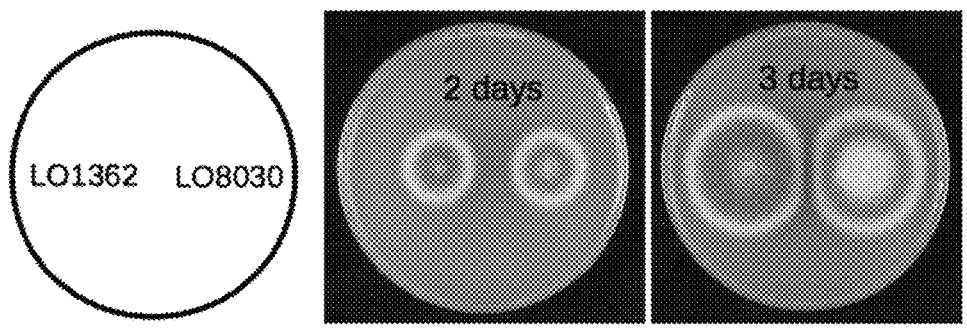
FIG. 1. Growth of a parental strain, LO1362, and a daughter strain, LO8030, in which eight secondary metabolism gene clusters have been deleted. Growth is on complete medium. After two days, the multi-cluster deletion strain grows as well as its parental strain. After three days, radial growth for the multi-cluster deletion strain is the same as for the parent. However, an increase in aerial hyphae makes the center of the colony white.

This example provides a description of engineered a strain (LO8030, genotype in Table 1) in which the clusters responsible for the biosynthesis of the following major SM producing clusters are deleted: sterigmatocystin,[3] the emericellamides,[4] asperfuranone,[5] monodictyphenone,[6] terrequinone,[7] F9775A and B,[8] asperthecin,[9] and both portions of the split cluster that makes austinol and dehydroaustinol.[10] Deletion of these clusters reduced the size of the *A. nidulans* genome by 244,061 bp. LO8030 is surprisingly healthy (FIG. 1). It forms aerial hyphae upon prolonged incubation, but it is not difficult to work with nor to transform. Production of the products of the deleted SM clusters was eliminated under all conditions resulting in a low SM background.

For genes and the gene clusters disclosed herein, the deletion comprises a deletion of a contiguous sequence that contained all of the genes listed as well as sequences between the genes within the same cluster.

In one embodiment the disclosure comprises an engineered *A. nidulans* strain comprising deletion of the Sterigmatocystin gene cluster. This deletion comprises a deletion of part of AN7804 (has been re-annotated); all of AN7805, AN7806, AN7807, AN12089, AN7809, AN7810, AN12090, AN7811, AN7812, AN11017, AN11013, AN7814, AN7815, AN7816, AN11021, AN7817, AN7818, AN7819, AN7820, AN7821, AN7822, AN7823, AN7824, part of AN7825 (has been reannotated). In an embodiment the deletion comprises an *A. nidulans* strain that has been engineered to lack the nucleotides of SEQ ID NO:1, with the proviso that 34 bp of the coding sequence of AN7804 was not deleted and 661 bp of AN7825 was not deleted. For clarity, all of the nucleotides in SEQ ID NO:1 were deleted. This is the case for each deleted cluster and SEQ ID for the clusters of this disclosure. With respect to AN7804, the entire gene was deleted per the annotation at the time of the effective filing date of this application; the gene was re-annotated before the filing of this non-provisional application or patent or PCT application and thus the indication that only part of the gene was deleted. Any non-deleted portions are non-functional. The same applies to any other gene where a reannotation is indicated. Irrespective of annotation the strain comprises a deletion of SEQ ID NO:1.

The engineered *A. nidulans* strain comprises a deletion of the Terrequinone cluster which comprises a deletion of the following genes: AN8510, AN8511, AN8512, AN8513, AN8514, AN8158, AN8516, AN8520. Thus the strain comprises a deletion of SEQ ID NO:2.

The engineered *A. nidulans* strain comprises a deletion of the F9775 cluster which comprises a deletion of the following genes: AN7906, AN7907, AN7908, AN7909, AN12004, AN7911, AN7912, AN7913, AN7914, AN7915. Thus the strain comprises a deletion of SEQ ID NO:3.

The engineered *A. nidulans* strain comprises a deletion of the Monodictyphenone cluster which comprises a deletion of the following genes: AN10023, AN10044, AN10038, AN10035, AN10022, AN0150, AN0149, AN0148, AN0147, AN0146, AN10049, AN10021. Thus the strain comprises a deletion of SEQ ID NO:4.

The engineered *A. nidulans* strain comprises a deletion of the Emericellamide cluster which comprises the following deletions: part of AN2545 (which has been reannotated), all of: AN2546, AN2547, AN2548, AN2549. For AN2545 11 bp of the coding sequence was not deleted. Thus the deletion comprises a deletion of SEQ ID NO:5.

The engineered *A. nidulans* strain comprises a deletion of the Austinol/Dehydroaustinol cluster which comprises a deletion of the following genes: Genes deleted: AN9246, AN9247, AN9248, AN9249. The deletion thus comprises a deletion of SEQ ID NO:6.

The engineered *A. nidulans* strain comprises a deletion of the Asperfuranone cluster which comprises a deletion of the following genes: AN1036, AN11287, AN1035, AN1034, AN1033, AN1032, AN1030, AN1029. The deletion thus comprises a deletion of SEQ ID NO:7.

The engineered *A. nidulans* strain comprises a deletion of the Asperthecin cluster which comprises a deletion of the following genes: AN6000, AN6001, AN6002. The deletion thus comprises a deletion of SEQ ID NO:8.

The engineered *A. nidulans* strain comprises a deletion of the Austinol/Dehydroaustinol cluster which comprises a deletion of the following genes: AN8379, AN8381, AN11871, AN8382, AN8383, AN8384. Thus the deletion comprises a deletion of SEQ ID NO:9. The genotypes and deletions are summarized in Table 1.

TABLE 1

| Strain | Genotype |
| --- | --- |
| LO1362 | pyroA4, riboB2, pyrG89, nkuA::argB |
| LO8030 | pyroA4, riboB2, pyrG89, nkuA::argB, sterigmatocystin cluster (AN7804-AN7825)Δ, emericellamide cluster (AN2545-AN2549) Δ, asperfuranone cluster (AN1039-AN1029) Δ, monodictyphenone cluster (AN10023-AN10021) Δ, terrequinone cluster (AN8512-AN8520) Δ, austinol cluster part 1 (AN8379-AN8384) D, austinol cluster part 2 (AN9246-AN9259) Δ, F9775 cluster (AN7906-AN7915) Δ, asperthecin cluster (AN6000-AN6002) Δ. |
| LO8096 | AN7884 (atnA)::AfpyrG in LO8030 |
| LO9345 | AN6448::AfpyrG, AN8694::AfpyroA in LO8030 |
| LO9587~LO9590 | atnM::AfpyrG in LO8030 |
| LO9627~LO9630 | atnL::AfpyrG in LO8030 |
| LO9595~LO9597 | atnK::AfpyrG in LO8030 |
| LO9598~LO9599 | atnJ::AfpyrG in LO8030 |
| LO9601~LO9603 | atnI::AfpyrG in LO8030 |
| LO9604~LO9606 | atnH::AfpyrG in LO8030 |
| LO9608, LO9610 | atnG::AfpyrG in LO8030 |
| LO9591~LO9594 | atnF::AfpyrG in LO8030 |
| LO9611~LO9614 | atnE::AfpyrG in LO8030 |
| LO9615~LO9618 | atnD::AfpyrG in LO8030 |
| LO9619, LO9621, LO9622 | atnC::AfpyrG in LO8030 |
| LO9623~LO9626 | atnE::AfpyrG in LO8030 |

Note that since the deletions of entire gene clusters are novel, there is no standard nomenclature for them. However, for LO8030 we designate the deletions by indicating the genes deleted fully or in large measure followed by the Greek letter delta (Δ).
Note also that for the sterigmatocystin gene cluster, 34 bp of the coding sequence of AN7804 was not deleted and 661 bp of the coding sequence of AN7825 was not deleted (based on the most recent annotation as of the date of submission of this application. For the emericellamide gene cluster, 11 bp of the coding sequence of AN2545 was not deleted. For all the other clusters, the coding sequences of all the genes were deleted in their entirety.

Figure 2A:
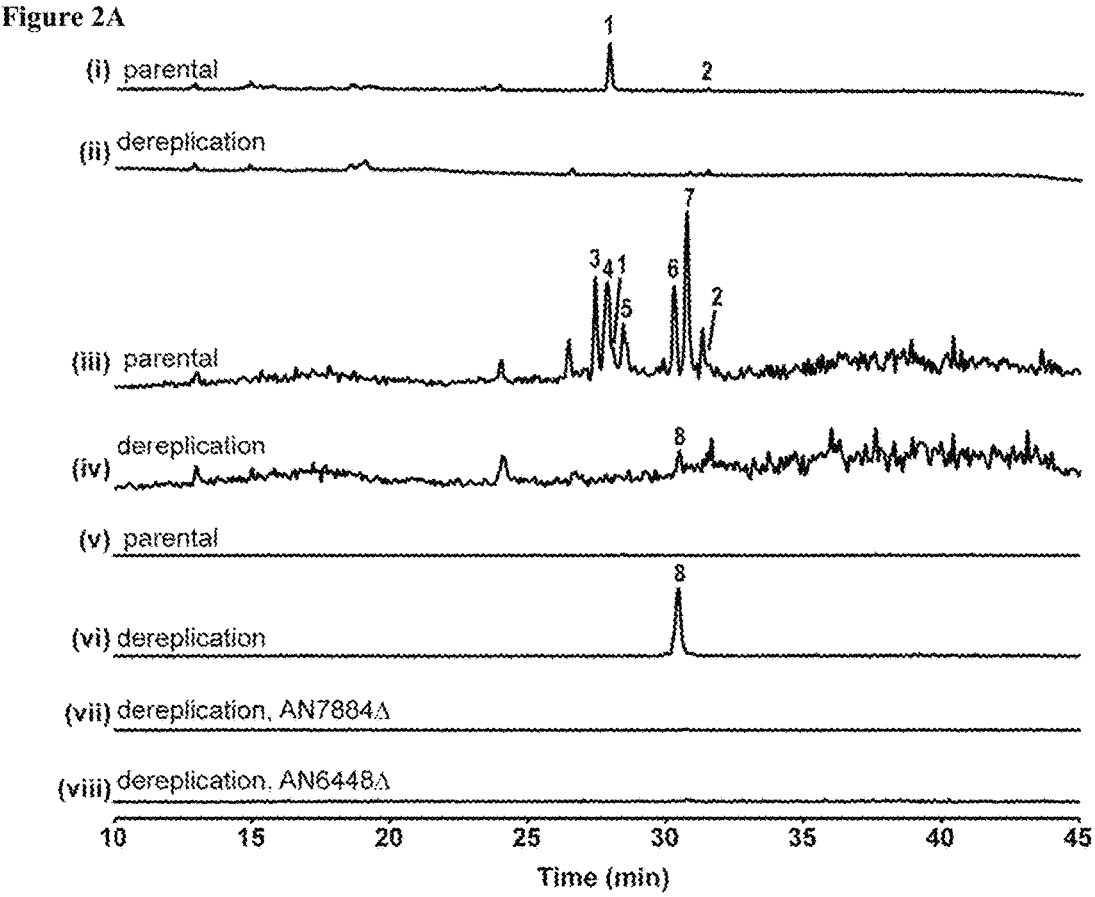
FIG. 2A. HPLC metabolic profiles of the parental and genetic dereplication strains. UV-Vis total scan from 200-600 nm (i, ii), total ion current (iii, iv), and extracted ion chromatogram at m/z 934 (v-viii). All strains were grown on glucose minimal medium plates. 1 is sterigmatocystin, 2 is terrequinone, 3-7 are emericellamide C, D, A, E, and F, respectively, 8 is aspercryptin.
Figure 2B:
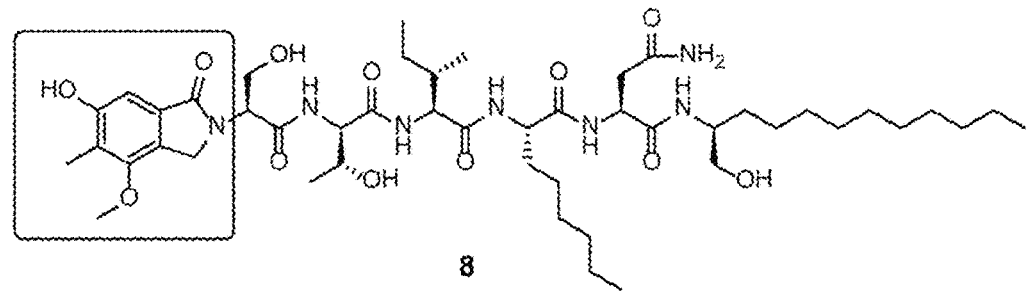
FIG. 2B. The chemical structure of aspercryptin (8). The box indicates the cichorine moiety. Strains: parental=LO1362; dereplication=LO8030; dereplication, AN7884Δ=LO8096; dereplication, AN6448Δ=LO9345. Genotypes are given in Table 1.

On glucose minimal medium (GMM) plates, sterigmatocystin (1) and the minor SMs terrequinone (2) and emericellamindes (3-7) were produced in a parental strain but were eliminated in LO8030 (FIG. 2A, trace i-iv). However, one MS (mass spectrometry) detectable peak (8, MW=933) was identified specifically in LO8030 albeit at low yield (FIG. 2A, trace v and vi). The molecular formula of 8 was predicted to be $C_{47}H_{79}N_7O_{12}$ based on its HRESIMS data, suggesting that 8 could be a metabolite biosynthesized by a non-ribosomal peptide synthetase (NRPS) pathway. The MS/MS fragment data of 8 indicated it contains several non-essential amino acids (see below). This is a common feature of metabolites produced from NRPS pathways since these mega-enzymes can incorporate unusual amino acids during the elongation steps. We were able to obtain 3.0 mg of 8 from a large-scale culture. Because of the large size and relatively low solubility of the compound, we took advantage of the high resolution and sensitivity of an 800 MHz spectrometer equipped with a cryoprobe to obtain NMR spectral data. From $^{13}C$-$^1H$ HSQC-TOCSY (Heteronuclear Single Quantum Coherence-Total Correlation Spectroscopy), six possible spin systems including threonine, isoleucine, aspartic acid/asparagine, serine, lysine-like, and an unknown spin system could be identified. Analysis of the $^1H$, $^{13}C$, 2D-NMR data and MS/MS fragment data revealed that compound 8 is a cichorine derived hexapeptide with 2-aminododecanol and 2-aminocaprylic acid residues as shown in FIG. 2B (for details of structure elucidation, see Supplemental Information). We named compound 8 aspercryptin.

The structure of aspercryptin indicates that it is an NRPS product. There is only one NRPS gene, AN7884, in the genome of *A. nidulans* containing six adenylate (A) domains.[11] Andersen et al.,[12] found that the genes AN7872 to AN7884 are co-regulated, suggesting that they may form an SM gene cluster. Bioinformatic analyses of genes in this cluster indicate that they encode a fatty acid synthase, aminotransferases, a P450 hydroxylase, a short chain dehydrogenase, and transporters, most of them reasonably predicted to be involved in the biosynthesis of aspercryptin (FIG. 3).

Figure 4:
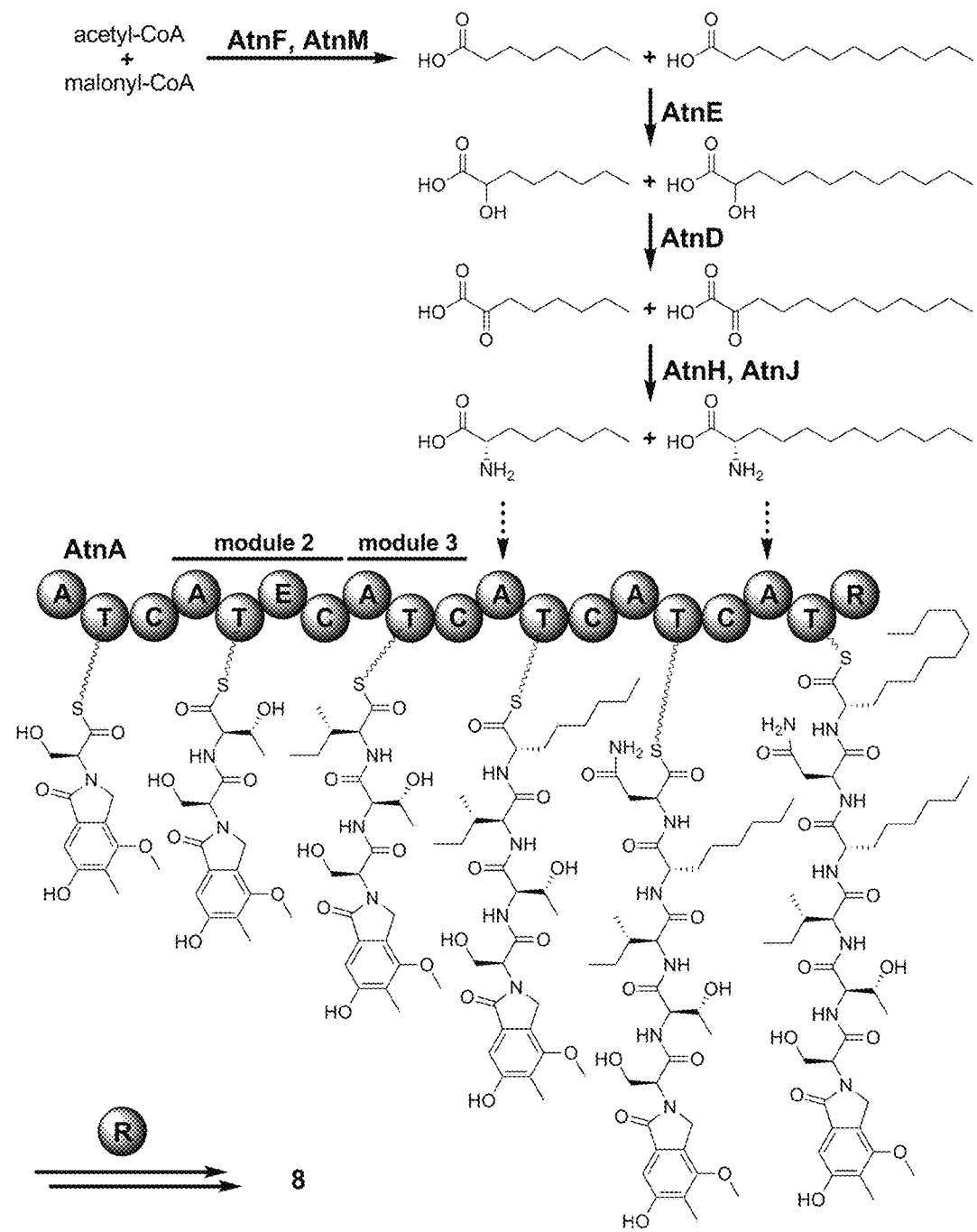
FIG. 4. Proposed biosynthesis pathway of aspercryptin (8).

To determine if this gene cluster encodes the aspercryptin biosynthetic pathway, we deleted the NRPS gene AN7884 and, indeed, deletion of AN7884 eliminated the production of aspercryptin (FIG. 2A, trace vii), indicating that aspercryptin is synthesized by the AN7884 cluster. We designate AN7884 as atnA and give the other genes of the cluster the designations shown in FIG. 3. Aspercryptin was found to be produced at a higher titer when LO8030 was grown on YAG (yeast extract, agar, and glucose) plates. In this condition, a new aspercryptin derivative 9 was identified, albeit at lower intensity than aspercryptin. The MW of compound 9 is 14 Da less than aspercryptin and the MS/MS fragment data indicated that 9 is aspercryptin with Ile replaced by Val. To gain insights into the functions of atn genes, we deleted 12 additional genes in the gene cluster (from atnB to atnM) and analyzed the metabolites produced on YAG plates. Deletion of the two fatty acid synthase genes, atnF and atnM, eliminated >99.5% of 8 indicating that the two FAS subunit genes are necessary for aspercryptin biosynthesis. The tiny amount of 8 detected in the FAS deletion strains suggests that fatty acids generated by other, endogenous FASs can be incorporated, albeit at a significantly lower rate. Deletion of the dehydrogenase (atnD) and cytochrome P450 (atnE) genes abolished 8. AtnD and AtnE are likely involved in the oxidation of the α carbon of the fatty acids. Deletion of the amino acid aminotransferase genes, atnJ and atnH, eliminated approximately ~70% and ~40% of 8, respectively, suggesting that AtnJ and AtnH might be able to compensate for each other but with less efficiency, or that other endogenous aminotransferases could partially compensate for their functions. Deletion of atnI, an RTA1 superfamily protein, eliminated >70% of 8. Deletion of three genes, an MFS transporter (atnC), an ABC transporter (atnG), and a thioesterase-like gene (atnL) did not alter the yield of 8 significantly. Interestingly, deletion of atnB and atnK, decreased the titer of 8 by greater than 80% but increased the titer of 9 more than six fold, suggesting that AtnB and AtnK might participate in the selection of Ile versus Val residue in module 3 of AtnA. Without AtnB or AtnK, the module 3 of AtnA prefers to incorporate Val and produces 9. Analysis of the deletion mutants allowed us to propose a biosynthetic pathway for aspercryptin (FIG. 4). The fatty acid synthase subunits (AtnF and AtnM), dehydrogenase (AtnD) and cytochrome P450 (AtnE) and amino acid transferases (AtnJ and AtnH) could be involved in the biosynthesis of two unusual amino acids, 2-aminocaprylic and 2-aminododecanoic acids, which are then activated and incorporated into the growing peptide chain by AtnA. Inspection of the domain architecture of AtnA revealed that the second module has an epimerise (E) domain, suggesting the second residue of 8 could be D-allo-Thr. Indeed, Marfey's analysis[13] showed that 8 does contain D-allo-Thr and the L form of the remaining amino acids. After condensation of the hexapeptide of 8, the C-terminal reductase (R) domain might be involved in the reductive release and production of the aldehyde hexapeptide.[14] Further reduction would generate 8.

Our proposed pathway postulates that aspercryptin synthesis uses chichorine-Ser as a precursor. Cichorine is a phytotoxin originally discovered as a natural product produced by members of the genus Alternaria. We have previously identified the cichorine biosynthetic cluster in *A. nidulans* and found that the non-reducing polyketide synthase AN6448 is essential for cichorine biosynthesis.[15] If cichorine-Ser produced by the cichorine pathway is the precursor of aspercryptin, deletion of AN6448 should eliminate aspercryptin production. We consequently, deleted AN6448 and found that production of aspercryptin is, indeed, eliminated (FIG. 2A, trace viii).

Our data demonstrate that genetic dereplication strains are valuable in discovering novel compounds from unknown biosynthesis pathways. The fact that the SM background is lowered dramatically may be particularly valuable in detecting compounds produced by heterologous expression of SM genes from other fungi and in searches for genes that regulate cryptic SM clusters. They may have an additional advantage in production of compounds or proteins for human and animal use because they are incapable of producing major toxic SMs such as sterigmatocystin (1). Our data also lead us to the fascinating conclusion that aspercryptin is made of building blocks from two distinct clusters that are physically separated in the genome, the AN6448 (cichorine) cluster and the atn cluster. They raise the interesting possibility that differential gene regulation could result in the production of cichorine or aspercryptin. This, in turn, raises the exciting possibility that *A. nidulans* (and by inference other fungi) may use differential regulation of SM gene cluster expression to expand their repertoire of natural products and tailor their SM arsenal to achieve maximum competitive advantage. Forseth et al. found that a somewhat similar situation occurs with the lna and lnb clusters in *Aspergillus flavus*.[16] These clusters are closely related to each other and contain homologus NRPS-like core biosynthetic genes. They are partially redundant in that when the lna NRPS-like gene (lnaA) is deleted, the lnb NRPS-like gene (lnbA) and perhaps other genes in the lnb cluster can modify intermediates produced by the lna cluster to produce two of the major products of the lna cluster, albeit in greatly reduced amounts. In addition, Forseth et al. also found evidence that intermediates of the lna biosynthetic pathway are modified by the lnb biosynthetic pathway. The situation with the cichorine and aspercryptin clusters differs from the lna and lnb situation in significant ways, however. The cichorine and aspercryptin clusters are not homologous and the core biosynthetic enzyme for the cichorine pathway is a PKS whereas the core biosynthetic gene for the aspercryptin cluster is an NRPS. The cichorine and aspercryptin pathways are not redundant. Rather they function in a serial fashion with the cichorine cluster able to produce an important metabolite on its own, and the atn cluster using that product to produce aspercryptin.

Deletion of entire SM clusters was carried out using established techniques and as described herein. Most clusters were deleted using the loop out recombination procedure based on the procedure of Takahashi et al.[17] Correct deletion of clusters was verified by diagnostic PCR amplifications using primers outside of the ends of the clusters. Atn cluster genes were deleted and deletions were verified by diagnostic PCR using the methods of Oakley et al.[18] Growth media and conditions, as well as extraction conditions, are detailed in the example below.

REFERENCES CITED

[1] N. P. Keller, et al., Nat Prod Rep 2012, 29, 351.
[2] Y. M. Chiang, C. E. Oakley, M. Ahuja, R. Entwistle, A. Schultz, S. L. Chang, C. T. Sung, C. C. C. Wang, B. R. Oakley, J. Am. Chem. Soc. 2013, 135, 7720.
[3] D. W. Brown, T. H. Adams, N. P. Keller, Proc Natl Acad Sci USA 1996, 93, 14873.
[4] Y. M. Chiang et al., Chem. Biol. 2008, 15, 527.
[5] Y. M. Chiang, E. Szewczyk, A. D. Davidson, N. Keller, B. R. Oakley, C. C. C. Wang, J. Am. Chem. Soc. 2009, 131, 2965.
[6] Y. M. Chiang, E. Szewczyk, A. D. Davidson, R. Entwistle, N. P. Keller, C. C. C. Wang, B. R. Oakley, Appl. Environ. Microbiol. 2010, 76, 2067.
[7] J. W. Bok, D. Hoffmeister, L. A. Maggio-Hall, R. Murillo, J. D. Glasner, N. P. Keller, Chem. Biol. 2006, 13, 31-37.
[8] J. F. Sanchez, Y. M. Chiang, E. Szewczyk, A. D. Davidson, M. Ahuja, C. E. Oakley, J. W. Bok, N. Keller, B. R. Oakley, C. C. C. Wang, Mol. Biosyst. 2010, 6, 587.
[9] E. Szewczyk, Y. M. Chiang, C. E. Oakley, A. D. Davidson, C. C. C. Wang, B. R. Oakley, Appl. Environ. Microbiol. 2008, 74, 7607.
[10] H. C. Lo, R. Entwistle, C. J. Guo, M. Ahuja, E. Szewczyk, J. H. Hung, Y. M. Chiang, B. R. Oakley, C. C. Wang, J. Am. Chem. Soc. 2012, 134, 4709.
[11] H. von Dohren, Fungal Genet Biol 2009, 46 Suppl 1, S45.
[12] M. R. Andersen et al., Proc. Natl. Acad. Sci. U.S.A. 2013, 110, E99.
[13] P. Marfey, Carlberg Res. Commun. 1984, 49, 591.
[14] N. Gaitatzis, B. Kunze, R. Milner, Proc Natl Acad Sci USA 2001, 98, 11136.; L. Du, L. Lou, Nat. Prod. Rep. 2010, 27, 255.
[15] J. F. Sanchez, R. Entwistle, D. Corcoran, B. R. Oakley, C. C. C. Wang, Med. Chem. Commun. 2012, 3, 997.
[16] R. R. Forseth, S. Amaike, D. Schwenk, K. J. Affeldt, D. Hoffmeister, F. C. Schroeder, N. P. Keller, Angew. Chem. Int. Ed. Engl. 2013, 52, 1590.
[17] T. Takahashi, F. J. Jin, M. Sunagawa, M. Machida, Y. Koyama, Appl. Environ. Microbiol. 2008, 74, 7684.
[18] C. E. Oakley, H. Edgerton-Morgan, B. R. Oakley, Methods Mol. Biol. 2012, 944, 143.

Example 2

This Example provides a description of materials and methods used to obtain the results described above.

Molecular Genetic Methods. Deletion of entire SM clusters was carried out as previously described.[1] Most clusters were deleted using the loop out recombination procedure.[2] Correct deletion of entire clusters was verified by diagnostic PCR amplifications using primers outside of the ends of the clusters.

Fermentation and HPLC-DAD-MS Analysis. For agar plate cultures, *A. nidulans* strains were incubated at 37° C. on GMM (10 g/L D-glucose, 6 g/L NaNO$_3$, 0.52 g/L KCl, 0.52 g/L MgSO$_4$.7H$_2$O, 1.52 g/L KH$_2$PO$_4$, 15 g/L agar, and 1 mL/L Hutner's trace element solution[3]) or YAG (5 g/L of yeast extract, 20 g/L of D-glucose, 15 g/L agar, and 1 mL/L Hutner's trace element solution plates which were supplemented with riboflavin (2.5 mg/L), pyridoxine (0.5 mg/L), or uracil (1 g/L) and uridine (10 mM) when necessary at $1.0 \times 10^7$ spores per 10-cm plate. After 5 days, three plugs (7-mm diameter) were cut out and transferred to a 7-ml screw-cap vial. The material was extracted with 3 mL of methanol followed by 3 mL of 1:1 dichloromethane-methanol, each with a 1-hr sonication. The extract was transferred to a clean vial and the solvent was evaporated to dryness by TurboVap LV (Caliper LifeSciences). The residues were re-dissolved in 0.3 mL of DMSO:MeOH (1:4) and 10 µL was injected for LC-DAD-MS analysis as described previously.[4] MS/MS was conducted with a normalized collision energy of 35 and isolation width of ±1.0 m/z.

Isolation of Aspercryptin (8). Aspercryptin was found to be produced at a higher titer when the producing strain was grown on YAG plates. For scaling up to isolate aspercryptin, 50 15-cm YAG plates (3 L of medium in total) inoculated with *A. nidulans* strain LO8030 were incubated for 5 days at 37° C. The agar was chopped into pieces and extracted with 2.5 L of MeOH and then with 2.5 L of 1:1 dichromethane-methanol, each with a 1-hr sonication. The extract was evaporated in vacuo to yield a residue, which was suspended in 1 L of dd-H$_2$O and partitioned with 1 L of ethyl acetate five times. After removing the solvent in vacuo, the total crude extract in the ethyl acetate layer (~900 mg) was applied to a reverse phase C18 gel column (COSMOSIL 75C18-OPN, 20×140 mm) and eluted with MeOH—H$_2$O mixtures of decreasing polarity (fraction A, 1:9, 250 ml; fraction B, 3:7, 250 ml; fraction C, 7:3, 250 ml; fraction D, 1:0, 100 ml). Fraction D (~300 mg) containing compound 8 was subjected to purification by semi-preparative reverse phase HPLC [Phenomenex Luna 5 µm C18 (2), 250×10 mm] and monitored by a PDA detector at 240 nm. The gradient system (5 ml/min) was MeCN (solvent B) in 5% MeCN/ H$_2$O (solvent A), both containing 0.05% trifluoroacetic acid (TFA), with the following gradient condition: 40 to 74% B from 0 to 17 min, 74 to 100% B from 17 to 20 min, maintained at 100% B from 20 to 22 min, 100 to 40% B from 22 to 23 min, and re-equilibration with 40% B from 23 to 27 min. 8 was eluted at 14.5 min and 3.0 mg of 8 were obtained from repeated semi-prep-HPLC.

Detailed Structure Elucidation of Aspercryptin (8). Of the six spin systems identified from $^{13}$C-$^{1}$H HSQC-TOCSY, threonine and isoleucine residues could be readily confirmed by the $^{1}$H-$^{13}$C one-bond (HMQC) and multiple-bond (HMBC) correlations. The aspartic acid/asparagine spin system was assigned to be an asparagine residue due to the long-range HMBC correlations between the γ-carbonyl ($\delta_C$ 171.55) and the two exchangeable amide protons ($\delta_H$ 7.31 and 6.85). Interestingly, there is no α proton to amide proton connection in the serine spin system. Instead, two carbons not belonging to the serine at $\delta_C$ 167.96 and 46.05 have long-range HMBC correlations to the α proton of the serine, suggesting an N,N-disubstituted serine residue in 8. Analyzing the $^{1}$H, $^{13}$C, HMQC, and HMBC NMR data further revealed that a cichorine moiety is attached to the serine residue. Moreover, the HMBC correlations between the amide protons and carbonyl carbons established the Ser-Thr-Ile tripeptide sequence. Subtraction of the molecular formula from the formula of cichorine-Ser-Thr-Ile tripeptide and asparagine residue revealed that 8 is a hexapeptide. The b-type fragments of the MS/MS data supports the cichorine-Ser-Thr-Ile tripeptide and asparagine moieties. It also revealed that the two remaining residues have molecular weights of 201 and 141 Da, and neither are proteinogenic amino acids. The lysine-like (141 Da) spin system has long-range correlations to the amide carbon of the isoleucine and the amide proton of the asparagine, indicating this residue is connected between Ile and Asn. The residue (201 Da) of the unknown spin system was assigned to be a 2-amino fatty alcohol based on the HMQC and $^{1}$H-$^{1}$H COSY correlations. The 2-amino proton correlated to the amide carbon of Asn in HMBC, establishing an amide bond connection between the Asn and the 2-amino fatty alcohol. Based on the molecular formula, all the hetero atoms have been assigned. The remaining unassigned carbons were CH$_2$ carbons and two terminal CH$_3$, indicating saturated linear carbon chains in both lysine-like and 2-amino fatty alcohol residues. Due to the overlapping of the CH$_2$ signals, the chemical shift of these residues could not be assigned precisely. However, since only 2-aminododecanol and 2-aminocaprylic acid residues can cause the neutral loss of 201 and 141 Da during MS/MS fragmentation, respectively, the structure can be assigned unambiguously as shown in FIG. 2B.

Stereochemistry Analysis of Aspercryptin (8). Marfey's analysis[5] was performed to establish the stereochemistry of aspercryptin. In brief, 0.2 mg of aspercryptin was hydrolysed in 200 μl of 6N HCl at 100° C. for 20 hr. The HCl solution was removed in vacuo after hydrolysis. To remove traces of HCl, the residue was resuspended in 500 μl of H$_2$O and dried by TurboVap LV (Caliper LifeSciences). The resulting hydrolysate was dissolved in 40 μl of H$_2$O and 80 μl of 1% FADD (1-fluoro-2,4-dinitrophenyl-5-L-alanine amide) in acetone and 16 μl of 1.0 M sodium bicarbonate were added. The reaction was incubated at 40° C. for 1 hr followed by neutralization with 8 μl of 2N HCl. The FADD derivative mixture was analyzed by HPLC-DAD-MS as described.[3] The retention times of the derivatives were compared to those of authentic derivatized standards of D- and L-forms of Ser, Thr, allo-Thr, Ile, Asn, Asp, as well as DL-2-aminocaprylic acid.

Spectral Data of Aspercryptin (8). NMR spectral data were collected on a Varian Mercury Plus 400 spectrometer at USC or on a Bruker Avance 800 MHz at the Bio-NMR Core Facility of the Del Shankel Structural Biology Center at the University of Kansas. High-resolution electrospray ionization mass spectrum was obtained on an Agilent 6210 time of flight LC-MS. Optical rotations were measured on a JASCO P-2000 digital polarimeter.

REFERENCES FOR THIS EXAMPLE

[1] Y. M. Chiang, C. E. Oakley, M. Ahuja, R. Entwistle, A. Schultz, S L Chang, C. T. Sung, C. C. C. Wang, B. R. Oakley, *J. Am. Chem. Soc.* 2013, 135, 7720.

[2] T. Takahashi, F. J. Jin, M. Sunagawa, M. Machida, Y. Koyama, *Appl. Environ. Microbiol.* 2008, 74, 7684.

[3] S. H. Hutner, L. Provasoli, A. Schatz, C. P. Haskins, *Proc. Am. Philos. Soc.* 1950, 94, 152.

[4] J. W. Bok et al., *Nat. Chem. Biol.* 2009, 5, 462.

[5] P. Marfey, *Carlberg Res. Commun.* 1984, 49, 591.

[6] R. Bhushan, H. Brückner, *Amino Acids* 2004, 27, 231.

While the invention has been described through specific embodiments, routine modifications will be apparent to those skilled in the art and such modifications are intended to be within the scope of the present invention.

What is claimed is:

1. A modified strain of *A. nidulans* comprising a deletion of a combination of gene clusters comprising the sequence of SEQ ID NO:8.

2. A method for making a compound comprising culturing the modified strain of *A. nidulans* of claim 1 in a growth media and separating the compound from the fungus and/or separating the compound from the growth media.

* * * * *

SEQUENCE LISTING

<160> NUMBER OF SEQ ID NOS: 9

<210> SEQ ID NO 1
<211> LENGTH: 51656
<212> TYPE: DNA
<213> ORGANISM: Aspergillus nidulans

<400> SEQUENCE: 1

| | | | | | |
|---|---|---|---|---|---|
| attgtttgga | agggtatgtc | ctttctcgag | ttgctttctc | agtatatcga | catcaccacc | 60 |
| aatagatttg | aacctattgt | acagttaggc | aggtcgcaga | aaatcaaaca | gaaacttacc | 120 |
| aaactgggtc | aatgttctct | aagcacagat | gtggcgacac | gtccgcttgc | tttccgcccg | 180 |
| ctctatcgag | catcgtccat | cccatcccca | gatgtgccca | tggattagca | tccgcgtagg | 240 |
| aaatctcaaa | gtcctcgtat | cgcggccgct | caatgacagc | ttggtagtgc | agagaggagc | 300 |
| cgggccagat | ggcgtttact | cggccggtct | cgttgttctt | gtaccctggt | gtttgatcag | 360 |
| tatattctaa | gaaagcttaa | gtaggagaaa | gaagaaagaa | aaaaaaaaga | atggtgctgc | 420 |

```
attcacaagt gctaacgtac agctgcgaca ttgatcactc caaactgtgt gcttcaccca      480
ctcctgtaca tgctcgttga agcggtccgt aatctgctgg cgaggcgccc aggcccggat      540
attctcgttc tgcatctttt tgaggaactg aatcgcatat tcagataccg aatgcagcgg      600
cgccatcaca ctaccgtttt gaatcggcca cgagggccca atgaaggtga gtagttggg       660 catatctggc acggccagac ccaggtatgc ttcgggattt gtcttccatt tatctcgcag      720
atcgacgccc cgtcggccga tgatgggaaa ttgcggacga tatgtattgt cgaatcctga      780
cgcacagacg atggtgtcga ccaatcgctc aatcccatca gcgccaacga tgccatcttc      840
agtgcagctg gctacggcag tgaaatgtac atcgacgttc gcctgctgaa tggcgtgcat      900
atacgggtct cctggtgtga tgcgacggca tccgaaacca aaagtcggcg tgaagccctt      960
ggccagtcta tcatctttga taatgctcgc catacgctgt cgaaagaagg ccgatgcgcc     1020
cttctgcgcc atagaatccc ggtagaaggc cccccacatg ccgtttactt ctgcctcgat     1080
actctttgta tgctcgacta gtgctgaagg attggacctg aattgcgcgc gctcggcctc     1140
gctgtagatt ttggttggcg cgccggtgtt tcctgcaagg actccaaacc acacacccgt     1200
ccgcacaaag atatcgagat gaccgacatg aggttgtatc ccagccacgg cctggatgga     1260
agaagcacca gagccaatta cggcgacgcg atcgctgttc cactgcacct cgccatagtc     1320
gtcaggccaa gctgccgtgt gaataacgcg gcccttgaag cgatcgtgga gtccaggcgt     1380
atctggccac tgcagcaatc agatatggac caaagaaccc agcctagtcg cgcacctttg     1440
gattactcaa gaccccacat gcattcagca gtatatggca atggtcgtcg aactcttccg     1500
gttcctgtcc tggccgctgt cgccggagac gtaccttcca ctgcccttcc tcttcgttcc     1560
agcaggcttt gatgacctct gttcggaact gcatgtactg tcgtaatttg aaggctgcac     1620
aaactttgtc tagatactcc cagatatccg acgcgtagga gaagtaacga ggccaatcgg     1680
ggtacttgca agccaagtca gatggactct atgtatatca acagacagga atacaaacaa     1740
gtgcaaaccg atacgtatac gcatgactgg gaacatcaca gcctgcatta gggtaacgat     1800
ttgtgagcca agtgcctgcg cgtaattaga ctcatccaca tatgggagtg ggaggaggca     1860
tacctccaat atcatgattc ttctcgtaca ccacatgttc gatatttgcg cattgcttct     1920
ggatttgata cgccatcaaa attccagaaa agccagctcc aatggtaatc acccgcaggc     1980
gacggttgtt agggtccatc catgttgtat gttgcgggat gctataccgt gactcttgag     2040
gctctgggcc ttcgtgaaca tagtgcacag tcattgcggg gggtattgtg tgctgtatgg     2100
tctaaaacgg atatgaatcg cctttagata tcccaatgtt catataatgg acacattata     2160
gtcagggttc ggccagcgag tcggttaatc gcatgccgag cattgcatga caggttggca     2220
gagcggggtc catggctata agtgcgtgtc ttgacggttc aacaactgct caacagcatc     2280
atatctgtac tcagcaagaa caatatggca gcccctccag cacctcagcc tccaagtctg     2340
ctcggctacc accgggttct ctcgcccttg gccggaatcc gcgtctcccc gctctgcctg     2400
ggcactatgc atttcggcgg gcaatggacg cgggcaatgg gcgatgtgac caaagaaacg     2460
gcgtttgccc tcctcgaccg gttctacgaa gccggcggga acttcatcga cacggcgaat     2520
ttctaccagg gtgagggcag cgagaagtgg ctcgggagt gggtggcatc gcgcgggaac      2580
cgcgacgagc tcgtcctcgc gaccaagtac acgatgtcct acagactgac agggcccgag     2640
aagatcaagt ctaatttcca gggcagccac tcgaagagtc tccgtctgtc ggtcgaggct     2700
agtctggcta agctccgcac ggactatatc gatctgctgt atgtgcatat gtgggatttc     2760
```

```
tctacgagcg tcgaagaggt catgcagtcg ctgcaccatc ttgttgccgc aggcaaggtg      2820
ctcaatattg ggatcagtga tgccccggcg tgggttgtcg ccaagtgcaa tgagtgtatg      2880
ctcctgaatg acccttatgt aatacctcgc tgaccgagcc agacgcacgg tttcacggcc      2940
tcactcgctt ctgtgtctac caaggccgct gggcatgttc ctaccgcgac tttgagcgcg      3000
agatccttcc tatgtgccag tctgaagggc ttgcgctcgc accctggggt gctctcggcc      3060
gcggccagta caagtcggcc gaagagttcc agcaagaagg gacgcggaac atgggccccc      3120
aggaagagaa gcaccggctg atgggcgcaa agctgaccga ggttggggag cgcaaaggcg      3180
tggccgcggc tgcgattgcg ctcgcatacc tgcttcacaa gtcgccgtac gttttcccgg      3240
tgatcgggtg ccggacggtc gagcagctgg aggcgaatat tacgagcctc ggtgtagagc      3300
tcagtgatga ggaaatctac gagattgaag acacgatccc ttttgatgtc ggcttcccca      3360
tggcgttctt attcgaatcg ccccagcaga agtaccgtag tgatatgacg accaggcata      3420
tctggcaggt tacctgcaat gcccggatcg agagtgtgcc taagccgaga gtatgtatct      3480
ctcaacctga atttatgatt tcgctaatcg aatttaccag cctatcgagc caaagcaggg      3540
gtacaagcag atggatcgga agtagttctc ggtagcatta ccaagcatc gggtcccgag       3600 cgttcaagta ttttatatat gagccttgtt tccttcctat gtcatggtag ccagtatcca      3660
taaggtatag gaatcaacca tgtcctcctc cgataattac cgtctcgatg gaaaagtcgc      3720
tctggtaact ggggctggcc gcggcatcgg agcagccatc gccgtagccc tcggtcagcg      3780
cggcgcgaag gtcgtcgtca actacgctaa ctcccgtgag gccgcagaaa ggtcgtcga       3840 cgaaatcaag tcgaacggct cagacgccat ttccattcaa gccgatgtcg gtgaccctga      3900
tgccgtcacc aaactgatgg atcaggccgt tgagcacttc ggatacctgg atatagtctc      3960
atctaacgcg ggaattgtct cgttcggca tgtcaaggac gttacgccag atgtatgcgt       4020
cccatctcct tacgaaagtc ctgtagagct ctgacctcag caggaattcg accgagtatt      4080
tcgggtcaac acgcgcggac agtttttcgt cgcccgcgag gcgtatcgcc atctgcgtga      4140
aggcggacgc atcatcctca caagttccaa cacagccagc gtcaaaggcg tccccaggca     4200
cgctgtgtac tcgggctcta aggggcgat tgacaccttt gtgcggtgcc tagctatcga      4260
ctgcggcgac aagaagatca cggtcaacgc ggtcgctccc ggcgccatca agaccgatat      4320
gtttctatcc gtgtcgcgag agtatatccc caatggggag acttttactg atgagcaggt      4380
ggatgaggta cgtttgtctt tgtgtctagt atctacggcg gctgctaact ggacagtgtg      4440
ccgcgtggct gtcgccgcta aatcgggtcg gattaccggt tgacgtggcc cgggtggtca      4500
gctttctagc ttcagatgcg gccgaatgga tcagtggaaa gattattggc gttgatgggg      4560 gggccttag ataagtcaca tcatatactt gaactatata gggtagacat gcaatgttcg       4620
ctccccgctc gcttaccgat atctgccgat catcgtcagc aaccattagg tcacgaaaaa      4680
aagagtatac taagagtaaa catccgtgca tggtatgaac ttagttgggt acaccgcagt      4740
tagtcacacc gtacttaagt acactcagcg attcacttag gcggctgaat cggcatttca      4800
tactctgcca gcaccggagg cccagcaaca tcaacaacaa taggcaaagc atgcacacgc      4860
tcaaaccagg tagataggtt gcggtgctca tccctccagc gtttatcaag gaaaaaccgg      4920
aatgcgccct gcacaatccc gagcacaaac agatcagcta ggctgagggt tccccgacc      4980 aagtactctc gcccacaaag atggttgtca agaatcttta gccgtgctaa agtgtcatct      5040
ttgctttgat atatgttgtc agcattgaag ttggctcgtc cgatgagcgg gttgaaccag      5100 cccccctaacg ctgggaggat ttcggtgatc ccgaaggcca tccagcgaat gatggaggca     5160
```

-continued

```
tattcttgtc cggtagtccc aagtaaagtc gtatttgaat cttgagatgt tactatacct   5220
cttagtcagg aattgaatag atggaattgc agtagcagca tggtaccata gagagcaata   5280
gcaatagatt ccgtcaatac gtagccgtcg gcccccacaa acgtaggaat cttgcctaga   5340
gggttgagct ggagatactc ttcggtagca tctttgaatg aagtgatggt cttgattttc   5400
agaggcaaat tgttcgcttt tgcaatcgca agaatcgcca gcgaccgcgg gttgaacggg   5460
cgagtgtaca gagtgccgaa cggcattgca gaaatattct caattcagag ctgattctcg   5520
tattgtatgc ttgtggcaac ctgctaaata caaatactga cagcaaatca actatatgtc   5580
aagaccatgc ccttcagctg tccgcgtaac cctaacttcc cccaggacaa cggccttcat   5640
ctttccccga tccgtgaaac ggtcctcgtc cgccataact tcgggctgc tcatgacggg    5700
gacaaactcc tcgaaggtgg cttggctcgc aaattggaca acagcaaatg cgtcgaaggt   5760
caaatcgatc gagtcgccgg ccagcggggt gaccggttgc tgcaggtagt gtcgggtgtg   5820
gctgactgga aaggccctcc cgccgagtcg ttgcagcagg gggatatgtt cggtctccca   5880
gtggttacga aattcgctgg gtgtgaggtc gccgcgacgg gctacaagaa tcaagacagt   5940
gaacatggtg gagtgaaagt gctgtgtatg tttgtccaca cttgcttcca gaatctcgcg   6000
caatacgcct ctatatatgg cctgtcccta tctcggtcgc cgaacgaact aaacaattat   6060
tcagagagac tcttcttaca ttttttgtcat tgttgccaaa gtcacttcac tcattgctgt   6120
cctccaacca tgtacacaac tatcatcaca gcggtatgcg tgctattcgc tcttcacctc   6180
ctggacagct tctatcaagc ccggcaggag gtatgggccc tccagcgggc aaacctagta   6240
cgagccctct gacccaatga ttggctagag gacgattaac tggtgataca agcccatgcc   6300
ttctttcagc ctgctgaccg gccactttgg tgccctcaaa caaaccatcg atggcatgcc   6360
gcccaacgca accctgcata gcattatgct gaaattgtcg caaaagttcc gctcagggat   6420
gttctacatc aacatgtggc cattcagcgg tacatggcta gtggtcgcaa caccgtctgg   6480
cgcggcccag atccagagtc tgaatctttc gaagccgaac atcctgcgaa accgctgga    6540
gactatcacc gggggcccaa gcttgatgag tatgcatggt gaaacatgga acggtggag    6600
ggcactgttt aatccaggct ttaaccccaa ctacttgatt gggctggcgc cgctgatcgc   6660
cgatgaggtc gttgttttt gcgagcagct acggcagaag gccagaacag gaacagtttt    6720
ccagcttgaa ccgctcactc tgaggttgac agttgatacg atttgctctg tgacgttgta   6780
tgtggttact cccgttgggc gatggcccctt tctaacccct gacttagaga ttcacagctc   6840
caccaccaaa ctcaggacca cccccttgcc tcagcgctgc aacggcagat cgaatgggcc   6900
tcgtttggaa ctaccttcaa ccccttttaag cggtacctga ccgtgcggcc tctggtgatg   6960
tggtacaata accgcttat gaaccgcttc atcgaccaag aggttgaccg agcgtaccgg    7020
gagcagtctg gccgtcagtc gaaatccgtg atctccctcg ccctcagaga ttacatgaaa   7080
gagaaagatg gaagtctgga gacttcaaa cgacgtgttg cgccacagtt acgggtcttt    7140
ctcttcgcag gtagagatac aacgagcagt acactgctct atgcattcta cctgctttcc   7200
cgacatccag aggccctagc taaggtgcgc ttagagcacg accaggtctt cggcccatat   7260
catcaacaag tacacgagaa atccaccaa gatgcgaaac tcctcaacca actcccctac     7320
acaacagctg tccttaaaga gactctgagg ctcttccctc cgtctgcctc catgcgtgaa   7380
ggccgtcccg gcgttgaaat caccgacgac aacggccaag tatatcccac tgcagggtgc   7440
aacgtctgga cgctcaccgt ggcactgcac cacaacagtg cgcactgggc tgaagccgag   7500
```

-continued

```
tcatttatcc ccgaacggtg gctcgtggga tctgaccatc cgctgtaccc agccaaaggc    7560
gcatggaggg ccttcgagtt cggcccgcgg agttgtatcg ggcagacgct ggcaatgttg    7620
gagctgcggg ttgcactagc gatgacgctc cgcgagtttg atattgcacc ggcgtatgat    7680
aagtgggatc acatttatcc aaatgacgcc gtcaaggagt tcaatgggca tcgggcatat    7740
caggcagaaa agggggaggg gggtgcgcat ccggcagatg ggatgccctg tctggttaca    7800
tttcgggtgt aaagtatata gtaaagaatt attgaatacg tgaataatga cataactgga    7860 cttttctctaa gaagacctgc tgatggtgtt agtttcgaca ttctcttttg tttgtagatg    7920 tctaaccccca tggttgcatg ctgatacagg agcctcgatg gtaaggagac gacgagaatc    7980
tatacgaggc gccgagaggt agatcagggt aatgcatctg atactttgat atgcacttca    8040
atctccgtaa gaaaaagta tcagttaact ctaatccata tttaccaatc ttgctgcaac     8100
attgcccatc ccaggcttat caggaaactc atcccaggcc ccctcgacgc cgcaccaacg    8160
cacccatctt accatgacgc gaatgatctc ttcgtcctgg cgcatctctt cccctacctt    8220
cttccgaatg ctctccggaa ccttatactg ctccggtcca agcatccttt ctacagaatc    8280
aagacccata tgcgcaactt tgataaaatc ctccttccgc agtggaaatt ccggacgcgg    8340
gtcagggagg ccttgggcat ggaggagagc ccgtgtcacc ttcgaaatat ggccgtcgtc    8400
gccgtagatc gacgcgcgat gcgctagctc catccatcca tcagctggtc gcttgggcgt    8460 ataccggta atgcggtctg cgtagagggt aggacatcca cagcctgcat acgtcacaag    8520
atcgccccaa actttaaaat gcaggagccg agctttattc gacggtgaga tccagtcttg    8580
cgccaggaaa gtcgtgtaga agatggagag ggtgagcgta tgcaacatga caaagtccaa    8640
tgcttcgact ttgccagggc tctgggctgc acccaccatg tatgcgcagg tgtgcaccat    8700
atctgttgtc tgctgtgcca gctcctcttc cgtgggactg acgcagtact gagcgagata    8760
cggaatgagc ttgtcacgga ccttggccag cagcccgtca ctgattttat ttatcggatc    8820
tgtcagctgc actgcgttgc ggatgactgg gtcactatgt agttcatcca tgatgtctag    8880
catcgacttg aacggcgcct tcgaatgggc agtctgcatc tcctcggttg gaacaaaaa     8940 cgaattgggc cagtcatcgt gcacgcaacc ggctgcgagt gcttctgcta tgagcagggg    9000
ctgattgaac tccagcgcgc atccgagatg gatcatcggg tgaagaaaac ctgcctctca    9060
ttgagcgaaa gattaccact cgaggaggtt acctaccaga gtgcatgcgg cccaggacat    9120
cattggaaat ctcatcattc gcgaacaaat actcgttgat gacatcaggc acgcctctct    9180
gcgcaatctc gtcctggaag tagcgcagaa agctgtcgta gtagctgagg tcgccaatac    9240
actgcttaaa gaaggtgcgg tctttcagct gcacgacgac tgaggctgga cggtactgaa    9300
cgagtgactg ataccaaatg ttgaggtcat acatggcccg gatctcctct ggggtggctc    9360
ccagggcaaa cagggtgagc aggtggtgga cggtgtgatc tgtacaggtt cagggtctgc    9420
acttttccag atgattccac ttactatgga agcccaccgc atcaaagagg gtatgatagc    9480
gggcatagtt gatcatcagc aactcagaga cgcggtctgc gctctgctgc gtcaagccat    9540
ctacatgcgt gttcccgggt gtcccatcgg ccgacagctg gatgttgtac ggaccgctct    9600
ggggcctcgt tgggcctagg gttgtggagg tgaacatggc tactgcatgc cattctattc    9660
tggatcacaa tgtgccaata tttgtgatgt aatactagcc ccgaacccg aagcacggtg     9720 aggctcgctg agcgaagcca aaatcttaca ttaagtccag atcttggtgg tgcaaatacc    9780
ctcacagaac caaacaatgc cttcctatgc ggttctgggg gctacgggta atactggacg    9840
ggcgatcgtc caggtactac ttgatcgagc agacaccgac accagaattc acatctgcgc    9900
```

```
ctactgtcgc tccaaggaaa agctcttccg tgtctgtccg gcggccgaga cttcgaaaag    9960
cctttcagtc tttcaaggac ggctggatga tgatagcctc atcgatgaat gtctcagggg   10020
caccgatgcc gtgtttctgg tagtcgccat tgtcgacaac atgcctggct gtacggtggc   10080
catgcagact gccgaggcgg ttgtagcgtc tttgcaacgg cttcgcgcta cagaccctgc   10140
aatacgtctt ccgcgactag tgattctttc gtcggcctcc ctggagccca cgttctgcaa   10200
cgatgttccc gccccggtgc actgggtcct caaaactgcc gtctcccatc tttaccgcga   10260
cctcgccgct gccgaagcat acctccgcgc ccaatccgac tggctctcgg cgacctttgt   10320
caagcccggg gggcttgtac acgaccaggc ccgcggtcac aaggtctgtc tcgaccgggc   10380
tcaaaccccg ctctcatttc tcgacttggc tgcgggcatg gtcgaggtgg ccgacgcgga   10440
tgatggccga taccatatgc gcagtgtgag tgtggtgccg cgtcaaggg ttgcaatatt    10500
tccatgggac ggcgtttact atacgtttac gggcttgctg tttcattttt gcccgtggac   10560
ttaccggttt cttggtgaat ataagttgca gtcgagaaag gagagggaca agcaagctta   10620
ggcagactcc atatttcacc gttctccgta cttattactt cccatttcg gaggtgaaac    10680
tatttactct tgtctgatct atctatgcat attctaagcc ggttcacctc tctgtagcat   10740
ccatacattt atcgctggtg ttggttgttg actgcacgtt tatcaataat atggacgcca   10800
tcttcaagca aatcaaagat gagtacgccc gtgccgacga gcatggcaag cgagagattc   10860
aaggctatat ccgcgagttg caggttggct tctattcgga ttgggatgtg gtgatgcggt   10920
tgagcagtgg tgtatgttcc ctccttacta tccacttcag ctaccgacag tgtgtagccc   10980
ttgcaagttg cacttgccaa aatcgccatc gacctggacc ttttccgcac cctcaaggag   11040
agtgaagctc cgctatctct ggcacagttg gcagagaaga cggggggcttc ccccaagctg   11100
cttggtaagt atgcagcgtt ggctatgttg gattgccctc actaagtcac aacagggcgc   11160
attctccgca cgcaggctgc atttggcctc atcaaggaga ctgggcccca ggaatacact   11220
tcgagtgcat tcactgatgt ctttttccaac cccgatgctg ctggtgccat tgcacagctg   11280
tatgtctcat tcctccacgt caaaggcaca gtaataaatt tcttctcaga ttcgacatct   11340
ccggcccttg cactcagctt ctgcccgact acctcgcgga gactgggtat caggagatcg   11400
tctccaacaa agaatgcccc ttccaaaagg cgtttcacac cagccagacc ctatttgaat   11460
ggatgcccca gcacccaaag cacatgaagt ctctcggcca cttaatgcc cttcaacggc    11520
ccacggtctg ggttgaccac tttcctgttc tcgagcagct aggcgagttc cctaacccag   11580
acaaaacact catggtcgat atcggcgcg gcttcgggca gcaatccaaa cgctccgtt     11640
ccagatgccc caatgttgaa ggcaaaatca ttgtccagga catgcctcag acgctagcca   11700
gcgctgagcc agcagaaggc gtagaattct ccgaacacga tttcttccag ccgcagcccg   11760
taaaggggc caaattctac tatctccgcc acgtccttca cgactggccc gacgagcagt    11820
gtgttcaaat cctgcagcag gtcattccgg ctatggcacc tgagtcgcgc attctgattg   11880
acgaagtggt aatcccggtg accggagtgc catggcaggc agcgtttatg gacttgctga   11940
tgatggagtc gtttgcgagt atcgagcgca cgcgagcaga atgggaggcc ttaatggaca   12000
aggctgggct gaagattatc gaggagtatt actatgatgg gaaggagcag gccatactgg   12060
tggttatacc gaagtaaatt attgtacttc tactttaggg tagaatggag tctcaaaccc   12120
tccgtgacaa atttaaccaa gaaattgaga atatatattt atacctgcat aattcctgca   12180
ccttctctat acattctatc ctaatcctac atcaggatgc cttcgtacgc ccttctagga   12240
```

```
gccaccggcg ctactggatc cagtgtactt cgccatctgc tttactcagg ctcgtccagt   12300
gacctcacag tgaatgtcct ggttcgctcc aagtccaaac tgctggctgc ctttcccagc   12360
ctcgacaagc ctcgaccatc cgtgacgtcg tccatcccga cgatccgcat tttcgaagga   12420
gactctacca atcccgatgt actttgcgcg gttctccaag acgctagcct cgtgttcatg   12480
tgcgtcgcgc agaacggcag tccaatgggg acaaccctag tgcagaacac ggccgccgcg   12540
ctgattgagg cccgacgccg acaggcacag ccacgcggtg agctaacggt catccagctt   12600
cggtcggcgt cattgaaccc cgtgcttgcg gttcaagtgc cgcgatttgt gcatcgcgtt   12660
gtttgctttt gcttggctgc tggctatgcg gatctccgac gagcatgtgt cctctatgaa   12720
gcagcggcga cagaggggct gttgcaatat gtgcttgtag acccgccgac tctgcatgat   12780
gcgcggggta cgcagacaac tggttacagg ttaattgata ccactgacat gaaggacaaa   12840
gaaaaccaga ggcaggcgat ttgtctgagc tatgctgatc taggggttgc catgtgtgag   12900
attgccagcc gtgcggatga gctgcatgga caaggtgtag gggtgaccgc cactggccca   12960
gtcaggcaga cctgggcagt gttggctggg ttcttgctag agggaggact gggacatctg   13020
gactacagat atggcagaga aaatgttgta gtccttgggg tttgtatttt gttgctgctt   13080
gggggtctgc tatatagtat caaagcctag gtggacaata ttactgctag tcgctcattt   13140
ggtctcaatt ccagcaata atatcagcgg caaccttctc tgctaatgca tagacagtcg   13200
ccatgggctg gccgtcaatt gcaaacggaa atgcagacgc gtcgacaact ctgagtcctt   13260
taacgcccct aaccgttgcc tttgagtcga gcaccgcaag cggatcatcc ggttttccca   13320
tggcacatgt gccgactccc gcatagtacg cgtccgaagt ctcggcgatg tagtttagga   13380
tctcctcgtc ggtctgatac tcgaaccccg gcagcagctc gggtccgtca atgacttgct   13440
gcatcgtctc tgaggcgaca atctcgcggc atcggcgaaa cgctgccaca gccatctcct   13500
tgtcgcgcgg gtcgtccagc caccgcgggt ccacgacggg gttgtcggcc gtgttggtgg   13560
tgttgatggt gacggtgccc cggctaaacg tggccagcag cgcagccgac atactgaagt   13620
agttcttgcc gtcatactga ggcacaaatg tgtcatccag cgcaatatat gagaaggtcg   13680
gccaatcagc cggaaaggcc ttgtcgatat cggcagcagt cgcctcgcta aggttttcctg   13740 gctggtgctt ttcgaaggca aagtagtctt gccccgggtt ggtgagcaag cctgtgcgga   13800
agttgttgta ttcgtagatc gagcgaggaa gagtctccett gctgcccatc aactggctgt   13860
ggctctcgac tttcacaggg ttcgtggggc ccaggatgat ggtgtcctgc atgttctgcc   13920
cgacgccagg gagatcagac aggacgggaa tgtccagctt ctcgagtgtc tctctagggc   13980
caagcccaga gaccatcagc agctgaggag atctcattac tcctgccgac aggatgactt   14040 cctttctttgc gccaatctgc cactcgaacc cgccggtatt gacaacgacg cctgtcgctc   14100
gcttctcctc gtcaaagtcg atcttcttca ccagagtatg tgtaatcaca ttcagactat   14160
tactcgtccg aagggccgtc tgcaagtacg aggtagacgc agtatcccgt cgacgagtct   14220
taggatgaat agtatgcgtg atgtatgagc ggcccagcag ctggccgttg gagaatccct   14280
gggcttcagg aaaccccatc ttttcgaggg ccttgtctac ccacgacgaa atggcgttcg   14340
taaggtacgg atacgcaacc tggacgggcc cctcttcttc tgcagttgct gcaaatgctg   14400
agacgtcatt cgaggccgtt gcgttggcgg ggcgagggtt cgtcagtggg cctgagaact   14460
gcacgctttt cttgaagaaa ggcagccaat gtcccaagt gtagctgtcg tcgcctactc   14520
ggtcagccca gagttgatat gcgccttttg agccctgtc tttgttagcc tgtgattatc   14580
aggatttgag gagagatacc gatgatataa catggctcca cgtgcagtcg agccaccaag   14640
```

```
ggttttgcct tgcatgtaga acatttttcg accggccagc ccctgaaact gtaagcatct    14700
gagctatctc gattgtcggg taagcatact ggctgggctt cggtatattg gtaccagtca    14760
aacagcgggt tcttgacatg gccgttgtca aaaagtagt tgaacaggaa cattggcact    14820
tcagtggcat tccctgcctc aatttcgtag aatcctccgg cctcaataac cgcaacagag    14880
ttgctaccgt cctctgacag ccgatgggcc attgctaggc cggctgtgcc gccgccaaca    14940
atcacatagt cgaaggtttg gcccggccac ccgtaccagc caaagtgaga gctgaggagg    15000
ccacggcctt ggatgcggcc gtccattgct gcttcatgct gctcagcggc ggtgccaaaa    15060
agggtctccc atggtgagga gaagaaggtc gtttgaccgg cgaacatacc caccactggg    15120
agggcggaga ggacgaggag ggaccaggcg ggcatagtga cgatggtctg tctgatggtg    15180
ctcgtctgta gcttaggctc tcgcgaagtt aataaaccgg ccaccacgta ccaatacttc    15240
ggcacatggc ggagccctca ccgatcgctt gccgagaccc atgtaggcgt cggtataaga    15300
cgagaaaaag agacctggca gatacccccaa gcataagttc atactcctgg aactcttcaa    15360
aaccatgagt aacgctggag tggaagccat agccgttatc accggcactt tcctgtccgg    15420
taatgctgcc acgtcccttg ccggccgcct aactaatgcc accaggtgca atgatgagcg    15480
tctacctcct agcggtcccg tccctcttcg aaacaacaag tagtcctgac cagctcgtcc    15540
gccactggag ccggatctac ctcaacgggc acataaaagg ccccatcatc tgcctaagca    15600
caaccgcgtt gtacggactg gcggctgcga ctaagtactc ggccggcgag gactggggcg    15660
tcttcgctgc cgcgggcgct atcaccatta gcatggtccc atttacgctg acggtgatgg    15720
cgccaaccaa caacgcgctt ttccggctag aggggggaagt caagaaggga catacccccgg    15780 tatggtcaga tgcagagcgt ctagtccgca ggtggaaccg attcaatgca actcgggcct    15840
tttgcccatt agttggggct gttttagggc tgttgggagt tctgaagatt gtttcgttct    15900
agctgaatgt acatagggct gcccggtggc cgaggacggg ttatacttgc ttggaaatga    15960
ggctggtcaa tcaacctatg gctgactcta tcgtaaatcc gtcgctctcc gacatatcag    16020
aggacctaga aaagtcccac aatagtcctt ttacgatgcc atgcttaggt ccatggtcta    16080
gcaggatggc tttcctatcc cttcctatcc taacagcgct cggcgcagtc gtttacgtgc    16140
tcttccaact cgtgtacaac ctctacttcc acccactacg cgactatccc ggtcctctgc    16200 tatgcgagc cagctctctt ccttggaaac tgacctcct tcgcggcaca atgcatcacg    16260
acctgatgcg ccaccaccag acgtacggcg atactgtgcg cataaagcct gacgagatta    16320
gctacgcaaa tggccaggcc tggcgcgaca tccacgccca cgtacctggg cgcccagaat    16380
tcctcaaaga ccctgtccgc ctgccactgg ctccaaacgg ggttatgagc attctcgtct    16440
ctgacactcg caaccacgcc cggttccgga gtctgttcgg ccacgctttt agtgacaagg    16500
ggcttcgcgc gcaggagccc acgattgccc gctatgctga tttactggtc gaagtcctcc    16560
gcgaggttgc cgatactggc aagtcagtcg agatggtccg ttatttcaac atggcgatct    16620 tgactccat tggcgcgctc tcatttgggg aatccttcga cagcctcagg aaccgcgagc    16680
tccacccgtg ggtagacacg atccacaaga atctcaaaag tgtcgccatc tcacacgttc    16740
tccgcagcat gggcgtcgag ttcctggccc cctatctaat gccggccgag ctgcgcggca    16800
agcgacaaga gaactacaca tatgccatag aaaaactcaa gaaacgtatg caaaagacgg    16860
gtgatcaggg cgacttctgg gaccgggtaa tcgtcaaaag tgccgacggg aaccaatcag    16920
gagatggaat gagctatggc gagatgatca acaacgcggc ggtcatggtg gtcgcccggt    16980
```

```
ctgagacgac ctcgtcggcg ctatgcggct gcacgtatct actctgcaaa tttgataaga    17040
tggacaaggc tgtcgccgag gttcggggcg cattcgcggc cgccgaccag atcgacctgg    17100
tctctgtctc tcggttgccg tacctgacgg ccgtcatcga cgaaaccttg cgcatgtacc    17160
cctcggtccc tggacagccg cccagagtgg tgccagaggg cggagcaata gtatgcggac    17220
ggttcgttcc tgctgaggtg tgtatcatat aacctaaccg tttagtttcc tgattgccgt    17280
ggctaacaag cagcggcctc tagacccgcg tcggtgtcag ccacctgggc gcttactacg    17340
cgccatacaa cttcagccat gcggacaagt tcattcctga gcggcatctg gccggtgcca    17400
agttagagga gccgttccga cacgacaact atgcggcgta ccagccgtgg tctgtaggag    17460
tgcgcaactg cattggacgg aacctggcct atgcagaggt caggctgacg ctggctaaac    17520
tgctgtggca ttttgatata gcctggacg aggagaggac ggggaacttt ttggaccaga    17580
agatctggtc aatttgggcg aagagggagc tgtatctgga aattcggacc agggaatttt    17640
agcatgtagg tagggtctaa atgaggctgt gctagttttc actaagtcag aacgaacttg    17700
atactttatt acgtgtacct tccatttcat ccatttagcg gccgttctgc cgatatgata    17760
taagctaaga acatgtacca gctacctatt ctcttcaacc cgccgtaaca gctctagtaa    17820
cggccggctc tgcgttaccc cttgtaccaa tcgaatatat ggtgcgtcca acgcaaaggg    17880
cttccctgtt acattgggga tccaccgtcc aacgagctct tccggcttga tatcagacac    17940
ccgcagatgt gcctcagat attgtctgta gccatcaata tgtccccgta gcatctgcga    18000
gtggaacgga atatcaaccc cggcaagtgg aatggttgca cggccacggg atagttcagt    18060
ttcattcgtg acagagcagc tgctggggat atggtgagca atgcattcgc tcatggtttg    18120
tgggctattt ggcgatgtcg accgggatag atcgtcgcac gcgtggctga gtacccagag    18180
agagcggacc tgttcgctat taggcctgat aggaaaacag aaaatagtat gacagggagt    18240
ttgagcgaga acatacatgg ccggcacata cgtactgccg cgaatgcacg ttgtagttga    18300
ccacctccag caacacgcca gttgcctgac tgacaagtcg cactagctca atcagtcggt    18360
cttcggtgaa gtctacgaaa tgttaactca gaatgtcgcg catgatcagg gaaaagagat    18420
acctgatcgg attcgcgatg gatcggcagc gaccatgcca tagtcagtac gcccgttagc    18480
gttgcgcggc agggtattct gcattttgag ccctctatag aggatcaacg ataaaagcga    18540
ctcaaaaggc atgatagttg tacaggcacc gaggctgcta tactctccca gcgagtgtcc    18600
agcaaagatg gcttgtgttt ggacgacgcc ttgcgcctgt aaatgcgcat actcggcaat    18660
ctccatgacg gccaacgcgg gctgggcaaa ttgtgttgac attaggagcc cagaaggata    18720
gttgaatgta tatgatcgtg agtcgcgagt caagccaggc agcatagatg gatcagagtc    18780
ggacatagaa agataaatat cacggatttg ccgaccacgc cgactgccaa agttgacagt    18840
aaggctcgta ggattctcac ggactatgtg aaggagcgaa atgcctgtaa tcggtattag    18900
agttgcccgt tctgtcgagc tcgggttgag gaggtaacgc accatattgg gatctaaagt    18960
gccgttctgc tctgtcccat actgctcgtg cagcagcatt cgtatcatac aaggccatcc    19020
ccattcctct ctcctgcgtg ccctggccgg taaagacgta tgttgtctgg gcctgctcga    19080
gtaccgcctc tgcatgcatt acttgctcac ccgtactctc cttaagcact cttacatgga    19140
ccaccataca cccgtccgcc attgcaaagt gttgtatctc cattcgcaac cggtcgtttg    19200
cccggacaag tccatcgaag gagggcgccc agctgcagaa acgggtccgt tcattgtcgc    19260
caatgatcca ctccagaatc cgccgcacgg tggcagacag gtgcagccca tgcacaacag    19320
gctgacccag cccggcaaaa cgagagaaca gagggcaaac gtgaatagga tttgtatctc    19380
```

```
cagataccat tgcataaccc tcgctttggg caggggcagt aaacgatata gatgcagcgt    19440
catcgccagt ccagcctgcc cgtgggagcg gctgtctctg gactcggggt gcaccgtggc    19500
ggttcagaaa atccatgact ggattcgctc caaaccccct ctcctccatg tatacacgtc    19560
caatccgggt gccgaccgaa gagacacaga caactgaggt atcagaaggg gccagtgaaa    19620
ctgatccaga aacttgcagg gaagcaggtg ctcctgcggc gtcgaatacc gtttgcgaat    19680
gcagttggaa tatcaatatc ttcccaataa gatctgagca aggtccatct agcaagaacc    19740
attttcgact cattaagact cttaattttg tgtgggagtc aacacgtatg accatatctg    19800
gctcttcaac gcaacgaaac tgctgctggg atacgctctc ctctggccgc cgctggatta    19860
taaatgtcgt ttggagtcga accaccggtt ttccctctct gaggagctct gcagaaatct    19920
caactcgctg gcctatggtg gtgattgtgc gctcggttat gcgcgacgaa gttgtcactg    19980
tatctcccac atgcaacggg cggatgccag gcacgaaacg agttgaagca gactggtgga    20040
ggagtcgaag agggtccgca tcaagtgctt cgagcagtat tggctttgtg agtgcagtcc    20100
aagctataac gacagcataa tcaattggca caactgggcc ccgtgtcccc caagctcgac    20160
aacgggccgg gccagcttga ccgacaatag ccaggaacgt attcacgtcc tcagctgtta    20220
ttgtcactcg atcgccagta aattctgaat tcagaccgac agaagttggg ctaggaaggt    20280
ctcgaccaat ccacaggtcc gtgtacaggc gcctcacgct gtccaagtaa tcagtccggt    20340
gcattttgag aattaaaggg cccatggttc ctccgagcaa ttccatctta aactccagcg    20400
cgggtcgttt gccctttgag cgagttagca atgtcactga taccttattg ccgtctagat    20460
gtatcagtcc cagtgctgca cgtatcgccc tggggtctcc ttgccgacgc aaggaatgat    20520
acaacgtgat ttcacgaagg cagccatcca tatattttgc ctcaatgacg tctccaatat    20580
ctggcttgaa agcgtcccga atcggatttg gagcgcgatt ttgcccaaaa acaacctttt    20640
tttggctgag ggcagcatag cccccaggcgc actcaccaac aaggtgttcg actattgcct    20700
ccgtcgatgg gagggtaggt ccgacaagat aataccggca cagcgagcct tcctggcttg    20760
tttcaatgcc aggtaagcga ttgccttttct catcgcgctg gttagcccaa gtgtaaccgt    20820
tgtcagaagc tgcctccttg agcatcattt tcaaatgcgc ctcagtaatc ccatcaagaa    20880
tgtctttaac tggctcatcg catactcgcg aatgacgcac ggctacaggc ccttgtatga    20940
tgcaaacacg ttgtgcatcc tggtccacca cagcgtctac atcttcagac tgccatagag    21000
aatctttctt aaaccatgtc tggaaatctg catcgagccg cggaataaag ggcaccggct    21060
tctgaccttg tcggcggaaa agattgatga gaaggcttac atcttccgga taaagtatct    21120
ggtcgccttg cacgccgtag gctgcgtcaa cgacgcttc cagctctatg ggagtgttgc    21180
aggaaagaaa gcgtaattca gcttctgaac ctgagcccag gcgtccttgt gcaagacgga    21240
gaaagtcatg caccaagctg aggtaggaag aatcgatcca gcgtgcctga tgctgcacat    21300
atgtaagctg gcagagacgg cgtaagactt gcctatagct cagctcctca atctctgttg    21360
gtttactgct gtctgtttgc gcgaaccacg gccgggcaaa gtcgttattc agtctattaa    21420
tgatttcaac acgatgttgt tttaatgcag cttttaaccg tttagggtcc gaattgaga    21480 agaaccggtc atcgaactcc ttccacaaac gcattgctcg agtcgcaagc acatggattg    21540
gttgacccat ctctgaagtg accgagataa caccgccaac tgcgtcatgt tcacattttg    21600
cccaagcacc gttgtcattc ccatcatcct tgactccggg ggcttcgact ataagctgct    21660
ttacagcgaa cgatgtcttc gcctcacgag ccaccatcat gcggctccct aggaggattc    21720
```

```
catcaaaggg cataggcgca taacccagtt tacaagacca agagccattc atgtatggcc   21780
aagtgtcctc agcaccccg  aatccactgc cagccacgag aatgacgttc tcgcagttcc   21840
tgatacgggc gtaacagtcg agaatcggta aatggaagtc ctcacaagaa tggtgtcccc   21900
ctgcacgacc cccggtccat tggatcccaa cggggagtgt cggatattgc cttgcgatgg   21960
taaggacgcg gtcaattgca tcaacagacc ccggtttgaa ccaaatatgt gaaattgcca   22020
acatgtcaat ccactccttc acgacctcgg gcgatgggat cccagcgccg accgttatcc   22080
catcaattgg caagccttct tccataatca ggcggcgcaa cacctggatc tgccaggaaa   22140
gtgctttggg ggaagcatag atgacattgc aggtgattga gcgatgggga gggatggacc   22200
tcgacagctg ccggagtgct gtttctagcg ttgctcggtt gtaatagcca ccacaggcaa   22260
attcaacatg atagtccgcc tgaatgatag ccgctacaag ctcaggtgag catgttgttg   22320
gcgtcatccc tgccaccata acatgtggtg ttcctagcag ccgcgtcatt ttggtttcaa   22380
tggatgcatg agcactccc  tcagctgctt ccgtagccg  cgggcgatat ttgcgacccc   22440
agtctttacc aagtgggaga gcaaaagcag acagattaag caacgataga ttcgaagcca   22500
tagactggcc ggacagatta acgacgttca tacccgttcc ctccaaaaca tcctgcacca   22560
ggctcccaac agcgccaggc ccaaatgaga gcacatgggt agcatcgttc attgcccaac   22620
acaaagcggg ccagttaact cgctcaacag taacggactg tatgagggtc aaaagaatat   22680
cgtgcgtgcc ataatcctgc aggttccgga gagatccatt cgcctggcag taaactggta   22740
tagcgagatc gttaccccgc aagcgaaggc cgccaatggc atcagtcact cttagctcga   22800
ctgatgacag aagagaagag tgataggag  ctgacactgg aaggaactgg acatcgacga   22860
cggaccgacg caggggaaag ggaacgcggc tttggtcgag ctcgggcgat gccttgacgc   22920
tacgaagtgc tatgcatact cctcgcagag catgtggtgc tccagccaga acgaacttgt   22980
tgtggccatt tataagggat atatagagcg aatctccacc ttggtcgttg agctttcgca   23040
ccagccgctc caaatgatta atgtctaagc ctgtcacact cagtaaatgt gacggagcgc   23100
cttcaccatt ttccaggcag tcgataactt catttgcaca cagaatactt cttggagaag   23160
catggtgtga ctccagcccg acccaaaacg acagttgcag gcaaggtca  gccgcgcggt   23220 agaaggatgg ccatccgtgg tcagtgtgag atatggcgat tgcggcggcc acaaatacac   23280
cttgagagtg tccgatagct ccctggagct tttggcggag ctgaccaggg tccagctgga   23340
ggctgtacgc agtaatagca tagtgtagga ggctcagcag agtgttgatt ggaaagctat   23400
aaggagacag cgccaaatct tccggcgtg  gtgcggatgc agcagcgtcg ttgagccagg   23460
cctgtaattg gaacccgcgc ccagcaaaaa atgacgatcg gtgtgggatc gctgctagtg   23520
attctagacg gcgggcagaa gagtcgagca agtcctgtat aggggcgcag tccgcgtagg   23580
cgtgcgagag atggactaac tcatcgagtc ccgcccaatt actgggccct tgcccaccaa   23640
agcacgcata taatcgtgat aggccagcgt cgacagcatc gagaaacggt gatggagtca   23700
ttctctttac aggtcgtcaa actgtaggct aacagatcag agccatggct gggaatgagc   23760
aagtatatcg tgtagccggg accaccacct atacgagagg gggagaaaca agtcagcgca   23820
gggtcggctt acgagcaatc ggagatcggg cgtggcggtt ctcaagttta catatcagct   23880
gttgttcttc agtctttcct gcagaactag gccataacat gaatacagcc atggcgatac   23940
gaaacatgga acagacaatt gcctacgagc tactgattga ctttttatcg tacgtttcct   24000
tataggtgtt gagcaaaaaa ctgatcagca gcagccatca gtttgcgttt ccggtgcaat   24060
ggtaggtcaa tagcgactgc gatacaccac taggtacgct gacgcggctt cgcgcacagg   24120
```

```
atagaaacgc agaaagctat attgcgagac actcgtcgcc tcgtcgaaat tggtccagcc   24180
aagacgctta ttggaatgac ccaaaagact atacagcagg tcccaagaca gggcttagag   24240
ttactggcca gcacgcagga ccttgcccag ctctgctaca tctatggcga gcctgccgag   24300
ggagaggatt cgaccgccga cgagtccatt attaatacgc cgcagtgtag cacaattcca   24360
gaggtagcgg tagagccgga agttcagcca ataccggaca cgccgctgac cgcaatattc   24420
atcattaggg ctctggtcgc ccgtaagctc cgcaggtcgg aaaccgagat tgaccccagt   24480
cgctcaatca aagagctgtg tggcggcaag tccacactac agaatgaact gattggcgag   24540
ctgggcaatg agttccagac ctctctccct gatcgcgcgg aggacgtctc cctagcggac   24600
ttggatgctg ccctgggcga ggtctcgcta ggacccacgt cggtttctct tctgcagaga   24660
gttttcacgg cgaagatgcc ggcccgcatg acagtgtcga atgtgcgtga gcgtttggcc   24720
gaaatctggg gccttggatt tcatcgacaa actgcagtct tggtggccgc acttgcggct   24780
gagcctcact cccgactcac ctccttggag gcggcatatc agtattggga cggtttgacc   24840
gaggcctacg ggcagtcatt gggtcttttc ttgcggaaag ctatctcaca gcaagctgca   24900
cggagtgacg accaaggcgc tcaagctata gcccctgcag actcgctcgg gtctaaggat   24960
cttgcacgaa agcagtacga ggctcttcgc gagtacctag ggatacggac cccaactacg   25020
aaacaggatg gtctagatct tgcagaccta cagcagaagc tggactgctg gactgccgaa   25080
ttttcggacg acttcctcag ccagatttcg cgtcgcttcg acgcacgaaa gacgcgctgg   25140
taccgcgact ggtggaactc ggcgcgccag gagcttctga caatctgcca aaatagtaat   25200
gtacaatgga cagacaaaat gcgtgagcac tttgtccagc gcgctgagga aggccttgtt   25260
gagattgctc gggcacattc actcgcgaaa ccccttgtgc cggacctcat ccaggccatt   25320
tctctccctc ctgtcgtccg gctagggcgt ttggcgacca tgatgccacg gacggtggtg   25380
acccttaagg gggagattca atgcgaggaa catgaacggg agccttcttg ctttgtggag   25440
ttcttcagca gctggatcca ggcaaacaac attcgatgca ccatacaatc taatggggaa   25500
gacctcacat cagtattcat caacagtctg gtacatgcca gtcaacaagg ggtttctttt   25560
gccaaccaca cataccttat aacaggggcg ggaccaggat cgatcggcca acatatcgtc   25620
cgtcgcttgt taacaggtgg tgccagggtc attgtaacca cgagccgcga gccattgcct   25680
gccgctgcct tcttcaagga gctgtatagt aagtgtggaa atcgcggatc gcagttacat   25740
ctagtgcctt tcaatcaggc cagcgttgtg gactgtgagc gtctgattgg ctacatttac   25800
gatgacttgg ggctggatct agatgcgatc ctccccttg ctgccacaag ccaggtggga   25860
gctgaaatcg acggactgga tgccagtaat gaagcagcgt ttcgactgat gctggtgaat   25920
gtactacgtc ttgtagggtt cgtggtatct caaaaaaggc gtagaggtat ttcctgccga   25980
ccaacccaag tcgtgctgcc tctgtctcct aaccatggca tcttgggtgg tgacggtctc   26040
tacgcggagt ccaaacgcgg gcttgagaca ttaatacagc ggttccattc agagtcatgg   26100
aaggaagagc tctcaatatg tggcgtcagc atcggctgga cccggtcaac gggcttgatg   26160
gcggccaacg accttgttgc tgagacggca gagaaacaag gccgcgtgct gacattctct   26220
gttgatgaga tgggagacct catctcactg ttattaactc cgcagttagc cacccgctgc   26280
gaagatgccc ctgtcatggc ggactttttct ggaaatctct cgtgttggcg cgatgcctct   26340
gctcagcttg ctgctgcccg tgcaagcctt cgtgagcgcg ctgacactgc ccagctcta   26400 gcacaggagg acgaacgaga ataccgttgc cgacgcgcag gaagtactca agaaccagtg   26460
```

```
gaccaaagag tctcgctcca tctcgggttc ccatcactcc ctgagtatga cccactgcta   26520
cacccagatc tcgtgcctgc tgatgcagtg gttgttgtcg gcttcgctga gctgggccca   26580
tggggaagcg cgcggattcg gtgggaaatg gagtcgcgcg ggtgtctttc tcctgcagga   26640
tacgtggaga cggcatggct aatgaatctc atacggcatg ttgacaacgt caattacgtc   26700
ggatgggtgg atggggaaga tgggaagccc gttgcagatg ctgatattcc aaaacgatac   26760
ggcgagcgga tcctatcgaa tgcaggcata cgttcactgc catctgacaa tcgagaggtt   26820
ttccaggaga tcgtgcttga acaagacttg ccgtcatttg agactacacg ggaaaatgcc   26880
gaagctctgc agcaacggca cggcgatatg gtgcaagtca gcacactcaa aaacggcttg   26940
tgtctagttc agctacagca cggcgcaaca atccgcgttc ccaaatccat catgtctcct   27000
ccaggtgttg ccggccaact gccgacaggc tggtcgccag aacggtacgg gattccagcg   27060
gaaatcgtgc agcaagttga ccccgttgcc cttgtgctgc tctgctgtgt agcggaggct   27120
ttctacagtg ccggcatttc cgatccaatg gagatatttg agcacattca tctatcggaa   27180
ctgggcaact ttgtaggctc ctcaatgggt ggggtggtga cacccgagc gctatatcac    27240 gacgtctgcc ttgataagga tgtgcaatcc gacgcactgc aggagacata tctcaacact   27300
gcaccggcgt gggtgaatat gttgtatctg ggtgcagctg gtccaatcaa gactcctgta   27360
ggcgcgtgtg caactgcttt ggaatcagtt gactccgccg tagaatctat caaagccggt   27420
cagacaaaga tctgccttgt cggtggctat gacgaccttc agcctgagga gtcagcaggc   27480
tttgcccgca tgaaggctac ggtttctgtc agagatgagc aggcgcgcgg ccgcgagccc   27540
ggcgagatgt cgcgtcctac agcggcctct cgctctgggt tcgtggaatc ccaaggctgc   27600
ggtgtccagc ttctttgtcg cggggatgtg gcgttagcaa tgggtttgcc tatttacggc   27660
atcatcgctg gcactggcat ggcctcagac gggattggtc gctccgtgcc tgctcccgga   27720
caaggcatcc tcacttttgc acaggaagat gctcagaacc ctgccccgat ccggacagcg   27780
ctcgcgcgct gggggttagg gatcgacgat atcaccgtgg cctcactgca tgcgacctcg   27840
acaccagcaa acgacaccaa cgaacctctc gtgattcagc gggaaatgac tcaccttggc   27900
cgcacctccg gccgtcctct gtgggcgatc tgtcaaaaat ttgtgaccgg ccatccaaaa   27960
gcccccgcag cagcgtggat gttgaacggg tgtctccagg tgctcgatac cggtcttgtg   28020
ccgggcaacc gaaacgcaga cgacgtcgat cctgctctcc gatcgttcag tcatctgtgt   28080
ttcccaatcc gttcaataca gaccgatggc atcaaggcat tcttgctgaa ttcgtgcggt   28140
ttcggacaga aggaggcgca gcttgtgggt gttcatcctc gatactttt gggtctactc    28200 tcagagccag agttcgaaga atacagaacc cgacggcaac ttcgcatcgc aggagctgaa   28260
cgagcctata tcagcgcgat gatgacaaat tccattgtct gcgtgcagtc acaccctccc   28320
tttggtcccg cagagatgca ctccatccta ctggatcctt ctgctcgtat atgcctggat   28380
tcatccacca attcctaccg cgtcacaaaa gcgtccactc cagtttatac gggcttccag   28440
aggcctcacg acaaacgtga agatcctcgt ccgtcaacga tcggcgtcga taccgtaacc   28500
ttgagcagtt tcaatgcgca cgagaacgcc atcttcctgc agcgcaacta caccgagcgc   28560
gaacgccagt ccctgcaact acagagccat cgcagcttcc ggtccgcagt cgcgagtggc   28620
tggtgcgcca aagaagccgt tttcaaatgc ttacagacgg tatccaaggg cgcaggggcg   28680
gcgatgagcg agatcgagat tgtgcgcgta caagggctc cgtctgtggt ggtaagttgc    28740
cttctcttct tcttgaaacg acgctgacgc gcccagttac acggcgatgc acttgctgca   28800
gcgcaaaagg ctggtttgga taatatccag ctaagtctga gctatggtga tgattgtgtg   28860
```

```
gtcgcggttg ctttaggtgt acgcaagtgg tgtctttggc cgttggcctc tatcatccgt    28920
taagcaacgg ctccagacat gtcaggttcc tcatcctgtt ttaagatgaa gtataatact    28980
tagaagatat ttagatcctc atcgcaattc tatctggctt tttacgccat ggttgacgag    29040
aaatcgtagg acagcgtcag acgttccttc ctggcgggac attgtttctc cgatccgccg    29100
ccaaaatgat tacctaatag ggtcttgtga tgttttaact atgtggaaag agcacacagc    29160
tcatccgagc tccgccagag ctcatatgag cgttacccct caaagcacgt gacgccaagg    29220
ccattaacaa gcagaacgtc tcgagcgagc tacaaaaaaa attacggaaa tactttgaaa    29280
ttcaataagc tcgaggcggc cagcagccac ctcacggagg taccactggt accacttcta    29340
aaaccggcat attagtaatt gggctgtaaa aaagcgaatt taatgataga agccgctgtg    29400
caaacaatta ttaagtactt tctgaataat taacttacgt tgttagagag agaggccatc    29460
acgcagcttg ttttggttgc tggtaatcgg aagcgaagac ctggctcgag acgaaatttt    29520
ccacaagctc gctcgagcgt cacatgggca aaaggccatt acataagcca tttcgtctcg    29580
agcgagccaa accacaaacc acaaacctgt accccggctg acctgtaacc acatgtggaa    29640
gggacggaca attatcagta ttggatggcc aacgtggccg cctatccata cctagcttac    29700
taaataatga ctaagcgagc tcgaccccta ggggcaggcg gtgccatagg acagtatgcc    29760
ccgacaaagt atgattcctg agtgccacct gacctgtacc tgatgattcc taactctgat    29820
cgagccttga cagaaccgga agttctgtaa gagtattcat cctgatatct ttgaattggg    29880
tagtatcagc tcctggtatg ataatatgtg cttgatgacc catagtactt aaagaatgat    29940
atctagacga ctggcgctaa ccgttccgc tgatgcctag attaatatat atttgctgcg    30000
cctcacaatc aacccactgc cttagggcca aatgtataac tatgggttct gacagacgcc    30060
cggcattgcc ttactcacaa acccagcata ttccacttaa cagatttccg aagaagagtg    30120
cctgatgttc cctcagtgct ggtgacggaa atagccacga gaaatgcgga tagccaggat    30180
actcatcgca ctttaccggg acttccaacg cgactagagc gtccctcatc aggcggacgt    30240
cgtccctcag ggtgtcggcg tcgccaacgg ccatgtagac tttattcagt tttccaagac    30300
ccggatgcag aagacatgaa agccggggat catccggtgg tgcgccatag caatcgaaga    30360
acgaccgcat cgcggagccg gtgttgattg tcaaccggtc attctcttca taggatgtat    30420
actctcctcg gtctcgattg tctgcggaca cggagtcagg atgaacggtt accggcgcga    30480
gagcaaccac gccttggact cggtctccta ggccgtcact aaccagggta agtgccgtac    30540
tgaacgccat gtttccaccg gccgaggcac cgatgaaaca gattgattgc acgggatacg    30600
tttccaggac cgatctcgca acagttagac aatcgtcaag cgccatcggg aatcggaatt    30660
cgggggctag acgtatcccc acgctgaaga ttctcgtgcg ggccagttta cagagagtgc    30720
ggacgaagcc gtcctcctcg tcaatgctgc ccatgaccca tccgccggcg tggaagtaga    30780
gggccagcgg tgggtcagct acatccgcg gcgtgtagat gcgtgtgggg acgccgccga    30840
ggatcttgtc ctctgcctga acgctcaggt ctggaagagg aaagtcgtag cggctcatca    30900
gcttgccgac tatcgtcttc catccctgca tgagcctctc gtacggcccg tcaagagccg    30960
gcgaaaagcc aagctcttct atgaactggt acagtcaatt ttacgcatca ggtgcttgga    31020
ggactgttcg tacctgctgc catggctctg atagcttgga atccattgtt gaagcgatct    31080
gttgtctgct acggactttc atcgcgaggt tcgatttgtc ttatgttgaa tgtcggtcac    31140
cgagctacaa tgttcttaat tggatcttca tccgtctggt aaatgtccac cataacgtat    31200
```

```
ggcgttattg tatctgatcc gtctgcagcc cacttagcta ccccccctgag tcctcagtat    31260 gccggtatat cacgtcggta tgcatacccct aggcgacaat gaacactgag actgatctat    31320
ccaccgacag ccctattcaa actcaaacca gacgccgacc ctaaccgtat ctgtttatgg    31380
caggagctcg cgcacgcaat ggtcggcaag gtacctggcc tactggatct gcaagctggg    31440
cctcccctcg acttcacggc tcgactggcg aaagggtttg atatgggtgt agtcgtgctg    31500
ctagactatg tggagtctct cgctaccatg tttacgcatc cgagccatga ccagtaagtg    31560
ttcagaatga atggccttcc gtgtttatca tcgttgatgt acgacagagt tcacgaattg    31620
taccaggagg tttgcgagga cgggagtact gttggttacg atattgaatt ctagagggct    31680
aggttgcagc atatcctcta gaactgttct actccgaact agtgcaggca taaccgtggg    31740
aatgtgtata taatcagaca tcgaacccag catcccgccg ccgctgcata ataggcctca    31800
actgattccc accccatccg tcctccaaat catctttcag gtcaaaagta ccctccggct    31860
gtactgccaa ggcacgtcct gtagagccac ttagtattat cccagccaag ccaataagat    31920
agaagagaaa ataggagtaa aatgtaccat gtatctctgg gcttgcaaca caataagtcg    31980
cggcatcaac gcatgcgtca atagacgtaa acgtgagtac cttggccata tcgactccac    32040
gcgctgccat cgcatgcttg attggggcaa tgagcggaga atcgaagaac cacggcgcaa    32100
gcagattgca gcgaacgccc aactgcttgg tctgagaacg cgtgctgcga aacagcccgc    32160
ggacgccgaa cttgctggcc gggtacgtgg acgccttggg gctgtccata tatgctgcga    32220
tggaggcgca gaagagaagg catttgttgc tgggcaactc ggggtcagtt cccgtgcctg    32280
gtatacgcag gtaatacagc cccagccagg aagtgaagta acttcccacc agattcacct    32340
cgatattgcg gacactggag ctcggccggg gaggatcgac ctctaggctg gaacacccg    32400 cggcaaggac gtgatctatc tggtttccgg gggcgagagc cgttccggca aagcaggcga    32460
ctatatccag ggcgccgctg ggtgagaagc gaagggcgct cttaaaggcg gccacttgac    32520
tctcccagct cgtgacatcg cagtagacat agtgaaaaca gtgcgcgagt ccaggctgga    32580
ctgggctcgt tggcggttgg atgtcggcga tggtgatata gaccccggcc tctgcccatt    32640
tccgcgctgt ggccagcccct aggcctgaag cgccgccggt gatgaatgcg gatttgccgt    32700
tgaggctagt caggtcgcaa gtgagatcga ggggctccat attgagtccg ggtgagtagc    32760
tatgggttat cttttgcgcg cattgggttg gtggtcattc atttatagcc ctcgggtat    32820 agagttcgga gtctcagaat ctgaacaagg tcgtagtgct caggaagaaa gatactaaaa    32880
tcgccgtctt cgccttcgtg ggtttctaaa tagctccaaa cagccaaaat ccaacattat    32940
tcggcatgat tctgcctctg atattggtct tgtatctgct ctctacggcg gcttaccgtc    33000
tatggctgca tccgctgcgc aactaccctg gcccgtgctg gtgggctgtt tggcgagttc    33060
catatctgaa gggcaccatt cgagggacga ttgtcagaga tatccagcga ttgcataacc    33120
agtatggtcc cgttgtacga atcgcgccag atgaactttc ctacatcacg ccagaggcag    33180
caaaaccaat ctacacgtcc agtcccgaat tccccaaaga cccaatgcat ctccctccgt    33240
ttcataatgg cgcccctggc attctcgctg ccgactacgc ccaccatcgg cgatatcgac    33300
ggcttcttgc ctctgccttc tctgaaaagg gacttgcgc acagcagggc atgattcaga    33360
gccatattga tcgactaatg actcgtctcc aggggaattg ctcgtcgggc tcgctggaca    33420
tgaccgtctg gttcaactgg gcgaccttcg atatcatcgg cgatctcgct ttcggggagc    33480
cgttcggctg tctcgagaga atggagacta acccatggat tgcctcaatt cagggcaacg    33540
tcaaatccat cccgatccta aacgctctac gtcggtaccg tctggacagg ctcattgagt    33600
```

```
tcctcgcgcc tcccaggcta ctggagatgc gacggcgtaa tgcgcagttc acagcagaaa    33660
aggtcgatcg ccgactgaag catgcaacga ccacgcgcgg cgacctgtgg gactcggtgc    33720
tggccgaccc tccagatggt gagcctccga tgtcgcgcgc cgagatggtc agcaatgcca    33780
gcgcaatcgt tcttgcgggg agcgagacgt cggcaaccac tctgagcggg tgtctttggc    33840
tgcttctcac gaaccctgag tatctgcagc agctcactga gcgtatccgc gctcggttca    33900
gcacggccac agtcattgat gcacagacgg tgacgcagat ccaggggctc caggcggtcc    33960
ttgacgagtc gctacgccta tatcctgcag tgccaatgca aagcaaccgt attgttccac    34020
caccgggcgc ccgtcttgca ggcagctggg ttccgggagg ggtaagtctg cagccactca    34080
tcctgccctt ttccttcttt tctctttcag ccgatgggcc tctcgctgac cgattgatta    34140
cagacctcgg tcgccgtcca acagtttgct gcctgtcgct cccccaccaa ctttcaccgt    34200
ccagacgagt ttattcccga gcggtgggaa aaggaaggtg agttcatcaa tgatcggcgg    34260
gaggcctcgc agccatttag cattggtccc cgcaattgca tcggacgcca gttggctctt    34320
gccgagatgc ggctgatcct ggtccacctc ttatggcact ttgatataga actggaccgg    34380
cggcgcatgg aaaatatgga ctggatggcg gtgcagggga tctggatcct gtgggacaag    34440
aaaccgctgt gggttgtgtt gaagaacaga agtacgtagg caccaaagtc tttgcagcgc    34500
tagtatggat gctagtactg ccactgtaca gcttattgct ttactaagaa attaaagtag    34560
taatgcccgg caaaagactg tggtagtatt attcacgtaa gaaagaagat cataataaga    34620
taaactagca caaataaagc tagaggttct tccagaccct agagttaggc cttcacatgc    34680
ggaaagctgg ccctgatctg tctgccctac tgccattcca gctataagaa ttataattct    34740
tacagccctt ctatgcttaa tggctctaat atgttgtgta acccactgta tctgccttaa    34800
gtatttacag cttagaaata tcctttgata actggattat tcgccatctt tcaattagtc    34860
aagtttagct ttcaagtaca gagcaggatt atgggcatgg tgtgtacctt ctggctatgt    34920
tctgcgttgt ataaatgttt gatctaagaa tatcgggtat attagctgtt ttaatctggg    34980
cccaataaga aaggatatat acttgaaatc gtttagataa ggtattggca ttcaaggact    35040
gcaggcagga agggggcgcat acagttcgaa ggcagattaa aagcaggcat atttgcggaa    35100
atgtactttt cagcctcttt aaactagttt gatctgttag tagcagtctg gaagctttaa    35160
aaatagaaaa tggctatgtt aatgtttgct ctggaagatc aatctcaacc aataacctag    35220
ttgtctaata gccggtaatt atatcatatg atatggcatc aaatattact agcgcggcaa    35280 aaaatcctg tgcacaccct cacaatgaca aaccttttac agcgtcgtgg acttgcagta    35340
gggcttctcg gcagccaaga caggaaaatg cacactaaag ctaatccagt gtccaccaat    35400
cacttgctgc cgtttagctt tttatcagct gcagtcatgc tataatgttg ggcgtcaaag    35460
cgtagtccat gatgcggtac ccctccgacg tggcattcct tagtgctttc tagcagacgg    35520
ttcgtatcgc acctctagcc caattgcagc actggctgtt gtgtgtatct cgcgtgtcac    35580
cactaaacag cccccctgagt ccctgatgcc ggtaacaatc tcgacgatct ctgtcttggt    35640
aggctgccgc tcattagaca actgcaggag cgacatgtcg cgcagtcgca ccatggattc    35700
cgtctcctga ttgactgttc caggcgacgg caggactaag gccgctatca tcaggcggga    35760
agtgggctga gtgcggagaa cctggagatg ggcctgcagc tccatcacag tttggctccg    35820
caatttcgtc caaggtagca tgggtgaggg ggacgggatg cggacgatgt agaccgctgg    35880
acctaagacc gtctgggggg cgccggcccc ccgcgaatgc accgagacac gattactgat    35940
```

```
ggacggtggc agctggtatg tcacccagga tggctcagag cccgttatcg ggcccgactg   36000
gccgttacca ggcgagcttg tctggataac taactgggcg gcaggaccca gggcagcaat   36060
catgccgatg gtgctggtgg acggggatg gatctggatg ctgtcagcgg gatgatctgg    36120
atcgacgata tggtaagctg acatccacga tggtggccgg cccaatggca ccccagtcta   36180
ccaagcgaag cacctcatca acggccaaag gctcatcaag aatccctcga gcaagatagg   36240
ctgcaaactg gcgttgcacc ttgggttgtg caggatcagg tctatcttcc aatcccgttg   36300
ccctactctc tgatcgagca atcagcgacg gagagaggcc acgatcataa gggtccggct   36360
ggcacgttga gcgtggcatc ttcagtgccg ccggaaccgc aacctgggcc aggaaaagcg   36420
ctgcgtctag cagctctggc tccgtgacaa aggaggctga tagtggggta tgcgcaacgt   36480
gcccgctagg tctctcgctg aggaatcctg cagtcaccat caggcgtacg actcgctgca   36540
gctggtccac agggacattg ctgatatccg cgacctcctc gaaagccacc tctccgtcca   36600
ggggaatgca ggccaacact tgaaactcgc atagccattg tagattggcc aggagttgcg   36660
tctttacttt gttagcaccg gtcattcttc cgggactgga agcaggacga tcccaagggg   36720
ggaacacaaa gacttgcctg aagcgcgaac tgttgcaaaa agccagctgg ctgagtcgcc   36780
attactaaaa agtctgtaca gcaaagacaa agatatgcgg tgggaagggg agagcagcgt   36840
ctcgaatagg aaagcccact gcttgcgggc cctaggtcga agccttgata tagcccagcg   36900
gctgccgact cctagacccc gacagggcag cttgcggtgc tcagccttcg cttaggataa   36960
gtaatggatc aagctaatgg ggttatcgta tggctcatgc agtcaaccag ttctagcccg   37020
cagtatcccc tctctggagt cgtatctcct catggcgaat ctccaggcta agtttgcaac   37080
ccttgaaacc catagccagt aaagttgaat tgttatttct tgtgtcagtc ggtagatatc   37140
gagccctgta atccctgcgg gaatattgac cccaagtaca gcttacacag tacagcttac   37200
tccccatctt ctcttcactg atatatatca tccagatctc gcggttcaat ccgcaatgcg   37260
ggcctgtatc atatgcaaat atcatggagc ccccagcgat cagccagcaa tccacaccca   37320 cggcccccggg gggaacgcaa gggacacgca aactgcgcga gagttgcatc tcgtgctcca   37380
gatccaaggt caagtgcaat aaggagaagc ccacatgcag tcgatgcgtc cgccgtggtc   37440
tgccttgcga gtatatggtt tccaggcgca ctggacgcac tcgcgtcatt ggtgttgagc   37500
agccaaagac agcaccatca ccaacaacac cgacgaatac gacagcagct actacagcaa   37560
cgaaggcagg accaccagtt acaacagaca gtgctgttca tacacctgtc attactacgg   37620
cgccctctcc caagccggtg cagatccagt ctcctccagc cgaaccagat ctctggggcg   37680
ccatcctgtc tccgaatact tccacctcca ccgacctatc gtcactcctc tcggtgaata   37740
caaatttcag tcagctcttc gcctcgcttt tccttcgct tcttgagggt atggatggca    37800
tggatgccga aatgcacgcg ccggagctgg gcgcattgtc ggtcgccgac ccatcgtcct   37860
ccatgatgca ggggttagag gcccctaacg ctgcccaacc accgtcttcg aacaccacaa   37920
gccactccta ctgcctgtcc atctgcctgg atactctcat gcggctcttt ccgaatgctg   37980
gcgctaactg cgagcgaccc gggcacgaga gcaaccccgg caaactgttc actatcgagt   38040
ccgttattga ggacaacaaa caaatctggg acacagcgca gacaatcctg gcttgccgct   38100
gcgccgagga tgagtacgtg gtcactctcg tctcacttat tgtcttcaag gttcttggat   38160
ggtacgtcgc cgcggctcgg gataggtcgt cggacccggg gcgcgaagaa gacttcaact   38220
ggtcgactgc ccaagacagt cgtagaggtt cggtctcttc ctttgaggag caggtgctgc   38280
atcttcccac cgtcgtcggc agttattgca ttgatggcca tcatcagagc cgcatggcag   38340
```

```
cccagctggt gctgagcgag ctataccgcg tccaacgact ggtgactcag gtaagccgtc   38400
gcctagaatc tattcgccgc cgctcctcga gcagctcgag ctctgcctct agtaatacaa   38460
cggactctga cggcgggatg tcgaccccct tgtcgtcgac caccctggtc catctagaag   38520
acgatttgcg caagcgcctg cgtgccgtct caagcgaaac gatcagcatc ctccgccacg   38580
cctgaggttg aataatctgg aatgatattt atgcgatcaa agttcattat gacgagtgtt   38640
gggtgaatgg tatgcgactc tagggttccc tgccgaatgt ccagcttatt tgatacagtg   38700
gtggacaccg agaagcattc aacgaggagc attcattcta cattccgggc gttcattaca   38760
gccagtagta taactacact acatttgaat tattcataga gttaggcgag cacgttgagg   38820
tgcaagaagc agcgataatg agttcatgat atactgattt taacaggatt cagcacatgg   38880
tagccaagta acaaaggtag tcaccaagta aactaccagg gcacgtctga gccgtccgaa   38940
aatagaataa agcgcccaga cgttgtattc ttgtcggcct cggtcatctg tcctcacagg   39000
attagttcga tgcagaatta gcgaaacgga aacatacccct ggcacagata ccagccacgc   39060
tttcctctat cgtcgtgggg gcctctttgc gcccgaacaa cctggcagcc tgggcgccca   39120
tatctgactg gatgtgtcta ccggcccgat ctcgtcagcc aagatgaagt gcgcttcaga   39180
cagtcataat cgaatccggg cattctcacc cagggtcgac aatgtacgca acaagccact   39240
tattctcaaa gtggatcttg cgcaccagat agcaggcggc cagctttgaa agtgcataat   39300
ttgtgagcgg tgcccgcgca cagctctcca tctcggtaat cgtgctaatc ggggcccga   39360 cgcagatgaa ctgcggcgat ttggcggcct ggagaaggac cctagtcgcc tggaacagta   39420
gcagggccgc gtatgcgtta atctgcatgt gagtctccag atactcgaga ggcatggtcg   39480
aggctggacc gtagttggcc gcaatagctg cgttcgcgat cactacatcg agatgcgtaa   39540
tgccgtaatc gcgctggaga atgctgaccg cgtcggcggg atcggacttc gatccactgt   39600
ccagttggac tgcgatcagc gaggagttct cgcctcttgg gagcgcatcc aaggcccccg   39660
cctgcgaagt gcgattgcgg agaccggcga tgacgatgct gttggggcga aggagaaatg   39720
cctgcacgag ccccctcccg aggcctgcag ttggtgttta gatctgtgtt aaatctgttt   39780
caggaatgca ggcgaacgta cccctgctgg caccggtcac taggtagacc gtcttgcggt   39840
cggacgaagg aacttctggt acagaaacgg ctgcagatgg catggcggca gtacagaact   39900
gagctgagaa gactacagta tatggatttg cggaagatgg tgaccgtctt atatttctcg   39960
ccgggcgtac aagtagcctc atcggccatt atagggaagg atcggggatt tgaccaagtg   40020
ccgaagcacg atcatatttt gtttggttgc ttttgtagat atgcttccat atctccatat   40080
ctccttattt cccgattctc aatggcctat aacccaataa cccaataatc aaataaacca   40140
tcaaccatgc aaaagggcat ctggccgatg cgcaggcgaa cccttacccg attcaactcg   40200
acactagtcg tctagtcaaa gaggcccaga aaagccgccc cgagggccgt catcattggc   40260
gcatacgacc aatggcccca ttctcccttt ccccagctat agcagatcgc gccgtcggca   40320
aacgcgacca gactgccggc cacgagggtc cagcccgtcg acttgcgggt cccgaacgcg   40380
ttggcaatgt agaacgaaaa gccccagaag atgtcgcgga ccccgtacac gtaactcagg   40440
ccctcgacga gccgtctttc ggcgggcgaa gcggcagct cccactcaaa gaaagagagc   40500
gcgtgcgcag ggcgaaggag cgcgttgacg ccgaatccaa tggcgatgag cgcaaacgca   40560
ttggcgccga tgctgagggc cgggtgctga gagacgggca ttttgaagta ttgtttaacg   40620
gattggtggc ttctgtcagt gttagtattg atgtcaagat tcagtgcagc gcagctccag   40680
```

```
tgcagtcgag agtaattta gtgccagtgc cagtgcagtg ttgatggatg tcaatagaac    40740
aaaatcaaag tcagcttctt acctcgtaaa tcaatccaga ttgatggtta agcagtattg    40800
cgacgagaga gagatgaaga atgtgcagtg agagaagacg agatttaagg cgagggtcg     40860 ggagttaggc acgagatag cagttctttg tcttggcctc tgccttgtct cacactcatt     40920
tccacacaat aaatgtcgct tgtagctagc ctcgtctcgt tggccatcag gtctgttggt    40980
tggttggcct ctggtcgacc gtctgtcagt cgtctggcca gtcgtctggt cggtggtctt    41040
gcagcgcgta ctagtcatct cagctctcag catctcacca tccagggccg tccctctgcc    41100
actcccaggg ctgagatcac aggtaccaga tcaagttcta ttcatagcgc aatccttctc    41160
agtgaacccg tgcccggcgc taggatgtcc gcccagggca cagttctcaa gggccaggaa    41220
gcagccgcag ctcgcattcg cacagtcccc attcgtcagc tgcctcgtgg cagtaccgta    41280
aagccatcgt gagaccattt tggaccctgc agagaacgcc accttgcttc ctagttctaa    41340
tttcgtcgcg tggcccccat gcggtctcat cctcgaactc tctcgacacc tgtcgcagtc    41400
attccgcgcc gctcgcgctg ggttaacggg ccatagacaa tagccagtgg ccgcttagaa    41460
tcgggctgaa gggcttcaca gccccttcgc acgcgaaggg gcaatacgag ccgaccagtt    41520
cgtgatgcgg ttgagcggga gatgcccgct agatcgtgct gttcatacca tggataagaa    41580
tagagcatca gcagtagaat ggctatataa accacttggt cttcgccggg atgtccttgc    41640
tcgaccagca atctcaatat cttctgtctt accaagaaac ttgcgcgaca gaactctcg     41700 cgacacaact ttcgctatac aatgttgctc aagagcatcc agaacattgt ctgtggcctc    41760
gtgccaacgt tcttcctgtt tggctctgca gctgccgagc tggactttga acagtggcat    41820
ccagcgggac tgggagactt gcgctgcggc tgcccggcca tgaacagtct tgccaaccac    41880
gggttcatca accataacgg cagcaacatc acggtcaacg aggtcatccc gttgatgcaa    41940
gaggtctttc atctcagtga agagctcgcc acgattgtca cgggcctcgc cgtcctctcg    42000
gcggacgacc ctgcctcggg tattttcaac cttgatatgc tgaaccgcca caacattttc    42060
gagcacgacg cctcactgac ccgcaaggat ttctacctgg gcggcgacgg acatactatt    42120
gaccagccca cgctggacga gttcctcagc tacttcgacg gcaaagaatg gatcgacctc    42180
aacgacgccg cagcagcccg ctatgcgcgc gtcctcgact cccgcgagaa gaacccgagc    42240
ttcctctacc aggaccagca gctcattact tcgtacggcg agacgatcaa gtacttccga    42300
accatggtcg acccgcgctc aaacaagaca tccgccgagt tcgtcaggat cttgttcacc    42360
gaggagcggc tgcccgtcag ggaagggtgg cagcgcccgc gagaagagat cagtgggttc    42420
tcgctggcca gcgatgtcgt tcagctggcg ctgcgcaccc cagagaagtt cattggcatg    42480
ccgttcgacc agcgtccgtt tgcagagcag gcctttgacc cgctgccatg gcagcggcct    42540
cccatctgga ctcccccgaa ctacccgggt ttcagtaaga ggcatttctc tgagcttgtc    42600
gggaggtttg cgaagaaggc ccttccgttt cgtgcttgat agacatctat ctttctgagg    42660
ctttggtcac tgccttcgct cggcgttgca gcgcaaaact atatacacgc acatatatat    42720
ttctctttcg tttgtctata gtactagaat tggtcttgtt tgtacaaaca taattaatca    42780
ttggcatcta tcaattcaaa gtaccagctc taaactgctc taccaatcca ggtaataatg    42840
atcccttata gtatgatctt acttaatgct ggcatgttgc tggcgtgaga ataaagtgcg    42900
gcagaggatt cagtagtgga tccactgcgt ggtctaaaca ggccggtgcg agtttaacat    42960
ctgcctgaga tctactagtg gctacgagaa cagcaggaag aaacacaagt caagaaaggg    43020
cttgggattg gaaaaatatc actatccaga gcgcatgact aaactgacaa gggtgagtat    43080
```

```
ttttaatgga aattcggaac gccaaggtca atgttaaccg cgatcgctaa actgggctta    43140
gcgtagggtg tttgacacgt gactaactag cactgtggaa agggacggac aattgtcatt    43200
attggtggcc aacgttgccg cctatctata cctagcttac taaataatga ctaagcgagc    43260 tcgacccta gggcaggtga cgcgacttga aactcatcat cgtctttatg gtcgcgtgac    43320
agtcatgact aatgttgctt atataaccaa tttgtatcgc gcgactaaaa atcaggtcta    43380
accgagctgc aatctgggcg gtgccataga acagtatgcc ccgacaaaca tcgcgcatcg    43440
cgtcggctct atccgaagcg agttagaaaa ttgttggtgc gtctggcatg gtacgccaga    43500
ctctccacga cagcgtctcg ttccatcaat cggcgtctat gtcagtgtaa tggcgcatcg    43560
acgatcgcgg ggaacgcccg ctatgaaact gtctaccacg tgcatgctct cgtccgtcac    43620
cgatcgtcct aatcgcgccc caacacattc gcgaaaaaac atggccgcag ccagacgcat    43680
ctccatacgg ccgagatgaa tacctaggca ctggcgtgcc ccgtacccga acggggttgaa   43740 agccagcttg gcttggtcag tgattctcga gttggatagc cagcgcgtat gatcgaacct    43800
agccgctctg tatcaacact gccatccgca tttttttgt tgattcgctt ccactgggct     43860
tccacttacg tgtctgcatc atcccagata ctcggattgc gctgaagact ccagttctgc    43920
gtagcaacta tggtgtcgtc gggaatgaaa tacccccaa ttgtcacacc cccggatggt     43980
ggactgcgag gcatgcatcc tggagccgcc ccgtatagcc gtagactttc gtcgatgacc    44040
gcattcagga tgggcaaccg ctcgcaggct tcgtcggtca gttccccttc aagagtggcg    44100
acctcggcct cgacttgctt ttggacttct ggtcgactca gcacacacca gagaaggaac    44160
gtcagagaga ttgccgtcgg gtcggagccc gccagtagta gagccccggc gtcagttatg    44220
atatctgtat cagtcaagtt tccggcctct agggccttat tgaatagatt tctcggttcg    44280
gcctgggcct tctttgcctc tcgcgctcgg gagaccacgt cgcctcccgc agcgaacatt    44340
ctctcctgag aatagaatat atcctggaga ggtgggatga accaagccaa cgcacggcca    44400
agatagtagc caggggagc gaagtgcttg agcagatgcg caaggtctcc catccgccgt     44460
tctagcataa gaacgaaggg ttccttgaca cctttggcga cgatgcctgc gccaccgccg    44520
aacgtaagct ggcagactat ttcgttggcc atgagagtcc accacccat gatctcggcc     44580 tcgccctta cggcgtcgca tttgatcttc tccacggtca gcttgatgat atcccgacc      44640 tttggctccc actcgtttcg taagctctgc agcgtgaaac cccgggcgta aagtttacga    44700
cgcgccgcat ggagttttgg atcccgaaag ttgaagatat tgtctaccgg ccctggtgat    44760
agaagctcat agaagggagc tttcatgaag ccagatccca tgcggtggat ctcgcgtcct    44820
gccacaggat ctgccacgtc gatttcttga ggtccgatac ggacgatggg cccatacttc    44880
tggtgcaagc tatggacgta gtggattcga ttgttggcaa agacggacca cgacaggcgc    44940
agccctgtca acgacgcata ccagggacct ggaatatgtt tcaatggagt gaagtaagct    45000
atgcgaatgg cctgggatac atcagcgcca gttgcctccg ggccggacga aatacccttga   45060 ttatgctaag tagtatgaag aagctgccga cataactgag catggagagc catttcatgc    45120
tcagaagggc cgcatagaag tctttactgt ccgaagtcat tggactcgca atcagagggg    45180
gacaatctgc atcatgaatt cccccttctgt tggaacgcct gatatagtac gcttgtgcgg   45240
ttgaccccag tgtatcgggc actcaaccgg tcatctattc ttgactcggt gaagagagac    45300
tgcaatcggc agatgctcgg gtatcgctaa agaatactct gtcctcttcc cagtaaaccc    45360
cggtacagtc agcgacggat cacggtcagc gaggccatga ccgactcggc agctccttga    45420
```

```
ttgacacctt gcacatgtaa gataaaatag gcaatctgaa tctcaccgtt agcttagaat    45480
catggaactg cagaccatac tattttcgca ataaacggct ccaggatggc cagtcacgct    45540
gagccaacca ggctcttcct ttttggggac cagacctatg acttcgttgc agatttgcga    45600
gatcttctca atattcgcaa caatccaatt ctagtggcct ttctcgaaca atcgcaccat    45660
gttatacgtg cccagatgat ccgcgagctg ccaccaaaag agcacaagca agctcggact    45720
gcgtccttag cagagttact gcagaaatat gtcgatcgaa agctgccgtc tgctttccag    45780
actgccctct cctgcgttac tcagataggg ctatttatgc gtcaatttga tgacccgcgt    45840
gttctttacc cacacgctaa cgacagctac gtcttgggag tctgcacagg atctcttgcg    45900
gcagccgcca ttagctgcag tacttcttta tctgagcttt taccaattgc tgtccagacc    45960
gtcctcgtcg cctttcgcct tggcctttgg gcagagaaag tgcgcgataa ccttgaaata    46020
tccgaaacca accaaacaca gccctggtcg gcagtgtgtc atgttccacc ggaggaggtg    46080
gccattgcca ttgacaggtt cagtcataaa aaggtccgta gccctgtata ccgtgctcaa    46140
aggtcttgct aacccattgt ccacctgaac aggcgctatc gaacacgcgc agaccctgga    46200
ttactgcaac atcagccaaa actacgacag ttagcgcaag ccctgatatc ttgagccagt    46260
tggctagtca agcacccttc acgaatagca aactgtggag ggagattcca atctacgttc    46320
ctgcgcataa caaccatttg ttctcctcaa gggatgtcga cgacatcctg gcgaccacga    46380
atgagaaccc ctggtccacc ttcggcgccc aaataccgtt cctgtcctcc gtcactggaa    46440
agttggcttg ggtccgaaac taccgtgacc tcctacatct ggccctctcg caatgcctta    46500
tcgaacctat acgatgggac gtcgtcgagg cagaagtgcc gcggctcctc aaagaccgtg    46560
atggtctcga tacgctgaca attgtagcct tcacaaccgt gctttctaaa gtttgtcca    46620 atgctctggt taccgaagga ataaagccag cagaacctcc gacctctata aataagaccc    46680
cggagcgata tagccaccgt ccagggtctg acagaggcaa actggcgatt gtgtctatgt    46740
ctggtcgatt tcccgaggcc ccttctaccg attcattctg ggatctgctt tacaaaggcc    46800
ttgacgtttg taaagaggtc cccttgcgtc gatgggatgt aaagacccat gttgatccga    46860
gcggcaaagc gcgcaacaaa ggggccacac gttgggttg ctggcttgac tttgctggtg    46920
aattcgaccc acgcttcttt agcatctcgc ccaaggaggc gccgcaaatg gatccggccc    46980
agaggatggc attaatgtca acttacgaag ccatggagcg aggaggcatt gtgccagaca    47040
cgacaccgtc aactcaacgt aaccgcatcg gagttttcca cggcgttacc agtaatgact    47100
ggatggaaac gaataccgcg caaaatatag acacctactt tatcacgggc ggaaacaggg    47160
ggttcattcc tggtcggatc aatttctgct ttgaattttc agggcccagt tatagtaatg    47220
acactgcatg ttcctccagt ctggcagcta ttcatctcgc atgtaattcc ctgtggcgtg    47280
gtgactgcga tactgcggtg gctggaggca cgaatatgat ttttaccccct gatggacata    47340 ctggcctgga taagggggttt ttccttttctc gaacaggcaa ctgcaaggct tttgacgatg    47400
cagcagatgg ctattccgt gcggaaggag tcggtaccgt cttcatcaaa cgtcttgagg    47460
atgcattagc agaaaatgat cctattctgg ccactatcct cgacatcaaa acaaaccact    47520
cggccatgtc ggactcaatg acacggccgt ttaagcctgc gcagattgac aacatgtcgg    47580
ctttattgag tacagccgga atcagcccgc ttgaccttag ctatatcgaa atgcacggta    47640
ccgggacgca ggtgggtgac gccgtcgaaa tggagtcggt tctgagtctc tttgctccgg    47700
acgagacatt tcgaccccga gataaaccgt tgtacgtggg atctgccaaa gcgaacattg    47760
gccatggaga aggagtttcc ggcgtcacca gtctcatcaa ggtcctactg atgatgaaaa    47820
```

```
acgacaccat tcctcctcac tgtggcatta aaccgggaag ccgaatcaac cggaactatc    47880
cagaccttcc agctcgcaat gtgcatattg cttttgagcc aaaaccgtgg cctcggacag    47940
atacacctcg acgtgtgctc atcaacaact ttagtgccgc tggagggaac accgctgtcc    48000
tggttgagga cgctcctgtt cgtgatcccg taactgcatc agatccccga actagccaca    48060
ttgttactgt ttctggccac gttgggaagt ccctcaagct gaacttggag aaattgcggg    48120
atcatttggt gaagcggccg gaaatcaatc cttcggagct ctcatatacg accactgccc    48180
ggcgatggca ccaccctcat cgggtgagta acaggagc taacactatg gaaatcttgc     48240
gcaatgtaga aagcgctata gcaagagggc atggagtcaa ccgccccgca actaagccga    48300
aaattgtcat tgcttgtagt gggcaaggct cccagtacac agggatgggc tggcagctat    48360
acaacagtta tccgactttc cggtctgacc tagagcgatt tgatcaattg ctaggagct    48420 atgggtttcc cagtttcctt gaggtctaca cctccaagcc agtcggcgac agcatggaag    48480
atctcctccc cgttattgtc caattggctt tggtgagtct tgaaatggct ttgggaaacc    48540
ttctgggctc cttcggtctg aaaccaagtg cagtcattgg ccatagtctt ggcgaatacg    48600
cggcattata catcagcggc gttctttcag ctgccgatac attgtacttg gttgggatga    48660
gagcgaagct gcttcaagaa cgctgtcagc gaggcaccca cgcgatgctc gccgttcgag    48720
catcaccggt cacgctgtgt gaagtattgg ccgaatccaa ctgtgaagta gcctgtcata    48780
atggccctaa cgacactgtt tgagtggac cacttaagga ggttatgaac cttcagaatt     48840
ccctgtctgc gacaggtatc aaaggtactt tactgaagct gccatttgcc ttccattctg    48900
ctcaggttca gcctattcta aagagttca agaacgtggc ccgtggtgtg accttccaca     48960
agccacagat accagtattg tctcctcttt tggttaaggt gatcgatgaa aagggcaccg    49020
tggatccagt ttacctcgcc cgccattgcc gggagccagt caagatggtg tcagtccttg    49080
aacatgctcg cgatcagcat atcatcacag atcgcacaat tgtcattgac gttggaccca    49140
aggcattaat ggctggaatg ataaagacga cacttgataa ggacaccagt tcggctctgc    49200
caactctggg acccagtcta gacgtttgga gagcctgac taatatcttg ggtacgttgt     49260
attcacgagg gttggatatt aattgggttg cgtatcacga gccgtttgga tctgcgaaga    49320
aagtcatcga actcccttct tacggctggg acctgaaaga ttacttcatc ccatacaagg    49380
gtgaatggtg tttacaccgc catgaaattc gttgcagctg cgcgactcca gggaaggaga    49440
ctgcaacgag cgactaccag cttccttcag atgagcaggt cgcagctaag aggccttcaa    49500
aacaagatga aagcaaggaa gcatatcccg agatagtggc cactacaaca gtgcaccgtg    49560
tagtggaaga gaagactgag ccacttgggg ctactctggt agtagagacc gatatctctc    49620
gcccagacgt gaaccagatt gctcaaggtc acctggtgga tggaatacca ctgtgtaccc    49680
cgtcagtata tgcagatatc gcccttcatg ttgggaggta ttccatgaac cgccttcgag    49740
caagtcaccc cggcgccatg gacggtgttg tcgacgttgc cgacatggta atcgacaagg    49800
cccttattcc tcatggcaaa tcgccacagc tgcttcggac gacgctgact atgacatggc    49860
cgccgaaggc tgcagctacc acacgttccg cgaaaatcaa gtttgctacc tacttcgccg    49920
atggcaagct tgatactgag cacgcgactt gcactgttcg cttcacaagc gaggcgcagc    49980
tcaagtcatt acagaaaaaa gtacccgaat atcaggaacg aataaagaaa ttaggagagg    50040
gccttcgcca gggccagttc attcgatata cgaccaagag cggatacaag ttgatgagca    50100
gcatggccag tttccatcgt gactacaagc tcctgaacca tctgatcctg aacgaggcgg    50160
```

```
acaatgaagc ggtctcgaca atggatttct ccgcagccaa gagcgagggc acattcgctg    50220
cgcacccggc atatgttgat gccattactc aggttggcgg cttttgctatg aatgccaacg    50280 acaatacgga tatccaacag gaagttttcg taaaccatgg atgggactcg ttccaggttt    50340
accagccgct cgtcaagggc aagacttatg aagtgtatgt gcggatgaca gaggacgaga    50400
aaggagatct tgttcatggc gataccattg tgctgtatgg cgatgctgtt gttgcattct    50460
ttaaagggct ttcggtaagt ctgtctcact tataggagac ccagctaacg tcgtggtagc    50520
tccgccgtgt cccccgaaga ggccttcgaa tggttctgca gcaggcgtcc gacaaggcag    50580
ctcgtctaca tgggaatcaa caagccgtca aacccaggc accacagcgt gcagctctta    50640
aacaaaaacc ccagtcgtca ccaacacagc cgcatgcatc aaaggtggct tactcaagat    50700
cagcaacctc gccaacggct ggaaaaccag tggtggctgc gagagaccta tcgcgagaag    50760
gagatgataa attcaaggcc gttttgagcg ttatatctga ggagagtggt gttgcgttgg    50820
gagaactcac agctgatacc aattttgctg acatcgggat agactctctt agctctatgg    50880
tcattggtag cagactacgt gaggaccttg gccttgaact tggagccgaa ttctccttgt    50940
ttatcgactg cccgactgtc agatccctca aaacgcttct ctctggatca gcggtaagtg    51000
tgaataacga caaggatgag ctggagcctg gtcaagaagc agagacggcg cgccagagc    51060 aactagactt acgcattggg gacgccgcgc ccagcaaagt tagagatgcc aacatcgagc    51120
cactcgatct tggggatgag ctgttccgga acgtgctcag aatcgtttcg gaagagagcg    51180
gagtggcgct cgatgagttg agcgctgaga ctgtctttgc tgacatcggc atcgattcgc    51240
tgagctccat ggtgataacg agccgcttcc gtgaagacct tgggatgtct ctggactcgt    51300
cgttcaacct atttgaggaa gtaccaacag ttgcacgcct acaagagttc tttggcacca    51360
caagcggaag cacgaccggt tcgtcaggct cgggcagctc tgaggacgag accgatagca    51420
tcccatcgac tccggaggaa tacactaccg cagatacccg ggtccctgaa tgccgtccaa    51480
ccacttcggt agttcttcag ggtcttcccc agatggccaa acagatcctg ttcatgctcc    51540
ccgacggcgg cggatcggca tcttcgtacc tcacaatccc gcgtctccat gccgacgtag    51600
ccatcgtcgg gctgaactgc ccctacgcgc gagaccccga aaacatgaac tgcact       51656
```

<210> SEQ ID NO 2
<211> LENGTH: 9855
<212> TYPE: DNA
<213> ORGANISM: Aspergillus nidulans

<400> SEQUENCE: 2

```
atatataaaa tatacacaag ctccctcacc cgctagggaa aaggcacaag ggaagggctc      60
tcactacagg ccccgctccc tcagtacatt cttcaatgtc cctgcaaaag cctcaacata     120
ctcccgattc aacatggtgt aatgtgctcc ttgcacatcg tggaaacgca cgtcctcccg     180
cacaaactcc ttccaggcac ttaacctccc ctccacccag tcgattcggt cctttgcaac     240
atggctcaaa gggtccgcca caaacacatc catacacttg actgatcccg agggttcata     300
gtccaccgcc agactctgca tattagatgc tagacctacc cagagaagat agtactcctc     360
tgaaaggccg agctcgtccc accgtgcggc atcgcagtgc tggcgcaggt accggatggc     420
gtccagacgg cggtttgccc gattaaactc ctgcagagta ggtttatgcg tatacgctgc     480
cagctcggtc atcagaccga cgaagtagaa tagatggatc acgcactcct cccagacgag     540
ctcacgcatg cggaacttga tatgcggcgg aagattccag ctcccgcagt agcggaccctc    600 atcgccgtcc tgttcgagaa gcttgctgac ttcaaatgcc accatcccgc caaacgagta     660
```

```
ccccgctatt gcgtagggcc cgtggggctg gcgttcttta attgcgtcgc ggtaggttgt    720
gaacaattcc tccagtgagg tgaaggggt  ttcgggcaag ccggccgccg cgttgaagcc    780
ttttgcgcgg aaggcgtaaa cgggtcggtc tgtaatgtga tgggccaggt tcacgaagac    840
taggacctca ccgacgcccg ggtgtaccag ccatagagga ctcttggtcc cgtgcggttg    900
cagggtcacg acgggtcgt  agacgtgcgt ggaagactga tcctgtgagc gaggcgcggc    960
ccctgttgcg agggcgacgg ctagccccct ggctgtcgag tctttgagga tgtctgttag   1020
gcggaggggc tgagaaggct gtaggcactt attgatgcgg tggatgatag cgactagatc   1080
catcgacgtg gcgcctattg agaggattga atcgttgacg ccaaagctgt catcatcaga   1140
ccggatctcc agctgttcct tgataatatc cagaattact gcttcatccg cgtctctgg    1200
gctcgcacgg gtcttttgct ggtagcgtct tatagcctcg tcgttgatct gctgctgcgt   1260
agcgaactgg ccttcttcca gagccgtctt cagttttgcg cgcgacagtt ttcccagcgt   1320
gctctttggc atatcctgcg gacgcagcgg cactacgcgc ggccgggacc gcgtgtgcat   1380
ggccacgaca cggatgatgc tgcttttgcgt gctgaacctg gcttcgtcat cgctctccac   1440
ataagatgga aggtagagca caaccacgac ctcggtatcc atggttgcat cgcggctgct   1500
gaacgtgcag aagtaactag gtgttgcgcc tgggatctgc gcctgctcga gagcagcatc   1560
cagttcgtac gggaggtatt tgactccatt gatgttgatc atctccttcg tgcgcccgtc   1620
gaggtgcaga ttgccgttgc tgtcaatgaa cgccagatcc ccgtccgga  accatccatc   1680
gctggtgaac gcctctgctg tggcggcagg attattgtag taacctttaa agacaacttc   1740
cccggttact tcgaggctgc cgcgctcacc ggggctgcc  tcttcgctcg gagtgtcaag   1800
ccgtgtcacc cgcattcgca ctccaggcat cggtttcccg agacaggcga actcatggcg   1860
ctgggcgtga tcatagcttg ggcagtgcga gttgaagata catccggcca cggtttcggt   1920
cataccgaag gagggcttga aaacgttgtc gggagcccc  taccggctga ggagggattg   1980
gagtgcaata caaacctctg tgacgttcgc ctcaccaccg gtatcaatat agagcgtctc   2040
aaggttgagg ccggggtcca ggatatactc tggactcccc gactccagct gtcgccgcaa   2100
cttggcgcag aggaagttcg gcatgaacgt gcgcgagacg cggtgtctgc ttatcaggtt   2160
aagaagctga gccgggttga tgagaagatc cggagcaggg acttgaatct gtgatatgcc   2220
ggacacgatg gcgaagatat ggcagtggac tagattggcg acgtggtcca tgtgcaccca   2280
ggagaggaac gggctgcggg ggaagcggag gctggccgcg gtggacttgc ccctgaaggc   2340
cgcaaggagc tgttgatggg tcagagggac agcttttgcg ttgccgctgc tcccggaggt   2400
cagcatgagg gcaagcatat cggtcgaaga cggggttagg gcaggcagag gtgcgtcagc   2460
aacgtccgca atttcgggag ctgcgaggat ctcatccact gttcgagctt tgatccggtc   2520
atccgctgtc tgctcttcaa aggggggccaa gagggcaggc cgggtcagac agaccggtga   2580
attgagcgtc tcggacagat gacgcagatg cctctctcta tctgccgggt tctggctgaa   2640
catcccaggc ccggtgaggg caggtatgcc cccagccaga aggacagacc agtaccatac   2700
gatgctgtcc agtgcggact caaagtgaac gaggacaatg gacttggggc tacatagctt   2760
ctgctgcaac agtctggtgg cattcgcctc tgcctgatgc agcagatctt tgtaggagac   2820
tgtctgtgga ggtgatgagg tgctgatgct gttгggtgg  tatactataa tgccctcatc   2880
ggtatgagca gcagcatgtc gaagagcgtc cacgatgttg ccaaacgggt acttggctgc   2940
cctgagcggt gcgatctcgg tcttgcttgg tgccatcttg ttacagtcta agaggaggtc   3000
```

```
ctagcctggc cagaagggtc tcaatgagtg agttatgagt aagttgggtg agccactgtg   3060
cctgtttctc cgcactcaag acactttaag tatgcagcct gccctaatac gagatattcc   3120
cgtcctcgcg gggtaagtcc aaatcaggcc cgtgttgcac aatgacgata ctattattat   3180
tactcgttca tattacacgc tgacgggata cgaggttgca ttccgccaca cgagatacca   3240
attcaaggtc acaaaaggac aagctgcagc cgggcctgga ccatggggcg tatatatgat   3300
gacagtagag tactctgaaa ttccttgcaa acagtccttt cttttgcgca gaaactgtct   3360
tcatcatggc tacagaatac tggtcccgtc atctacgctc agtgctggct ccgctgttcg   3420
ctgcagctgg cacatactct cctgaagatc aggagtccca tctggccttc attgacgagc   3480
acattgcgcc caacctgggc cctctccctt gggagcccca tggaccctac agcactcctt   3540
cctccctcgt gggctccccc ttcgacccca gcatcaacat cgtctcatcc ggaaaggcca   3600
aggtccgttt cgactttgac gtgatcagtc cacctgatcg aacaggccca gaccccttg   3660 cagagggatc cgccagggag atcctccacc gtctcgccga ccttgtcggc gcagacacac   3720
agtggatggg ctacctcatg gatgctctct acctgacccc cgcggaggct gaggttgcga   3780
aaacgaagtt gcctccaggt gttgctatcc cgcccagctc agtgggcttc gacttcgacg   3840
gccccgagcg gacgctgaag ttctacatcc ccagtgtgcg gaaagcgcta gcaacggggc   3900
aggatgtgtc cgaactcatg ctaaagactc tacgtggatt acagccactt gggtctgagc   3960
tagtgccagc gatggacctg attgcttcgt aagctctaac ttcacatctc tagattattc   4020
tgtattagcg cgatgcaagc tgactgaacc aggtatctct caacccgcac caacgacgcc   4080
atgctcccgc tcgtcgggat tgactgcctc gatccaagga cacataagaa cgctcgggtc   4140
aaatgctacc tgcacacgag cagcaacagc ttcgcagtcg tccgcgacgt cctcacgctg   4200
ggaggccgtc tcagcgacga cacctcgctc aagcgagtcg agacactcaa atcggtctgg   4260
cctttgctga tcaacgagct agaaggtcca cagagcgacg cggccaccat ggacgaatcc   4320
tggtccaagc cagagcggct caaccggaca gggtactcgg ggatccagta cacgattgag   4380 attaccccg gtcaggcaat ccccgacacg aagatctacg tcccgttatt ccagtacacg   4440
gacagctctg aggtcgctga gcggaacttt gagagcgcgc taaagaagct ggggaatgag   4500
tgggggctga gtggcaagta taggagcgtc atgcaggaaa tcttgtgagt catttcttct   4560
atttcattta tctatttttt attgttatac gatcccttct gacggccgca aagcaaggat   4620
gtagagaact atggccagac gtacgcatct ttctcctaca cggagggaaa gggcgtctat   4680
acgacctcgt atgttgctat gcctattaag gatgagggag ggggtagcct cgctggagat   4740
ttcggtttca ggaactagat caagtactcg gtgctgtagc gctcaatcag atactagtct   4800
aatcaaatca ttggctgtcg ttgattcgga gtgtaggaac tatttcttag tagacatctt   4860
cctctcacta cccaagacct ccgccaaaac ctagcaccca aatgagcgcg gagcatccgg   4920
ctgtccccca cattgacatc agatgccaag catcgagcaa agtaaagaaa ggtctcgacc   4980
agatctctgc ctcattcctt ttgagtggga tttcgtcagc tgcatgccca gaaagctagg   5040
gctgcttagt acgggacggg ccagctgcac ctgcagcttg gcttcgtatc ccagaatagc   5100
caacatttat ccggagactc gcacattgta tccccttgtg gcgattcgag attttgagct   5160
tctttctatc agggtctaat tcttactgca taatgcgggg ttgattgtcg tacgtactaa   5220
ggtcaacatg cacacggcct acctgcaacc tttcagccta caagatgtaa cccaagaaaa   5280
cccagagtat aaaaaagcgc aaataatata ggctgacctc gactccatct cattcttcag   5340
cctaccatct tgctatttag gttaactccg catcgcagag aaacgactca cccagaacgg   5400
```

```
aaacgactat gcatgccgct ctcgtcccaa cctggtcctc cccctgtccc atctataccg    5460
agattccaga cccggggcct ccgccaccag aacagctcca actgaaagtc ttggccgttg    5520
ggattccccg cgttgtacgg ctccgtgctc gagggatcca cccgactgcc aagtcagcca    5580
gtctcccgta cgaccccagc attgacggcg tagggattga cgaacaaacc ggcattatgt    5640
actacattct tccgctctcg gcgtcttgtc ttgcggagaa agtgaatgtg gaccgggaca    5700
atctggtccc gctccagccc ggggcaccta aacctcaacc tcgaaatgga cctgaaaatg    5760
gatatggaat tgcacttggc gatgctgctg accatagagc tgagacgctg gaccccatcg    5820
caattgcggg gctcgtgaat cccgtgtcga gtagctggat ggcgttgaga caagggtgg    5880 atggcgaaat tacggggaaa acggtcctgg ttctggggc aacgagtaag agtgggcgag     5940
ccgcagtgct cgttgcaagg tttctgggag caaataaagt gattgagtg gcgaggagag     6000 aggaagggct aagaagtgtg gaagggttgg atggctgggt tacctcgggg gatatgcttc    6060
ctggggagac cggggttagg tttgctctac cggactgggt tgggccagtg catatcgtcc    6120
tggattacgt tggaggcagc gttgccgcgg gagtcctggg cagtgctgag attgaagagg    6180
gtagagagtt gcaatacgtg caggttggga acctcgcgct tgagctgggc acggagaga     6240 agcatatgtt tgaaacctta ccaggccacc tgatcagccg gaagcccatc tgcatccgcg    6300
gatcagggat gggaagtttc agtaggaggg atctggtccg agagatgcct ggcttggtgg    6360
catttcttgc acgaatgaag gcgccgtttg ggattgcgag cgcgccgatg tgcgaggtgg    6420
cgtcggtttg gcaggatgag gatacgaagg gaagccgagt ggtgattgta ccttgaacga    6480
cacttgtacg aactggggcg gtttgtcatg acacattcaa cacggactga cagttacaat    6540
catggtagta gtagcctgag atcccgaata cgaagccatt cctgtggttc atcgccttct    6600
atgctatata gaggctttta attttgctgg tgtctagtat caaacccact actgtagacc    6660
atcgtgctac tgaatatcgt accaacatca ccatgggctc aataggggcc aataatgctg    6720
tggcggaccc aactcctctt ttctcgtcac gggtgcagaa atgggagccc ggtgcaagta    6780
agccacgttg gccatgacag cgcaattcca agctgaccag atcttcagtc cggagcctac    6840
tccctctcga agcccttcct ggcatgatct ccctcgtggc aggaaaaccc agtcccgaga    6900
cgttccccat tgctgagatc gccatctcac tcaaggatac tccagccggg acaggtagga    6960
tcgtggttga tggggacgag ctcaaccagg ctcttcaata tggtcttcct cgaggaaatg    7020
cccagctaat ccaggtttgc tctgtcccctt agtctccata tttcctactg atcattgttg    7080
ttcagtggtt cgaaagtctt cagaggagcg tccacggcct cgatgagaac ggaggctggt    7140
cgtgctgcat tggcacatgg aagtcaggag ctcattcatc gcgtcatcca ggtcttcact    7200
gatcctggga cccagttct ctcgaaacg tgggtctcac tcccttgta tgcattcccg       7260 gacgcaggcg ccgctgactg aagccataga ccagcatatc cgtatgattt cctccaggaa    7320
ttttcagagt ggacatttta gcaccttgct gacaggacc acagaggcgt cgccgggttc     7380
cttcgcgcag acggacagga gcttatcccg gtctactctg acgcccaggg cctcaatccg    7440
gccagcctgg agcaggcatt gtcggagtgg cccggagact cgccgcgccc caaagtcctc    7500
tatacaaccc cgactgggtc gaacccaacc ggtcaatcct gcaccgagag ccgcaaggcc    7560
gagatgtaat tactcctctg cccagccact gctccagacc tgagactgac agttccatcc    7620
cgacacctat agtctccgtc tggcaaagcg attcaatttt atcatcctcg aagacgacgc    7680
atactattat ctcaactacg gagacgacaa acagagagcg cggagctatc tcgccctcga    7740
```

| | |
|---|---|
| aagagacgtc aatggagagt caggccgcgt cgtgcgtttc gactcgctca gcaagatcgt | 7800 |
| cagtcccggc atgcgtctgg ggatcctcac agcacaagca gcggttgttg acaaggtggt | 7860 |
| gcggatcact gaaaatataa agtatgttta tccttctctc ttctcctgtc ctgttctggc | 7920 |
| tgcttcaaat gactcgctca ctgaatccca gccttcaacc ctcctccaca actcaacttc | 7980 |
| tagccctctc tctactccgc cactggggtc aagctggctt cctgaaacac tgtgcagaag | 8040 |
| ccgccgaggt ctatcgacgt cgccgagacg tctttgtttc tgcggcggag cggcatctcc | 8100 |
| agggtcgagc tacatgggtg gttccaacgg ccggcatgtt tgtctggctg gaacttaagt | 8160 |
| tgccaccgga atggatagc ttcgagcttc tgaagagcca gggaatgaag aatgggttc | 8220 |
| ttgctattcc tggtgttgcc ttcatgcctg gaacgagca aacgtgctat atccgggtga | 8280 |
| gcttcagtct agttcctgag agagatatgg atgaggcgtg taggcggatc gcgggtctag | 8340 |
| ttgatcgatg tgcttgccat tcctaagctt attatacttt tgttcgatgg ttctaatact | 8400 |
| atttctcccgg tcaaaagatc ttcgccatga atttggttca ctcgctatct gtaatcacgt | 8460 |
| cggatccagg tgcagctggc ttctgcccat acacaacata tctattcgct cgactcagca | 8520 |
| tataagacct cgtaggacag tcatgaaaag ggatggtaga cttacaccgg ccagtaacca | 8580 |
| tgcacaccct cattcatcag ctcctccttt acgttcccca agaacgtctt tgcatcatcc | 8640 |
| atctcccatc caagtacttt taccaacaaa gccaccgaaa actcttcaaa gcgctgcaac | 8700 |
| acattgtaca gattccaaag acccaaggtc ttacccttttt catccgcagg ccacgggttc | 8760 |
| gtgggccaat tatacgcaac ggtgtggcaa ttcacgaatc cggcctcgcg catccacgtc | 8820 |
| tcatatttgg caggattgtc cacgggacgg ttcatcttct ttgaggcctc tataagaaga | 8880 |
| cggccccatt gggagagcgg gttgttctct gatagggttc cgtcgtcgct tgtgacgggg | 8940 |
| ttactgagtt cttgcatctc cagccagccg ccgggagtga gggagctttt tgccagtgag | 9000 |
| accgggctca gcacgattaa gcgaatggta cttgcctgaa cgcctgcttg aagagtcggg | 9060 |
| gctcgtctag gcgccggtga tgctggcggc aatggacaaa gtcgaactgg cgggtgtatg | 9120 |
| tccatggttc gttggcgtcg cttgcgtctg gaataacact gagacctaga ggtatttttac | 9180 |
| ttgtgggact aggatcgttg gccacgatat acgcagaagg attctgttca gctgctaccg | 9240 |
| gttaggggat atctagtgta tatagaccga gaatgctgca gcctaccaaa agcatggacc | 9300 |
| catgttgagt ctcctgttgc tatatcgagc acagattgca ctggtgacgg taggggagat | 9360 |
| aactgaagtt tcccatctag ggttagatgg aagagctggt gctggagtgc ttggtggtgt | 9420 |
| cagtctggta cgccttgaag tttctatgca accactctat cttatccacg tagacggacg | 9480 |
| atggactaag cttaccaagt cgctctgtct gtgagacagg tttcgcgtca gcattgcgtt | 9540 |
| catagtcagg gatcataaac actgcctgat acggacctcg atatcccgtt ctgtaagggg | 9600 |
| ctcaattagc ttagactggt aacgtataca tctaaatctt catacctcca ttattggttt | 9660 |
| tctgaaacag tccattcctc gcttgtccac tgttgtccag gtactttttgt acggactcgg | 9720 |
| cgaccgcatt ggcaaggtcg ttcctgggtc agttagatat tgctgtaaaa tatgtctact | 9780 |
| agtgtcaagg acgtacatgt ttgcgtacgg gcggttaacc atggcgacgg attgttaata | 9840 |
| agattcttgg tacct | 9855 |

<210> SEQ ID NO 3
<211> LENGTH: 24650
<212> TYPE: DNA
<213> ORGANISM: Aspergillus nidulans

<400> SEQUENCE: 3

```
agcaagatgg cagcccctgg agatatcaca gtgaaaaccc ttaaagggtc gtggacattg      60
gtatacttgc tcctggcttc cccaactggc atattacaga atgctgacgc taagtaggac     120
aagtccgttt ctgatagcat ggacggtatc ctcaggctgg taggagcgac cagaacgcac     180
cagaattatc gactgacatg gtcttctagc aaggcgtggg ctggctcaca cgcaaaggga     240
tcagcgctgc aagcataaca ttgcaattca cctcgggcgt cgagccatct ccatcttcgg     300
gcgaacccac ggtacatctt acaatgcgcc aaacgctgac cggcggaatc ggagcttcga     360
ctgaagagcg catcacggac tgggtcgaga gagaacgaag caaccacatc tacggcgacg     420
tgctctcgcg cagccggctg atcgctggtg ttcgggagga cggttctgtg cgaccagatc     480
tggatctaca atcgaagcct tccaatgacg cgatcaagga ggaggtccag aaattcttgc     540
gtggagcagt gggtcccacg gataccgatg accttacaga tttgtttatc cacgactttg     600
gacgcaatga aaagtccggc tggacagcag agcaggtatg ggcactgaaa ttcaaacggc     660
aacctcgacg ggtactaacg atagtctctc tgcagatttg gagcattgaa actattaact     720
ctgagaaatg tctcgttcgc cgtgttgcgg tcgtgcagga agaagggtat gaagtggccc     780
gcctggtata taagttcaat gggctctaaa tccattactt cgcctcgtgt ggtgaactac     840
cttactgtat atcccgcctg gcgcgcatgt ttccctgtgg atactctacg aatcctttac     900
gctgcattaa gcttgaaata gcaattattt gaaatatgga aattgagcac aacctaatac     960
ataaaggcct tttatagttt gccagctcga tattccagtc ttcaaagtca tttagctttt    1020
ttattgctct tgaattctgt aatatatggt tcttaatctc cgctggtccg gattaacctg    1080
ctagcaatct cacgccgccc tatctggcca ctggcagctc tacaacagcc gcagggcgta    1140
ggtgctgaag aagaccacgc gtcatgatat gatcagtgta ccgtaaacaa ctaaaaccga    1200
cttaactcca taccgcaaaa acatatggag ttcaaggaat ggttcaggtc tcagacaagt    1260
tcatagaagc taataatgcg gccagatccc cctcgacgca atctcggcaa ggtgcccatc    1320
aagatccgca aaataaatgc tcttcccacc gcgttcccag ttcgtgcagc tgataatcgg    1380
aacccccttt ttctggaggt atgcttccca cttcgctaca tcttcggtac tctgacggc    1440 gacacagaag tgctgcttca ggctgtcaat gtcgccatcg ccctctttgg ctgcgttgag    1500
cttcgcgacg atctgcgcgc tgggtccatg ccaggaatg acgccgctgg gagtagtaat    1560
atctgcgtct gtttggccca gttggaagag gaggagagtt gtattgccta gggagaagca    1620
ggcactgcgg tgctaggaag ggtatcagcc tcaccttaac agttgcccaa cattgttggt    1680
gaaaagggat cgtaccgatt gcatgaacgg cttaatgttc agcacatcct cataaaattt    1740
ccttgaagca tggatatcgc gcacgtagag gcatgtctcg aggacgtggg tgaggggagg    1800
tgggttgttt tcagtggcca tgatccgatc ctgtacagga acgtatctag ttcaatgttc    1860
aaagagagtt ctatatccta tctcgtaagg actaaacaaa tatggattga gcacagttgt    1920
ggatcaagat acagtgagcc agcttctacg gagcccgtcg aatccattta tgtctaattg    1980
attgaaaatt attgggtttt cggctcgcat ctctggcctg aggcaggctc tcacttcagg    2040
atgacgctca catagttgcg cgtgacccat aaatacggac tgccggagat ctaccttact    2100
aagcacatta gcacctcggc cgagtgctta accactgctt aacctggttg taactgccca    2160
aataatttgt taacatttcc ttcaatgagg ctctttttaa gagtctcgaa aagctacaaa    2220 ctgttttat atcatggata gggcatcaga tctcaattat attcgtttgt cgcagacgat    2280
ggtcacatga tcaagatcga cgctagcagc tcttagagtg cggggtctta gctcggcgtg    2340
```

```
gcttactctg aattccgcga acatggctca gagcgcggaa cggataaaca ttttaaacat    2400
ccgaaataaa gttctgacta atatactggc tgtcacatca acatcttcgc ttcgcttcag    2460
agtctgtccc agattacgaa gcacattcat gaaaacgcct aactacgctc ctaaacaggt    2520
cttagaaagc ctaatcgttg agtacgatta tcttttctat taagttgttt caattttagt    2580
tattttatac gagcctattc actagtaaca atacttgtaa caatacttgc ttctgatgaa    2640
ttctctctca taaggcttta tcctacaatt attagagaga ctttctcta ctatagcttc     2700 aggtgcttat gggctgattt catagtctca tcacgtatac tagtgaagaa tgtcagaatg    2760
caagatgcca gaattgtctg aaatatctac cgttagttct cgtacttgtt aaagatggat    2820
ctaaactagg aagttggtga acacacccga acttaccagc cttgattgta gactcccgca    2880
acagcttcag agcccaacca aagccacaat atagaagata tgtcgttacg cgtaaatcac    2940 tcagggaac gcatttccgg atttctgcac gaacgatatc tatctgctgc gcttgacaag     3000
aaaaactcca gttgctctgg gtggtattac taattccacc actggctaat ggttgctgtt    3060
tagaatagga ggaaacgacg ctaaacttct gtgtggacgc tcgcgtcggc gtcaagttag    3120 tggcttttggt ggacaagtcg ctcgtaaagc ctgggtttag atgccgtgat gtctatcatg   3180
atattcattg taagaaggag gtaaaagaga tctatgatag ggagaggctt gtaaacaaag    3240
tcttatagac agggaactcc caggtacagc atcatctcaa ccgttcactg gggagttgat    3300
acatacgagt acggcgaatg agagaagcct acatacctaa attgctatga tttgctaata    3360
ggccagtttt agtgcaatta caatagttta gactccgtca gtggatagcc tgcgggaaag    3420
agatggacct ctaggccgcc agctgtgatg tcgggagcat cgcacgaaat caaccaaata    3480
cgtgtaccaa agggcgctgt gacgatatat accaccgaag ctctcgataa ggatctgtga    3540
tgcgttcgga ggagtctctc gttgtcttct ctgactgtct gctctaatcc agcgcggaag    3600
gttgtcctct caccactgcc ccattccaat gactcggctc ctattcatgt tagtggtaca    3660
gatggtatag ggggctcgcc ccttatcttg gttgatgtac tttgtattag acggtactcc    3720
cattcacgct tctctggctc cgggcggcgg tgcgaatctt gccgcgtcat tgacagccag    3780
gtactgatat agggtatggc tgctcctaaa atgttcggta tccatatggt ataagcattc    3840
ctggtcttga gagtgcccgg catggccaag gtgaaaccta tgcgaaagag ccttccgggg    3900
aacaatccca ggaagatgtc actactgcac aatcaaactt tcacaagcaa atatagaccc    3960
ctacggttta tagctgacga ttctgtatct attactgtat catgctgggg gttatggaag    4020
tacagtcctt tgtgctgcca ttccgtagct cttgtatggt ctatagggtt gctttctttt    4080
taaacagcaa tgaaagttac tgagctaatc ctcgactatg agtgacaaca aaagcccaag    4140
tcagccatga aatatctttc tctgccttat caacaaccaa tacactatgc tgagccagta    4200
aaaatgcagg aatagacggc ttcctcctac cggtcattaa cccctcgact acccttgccc    4260
ctgcttcgcc cacggccacc actccatcat tcagcaagca aggttccct tgctcacagt     4320 cccctggcaa tcaatacgct ccatgttgat gccatctaac atgtcataat tgtctataat    4380
tctaacatgt gttctccaag gcagaacatc ccgaagaaag tacgtctgga caaacaaaaa    4440
cacatctccg ttgcataccc ggggatatac actagtatct tgctacgcgt ctggggaaaa    4500
tggtggttct accgtgaaat gatcccaggg acacgttggt agttcatatt tgaaaatatt    4560
actacgcaaa ggctaatttg cctacggttc tagttttaaa ataatagatc attatatatc    4620
tactacgtga ttatattttc tgtctcgaga ggcttcagtg attactcgtc cgtctggcat    4680
aacgttgatg ccagtctttta gcgctaatgt catattggta tttaacgcgt ggaaggactt    4740
```

```
gttgaattca ataagacgac acttcctcag tgagcccacc gcttcttcat tttatgtttt    4800
ggtaacgttt actggcccag ggactaatta gacgttctaa tccagtctat tagtacatat    4860
cgagccctct ctacaacaca caacacctt tctcttctctc tctctctctc tcttttttt    4920 ttataatttt ttttttttg aggttgtctt tatatattga ttcctgccag ttgtttggta    4980
aattcgaatg acatggcaga cctaaaaaat acaatagtcg cggcggcatt tccttcgacg    5040
ggctataatt atttgtttca gattgtttcg aagtatatac attctaagac gctgacccac    5100
aatcaagtaa caagacggca tgggtagctc caccttcct ttcccaagca ccctcacttc     5160
agggtgagga gccctggccg atatggcaga aggtcgtagc cggggttgag gctgggatct    5220
cggccctgat agaggagctg caggttgcaa gggtcgatgc tcattgtctg atccggggta    5280
ctgcgcacaa gatcgccatg gctgatatcg tccgtccagg tggcaccgct gttggctttg    5340
ccagcaaaag gtgcgctctc agtggccgcc tgcggtgtcc atgagccacc aaggctgtcg    5400
gcagtgaatg accggaaata cgccccctgt gccccgatcg cttcgacaat cattaggtat    5460
gtgtctttgc tttgacctga gaccgtgtac acctggacag cttcgaacaa gttgtttctt    5520
tcatctgaca ggataatctc ggactcggta ccgaaatcgc cggggaattg gtcgatgggc    5580
atactggcgc gatagatgcg gccgttgtct cccgcgaaaa agaggtacat tgttgtactg    5640
tcgccgatga ctgtctggtc aatgaccccg gtgtctgagt ctgaaattga cccggaaaag    5700
agcggttggg gtgatgacca accattggca tcggttggat cactcgacgt caggtaggaa    5760
aatgcagtag ggccccattg gtacgcgagg atccagacat ccttgggctc gaagtagaat    5820
agcgtgggcg cgacagtcga ctgagtcatt gcgttctggc tcgccgtggc catgtcggac    5880
cagttcgaga agaggccgaa attcatggag ccccagctcg tgcccgtatc atgataagtt    5940
gcgtacacaa gatactgccc attgtacggg accgcagtga agtccttgag tgatgcccat    6000
ccgtccttgg gttcagcgag cgggccagtc gacgttccagc tgtacgttga cgggagaccg    6060
cactgcgcca ggacccttgg agcagaccaa aggagggctg cgaatgtggg ccaggtactg    6120
aggtttctca ttgtagcgcg ttggttctag gagtcaagat gagatgcagg aagagttcgt    6180
ataaattgtt ggtctcagct gaaatgcctg aataccgtca accttaaata ggctgtatgc    6240
aacggattgc ccttttctgc cacggggctt gtcccccacg aagggtcat ttgtttcacc     6300 ctgtggggga tccagacaa tcactcagta ctgctccacc gacgcaaagc actgattcgt     6360
tttctggacc ttgaatctcc aagcccgccg acgcaaagaa agggtgcttt gacacgccaa    6420
gcaaagatcg gcctttgggg aatcttttgg gtcgcaaccc tgattatccg gttaaagtca    6480
acaatcttct ccctcaataa ttacccggac gaatgctgaa aggcgtcatt ttcgagggcg    6540
gatccactgt ttcttactgt gctggttgtt gatgtcgtgg acgtcaggcc ggtccccaa     6600 ctatgtcgca tgcgcgcaag ctggtgagta tgttactgtg gtatgttcta ttgtgatatg    6660
tctttggaga cgtgcacatt ataccgttg ttttcatata aactctaaaa gcatcaaggt     6720
ctatacatct ataagtgaca atctattcca ccgcccgagt cacagtttca ataacaatat    6780
caccaacctc acttgcatag ggcgggcaca tcatggagaa gtgatctgaa ggccaagtta    6840
gtaagttacc atagatgggg gccagtatag ttccaacgta cctccattga cggtatagac    6900
agcgatatgg tctccaagta aatcctccca cccattcgtc ccaaactgct gtcggcgccc    6960
atagaaccag gagttgaaat agcgctcaaa ctcatccagg ttcatctcgt acatactctt    7020
gccgatatcc aagccaggtc gacccatgga ggcaattggg gcatccggcc gattatcgag    7080
```

```
acccagtaag gcccagacaa cggcgacttg ctttggctgg cggtccgatg ggaacgccgg    7140
tgcatcgtag cgggagaggg cccggcaagt tgccatgaga tgggcacgct ccttgactga    7200
gaggtcttca gggaggtcgc gtgcgcggtt aatgccctca aaggtaccga gcttgtcgac    7260
aaaatcggtc gttacgatag aggtcggaat gagcgagggt gcgcgcatgt cgaggatgat    7320
aagggcctgg atggtttcac cctcgcgtgt cagacggtgg gcaacctcgt aggcatacat    7380
agagcccgcg gaccaaccgc cgatgaggta gggtccatga ggctggatgc gccggattgt    7440
gcgcaggaaa atggtggcca tctcctcaat ggagaggtcg aagagctccg gctgctcgag    7500 gaaggggggac tcgagggcgt aaatccgccg gcccttgggg agggcttttca ggtgatgta    7560 ggactcaacg gtcccagaac catccgtcgt caggaagaga ggggcttcgc gggagcgaga    7620 ctgaccccctt tagtagactg cacgcgagac ggcggcatcc agtttgtgct ggcggctgga    7680
gtcgatcgtg gtctctttcg ctgggttcgt cgatgtctgg gcaggggcac tctcctcctc    7740
tgcgtcatca tccagagctt cctgggcggc gcccactgta gggttggcgc tgaagaacgc    7800
agcagggagt tcgatccccg tcttggcgtg aaaggcagcg gtgattttga tgctgagcat    7860
cgagtccata cccaccgagt caaaggtcgt cgacggcgtg agatcactgg cttccaatcc    7920
cagcgcttga gccacgagag agagcaggtg ctggcttggt gccgggcctt gcttccgggc    7980
ttgggtctgt tctgggctag ggtcggcctt ggtgatgtcc tcctccaggt catccagtgc    8040
tgagcctccc agctcggctt cggcgtcagc cggagtaggg aagttggtga agaaggctgc    8100
cggcagctct acggccgtag tgcgctggaa gttagccagg atggagatgg ccatctgcga    8160 atcgacccccg aactcggtaa aggtggtgcc gggtgagctc ttcatctccg ccacactgac    8220
cccagtctgc tcagctacgg cctgcagcaa ttctgtgccc aagtcgacca tatctgacac    8280
gctgctaggt gttggtgacc tcgacattgg ggtgttcgag ccggaagagc tgctggggct    8340
gggcgatgga gcgagctgcc gggcacgctt tgccatagac ttggccggcg cagcagccac    8400
cggcttggtg gagcggccgc gggtggcacc agtgagcagg gcaaagaagt ctcgctctag    8460
cttcttgaag cagatgtccg agcagactgc aacaaggcgg tcctggctat cggtggtata    8520
gacgtcgcac agacttgtgc cagccttctg atcctgctcg cggatcgtcg cgtagacgtg    8580
gtacgggcca ggcgaagaga gatcgcccac gatccgcaac gagccaatgt ggttggcaat    8640
gtggacttca ttcttcggtc ggcggacgtc tgcgttgagc aggaagccgg caacatggac    8700
caaagcatcc acgcgaagg ggctgctggt gaaggtaccc aggtcagcgg tgggcgtcag    8760
ttggagagtg acagcagcgt cgtggaaatc agcggctatc actgcttctt ggactgcgtg    8820
atatggcgcc gagtagtcaa cgatctctga gaagaccttg tagaagagcg ccgtgtccat    8880
ggcatggact tcgcgaggcc ggacggagcg gttgagggtc tgcacgcgcg cccttaccag    8940
cgactggatg cgagaccagt cccttcgaac ggccgaatcg ggctggccta gacgcatcgt    9000
cgccgagccg tacccaactg ctcctttcga ggtttggccc ttgaagtgca cagacacggc    9060
attggacttg atgtcgagga ccgcctcgac ccagacctgc ggcaggactt ctatatcctc    9120
gcggagcacc agcgggctgt gcatctctaa actgctcagc tcgtaggtgt tcagtgcagc    9180
accagcgccc ttctcctgct ctagaaaaac tgccgcggtg taggcatgt cgatgaagat    9240 actggctggg cagatggccg actcatcgac gacatggcca cagatggcct tggccagctt    9300
gggatcggag aggtctactg taaatgtccc caaaatcttc ccctcctctc gctgcaactt    9360
ctcaactgca tgaagtgtgg tagatgccag cctcgagagc ccggtagtgg atggtgtggc    9420
cgacgcggcg ctcacagccg cagcaggggt tttgtatgaa tgccaaaagg tcttgaggtc    9480
```

```
gaatgcatac gtggggagat cactgatcaa gcgaacagtg tcaagatggt ccttgtggaa   9540
ctcactccag gccaccggga gctgcgcact gtgggctgca gcaagagtcg aggagaccga   9600
ttgccaatca tcgccgccgc gacggaggct gggccaggcg ttaattttgg ccgactgcag   9660
gcaggtagcc atcagactga tgcagatagg atggggcccg atctcgacgg caaatgagcg   9720
gtctggtatg agtccctctg tctcgcaagc gcgcacagcg tcaaggaagg ccactggctc   9780
ccgcgtgtga cggcgcaggt agttggcatc gaaaacgccc tgctcgccgg gcctgacaat   9840
gcgtccgagg acgtgctcg ccacaggaag ggtcggagcg tggaaaggga cctgggctgc   9900
actggcctcg agctcgtcca acaggacatc catctggcga gtatggaaag catgctgcac   9960
tcgcagacgt gtggtcgaca ccttgccatc cgactttagg tattcgtcga gggcctggat  10020
ggcggcgaca gggcccccta ccacggtgct ggatgggccg ttgacacagc aaacctcgca  10080
tccagtggtg gccgctgaat cacggatgcg atactgcaca gtgcgcatcg gcagtccaac  10140
agccagcatt gctgcttcgg atggcggaca ccgagtgaag atgagcgtgg cgcgtctgaa  10200
ggccagggcc agagcatcgc tggcagacag caccccggcc acacagagcg ctgcatactc  10260
tcccaggctg tggccgatca gcaccgtcgg tcggatgccc agcgaccgcc agtaccgagc  10320
gagagcgatc tcgagggcga cagtcgcaac ctgcatgtcc acttcggtga cggtagcgcc  10380
ttcggcgccg ctaccgcgga tggcgttgag gaacttcgtc ggcagcccct gcacctcgca  10440
gatcgactgc agagagtcca agaggcgacg gaaggtgggc gacgtgctat acagagcacc  10500
ccccatgccc aagctctgtg cgccttggcc tgtgaaggta aagacgactg cgggtggcgg  10560
cgcggattcc accttgtctg ctaatggctt ctcgagctgc cgcacaaggt cgctagtaga  10620
tgaggccaca tacgcctcac ggtggacgtt gtgtatccgg cgtgcggtcg tcgtgtaggc  10680
gaggtcggcg aggttggtgt ctgggtgcgc agagagatac gcatgaaggc gcttccgatt  10740
ggcctcatgg gccgttgcgg tgcgtcccga ggtgacaacg acgtggtgtg ttcgaagacc  10800
aggcccagaa gctgggctg gcagggcaaa cgccggggga tcttgtagca gcatgctgac  10860
attgcctccg gcagcgtcga agttgttaac gaagatatac cggggctcgg cgccgttccg  10920
ggtccaagac tgtccatttg ctagctggat ttgtttcccg atcaacggtt caagatatgg  10980
gttcattttg atgggctggt tcggctgcgc tggaatcttg tcgtgctgca ggatgagaat  11040
tgccttcatc agggagatga tacccgcagc ggcctcactg tgtccgatat tcgccttag  11100
ggcgcccaca atcagcggtt tctcgcgctg gttcccgttt gacggcgcaa agacgctctg  11160
aacggcatgt gtctcaacac ggtccccagc ctgggtccca gttccatgca tctcgacgac  11220
gtccacttgc tccggcctga cggccgcctg gcgcatcact cggcgataga gagcccctg   11280
ggccttctcg cctgggtagg tgatggagcc agcgcccgca ttgcagttgc gagatgcacc  11340
ggcgattact gcgatgacgt tgtccttgga ccggacagca tcagccagac gcttgagaat  11400
tactacaccc acgccctcac cacggcagta gccgtccgcg ctgtctgagt acgtcttgca  11460
agcgccggta ggcgacagga aaccccctg gctcagtcct gcaaaccatt ccggcgcggt  11520
cagcagcgta ccaccgccga caacggcggc gtcgtacttg cctgccgtca gagcgtcccg  11580
cgcaaggcac agtgctgtcg cgctggatga gcagcctgtg tcgatgctgt agaagccacc  11640
ggcccactgg aaaaagtggg atagtcggcc aggcgcaaaa ccacggttga caccggggag  11700
atagtgggtg tctatcccct gctggtcgtt gatgctcttc cagtcgtcga ttgtctggcc  11760
aaagtaggtt gcaatgcgag gcggcgcctg ctcgctgtca ccgggtgcgg cggggggttgg  11820
```

```
aggtgagtag cccgccatct ccagggcttc gtacgtggtc atgaggagca tgcgctgcac   11880
gggatccatc tgcatcgcct cgcgaggaga gatgttgaag agtcggtggt caaagtcgcc   11940
ggggttcttc aggaagcaac catagcgcgc caggagcgcg ttgtgctttg cgcgagtagg   12000
gtcatagaag tcatcgacat tgaaccggct ctcggggatg acctgatggg ttgtagttgc   12060
cgtctccagc agccgccaga actcgtcaag agtgtcgctg ttagggaagc gtccggacat   12120
gccaacgacg gcaatggcgt cggctgggat gctgtcgagg tcgtttccat acggcctcgg   12180
cgtaggacta agctgcccaa gctccaccgc gaggccattc ttctccagga gactctggat   12240
tcccgacgtc tcagttgagg cgccgatggc agtgaggacg atgtctgtga tattggccct   12300
atgcaggtca tgaataaggg cagtgacggc ctgatgaacg tcgatgggct tgttagcgac   12360
ttcctccaca gcaagcttcc aaagctctgt ggcctgttgt gacgaagaag ccgcaatcat   12420
agtcgcgctg ataggggggca gatgagcccc atgcagcggc acctgggcca gtgctgaggc   12480
agggctggtg atcgttgcat gggcgagttc cggtctcttc gccagggcgt ccaaggtgga   12540
cggtggtcca aagacgaccg tgcttttcgt catgacctcc ccgatatatg cttggtttat   12600
cggtctgagt gaggcgttga tcctatccag tgcctgttcc aggtctgcaa tggtggtggc   12660
gctggagatc acttgcgccc atgggccatt cgagtcttcg atgtcttttc ccctccgctg   12720
gagttctacc cccagacgaa aggccaccga gacagcctcc aggcccaagt tgactatccc   12780
atccgctgac gtggcggctg cagctacacc agcggccacc agcccggcgc cgaatcccat   12840
gggaattgcc cttgcccctg catgtccgga taagatcgct ggatcatctt cggcgaggct   12900
attggaatac taacgtcaga aagagacttc aggaatttcc gggtcaagaa gacgtacaca   12960
agcagctggc cgatctggac ggtggtcaga agtaccaggt cagcgacaat gctaccccgg   13020
gtctgggtgg tctgccgctc agcgagctcc actaagtcct caaaggaacc gatatcggca   13080
cgctcgagtc catcaagaga tgctgtccag tgctgtacga cgtttgatgc cgcagccaaa   13140
aggctctgga gtctgcggcg tgacttagag cgcacgttta agtcgtgcac ggcatcaaag   13200
gtgacccgct cctgcgggaa aaaagaacg tgatttggag ccatggtgac ttaaagagaa   13260
gataattaga tattgagatg gggaaatatg tctatgatat tatagcggca ctgctgttct   13320
attgccgtga agagtcaagc tccgtgataa ctcaagctca actccaaagc aggtgcaatg   13380
ggatgtttta tatagcctcg ccttgtcaag taatccgcct cccaaatcct ttttcttctg   13440
gctcacttaa tcatggctgg aagctgaagc cgggcaatcc ttcagctgcg ttgtagcctg   13500
cccccttagg caagccgggc aagaggcata gccatgctcc tctgggtact attcttgtcc   13560
gtacgagggt ccagagtgcc agggtacgca gtttacgaaa gaatgtttcg gtagtggagt   13620
gtacgcgact ctggtccgtg agtatctgtt gagtatacac atctgataga gccccaatct   13680
ggccgttgat gtcagcccag aagcgacatc agcgttacaa cgatagtaca tcgtaagacc   13740
acacttctgc aagcttatcc ttgggcaagt ttcagtgcga tacgaaagaa caaaagaaat   13800
tttccgggtc agatcatctt gtgggcgaat catcagccct atgacggcat acgcctccgc   13860
tgcagcttat actctggtcc agatgtgaat catcatagat actctgctcc tacagtaatt   13920
cagaccgcat ttcattcatt tgcagcctcg atactcagca atgtttgaag aggtactgcg   13980
gtcgagcccg ctgataagga ctccaaaggc ctactcccat aaacctaccg gcccaccata   14040
accctgtcaa atcgtctcat tcctaaacat ggctactgag attgccgaga tcaccaatct   14100
tctgaaacgc gagcgctact accgggacac tgctcagtgg gagctgtgcc gggacgccta   14160
tcatcccgac gcgagcatga cctacattga cgtttcctgg tacgcacaac cagcccagac   14220
```

```
aacagccggc tgcacgctga ctacgaacag gttccaggga aatatcgacg agtttctgga   14280
acgctcagcc agggtgcatc aaggtcgagt caacgtgatc cactcctcct ttgatccggt   14340
cgacgtccaa gtccgcggcc gccgagccac cagcgcggca ttttgtctca tcaccagctc   14400
catcacgcta gacggggttg aatatgagct ggcctcgtat atgcggcttc tctcccgatt   14460
acagaaactt tcagacgccg gtccgtggcg aatcctccgg ctagaagcaa tctatgtccg   14520
cgaccgactg gtatgctcct ttcccggccg agacgctgcg gcgccgctgg tgataccgga   14580
gaaggcttta gcgtatccca cgccctaccg ctgtatggcc tttgtcatgc tacatcgagg   14640
gctcgagcct cgcgttgacc ttccaaacga ggatgatcaa gatagcgtcc ggcgagtggt   14700
ggagggcaat gtggcatttc ttagtggtgc cgaggatata gttgaaggca cagtagcata   14760
ggcaggcgtt gattatgtcc cattcgacag tgctatcttt atctctctcc cattttccaa   14820
atatagactc aatcccggga accgtactgc aataggccaa ttcctactgg tttatcactg   14880
ctccttcttc atatgcacct taagcaagtc ctccgcgttg cggtaggcca ccatctccaa   14940
ctgctcttcg gtcaacaggc cactgccctc gagttccttg aaccactcca gtccccgctc   15000
gttggattcg aaggggtagt caacgctgta catgatgcgc tccacttttg tgttgtggag   15060
gatgcacttc agaggcgcga gactccaact cccagatgta gtaatccaga tattctcatc   15120
ccagacctgc cggagcggtc ggtctcgagg gccccatccg ccccagcgag tactcatgtc   15180
actggctcgt tcgagcatat agggaagcat ctcacccatg tgcccacga tgatcttcag   15240 ccttgggaag cgatcaaaca cccccgcagc gaacagcttc agcacgtgga ggccaacatc   15300
gggatgccaa ccccagcccg ggccgccag gctgatgccg acgggactg ggtaggagcc   15360 catgaagttc tcggccatgc gggccgaggg ccaggtaggg tgcaggtaga tgggcacatc   15420
gagctcgcac gccttggccc agagaacatc gtagtcgtga ccgtcgaaat gctttccgtc   15480
cgcatggttg tcaatcaacg caccgacgaa ccctagttca gaaacagacc ggtctagctc   15540
cgccgccgac gcagttgggt ctgcaacggg caggactgcg aaggcagcga agcgctgggg   15600
atcgctgatc tgggcaatct cggccgcaag ctcatcgttg cctgctctgc aggcttcggc   15660
actgggtcca cctatcgatc tatgcagtca gctcgcgtgg cttttgtgct attctgggtt   15720
acattaggtc ttactgaccc ggagtaaaag catgggagac cacctgcagc gagatgttcc   15780
cacggttcat tgcctcgagt cgcccatctc cgaggcttcg cagctggtcg gcgagaccag   15840
gcacgccttg cagggttcgc tggaaggtct cgccaatcga gttgaagatg gcggtcgagt   15900
agtagtgttc ttcgagggcg aggagtggcg gagtcattct tgccagtaga atgctaagtt   15960
gatctggatt ttctctttgt tgggacacct taaggcagac cggccattca tactctccct   16020
atatattttc cccatagagg ctccagtcta aatgctgacg tggatcgata aaaatattcc   16080
cgtatacgcc gggtattagg gcacagcagc tggagcagcc agggaccgcc ccaatacgag   16140
gcacaaggtc gtctgagaca tcatccgccc ctttgtttct tgacgcatag ttcgtgtttg   16200
aacggtggtc tgattgccga gggaaagaat tgcagggcat ataaaatggg ctccgtcttt   16260
tcttctgggt agctacggtt aaccatcaat tacactaggg ataaccatgt tggccttcaa   16320
cccgcttgtc acagcgcttg ccgctctcat tttcctcttc tgtcaagcaa atgccaatcc   16380
gccgcttatg cagaggctcg tccatgagta ccaatggaag accaagcagg gcctacctag   16440
gcaaggtgct tgcaccccc ataaccttgc ggttcgcaga gagtggtatg tatacgtcca   16500
tgcggcgctc tccccttcc gcgacttcta tttgctgacc ggtttgccag gagcaccctg   16560
```

```
gatgtcgaga cccggcttga atacatcgaa gcggtcaaat gcctggcccg cttaccctcc   16620
atcattgatc ctgagctggc tccaggtgcg cggtcccggt tcgatgactt ccaggccacc   16680
cacatccgcc acaccaggac catccacgct acagggtcct tcttcgcctg gcaccgccat   16740
ttcgtctacc tgtatgaaaa ggcgctgcgc gaggaatgcg gatacacggg gtaccagccc   16800
tactgggaat ggtcccactg ggctaatctc cccatcacgg ccaacccccct ctatgacggc   16860 tccaacgcgt ctcttttcagg caacggagtg tatattccca accgcaacgg cacccctccag   16920 cttttcccaa ttcccaaccc gtctcccgat accgctatct atactcctcc cggaaccggc   16980
ggtggatata tctacgacgg ccccccttgtc gactgggagc ttcacctcgg gcccgtcctc   17040
tattcgtacg ataacggcca atacatccct ccaaacccac gtccggacgg attgggatac   17100
aacccacgtc ccctaatcag agacttcaat aacaccctcc tccagcaagg cgcctcctgg   17160
gacatcatcc tcaacatgct cgtcaacgtg accgacatgc atgaattcca tcctttattc   17220
ttccaaggcc cgcatctggc cggtcatatc ttcatatcgg gcgtcgacaa tgatattttc   17280
acttcgcctg gggatccgct attctggttc caccacgccc aggtcgaccg catctggacc   17340
atctggcagg ccttggacct ggagacgagg gagtatgccc tggacggcac gctaacgcta   17400
ctgaactgta agaacctacc tttccgccgg attttagcag gcgagctgac agtctgcgat   17460
gatagtaccg cccagccgta acgcaactct aaacgacacg atggtattcg acttcagccc   17520
cgagattaca atcgggaccg ccatgagccc taccaagaac gaatattgct atatatga   17580 gtaatcgtga gacgtaattg gcgaatgggg acactccacg gatgagtggc tctcttggct   17640
ggtaccggct tggaccccga gtatgcgcct gctgcatgca gtttgttcga ggagaaaacg   17700
tagtcagtgc ctagtcggtg cccggtcgga atcgcacggt ctcgcgatat tgcctgattg   17760
tataattata gaagctttga ttagaagata tgcatatcta aatttaattc ttcttgtctt   17820
gactgagcac agccagctta ggttatgtat gatatcactg caggctagta tgtatgcttc   17880
tatcagatgc aaggatatcc tagcagaaag cgccccggcc agctagccag attatcaaat   17940
cttcaggccg tgctttggca aagggctgta gcgaaaccgc atgtgtctgg taatcattag   18000
tctaggccga aatagtaagc gcaacaagcc gctgcacatt tccgtcatcg tcctccggca   18060
gtcgctcagc gatccgtagt aagatcgtca tggccaaccc cttgactagc cagcatccgc   18120
agcgctcggt tcgattgacc atcagtgctg cccaatgggc gaccaccacg agagatgctg   18180
gatagtggcg tgccaccagc tccttgaaac gaagcggcac tcgcgtccac caggtcgcca   18240
tcccccacca cgctggtcca acttcctccg acgcaaagct cgtgtcacag cactcaccca   18300
tagctgcgag ggctgacagg aggacaagaa cgtcctgaat attctccggt ctcccaaagg   18360
tatcggccat gcgagctggt aggtcatgaa gacggttccg gatctccgca aggacgctgt   18420
ttccggcctc tgaggtgttc catctgagaa ttcgtgtcgc gtaggccgac gtttcagctt   18480
cgtgtggtgc ggccgcggga acagtactct gaatggtgct gatgatggac tggaggtgct   18540
ctggtacgcc cggctctggc atgatgcgtt gatcgcaggg ggattcagcc aatgcccaat   18600
gtgcacaacg tagcaaacac tcaatctcgg tcgctacctc tcgcagaccc tcaccagatg   18660
tgtcggccag ttctctccat cccgttcgaa actcgaggga gaattcagcc gctcgtttgc   18720
ggtgctgttg gccagccgcc gcattgtccg ggaatgcggc caagtgacag gcagcgagcg   18780
ccagcagacc gcacatcaac catctctgct ggagcgcttg agggactgcc ttttctttcc   18840
agtattgagc ccccgactgc atatcctgcg gacatggtaa tgtcaggctc gttgccgaca   18900
tgaaatggtg aaagtaggac agggtttcaa ggtccacgtt gacagaggga gcggaagggc   18960
```

```
cgggagaagt tgtgaccgtc gttgactgcc gaccaccgtt gtcgtcttcc tgctcttcca    19020
aatcgacatc cccttcttcc tcgtcattct cgctctcgtt ttcctcatcg tcctcatcct    19080
ctgtcgtggg agtcacctca aagtagcgga tcttagtccc ccgaaagaaa gtctgtagct    19140
tggctggacg cgcgagtgac gcatccgcaa taccatggct ctctctccaa tggcccttca    19200
tgcgcttcag actcgcacag agattagcgc aacccggggc tgtacagcgg taccccgcga    19260
tgaccggcag cccgtcgatc gggggtgact ccggaggcgg cagcaacaca tcgtcaggct    19320
cgagaagatc gagctcatta atcatagcga ccagctgctg gcggtcggca cggtagatct    19380
tatggcgcag caggtggctc tgcagcgcgc tcttctggat cgcataccgg cactcgtggc    19440
agatcagaac cccgtagcga ccgtcgtact cgaggatctt ccggggtcca aatctcactg    19500
ggggcatctt gtcgtgcaag agacatgatg agctccagag gaaggagtgc gattgaggtc    19560
ggagggaggg aggttgctca cagacgagag gctttacacg actcgagcag gattgagtga    19620
aatgagaaga atgccaagcc gaacaggcaa cgacagtacc atacagtacc gtaccgtacc    19680
gtcctgttta aagcatagc tgactaagag tagaaccaca cctgctgttc ttattcttgc    19740
aagcggcttg caataagcga gagagaacgg caggtgccgt tctcttctat gtactgggat    19800
actctggact caccctcgtc accttgtccc ctcgtcctca tctcttctgt actgctacag    19860
aatcgcacct gccatttggt tgattgttaa aaatccttga cagcctcaag atgtatatat    19920
tgccaccgtt tcaccatcat tgccctgatg gtttcccatt ccatgcccat tgtccagtct    19980
cgtctctgtc catcttcaaa cagcaatctc tactcagtct cttcatactc actccataac    20040
acataatctc ataaaacaag atggcaacca accaagccgc gtggctcacc aaggcaggca    20100
atgacctcga agtcggtgat gcccccgtcc ctacggctgg cccaggcgag attgtggtta    20160
agaacgccgc ggtggccatc aacccactcg acacccatat gcaggacgtc ggcgtctttg    20220
tccagcagtg gcccaccatc tttggctgcg acgtcgccgg tacagtgcat gagacgggtc    20280
cagacgtcga gcggttcaag aagggggacc gggttattgg gtaagttcat ggccattgac    20340
ttgtcgtttg gctcgtgact gactctgata ttgtagtcac gccatcaatc tggtcaccgg    20400
gcggcctcag gatggtgcct atgctctcta caccgtcgtc cccgcaaca aggcggctat    20460 cctgccggac gctatctcct tcaccgacgg agtcgtcgct cccttcgcgg tcgaggcggc    20520
cgtttgcgtc ctctccctga aagagcccgg tgtggccatg cccggcgtct ccacgccggc    20580
attagccctg ccgtatccct ctcttgacga tcccgtcaag ccgttgggca aagtcctggt    20640
catctggggc ggctcttcgt ccgttgggtc catgacgacc cagattgcca ccgccgctgg    20700
tattcaggtt attgccattt ctggtgctca aactttgag ttaagcaagc gctgtggcgc    20760
taccgaagtc tttgatcaca aggatcccga ggtcgttgac aaggttgttg ctgccgtgca    20820
gaaatccggc caggagtttg tgggaatctt tgacgccgtc gctacacctg acacctacac    20880
cagcgatctg gtcatcctcg agaaacttgg aggaggccat ctggctgcgg ttcatcctcc    20940
gcccgcagaa gtcccgagca acgtcaaggc cggcatgatc ttcgcggtca cgatattgc    21000 aaccccggta tggaatgact tgtcacccc tgctctcgag agcgggaaga tccagtgctt    21060
gcctccgcca acaatcgtcg ggaagggtct tgaggcgatc aacgaagggt tgaagaggtg    21120
caaggcgggc gtgagcgcga ccaagctggt tgtggagttg taattgcgtg ccggctgcaa    21180
catattagaa aagaatattg tgtacaagtt caagatagca tacaatgaac gattggtcct    21240 tttcttatt ttctttatt ttctttcgt cactctctag caccaaacaa tgatgatgtc    21300
```

```
ccgcatgctg aaattgcgcg atttctagtt tgaaaatcct gtaagtgacg aagtagaata    21360
tttcggcttc cccaggggat acggcaaaga aattaggctg cctttttgcat tgttcgatct   21420
tcgttggatt tcttagccca caaagctccc acgctgaact cgtattgcct tagcgttcgt    21480
gatatcaaaa cgcccctcct agtaatatgg ttggataaac agctattatt ggcttcactt    21540
gggtcgagag actcgttgtc gtgactcgca ggtcgtatgc tgagtggcgg ctcactgctg    21600
atatgggaac ataccaggct gaaactggta taagctcagt ggtacattcc acacctgtta    21660
ttttaatagt ttcttttaccc tttctttcaa tggctgtgcc catcagacgc tagactgtcc   21720
caagcggcgt ccatgttact gtttaaacat ccttggatgt cggtcttcct actcgcacgg    21780
ctctgaacaa ccaggcttac atagcagcaa ctcctcaaag ctggcactca atacttgaag    21840
tgaggaagtc ggtttgcgat ggttatgggt agcttgcatt ggattcaggg tttcatcacg    21900
gacatattat cttctccgca ggtgactgtc atgaagcttt gggtggcctc gcagattgtc    21960
atgtctagca aatgaagcga atgcttattg agaactctag ctgggaattg ccgtgacact    22020
aaaacaagag tgactccgaa gatagtgact gatactgtac aggtagttca attacaaagt    22080
ctatcagtca gattttttgcc ttgacgcctt gacgttttgt ttcacgcctt agtcttgaca   22140
acaaagagc catgcgttct gagatccctg gagctggcgc ccacccaagc ctcgtacgta     22200
ccaggagcaa ctgcccactt ttggtgctgg acatcccagt aggagatgtc acggcggcgg    22260
agctcgaagg tcaccttggt cgactgaccc ttcttgatgt agacattgtg gaaaccacgc    22320
agctggcgca ctggctgctt cgcgacgtcc gggtacgaga tgtagagctg aggcacctcg    22380
gccccatcaa gagagccggc gttgcggatg gtcacggtca ccttggcgac tgtatcccac    22440
agatcttcat agccaccgac cgcgagctga cctgtagggt aggtggagag ggcagagggg    22500
ccctggatgt ggaggtttga gtaggcgaag tcggtgtagg aaaggccgta gccgaactcg    22560
tagcgaggag taacgttata ggcgtcaaaa tagcggtagt cgatatagtt accctcggtg    22620
aagttgcact gcgctgtgta gcagatatcc acattgtagt cggattcggt cttcgcgatg    22680
gtgtaggtga ggcggccgct ggggttgaca tcgccgtaaa ggacatcgac aatggaattg    22740
cctgattcct gacccagcag actgccgtac agcacggccg tgacatttttc gtgctcaatc   22800
caactgtcca ggattctggc gccaactgtg ttgattacga ccacggtgtt gtcacagttg    22860
tctgcaacct cgttaatgag attgtcctga tcggtgttgc gcagctccgt gcgatcagca    22920
ccctcgccag ctaatgcgtt gataaaaact aggcagacat ccatgttctc ggagtatgca    22980
ctgacgagg gcgtgacaga ggtgctggat gagccctgca tgaccaacgc agagccagtg    23040
gaggaggagt aggtgtcgtt ggcaatccag cgcagcatgg tgccgtcctg gctcgccttg    23100
atgttgagag cgttttcggg cgtgatcagg tatggcagag aagcctgtcc agatcccgag   23160
tccgtcgcga tatggccgtc gtacgtaggt ccagaaccct cgacactgaa ctgcatgtta    23220
gggccagcca ccgccgcacg ggcgtgcgag ccaaagatgg ccatcttgtg aggcttgtag    23280
aggggcaggg tattgttctt gttttttcagc aataccatcg acttagaacc atgagaacgg   23340
atcagcttgg cgtggttggc gcggacatcg acatagtcat cttgcgcggc agtagagggc    23400
tgggttccgt tatcgaggtt gacgtagtag tagcccatca ggttgcgaat agccatgtcg    23460
ttcagacgag cttcggtgat gttgttgctc tcaaggtacc cttcaatcgt tgattcactc    23520
cagaggctgg acgaaccgta atcaagtcca ttagcagcag aagcaagggc atcctgctgg    23580
ccgttcgtat caggccagac cataccgggg aaaccaagct cggtcttgag aatgtctaga    23640
aggagggagg agctttggca tgagagcgtg ccgttgactt tggtcatggc gcacatcaca    23700
```

```
ccaccaaggc cggaatggac cgcgtcgtag aaggaccaga ggtatgtctc gtggagggtc    23760
ttgtcatcgg cgttggatga gtagggagcg ccggaggacg acgaggacga gaaagcactg    23820
ctaccagcca ttccaccacc cattccagag ccgccggggg tcgaagtgga cgatggaatg    23880
gctcccgcag agcttgtagg agacatgccc ccagggacac tagagctaaa ctcagcgcct    23940
ctccccatgc cgccaccacc aggagcacca ccgccacctc ccatgccgcc ggtccggttg    24000
gtctcctgct cgttaaggat aaagtgctaa accgcattag ataggcagta atttgtcggt    24060
caggtgaaat gcttacctta gccccggcga taactcccac gtccgcatag ccctagttt     24120 ccaacccggt tgcaatacca ttcagatacg gatcaggtcc aaagctttcc accagtcggc    24180
cgccccatgg agtacggcca agaggctgcg aggtcggacc ggcaaccatc tggattccct    24240
tgccgtagaa ctcagccgca atggccctgc cctgctcgta catggcctcc ttgtcccaag    24300
tcatggccaa ggcggaggac agactaaacg ccgagacata atagtaggct gcgcgcccca    24360
tgtcaccgtc gagaatgtcg agagccgtaa atgtctcgcc attggtagtg gtcacactgc    24420
tgccggtgat gagcttgatc ttctcggtgg tgttgagctt ggcaacaaat gcgaggctt     24480 tctcgtgtgc ggatttccag tcaccgagag acactgtcaa gagtcagcca ctggcaaaga    24540
actggtccct agtgcagaga ggataccttt gccgctggac agaaggccgg cttcaaaatt    24600
gctggcggcg ccagcgcggt tgccgagcag aaaggaaaga actgataacg                24650

<210> SEQ ID NO 4
<211> LENGTH: 24502
<212> TYPE: DNA
<213> ORGANISM: Aspergillus nidulans

<400> SEQUENCE: 4
aattgaactc ttgtcgatgc atagattgac tgctatcgat agacctgtaa agagtagaga       60
gtagagtcac tcttggcttg ttgatcgtac tagatggcca agaccatat acagcactgc       120 gtatatctaa tcaatcagac gactgcactt tgaagtcctt ccaagccccg tccatgcctg      180
ccataaccac ccaccgattt tgcatgttcg tctcaatcgt cgtctcatac gccatcctcg      240
caatcctcaa ccacatatcc cccttgacca taaactcctc tccatcctca aactgcccgc      300
aaacctcctg cccgttcttc agcgctcgca caaacttcgc cacatgccca tcatcatgct      360
gctcattaac aatcgcaaac aattccttcc aggacatagt ccccgttctc tcccccctgt      420
aggttctcac aaattcgaaa tcaagctcgg gtacaccgca gagagcatac cacatcagat      480
ccagccggcc cttccactcg actaaccta ctctatcccg catggaaatc cagtcctgac      540
gcccgagaat agagaagaag atactgcttg ttacgcagtg catgaagaaa agtcaatct      600 ttggctcata cccgtccttc gtcctctgcg acgaccagc caagtaagca cagaggttta      660
gcatctcggc agtctttctc gcgagcgttt cctcggtgac tttaaaccgc gacgcaatgt      720
ctattatttc atcagctgca ttgacagaa tagactttct catcttcatc gtcccaatga      780
ggccctggac gcgtccggct tcgacaagtt tgggtgtgtc cctgattttc tgtaaaaggt      840
tcacgagagt ctctccctct tcgtttcgcc cagcagctcg cttttcggcc gtgaggaaaa      900
agtaatcggt cccaaaagag tcgtgcgcgg ccgcctgcgc caatgcctca gcgatgatcc      960
ccggctgttc gaactcgact ccaagcccga gatgaataat tgagtgaaag gcgccgtcgt     1020
acataagcgg gaggatcttc tcagcaatgg gcgagcgcga aagacgtac tctatcacga      1080 cgtccttcca tgagtctcgt cggtcgatct ccgcttcgaa gaaacgtagg aagtttgtat     1140
```

```
actggtcaat ctgtgtaatt tgggactcga agtaggagtt gtcagataac ctttccacga      1200
tagaagggac gagaggcggc atggcgcgct gagtagggag gtcatcgtcg taggcggttt      1260
ggagttgctc tggggttgca cccagcacta gccgagtgag aaggttatgg accaggtggt      1320
tgtggccgtt tagattgcgg aaaaagatgt gcagcgtgtc gtggttcttt tgtaggaggt      1380
gatttgtcag agtgagagtc tgggagggg  gagtttgggc gtagatgttc tggccgagtt      1440
tggttgagag aatattgatc gaagaggaca tttttgacgc cgtattcgtg ctttcttgtt      1500
gacttggtat ggtagatggt tgggttttgc tgactggttt aatgtcctga gcccaaagat      1560
atatactgca cagctagctt cggataacga gacctcgaag cccgatgacc gagcagccat      1620
attcacatat tgtcgactgg actggttctc tatatctagc aaatggcaaa ggtacgccga      1680
gcgtgactag tacgaatgag tgactgaggc cttaacctcg atcagggcta cgttttgcgg      1740
tgttgggaat ccataaaatt gacccatcta ataaccaaaa cgtcctccta gagacccaat      1800
attacatacc ccaggctaca atcccaggcc attaggaagg ccccgttgtt ggcagaaatc      1860
gatgcaaccc cgggaagaaa tgcctgagca agccaacaat gatacatttc ggagttccag      1920
gcggaacct  cgccttgccc ccgtattaa  ccacagagac gttcctccca tcatacctcc      1980
catctgtatc atttgccgcc tcaagcatgg cagccgccag atccaggtac gagatgaacg      2040
actcctgctc gtcaaagtcg agtttgtgac cacgctgaat gtcgacgctc aagccggcag      2100
gcttgatgaa aatgcttgtg acccaggact cgttcgctcg cagcatctcc tctgccttga      2160
tcaggtcggc gtagacgtta ctcgcagctg ttttcataat cggtaagaac cacgagggca      2220
ttttgcggct taggtgcgga tctatcgtcg cggaggagag aaggaccagt tcggcacaa       2280
ctgcattcgg ttccgctgta cgaatctgct tgagtgcctc gagaaccgtc tgcaccgagt      2340
cctgactcag tcggcaaccg ggaatattgt cgtttgaagt gacggtcaag aagaccgcac      2400
gtgtgttgcg tatgcatgcg gtgatgaggg ataagtcggt gatggagcct tcaaagatag      2460
tcacattttt cgtgtcgttg agttcgggca agaggtttaa gagtttgggc ttgtttcgac      2520
agtaggcgtt tatgtgcatt tctgaagatg gtggcgagag cagattctgg atcagagccg      2580
tgccagtatt gccggttgcg cccagaacgg cgtaagtggc cagaggcatt tcgattgatg      2640
atattcagaa tttagtattt cgtaaccaat acggtgccgt gaggattatg gttgatggtg      2700
gttgggtgtt tataaagcac tcgtatagag agctatggca gtcgggtacc gtagcctaaa      2760
ccgtcgtttt cagacttcaa tgtctcaaat atctcaagat acgaactata ccgtgctaga      2820
tgctggatat caagatctgc agtgcaacct caacccccgg ccccgaaat  ctcggagttc      2880
atcgagcgta tcgcagtcgc agaccccgg  gttccggttc gacggagtag atataatcac      2940
cgacagccca tacccacccg cattatcatt tccaaacaga ccagaccgca caaatgtcat      3000
tcggaacact ctacacccat aacgtatgtt cttacacctc agggcccaga attagaattg      3060
ggggtttagc taaccttgaa tcttgcagcc aacgcctcgc tcgacgaccc tcatcgctct      3120
agcaaagctc cacaacctcg acgtcaaaat catacacgca gaaagaaga  ataagagggc      3180
atttgaggag ctttgcagat ataatccact cgggcaagtc cctactttg  taggcgcaga      3240
cgggttcgtg ctgagtgaat gtattccatt gactctttac tgtactcagc ccgacactc       3300
cctggttaat gaaagaggac tgaaaagtcc tgctgagcag ttgcatccca gagtcaggac      3360
ccgataacaa aatccctcct aggcaatgac gaacgctcct cgctcaggat cctccaatgg      3420
atgtctttg  caaactccga cctctttcca gcagtcggcg gcgtcttcct cccacgcatt      3480
gggcaacggc aaataatcca gcaagatgac ggggactcac tgcgtgcgat gctgcagcgg      3540
```

```
tgcaagtacc tagatgagca tctgaagcgc agcagatatc ttgtggggga aagtataacg    3600
attgcggatt ttttcgccgc gagtctgctc atgggagcgt ttgcggcgtt taggagatcc    3660
atgcaggaga ggtttggagc actgtgcagc tggtatgatg gggtccttga gattggctgg    3720
tttaagaagg ttgcgggagg tgtcccggat ttgggacttg agttagagat tccagaggat    3780
ataaaatggt aatgattaga atgtctaatg ggacaacccg agtcggctag ttggagccat    3840
gtcttgacgt cttgagtgat ctgatgtacg atttcggtgg cgttaagaat agcatattga    3900
gacgccctca gcacacaatc catctatagg tagggttcta tctactggta ggctcagtct    3960
gcaaataggc cagcatagcc ccctccacat ccccacgagc aatcttatgc gtcccattaa    4020
ccggaaacct ttccagtccc aactggtgca gataaattac tccgttcaac gcattgctct    4080
tcccaagtgc ccgcacaaca tgtcttctga tctgggcttc tttcttgccg gtatatcgtg    4140
ccaggacagc aaaggggccg ccagcattta ccacacatgt ctggtatgct tgtttagatc    4200
tcagatctga ggcaaatgtg gtggaggtat gggggaagaa taaagaaaga aaacatacct    4260
gaacagaagt atatttctca aggcaactct caatcggggc aggcatcact ttcccattaa    4320
tcatatcctt catccggcca aggataaaaa caacgccctg cttgtccatc aagcccacat    4380
cacctgtttt gaaccatctt cgcccatcct cgtcgtgaaa cgactgggct gaaactccac    4440
ccagataccc cgggataata cttgggcagg agacatggag ctcgcccagc tctcctcttg    4500
ccactgtcgc gtttgcgcca cggatcctga cagcagcgcc tcgtgcaacg gatccaacag    4560
gactcatctc accatagaac ggaatatctc tgggcctgtt gaaaggccaa acaaacgccc    4620 ctccacccte cgtcatcccg tgattcacga caactctcgc tttcggaaac aatcgcgtac    4680
atatctcaag tgcgcctctt gtcaccgcat cgccaccgat ttgaactgtc ctgacagaat    4740
cagctgcgcc atttctaccc ttcaactcgt ctgcaactgg atgaaccatc gccggcgtga    4800
gcaccacgaa actaaccgcg tgcctttta ccgcatgcac caaatcgccc gcattgaagc    4860
cattccccgt catgactact gtcccacctt ccctccatgt ctggagtgtc tgtgcaatgg    4920
caatgccccg acacggatgc gcttgttgca gtgcccgcgt gcagttctct gcgttgacca    4980
gccacgactg ggattggaga acgtagctca ttcccgaaat atgcaacggg cacccttag    5040 ggaccccgga tgttcctgac gtatagagga tggagtatgt acgggctgcg ttggaagagt    5100
cccagcgagc agaagataga agagactcgg tttcagaagc tgaaagagct ggtgtcagag    5160
atagggacag aagggatctc caggctgagt ctggttgact tcccgcaagc tcggatagag    5220
tgatcttgag gatatccggg tcaagcggta gattccgcaa cgcgacatcg atcacatccg    5280
cgccttttac gtcttgcaca acaataaccc ttggattgat agtctttagc attctgcgta    5340
actcatcatg ctgctcaacg ttaagcagtt cctcatcgag acagacaatc gtcacgcgga    5400
gaacaaccgc agtccaaagc agaagacaga actcggcgcc gttggggatg agcaagagca    5460
ttctcgtgct tggctgggca tttctcgcca gcagccccgc cgcaatccgt aacgcagcgt    5520
ggtggagttg tgtatatgtc caggcgaggc atgtcccegg ttctctctcg accgcatcat    5580
agtttggcgc accgccattt tcagtcccac ttcctgtctg aacaagcgca gagaaatgac    5640
acggttgttg atgggtactc tgaatagcaa accctgtgg attctgatgg aggccacgct    5700
caatgtgtgt aaagaccgaa gggtcaacgg gtaggtgccc accatcgatt tctgctggga    5760
ggaaaggcct gaagcacgag cgtgaaaccg acattctgtt tgataggtgc ttgaatactc    5820
cactgtagac tctggtcact gctttgactg tttcaaaata cgagccgtgg tgactggaca    5880
```

```
tgcagcgtca gcgtcagcgt cgtgctatcc gagctcgggt ttcagtggaa ctgtcggggt      5940
ccggtgtgca tctggaactc agtaatcaga taaataaaga agacgaccaa gaaaaacaaa      6000
agtaatcaag taatagttgt catatcaaca aacagatacg gttgatgtcc cgaagcgact      6060
ctaggtaact aactgctccc tgaccgtaag ccttaggaca gaaaccatta cccagaccaa      6120
agaaaccctg ttatttgaac gaatagccag aaaatgataa aaaaattgtc aaacacagat      6180
tcccaccccc agcactgccg ccatcagtgg aaataaactc ctgaccaggt gcatccattt      6240
ccaacgcacc aggagctccc tgacccttc caaagtagcc atctcaacac caattccgac       6300
actaacatta ccaaggccat gactctgact tgaattcgca cctttcaagc cacttcggtt      6360
ggcaccctgc tcgaaaaatt ggctgtggtc ccgattccca gcctccagcc caaagagcat      6420
cccgttcgtg gaactcatca caatccacgt gaatggaacc atgacgatcg tcagaaaccc      6480
gacaagagca gctttgcgcc acggctgctc ccttgccccc tgataagcag cgatgtagaa      6540
gtatagaata gccgtggcga tcgagatcgt aggcaaggaa atgtgcccgt agtggtaggt      6600 gcggaccat tggtgcagga gttgggggtgg atgggtagat gtctcgagga gaacagggac      6660
cgtgattgtg ctgagagtta tcattgctcc tttcattcga gaatgagggt atgagttatc      6720
tttccgcaaa gggggttgga aaggtgaagg gagataccag agagaaaaga gcccgtgacg      6780
atggcggtgt tcttgagggt tgtgagggag gccatgatta ggctgtactt aatgttggca      6840
gaaagattac tggaagcgct gatatgcaga ataaagctgt ttgtttgact gaaccctgct      6900
aggctgtgag caattttaaa tctactcttc cctgttgagg ctgaccggca gctcggtgat      6960
ggttgatctc gctgtccgat ggaacgcact gcgttgttgg aatgaacccc ggactggaag      7020
taacacactt gcattgaata tcgaatgtgg catatggact cagtatacca tgctgcatag      7080
cgagtagcta cctacttctt cgggcctgga aatccctcaa acccttctgt gacaacgccc      7140
cgatcaataa actgcgtgat ccagccgatc gtcatcctgc atgcgttagt gattagccct      7200
catttccttt atcttgatta tcattccatc cagctgattg accttcgcca gaagggatgg      7260
gacgggacgg cataggatta aggacgtact tgcttctctt cgtatccgcg aaattctcat      7320
ggtcccctac aagatgttcc ttataccagg ggtcatcctt gattttcttg tagtcctcga      7380
agttgcgaaa taccacttgg ctaaagcagt cgtagtcggc aatattcgcc atttgcgggt      7440
ccatgatctc gtacatcagt tcgcgcgttt cggtgggggtt gtggatcttg cttctgtcag      7500
gacatttctg acagagtacg gtatatgtct tcaaggaaag atatggttgc ggtggtggat      7560
gcacgtacga cagtccatct caaaatacca tacttgatca tcagatcctt tgtcaacggt      7620
gcagagtgct caatcatgtg tttgcggtaa gcttcctcac tcatgccttg tttgcggtag      7680
ccgaggatag tgaggcagag gagacgatcc tcggaggtgg tggagtttgt tgctggggga      7740
ttgggagtgg acatttttctt tgaattgatg cgggtgaatt ctgagctggt cgatgtggtt      7800
gatgagtgag gatgggcgag tggaggctcc ctatataatg caaaatgacc cgagacgaga      7860
tccggacagc ggcgggaaat taagcacaga tcgggtcatt aagctgttat ctacgacgat      7920
agatcacatc gaggcttact tcgtcgcgtc aaggatagtg aaatatgcat agaccagtgt      7980
tttcatctgt acctatatac cataactcta acaaccgaaa gcaacagcgc agcccttttca     8040 ctaccggtta acatactgcc taattatagt actctaatag ccagcttcgc agatcgccga      8100
tggtaggata ctccaggaac aaactaccag tcaccgtgac ccccagctcc tcccgaaact      8160
tctctgctat caccaggctc atcaagctgt caaccccgag gttggcaaac gaggcatcgt      8220
ccgtgagatc cgaaagctcc agcgcagctt ctttggcaat aagcacaaga gctttggctg      8280
```

```
ctacgctgtc gctctcacca gcggcggctg gtgcagctgc aggtgtaggg ccaggagcag    8340
gggccggagc aggggctgga gtaactgacg ccggtgctgc aggagactgg gcaactggtg    8400
cagctgcagt agccggggta gcgactggaa caggctcggg tttggttctg ggggctggcg    8460
tactcgaagc ggcggcatgc gaaatggctc ctgcctcttc cggtgccgtg aagaacctat    8520
taagcaggat gcgtggatac cgccggaact ggattccacc acacatccca atgatcgccc    8580
cgtcttgcat aatgtataca tcgccgaggt aaacagtagg atcctcttcg gtctgaatca    8640
tcttgacgta tgaccggtat ttggcacctg ctacaagcgg tttggcgaat cgcagagact    8700
tccatcccgg agtcacgcag tagttggcct tggtatcaat agcgtcggac acattcatca    8760
cgaacccagc gagatgcgcg acgctgtcga taaagtaagg cggaatagtc caggtgccac    8820
tcttctccgt ggacagcgtg atatcggcga atgcttccag ctcatgcaga accacagact    8880
gcataccgcg gtacttctgc gcgtagtcca cgaggttgtt ggcaaagagc aggtaagcca    8940
tattgcgggt aaagcggttg gcaatgccat cttccgcaag tcgctccaaa gcctcaatcc    9000
taccctgaac cagatgcgtg cttggtatcc aagacttgag ccacagagcc gcatcgtcgt    9060
ataatatcga ggcacttgca aaaggctcat ccgctgtgtt gtcattgagg acgttctgcc    9120
agatgagctc agcaaccccc gaattgatat ctgtggttga aatggtgact cggatatact    9180
gcggcttttt ggtgtttttc tgcgcaacaa gtcccctcaa cactacaaga ttggccatgt    9240
tcatatcagg cgccttgcca cctttgacca ggttcttgta cagatacct cccagagtaa     9300 aaccaatgtc gccgtgtata gactataaaa tgtcagatta taatgggggc gctgagtgga    9360
atacttaccg aagttaccac accgcatccg ttcatcttat gtccatgtgc agcatccaaa    9420
aaatctggct gcatcatatc ggactgcatc accactttac ccgccgagcc gttgaagctc    9480
tcctcgataa tctgctgaac agtggacgtc ctcagcccgg atggtacgga ggccaattgc    9540
cctgtttgct gtgccttgag tgacttttcg gcatcgtaaa aggtgttccc ttttgtcaat    9600
gcccagtcgc cgttgtactg gatccagtac gtcttgtcgt tccaggcgta tgtaggaagg    9660
tctaacagcc tcagcccttt ttcgaacggg cgttggtatt cgttccattc gattggcaca    9720
ccagcacagt gcaaggcagt aagactatta cataaagtca cccagttgtc ctcacctctc    9780
ttcattgagg cgaccgtctc attgacagct gggagagtgg cattcacaaa gcccatgcaa    9840
acgggatgcg gcccaatttc cacccaaaca gtctcttcat caaccgtcga aaagtctgt     9900 gccatctcaa gtgcggataa gaagtttact gtctctcgtg tggcacggcg catgtattta    9960
gcggtaatgg tcttgtcatc aaaaatgact ttgcccaaca ggggagatat cacgggcata   10020
ttaggcgcac gaaacaatac tccatccttt gcagcttctt caaagtcatc aaggatagcc   10080
tctgtttgtg aggagtgaaa tgcaaatgcg acgtcaaggc tggtgcatcg atagcctact   10140
gattgtagga tttcagacac aacctcaacc tgcgcctgcg atccgctgag tacggtttct   10200
tttggtccgt tgatgcatgc aacttcatag ttcgtgccct ctaaggcttt ctcgatatca   10260
gccaaaggag cacgcaccgc cagcattttg tggctgccga tctgacactt ttcctccagg   10320
agctgcgcac gacggccaac caagaaaaga gcatcgctag cggaaagcac gcccgccaca   10380
tggaaagccg catattcgcc aagactatga ccgacaacag cgttgggctt gaccccaagt   10440
gaaatccaat acttggcaag agcaatctcc actgacacaa gtgctagctg cgtgacaacc   10500
ggcgagtgag cgtagtcttt ctcgtggctg ccatccactg ccggaataaa gctaggaaaa   10560 ccttgcccctt gtgccaaagc gtctagatga agaagttgag atcgaaagta tggagagtga   10620
```

```
tggaacaact ctaagttcat tgacttgtac gatgcacctt gacctgtaaa ggcgaaggca    10680
acctggggcg gcccggtggc gggaatgggc ttgtgcgctt caactttatc tatgtaagac    10740
agaagcttct tcttcacttg agctatatca gtagcagcaa ctgaagctcg gtggttgtgg    10800
tggtaacgtc gggcagtcgt tgtgtaagac aggctagcca aggaggtatc cggatttgcg    10860
tcgagatagg cgacaaggcg ctcaaggttt ttcttgaaag agattttgct ctttgccgag    10920
acattgacaa catgagctgt ccgcgggtca acatagtctg tctccctgag cggtggctct    10980
tcgaggcaaa cggtggtatt ccaccagct gcactaaagt tattcactac agcatagcgc    11040
tttttacctt tcactcgcgg ccatggcacc ttctggtacg gaatgtgcaa gttccgcttg    11100
tccaagtctt ttgggaataa agggttgagg ctgtttttaa tgccaacatg cggcgggatg    11160 gcgtttttt ggtacattag caagaccttg aggagggcag tcactccagc aacggcctct    11220
ccatgtccaa cattggcctt cacagcaccg atatggagtg gttgttgggc gcttcgtcgc    11280
ttagtgatcg gagcgaaaat gtcagttatt gaagttattt caactgaatc accggcctgg    11340
gtaccagtgc cgtgcatttc gacaaagctg acatccagcg ggtcaatacc agcggagctc    11400
atgacttgcc ggtacaaata agcctgagca ccagcgtgcg gatgagtgat tgaaatagct    11460
tcagccgaat gattcgttgc tgcagcacga atgatcccga tgatattgtc gttgtctgcc    11520
tcagcatctt caaggcgctt catcacgatt gagcctatac cgtctgcgcg gcaatatcca    11580
tcggcgttaa catcccatgt cttacaggcc cccggagtct tcgaaaggaa gtggccatgg    11640
ctgagaccag cgaaagcgtc ggaatttgtg agaacattca ttccaccggc gacgaccatg    11700
tcagtatcac cgttccacaa agaggtacaa gcagcctaac aacgttagtt tttctataat    11760
tcaagtgaaa cctccatacc tgaattgtgg ccaaacttga cgagcatgca gtgtcgcagc    11820
tgaaactggg accggaaaat ttgaaaaagt agtttatgcg ccccggtcca aaggcacgac    11880
aaccgccagg gatgaagtaa gtgctaattt cctgagctgt attgacctca cgataatcat    11940
cgctagcttg accatagaat gtcccaatgc gatgaaggtt agtggctggt gtgcgattag    12000
ctacgtaacc cgccctctct agtgcctcat atgcggtgac aatcgcaaga cgctgcattg    12060
gatcggtttg ctgtgcttcc ctgggcgaca tattgaagaa cggtgcatca aacaagccag    12120
gctcatcaat aaagcatccg tacggtgtat ggctcgtgtt gacccttttc cctttcggat    12180
cataatgagt ctcgacgtca aatctatcag caggaatttt tctagctacg tcaagccctt    12240
gctcgagcag ttcccaaaac ttttccgtat cagttgctcc gccaggcatg cggcatgaca    12300
tgccaatgat cgcaattttt gactgtgcag ttcctcgcgg gatttccata tcagatttct    12360
gaagaatcca cggaatcaac tcctcggttg acgtttcgaa tccttgcagt ttagagccaa    12420
gagcagtccg cagatcgttg attggcaccg aaatgcggaa gaccaaaaca tcacagctag    12480
ttgctgatgt tgcgtatgcc tggtcaacaa cgccttggac gacattatcc cataggatgg    12540
gctgtgtgag aagttccaag actagctgct caaacaatcc tttggccgta gaagccgtaa    12600
atggtcggcc agttgaagtc tgatagacag gaattgccgg cgagtaaagt gcatttatgg    12660
agtccataga tctcgtggat atgatctcac gtgcatgttg ttcgttgtag aggtgtttgg    12720
catggcacag accgctgtac acaggaaggc tcactaccct gtgtcgcctg aagaattcgg    12780
ataggcgcaa aacacgcctg atccgtgacg gtggaccact aattgtgacc gaccctcgt    12840 tccaggcact gataaatatc ttgctaggtt ggggtgtttt ctatcaagat gttggtaagc    12900
tttaacgcgt taccacggta tggcagctta cctctcttgc gtggatagcg tccaactcag    12960
cttggacttc ttcaaccttg gcgccgggaa caacagaagc ccaggtgtct ggggagccgg    13020
```

```
acgtatcgcg aggctcgagg ttctgcgaga tctcatccac taacgttccg agacggaaag   13080
aaactcgcac tacctcggca ccaataactg ggacgtcggc caatgcagag cataaagcaa   13140
cagcagcggt tgacaaaagc ccaagaccca ggccagccag gtacgtggac acggcatgta   13200
ggtcaaatcg ttcggaagca ttctcatagt aactacaaca gtcagcagcc tctttgaagt   13260
aaagtcgtgg tacatgccct atcagagtcg ctatctctag cacgcagaga gaacaccct    13320 ccaaggatcc gccaagagga cccttccgaa gttcggggta gtcggcaagg ttcaagactg   13380
tttcaaaggc aggaacaaga gcctttacag ccgtcggtaa ctgccgcact tcttcacgga   13440
cagcgagtgt agcttcatgg ataaacctag cgaggagggg atatcgtcta tctttgctgt   13500
ggttgtacag acggcggaag aggccttgga gatcatcctt cgggagttcg ttgctaaagt   13560
aaaggagctt catcttggag tactccggca gtgagcctga ttgaggagta tatacgggca   13620
ttctgaggcg atggaaccac caagagaagg tggaaaacaa caaaaaaaaa aaagacagga   13680
aaatgcagac tcggcctgag ataataagga gagcagtctg caaaattgga atcaagtgca   13740
agacagattt ttgttgcacc aggtcagctt tattgtgatc aataaagact gctatcaggc   13800
tgccaagtga caagcgtcag atcggccaat ttgaccgggg cggcattcgg cgatgagtac   13860
tctggactcg tactcgtact cggaatacta gatccccggt cggagtccag tcgatttgcg   13920
gctgacgggg ctattattag caatgccgat agtatggaag tgttgtaatg tttatttcgc   13980
ccagttcagc ttgatatgtc ccagatgatt ccagcttttt tccactgctc tcaataaggt   14040
gcaaaagcat cggctagact tggggttgtg cattttctaa ccagacacaa tggctcagcc   14100
gcagcagcat aaaggcgggt acaaacaaat caacaaagct ctcaacatat gtgcgtttga   14160
ggattacctt tccgcccagc taaagcactt gccgcaactt gcggatgtag agcagctcag   14220
tcctcgagtt atccgtgtcc tggggcagaa cgctgggaag gtaaatgccc cgaatcggcc   14280
tcttttctag ctaacgaatt ctgcgcagtt cactttgcag gggacaaaca catatattgt   14340
cggcaccgga ccgcaaagac tcatcatcga taccggccag ggaattccgg aatgggcaga   14400
catcctcgat gctaccctca aagaacgctc gatctccttg tcgcacgtgt tcctctcgca   14460
ctggcatggt gatcataccg gaggagttcc ggatctcctt cgtctttacc ctaatcttgc   14520
cggcgccata tacaagaact cccctggcag cgaccaacag ccaattgacg acggccaagt   14580 cttcgtgtc gagggcgcta ctattcgagc agtgcatggc ccagggcact cgcatgacca    14640
tatgtgcttc atcctcgagg aggaaaatgc catgttcacc ggagacaacg ttcttggcca   14700
cggcaccagt gcagttgaag agctaggtgt ttatatggag actcttcgaa agctgaattc   14760
acaccattgt gcggttggct accccgccca tggcgacgtg atcaccaacc ttcccgcgaa   14820
gattgctggt gaactagcgc agaaaatgag acgagagaag caggtccttt tgacactgga   14880
caggatcaac aaggagtcca gacgcacggg acaaggtaag aaggctagct gttacggtta   14940
aagagctagt ggtgctggtg catggagatg gaatcgacga ggaggttcgc aagatggcat   15000
tggagccgtt tatcgacgaa gtgttacgca aactggcaga ggatggcaag gtagcattcg   15060
aaatgcgagg aggtgtaaaa cgatggtttg gagtaggagt gctttagtta agcgaggcat   15120
tggatggagt gaggttggga tgccaagcct gaagctttca ctttctttca tactccacct   15180
tcgctctcca acaacacatt aaacggattt ctacgattgc cgacaacctg ttcactagat   15240
ttatcaaacg attttgctgc tgcctagatt gtcactctaa gattatcaac taaacgcaga   15300
ttacagtcta cttcagtcct ctgttgacgc gcgtctttgt ccttggcgtg gattcatcga   15360
```

```
cgtacggtaa tacacatcta accgtcaact gctcgcagtc tcgactctac tattcaccat    15420
atacactgta ttgatgacca agctgatcgg ttcgtgtcaa cagatagacc gtgagcgtcc    15480
aattgcgcgt tgtagccgaa gtagataaga cgatggctag gccgtctcta cttcagatat    15540
gcgccgttga caggggaact gctttctgcg acacgaggca acagacaaat tccataaacc    15600
cattcttgac gggctatacc accccgaact ctgccaaagt gacgagtgac gacaaaataa    15660
ggtcgaattt agcatgcccg ctaagctgga ctaagaccgg ttgcgaatag cgtgccgata    15720
gttgcgggtg gatctgcagt gcagtactag ccgattgggt tatactatgg atagtttccg    15780
atcagctcaa cggcactgag caagccacgc gagatacctt ccgaccctct cttttgcgga    15840
ttccaaacat tcccgttggc ttttttgaaag tttcctatcc ggtttcccgt tgatgaagcg    15900
gtcatcttcg aatcgccttt tgcgatgaca actgctaatg accggacagc ggcggtgatg    15960
tcggtcaccg ggaacgacgt gggggccggt taacctgggt ccgaaagtct ccacatctat    16020
tccgttaccc gtaagcgtac atctgtactc gtctccgaag taggtacgag tagggcgcct    16080
ggcttggtta atgcttgatt tatagtttcg ttgagatgga gttatcggtc gaatgggatt    16140
aactgcgatg agcaaagtcc ttctcctccg ttaaatccga gacctgactc cggcaaatgc    16200
atgataaaat cggttgttgc tagcactata gtgcatatga atggattgcg gctcccaggc    16260
cactctggct gatcaccatc actgtcgggg acagcaagac ttgacccgcc cgaaacaaaa    16320
ggatcatgag cattgccagg ggctgttttcc cggatcccac tctgggcatc agctcaggcc    16380
ccggatggag tttagagact ccaatggtat ccaactgtaa gctgacatcc agcagctggc    16440
ctggtgctat caaagccaat gaaccaagcg gtggccatgc gagcatggag tcgaatcctt    16500
cctgcagatg ctctcttact ttaagcctgg gcccctcat tttcccacgc tgtaatcccc    16560
cgattgatat cgcctcactc ccactatgac atcttcagag ggtccaggta tccccgctat    16620
caaaactccg ccagtcaagc tgcgaggaag ctgtcacgca tgtgccctgt ccaaattgaa    16680
gtgcagtcaa gataaaccta cttgctcacg atgcgtcaaa agaggtacag catgtcagta    16740
tctcgccagc aagcgcgcag gtcgcaaaca aggcagtaaa acaggcagct tcaagtcatt    16800
ctacaatatg aagacagact attccacgtc tatcaacaaa gatgatgatc ggagggagct    16860
catggaggtg tcgacagagc tcatgcaata cgctcttcag caggaccgaa gcctcgaagt    16920
ataccgaaga aatcaatatc accagcgcac accaagctat ccagagagta taccaagtct    16980
tctctcatca accggccccg gaacctcagc tacaagccct cttaccttgg ggcccctga    17040
ctacgacggt tatcttgctt cgcctatatc tctatcgctt ctcgatgtgc ctgacatgga    17100
ttacttccct ggagctgata tgagcgcgaa tgtcatggat ggttttcctg atcctccgtc    17160
attcttccca tctggagaac cgataccaac gctccaagag aatatcttga agaccagttt    17220
cgcggattct cccgttccgg caaattcgcc ttcagttcct cctacaccag atgtaaccag    17280
tgttgggaca ccacggcaat gtttctgttt cccacgtgca ctgacactgc tgcgcgaact    17340
cttttccaaac ccttcactat catgcgtgac tccctcaagt gaaagtggca gtgcaagtcc    17400
tcctacagtt caacaagtca tcactaaaaa tgagcagact ttacgagata ttactgagat    17460
catagagtgc tcctgctcgg aagacggcta caccatcaca atcataactc ttgctgcctt    17520
caaagtacta gcctggtata gcgccgtagc gcatatctcc cctatatctg aagacagcca    17580
agcattagaa gagatcgaca ggacaccggc tgttgtcagg ggctacaata tcgatggtga    17640
agatcaaggc cgcatggccg cacagctagt tctcagcgaa ctgcatcgcg ttcaacgatt    17700
agtgggcaat ctctatcagc gactgaaaga ccaagtctca ggcgggaagc ctgctaggtt    17760
```

```
gagtaccact ggggtcaatg acagcaatca ttactctctc cctttcatc tgctggaaag    17820 gctggcggtt gatctcggag ctcaacttcg gagcctgtca agtgagattg tcgaccgatt    17880
gcggaggggt tgattgtcaa acattatcgt accggaatcc atatacctg ttccattgcg     17940 tttcgtgcgc gcgttgtatt tgcaacttag ttgttacaat aagacctagc atatgagtgg    18000
tcggagtctt tttcccgtgc ttatcagtgc cgtaatagta tccatattat gaccagcgta    18060
tagaggggta atttggatta aggctattaa gttcccaatt ggactgggca gtcccgttca    18120
agaactaaat ttatatcccc gagcatatca gctctcctag ttggaatcca aatgtgttat    18180
gtcagcgtct gtgactttca atggctctat ccgctgcgat cttctagtct agatattaac    18240
tagttgtact agaaagtatc gagcacaata gccaagcttc agtgacagtt tctatcatct    18300
agtgctccct caatcaacac aggtagccct agaccaccgg ctcggtgctt caatgaccct    18360
acccaacgca ctacctactc ggcccaggtc cccaaacacc accagcactg agagtcacaa    18420
tgacccattt ccccgtcaac atcgccagtg acaagcagga atttgatcca gagcgctggg    18480
caaagacgcc tactaccgaa agcagtgtta acggcgagaa tggcactgct cctacctctg    18540
gtcttccatc tcggcacccc tcgaccggaa tctccgtcct cattgtcggt gctggaatgg    18600
gtggactgat gacggcgtta gaatgctgga gaaagggcca tgatgttgcg ggaattctag    18660
aacggagtga gggacctgtg tattcaggta ttttgttgat acgtctcgtg tattccccca    18720
gagcatgaga aaccgagtag ttaactctat actttctcga gataggagat atcattgtca    18780
tgcagccttc tgccgtatct ataatccggc actggcccga catgctccat gatatgaaag    18840
cggagcaagt ccacgccgtc gttagctacg aaactcatga tggacggcac atttacggcc    18900
caaccgtccc ctcgttcaat gaccccgagc acctggaaac acgcaaaggt ccatttgttg    18960
cccccgctca ggttcgccgg aaattctacc gcatgctcct gcgccaggtc gcaaggtgcg    19020
ggctccgcgt tgaatatgga aagacggtga agagctattt tgaagatgaa aaggatggca    19080
agggcggcgt tataatcgca acaacaggag aagcagaggt cagagtggct gatatcgtcg    19140
ttgcagcgga cggcctcaaa tctccttcag agatattgat agccggtcag catgttcctc    19200
caagatcaag cgggctgagt atctatcgca ctgcatttcc gaaagattta gcaatgcaga    19260
atgagctcgt acggaagcga tggagcgata gtccacccat ctgggaatac tggcttggac    19320
cgggcatgta tcttggtgtc ttcgtcggcg acgatattat ctccttcgga ttcacgcccc    19380
gtgatgacat cgttgaaggc acagccactg aatcatggga gcctgataca gatcccgaga    19440
ctgtggcgca ggctatgctc tccggtgcag gagactggga tcccgctgtg ctagcgctca    19500
ttcgaagcgc gccgaaaggc gcaattgttc attggcctct cctctggcgg gaccttcgcc    19560
gcgagtggac ctcacctgcc ggacgggtag tgcaagtcgg cgacagcgcg cacagcttca    19620
ttcctacctc aggaaacgga ggctcgcagg ccttggaaga cgcaatcacg cttgcaacat    19680
gcctccaatt agccggaagc tcgcagcgtg catatcttgg gaccaagatc tacaatcttc    19740
tccggtatga gcgggtctct tgtgcacaaa aaatgtcgtt cgtgaattct cagctgaaga    19800
cgggcacgga ctgggatgcg atctggaagg atcggcgaa gatcaggaca aggtttccta    19860
agtggatctt tcagcatgat ccggaggcgt atgcatatga aaagtcggc gaggcgtttg    19920 cgcatttact tgatgggaga gagtttgtga atacgaacta tcctccgggc catgagttta    19980
gggcttggac ggtggaggag gtttggagga atattgcaga tgggaagaga gtggaggatt    20040
tgttggatgg tgattggtct tagttacctt ttctccaaag atttagaata tatattgatt    20100
```

```
tggatatcat cagtcgcaat gtgattgagc ttaaagctgg cgctcaaggc tagattcata    20160
aatggtttga tattcgtatt tcccagaaaa tctaagtagg gcgacctagc tagcagttca    20220
tccttgatta agagacaatg attctgatct actgatatca aagtcattct tctcaaccat    20280
ggatacttaa cgagtgctac tcagcaataa tggtaactct tatattctct tggtcgggcc    20340
aaattgatca catattcaca gctcgtgttg caacacgctc atgcccatcc tcaaggcaga    20400
agtaatagta ttatatgcag gtaaaacatc gctgtccgta ctcgcataat gcatctaagt    20460
caccgaaacc tctctcttat cccctgcgcc caagttacat atcccgatcg agactcgggc    20520 accgtacccct tgcacaccat gtgcttacga acttagggct ctaatcatcc gtttctaaga    20580
aacctgagcg caagatacat aaggtaggta ggaaagcacc aatgtctcca gcaatccaac    20640
gtctctccct cgtgtcctcc cacctcaatt ccaacgtcag cgcgctccca aaaatgaccg    20700
caaccacgca cgcccatac cgcctcgaag gcaaagttgc ccttgtgact ggctccggcc    20760
ggggaatcgg cgcagcaatg gcccttgaac taggacgact cggtgcaaag gtcgtggtga    20820
attacgctaa ctcccgtgaa cccgctgaga aattagtcca ggagattaaa gagctgggta    20880
ccgatgcgat cgcgctgcaa gccaacatcc gcaacgtgag cgagattgtg agggtcatgg    20940
atgatgcagt ggcgcatttt gggggcctgg atattgtttg tagtaatgcg ggggttgtta    21000
gttttgggca tctgggcgag gtcacagagg tatgaacccg cttttcattc gactcctggt    21060
tgaggtattg acgattttc ataggaggaa ttcgaccggg tcttcagtct gaacacccgc    21120
gcccagttct tcgttgcgcg tgaagcttac cgccacctca acacccacgg ccgcataatc    21180
ctcatgtcct ccaacactgc taaagagttc agcgtccccc ggcactccgt gtactctggc    21240
tccaagggcg caattgagtc ctttgtgcgt gtgatggcta agactgcgg cgacaagcag    21300 attaccgtca atgctgtcgc ccccggggga acggtgacgg acatgtttta cgacgtggcg    21360
cagcattata ttccaaacgg cgaaaaacac agcgcggaag agctgcaaaa aatggcggca    21420
acggtatcgc cgttgaagcg gaatgggttt ccagtggata ttgcaaaggt tgtcggtttt    21480
ctggcgagta gagaagcgga gtgggtgaac ggaaagatca ttaccgtcga cggaggcgct    21540
gcttagttct gctagattta gtagctaagt cgtagccaga acaataaaat ggcacattgc    21600
gttgatgatc taggctgcat tgaaatgggt tccactcaaa tataggtacc ggacaccgaa    21660
ggtcggggac caagtaaaac ccgccttcat acggtactta gcaagtcacc gacctgaagt    21720 accccttgcat ggtcttcccg tcctagacac tgtcttgtga gttgggatcg acttaaaata    21780
ttgcttttga gtctacccttt tctccgtttg tcccatcttg tagagaaaca gggacggcac    21840
aatgacgctg cagccaacat ttgaaggtag daccccctgaa cagtgtttga atgtgcatac    21900
tgatagccat ccagacatta cgggctgtca agctgccctg ttcgaatggg cagagagcta    21960
cgacagcaaa gactgggatc gcttaaaaca atgcatcgcc cctttccttc gcgtcagctt    22020
cccagtctcg tcctatataa tcagtgctga cggtaccaga tcgattacag agccttcttg    22080
gacaagctct gggagaagat gccggccgaa gaattcgtgg ctatggtctc tcatccccac    22140
ttcttgggta acccactcct caaaacgcag cactttgtgg gaacaatgaa atgggagaag    22200
gtcgacgact cgaaaatagt tgggtatcat cagatgagag tcgcccatca gaaacacctt    22260
gattctcaga tgaaagaagt cgttgcaaaa ggtcacggtc atggctcagc gacggtgacg    22320
taccgcaaga tcaatggcga gtggaagttt gccggaattg aaccgaatat acgatggact    22380
gagtttggtg gagaggggat cttttggaccc cctgagaagg aagagaacgg agtcgctgca    22440
gacgaccaag tgatgaactc gaatggttcg agtgaggtag aggagaggaa tggtcatgtg    22500
```

```
gtgaacaaag cggttgaggt caggtccgtc tgatcatgtg ttagacggct ggtatatcca    22560
taaactatat aatatcgcct acaacctatc gggtaattag ttccatatat cttggtactg    22620
aggaaaggta gtttctgcgt cggaatcgcc tcttgctccc catcggggtt tgtgtaaggc    22680
cgttattcgt gttgcttcac tgttcgcggt catgttcggc tgcatatgca ttcttctgct    22740
gtgttgcctg aaatatcccg agtgaggttc aggctctatc ggttgtgctt atatagctca    22800
gaacctttcc tgatgtgatt ctactaatat atactgccca ccaatatatg gtgtcaaggg    22860
acttccagga catgatgtct agtctatccg accttgaaac ccacgccagt gagctcacaa    22920
gcgctgtcaa gacgatcatc tcgcaatgcc ctcgccaaaa tgccgcctct cgcagcagaa    22980
ctcaaccccct catcacctct agcgcttcca aggaagcgca tcgagcccaa caatcgatct    23040
tatcaaccat ttctggcctc cagaagctcc tcaccagccc aaccgacttc ctccaccacc    23100
tcgccgttca gaaccagctg cttgcctgcc tacaatggct cggagagttc caagtcctcg    23160
cttgcattcc cctcaccggc accgttccca taaaagatgt cgctgagctg gccggtgtcc    23220
cagagactca tctctcacgt attatccgga tgacagccac cgctggcttc ctggatgagc    23280
cagaccccgg tcaagtcgct cacagcgcgc tctccgctcc tttcgtcacc aaaccgtctt    23340
atcttgacgc tgtgatgttt ttggctggca ccattgcccc ttctgctttg cagatgccta    23400
ctgcaacgca gcgatttggc gcgagtttgc gtccgaacga gaccgcgtac aacctagctt    23460
taaataaccc agcgacattc gccagtacgt ctgagcaacg gccaaagctt caacgccagt    23520
ggcctgcttt tcttcagtat gggaccagtg ataccgacga tcgagtgacg gatctgttgt    23580
cgaggctgga ccattttcga agaggaagta tatctgtcgt tgaggtactt catccaatcc    23640
atcttcattt tgagatcatc catacgattg tctaaccaat tgcccaaatt ataggtcagc    23700
gcccgctccc tcgaccgcgc aacaacccctt gcaaacctct acccatccat caacatcaca    23760
gtccaaatcg catccccagc aggcccaact gcctggtcac cagcacaccc caatcccatc    23820
cgccccccaa ctcccggcgg tagccacaaa cacgacgacc ttcgcgcact cactgcaagc    23880
acggccagta caacaccggc tctagccac aaccacaccc atacgcatac caccaatagc    23940
ataccccagg cctccaacat aacgatccaa caccggcttc caacagcacc gcaacccatt    24000
acctcagcaa atctctacat cctacacctc ccctctccct caccaacagt tcctttcgcc    24060
tcccttgcaa cgcacatcct cgcagaactc cgctcacatc tcgacatcct ccgctcaaac    24120
ccatcggcga ccctgattct caccccgcgg cccttgcctg aaccctcagc tgtgcatagc    24180
gaggtcgaag caagcgcgcg actgcgcgac ttgacgctga tgcagttggc aaatgagcgt    24240
gagattgagc tggcggagtg gattaatctg ctgagcaatg tcagtgatag tatgggccgg    24300
ttggtggtgg tgaataagat tcagtccaga gaaagcacgg tagttttgtt ggagattcgg    24360
taccaggcct ataacaggtg acggttggaa atttttttt gagtttgtga gatgttcagg    24420
atggtccatc tatttcatgc atctatcagg tcctaagact gattccgcaa ctgcccggat    24480
ggaacggttt ggaacgagcg ga                                              24502

<210> SEQ ID NO 5
<211> LENGTH: 37665
<212> TYPE: DNA
<213> ORGANISM: Aspergillus nidulans

<400> SEQUENCE: 5
acagactaag gcctcggtca acaacttcat caacagttac ttcatgacct ctcttctgga      60
```

| | |
|---|---|
| gttcaaaggc aacaagactg gcatcaacca gatcgccttc aaactttgga gcttcattca | 120 |
| ctccttgagc atttagctca gacacacaat caacagtagg tagctcagca tccagagccc | 180 |
| cgttcataaa cgcatcaaca gtctcgcaca gttgactgag tagcttctcc gcaacctcga | 240 |
| cagtaacccc atcttcgagg taagccatgg caatctcaac atagtctgta ctagcagtcg | 300 |
| atgtaaccga cacatcagag acatcacccg caccttcagt cttcgcaaca gagacattgt | 360 |
| atttcccatc atcaaggtca agcgtccact cggatgcttg gtccagatgg ttcaggagcg | 420 |
| aggtgaagac tgtaccaact ggcatatccg tacagttgcg catcaagtcg cggaatccga | 480 |
| gggattcgtg cggcaggcgg gaaacaagct gttgctgcac agatctgagg aggtcatgtg | 540 |
| tggtccaggc tgggtggata gtagcgcgca caggaacgag atttgcgcag catccggctg | 600 |
| ctctttcggc aatggggtcg ccgttgcggc ctgagacgac ctccccaaag agtacgtctg | 660 |
| ggttccctac gtgttggcct agggtcagag cccacgccga tcgcacgatc gttgagagag | 720 |
| tgatgcctgc tggaagggtt ttgaaactaa cacggcgaga atcgtggtag acctgtctag | 780 |
| atggtagacg tctgggttgc gaggatgagc tgatggccgg cattgtacag cctttgagga | 840 |
| gcgagcgcca gtactcacga ctagaccagg tgtcctggtt cgcgaggctg gaaatatact | 900 |
| gggggaagcc aacgtactcc gtggtggact ggcgctggta gatctctctc aatgagttga | 960 |
| caaagtacga taatgatatc gcatcgtact cggcgtggct tagtcggaaa aggacgcgat | 1020 |
| gccggttggc gacgggagag cagatgatgg caaactcaag gaaggggtaa cccagttggg | 1080 |
| gtggtcgatg catgtcatgc gcgatgaact cttggtgaa ttcttcgata gactgatctg | 1140 |
| tctgatagtg ggttacagca ggggcgtaat ctcgaagaac aacctgaagg agttgatttt | 1200 |
| tgtacacgac ataagccgtt cgaaggatat cgtgcttctt gactacctcc aagcaagacg | 1260 |
| ctctccatcg ggcaaaatta gggctgccaa ttccatcaat actaacgtac gccattaggt | 1320 |
| cacgagaggg tcgcaacgat gtggcaatcg aaagagactg gaggtccgtg gtaggcgcaa | 1380 |
| cgtcaattat ctcgctgggt actgagagga gaggcttgat ggagtcgcgg atggcataat | 1440 |
| catcagtcat tgtagagaac gggcaatatg ctggctttgt cacagttgtt tttcgatcta | 1500 |
| tcagtgtggc catgtcggat agtattggat gacggaagac atccgccacc ttcaacgaaa | 1560 |
| tatgagcgtc ctcacgggcg ctggcaacaa gtcgcatagc cgagatagag tctccaccag | 1620 |
| agcggaaaaa gtcgtctttt gcgcctatgg aagaggcagg aaccttgagg accgtcgccc | 1680 |
| atagactttg caaaaggcgt tcggtgacag tagcgggctc tgccttaata tcatccacca | 1740 |
| ggaaatactg cgaccatgac ccgcaactgt gaatcatttc ccacgttgct cgacgattga | 1800 |
| gtttgccgga atctgtaagt ggtagtttgg cgaatggcag gtatagttgg gggaccatgt | 1860 |
| acgaaggtac aacagtaagg aggttgcggc ggagttcgcc aaatgcttcg cgaagttcgt | 1920 |
| cggacagtga tagcaagccg gacgattcaa cagagcttga tggcacttcc atcgcaacag | 1980 |
| ccaggagggg ctcatcctct tcgtaaatag gtttaaacag gcctgccaca acttcacgta | 2040 |
| catctgggag tttgttcttc acccagaact caatttctcc aatctcaaca cgttgcccat | 2100 |
| gaatcttgac ttgggtatcc cgtctaccaa tgtaaatgaa agagccgtcc aacttctgct | 2160 |
| gaacaagatc tccagtcctg tagaatcttc tcccggaaac ggggcctaga tcgtattgct | 2220 |
| gtagccaggc tgggtcggtc acaaacgcct cggcagtttt cttcgcatcc ccaagatatt | 2280 |
| cccgagctaa cagaggtcct tcgataagca gctcgccgac catgccaacg ggaagcagat | 2340 |
| tgtggtaatt ggacggatca acgacgaaca ggttactatg tgccaaggga aagccgatat | 2400 |
| tgggtgcttg aactgggtcc ctaatgcgct ggctgaaagt cgtcaggatg cttgactctg | 2460 |

```
caggcccata cgcgttgtga agttcgacgt gactggagct ccatggctca gcaacttcag    2520
ggcgaagagc ttcgcccaca agtagcaatc ttctgagaga aggcacctgt tcaggtttga    2580
gaagactagc aactgtaggt gtgaggatgg cgaagttgac agcagcctcc tccattgcct    2640
ccgcgaggcg actgacacga tcatcttctg aaataacgca tacacagcca ccaaaggaaa    2700
gagtcgtgaa tatctcggcg atactgatat cgaagttcaa ggcggagaac tgtatcgctc    2760
gagtgtcggg gcttgcgtag agtgagccgt ggccttgtac catgctcgaa acaatggcac    2820
cgtgttgaag caccacggct ttgctggtcc ctgtcgaacc agaagtgaaa atgataaagg    2880
cggagtctgt agcttgtaca actgggtgag ggttgtcgga atcaggaagc tgcgtgaaaa    2940
agtcttgatc gacctttaga acaggaccag tgacaagacc ttggaggcgt ccagggtctt    3000
gtgaggtcaa gatgactcga gtaccgatgc tctgcaccaa agcctgcata cgctgcttgg    3060
gatgctgatg attgactggc actattgttc ctcctgcttt tagtacggcc aagtaggtga    3120
ccaccaccca tttggttttt tcgaaaatag tagcgaccgg cacttgggga cctacgccta    3180
gaccttcaag atggtaggca agtcgggtgg caagacgatg gagttctcgg tatgtcaaat    3240
gtccgtcgaa ggcatggaca gcctgcgcat cggggcaaga aagtagttgg tgatgaacga    3300
gatcgtggat acagccatca gccatggtca ttctttcatc gaaatggttc catttctgga    3360
tccgacccag gtcctccggc gtcatgaaga taacgtcgct taccaggacc tcgcatgtcg    3420
cttcatttgc agcgctctgg agctgtccaa atacgtgggt aaagcgttcc aagatcgttg    3480
ttgccttctc cacagagagg acagcagggt cgaattgaag ttgcaaatca acagcactgt    3540
cagtatcggt catgttagtg ctgcactcta ttacaagagg ataattgtgg aatccatatg    3600
tctcaaacgg cacaggcgta agtccttgga agccggagtt tgcctggtcg agacggtcaa    3660
ctgcgggctg gacgacaaaa agatgctgga agttgagagg caacgacgtc atccggctaa    3720
tgttgtgaag accagcatgc tcaaacggta gcatttctgt ggcttgttgc tggattgagg    3780
ccaagtacgc cgagaggctc tgggcagggt caacagaaac gcgaataggc acagtggtaa    3840
tggtaggccc caagacgtcc agaatcccat ccactggagc agtgcgacct gaaagcgctg    3900
ttgggaagcc tacgatttgg cttccagttt cctgggacag gattagtgcc catgtagctc    3960
tcaggagcgt ggagagagta aagtcattgc tgttattggc gggaatgcgg caactttgaa    4020
ttctgagctt cctgggagaa ccgttcttcg gagacccggg gaagctaggg cctatgccac    4080
cctcgagttg agacttccag tagtcgcggg tctcctcggc agagtttgac tgcagatact    4140
gcacaaagcg agtgaatgga tggaaagacg gcgcgggatt attggagtag agtgcaaaag    4200
cagcctccat caactttcgg gctgtccatc cgtcatacgt gctatggtgg gcagtccaaa    4260
cgaagaatcg cgcctgtctg ctggttacaa ctgccaaacg caccaacgga tctccgaagc    4320
ccatgggctt tgcagagtcc tctgcgatat aagacggcag ctcggacagg acgttattcc    4380
atgttatttg ctgctgaaga accacttgca ttccaccagc cttgggatct tgtataatgc    4440
gagtacgtaa aattggatta agttcaacca acgttctcca agcttggcaa aagcgagact    4500
catcgatggt gtcttccaaa cggaagaccc accgactgat atatgcctga gggtgttgag    4560
ctgtgattgc catgagacct tgctgcaaag gtgtgcacgg gtaagcatct tcaatgacgt    4620
cgacttcaac tttgcactgc gaggcaatct cctggagacg tgcctgtctc tcatgttgag    4680
ggtagggcaa cagcaaaaac ggtggcacat cgttgtcata ttgacagttc tcagtggatt    4740
ctgaattagc aattgtattg gccatgtccg agagaacggg atgcttgaat acgtcactga    4800
```

```
cagataacag gataggaggc tgtgcggttc gagctaaagc gactaggcgc atagcagtga    4860
ccgagtcacc accaacgcgg aagaaatgag cgttggcgcc gaattctttt gaggtgttga    4920
gagcggctac ccagactctg gccaaacggc gttcggtctc agtcgaaagc gcgacattgc    4980
caccatcagc caggctgtac tgtgcaagct gctcctcttt taggccccct atcaaggttc    5040
gaagtgctct tctgtctagc ttaccagagg ctgtatttgg catgttcttg atgggaatgt    5100
acttcgaggg taccatgtat gagggtaatg ctttgagaag ggccgcctgc agctgtagga    5160
atgattctct gagctgatgg ttgacgtcca ggaagacaca ttcgttgctg gaacgatcct    5220
tgcgcaactc gatagcagcc actaaggcta cgtcgcctgt gcttgcacca ataacgtcaa    5280
cagcgacagt ttgggtgtcg aagtgttgcc gaagccagta ctcaatctca ccgacctcga    5340
cacgttgacc gcgtatcttg atctgaccat ccgctcggcc gacaaacatg attgaaccat    5400
cagtcggatc ttgcctgacc agatcaccag tcttgtagat tcgcttttcca gcccaggaat   5460 ggaagccgta tttagaaaca aaggcaggat ccgtgatgaa ggattgtgaa gttcgctcgg    5520
tgtcatttag atagccacgt gcaactagcg gccctgagat gagaagctca ccaactacgc    5580
ccaatggaac gagacggttg tgatcttgtg tgtcaaccac ccagatagcg ccagcaaggg    5640
ccgtgccaac actagaagct tgctcttctct caataatcgg gccgttggta gtcgcaagaa   5700
tggtagattc tgctggtcca tacccattaa agagggtgac atgacttgcc caggtttcga    5760
cggcgctgtg tggaacaact tctccggcta aaactaaggt cgacagcgtc ggtactgtcc    5820
gagggtcaat aagactggcg actgtgggcg tgaggactgc aaagttcacg gccatagcct    5880
ccatctttgt agtaagactg ttggtatcaa cacgatcttc ctccgagacg acgcagacac    5940
aaccgccgaa gcgaagagta gacaggatat cgagaaggct gaggtcgaaa acataagcgg    6000
agtattgtaa tgctctagta tttgaccca tttgaagttt tggcccatgg ctttctatac      6060
ttgtgcagat tgtcccatgt gtgaggacaa cacccttggg tgtaccggtt gaacctgagg    6120
tgtatatgac cacagccgca ctttcagatg tcagactact ctcgctgggg ggatgacaag    6180
ggttgggtag tgttgctata aatccaccat caatagttag gacgttggca gaggtaatat    6240
ccctgagttt ggaggcatgt tgtccatgg tcagaacaac tggggctgtg atctcgttca     6300
ggatatgctg cagacgctgg acaggcatct gaaccccaag aggcacaatt acaccaccag    6360
atttgagaac agcgatcatg gacacaatgg tccacatgga cttatcaaaa caaagccccca   6420 ccatcacttc ctcacgcacc cctaagtttc gtaagtgatg agcaagccgg tcggacatgc     6480
ctgtaagctc agcgtaagtc agctccccgt cccagccgca cactgcctgg gcccctggct    6540
gagaaagagc ctgctcatga atcttgtcgt gtatactgcc gggaacagtc tctccgacgg    6600
ttgagttcca gatatgaagc acttcaacgt caccagttgg tatcacatca atctcatcga    6660
tgtttgcgtc ggggtttgcg gcaatagaag ataatgcgcg gccgaagcta cccaacaggc    6720
gtcgggctga cggttcgtcg ataaaagtgg tggcgtattc aaggtctagt gatagacttt    6780
tatcgtcact cacaatttta acctgtacat catattcggt aggatcttcg ccggcgaggc    6840
tttcaatcac cagacttcgc ttttcgtgag tatccatcat cggcttgggc ttgtagatca    6900
tggttgtatt gaagaggccg cgctcagata gatgaagagc gtgctggata tcgctaagag    6960
aggttcgctg gtgattgaag gcatctaaga aattgtgctg aacctgcttc gcggcttcag    7020
ccacggtagt gccggggtgt gcgagttgaa ctctagacac cattaagtta atcatgggcc    7080
cgcacatctc gtgtatcccg tcgattggag catccctgcc atttgaaata tagccaaagc    7140
tgacatcgcg ggaaccaaga taccgagata aaaccgtggc ccaggcgagc tgtgtgatgt    7200
```

```
ttgcaatcgt aactccatgc gtgtctctga aatcttgcag aggttttatg ttatctactt    7260
cgagagaaac cgttctcaag gagcgctttc cggagtctag attagaagag gcaggaaggc    7320
atgacggctc tgcaccagca aggtgattcg tccagtagtt cagggagtcg aaagcgaagg    7380
tctgttgcag gaacgagaca tagatgccat atgatggagc aggcgagtct ggaagcatat    7440
tatcatatgc cagaatgaga tcattgagaa ttagatccat ggatgaggcg tccattagaa    7500
cgtggttgac atcaacctgg gcgtaaactt gccctgtaga agcttgggct agggtgagct    7560
ggtaaggcgg ctgcccgggg gcgtactccg gacgttcgag tccttcgaat tgagcaagga    7620
aatcatcact actgcaagac tgcagcactg gtattgttgg agtgtatctt ttgagtacaa    7680
cttgatagaa gagttcccgt cccgatggac tagggacaaa gaatgtacgt agaatagcat    7740
gtcgctgcac aaccaactgc cacgcgcgta ggagtcggtt catgtcgacc ggtgaagaat    7800
cagcggcacg aatctctccg gcctggcgca cttgatatgt tgtgtggtcc ttgatctggc    7860
tcatcaagat gccttgttgg ataggggagc aatagtaaat gctctcaatt gcagaaaggt    7920
tctcgacgcc ggtccgcgga agcacgtcgg tctcaagctt agacaagtcg ctggcgttga    7980
tatcaaaggc cgttggtgcg cttgtagcgg ctggagcttg atcgattgaa gaggtagaga    8040
gctgagtgtc agtgttggga ctcgtggtct taatcacagc cttcttcgcc agttgagaga    8100
ttgattcgca ttgcagcaca tcgcgaacag taacatagat ggaatattgg ctgcgacact    8160
ttgacacgac ttgcatagca gtaactgagt caccacccac agccaagaac gggcgactca    8220
tagggacctt tccaatcgaa gcgtggagta catcggccca gacagcttgg atgttttttt    8280
cttcggatgt gcttggagtt gtcgtaccct ccgtgtagct ttgcgtgagg atttttaaaat   8340 gttccacctc catggtctcc agccattgcg tgagtcggcg acgatcaatc ttgtcggaac    8400
tgttgtgcgg cattgctgca agtgatatcc aggagttggg aaccatatac tcgggaatac    8460
aagagtgtag gtgatcacgg acggatgaag cttgctgcag ggcatgggga agctggtcga    8520
ggggcgtggt ttggattccc tcatctgcgt cagaagaaat gaatccatgc aatgtcaata    8580
tcccaacgag ctgcaactgg gctgggccac agtgagggta aactatcaca ttctctacca    8640
cagaaggatg ctcggtgaca tggtgctcaa tttccccgat ttcgactcgt tggccgcgaa    8700
ttttgacttg accatcgcgt cgtccgacat agataagtga tccgtcttcc atctgacgta    8760
ccagatcacc agtgcgatac atgcgccgct cgcggcgctg tgaacaatgg tcgtgttcag    8820
agtaccggga gatccaggca ggattgcaaa taaatgcatt ggctgtctta atagggtcgt    8880
tcaagtagcc tcgagcgagt agaggaccct cgatcagaag ctcacccact gccccaagag    8940
gtagaagtcg gttgtagttg ttctcatcca ccacccagag gccacctgct atcgcacggc    9000
cgatattcgg cacatccgct ttattggcaa cctcattgca ggtggcggcg atactacatt    9060
ccgcggggcc gtaggcattg aatacacgaa caccatttag ccagggttcc aggtattctg    9120
gttgcaccgc ttcaccacct accactaagg tcttgaggcc cggcacgtca gacggcttga    9180
tggtatgtat aacacgtgga ggaaggaacg agtagttaac tcccatacga ttcattgcat    9240
cggccatgtt atttactcgc tctctttctg atggcatgca aacacagccg ccgaattgca    9300
gcgttgatat aatgtcatgg agcgagatgt cgaacgtaaa gtgggcgaaa ttgaaggcgc    9360
gggtctctga gttcatgccg aacttcttgc catgtgcctg catgctggtt gacatagcgc    9420
catgctcaac gacgacaccc ttgggggttc cagtcgaccc ggaagtgaag atgacgaacg    9480
cagcattgga aggtgtaacg gttgagatgg gctgcgtgac agggcttggg agcgactgga    9540
```

```
tcagatcatc gcctatagtt attacattag gcactaaacc ttcaagcgcc gaggcaaagc    9600
cctcagaggc gaggatcgtt gtaatgccag tctgttgcaa gatgttttgc acacgctgaa    9660
tgggatcagc tcgaataggg acaaccgcgc ccccagcctt caaaacagcg aggtttgcga    9720
ccaaagccca ttttgatttt tcaaaacaaa gagcaaccat ggtctctggt attaccccaa    9780
gcgtagtgag gtatagagct agcttgtttg ctaggcggtc tagctcttca cgcgtaagat    9840
caccatccca agcacatacc gcaggggcat aagggttggt tgaaacatgc tgagaaacta    9900
gttcatgaac caaagcttgc ttgaccgggg gaataccttg gttgaactgg aagagtcgtc    9960
tggcctcgtc cttgctcaat aaatcaagat actttagttg cgtttgatct ctgccgttag   10020
taacaagctg agtgacaatg tgactaaagc ggctgagcag atcattcgtc tgggaagctg   10080
aaatcattct ttcatcaaag tgcgcctcaa tcgtaactgg gatatcggat atatcactag   10140
taacgcactc gacggtaagg gcataaccgt cgaggttgag ctctggaaca tgaccatgct   10200
cgtacgctag gagcttacca tgtacagaac tctcacgttc ttgcgctggt tgcacggcga   10260
aaagatgtgg aagatcgatc tggccaacga agcggcgaat gttctgcaag cctgtgtgct   10320
cgaacggtat catgtcgacg cttttgcttgt gaaccatggt gagatattga ttgatcgttt   10380
gttccgggtt gatatgcaca tgaactggga cagttgtaat tgttggtgcc gccatgtcca   10440
gaatgccggg aactggcgca gagcgcccag agagtgcaac tccaaacaag acatcattgc   10500
caccgtaggc ggagattgcc agtgcccaag cagcccttag agaagaagct agcgtattgg   10560
gccctccaac tgggcgaatt tcgacgctcg agctcaactt ctgagtaggc tgtggccggt   10620
acgaaagctt gtgaagagag gggaacggtg ccccaacttt tctcttgatc tgagactgcc   10680
agaacgactt agcggccttt agatcttgtt gacctatgta cgagatgaat cttgagaatg   10740
caggagttgg agcgagctct tttccatcat agaggagtgc caccgcgtca aacagctttc   10800
ttaaactgta cccgtcgtat acactgtggt gagctgtgag tacgaagtat cgcttgttgc   10860
cgctgtaaat taaggcttgt cgcaccaagg gctggccgta accgaaagat tgttgtaggt   10920
ctttatccaa gtactgcttg aggttcaggt ctccacccca cgcgacagac tcacggacta   10980
ccacttgaag tccacctgac tgactgggcg caatgcgcgt acgcaggatt ggtgcctttt   11040
gggtcagtga tgaccatgcc cgtttaaatg cgttagtatc aacagcttct tggattcgga   11100
aaacccagcg gccaatataa gaccctggtt gctgagtggt gatagccatg agaccttctt   11160
ggaggggtgt acatggatac acatcctcaa tatcgtggac tgcaacatca cataactttg   11220
caacacggag aagttccctc tcactgacag aagcctctgt ctgttgggct tccttccaaa   11280
gcccaaaccg aggaatatcc tgtacgtccc ggcggcgccc catctgagct tcaagatgag   11340
cggccatctc ctgcaactta ggataccgga agacgtcggc aacgcttatc gggatgtctt   11400
tggcatttgc cagggaaacg aggcgcatcg cggtgaatga gtcgcccccg cagtgaagga   11460
agtggtcttg gacacctaca tggtcctggt ctacgttaag cacagtggcc catagcgact   11520
gtaacttctt ctccataaag gtggatggtg caacactcaa actggttgaa agggagtact   11580
ggaagaggac atcacccggc aggttctcca gcatctgctt gatcgtgcga cggtcgagtt   11640
tgctagacgt tgtctgaggg aggtgcacta ccggaacgaa aagccgtggc accatgtacg   11700
agggtaggac ctctagtaga gaggcatgaa gctgagaaaa tgcatctcgc aggtgagggg   11760
cgttggggag gaatatttcg tgaaatgggg cggataacaa atgcctctga aggaaatcat   11820
cgctgagttc catcgcaaca gaaatcatta tgttggggga attgccacca ggggtgataa   11880
ggcttgccac aagactcttc acagctggca ataacttctt aacgcggtac tcaatctccc   11940
```

```
ctatttcaac gcgctggcca cggaccttaa cctgggagtc ctttcgagct tggtagatca   12000
agtcgccgtt tggagactga cgaacgagat cgccggtgtt atagaatcga tgaccttcaa   12060
gtctgattgc cttcgcccac ttagggttcg tgacaaaagc tgccttcgtc ttcttcggat   12120
cgttgtgata cccgcgagcc agtaacgggc cttcaaccca gagttcgccg acagcgccaa   12180
tgggacaaat ggattcgccg ttggcaatta cccagacgct ccccacaagc ggtcggccga   12240
tgttgagtgc ctgtttcttt tggacgagag ctgcactgca ggtcgtgtaa atcgagcact   12300
cactcggacc atatccgttc aaaaccttga ctcttcccgc tgccttggcg tgctcctcaa   12360
tcatggcctc cctgacggcc tctcccccga gaattagtgt ggtaagacac ttgatgttcg   12420
caatatccag caagctagcc acagttggag taacctgtgc gtgagtagca ccataagcct   12480
caataacgcc ctgaaggttg ttcatgcgct cctcttctga tatgacacag acgcaccccc   12540
catgcgacat agtgcccag atatcactaa tgctggcatc gaacgtgtag gcagcgaatt    12600
ggagtgaacg agtactggga gacatttcgt aaatcttgcc atgagcgcgg aagctggaac   12660
atagagaaag atgggttaaa atgacacctt ttggcatacc ggtactgcca cttgtgtaga   12720
taatgaaggc agcgttgttg ggggtaacat tcgtacttgg aggctgggg t tgtgaagaaa   12780 gggcagaaaa tagtgtctcg tccatgtgca gaatatgcgg acaaggttc ctgaactgag    12840 atgaatactg atgcgacgtc agcatcacct ttgcgtttat atctttgagg acagttcca    12900 ggcgctgcgt tgggtgcttt ggattgattg acacaacgac gccagctgcc ttgaggacac   12960
tgagctgagc aatgatggcg aatttagatt tatccagaca cagcgctacc attacttcgg   13020
gaccaattcc caaggtcact aggtggtgag ccagcgcatt gctcatctcg tccagttgtt   13080
ggtatgttaa gtcgccatcc caggcacaga cggctgttgc gttaggtcgg agtagccgct   13140
gttcattgaa taagtcatgg ataagacaat atccatcaac ggcaggaatc ttgtcattcc   13200
aagcacggac ttgcaggata tccttcggcg ttacggtgtt tagctgtccg acatgggtat   13260
ctccgttagt aacgagggat tggattccct gccggacaca gccgagcaac ctgttcgcgc   13320
tatcgtagga aagaaaatct ggcgagtact gcagagaagc ggatatcttt tctggcgatg   13380
cgaacacact gaccgtcaca tcatactctg tgggatcctc accggtgatc tgctctagcg   13440
cgagactgag ctgatgtttt tctgctgaaa caatatggcg ataggaaagc gctgtgttga   13500
acaagcttct gccctggagc tgaagggcgt gccaaatctc aaccaagggt gctctctggt   13560
agttgaagct ctcaaagaag ttctcttgta tttgcttgag tgtgttctga gcactggcct   13620
ccatgtctag tttgatatga gtgaccatca tgttaattag ggggcctacc atggtctcaa   13680
catctttgac agggacgtcg cgaccacttg atagatagcc aaaggacaca ttaggcgagc   13740
cggtgtactg ggctaaaacc atggcccaga cgagctggaa cacgttggca attgtgacac   13800
cataggtttc ggtgaagcta tgtagctttt caatgcagtt gatgtcaatt gatactgttt   13860
gcatgggcct ccttggtgtg gagtcatcag cagtagctgg ctgcattcca tcctctgtca   13920
tgcctcgaag gtagcatggc tctgcgtcag caaggcgctt ggcccagtaa tccaacgcct   13980
gatccgcggg tatcttctgc agatgcgaaa tatattcgct ataagcagcg ccgatggtgt   14040
caggcgccag cttgccatca tatgcctggg caagctcggc ctgtatgatc atgagagatg   14100
aggcgtctac gagtgcgtgg ctgataatga tattgccgaa cgtccggttg gaagaggtcg   14160
aataaatcgt aagcttatga ccgatgcgct tgtcaatatg tcgttcatct agagtagctt   14220
tgacggcaag gtttctgaaa agatcgtcgt ctgtgcactc gacatgctca gcttcggcct   14280
```

```
tgcacgactt gaggaccacc tgatcaaaca aacgctcgct tgatccggat gccgaacgga   14340
cgaatcgtgt tcgaagcatg gggtggcggt ttatcaagac ctgccaggca gcaagaagac   14400
gagtatggtc aagtttgcca gaggaagtgg tcggtatgat ctcaaaagat tgctggatat   14460
aatattcgga tggtgatttc acttggctga taagtatgcc ttgttggatt ggagaacatg   14520
ggtagatgtc ttcaacatca gagcagttca agccggcgtc aggcaaaatt tcatcttgaa   14580
gaaccctgag gctctcagat gttaaatgca gcagtgggaa atcagtcaca gttagagtcg   14640
gcgacgctcc tgacaactca gtaccaaggg cactgatggc attggcatag gagtcagccc   14700
aatcccggat cttctcctgg tacttcatgt tgcgattgaa cttgaagcga atacgcaact   14760
tatcggggta cgcaatgacg ttgacattaa acacacatcc acgacgggta ctcttgccaa   14820
ctggagatgt cccaggtcca gtgagatcta ctgtctcgaa aatagtttcg cttgcgagtc   14880
cttcggaata ttgaaagagc acttcaaccc atcggtcagt gaaagcttgt tgaccgtccg   14940
atagaaccct tccgaaggcg ctgcgtcttg cgtccttagt ctgtcttaca atatccaagc   15000
cgttgtgtgg ctcatcgaga aagatgtgta taggtgtcat acattcgaag ttgccaactg   15060
tgtttgagaa gtcaagtcca ctatcaccta cgtttcggcc atcgttaatt tcaaaaacgg   15120
ctgggagtcg gcgatttggg aaagttttct ggaaggactt caacagtgca gcaagaagaa   15180
tctccacacg ttctgtacgt aaggctctgt ttgcgtccct aaagtatgca ttcgtgtcgt   15240
ggctgttgaa gatcacttct tcgaccgttt cgtcctcgta ggtattgcca tcgttcaagc   15300
cccagtactt aaagtcagca ggtggcagat cagatctgaa aactattccc tcaaggttct   15360
ggctccgttg ggcttgtagt ttgatccagg tctggaatga tagcgggtta gaagttggaa   15420
actgctgtcc ttccagaagc acacttatat ctcggcgaat gatgtcccag gacacttcgt   15480
cgactaccag gcgatgggct gtcatgaata gaagatctgt atttcgagcg tcttccactt   15540
ggatatactc aacgaagaat acgggacctt gctctaggtc taaactgccc tgagcctcca   15600
caataagggc ctccgcctcc tcgctggtag atacagtgta atgcctcaac gcaaacggtt   15660
gatcaccatc actgtgtaga ctctgttgcc acccagcgac gttatgacgc tgaaatctgg   15720
aacgtaaaat aggatgtctg tcgacaagcg cacccacggc ttgagctagt tctgaatatt   15780
caaaaagttt gcgaggtacc aagcagatat tggaattgta tctgtgggca ccactggact   15840
tcagaggcaa ctcaggatcg gcaatggact cgaaatacca cttctgcata ggcgacagaa   15900
gagattggtg gccttccgtc ttctcatcct ttacttctgc ggtttgcgcc aactgagcca   15960
cggacttgct ttcaagcaca tctcgcaccg ctaccgtaat cccccgcacc cgcagccagg   16020
acacgacatg catggcagtg atggagtctc ccccaacact taggaatgac ttgtgctcta   16080
taggaatttg agtaggcggc aaacgcaaca catcggccca tgcttgttgg acttggcgtt   16140
ctagaagcgt ttcgggctct cgactctcag agccagcgtc agaagacttg gtgagagctt   16200
ccaggaacgc tgtatcaata gcctcaagcc acaccccccaa ttttttgcgg tccaattttg   16260
atgagtcgtt ttgtggcatc atgctttcca aaggaatcca gatctttggg accatatgct   16320
caggaacatg atttgagagc tcttccgatg cagcagccag ttgactttt gtgtgagaaa   16380 gttttccact tggtataggt attatgtctt gtcctggacg ttttccgcaa aagaaatcgc   16440
gcaaggtgag aaggccgacc aatcgatctt tgcagggtcc ttgtttaggg tagattatcg   16500
ctgcatcgag aactgcgtct tgttgtagga ggtggtgctc gatctcacca acctcaaccc   16560 gttgtccccct cactttaatc tgtgtatcac ggcggccaat gtacgtgatg gaaccatctg   16620
ggttctgctg tacgaggtct ccagtccggt agaggcgtcg gccggatcca aacccgttct   16680
```

```
ttatcatcca tgccgcgtct acgacgaacg ctgctgcggt tttctcggga gagttgagat    16740
acccacgagc ttgcaatggc ccttcaatga gtaattctcc tggtgctccg attgggacaa    16800
ggcgattgta gtcattgggg tcaacaaccc aaagagcccc cgcaaacgcc cagccgatgt    16860
ttagtgcatt gcaaccaggt gtcaatcggt tgatactggc ttgcatcgaa cattctgacg    16920
gcccatacgc gttgtagacc tctacgtgac caatccattg atctacgacc gcttgcttga    16980
cggcttcccc gagtaggacc aacttcttca gggttggcac atcttgcggg aatatcgttc    17040
cagccaccgt tgaagttagc cccgcacaat taacctgata tttcaccatt tccggtgcta    17100
gattgctgat acgatcctct tctgagagaa tgatcaggca gccgccgtag tgccacgtgg    17160
tatatatatc ttgaatggaa atatcaaagg tatatgccga aaactgcact gtgcgagtat    17220
ctggactaag cttgaatcta gcacccatat gctcaagact cgtacagaga cttgcatgag    17280
ggagcacaac acccttcgga acaccagtgg atccactggt atagatgata aaggcggcgt    17340
tatcgactgt tgcaaggcag gggaccattt cggaaggtgg tagttcggcc atgaacgctt    17400
catcaatgac cactgtatgg gtcacgaggt ccatgaagcg ggaggcaaat ttccctgacg    17460
ttaggatgat tgtggcttgt aggtccttta ggattagcct ggttctcgat gctggttgtg    17520
tcgttccaag aggaacaacg catccaccag ccttgaggat cgctagttgt gatatcactg    17580
cccatttcga tttttcgaag cagattggga tcttagtctc gggctgcacg cctaagcgaa    17640
tgaggtagga tgccagctgg ttagccgtgt cgtccagctg ctgatatgtt aagtcgccgt    17700
cccagccctg aacagcccaa gcatcgggtc ggcggagtcg ctgttcatac actttgtcgt    17760
ggatacgata gtctgccttt ggtgggatct ccttggccca ttcacgaagc tgattgattt    17820
cttgagtggt actaatatca atctctccca gcacggcatc ttcttctttg acgatgttca    17880
ggagcgcctg ccggaaggat tgtgccacac tctccaccgt gcgctggcca atccgtgagt    17940
tccagtaatc aatcattact tccaatccct catgccctac ttggatgttt atggacatgt    18000
catacttgcg cacttgttag cgtcgaatgg actgtaaggg atataatcac tacttacttc    18060
attggggttg gcagcatcaa caagctcaaa agcaagccca gatcccgcta attcagttgc    18120
agcttttcgt tggcatgaca ttaatgtgtt gctcttgaaa cgggcaaagt ccccagattg    18180
cgcatcatcc aaggctaagt agtactgatg tgagaggctt tccacgaagt cgttcctagc    18240
tttcaccaaa gcctgcggaa ctgttgcagt aggcggcagc ttgatgcgac agaccactgc    18300
gtttaggaag gctccaaccg tattgttgat tcctttaaga ggaacatccc gccccgacgt    18360
tgcatacgag aaacacacat cttccaaccc ggtgtaggac ctgagcacta gtgcccatgc    18420
tacctggcaa atattagcag gcgtgatgtt gaacttacca cagaattccc ctaggacatc    18480
agagcccagc tgaatgtttg atctgacggt acgaaggtct tcgcgactca actggtctcc    18540
gtacaatggg aaatgggatg gctgggctcc tgcaaggtag ttggaccagt aagtcatgga    18600
ttcttgcata ggcagccgtg attggtagtt gacaaagtct tggtaggcca tgacacgact    18660
ggccagcttc tgtttgctat agagttgaaa aaggtcccgc atcaggacca gagcggaaag    18720
cccatcaaca acggcgtgtg acatatcaag acggaggtag acagaggatg gtgagattct    18780
gcaaaatgtc acttgatgag tttggccgta gctcttgaaa gttactggac ggcgacacgc    18840
gagacggcga gctgcctctt caccctcgtt ctctaagaaa gtgatggagc taatgccctg    18900
cttcattacc acctggtcga agtgcccttg gcgatttggg ctttcaatga acacggtccg    18960
aagagctgga tggcgtgcca cgaggcgaac ccaggcgtct cgaagacgcc cgcagtctag    19020
```

```
ttcgacattc agatcctcgg agctcaattt aattacaaag gaacactggt acagatcggg   19080
gtaaacagct tgagccacca agaaggcttc ctgtcgcggc ccacagggga atactgcttc   19140
cacgtcgcgg aaagggtcgc ccgttacagc cttgagccga gatgaaacaa ggttgtccag   19200
ctctgagtat gtcagtttga ggaaaggaaa gtcgcttagt gttccttgca cttcgctcat   19260
ctcacactca gcaatcagtt ccttcagggc agcgcgaaac aagccagcaa gctgacctag   19320
tttttcccgc cctagctctg cagacctgga ccgaagacga agctttagct gctgttgctc   19380
caagaaaggt tcaacaaatg ctaggcaccc gtgaggaagt atggagaagt catcctggtg   19440
gaaaagctca tggagggtat cagctattgg cgctgtcgtt ctcccagtt gccccatatg   19500
taacagaaca tatcgactgc gatcctcgac tcctgatatg cgagagacat aaagaagcc   19560
catccgtgta tccttgactt tccgtaggaa tccaagtcca ccgtcctctt ctgctctttc   19620
cacggaccgg cggatgatat tgtcgaagca ccctactgta gctgacagct taggaccgcc   19680
actgtgcctg ccgtttgaga ttataccaaa gctcaacgtc tcctccgacc tggttactcc   19740
tttaagtgcg atatgtagtg cggcaacgat aaaatcctct ggctgagtgc gaagcacaga   19800
gtggatgctt tcatcctcca gcttcgccag accagctgca tctgtttcca ggataaccac   19860
atcagccaac tcgattttgc catcattttg gtgtctattg tgttgtcttt catttgtgtt   19920
ccgctcatcg tttgtgcttt cgaccggcgt cgagcgtctg aatgtaaagt cgcttaggtt   19980
gtgagtggaa gcccaggagt caaacgaagt ctctggatac ccgcgagcaa gcggctttcc   20040
gagtactgca tggtccaaat cgcgctgaag atatcccaa acgagacat cgatgatggc   20100
ccggtgaaag tcgagccgaa gatagcgggc gaggcacgtg ccgtggtcac ggtctttttg   20160
cacaaatacc gtggcggcga agagtccatc ctctctcttc ccgtccgctt cccagcccac   20220
ggtcaggtat ccctgctctg cttgcgttga gatcgtcgga atctcgattc ttcgatgggc   20280
gaaggcgtcg atcgtatcat tgtatgtgag tcccaagtca ttatttcaa gtgttgtaaa   20340
gttcgctcgg aggatggggt ggtggctgac gagcaatttc agtgccgcat aaagcgtcga   20400
ttctgcgatt ccaccttcta acttgaaaac tttggcatcc caagccttcg tcgaggcata   20460
caacttctgt gcctctgtta atggcttcgt ccgtatctcg gcaggctgcg caggcccgtc   20520
cagcaccggg cctgagctga gcttccctgg cgcgctgctc ccctctgcta gttttacaga   20580
ctggcataac tctcggatac tcgtcgcttg gagcatatcg ttgatggtga ttgtataccc   20640
cgcctccccg cagcgcgcca tcagcttgat tgcgagcaaa gagtcccctc cttgcgcgat   20700
gaaggacttg tccaacttga tctttcccac cgggcggcgc agcacctctg cgcaaatctc   20760
cctgatgtcc ttctcaacaa cctcattatt cgtaactgtt cggtttggcg aaccggctgt   20820
cgcaaacgta ctttgctcca ttgcaaacga ttattatgat tatgattaga ggccgctatc   20880
aaaggcgaag aagaaagtta ctgccgttcc aagctggtct cagtctccgc gaagataaag   20940
ccagcaacaa cgtgattatc gcagaacgat atatccagga gtattactga gctgagtcaa   21000
agtatgaaag ccgtgagcgg tacatacgct ttggacctac gcgaagacag ctgatcaaca   21060
atgccgctac tccagaccac cgtatactcc aattcgccga agttctagct ccgtatcctt   21120
cgtccttatc caccaaagtg tcgatcacgc tgttccacac ctctcgaacg agatctgtgc   21180
cttcggccca cttgaccttc ctcgtcttgg cacgacattt ctggtatccg cagcaaagcg   21240
ggccgggttt ggaaaagttg gaattaagag gaaccttaaa ggaagctgat gccgctttca   21300
tgatccaagt acccgtacgt attgaacctt tcaggcaata tccacgaatt cgatccggag   21360
tctgaactga ataaagaaaa tgctcgtgac gtatcatttt cccagcgcag ggagcaggaa   21420
```

```
accatgttcc tcgtgaggtt cataggagtc aagtgggatt cgatagtcgg aaaccttcac   21480
ctcccgacca tctacatact tgcttttccc ttaggaaaat cgggtatgac tacagcggct   21540
tcatcatcac tatgtcaaaa gcaaagcaca ctctggctta catcgatttt gttttttaca   21600
tcgacattgt tcgcaatcat actcaaggta tacttaacgt acgattggtg gatatattcc   21660
attggtgctc aacaacaacc acaagaagca ttgaatccaa tcatgctgat catgagagac   21720
gccctccgat actggttcgc acgcgagcga tcccgcgagc tagtacatta agctcggac    21780 agcccttgac cattcaatca ttttcgctct gatattcaag agttttctca gtctgaaccg   21840
gactgatgga aaccgatcta atcggcggac gtgccctga tgcaataatg acttttgctt    21900
ttgcttctta tccaggtcta ttttatgtat cttacgtatt agttttatc ctttttatt     21960 tgcgttttcc ttttttgtct tttttttttt tttttcaaa ccgagaagga cgggacgcct    22020
agatcatttg gcaggtacca gaaccacatt attcatgatg cgacgagtcc aatattgtcg   22080
gagcagcgac gatcaacaag gcagggctgg caaagatcag gatcccgact ttaagcctgc   22140
tagctgctgg tggcggggag aggcagagct gcaagttcca gaagcgagat actccgaggg   22200
cttgtttact ttttttcccc gattgcgtca actcctgcac aagaacaagc cggaccaatg   22260
gtctattccc acgcatggcc gtggcactat cgaccctaaa tgcagtggct ctaatggtgt   22320
gccgacgtgt ccaaagtaca gatccctggg cctcaggtac ccagtcgcga atctgagcct   22380
cgttcgcaag cttgtattga tcgtcgaatc caagacatac tggttccact gagctgctat   22440
ccggtcgcta gcaccccaa acgccaccag tattcaaata tattttctca tcggacactg     22500
cacggtaaat tacagcgctg tgggccagat tgatggggaa gtcttctgcc atgctgagtc   22560
tatgattcaa ctcagctgag ccatgtttgg tgtcgcgttg acttggctcg ccgcgattgt   22620
tggcagcttc gtatccgaat gctactctcc tagatcactg taatcagctc gagagtcaga   22680
cgcagtctgc gtgcctgtcc cagtcacagt gttccgctgc aacacttctc ctgtgcctcc   22740
gtgccgcttc gccgagtttc ttggtcttgc tctctcgtac cttctcctgg atgtttctac   22800
gttcaccact tgcattctca aacgctggta aatcacctct agatcattct gtcgaaatct   22860
agccttgaaa cgcgacactc ggtttctttc tgttcgcgct gagctttgcg tcaataatgg   22920
cgaccttcga caacccattt tatagttttc ccacctcgcc tttcacagaa acattctgga   22980
cgagttggaa cttggatgat ttccccgttt taccccagaa tgacgaattg aagacagatg   23040
caagctggca gtctgccatc tcgatgccgg attattcttg tctgcccctc aataacttct   23100
caagcttggt ccctactggc gattcaatct atatcccaca aattccagat agccaatttg   23160
atcccccagg ttgggtaccg ccagccgaca cttttggggc tccagtgtta ccagcggctt   23220
ccacagcttt tccatgcgcc cataatttca caaccgactg caatccgttc caagactcgt   23280
cgcacccgcc gtccggcgta tcaaccccaa ccgatcgctc ctctccatct gagtctagca   23340
gcagccgtcc ctcgcccacg ccctctgccg ttaccaggac caagcctaac cgcgacataa   23400
aaggccctat ccgatgctgg gagcacagct gcggcggtcg ggctttctct tctcttggaa   23460
actatgagcg acacctacgc gagaaaagtg gacgagctaa gagctttacc tgcgagcagt   23520
gcggccagcg cttcacccga tcgactgcga agaacaaaca cataaagcac ggccggtgcc   23580
gagcgcaaca ggcctgataa actaccaacc aaggacatca tcacttacac tttatacccg   23640
atttcttttg cgaatgcaca tatatacata tattgagctg ggatttggag cgacggcaaa   23700 aattttttctt ttaccccttgg aatgagatag gagttgatac agcacgcaag cgctgtggct   23760
```

```
ggcatggact ggcaggatac taattggacc acaagcatct gtagggtatt ccacctaaat   23820
aagtaaatat gtaaataatg caacctgttg cgatattgtt gctgcgattt ggtacagttt   23880
aatttaaggg gctcgactaa attaagctta cttcagcggt gcgaacatgg ttcggatagc   23940
cgatgctagt tccgatctca tgaacgccct aaaggtgacg ctatttaaac taccctttatt  24000 gcaacagata attttctcca gataggagag gcagagctat atagatctaa agcatatagg   24060
ataccagtag cattgaaggt gattacttca gacatgggca cgttcgattc gaaagtgcgc   24120
tcaatgatat taagatcgtc caatttcccc atagcgtgaa tataaggtcg ctgactgctg   24180
ataacagata tcctggagaa agaaatagca cccttgattt attaggctct aacactctac   24240
gaagaatagc aagcttgcta agatgttctt gatttcaaga ctccacaaac tgatgtacta   24300
tattgaggat tcgaggtatg gagctgtgct atgctagtac ctggtcagtc acttatgcgc   24360
ttttcctata acctaccgca gccgaatcca tcattttgaa agaacacatg tgtgagcatc   24420
caagagataa acattaatat ctaagaatag tagttatata taaacgcgta gacacattag   24480
aggtagcaca ggatatatcc cgaagaatat tgtcgcaaat tagtctgtca caaagtgtat   24540
caagagaaca caaatgtgg ttagatttaa ccatcttgat caattaatca atgaaaaaaa    24600
gacatattga gttaatatga gcaagattag agcttgacaa ccctcgactc cttcgccaca   24660
attgccgcca gttgcgagat gctccctgtc ccgcgaataa ccataagctg gacattcgca   24720
tgcaagtacg ccccgatcca gtttcgcaat tcaacagcaa caagcgagtc gacgccgtaa   24780
ctgtcaagac tctgcgcagg tgaaagcatc tccacaggcg tgactataag cttgcttagc   24840
tggttgagaa tcgcgtttgt gacgatatgg acagcttcgt cgagttgtgt tgccgctgat   24900
aggagagtga ttgcgtcgag agcctcaccg gcgctcttct gcttactgcc gttgtgcttg   24960
acgagttgag aaaagcgacg gtccgtcatg aggaaatcgc gtccgttctc ggattcgtcg   25020
tcggaggcga tgagcccgat tgatgcaacg caggtgcttg ggttggcacc gcgagcgttc   25080
aagatggcgt ggttcagaac gatgaggacg tcagacacac cgattgaccc gagcccgttg   25140
cggcggaggg cctctgcgac ttccgggttc tccgagacat atccgacgtc gcggatgggg   25200
ccgatattga tggagaatgc gggctcgcct tgctgtacca tgtggcggac aaacgtgtcc   25260
tggaagctgc acgccgcgct gtaatttgac tggccgtagt tgccgcgcac agcgacgata   25320
gaagacatca tgacgaagaa gtcaagcgat ttaaatgttg tgtgcagatt ctgcgatccg   25380
cgaaccttgg aggcgagagc agtgcgccag tcgtcttctg tcatgttgtc gaagagagtg   25440
tcgcggagga ccatggccga attgataact ccgcgcacag gcggtaattc tgagcgcttc   25500
agctcttgag ccaacgcaac cacggcgtca gcgcagacga cgtcacaagg tggtgcaatc   25560
agatttactc cgcggccacg gatgttactg atgaatgtgc ggctgtctgc atcctttgca   25620
cccgagcgtg agagggcgac aatgtgcttt gcgccatgat cagctaacca ggtggtaagc   25680
cagcgtccta gaccacccaa gccaccgaca actatgtacg atgcatcttc gtgaagcctg   25740
gcctgctttg gcatagacgg gacagcctag acagatgagc aagttatatt cacgtgtagg   25800
aagtatttgg gacttaccgg tacttcttgg ttctcttcca ccgtgaggac aatcttccca   25860
gtatgcttgc cagcctggat ttgacggaag gcgatctcaa tatcagaaat cggcattgtg   25920
gtcagagtca ctggtcgaat agaaccagat gctgcaagat ccgcaatgtc atggagcaac   25980
cttctcgcca agggtttcct ttgctcaata atagccgtca agtcaacata agaaaaagtg   26040
atgttgcgta ggaggaactc cattggcatc aaagcatcat ccattagatc cttacgccca   26100
atctcaacga aacgaccgaa ggaggccatc aaattgcatg attcgcggaa catttcgccg   26160
```

```
ctcagagagt tcagaacaac atccacacca taaccgcctg tggatttcat gatctccccg   26220
tagaaagctg tcgtacggct cgagaagata tggtcgtagg gaacaccgta tttagcgtga   26280
agaagatcgc gctttgcctc gcttccaact gtggcgaaga cctcggctcc gagatgctgg   26340
gcaagcatga tcgcggcttg tccaacagca cctgcggcgg aatggataag aatcttctca   26400
cccttggaca gggagcccct atcaacaagt ccatagtaga ccgtagccca acaatcgga    26460 agcgatgcgc cctctgcgaa ggacagagag tcgggtatga cctgacagca gtctccgtga   26520
acaagaggat agttggtgta ggagcgggaa taaagtgcgc agacccgatc tccgggcttg   26580
aagcggtgct tcatgttttc gcccacttcg acgacgacac cgctgcagtc gtttctcatc   26640
tccgtgatgc cctcaagctg gccagcagcg ataagaacat ctttgaagtt gatactagct   26700
ccacgtagtt cgaagcgaac atcatcaggt ccgagaggtg ggcattcaat atcgtccttc   26760
cagcgaatgg tctcaagtag acccggaact cctagctcag cagtcaaaat tctgcccgta   26820
ctgacgaatg gaaccggttc tgaagctgct tgtcgactag tcaaatccac atctctactg   26880
atatcaggtc tgtatgcgta gcgtgataca aacagctgcc catccttttc cgtgaactca   26940
ttctcaactt cactactgag acagtcaagg tcaaagctcg aactgttaag gattatcggg   27000
agaacttctt taagtttgct catgactggc acgttgggag tctggatgtc caatacaacc   27060
tggcgcagat ttggatattc cagacgcatt gttcggcgga agccagccca caagccggtt   27120
tctgcatgag aagaatccgc catggtgcag ttgctgacca agagcacggc ccgcgatttc   27180
aagatccagt ttttgaaaga attccagaca ttcacatctg gttcagcgca taacagcttg   27240
gcaatttctg gaagcaagat ggcaactccc ccatgctgac atggatgagt aatgggcaat   27300
agagctaccg acgtctgaca ggcctgctga atctcttgcg cctgctcttc tgtggcgttg   27360
gatgcatttg aatctgtgag gagatggatc ggaagcgatt cattcctcct cgggaaaggc   27420
gcagtagata tgaagacgct gagactgccg ccatttttcat ggggtaatc aacaaaggcc   27480 tttttcaatat gagcaaagcc agccttttcc aatcgctgac accactcaga gtccgtaaga   27540
aggggggagc gcgtgcgacc ttcatcatag ccaagccacc aaccttcaaa taggccaaaa   27600
actatgttaa aataaagggt ataacgagag atctccatta gcataaactt gcctccgggc   27660
ttcaacaagg gtctgatgtt gcggagggtc tcatcaatcc gcggcgtcgc gtggatgacg   27720
ttgcatgcga cgatgaggtc gtatgcgcct tcctcaaatc cctgctcttg ggcattgcgc   27780
cccgcatcca agacgcgaaa ctcgaccacg ttggcaagat cacctagccg ctccttagca   27840
ggctcgaaga agccgggtga gatatctgtg aaatcataac gctggataaa tcggccgctg   27900
caatcgttca gggccttcag aatcggcagt gtggctgaac cagtaccggc gccaatctca   27960
agaaccttca gttgcgggtt gaaacgacct agctcgtgac aatacgcgct catctgcggg   28020
tatagtcttg atgagcacca ttcagtatag acacgggaca acaagttgtt tttcgtcaat   28080
aatgacaacg cagacgtctt gcccttgagg atatccacta gatgcggtcc cagaatagct   28140
attgcctcac cgataactcc aaggtcttcg ggtttgttct cgagtagtat attgtcgtaa   28200
gtttcgtctg caagagtacc catccactgg aaatagcgct ggagatgggt ttcctgaatg   28260
tcattcagcg agatttcacg tatagcgttt tgcgcaaagt ggatggttat tgcatccagg   28320
gcacggttgg tctccattag agagcctaac tcaattgtag ccctgcagac ctgatctcga   28380
tgttctgttg tccaagcatc aacatatgga acaagcgtct gagtgtggca cgcctccctt   28440
ttcgagactc ctgctgcaac gtcacctccc aagctagtga cacggatacc ctgcgcgaca   28500
```

```
acagccattt ggttaatctc atccttggtg tgaaggtcaa agactaatgg ctcattccgg    28560
cgaatcgtgg agcaagtcaa atagctccct ggagccacat gacgattcgc aacccaaagc    28620
tgttttatga aggtgggcac gtatgcggat gagcggccat cttccaagta gatcacagta    28680
gacagaccgt ggaagagggc agagtcaagc acggccgggt ggagcaaatc ctccattccg    28740
cctgatggca tctcgtactc gggaacgcga gcagtggcaa cgcacgaatg cttgctgcta    28800
cgaatttggt gcaagttgtt gaaagggtgc tgccaatcaa ggccgtttcg tttgccaacg    28860
gcatagaact tttgtggtat ggtgccatga gtgcactctg agtcgatacg agaaatatca    28920
gcaggcgtga atatactcct gaaaccttca acagagtcaa cctctgcctg gacgagaccg    28980
cgacagtgct ccgtccattt ctggtcgggt gtcacggtga agatacggaa ctcgttccag    29040
atacctgatg actcgcgagc ggttctcgct tgtggacgca gagatagcga gatctcgact    29100
tcggcgttct catcaggtag cacgaggcct ttcccaaagc taacatcacg gagacgaata    29160
aattgaattg tagaagctgg attggctgtg tgcatatgct ggcgaatggc ctggattgcc    29220
attgtgatat aacctgccgc agggaatgtg atgagcccct gtataatgtg gttacggagc    29280
caaggggttt ccttgaggct gacgaaccgc cgccagcggg gctctagttt gttaacatct    29340
gcagaaaggg ttccaaggag ttcatgcggg agatgttctc ggtgtctata gtccctagac    29400
aggcgggttt cgtgccaaaa gctacggtca tggtcgaagg agtaaggcgg caaatcagcc    29460
agtggctgga tgtcgctatc cttggaatcc ttgttgagat cacagagacg aaccgagccg    29520
ttcttgatgg ccaaaaatcc caggcatcgg agaagagcgg tttctgcgtc atcgccacgc    29580
ttcaacgtgt tggtgtagga ggcttggcca tggggccctg gaattgtctt gaggatctgg    29640
ttcactggac cactgagttg agaatgtggg ccaacctcga tgagcgtgtc aatgggcaaa    29700
ccattgtagt cctgctcaca catggttcgt agtgcctgcg agaagaggac tggactgacc    29760
aggttctgcg cccagtatcc accgtcaaga acagtcgatt cgtccagctc cttgcttgtg    29820
acggaactaa acatgcggat agatgaacta acgggcttgg cttccagacc cttgagcgct    29880
gcaatgtact tgtcctctat taatttcatt tggtgagagt gataggcagc accgtgggta    29940
atcagcttgc gattgaaaag ccccttccgta tccaaaacct cctttatacg gtcaatagcc    30000
gctacgtcac ctgatacagt gacactggat gggctattga agcaagcaat gcgcatgcgt    30060
ccaacatcag tacctagctt gttgatatgc tgctcggcaa tatcgggcgg tgcaccaacg    30120
gctatcatag ctcctgggga ttggttctca gcaaggagtt cactggccag cttcccacgg    30180
tagtatgata cacttatggc atctctgaag gaaagagcgc ctgcagcata tgctgccccg    30240
atttcgccgc tagaatggcc tagtacagcc gaaggcgata ccccaaattc gttcagaagg    30300
tcgaccaggg ccagttggat agccgtgcac attggctgag agaaagctgg ctcgttcacc    30360
cgagagtccg ctttgggccg gcagagttcg ctgagaagat cccacgtaca gcccagcctt    30420
gacagctgtt gacgtgcacg ctcaagagag cgaacgaaag agggatagct tttgagtaga    30480
tcgcggccca tctcggcata ttgcgcgccc tgaccgctaa atataagggc aatgcgatgt    30540
tgcccgaatt tctctcgtct agtaatagta gaatgtgagg cagtgattag ctgtttgatt    30600
aattcgtcaa gttctgatgc gacaaaaatg acgcgataag catgaataga ctgtttagct    30660
agggtatggg ctagacgagc gagcagggca tcagggttaa tggagtttcg gtgattgacg    30720
acaagatacc tagccagcct ggcacacacc ctctggcaag cttttttcgct tgcgccgctc    30780 accatgaaga ctcgcggttt ctcggagtga tacgataact gcaggtgtct gcttaaagac    30840
aaccgcccaa atgcagagat ggcctcatga gctgcatcta taattacgtg ggcatttgtc    30900
```

```
ccgccatatc caaaactatt cgccgttagt acattttgag tagttaactc tgaatcgcta   30960
gcatacctat taagagagat gcgacgcagt gtttgcctct caagttttgt ggggatctgg   31020
tagagtcagt gttgtcatgt tttcgacaga attcttacgt actcgtaaat tccactcctc   31080
cagatggatg tcagggttcg ttgtctcata gttcacctga ggcggaatca taccgttctc   31140
aagcataaga acggacttga tcagcccagc gagaccggcg gcactttccg tgtggccaat   31200
atttcccttg atggatccaa tgggcagagg ccgggaaggc gacctccttt gcgttagggc   31260
cgctgcaata gcgctcgtct cgattggatc gccaaccttg gttccggtgc catgggcttc   31320
cacatagtca gcatacaaat ccagctttgc ctgtctgtag gcccttatga tggcttcttt   31380
ctgggcaaca gcgctcggca cactgatacc aggtgtccgg ccgtcctggt tcaggacaga   31440
gtttctaata acagcccgaa cagggtcacc atctcgcagg gcaactgata atggtttgag   31500
aacaacaccc gtgacacctt cacctcgtcc atatccatta gcacgagcat caaatggaaa   31560
agatcgaccg tctttagaaa acattttaag ccggctctgg tagtgaaagc gttgtgggtc   31620
aagaagtagg ttaacgcctc caacaaagca ctgcgtggtt tcccggttcc gcaagctgag   31680
gaccgcttga tgtaacgcca ctaaacttga cgaacatcca gtatccactg tgaagctggg   31740
cccgcgcaaa ttgaagacat atgagacccg attgcttgtg attgcaggcc cggtgcctgt   31800
cacaaggtat agaggtggtc tctcaatatc acgagtagct atctcgtggt aatccgaagc   31860
ccactgaccg acgtatacac cggtattgga tccccacaat gcatccatcg tgataccggc   31920
gttttcaaag gcttcgtagg ctacttcgag catcaggcgt tgctggggat ccattgccta   31980
attgcagagg cgaagcgtta gaatcgcatt cgatcgctaa tttgagacaa aggcctgcgc   32040
catgcatatt ttatacatac ctgtgcctcg acagggttga tcccgaaaaa tgtagcatca   32100
aactttgata tatcttctcg aatgaagtgt cctcctgtgg catttgtctg aaaagaaatg   32160
aatcaattta gcacatactc ttcttgaacc atcaagcgcc gcttactgtt ccagacctgg   32220
tccctgtcgg gtcttggaag gccttcatgt tgaaccgtgt cccaggccct ggtgtccatc   32280
ccgagcgacc agatttcagc atatcccaaa gcccagaaac gtctgttgcg cttcctgata   32340
gtcgacatcc tataccaata actgcgattg gctccagtga gccggggcca gcccttgtgc   32400
tgcgctcatc agatgtattg ctatcattgt cgctgagtat agaccacggc gaggaagaaa   32460
gcctctcact gtctgactcg ctatcagcga tctcaacacg ggacctggat gcaggactca   32520
tggctgtaga aattaggagg tacggctaat cgttgaccgt ctgaatagca tggggtatcg   32580
tgatcaagat acgggatgtt tgaagaaaga tacaaggcca gcgttaagta cagcacgcaa   32640
taccagggaa cgaatcctcg gttctaatcc gtcatgtcag gtccacccag ggcatgccca   32700
gaaatcgagt taccattttc attacgtgcc atgatcgggg tcgttgctag gcttttccca   32760
ccaagggaac tattctcccct ccacggaatc actgacggac agattatctc ggtggcgaaa   32820
ctttcatttc ctgcagcgcc cgaagtatgc tatatccgag ataccttgg acgtgttcgt   32880
tgcagagtgg tcatggggaa tcacgggcca atcactaccg aagagaacag ggttagccca   32940
ctatgacgag acgaaggaaa taaaaggaag gtaggttact ccgtaactcc agaagagtca   33000
agacagatct gcgatgccca ggccatagga ccggccgaac tacttgcaga cgatcgaccc   33060
gccatttgac gcgaaggaat cacagatcga caggcctaat ctaggcgaag gaaagcagag   33120
tgggctctgc tgccatgcga tcctattccc aagaatggtt gagcgctaag ctgctggatc   33180
tgcattgata ctcggttacg taggatgttg tcagtatgtg actgtagggg tgtagtggag   33240
```

```
agaagaggaa cctgagagga acctgggaga atcgatattt ggcgattagg cttggcgttg   33300
cattaggccg gaacagtgcg tcgcgttatg tcctgctcca agcttcgcgc tccatatatg   33360
ctcttgttta cctatacaac tctttttttg caatgcaaag aacccggtca atcaagcatc   33420
tatacaagct ctatcttgac tttgggactg tgaccaaatc tcagggtttt actcacaatg   33480
gaagaaacaa acgtcaagct cagcgtacct ctaagcgagg acgtgatcaa gctctcggct   33540
ctagatcaac agataatgcg attctatgca aaggccgtct ttatctttga gcgcgattcc   33600
tcaaaaacct cgattgacat tgttcaccac ctgaagcaag gcctcgccgt gaccttgagc   33660
gagatacctg acctcgccgc gaccattgct ccagtcccga attctcaccg caaggacctg   33720
gagctacgca tcgggcccaa ttcgggcgtc cctttcaagg tcgtggatca acaaagcag   33780 gaatcttggg tatatggcac ctaccctgat ctggctgcga acacttccc caccagtgat   33840 attcctcacg atatcctctt catcccacag ccgcaaccaa gcgcggacgg actgcctgct   33900
gcgtttctgc aggtcaatat tattgatggc ggagttatca tcgcgatctc atggcaccat   33960
tcagtatgtg atgcgagagg catcagtatc ctgatcgatg cctgggccag gcatacagcg   34020
acgtcgctag caaacggcaa acccgatctg cctgcgacac cagcagaggg cagccgtgat   34080
cggtggcgat tagatcacgg cctgcgagag gttactattg accaacttcc cgaatacacg   34140
attgatagct ctgcccgcga agacccaagc ggttcctacc tgctcgaccg cgaaaacccc   34200
gtcacagtac cttattctgt aagcacctgg tatttcagcg catcatcgct caaagccctc   34260
cgcgatgctc tcgcacaagt cgaaaacgac gaatccaccc agttcactaa agtcgaggcc   34320
gtctcagccc tcgtttggaa acacatgagc atcgcgcgcc aactggacag atccaacccg   34380
gacggttcct cgctcttcac cacacgcctg gacttccgcg caagaacaaa gccacccttt   34440
cctgatacct tcattggaaa catcaacgag cccacagccc gcgtacgctt gcccatagct   34500
gagatctgcc gcgcctccac cccagaatcc ctgacgaccc tagctgaagc tgtgcgcgcc   34560
gccaccgaaa acactaccga gcaaagcatg cgcacgctca tcggtctagt caacgacgcg   34620
cctgcggtca ccgatgttgc ttggaaatat aactactttc ccggccctga cctgggtgta   34680
actgatatct cgaatatcga tgccatgaag aagaactggg gcgctggctt gggaaccca    34740 acttgtgtta ggtcttattc tagagaaacg ggtctacttt acctgtttcc gcaggatgat   34800 gatgaggct ttgaaattca ggttcagtgt gaggtggagg ctgtgaagag actgaaggct   34860
gatgagactt tcacaagata ttgtgagttc aagagggctt ccgcgtataa tgcgtgaatt   34920
ggtacaactg taaagatagg ctcttttttt atattttctt tcgatatta ttttttattt    34980 cggactttga tatacatttt atcgttagta aattatgagc tttaattgaa actaatgttg   35040
agtaatcaaa atatatatat tcttactgca tgttgcgagc atagggcatt gaccttagga   35100
aatggacctg tatgtgcatc aaagcgaccc tgcaaacatc acttggaggt agataaccta   35160
gtccactagc aaacaggtaa gtccatatcg tgctctcatc tacttgacat atactcttag   35220
cactatgtaa actacgaaca gtgaacaacc gctatcggcg gagattctga gctagccgaa   35280
gttaaccagt tcagcattcc actaggctac gctggctcca taaaagctgt accatagagc   35340
acgacaggca gtccttagat ataatcttta tcattcattt agtgagcatg tatctaccca   35400
attaagatta aaaagtatag atattcctcc tacgggatgg gtttagttca tggccttcaa   35460
atccttcttc aacactttcc cactctcact ctttggcaac ttctccagga acacaattcg   35520
atcgtgaagc cagtgcgatt catgcagctt tccctgcaca aattcgtcaa tctcgtcagc   35580
cagatcatcc tcgtccagat cttccatcac ggtcttcgag cgcacgatgt acgctttcgc   35640
```

```
acgctcgcca gagagctcgt ccggaacgcc gataacagct gcatcgatta cggctgggtg    35700
cgaaagaagg acggactcga tgtcccgtgg gaggacttgt tcgccctgtt ttgtattcat    35760
taagttgacc ttgctcatat atttaaaatt ccattcaaga aacgacgtac cttgactttg    35820
atcatatcct tgatgcgttc gagaatgaac aggtgagcgt gtccgttagg cgatttgcga    35880
aaaacaccga tgtctccgga cttaagccac ccctttcgt cgaaggtgtt cttgttggac     35940
tcgtcgtcgc cgacgtaccc gaggaaacaa ctggggagt tgaagtggac ttcgccgggc     36000
tcgtcgaggc cctctgcgtc tgtaccgtcg ggcttgacga gtcggatctc gaaacttgga    36060
aggagggaac cagaggagcc gtgccagaca tcgtgtgggc ttgtgagagt tgctaccaca    36120
ccggtttcgg tgaggcctat ttgtctcata ttagccgtta gctagcgcta gggttattga    36180
caataccgta tgcatggttg attttccacg tgggtcgcag tttattcagt ttcgcggcga    36240
tactacgatc gagtgctgca gcaccagtga cggtcgcttg gacggatgag aggtcgtgga    36300
ggtcaagaag gaaggggttc gctgctaatg ccgcaaggat tgggggaacc tgcgcaatta    36360
gtttggcttg cattcctagg cctgagaata caaaccacgt atagtctttc gacgcggaaa    36420
cgctcaattg tcttgagcat caactgcata tcgaaccggg ggcagataac gtaggtgtct    36480
ccgcggtaga ccatgatgtg cccaatgttc agtccatatc catgggtcaa cggaatcgcg    36540
ccgaatgcga tctcgttacg gccattctta gcatagctct cgtgcatgca cacttgcatg    36600
acattggcaa tgaagttgta gtgtgtgatt ttggccagtt tctacaattg cccgtcagcc    36660
atcatctcca ttcccgagaa gagccaccga cctgcttccc tgatgttcca ctggtagcgc    36720
agtagtatgc gacctgtatt tttgcgcggc ctttctccca ctgtaatggt ggaagtcgct    36780
gcaacttctc accctcagca atcagttgat ctaccgactt gaactggtca atcggctcgg    36840
gattctgaag atacgcttcg ggtaatgccg tggtatagat cttgtctccg ggaatagaca    36900
gctccctggc agcttccaaa gtgtttgcaa caagagactg acaggtgaat atgactctac    36960
attttgctct tttcatgtgc gctacgacct cggggacgat actaaacgga tggagcggga    37020
gacagatccc attgagacga tggacggcc agcagagagc aaaaaagtca agctattttt    37080
ttttcttcat cagcttatag caaaggaaga gcaatgcaaa cgagtgtcac cgaccgtatt    37140
ccagctgtag ataccgacaa ctttatcctc cggctccccc tcgttcggcg accatcccag    37200
ctcttgcgca agtgaccgcg acaagaactc tactcgatca accagtacct tagtcgagta    37260
tgactttccg gtaattgcgc agacaaacgg aggccgtccg ccgcattgcg ggggaagact    37320 ggtgttcct tccaacgcaa actggcctac aggaatagag tctgggattt cgcagggat     37380 ccgtggcacc caggagggag aagagaagac cataatgata gaatgtaaac aagggacttt    37440
gacaaagaac gtgaagtta actctctcga tggctgccgt ggtgttctag aatgagaacc    37500
gccctgagat gatcaacact atcgccgacc ggtgcgttca gtgagaattc attgattgcc    37560
gaacggttcc atagccgaag gaagccagct tgaagctagc tctggctccg cgatacgtca    37620
catctgacta gattgaaaga gtatgagttg gagctgtgat ctgca                    37665
```

<210> SEQ ID NO 6
<211> LENGTH: 34256
<212> TYPE: DNA
<213> ORGANISM: Aspergillus nidulans

<400> SEQUENCE: 6

```
tcttgacccg acggctcgct ttcctaatac ttaagtttgt tgatattgct taagagacga         60
```

```
cgcgataact cgagttatgg tattgagagc tacagatcgg ataccttgac ccggaagggc    120
cgatgcctaa cagctccaca gcggcattcc tcataacggc agcaagaatc aagtctgcgt    180
atacgagcat gatcgaggac atgtgtacat gtgaccgtca agtatgattc ttcaaaaacg    240
acattcgccc tccaaaatac actaagcgct ggagatcaag ccaagatgct ccccaatatc    300
cttcccatcg ttaccccaaa agtgcaccgt atcaacatca caatgctggg ttgaactgcg    360
gaacccaaac atcgcctgcg tgcgcggcga caactctgta gcaatttgca tcggaatcca    420
caacggaaac gcctgcacag ggcgtagttc tcggcggatc gtggaaaacg ccagcgcgcg    480
gcgctggtcc gaaagcgtcg cattgtggcc ggctccgtga atcaccttgc cactcatcat    540
atagcaatca ccaggttgca ttatggcagg cacagaatcg atcttgccgt actgcggaca    600
atcggtcgcg ttgatcagcg tgagctccgg ccaacggttg ctgcccggga cgagacgggt    660
ggcgccgttc tctacggtga aaggagttac ggcgcagaag aagttgacga ggcactcggg    720
agcatctggg cccatggagt tccaccacgg gtagagctcc tggtcgcggt ggaggcgctg    780 cgcggggggcg cccggttgca cttcgatgac cattgtgtcg ttgaagtggt agcccatgcc    840
ctcgccgggc ttgctaaaga cgcgctggag gagttcgtgc atgaggtcat tctcaaggat    900
ctcgtggcga aatgtcgggc ttgtggtgac gagcttactg aaccgcttca cgcggtcgtt    960
gctgttgccg tcgtttgtaa cctggacttg gatcttctcc atagcgggct ggatctcctg   1020
gctgaagcgg gccatttgat ccggcgggac gaaccctcg atgataacgc aaccatcttc    1080
cttgaaggcc gcgtaaatct cgtcggcggg ggctgtggca ggaaatttct ggagacggga   1140
tggagtagct gagcccattt tcagtgttac ttatttccgt tttatactcg aaatgaggat   1200
caagaaagcg cgggatggag attttagtgg tagaaggcga aggatgattt aagaatcact   1260
gggaggcata aaagtatgca caaagattga aaagcggctt cggtgtccga tatgcaaggg   1320
taacagcccc taccttccaa gtataacaag aacgagaaga agctagggaa gggctaagca   1380
atgtagcaca ggatttatgg tgagcaatat cagagctcag cacatagcaa gtaaggaatt   1440
gtccacgaca ccaaccggca gcctacgtaa tcactaatgc cagcagatat atcagtgtac   1500
caaaggccca gcatcactat gaccccaatc tctgttatcc tcgtcactga taataagctg   1560
taagttttca ttaagtccta agagccacat gattgcccta ctgacaggac aaggcccaaa   1620
accatgtcca ccacacgaga aaagctcctc agaacaacct ccagatttgt ctcaacgttc   1680
gggtcctttg acatagagga aattctctcc attcgcacgc caacatgcct ttaccaccag   1740
tgctgcccca gcttcaacaa aaatgtcgta acgaacgagg aaacccgtgc gaacttcccg   1800
cagttcatcg ctactttcaa acgatttgac ttttccatca tcgagccaga ccatacccTT   1860
gtcgatgagg ctgctaggag agtgatgatc cgcgctaagg cttccgcaga aagcattgtt   1920
ggagcctatg agaatgagta catctttatt ctgaagatga cggacgactg taggtttatc   1980
gaggagatct acgagttcta cgataccata aggctgaagg atctccaata ccggttagaa   2040
gcgaagcata tctcttacgg ggatgctgcg ccctttaaaa cgagggatac tcagttatga   2100
gagagcccat tatctggaaa ggggctcata atcaccggca gatggtcaga ttagggttac   2160
tttacgaagt tcttggagag atggataggt aaagcgaaca tcagaacctt atgttggatg   2220
catttggcag gatgacttca ttcctactgc gcgatgacca ctgtactcat cctcttaccc   2280
tcctagctcg actggcttac tttgagcaaa ataacagggt gcaccaatta tctgttgagg   2340
tcgcgtacat agatcgcggg aatgaatgcg cggtatcgag aaaggtcacc gcgctatgat   2400
aatctggccg acacggcggg ataaatctct ttcttgaatc ttgacttata gatgtcgctt   2460
```

```
cattccoctg taattgtagg caaagaatac tagagagagg agagcaagca aacaggattg    2520
aattgggatg atacttccgc aaggagttca aatgctatgg acgaacacag accgccactt    2580
atgcctcggt gtttggaatt ctggaggact gaagatggaa gaatccgtgc tgcatgcctc    2640
tagattcggc gacggctcct tgcgtgttcg cgtcttttg actctgatcc acagcgagcg    2700
cgtggctaag agttgtatgc ccatcccagg acaatatcgg gccagacttc aagaccagaa    2760
tcatgaaggc agcagcctgc aattattgct gcatggagcg agttgagcgc acgccacgtc    2820
cgcgtccacg caaacctaca actgatcagc aacggcatgg atagcgtgat gcgcataggt    2880
atcttaccag aagatctatt tgacacagta ctcaaaaagc cgcgatcgtc tccactatgg    2940
tgaaagcatc gtattttatt attataatca ttatttgttc gcgtcaacaa gcgtcctgcg    3000
aagcacccca ataattttcc aacaacccaa tagcggacag aagacagcta agaataataa    3060
aagaaacgac tagaggtcaa tttcagatca ctatctcctc cttccttcgg cggacacaga    3120
tcctagcatc gggattcgtg gctaagaaga tccccgactt gctgggtgca accgcgccat    3180
tatcaggaag tttaatgtcg tatttcataa gcatatggga caagacaatc ttcagctcgt    3240
tggcggcaaa gaatcttcca gggcacgcgt gtcgaccaag gccaaagcct agatgttctg    3300
gggaagccga aaccaggtag gcggaactat cgccctttc acgccgagtg gtaaaacggt    3360
caggaacgaa atcatcaggg tcggggtaga tattggagtc tcgcatggcc acgttggcga    3420
taaagactgt tgagcctttg gggattattg ttccgtctga gagtgtgatc tcgcgcgagg    3480
cgtatcgccc catcgttact gtatgcatgg ccaggttaga aaaggagggg atcaacttgt    3540
gaaaagaggg tgatagagga agcttaccag ttgaggctgg ctttaaacgt tgagactctt    3600
tcagcacact gtccatcagt ttaaggttgt tcaaagcgat cttatcccac ccctctccct    3660
gtagcgagga tatgatttct ttccgaagct ccctgaccag aactttccaa tctggtctca    3720
tgcagaggtc aaggaggacc tgccccagga ggtcactgga ggtatggaaa gagccgatgg    3780
caaggagcat ttgggataat ataggatcat agggttgacc tgtactgcga gacgtctcgt    3840
cgagccattc tatcgcgtcg ttatactccc ttcgatcacc ctggctctgg gcatggcgcc    3900
gttgctcaag gactgggaca agaagcgcac gtgcatcacg gatatatcga cgaagctggc    3960
ggcacgatgg ttttagacgg gcgatgaggg gtcgaagtat ctgaggccag aggttgagct    4020
cttcggctgc tgcaaaagcc tcggtgttgt atgatgttag gatgcgtatc caatccgggt    4080
tgcgcccgag gtcatcgcca acgaagacga gagaagagag ccgcgacaga ataaacagag    4140
ccgtctcatg cgggctcacc tccacccagt ctagtgcgag gtatcagtag aggttgtgtg    4200
acaaaagcgg gcggactact gatggactag atacctggtg catctttcca ttgggattgt    4260
agaagaaggg gagtctcgct agtgagaagc ggcgtcaatt ttgctaagag atttggtata    4320
tcaatatggt tcatccgaag gcgagaagca atgaggtgac gctattctag gacgaacact    4380
tactcagctg ccgggtcagt ctcgtcctca cagactcaga gatgacatca ctggttccca    4440
gttgtgcaaa cacctcgaat ccattaatat gggaattgaa ctcgtctcca gcgattgggc    4500
cggggttcaa gtcaggatgc tccgcgatct catgtgcata cgatggagca agtacgatgt    4560
tgactccatc tggggctgcg atccgaaagg cactcgccta tctctgggct cagcggttac    4620
tactatttgg aggatagatg agtaccttgg aaagcccatc tgcaactaat ctcggtagct    4680
ctgtggtaaa tgtcttccgt gagcgatacc ctcgtagtat accgatgcgc ccctttccgg    4740
gattgatcaa tggcaaatca gatttttcc gaagaggatg aaaaagaatg attgtaaccg    4800
```

```
agaagagtag taggagccag gggagcccgc aagtaaccag aaagccgtta ggaaatctaa    4860
ggctgtttgg aatcccaggc tcatgagatg aacgaaagaa atgtgtccgc aactctggat    4920
ttcccattgc cattgtagct ctagaatttt gacgggggac gaagaaagga ttgttagata    4980
gacgatcaca aattcagtgc agatattaat atagtcttgc acttgaaact cgtgtaaaca    5040
gtgattgaat atgtcttgtt cgcattcccg ctgtgtatga attaagttac gagccgtacc    5100
tttttagtta cgacaattcc attactagga atatatctct ggccctccta ggaatcacat    5160
acttcagtat tacaagcatg actgtgaaat gcagggattg cactaccagg aaaaacaaca    5220
tatgctcacg tcgtagcgtg cctctcatgg cattgattct tcccaatgag gtgtggcttc    5280
ccatccatgc ctcaatgctg atcacttttg tgcagcgaag caggggctaa tattaatcac    5340
taaatacggt gtggttggtc aacctatacg gagggatcag aacatagttg ccttcgtatc    5400
accgtacatc agcctacact cttcttgcct tatccaaccg aggcggcaga ccgcagcccg    5460
aggtatttct cattgtactg ggttccatca tctgtgagcc attcccaaac acaaccgatc    5520
taattcctcg ccgagaaatg cgcctcaatt ttcttccccc atgcatccct cgtcgccgaa    5580
tctgcaaact ggaaaaagtc ctccaccatt gttccttcct cattaatctg cagaatgtag    5640
acgtactcgg tctcaaatcg accaaccagg gagtcccect tccectcaat atgcagtaca    5700
accttcctcg caggctcgtc gatgactggc tccgcaccgt ccttgacgcg tagctggaaa    5760
ttgtagaaaa aatcctttag ccecttggaag tccgccttgc tttcttcttt ggtttgcaaa    5820
gctggtttgc cgaggctgga tggaaaagag cggagggtgc aactgggtga catgaacgat    5880
aggactgatt cgacgtcgag tttggcgaac tgacccacaa agtttaaagc cgtgcataag    5940
agctcatcgc gtgtaggagg cattcttttcg gtgatgagtt gaggtgatgg atcgagtagg    6000
gtagagcaaa gacagatggg ttggtcagta cggtggaaat agttgtgcaa ccgcttattt    6060
aacaactgct gccccataca aacttactgg gccttctgtt gtcattgtat tagaggtcat    6120
cccaagattg ccgacgatca tgcccttgct tggttcccgg caaggaggaa gttcgggaag    6180
gtcgtctgac aaaatttgac aaaggatatt tgtctgtttg cccgcagttc aattatgcgc    6240
agcttttctg ctcggtggaa taaacaaaca taccatgacc attgtgctgg cattaaggcc    6300
actgtaaggg ctcgtatgac cccaagtacg ccgctggcaa gatacatact tgtgcgtgca    6360
ctttcatagc cagaaactcc agacttgcgg atagaaaact ctaaaggaaa tcccatgcac    6420
tacgagcaat ccgttgattt tgagtctaac cgacatggtc gacaagatca gcgtaattga    6480
gttgaaacgc gtgagttttg atagagaagc attctatgag agtggtgttt ttagtatacc    6540
tatcctgttc gaaatacata atccaatcta gtcccagcgg atctgattga aagtaaggag    6600
ggactttctc tggttgacag gccgcataat gtggcataag ccaggtgtcg gggcatagca    6660
gtatccgatg ccgcctgccc ttcgggtggt gcccgtttag tcattattta gtaagctaga    6720
tttatagatc ggcggccacg taggccatcc aataatgtca atggtccttc accgggcgta    6780
cacgatgagt cacatgacat ttccttataa aaatttgtcg gctattgagg tggttgctag    6840
cgtcgatttt taatcatgtg attgatatct gtaatgagca actgtattga aggtcttaat    6900
ttcctaacta caatctgtat aggctattta tgtctttttca aaggcttcaa aagaatgttc    6960
tcgatatcgg tagatagttc aggttgtata ggcagatgtg cctgtcatat aggcaatatg    7020
atgtatcaaa tgagcggacg agcgaggtgc tgtatgttga ttagtaagga gaggctatct    7080
ccggtcgaca aaattcaata caattatact tcacgtaaat gaggcataca tacacctcgc    7140
cggtgaaatc ctggaatcaa catctcacaa gaattgctca agctccgaca ggtgtgctgc    7200
```

```
tacacgtcag ccttgcagtc gcatgggcct agaaccttgc ttttttccttg ctccaatagt   7260 gcccaacgta gagccggctc attcttgaag caatacatcg tactctcgtc cagcgttatc   7320
cgcacattcc agggcgcgga acctgccaca tccgagctat ttgcgcacaa ggggagaatt   7380
atacaggacc catttaccca cggtattccg gtttcgaagg cctggatttc ccctagctcc   7440
gctccaaatt gtagctcgta tgtcttgatg tgtctcaagc ttgagacgat agcgcaagcc   7500
gggaggatgt tcacagcctt ctgttcctcg tgggcgttca gaaaggaact tagcgagtcg   7560
atgtaggatt cgccgaatct cgctagtttg gcccggattg tataagccgt ctttgcgatg   7620
gcgaggaaga atgacgtgtt caaaccggtg ggtacttctc ggactgcccg atggaagtct   7680
ggagaggcgt gtcgttgaga actgacctcg aaacgtagcg ggatagcagc gttccccatg   7740
tagtcatggg ggagaggagg ttcaacgaac ttgcgcaggt ctacagccat aaggcactca   7800
gagacacttg gcttcgcatg gagcttctca tctctgtacg ggtgcttggc ggcatgccgt   7860
gcctgagcta tcgattcgca gatgagcgcc gtgagtacat cgttgatcga aagaaacctt   7920
acatctcctt gacctgtgac cgatttctga ttctcatgta acttttcaag tatagaggta   7980
caagcaatcc tcagctgttg gagttttttca gcgcaaaaga caaagcattc atccttcaat   8040
ggtgggggtg ctgcaaccgg tctgtgagag atattttcag agaattcaga tggcgaaggc   8100
gcatctacac gagcacggtt attttttttc agccgcgaac tcagagccaa caatgggctt   8160
cgcactcgtg cctgcgtgga agggattccc aatctcccgt ccattcctat tttgtcctgg   8220
ttgcgacacg attcggccag aagttttact atcaccgcgg ctccgagagc atcgaatact   8280
gcatgattga acgccagcgt caggataagg ccgtcattga ccaagttaat ctggaaacga   8340
atgacaggtg ttggtcgatt aggagttggg tatgcggcga gtggattgaa gagaccatta   8400
agcggaagac tcgatggtac gttaaatgga gactgttcta gtttcttgac cggcagggca   8460
caattggaat ggcgctttac ctggaccagt ggaacttgat cttcagactt ggccctgggt   8520
ggtcggacta aaggacatt gttcgcgtca ggaactgggg caggaaacgc gatctccccg   8580
ttcaaaaacg gcaccttttc aagaaggaca tcgatagcgt tatggatggt ttgaagggca   8640
gaagcttcat tccgcacccg atacgatatg ttatagaaga aaaaaacttg gccattcgcc   8700
tgatcgatag gggtcaatga gaaggcttcg aaatcagggg agggtggcat ttgatgggcg   8760
atcaaatagg gatttatttt caacaaatct tgatggtcgg aggatgggtg tccaagttgg   8820
tcgggttgac tgatagacag actatgtaag agaacctcgt cccgaaccta gttcaaggaa   8880
gagttcctgt ccaactttca cacattcctc cgtagctgca gctatgccca atgagttgca   8940
aaacacgaaa gttgaggaat gattattttc aacatctctg ccctcggtcc tcccaagccc   9000
atgcttcaag tatgtagggg cagcggtcca cgtagcacga gtggtaaagg ccagcttgga   9060
cagaaaatcg ccttgttact tggcgagtct gtatagaaca tactcgacac atcttagttc   9120
gtcggacgag agcttgttga acatcacgc gcgaccatgt tgcgacttcc catcgatagc   9180
gcaatgcacc ccttctcaac tctacctaac catgaactcg gcctctatat catgtggatg   9240
atgtctgctg tctttgtgat atttaagctg ctggcaccag ctaaatgcga tatcccaacc   9300
gtgaacggac gcaggcggtt tgagatagga cagtaccagg caaggcggcg cttttctgtc   9360
gatggacggg gcattatctt gaatgggctt cagatggtca gttgttacgt gtgtaattgt   9420
ttgattctgg gttggagact aaaataaacc gcaggcgcgt gtatttcgcg tggtttctca   9480
aaaagggccc aagataatcc ttgggcccga atatgccaat gaggttaaaa gccatccggc   9540
```

```
ctgcaatgcg gatgtcttta tagcaaagga gttccacgct cacgtatcag gctttgaggt    9600
cttgcggcca cagcaagtaa tgaaagatgc tatccggctt agactgacca ggtccatcgg    9660
taagagccag ctgtctataa gggttactag cttacgtttt ttggccttca aggggccttg    9720
atgaaaccca tctctgctga aactgcactg attctcgaat cacaatgggg gaatagtaat    9780
tgtacgtgac catgcagtct tgcaaggtgc cacactaatc tggtgttccc aggttggcat    9840
gagttagatc taaatttcac catagcctcg cttgtctctc gagtgtcggc agtcatgttc    9900
gtcggcgagg aactcggccg tgatcagaaa tggcttagca ttgtcaccaa ctacagctct    9960
gatatgttcg tggcggatct agatctttgc aagtggccag aggctctgcg tcccattgct   10020
acgtatttcc tgccttcttg cggtaaacta cgacgccata tccgagaagc ggcactaatg   10080
ctctacccca tactttcaga gggatactct gcgcatcaaa acaagcagaa ctttctagat   10140
tggcttgaag aaattgcagg tgatcggaaa tacaaccccg tgctggcaca gctttccctc   10200
gctgcagcgg caattgatac tacatccgac ctcataatta agactctgac tgatatctgt   10260
cgtttccgcg attcgcagaa actccaagaa gatcttcggg aggagatggt cagggttctg   10320
cgggcagatg gatgggagaa gtctgccatg tacaacctta aacttttgga cagcgtcctg   10380
aaggaaacac agcgtgtcaa acctgtcgtt gtttgtaggt gtcgttgctt catttatgaa   10440
tcatgttgag ctaaccctaa tgtcaccgca acacagtcgg tatgggtcgc tacgttactg   10500
aacagataac attacatgac ggaactgtga tctcaaaggg cgagacaatt aacgtcgtca   10560
atacacgaat atgggaccca gctgtctatc ccaacccgct agaatgggac ccctatagat   10620
ttgtacgtcg tcgcgactcg ggcgatcacg cagcacatct cgtttcgccc acaccagatc   10680
acatggggtt cggactggga aagcattcat gcccaggccg attctttgca gccacgaaaa   10740
tcaaaatcat actatgtcat attctgttaa agtatgatgt gaaaatccct gatgaggaaa   10800
tttctacagt gatttcttcg ggaaactttc tatttcccga ctcaactttg aggatctcag   10860
tcaggcgaag gcaagacaac ttgactatct gggactaaac acccttccct catagcagct   10920
gtctgtaatt ggaatgattt gatcatagac tttggaatct tgctaagact tattttggaa   10980
aggcgtgcag acaatatcag tgtttctctc gagcacaat acatttcata attgcccatt   11040
tatcatcaat tcctagatta ttgagcctcc tcgaggcgtc cctggaactg gcgaaaacgg   11100
gctgtgtcca agaactgaaa gatctcatcc accagagctc cctcctcatt catagccatt   11160
ataaacattg cttcgttctc gtagggtcca accgtcgttt cacacctgat tttcaccttc   11220
acgacaactt gtcttgacac ctcatcaaca accgtaatgt tgtcgtccac aatgctggca   11280
ttgactgatc gaaacactcc tcgcgataac atcatatgtc tcgtgtgttc ctccatactc   11340
tgagtaaact tgcaggtcgg tgcaactcca tgagtaaggc aggttggtgt gcgaacggtc   11400
ttcatagcac ttggatcgaa ctcgttgtac gcggcaatgt atttcgaaac agttgcaagc   11460
agtctttctc ggattgacat ggctctaatg taaaattaac tgctggtgga ctgatgatgc   11520
tttttagac tgaaatgtta acctgacaat agtcgattga tttctggccg atcaaaacct   11580
aacagtggac atgtgcgtgc tgtctctgta ggtatatccg taaaagtgca gaatcctacc   11640
tccttgggtt tctctagccc cttgctcttc cggcattttg tcccttacag cgcaaaaggg   11700
gcttgagatg gcaaattcgt tccatttaac ttgagcccat cacaatatct tcgaggctac   11760
atcgtaaagt gttcgattcg cgagccactg aagggttaag ctataccttt cccttgtcaa   11820
gtcggacgag tcacacggcg aagtattcaa tatagcagac acagacatgc ctgggtcgtg   11880
gagtgccaag tggccctcta tctgcagata cttttgggctt gaagccagcg aaactgttga   11940
```

```
cgatcagtgg acaaatatag acagcaggtg gcacgcgaac caagtggctt acgaaagaat   12000
gtacaccgag tacggactgc agaagcagtt ggtttcacca acagcttggt cgttggtgaa   12060
aataggtcat acgttgttct accagaatcg ggaactctgc ctcgataaga ctcggggact   12120
gggctttacc gaggatcatc ccgtcggatt tagctatttc caggttttcg aagacttcga   12180
gaggatgaag attatcctgg ctaaaattgt tttggcctcg ctgccgcgac gttttatatc   12240
agtgctaaat tgatttcgct agagcacatg aagagactcg acgaccgcta taccgaccgt   12300
tgttgatact gtgagaccgg cttccagcag atgacatgta tttagacgcc agacagatcc   12360 tattttacc gattattgag gcattttgca actgcgccgg gttgattgat ttggcgcgcg   12420
gctgtgctgg ggttttaatt ctgtcaggtt aacgtgacat attattaccg ctagttatgt   12480 attaaccta taaatggtaa aataaacgta tccgtatcaa ttcgagtcac ctagccctaa   12540
ctggtcactg cgcttgacat tttgatatgc agctatcacg atggctagta tacgcgccat   12600
agtacacatt cctcgccata aggacttgtg aaagggttac aacacatagt aagctctact   12660
atagatgata taagaagtaa ttatcaagct ttaagcttga tagtttattc atggccgaga   12720
gcgttcattt tgccgccacg tattcaggca agcaatatta tatatatttg ccgtatatgt   12780
ctgcggtgag tgtgctggaa aataagtttg aattagcgga tggcgtcaag cgtcagctgt   12840 accttttctag ttcgcaccaa tcaccagcac ttgataaaac gaccgctagt gcctggttca   12900
tgtgtccggc gaacataatt actgcgtgaa ttaacatggc gctggccgct tccgtgtaat   12960
ggtctcattc tcaaaggcca ggaattagat ctggatctcc ggctgtcgcc gtcttactag   13020
cacctttgcg gtcatgtttg cgttgattgc tgccgcaaac tcccacacgt gctgcccagt   13080
ctccccattg gccggtttaa tatcatactt catcaacacg tggcaaagag atatcttcag   13140
caccgctgcg gcgaagaacc gtcctggaca ggcgcggcct ccatagccga atcccaggtg   13200
atcggaggta ggtgatgtaa actgtgctgt attctcctgc cctggagcct gtcggagtct   13260
gtaaaaccga tacgggtcaa agtgcgcggc gtcaggatac ttgtcctcat cccacattgt   13320
gtgtccagat atgcggatag actggccttt ctgaatgatg aggccgtctt tcaacgttac   13380
gtcagcgacg gcgaccctgc caactgctgt ctgatagtta gggtgtgtcc gaaccaggag   13440
aagggatttg gcataccaaa caggattgga tctacccgtt gaacttcctt aaaggcactg   13500
tccatgagtt tcaagtggta cagcgccgtt ttgctccacc catgagtctc gtagacttgg   13560
atgacctctt tacgaaggtc gctgacgagc tgaggatcct cagaaaggcg caggaggatc   13620
ttaaccagat ggtcgcagag gccatgcatg gacgcaaagg caatccgcag gttaagtatg   13680
agctcgtcat attcttcccc gtgcgaggct tctttgaacc attcaaagaa gtttagcggt   13740
tcttcgcctg ttgatgcctg cagagccgtt ctcctgcgca tgtcacggct catgagctct   13800
cggccagatt tcatgatgcg gtagagctcc aggcactcag gtagaaactt ggccacaatc   13860
cgtcgtagca tcacaggcca cgcggagagt gccgccgatg ccatacccag agccatttcc   13920
atctttacca caaactcggg ccacgcctcg tccaggcagt acacagaaga tgtaccctgg   13980
gctatggtac gctcgaccac cgacccaaga actatttcct gccagcctgg ggattattag   14040
atagacgggt cagccacact ttcgcgcatg tcgacggaag tcatggttta cctgattcac   14100
taggccatct atcgctaatt gcttcaccga tatctgatgc gagcggctgg atcagtttgc   14160
ctggaaaagc ttgttagttt ggttgtgctt cacgtatcgt agctcctctt accaagcgac   14220
tgcgcgagct gtgttcgcac agactctatc aaaatgcgat cttcaaccgg ctgtgaccgg   14280
```

```
catagctcaa agcccggaag atgaccgtga tgcatctgac caagaattca gaaatccgat    14340
ttcttcccac aggcgggtgt tccattgact acctaccttt gcagtgaacg ggaatacctt    14400
cagcgaaggg tgattgcgga actggtccgc atattcagga gacgcaaaca attccacccc    14460
tacatccgta cgcattgcga agacattttt gtactagtgt cactggatga gcatacgacg    14520
ccgtttcatt cttgttcaat ttctgcgtgc gaacttacag aatcaaagcc ggattttatg    14580
agccgccggg catcgcgacg aaagcgattc actgctgtca cctgaagaaa gtcgaatggg    14640
cccccatcgt tcaaaagagg gagattgttg ggacgccatt gctgggtgtt gtagagcaaa    14700
tataaaacag cggagactac cacgaaaccg cgatcaaag gttggcccag cggggtgaga    14760
ctaatagttt cctgaagcat ggtgtagtgt atctaaagta agttttgag agccggacga    14820 gccgcgagta tatggttatt tagccatagt gctgctggat tggcgcttat gtggcatgcg    14880
tgtcggcaag gggccgaagt cggtcaggga tattcatagg cctcagaatc cccttacctg    14940
gaaggctgca atacagcgcg gcttccgatc ctgagactct catatgtcgg gtgggtggtg    15000
aggacaagct cgcataaagg cgaacggact cttctaatag gttttactgt agtgctacta    15060
atgaaaaaac cgaacagact gtatcgggtg atttacctcc atgttatcct attggtttg    15120 gatatgtgca aactgttatt gatataatac gaactaaagg ggtggaaagt cgttagataa    15180
cattacgaga caattatgct aatagacagt gggcccagc tacgattatt tactcagtgg    15240
cccttttgcc ttgtagcggt tttgctgtct tcaacttcag tccatcctct aagcacccga    15300
ctgatgtgta tttaacccaa ccgtactgag cactactggt ctaacagtcc tccagccaac    15360
catcttctgt gaaagcgggg gcatggttcc agagtaaccg ggctctcaag agcaactagc    15420
taacatcttg tgaagaaaat tagtagcatt cgtcttgtat tcggtgcctg attcgtatgc    15480
ttcccaccag cgtgcagcag ccgctgaggg attaccagca tgtccccagc gtttagctct    15540
gcttgcacgg cctggtcctc cgatggtgtt caacagcctc ccattttggc tgctgagaat    15600
gacccgcgtt gcaccgttgg caacagtggc gtccgtcatg gagacaagga gcgtcactat    15660
cagggatggt gatgtggcag gttggtactg aaggacggga tagagcaatg tgtcccggtg    15720 aaagcccttgt gctgggcttt gtggttttgt ggttcgtaag ttcccagtgg tcagccagta    15780
gtctcccacg tcgcggaaga cggccttgca tgttgtgagt actgccgagt tgttcagtat    15840
gtcgtcccgg tagggtggcg agcccgagga ggaaattttc tttccttcag aacgggttat    15900
catcaagcca aacaggttgg ttggagcttt cgacttcgtt ttggaggcgc taggtcacat    15960
caagagaccg gatgcatcta attaacaaca ccatcgtcgt cgaccgcttt tgacaatgtt    16020
tctagattgg tgtcagaagc aaaccgttgt aactgcgttt gggaatgata gtcatgatgc    16080
ggacacagag aagcagggat gatactgtga cagggcagta tagcgtagtt gagagctaaa    16140
tgaaccaggt agatacacgc ctcgcggagg cgagcagtgg ccggacgtac tataaatata    16200
tgctctagcg agacggctac aaggcaacat ttcatgtaga tggtcgtcct ggttatctac    16260
aacaactaac atacgaatcc tatatcacga caactgttcc tctcactgtt atcactgcca    16320
taacatatat tgaacgtcac tttgcaagca acgcatgggg tcaacttgag gcgtggtcct    16380
catctgaccg cagcctagcc cgtcaataat cccacatgat gggctactat cctgtagctg    16440
cgtgaaccgt tcgagaagta agggatgcgg gggttgtcct gcgcaaccac gtattcaccg    16500
gaagagtcag tttccgagca tttcttgtca ctcaaggggg gccttgtgg ctagatcatg    16560 taagagcaac gcctaagtac ccccatgcct taagccagct tcatcagcat tggcgtgaat    16620
tgatcgcaca cgagcttcca atcgccttaa gcttgctctc cggagtattc gcctttgagc    16680
```

```
attgaataca tcacctgacc tagtaggagg gtttagaatc ccttgctagt ccccgcactt   16740
cctcacggtt ctccagaagc ccttaatgat tgtagtacgg cggttgtgtg aggtttcata   16800
atactagctg cctctagcac tgctaatttt tcttttatct gtcctctggc aactttcttg   16860
gacgagtgct caggtatcaa aatggcggga ctgacaggtc aacccatccg caattattgc   16920
gatgtccggg tgatttcccc ccagaaccta tggtcagtac ttgtgaataa acagagtaaa   16980
ggaagcaagg tgccaccgga ccggtttaat gtcaatgcgt tctatcaccc ttctggctcg   17040
caggccggca ccgtgaatag aaatggggcc atttcatgaa gcggcaccct gctactttc    17100
gcgccgtgtt tttctgtgct ttcaaagcag gctcgagcaa tggatctgca gagccgtaat   17160
gctgaaatgt gcattctagg cgtttgaaaa cggtcagtcg agtgctacca cagaagctga   17220
ctactttctc tagccagtat gataatagac gattttgcag ggacacggac ggcatgttac   17280
gtccccagct ccgccgactt cagggagctt ctggggcagg acgagttgca gccgagatac   17340
aaatttacgg tgttcggagg agggatgctc gcaaaccgta tctcgtggtt ctttgacctc   17400
caaccaacca ttttaacggt tgatactgcg tgctcttcgt ctgtcgtcgc gcttcgtttg   17460
ggctgccaga gcatccgcac aggagatgct gatatggtgc gcattcctca acgtgtacag   17520
cgagattact tctattaccc tgcttacatg caaaaataac actccaggtg ttagtcggtg   17580
gcgccgatgc gaatttgtac cgcaggtgat gaccagttag ggtttgctcg gttttctcag   17640
ctcggacggc cgctgcaaag gcctctgagg agcaaacaga cggatacgcc aggggtgaag   17700
gaactggggt tgtccttctt aggccccttg atgcagcact ctccgatgga aatgcattac   17760
gcgccgttat ccggaccccg gcatcaccgc tttcctcagc agaggagcaa gagcgattga   17820
ttcgaagtgt ctatgaccaa gtctgtctcg atctcgttga gacgcctttt gggaagcgca   17880
tggaatcagg tacacgaaag gcgatttgac cggcgcttcg tcactggctc gcgcctttag   17940
ccacaggcgg ctgccgcaag atttgctcta tattggaagc gtcaaaacga acatagtgca   18000
ccttcgggtt gcggtggtgt tcccagata tcaagacagt tctggccctg gagaacggta    18060
ttattccacc aaatatataa cttaaacagc tatgtccaga cgcacctctt ggcagatggc   18120
gcctaaaagt gctggctgaa ccggtctcct agccagaggg tgaaagcgca gagcaaatat   18180
caacccctttt gggtatggcg gcacaaaccc gcactgtatt atgaagactc tagaagagta   18240
cacgggtcgc aaggtgcagc aatggctgga gccttgggtc aggagccaag gtgcaacaat   18300
gaggccaagt ctagagaaga agaagcgcca gttttgattt cttgcttctc ccgtgatacg   18360
ggcggtatct ctcgcctggc cgttcaatac gcacagtatc ttgaaacgaa gatcaagtgc   18420
catagatcgc aacagtctct cagcctcaga ttcattgacg gagcgggctt tctgtcgcag   18480
agctcggtgc gcgctgcaga taaggtctcc aaatttcaac tttctgcgcg cctaccttgc   18540
caccgaggct cgacttgata tctccgtgtt ggagctgatg cgtagtatac cggtgagaga   18600
acttgctcga gacgtggccc tgcggtcagg atacctagt cgctatactt tagaccagag    18660
ctatgtagct acgtagctat caactgcgga gtgaggcagg cgccctgaaa atgcgatatt   18720
aggagccaaa gggcgctatc ggtgtagtaa cgacaacgac tacttctaag ggtcaaacac   18780
ttccactaca atatctgtgt ggctagatcc attcccataa agcaagggga tgttgcctaa   18840
tcatacccccg attataccgc tgttacgata tatatacata gggcagaacc aacaattcct   18900
ccacttccgt cgaccttaca ctgtccccc acagcaacaa agtaagatca tatctctatt    18960
tttccaatca atcctgacca tcgtaaatag tccatgaaca ccacgcgcca caggctcctt   19020
```

```
gccaccgcgt cgcggtttgt cgagacactc gagagcttag acgtggatgc aatgctcgct   19080
atacgatctt caacatgtct tcatcatatg tgctgcccca gcttcagaaa ctacagcatc   19140
acgaatgatc agacccgtga agcgtttccc cagtggaaag ctacgattac caagtataaa   19200
tttggtgtcc tggatgacag ccaaattctg gtcgacgagc aagcgagaaa ggtcatgatt   19260
cacgccgaaa ccgccgcaga gacaacggtc ggtgactaca caatgaata tgtgtttatt    19320 cttcgaatgg cagaggattg caacacggtg gatgaaatct gggagtttta tgataccatt   19380
cgtctacagg accttcgtca caggctggag gccagccatg tgccaattgg cgttgacgct   19440
cctgctccct ttaccaccac tgcctcacct gcggccctct aatagcctgt atatcctagt   19500
aagactctta ttagtgtatt taattatggc tagtcaatca aatcacagcg ctgcaaggag   19560
acaatcgtcc cttacatttt cacattccat ctctgggaca ctcactatac ccgccttgac   19620
caccagggta ttcctagcca ctaattgtcc ctgttcgatc ttcaaacaac ctcgtattct   19680
tatcattgct atatcttaat gctatgacag gtacacgaat cctcgagctg ttcggcccgg   19740
cgccagaacc cccctccgag ttaggccgct accgaatcct ttcacccacg gcgggcatac   19800
gtgtttctcc cctccagctc ggtgcactat ctatcggaga cgcatggagc accgaccttg   19860
gctcaatgga taaggactcg gcgatggaat tgctagatgc ctacgccgct gcgggggga    19920 acttcattga cacagcaaac gcgtaccaga atgaacagtc ggaaatgtgg attggagaat   19980
ggatggccag ccgcggcaat cgggacaaga tggtgattgc caccaaattc gggaccgact   20040
accgcgccca tgaactgggc aaagggctcg cagtgaacta ttcggggaac cacaagcgca   20100
gcctacacat gagcgttcgc gactccctgc agaaattgcg aacaagctgg attgatatcc   20160
tctacctgca cacgtgggac tataccaccct ctatcccgga gctcatggat tcactacatc   20220
atcttgtcca gcgcggagat gtcctctacc tgggaatttg caatacgcca gcttgggttg   20280
ttagtgcagc aaacacttat gcccagcagc aggggaagac ccagttctct gtctaccagg   20340
gtcgttggaa tccgctgcgg cgtgagctcg agcgtgatat tctacccatg gcccggcact   20400
ttggaatggc cgtgacggtg tatgacgccc ttggtagtgg taagtttcaa tcacgggata   20460
tgctcgcacg ccgcaaggat caggggagg ggctcagagc tatatatggt gggcagcaaa    20520
ccgcgctgga ggaggcaatg agcaaggcgc tgggagttgt tgccgcgcag catgggattg   20580
aatcagttac agctgttgcc ctggcgtact tgctggcaaa ggccccatat gtctttccga   20640
ttatcggcgg acgcaagatc cagcacttgc atgacaacat cgaggcgctc tcactccggc   20700
tcagccagga ggagatcgag tatttagaaa gcgtgggaga ttttgacccg ggttttccgt   20760
atgatatggc tggggtcgat ccagctgata ctggaatagc tactccgatt gtggctcagg   20820
cagcgccgat ggcgttttgtc cagagatcga aggctatagg gtacgctgaa tctagcaagg   20880
gaagtcagat gttcggctga gttagtagcc tgtagcggag tatcaatgtt atggaaacac   20940
aattcaggaa ccaacttaga cagcttgcaa tatggatgaa tatgattcgt ctccatacac   21000
gtcacaaaga cctgtacagt atgttgcaac agtgtcgctg taagacgcat aatatgaatg   21060
gcacctgcgg tagtcagtta ggagaaaaag actggctttg atttggccgg ctttggaatg   21120
atacaaggat tggctgttaa tctgcacgaa ggggagctgg aatctgatct ttgataatat   21180
attgtctcta taggactgtc ctgttgctca ataccggga gcctggcatc gatagtctgc    21240
ccaatgtgta ccgtgtttac cgcgagcttc ttaacatact agagagcggc cacaagaacg   21300
atgacatgtt tcgtatctgt tcttttgcca acacttcccc gtagcaagcc cgatcgttac   21360
atatactata ctaaatacgt ctaagcgggt gcgagcatca acactgagtc gcttctctca   21420
```

```
gccaggatgc aatcactgtt gttattccct tgcaagcaaa gcgggtatgt ggatacaact    21480
aaggatcttg ctagggatct gctctgtaag gtggaatgct gatatttgcg ttatctgtgc    21540
gggtaacatg tctgccggca ccggacgatt gaaaaaaatg tcttcatgct ctgtgacagg    21600
gccactaggt ctcgcaagta tcggctgggg gtgctttggc atactcctta cggcgcagat    21660
catagtgaag gtgacagcga cggtgaggat agttcttatg tggagtttat tgaaggcagg    21720
gcaactcctg atcttgcata ttcttgcacc aacagtaccc tacaagtccc gagttgagcc    21780
aaatggttgg gtcctcagag gccaccagtc agggtaaagc gatcgacgct caaccggctc    21840
ttattgctcc gtttccacac atgcaagggc taatcgaatg acttagcgtc aaggggtatg    21900
ccagcttaga ccctaggccc ggcccgaaat tcagtagtaa taagagttga cttgggtcgg    21960
cacattccag accgactcat gtgtgacacg agacaagctt actggccctg caggcaaggg    22020
gccaggacta gatcagaact gaacatccac cacgcaaagt cgcccgcgat gggcacattt    22080
gagatgcctc tggatatgac aaaacggctg gaattatact gccgtcgtat tatatagacg    22140
ttttcctcaa gtaatgagag gctgctcacg tagggcagca aagggagtcg gttcaccaat    22200
accagaaagg ggaatccttt cctaagaatg caacgaattc caggagcata tgtacgacat    22260
gcccactcaa tgcatgctgt ggcaaggtag tgattatgcc attgagctcc aggccaatca    22320
gcatggaagg gaaatcactt cagaatgaac agccgtgagc gctcttgtta gtgagagcag    22380
gcctcgtcta caggcgttcc gtgaagcgtt gtgagaacta ggaatacttt cgagtttggc    22440
agctcgttct gcttccttca accgtttcgg acgagtacca acaattcgcc gttgctgcgt    22500
acaccctacg tccctcgtta ccatagttcc ctctatctcc aacctatggg tcgcagagcc    22560
catctttgca acctctacgt cctgtgactg tgttctttcg gccggtatac ccagaggtaa    22620
ccgagccgag ttcatatatc cgacaaaccc tttccgataa agcatctcca gggtggctca    22680
acgagaccat acaggggctg ccatctgtct ggcagggtat cgtgcggcaa tggtcagctc    22740
tcaagatttc aggtgagtct cggcccagcc agctgctcaa tacctactcc gcgggtcatc    22800 tagcccccgtt acgaagccac tgaacttgct gcttgttccc gtgacggtgt tgcggcatat    22860
tgtggaattc caaaagctca agagaagag taagaacctt gagattagag aggtctaagc    22920
gttctgcgtc gggctgtttg ctgctattac agcatgctgg gagcacgaaa tccccagagt    22980
tgacagcact gttctccggg tggttatcag tatcagggca ctcggagctc aacgggtccc    23040
cttctgagct tatgggcgtg taatggaaga tgaaatgtgg gtacagacat cttggggagg    23100
cccttcagcg gtagaaggtg tgattttgac cgtgtcaaac gtctagtggc ggctgacgag    23160
ataaaacagg atatattgcg tgcatgacca agacaaacgc gccacagtta cagtccctac    23220
tgaaaactac gtgtccttga cacaggaact tgtgagccac agtatgtcag tcaacagcgt    23280
ccttctacgt ggaaggttcc atacctctga tcataccct gccacgaatc agttgctcgc    23340
atctgtgcaa aggatcgatt tcaactgcca atcaagaaaa gtctacatct accaccgagg    23400
tctaatgtat atggcttgcg agtttcgagc aatctgctga ttgcagttgc ggtcgagtcc    23460
attttggcca agcgggccaa ctggttgctc acggggccga agctctcaag agcgagggc    23520 cgcaaaatga aaaacacgcc atgatcatca gagcaggaca gatctttctt agccagtgtt    23580
gagcacatct gagaccagat ggcgcccaac gacacttcac ttcatcggtc aagccacacc    23640
atgaatatac actccaccac gcaaagtaac ggtaccgttt ttttttggga ctttcgaccc    23700
aggctctcgt cgcgccaatt gcccgttact ggattcgcgt gtcggatccc caggcagcat    23760
```

```
gttgcgctct agtccaactt tggaatatcc ttttctaatc tcctactttt tatttttta    23820
ttttatattt ttatttattt tattttattt tattttttt ttgctatagc tagaatacta    23880
tgttgtgaaa ttgtctcgtt agcttattcg atgcctagag gcgctatccg caagtctgcc    23940
tgcgatttga accagaaacg tcaataccct gtacggacaa tggtattgcc aaaattagtg    24000
ctgttatgtc tgttggcaaa agccagcact gtgcagacga acttattata tgccaatatc    24060
tcgtcgagtg caagcgacga atgacccgggc gcagccagat ggaagtgaag gctggagatg    24120
ctgaaattg taccagcaac cattgactgc tttggggtga acgaattcaa tcccggatgg    24180
tgatcatccg ccgagacagg aacacgatgc gtgcgaacgc agtaggcctg gcactctgag    24240
agtgggttgc ccgtcttgga ggctcaccgg gttcaggact ctggtgtaac ttgtgagaac    24300
ggcatcgtag gcctctgccc ggccaatctc tcttggtaga ccggctggtt tcagcacggc    24360
gccaacttcg atagtggtat aaagagcttc cgtaaacctt gtctaaaatc tcaacaaggc    24420
ttttatatta tccagctcag acatattaga cacattttcg cccagtgaaa gcaccaaaac    24480
atctcgatga agcaatctac agttgcgctc cttggagtcg gcatgctggg cggcgccgct    24540
gctttgcccg caggacagct tgccaacggc cctcaggacg gtaagtgagg tgatgatcat    24600
tacaaccccc tgcttcaata catgcacatc atcatcctcc tccagcacta gccagaagcc    24660
gtattggtag tgataaattg aacccagcag cctccatgca taacctccag gcgcgccaag    24720
ttgccgggac caatgagcaa ggcatcgtgc caccggtcac cgattacgtg tttggctctc    24780
ctccagttat accttatcct acttggggca tgtttgctcc gggaaccgag ttcaatgctg    24840
atgcattcgc cgctgcgttc cttgaagttg gcggtctgcc atcgtcaact tcaactacgg    24900
tttctgaggc ttctgtgact ccagcagcca gtcccatccc tgcggtggcc actgctggaa    24960
cctcaatctc gactccagcg gcttctgcag cgacctctgc tgtttcaagg gctactcctg    25020
cctaggccgt gacacaactc gccggttggg tacggtctac tcctgccacc agggacacgg    25080
ctcgagagag tacgagtggg aaggtcattg tacggaaaca ttccactttt ataattgtgc    25140
tttgtttcgg cgtctttgtc gttttggcg ttcgcatggg gtagggtttt ggttacacgg    25200
ccattccttt cagtaaagcc agccatcaat gtgaaccaaa ttagtatttt tgcaaggaaa    25260
aacgatctcc gtccaataat aggtttcagc gtctgcattt tgcatagctc tgggtgtctg    25320
ggacattctt ccttacgtcg cttgacaggt ggatacgttc agttatgggt ttgataagcc    25380
ccttcatgat cttgccggat cctgctcgca tttcctagaa gcccctggat cttaccgaat    25440
ttgtagaaat tccgccagtc aatacaagcc ataaaagaag cctgaccacg gttatgaacg    25500
atcgcatgcg cgtccagccg tcgccggcac agttagctct agggagcggt gtctcattgt    25560
aagtgaaggc gttgaagctc ttctgcggtc gctgctgcca gcccgctccc tgactcgcaa    25620
tctcctcctt ctactatgcc gggtcggtga gggcgattac tgcgttcatt gacggcggcg    25680
ggagtccgtg gaatacgacc agcgagcggc tgtaccgcgc caggtggttg atgatctgga    25740
cagcgctggc gcctttgccc gagtattcca acgcgcttgt cagccaaccc agtgagcttt    25800
gaaatctcta atggctcgcc tgtgaactgg cagtcccaag cgtgcggtgt ggaagagcct    25860
cctcttgtac ttggtgatat ccgggtagct ggggacacga ggacttgcaa aagagcccga    25920
ggagaggagg acaatgtctt gaactgcttc tctctgcctt gtttgtatct gatacatttt    25980
caagcagctg tcagctacg taccagatct tcttgtcctc gtcccacgcc aaacctcgca    26040
caatggtgcg gaacatggcc cgggcctcta gtccccaatg cttgcaatac gctcggcatg    26100
ttcgcgaatc taggtgccac tggcgtacct gtgtcgtggc atgtatcctg tctcctctag    26160
```

```
gagcggcata taaatataac tctccgtgtt gcacatcaac ccgggtaccg attccagtac   26220
cacgtccctt agaaccctgc ggctgtatct gcaatggcga tattactcgc cttgaactgg   26280
ccggtctgga gcaggtgcac ggcgaatagg aggccgccaa aacctccgtt aaaacctccg   26340
ccaacaatca ggaccctgtg gcggcccTAA aagagtatat gggtttgcag gaagagcaaa   26400
tgtggcgatt ctcctgctgg ctctgggcag cttgctcagg ctcacggctg tgacaaagaa   26460
aagggcgttg aactccagcc gcagaatatt gcccataaac attgcccata ttctattgct   26520
gaatgagcat aggagggggt cagttgcgca gtcattcctg ttgataacgc gtggtcgact   26580
atttaggtga taggcaaggc actgcgacct agggatgctg gaaatcaatc attattcttt   26640
cccacacact cagttgtagc aaagaatcga cggatgatgg taagacgaga gcgccaaatt   26700
tcctgcaatc ttacatattc accaggacca ataatcgttc ggaagatgtt atgggtgtac   26760
cgctgtggta tgcattattt actcctcact tgcagtgatt agcaaagggc atcaatagct   26820
agttgcgcaa acattccctg cataatgcca cggataataa atgactgcca tgtagcacga   26880
ccgtggtctt aggcttatag cttTGTTcat aattaactga ggataccgtg ttatcgcatg   26940
ctgaagcagc actcatcgca gttcaggaca caccacaaca cgcacaacca tgtctcaact   27000
aacaatctcc aagatcattg aggaaccctt cagcgcactc tccctctccg aaatgctcaa   27060
gatcctcgcc gcgcttggtt ggtcgacaaa ctatctcgcc atggtctacc gcacgcaagc   27120
tgacaaactc cccgccatcg ccgtcctccc cctatgctgc gatatcgcct gggagtttac   27180
ctacgcgtgg atatatccac aggccagcgg ccactggcag ggcgtcgtgc gcgtgtggtt   27240
tttcctgcac acggccgtcc tggccgcgac cctgcgctac gccccgaatg actgggcggg   27300
cacgccattg ggtgaaagcc gaggacgact ggtgctgttg tatgcggcgg tgattgccgc   27360
gtttgcggcc ggccagctat gcctggcttt ggaaatgggc ggcgcgctgg gctttcattg   27420
gggtggcgcg ctgtgccagt ttctctcgag ctcggccgcc gttgggcagc tgcttacccg   27480
tgggcatacg agggGAGCCA gtttgcttat ttggtaagtt ccatgaattt acggttcgcg   27540
ttgctactaa caatgatcaa aagggggggct cgtgcgatat ccaccgccgg cgggtttgta   27600
aaactctgca tccgcttcca gcaccaggtc gatgggcgc catggcttga cagtccaatg   27660
tgctggtttt atatagggat cgtgctctca ttggatgcgt cgtatccggt gctgtaccaa   27720
ttgaccagaa ggcatgaaga agccagtggg ggtgggaaat caggaaaagt gaagaattgg   27780
tgattgcgct atatctgttg tatcgaaggc ctgctttgga gattaactgg cgtacaagac   27840
aaagaaaaac caaggatcac tggaaggtag tgtacttgca agttatacat ggcttgggtt   27900
acgacagggc catgtcaaac gagatgtctt atttccagcg caaaacaagt acctgcaagg   27960
ttcctgttga taacttgatt ctatttgttg tgaatgctca gaggggaaag gccagaagga   28020
aactgtatca agtacacgaa cgtagcctac taagaatcgg acgccatatg acgatcgatt   28080
ctctgccttt tgacgatag atctcttcct cctccctgta ttcttcatcc tgtcgtcctt   28140
tctttccccc cactatacct tctagaacta cgcgatgtat agtcaagcca ccagagataa   28200
cgtggccttg tattcctata tcattattga taacgtgtat tctggcactc tgaatgccaa   28260
tgtgccacct aaaatggaga tcattacata ttgtacaaga tggatatgca agagcataga   28320
aaacaatacc agcaacgaaa aagccacgag acaagtctca aagtccatat agcccttgtt   28380
caagcatgcg ccatgggcgg gattctcgat cccttgacgg acaggcactt gatcggcagc   28440
accccaaaca gtgctagggt gcatagcgca gtgccggcat aaaacacctg tgtaattgct   28500
```

```
agactgtatg cttccagagt ttgagggagg tactcgggct caattgcatt gcgtatctcc    28560
ctcggagaaa catcagccac cctcgccgta tccactcctg gaagcgccgc attcaggtta    28620
tgcacaaggc gactctggaa gacactttgg gccacaaagt taaataacgc gcccgaaaga    28680
gactgagtaa atgtgatgat ggcggagccc gtcgagacgt cgtcggtagg gagagcagtc    28740
tgtacagcga caaggggag cgccatgccg gatccgatgc cgacgcccaa taacagctgg     28800
tatgtgatcc aggcagccgg tccggaaaag acgtgcagtg tcgtgagcag tcccgcgcca    28860
atagatccga ccaccggtgc catgtacata aacggcacgt agtagccaac ccggctgacg    28920
ccccagccag agagcatcga acatacaact acgccgagga tcatgggaag attcatcacc    28980
cccgagcgcg ttgcggagac agatttgatg gcctggaacc aaatgggag ctggcaagca     29040 catatccatg ttagcatccg gattcagtag caaggggtg ttctcacata atacgtaaag     29100
accgtgaagg agccgtaaat gcaaaccgaa aaggctattg caccccagac actgcgattc    29160
cggactattc gtggcggaat cgtagccctc tcgccctgcc acagttgcac agcagtaaag    29220
gtcaacgcca gagagcccgc catgaccaaa agcacgatga tgcgccagtt gctccaggcg    29280
tattttgccc caccccattg aagtacgagc aacatgcaca tgacggcggg aaggatgaga    29340
ataataccga ggggatcaag atcaagcaac tgcgcccagg gggttttctt tactgtagcc    29400
ttttcgcgga cccgcggcct gacgaacaga acaatgataa acgctgtcaa ccctccaatg    29460
ggcaaattga tatagaagca ccagcgccag ctgacgtagt cggtgaatac gccaccaaga    29520
aggggaccca cgacgctagc gataccgtac agaccgctaa taagggcgat aaacagtggc    29580
acttgatgga gcggcatgat ttcgtggaca ataagcatgg agccgaggaa taccctgcg     29640 ccaccaacgc cggcaatggc gcggccgatg atgagggcaa gggaactggg tgcggcgccg    29700
cagactagtg agccggcttc aaacaaaaat agcgttgtca ggtatacca tttcactctg     29760 tacaagctgt agatcttgcc gtagacgagg ctgaagctgc ttatcgtcag gttgtatgca    29820
ctcacgtacc aggccatgtc gtgtagcgag ttgaattcag cagtgatctt ggggattgca    29880
gttgatagca ctgtgctgtc ctggacattg atctgttaga gtacatcctt gatgcggaga    29940
atgtggttgg ttccaggacg tactagggac atgcagaaca ccgccagtga taatccaatg    30000
agaacagcgg cgagtttcca gcctgataca gtaccagagc cacttgtgcc gtcgtcgacc    30060
cggtcatttg aaccatgttg gagctcggcc accgtgggcg catctccctc gttcggcgct    30120
ggcgttggat gggcaccccc tgcattgtta tcaccggatg cttcgcttag gccctgagta    30180
gcactttgct cgaggtgctc ctgcgatttc gtctcctcaa tgggttgggc gtcgtccggg    30240
ctcgcaagtc tggtggttga ctcggtgggc ggttgctgaa gacgccgaag gcgaaactta    30300
gtgtggcgct tgcttctgct gcctgtgacg cctgtcattc ggccaagcag gctggactgc    30360
atctttggtc aagggggcgat tggctgaaag atgaggcaaa tacggaacgc tgagacctcg   30420
ggagttatcc gtgcctttgt cagtcccaaa tttgaagctt tgaagaaatc atcgcggttg    30480
gaggacgtct tattcgaagc gagtgttttga tcatcgcatg taaccacagg gagaattctc    30540
atttgggcct cagaaataat cccttgctgc ggatagctgc ggcatccgag gcatttcagt    30600
aagatttatg tattttacga cattaaacgg gctcatgtgg caggtgccta agcaggggat    30660
acgcattctt accgattgag aatgactgca attgccatcc ccagtgatag tctcagcaat    30720
tgtgcactcg tcaagctttg tgtaattcaa gtgtctaaca tggaatagca ataaaaaaat    30780
cccagccagc atggtttcca tccgacatag cacattccag cctgttctga cctaaggaaa    30840
aattggcgtg acaaatacgc tagagtagac tagataacat aacattgaag ccaaaactgg    30900
```

```
tagcgaaatc accagccaag ggagggtcgg tgcgccaacc tctgggctcc cggcgtagtc    30960
gctccatcca gggcccgtcc tcttcggggt gggcaggaaa tccacctgag gggcacctgc    31020
aatggcttgc gacgttctct caagcacctg ctgcctgaag cgaggaaaga tgtagcggcc    31080
aacaaaggcc ttgagcgcgt cgtccctcgt gtgcagcctg cgccaaagt  acgcacgttg    31140
gtatgtgctt ttcacgcgct cgtacctcag cgaggcgtat tcttggagca cggcgtctat    31200
tgtgcaactc gtggccgacg agtcggaagt cgatagtctt tgtagcagag atgcgagcac    31260
tcctgcgtct tctgctgcgg tattggcacc ttgcccgata ttgggcgtca tctacactgg    31320
ttaatcacat cctgctgtcc gtctgttgat acatcaagcc actcaccttg tggatgctat    31380
caccgagcag gactacgcgc ttgaatctcc aggtctccag caggccctct tccagcgcag    31440
tcatggagac cgacgtcttg ttcccccaga gatctctcac gcatatatcc cccagaccg     31500
gtacattagc atactcggca caaatcttgg ccgcatcgct ggctgaaaag cgcggagtaa    31560
atgggtagat aaacctcttc tgtaacttga tgaggataaa ccaaaaaaca cggccatcct    31620
taccatggaa ggtgatcaca cagagcccat tcgagtaaga gttaacatgc tccccactct    31680
ccaggccgga gatagggctc gaaattccaa aaacacatgc atattcgaca gtgaatgctg    31740
caatctcatg attaacgtct gcaacaatga ggagatattg caaagcacac cttgtcgatc    31800
tcgccgacca acaagatcct tggcctggcg ccacatctcg gcacgcactg cactgtgtat    31860
cccatccgca ccaacgacca aatcccctt  gtatacggcc ccatcggctg tgagcacctg    31920
ggcttctcgt tcggttt gtc gaatctcagt caccttcttg ttgacgtgaa tgttggactt    31980
ggccgggtag cggttgtaga aatctccag  gactttctgg cgatcgagag atataatcgg    32040
atatccaaac ctacaattcc cgtcggtatc aagttcaaac agtgtttaga agcaacaaac    32100
cttctttctgga cttgcctcgg cagctcactg ctaaaggaga cccatctgg  aaatcgcacc    32160
ctcattttgt gtattggcac cgtgcacttt tccaggtctg catagacgcc cagctggtca    32220
aagattcggc ctccattggg ccagatgcct aggaacgctc cctcttgcgg gctgatctca    32280
gcgcgctttt cgagtactat atgatcgata tttgcgttcg ctaaacagtg tgccaacgtc    32340
aggccagcga cagaccctcc gactattatc acacgaagat cagtcttgcg cgtaggtgta    32400
tcgctcattg tggctcatcg gtgtggtgca actactcttc tccatcagct aactacggtc    32460
tattaattat agtaactagg ataattgagc ctagcccgct gagcagctat gagagccgtc    32520
cacattggtt cttatgctgc ttgcacaact cataacataa ggatcccttg cgagacgctc    32580
tctgcttcat tggctagcag caagctatgg gtccaaataa tacaagcacc cacccttgcc    32640
gagaagttgg tttcacccctt gctatgtgca tcaacgatga tagaagttgt cacacaacgg    32700
atgctctttc aggctctccg ggcatgatgg ccctcaggct ttccaatgga gagaaagatc    32760
tcctgctaat ggcattctga agacctagat gcatgattgc cggaaccctt gtcagtggta    32820
tctcccctta ctgggtaggc tttcgagaga tatccccgtt atttccgagt cggcggaata    32880
ctgggccata ttgaagaggc cgcctgcttc ccggcgctat atcgcccaag gccttgatgt    32940
tcctttaaca ccccagggcg cgctcaatcc tcttgatttc ctcctcctct ctccaccgcc    33000
caaacctttt gtgaaagaaa aaaaaatggc cgtcatctca gaattgaaga gacatcatcc    33060
caagacagga ctgctcagat atctccctac cggcgttgtt ccatacggag agctggtgcg    33120
catccaccgc gccctaggtt attacctcaa cacatctccc tacgtagttg gaatcgcata    33180
cactgccgca actgccgaaa caaaactgcc cctcgaccta ctcttggatc gcctcctcct    33240
```

```
gctcacgctc tggtctctta tccttcgcag cgctggctgc gcctggaatg atctcgtcga    33300
tgtcgacatt gaccgacaga tttcgcgcac acaaagccgc cccctccccc gtggcgccat    33360
ttcgctctcc gcagcaacca tcttcacagc atgtctcttc gtcctaggtt gttcgctttt    33420
actctttctt ccgcgagaat gcctattcga cgccggcatt aaagtcttct tcgcgctgct    33480
ttacccttc gggaagcgct tcaccgatca ccctcagctc atcctcatta acatcgcctg    33540
ggcaattccc atggccatgc acagcctagg tatggagcct tcgagccaga tcctctcaat    33600
gctctgcatg tgcgttttct tctcggccgt gattgtcatg atcgacctgg tttattcgcg    33660
tcaggacaca gaggaggatc tcaaagtcgg cgtgaagagc atggccgtgc gataccgaaa    33720
ttgtgtagaa acgatggcct attcgctttt tgccatcagt tccctggcac tactgtttgg    33780
aggcgtgctt ggtgggcttc gagtaccgtt tgtgcttttt tctgtgggtg gcacattgt    33840
gggcttttgg aggttcctgc gagcatcgct gcaggctgga ccggcagggg tggagtcgcg    33900
tgccaaatca tcctgcttga tagcgagtgt gttttgggtg ctggggttag gtatcgagta    33960
tgctgtgcgt gtttagcttt gcttttcggg gtgttggttg accacacgcg cgtaaacgac    34020
gccaaattgg tcgtggctca tacgaatttg catattttcc agataaccgg ctcaatgcta    34080
tatggatggc ctacaggaaa tggtcaaaga aaaggataac cccactgata agaagaagca    34140
tcctcattga gagatccaga aacgcttcca agtcagccct acacggtagt gcgcatctag    34200
atcgctggga aggttggcgt aagatcgtta ctggggcgat accaatgctg cctgcc        34256

<210> SEQ ID NO 7
<211> LENGTH: 32878
<212> TYPE: DNA
<213> ORGANISM: Aspergillus nidulans

<400> SEQUENCE: 7
tcagctatag atgcgatccg cgcctcaagc gcatttcaag ccctccctct tcaatacgtt      60
tgcgatacct tagagaaaca aatcaacatc catcaactgg cacagattca tctaccaact     120
caacgtgatt acccgtccag ctttgaccta aacctccata atccccatcc acaaggcacc     180
atgggcagca catcttccga gcccacatac gacagtgagc ccatcgcgat tattggcctt     240
tcgtgcaagt tcgctgggtc cgcagacagc cccgagaaac tatgggagat gcttgcggaa     300
gggcggaatg catggtcaga gatccctgag tcgcggttta accacaaggc cgtgtatcat     360
cctgatagtg agaagctggg gacggtacgt cttttccttct agacttgagt ttcagtggtg     420
aagtggatgg gaagcaagaa cctggccaga ctaacgcgga atcttcgcag acgcatgtca     480
aaggggcaca ttttctcgag caagatgtcg ggctcttcga cgcggcattc ttcaattatt     540
cggcggagac agctgctgta cggtccctat gaacgatttc aggatgaatg gccaggctaa     600
ctgagcatga tgtacggata gaccctcgat ccgcaattcc gcttcagct cgagtccgtc      660
tatgaggctc ttgaaaatgg taccaccctc cccccaacag cccttgcgca aggctgaaca     720
gagagtacag ctggcctgac gattccatcc atcgccggca ccaacacctc cgtctacgcc     780
ggcgtcttca cgcatgacta ccacgaaggt ctgattcgcg acgaagacaa actgccccgg     840
ttcctcccca tcggaaccct ctccgccatg tcctcgaacc gcatcagcca cttcttcgac     900
ctcaaaggag caagcgtgac tgtagacacc ggctgctcga cggccctggt ggccctgcac     960
caggccgtcc tcggcctgcg cacgcgcgaa gcagacatga gcatcgtctc tggatgcaac    1020
atcatgctgt cgccggatat gttcaaggtg ttttcaagtt tgggaatgct aagccctgat    1080
gggaagagct acgcctttga ctcaagggcg aatggatacg gacggggcga gggcgtagcg    1140
```

```
acgattatcg tgaagcgact cgcggatgcg ctgagggacg gggatcccgt gcgcggcgtg    1200
atccgcgaga gctatctgaa tcaggatgga aaaacagaga ctatcacctc gccgtcacag    1260
gaagcgcagg aggcactgat caaagaatgt tatcggcgcg cggggctgtc gccgtcggat    1320
acacagtact tcgaagcgca tgggacaggc accccactg gagatccgat tgaggcgcgc    1380
tcaatcgcgt cagtatttgg aaagaatcga gagcagccgt tgcggattgg ctctgtcaag    1440
acgaatatcg ggcatactga ggcggccagt ggtcttgccg ggctgatcaa ggtcgtgctg    1500
gccatggaga aggggttcat cccgcccagc gtaaactttg agaagccgaa tccgaagctg    1560
aagctggatg aatggaggct aaaggtggca gatactttgg aaaagtggcc tgcaccggcg    1620
gagcggccat ggagggcgag cgtgaacaac tttgggtatg ggggtacgaa cagccatgtc    1680 attgtgaag gggtgccgaa gagattatac acaccggcaa atggaaatga gaccggccag    1740
ataaagcatg agacagagag caaagtgctc ctcttctctg gccgcgacga acaagcctgc    1800
cagcgcatgg ttgccagcac gaaggagtac ctgaagaagc gcaggagca ggatcctccc    1860 atgacacctg aacaagtcaa gaccctcatg caaaatctcg cctggacatt aacgcagcac    1920
cgcactcgct tctcctgggt ctccgcacac gcggtcaagt actcgacctc cctggacacc    1980
gtcattgacg ccctcgagtc tccgccgccg gcctcaagac ccgttcgcat ccctgactct    2040
ccattccgta ttggcatggt cttcacgggg caaggtgcgc agtggcacgc catgggccgc    2100
gagctgatcg ccgcgtaccc ggtattcaag gcaaccctag acgaagcgga acagtatttg    2160
cgccaactgg gggccggctg gtccctcatc gaagagctga tgaaggatgc agccacgaca    2220
agagtcaacg acaccggcct cagcatccct atctgtgtcg ccgtgcagat cgctctcgtc    2280
cgcctgctca aggcatgggg gatcactgcc tcggccgtga catcccactc gtccggtgag    2340
atcgccgccg cgtatacggt tggcgctctc tcgctgcgcc aggccatggc cgccgcctac    2400
taccgcgctg ccatggcagc agacaagacg ctgaagagcg cagaggggcc caaggcgca    2460 atggttgccg tgggtgttga caaggctgcc gcgcaggcat acctggaccg cgttgagaaa    2520
tcggcaggcc gcgctgtggt ggcatgcatc aacagcccca gcagcatcac cattgccggc    2580
gacgaggcag ccgtcgtcgc ggtcgagaag ttggccactg aggagggcgt cttttgcgcgc    2640 cgactcaggg tcgagacggg atatcactcg caccatatgg agccaattgc gagcccgtac    2700
cgggaggcgc ttcgcgccgc attggcccag gaagatgctg agtctggtac caaggaccag    2760
actgatgtcc cgggctttgc ggatgccact aaaccgggca gcctagacca caccgtcttc    2820
tcctcccccg tcacgggcgg ccgtgtcaca gatgccaaag tcctctctga cccggagcac    2880
tgggtccgca gtctgctcca gccagtgcgg ttcgtcgagg ccttcactga tatggtgctt    2940
ggctccacag atagcagcaa tattgacctg atcctcgagg tcgggccgca tacagcccctt    3000 ggcggaccga tcaaggagat ccttgccctg cctgacttca gcagcaggaa tgtcagcctc    3060
ccctacatgg gctgcctcgt tcgtaaagaa gatgcgcgcg actgcatgct cactgctgcc    3120
ttaaaccttt tctccaaggg ccacagtatc gacctgctca gactcagctt ctcgtctggc    3180
atcccagagt tgcaagtcct gaccgacctc ccctcatacc cgtggaacca cagcatcaga    3240
cactggtctg agtctcgccg caatgccgcg taccgtaagc gcagccagga gccgcatgag    3300
ctgctgggcg tgctggaacc gggcacgaac ccggacgctg cctcgtggag gcatatcatc    3360
aagctctccg aggcgccgtg gctgcgcgac cacgttgtcc aggggaacat cctctacccc    3420
ggtgcaggat tcgtgtgtct cgccattgag gcaatcaaga tgcagtctgc catgagcggg    3480
```

```
acgaatgatg tgaccggttt caggctgcgc gatgtcgaga tccatcaggc gctcgtgatt    3540
gcggacagtg cagacggcgt cgaagtgcag acgaccctcc ggtccgtagg aggcaaggtc    3600
atcggcgcca gaggctggaa gcagtttgag atctggtcgg tcagcgcaga cagcgagtgg    3660
acagagcacg cgagggtct aatcaccgtc gacactgaga ccaaggcatc cacgctcgtg     3720
gcaagcactc tcgatgaatc cggctacacg cgccgcatcg acccgcaaga catgtttgct    3780
agcctgcgcg caaaggggct caaccacggg cccatgttcc agaatacgct gagaatcctg    3840
caggacggaa gggccaagga gccgcagtgc gtcgtcgata tcaagatcgc cgacgtatcg    3900
agcagcaagg acagcggccg gatgagtctt ctgcacccga cgacgctcga ctcaatcgtt    3960
ctctcctcat acgccgcagt acccagctcg gatccgtcca acgacgacag cgcgcgcgtt    4020
ccccggtcca tccgcagcct gtgggtgtcg agcatgatca gcagcgcccc gggccatacg    4080
ttcacctgta atgtgaagat gccgcatcac gatgcgcaga gttacgaagc gaacgtgaca    4140
gtcgtggacg aggccggagc cagagctgag agcatggtcg agatgcaggg tcttgtctgc    4200
cagtctctcg gccgcagcgc accagcagag gaccgagaac cctggacgaa ggagctatgc    4260
gcgaacgtcg aatgggcgcc tgatctctcc ctctctctcg gccttccggg ctcgtcagac    4320
gccatcgaca ggcgcctcaa cacctccgc gaccagaatc cagacgagag gagcatcgaa     4380
gtgcagacgg tcctgcgccg cgtctgcgtc tacttcagcc acgatgccct ttcctccctg    4440
acagaaaacg acgtggcaaa tctcgcattc caccatgtca agttctacaa gtggatgcag    4500
gataccgtca acctggcact cgcgcgccgc tggagtgccg acagcgacac ctggattcat    4560
gacagtcccg ccgtacggga aaagtacatt tcccttgctg gtcgcagac ggtggacgga     4620 gagctgatct gccagctagg cccattgctg ctgccggtcc ttcgcgggga acgagcgccg    4680
ctggaggtta tgatggaggg acgcctgctg tacaagtact acgccaacgc ataccggctg    4740
gagcccgcct tcgagcagct caagtcattg ctgggcgcga tcctgcataa gaaccctcgt    4800
gccagggttc tcgagatcgg agccggcacc ggcgctgcca cacgacacgc gctcaagacc    4860
ctagggactg atgaggatgg cggtcctcgc tgcgagagct ggcactttac tgacatctcc    4920
tccgggttct tcgaggcagc ccgcgctgaa ttcgccacct ggggcggcct gctggagttt    4980
aataagctgg atatcgagca ggaccccgaa gcgcaggggt tcaagctcgg ttcttacgat    5040
gtcgtggtcg cctgccaggt tctgcacgcc acgaagagca tgcaccggac tatgaccaat    5100
gtccggtccc tgatgaaacc cggcggcacg ctgctcctta tggagacgac acaggaccag    5160
attgacttgc agttcatctt tggtctcctg ccggggttggt ggctgagcga agagcctgag    5220
cgccacgcga gccccagcct gagcattgac atgtgggatc gggtgctcaa gggggccggc    5280
tttacgggag tcgagattga cctgagagat gtgaacgttg atgctgagag tgatctgtac    5340
ggcatcagca atatcatgag cacggctgtc ggcacggcgg gttcgagccc tgagaaggtg    5400
gatgccgccc aggtggtgat cgtgacgggc aacaagacgg gctttcagga cgattgggtc    5460
aggggactgc aggcagccat tgctcaggac tccgtagcg atgcccttcc agagattata     5520
tccctcgagt ctccctcgct cggggcagag gccttccagt cccggctggt cgtcttcgtc    5580
ggcgagcttg acagacccgt tctggcgtct cttgactcca cagagctcga gggaatcaag    5640
accatggccc tcgcctgcaa aggtcttctc tgggtcaccc gcggcggcgc ggttgagtgt    5700
acggaccccg actctgcgct tgcatctggg ttcgtccgcg ttctgcgcac cgagtatctc    5760
ggccggcgct tcttgactct cgacctggac ccagcagccc attcgcctgc gtctgatatc    5820
tcagtcattg tgcacctcct ctcctcgcgc ctacagccgg ccgttgagac agcggccccg    5880
```

```
gccgacagcg agttcgctct gcgagacggc ctcctccttg tgccgcgcct ttacaaagac    5940
gttgtctgga atgcactgct ggagcctgag gtccccgact gggcctctcc agagagtatt    6000
cccgaaggcc cccttcttcc aagccaagcg ccgcttaaa  ctcgaggttg ggatccctgg    6060
tctgctcgat acactcgcct tcggcgacga ccccgacgcg ctggacgccg ccgggcccat    6120
gcccgacgag atggtcgaga tagagcctcg cgcttatggc ctcaacttcc gcgacgtcat    6180
ggtggccatg ggccagctca aagagcgcgt catgggtcta gagtgcgcag gcgtcatcac    6240
gcgcgtcggc gctgaagctg cggcgcaagg cttcgccgtg ggtgaccggg tcatggccct    6300
gctgctgggc ccgttcagct ctcgtgcacg ggtgagctgg cacggagtcg ccagtatgcc    6360
cgcggggatg gggtttgcag atgctgcctc tatcccgatg atcttcacca cggcgtacgt    6420
cgctctcgtg caagcagcgc gactgtcgca ggggcagaca gtgcttattc acgccgctgc    6480
aggaggtgta gggcaagcag ccgtgatact ggccaaggaa tatctcggag cagaagtctt    6540
tgcaaccgtg ggctcgcagg agaagcgaga cctactgatc aaggagtacg gaatccccga    6600
cgaccacatc ttcaactctc gcgacagttc ctttgcaccg gctgccctgg ccgcaacagc    6660
cggacggggc gtggactgcg tccttaactc gctaggtggc gccctcctcc aagccagcta    6720
atcgaggttc tcgcgcccct tggccacttt gtcgagatcg gcaagcgcga tctcgagcag    6780
aacagcctgc tcgagatggc cacctttcacg cgcgctgtct ccttcacttc gctcgacatg    6840
atgaccctcc tccgccagcg cggcgacgag gcgcaccgcg tcctgagcga gctcgcccgg    6900
ctggccggcc aggggatcgt caagcccgtc caccctgtgt ccgtataccc aatgcgccag    6960
gttgacaagg ccttccgtct gctgcagacg gggaagcatc tcggcaagct ggtactgtcc    7020
accgagcctg acgaagaggt tagagttctt cccccggccgg ccacgcccaa attgcgcgcc    7080
gatgcatctt acctccttgt cggcggcgtg ggaggtctcg gccgctccct cgccagctgg    7140
atggtcgaac acggcgcaaa acaccttatc ctcctctcgc ggagtgcagg caagcaggac    7200
agcagcgcat tcgttaatgg cctacgggac gcaggatgcc gcgtcgccgc aatctcctgc    7260
gacgtcgccg acagggccga cctcgaccgc gcgatcgcgg ccgcctcaga gttgggttc     7320 ccgcatgtcc gcggcgtcat ccagggcgcg atggtcttgc aagactcgat cattgagcag    7380
atgagcattg cagactggaa tgcggcaatc aagcccaagg ttgccgggac acgcaacctc    7440
catgaccgct tctcccagcg caacagcctc gacttcttcg tcatgctctc ttccctatcc    7500
gcgatcctgg gttgggccag tcaggcctcc tacgcggctg gcggaacgta ccaggatgcg    7560
ctggcgcgct ggcgctgctc caagggtctg cctgccgtat ccctcgatat gggcgtaatc    7620
aaagatgtcg gctacgtcgc cgagtcgcgg tcagtctcag accggctgcg caaagttggc    7680
cagtccctcc gcctctctga agagtcgatc ctccagaccc tggcaacggc ggtcttgcac    7740
ccattcggcc ggccccagct cctcctgggc ctgaactccg gcccaggcag ccactgggac    7800
ccttccagcg acagccagat ggggcgtgac gcccgcttcg cacctctccg ctaccgtaag    7860
cccgcatcta cgaagtccgc tcagacatct tccagcggcg acggcgaaga gcccctttca    7920
tccaagctca gtcagccgat ttcccccgat gcggcggcga actatgtcgg gggtgcaatt    7980
gccaccaagc tcgcagacat cttcatggtc cctgtggccg atatcgatct gaccaagccg    8040
ccaagtgcgt acggggtcga ctcgttggtt gctgtcgagc tgaggaatat gctggtgctc    8100
caggcggcgt gtgatgtgag tatctttagt atcctgcaga gtgtgagcct tgcggcgctg    8160
gcggggatgg tggtcgaaaa gagtgcgcat ttcgagggaa gtgccacggg aactgtcgtt    8220
```

```
gttgcttgag ctgcatcggt catgttgttc ttctatagag ttgaagcaag gtttgtagtt    8280
tgctctgggt gtctggagtt gtctggagtt gtctggagtt ttgttatgat gttgatgggt    8340
acttcttcat actagcattt tggcatgtta taagaacata ttatcagtta aatgtctttc    8400
aatttaatca atttgttttt agaatgatgt tgtctgcctg gctatgtatc tagatcctat    8460
acaagctcta tcgactcgac ctaactacta cgacttgaaa gtcaagcgag aagtgatgat    8520
atgaacccat atgtcagacc cgctaaattt attagtgata caactatat tactcagagc     8580 ttttctttct agagtatgtt agaattgccc tttctggctc agtgggaagc tcgagaccta    8640
gtccttagtc acgtgctgct acatcatgta aatataagcc ctacatggct gtcttgtgca    8700
tgaggctaac accattatct gtcactggtc cttttatttg gttcttttct ttactttctc    8760
gggcgggggg gaaagccgct aacactgtct atcgcttgga cagaaactca ccagtttgtt    8820
cgcaatcctg aagcgtatgg gaagcttaca gttaaggagt agctcgagtc tggaccctgt    8880
tttcgacttg tacctttgat ttggatgact ggttaacctc agcttatgta tgatgtgctc    8940
tcatggtgtc aatatctggt agtctgattc tgagcaattt gatagtatct gatggctggc    9000
gagtaaggcc agggcgatga ctggtataaa gtcagcccta aaacttccat ccgagatgta    9060
aaaccatcga ttcccctcca agatctcctg acgagactaa acaaagatca agtggccttg    9120
tagtaactct agcaagcagc gacaaaatgc ctcaacacga gatgaccaag tcagactcgg    9180
aacgaatcca gtcctcgcag gtaagagcat caggacattt gctaatacca ttccgccccg    9240
ctaatctgct tgaatgcaca caggctaaaa gcggagggga catgtctctt ggaggattcg    9300
cctcgcgcgc cctgtctgcc gggactgctg ggtcaattcc cagtcctcgg ccactgcttc    9360
cggccacgcg gactcgggtg ccggatctgc aggcggatct cattcggccg cacctggcgg    9420
tgatgcgggg cagggaagaa gataaaagta ccctgttgtc tttggggcgt tgaggtataa    9480
tggcatcgtg gtagaccgac tgggcttttt tttttgatat agttgatcct gaagcggagg    9540
acagttggta ggataaatga aagatactga accatgcccg gattttgtgc tcaaggacct    9600
aaaactgaga agctgaatct gttcttgtct gggagaaggc ctgccagctg catccgagta    9660
tctatcttgc caggaccaaa ccgggtctgg gctcagttct tctaacttct tagtggagtt    9720
ttgcagtgta gattcctttg cactatctgg tatcctagta gcagcctacc aggaaataag    9780
agataaataa agtcttaatt ggcattatta tgtttctcag aactatatat ctcggaacaa    9840
agctgagcag acagaagttt accctcacat atggacaaat tgcgtgctca ggcataagtc    9900
ggaaacagcc ttagccaggt caacacttgt agccttcgct agacgacgcc ccagcttttc    9960
ataatggccg gcctggaggg agatacggct atccacccta gaacctcgga ataggtgtcc    10020
ccttcccaaa gaccccttg ggatcccact ttctcttgag atacgacagc tttggcagat     10080
tctccttgct ccaccacgcc tccggcccct catcaccaaa tgcataattg acgtagatat    10140
gtggctggtc agcaggaaac ccgctggtgg catggagctt ttcgcgcagt gagaccagca    10200
gctcgttcgt tggagcctcc agttccggat tcaagaatat attctcgtgc agccaaaaca    10260
tcttcgtgtc gcgccaggga tacacggccg tgtgcgcagg cgttttgagc gtgttgttgt    10320
tcgcgtatcg ctggaacaga ctctgcccca gatacccggg gtactgctcg tagaacgcgg    10380
tcatgtcgtc gaacacctcc tgcatggtgg ccgcgtctgt tcggcctagt cctacggtac    10440
cgccggagac gtaggctccc gtctggcagg gtcgtcgag gccagcgtac agctcgacaa      10500
gagtgacgtt cgatacgttc cggctgatcg ggccgagcgc ctcggcgtgc tcccagtggt    10560
cgacgaaagt ggcccagggg gcgaagtgct tgatgtccac ggtcaagagg gtctcgttga    10620
```

```
tggtgcggtc gtacccgatc gagagctgca ctcccagttc aggagggagg acattatcga   10680
ggacagagag gtactcgaag acgccgagac tcttggatga gttatacaca aacgtgccga   10740
tcacggcgtc gccgttgttc ggctggtcga acatcttgaa tgtggcggcg gtgatgatgc   10800
cgaagtttgc accggcgccg cggatagccc agaggagatc gctattgcag gtctcattcg   10860
cagtgatcag ctcgcccgtc gcagtgataa tgcggacaga gacgagtgcg tccacgccga   10920
ggccgaagag ccctgtttcg tacccaattc cgccgccgat agtggcgcca ataaccccga   10980
cgcagggaga gttgccgcgg gctgtctcta ttagacggca tgcttaagaa ggagaaggag   11040
agaatgaggg ggcatacgga tggccttgcc cgctttatag agcggctcag tgatatctcc   11100
cagctttgcg cccgcaccaa cggtgacggt gttggactcc agatcgatgt ccacgttgtt   11160
aaagttggcc aggttgatat caagcccttt gacggtgccg taaatcagac tagtgccgtg   11220
gccaccgctg gtggccatga agctgacatt gttcgcgacg gcgatgcgga cctgcctcgt   11280
cagtacacta tttccttaag aagcaacact acaaaggcaa acagagaaca agaggcataa   11340
gaagaagaag aagaagaagg gggtatacaa tctcctgtaa atcctcctcg gtctgcggct   11400
tgatcgcgcc tgtccaggtc ggaggcctcc attcggacca tctgggtgat acgacctcgt   11460
caaaatccgc gtcgccaacc tcggcgatct ctgtttcagg cgagacgtat gggccgaaaa   11520
gagattcgag gtcgatgctt gccgcgcgcg ccgcagcgac tagtgttatt gactgaagca   11580
gaaaccgcat cctggtgtga ttgggctgat taggacaggc cggatgggtg tgcaagatag   11640
gaggagagga ctggtacggc gaatgagctt taatagccgg tcagagattg cgcgtggctg   11700
cgcccagatc cagcagctcc agccatactc cagcatactc cggccagccg ggggcatatg   11760
gcgtggtcac tggagctggt taggatcaac tgctggttaa ggcttactgt gttgccatgc   11820
ttacggtgca ccgagaggga aggttggagt taacggagtt gtaactccgg ggatccaatt   11880
agggcttaca gtctgcaaat ccatgcaaag tccgctgcgc ccctgacaca gcaaggaaca   11940
gtgtagagtc cgattggata gcggagttga ggtgactggc tggttcctgt tagcccctgc   12000
atcgacctgc aatgtattgc atcaaattag ggctagcctc taactccgtt agactatccg   12060
caacgcctgt cacacacgtg gctaggcagc agatgatata cttttgaaag cagtactcta   12120
aatttgtggg gtatatggtg tggctatgct ggatcgtcgt ctaaggccca ttgttaccag   12180
cactatttaa gttgtcgaca agatctagtc acatactacc agcgagtgca tgcagggccg   12240
caggatatag accggactca gcattgagcc atgtctttac gtaccactgt agttagccac   12300
tgagtgatag acacattgca gcttctctag actgatcagt aatgacgatc tcgcttgata   12360
ctgtctgctt atgcagtatt tatatagtat agtgtagact acggacagat tgcatctatt   12420
ccgtgaggaa agggtcttca gcatctata aggaataaaa actcgctgtc actgtacatg   12480
ctctagctac ctaaaagaga tattgcaggt gcattgataa aggactatgc agagagctag   12540
atctcatgtt tctactcaag ttacagggca tggcctagcc taatatgcag ttgtcctata   12600
tgtgagctag ctggagccga tgggaagtgt gtttgatgaa actgattgga ataatatgga   12660
attgtaagca aagtaacaac agtctagata caatgaatca ttcccaacac cagaatacgc   12720
cagactaaaa ccagagttag cgaaacaaag aatatctgta agctcaagca atcaggcgag   12780
gtagcccata tccttccaag cctgcacata caacctcgca agctccgtgc caacaggccc   12840
aacccccgcc atagtggtcg agtgctcctt cgccttgctt gtgtcaagca ccaggccgcc   12900
acagctcatg cgctcgaaat ggtcgtcgag gaaatccacc agccgcgccg ccggattctc   12960
```

```
cgtctccatc ggcagcggag accgccgcac ccttgagatc cacgtcttga atgggatgat    13020
attcgatgcg ggaatatcga gtgctgacgc aagcacatgg ttcatggctt gccagttctg    13080
accgacagga ttgtccatat ggtacactgg gtatgcctcg tcgcctcgtg aggtgagatg    13140
gagcaggtcc acaacaccag cagcgcagta atccacagga atccactgca tctggccctg    13200
caggtccggc caagcacgca gcgactgcga agacttgact aagaaagcaa agtgctcgac    13260
cgggttccag aaaccgctcg tcgacgagcc cgagatctgg ccgggccgca cgaccatcgc    13320
ccggaagaga ccgggatgcc ggtgaagggt ctcatcaacc atgcgctcac aaatccattt    13380
cgcctcgcca tatccggacg gcagtgctgc agatagcggg acgcggtcct cgctcacgcg    13440
ggactgcccg cagaatccga cgacgccgat ggaggagatg aattggaagc ccacgcggct    13500
ggaaccattg aagggccgtt ctgcaatgtc acgggcaaga tcaagaagat tccgcattgc    13560
ctgtagctgg ggctcgaatg cggacactgg ccgtgtcccg ctcatgggcc aggcgttgtg    13620
gatgatatcc gtcgcgttct cgaggagcca gccgtactca agcggcggga ggcccagctg    13680
tggcttagaa gtgtctgtct ctaaaacgcg gagctttgcc cgtgcgccgg gggacagggt    13740
gatgccgcgg gctgttaggg ctgcctgttg gcgcttctct ggggtggtgc tgctgctgcg    13800
acggttgagg cacaccaccg tcgcaaccga cggtgtctcg gcgagtctct gaacgatatg    13860
tgagcctagg ctgccagtcg caccagtgac gatgacgacg gcctcgtgcg ctctgcgtcc    13920
tggtgctgcg tgcggcgcct gtgttttgcc agactccttc tcggcccggc tcgctaaagc    13980
acggagtttg ggcgtctccc agccagccgt gtactttgca actaggctct ctgctgtcgc    14040
tgtgcgcgcc tcaacattct cccggttcaa ctcggggatg agggtctgca cgggccctgg    14100
cttgggcaga cgggctccct gagccccgga cgcgagcgcg ataatgactt tctggaaggt    14160
attttcaggc aggttgccgt ctgtccagtc gacgtgccca aacccggccc tgtgcagctc    14220
actctcccag tgctcggccg gtacgacggc gtggtgccgc ccgtcatcga acagccacca    14280
cccctcgagc aggccgaaaa caagatcgac aaagggggacc acctcggtca tttccagcat    14340
catcaaaaac ccatcggggc ggagtgcctg atggatgttg acagcgaga ccccgagatt     14400
gtgcgtggca tggatggcat tgctggcgag caccagatgc tggttcctga gctcgtcggc    14460
cgggggcttc tcgatatcgt gcacggcgaa acgcataaac gggtattgct tgctgaaccg    14520
gcgacgggcg ttggcgacca tgctggggga aatgtctgtg aaagtgtatt caatgggcag    14580
ggcgcccgat tcagccaggg tcgccaggaa cggcgccatg atgagcgtgg tgcctcctgt    14640
gccgcgcccc atctcgagaa ccttgagcgt ctctccggtg cggccaatcc gctcagcgag    14700
gaggttcgtg acttcacgca tctgtgcgta actcatgcag ttgaaggtat gctcgcagta    14760
catgccgcg gtcagctctc ttccctcagg gctgccaaac agcacgcgga tgccgtccgt    14820
cgagccgctc aagacgcccg ccagctgctg cccggcgtag taggctagtc tgttggggac    14880
tgcaaacccg gggtctgatg ccaggacttc ctgcaggatc acctggctgg tcttgcgcgg    14940
ggccgtgatg tgcgtgcgtg taatctggcc gctggccggg tcgatgttga taaggcgtgc    15000
gtcacgctca aggaattcgt agacccattg catgaggcgg ccatgctgag ggaggaaggc    15060
gacgcgggcg aggggctggc ctggtgatgc cgtgcgaagg gggcatccga gttcatccat    15120
cgcctcgacg acgagggcag tacagagtct gttgcttcca gagagcatga cgccctcggt    15180
cttgtcgact ccgtactcct tcatgagggt gtcggtctgc atcttgacct gcccaaagga    15240
ggctagaatg tcggaagagg ataggcaag ccgagactcg acgggaggtg caatcgctgc     15300
gagcccagca gacttgtgaa tggccactgc cttgagaggc aaaggctgct cctcttcgcc    15360
```

```
agtgggcgtg aggatgcccg tgtctgagct ttcggagccg gcgtcgtcgc tctcagaggc   15420
agactcgctg gacgagttgt cgctcttctc ttcgtcttcg tcatcttctg cctccgcagg   15480
acctgcgttt ggaccaaaga gcgcattcga gacgcactgc acgaacttgc gtaaactggt   15540
tgcttccatc tgctcgttct ggtcgagagt gcacttgaac gcggcctcga cctccttgcc   15600
cagttccatg cccatcagac tatcgatgcc aaagtccgcc atctcggcgt ccagctcgag   15660
ctcgctggca tcaatgccag agactgtagc cacaaggttg cgcacttcct cggtaatatc   15720
tcgccaacca gagggcttgc tggacttgga tttggccttc gtaacgggct tcttctcttt   15780
cttctctttc ttcgaggtct tgctggcctt taccttcgcc ccaggttcag agctagctct   15840
tacctcagga gcagtcttta gagcagcctg aaggctgcc gctggtgttg gtcctggcac    15900
cagcgctttc gttctcagga ccgagtcgtc cttggtcatc cgtgcgagca tcatgctcat   15960
cgacgccttt gcgacacgca tatactgcac gcccagcatg atctccacga gctggccgct   16020
taccgcatca aatacaaaca ggtccgtcat gatcgctttg tcgccttgtc ttgaatggcg   16080
ggcataaaca tgccagacgt ccgcatcctc tctcggcggt gctctaggcg agcgcatgct   16140
cagctcgcag cccgtcgcga tgaacatgtc gctgctcggc aggtccgtca tcaagtttac   16200
ccagacaccg ccgacctggc tgaaactgtc gctgagcggg acatcgagcc atgtatcccc   16260
gcgactggat ctggggagtt gcacacggcc tgcgcactca gttcccttgc cgacgacata   16320
cttgaccccg cggtagacct cgccgtagtc gacgatcgag ctgaatgcac ggtagacatt   16380
gcggccctgc aggacctcga caccttcgtc ggtgtcctga tcgaggctta gacggagaag   16440
atcggtgcat tgcttgtgtg agacgagccg ctcaaagttg gcgaactcgc ggacgtgcgc   16500
ttggtcagaa gaggagcgca tttcgaccgt ggcttcggcg tgaatttctg gtgttttctt   16560
ggtcgcgtca tcatcaaggc tgaagatcct gaccgtccag tttgtccgtc tcttgtttgt   16620
cgccgtcaaa tcgaggtata cgacccggct gggatccttg cagatagggc tgtggttgat   16680
catctctcgg acaacgggct gcaccccatc ttgcctccac cctggctcga gactgaagag   16740
ggcctcgata acgatgtcgc actcgagcgt ccccgggcaa atgggcgcag tctgtgcgat   16800
gacgtgactg agcacgtagc ggttgtactt gtccgcggag gtattaaccc ggaatcgggc   16860
ctgccttgtc tcgtcgtctt gatagccgac gaactcccac accggcagcg tccggggtc    16920 ctgcggcgtg ccggcctgct gaccctgcag ccctgcccca gcgagggagc cgccgttggc   16980
agcgatcaag gcgagagcgg cttccttaac tttctcaacg ggggacttca tcgggagcca   17040
gtggcgggaa gaagtatcga actggtatgg gggtaggagg aggtgggcat actcagcggt   17100
ctggacagca tcatgcgccc agaaggtaac gcggagaccc tgcttccaga gcgcggttgt   17160
ggtatcggcg agagagtcta gggctgtctc gttggtgatg ctgacagcct ggaagtagtg   17220
gctctctgac gacgcctggc cctgagcaat ggcccggccg gccatgacgg tgatggtcga   17280
gctagagccg gcttcgagga agatcgcctg cgggtgtctc tttgcgagac gctgcactgc   17340
gtggttgaag aagacgggtt ggcgcatgtg ctgcgagacg aaggaggcat ctgtcgctct   17400
ggcagaggcc acctcagtgg ctcgctcgac ggggatgagg gggctgttga aggtcagcgt   17460
cttgccgata gagtccagcc cgtcactgat cttgtcaacg agcgaggagt ggaaggcgtt   17520
cgtgacattg agacgcttgc ccttgatcga gccgaattcg ggccgcgaga tcgtctgctg   17580
gacctgatcg acagcactgg tggacccagc aatcgtgaag ctgcgcgggc cattatagca   17640
ggcgatactc gcagagccat cagaccctga agctccgttg gcctcggaca gtagctggtg   17700
```

```
gactagtccc tcatcgcctt ccagagccat catggcgccc cggtcagcgc cccagctgtc    17760
ccggacgagc ttcgcacgcg ccgcaaccaa acggacggtc tcatccaggc tcagggtccc    17820
ggcaacgcat agggccgtga tctctccaaa gctgtggccc actagggcct ggaccttgcc    17880
gttgaggccg cagtctatcc aggtctgagc gcaggcgtac tgcatcgcaa agagcatcgt    17940
ctgaagctta acggtatctt caatgggctc gcggctgaat atatcgggcg cggcgtagat    18000
actgaccagc ccctgcgcct taacaacagt atccaccgca tctagatgct tgcgaaagag    18060
ggcaactgcg tcaaagaggc cccgatccag cccgacaaag cgcgagatct ggccgccgaa    18120
gcagaggatg acgggtcgtt cggccttgac gggggcaatg cccacactcg cggcggcatc    18180
cttgctgctc ggagccgcgg caacggcctg ttcgatcttc tcgtggagtt cggccagcga    18240 gcggcattg aagatgaatc cctgaggcag accgcggttg gattggcgac tgaggttgaa     18300
ggagatgtcc gccagggtcg gctcttcggc gcgcgagcgc aaccagggcc cgagtttggc    18360
acaatacgcc gttattgctc gagtatcgag cccaggaatc caaaaggggt agcgtgctcc    18420
tgcaacagcg tggcttctcg agtgagggcc tcggagatcg ggctgggtga cgatcatgct    18480
tgcattcgac ccgcaagcgc cgtagttgtt cagcaaggcc gtcttcctct cctcctccca    18540
ggcccgtagt cttgtcacaa cctcgatatt gtcgtccgcc ttgacgggga tcttcttgtt    18600
catcgtcttg aaactcgctt gcgggggat gaaccctcg cgcatcatca tgattatctt      18660
gacgagcgca atcgccccgg acgcgccctc tgtatgccca atatggcctt tgacagaccc    18720
aattggcagc ttcttcttgc ggcttggtcc acccagtgca gcaaggatgc tctcgtactc    18780
tgcaggatcg ccgacgggcg ttccggtgcc gtgggcctcg accagcgaga cgtcgttagc    18840
agtgaccttg gcctggcgca tgacgtcctt gaacaggtgc gacagggacg gcgagttcgg    18900
gacgaacagg ggcgtgcagt tctcgttttg gtacacggcg ctcgcggcaa tggttgcaat    18960
aacctggttc ccatcgcgga gggcatcaga cagacgcttg aggtagacga atgcagcgcc    19020
ctcagcgcgg cagtatccat cagcatcgtc gtcaaagggc ttgcactggc cagtaggaga    19080
cacaaagctg cccgccgcga ggttctggaa ccagttcatg tttgtgaccg tattggaccc    19140
gcctgcaagc gcagccgtgc actctccaga gagcaggttc ctgcaggctg tatggatagc    19200
caccgccgag gaggaacacg ccgtatcaaa ggtcatacag gggcccgtcc acccgaaatg    19260
gtggctgact cggccggtaa tgaaactctt gagtgcacca gtcgccgtga acgcgttcgg    19320
gtcgtagcac gagatgttat gctcgtagtc gacaccgcat gaacccaagt agacaccaac    19380
atgcatcttg tcacgcccgt ccggggtata cccgttatgg tcttcgacaa agtacccaga    19440
ctgctcaaca gcctgatacg cagcctgcag gacgatgcga ctctgcggat ccatcgctgc    19500
cgactcccgc ggcgagcgct tgaagaattt gtggtcaaag gcatcgccgt cgcggaagaa    19560
gcacccgtag aatttgcgct tcgggtcggc atctgcgttc tcgcggaaga gcatgtcgtg    19620
catgagtctg tccgggtga tggggatatg ctgcgactgg cccgtcttga gcatggcgac     19680
gaactcatct agatcgtcgg ctccggcggt cttgacggac atgccgacga tggcgatggg    19740
ctcagactgg ggcgagacgg gcatgactgg ctcgacgcgg tggtctgct gctgctgcag     19800 ttgcaggacc ggttgaagct ggggttgtgg gggaggtgat gattgcggtg taagccagaa    19860
tgaaggcttc tcagggtctt tgggaaggtc ttcgtaaaag acctgtcttc ctccgagagt    19920
tctcatcaga gttggaggga cacatctctc caggccaaag gtgaccacgt aagggtctgg    19980
gagggcatcc gccacggccg agaaggtgtc aaaccaccgg cattgctgca ccaggatcga    20040
ccgcaccacc atctcagtca tgttccctga gccagaaacc ggaatgcccg atccctggtt    20100
```

```
gtcgtaagtc tgcagagcga gcttcgacac ctctgcatac tgcagcccag gcagagaggc    20160
gcacagctcc accagggcat tcgtatgttg tttccgatca gcattggggc tatggatctg    20220
gcccttgatt ccaacctcgg ccaccgtgac tcctgcagct ctgaggcgct tcatgagcag    20280
tggcgcaatt gtctctgagg ccgtcaccgt tgcccgcgcc tggtcatacc ggacagcaac    20340
atacgcgtcg tttgacagat ccccaatgat tcggttcatc tcgtcctcct gtttctggcc    20400
gcgccaggcg acggcgtagg acgctgaact gcccttgccg gatgccttgt cccatacttc    20460
ttgcgcgtcg atgagagcgc cgatgagcat cgccagccgg acggcgacgg ctccgtattc    20520
ctcgaacccg gcctggtttc tggcgctagc cactgaaagc gcagcgagca ggccagcgca    20580
gaagcccagg atgaccgtcg gcctgctgcc ggactgtgtc tgctgcacca gctccgcctg    20640
cagatctacg gctggggcac tgccgtccct gatcatctcc agatgccgcc agtactgcgt    20700
cagctggatt aacaccacta acgggccaac caagatgctc ggcagagact cgtcgtcaga    20760
aaccgagagc ccggccgtgt cgaggctgtg ccgaagccat ctgtccagtt cagacaagga    20820
ggtcggcccg tcgatatcgc gggctatatc aggcatcttg gctgccaagg catcccagta    20880
tgttggtagg tcgcgattg tgcgcaaaat ccagtcgcgt tgtggcgatt gtgagagtgg    20940
acgaacgagc ttgtccatgg atgcctttgt gaatgtaccg acatgcgggc caaataggaa    21000
gactgttgag gcctcgtggc ctgacccaga ggcgcttgct cgggtcattg cgggagggta    21060
ggagggtagg agggtagcta ggtagttgat agtgctaagt gctctgccgg tcaactgtg    21120
aatgaatgag gtgtagttga gacacttgag gttgactttc caggcgagcg agcgggtcaa    21180
gagagcagag agaatatgat agactgggtg tctgtagtag atagacaaga tgtatgtctg    21240
tcccttgggg aagtagggct aatacttcta ccttagcaca tgttgcggga agccacgcac    21300
tgaggaaaca ctgacatcgt tggggcactc tgattggagc cggagattaa ggtaagatgg    21360
aatccttctg gctgcagcgc tgtaagccct aagcctggtg gcgcttctgg cggacttttc    21420
ggactacagg actccatcca agactccaga tcgagactca gcttcgctag tccggaagtc    21480
cgctggctga tgcttgtctc agcttttcgt ctcagctttg tcgtcttctg tagagccttt    21540
agggaaaccc caactcagca tatggatgca gggctggttg ggctgattgg gcgttgtctg    21600
gacttgtatc tgggtatggc tgccgtctgg ggatcaaagg taaatggggc agaaattgcc    21660
tgttgaaata gttattgcgg aggccaatgc aatatcccaa gaatttccca aaatgcaagc    21720
tactatagat gctacatagc cagatagagg ttgataatgc cacattttca atatatacac    21780
atacgttttgt gtgtataagt acataacacg actacagtgg ctgatatata tgcagtggac    21840
gcctttagac atgtttccat ttatgattat agagcgatcc tcaggcaagt ggttatacta    21900
gaccttcact acagcacgct catacgcttc tctcgcctgg tcgaccatgc cctgcacatc    21960
gaaatcccaa atcaccctgc tcctcctctc ccattcagcc ttacacttta ccccgtcacc    22020
cccaatgtct tcataccgcc attcgtagag atctcccatc tcccttgagc tcttcacaag    22080
ccactggcta cgctcaatcc tcacatcgct gtaagtcttc agggcaagct caatattaga    22140
cttcttctcc ttgaacgcgg agccgttctg gaccttctca gcaactcag cgagaacaag    22200
cgcgtcctca acgcccatac aggccccagc ccgtggaac ggactggacg cgtgcgcggc    22260
atcaccggcc agcgccaccc ggccagcggc atagtaagga agcgggtggt ccgcctgatc    22320
gaagatggcg tacttgctta gctgttccgg gaagaggctg gcaagttcct tgatatgcgg    22380
gccccagttc tcgaccgccg agagtatctc ctccttcgag ctgggcactg tcatggtgtg    22440
```

```
gccgtgagtc cactcgttcg agtcgtgcgt gaagaggaaa acattataga tctgggcgtt    22500
gtttacctag gcacaatcag cgccttcttg cagaatagat gcggcatgct aggcctggag    22560
gtaaggtagg gtaccggaaa agagacaatg tgcgcgtccg gcccgcaatg tgcgatctgg    22620
acatgcgcct tttcggtccc cagcgcatca attgctgctg gcataggcac agagcgcgg     22680 tagacagctt tgcgagagta cctggcgttt gcagcagggt gttctgcgcc gaggaggact    22740
ctgcgggccg tggagtggac gccatcgcat gcgatcactt cacccaccgc attagcatta    22800
tgaaacgtcc aatacccagc tcagggaaga aaaccaacca atatctgcct cctccacctc    22860
cccgtcctcg aacctcagca ccactttctg gtccccacca tcctcatatg ccaccagcct    22920
cttgccaaac ctcacaaccc tctcgggcag caaccgcgcc atctccgcat gaaaaacacc    22980
cctcaagcaa gcccagtacg ccatattctt ctcctcgatc tcaaacagca cgctcttctc    23040
tggatcctgt gcctcctctt tgcttttcgg gtggaatccg tcccagtacc gcactttatc    23100
atgcggattg cgctgcgcaa ctttggagag agcggataga attgcgggat caaggcgctg    23160
catgcactcg cgggcgattc cggtgaaggc aaatgcggcc ccaatgtcgg gccaagctga    23220
ggcgcgctcg tagattgtca ccttgccgat gttgcggtgg agaagcccca gggctgtcat    23280
aaggccgatg atgccgccgc ctatgatggc gatggagagg ggttcctgtt cctgctcgtg    23340
gtctgccatc ctgtttagag tggccagaag gtgtgtgtgt tatctgcagg atgccggtac    23400
cagtagggct gtatgtaaat acggctgcag tagtttcaag ttctgcttcg atcaagcgtt    23460
agacctagga ttgagcgcgg ctctggcaat ggcggctttt ctcatggtat agcatggcat    23520
agcctgagga tataggtact ccataccgag gtacagtac  atctatacta agaatagtga    23580
ctcccagctt gcctatcccc tgcttatccc ggagtttgca tctccgccag gaagcacgcg    23640
gactgaggcg gagtaattaa cagaaggcat ggcaatgctt actgcgtggg gcttaaaacc    23700
tgacctgacc tggcctggcc tggcctgatc tgatgtgaaa ctggttctcc ttctctatct    23760
ccctctgtca gattgatcgt caaaacctaa ccctaagtca aatttaaacg ccacgcaccg    23820
gatactctca actctgaata cggccttgat cagccaatca cagaagattg cgagctgaca    23880
gttcgtattg attactttaa agcctggcat agacgatctg ccattgattt gcaattctcc    23940
ggcccagttg cataatgccg cgctcgata  tcgcctcggc cccggccgca gtctatcaac    24000
agcaactcca tctcccacgc atcctctgcc tccacggtgg cggcaccaac gcccgaattt    24060
ttaccgcgca atgccgcgct ctgcgaagac agctgacaga cagctatcgt ctcgttttg    24120 ccgacgcgcc atttctctcg tccgccgggc cggatgtgac gtctgtctat ggcgaatggg    24180
gcccgtttag gagctgggtt cctgttcctg cgggcgtgga tatcagtgca tgggccgctg    24240
ccggtgccgc tagtaggatc gatatcgacg tggaggcgat cgatgagtgc atcgcagctg    24300
ccatagcgca ggatgaccgg gccggcgcga cagggattg  ggtcggcctg ctgggggttca   24360 gtcagggggc gagggtcgct gccagtctgt tgtaccggca gcagaaacag cagcgcatgg    24420
gtctgaccag ttggagtagg ggtagggatc gcaagcgagg tgcgacctct agcaccaatt    24480
atcgcttcgc tgtcttatt  gccggccgcg gaccgctcct ggacctaggc tttgggtctg    24540
gctctttagc cggctcgagt gctgcttctt cgtctgcgtc tgcgtctgta tctggatctg    24600
aatctgcggg tgaagaggaa gaggacgggc acctcttaag catcccaacc atacacgtcc    24660
acgggctgcg agatccaggc ctcgagatgc accgggatct agtccggtct tgccggccct    24720
cgtctgtgag gattgtcgag tgggaaggcg cccaccggat gccaataacg acgaaagatg    24780
tgggagcggt agtagcggag cttcgacact tggcgataag ccggaaatat gaaagcttga    24840
```

```
gatgttgaat tcagcctatt gagattacag ccacggaagt aatcctgtaa ggatcaggat    24900
gcaactccat gcaaggcgct aaggatcagg atccttttct tcaggattgt ggcaacggcg    24960
ccagcggcca gcgggcgcta tcgcgtcggt ggtgatggcg ttatttggat tcggaggat    25020 agaatccggt cagcctaatc aagccaactc cgtcggactt cggcgggact gtccggtcag    25080
ttagagctag agaaggaagg aggtagagtc ccagatagac aaaagacttg gctgctatat    25140
atcttattat tcaatcctca atcccgctag ctgtcaatag aatgatcctc agccgcactt    25200
gaagtcttgt ctacatcccg aatccaggcg caatggctga gacggattcc tcccacaccc    25260
gtgggcccgt agactcaatc cagaagaacg acgcctcaag cgacgatgcc gaggcagaga    25320
ccaagatcca gtatccctcg ggctggaggg tcacgatgat cctgacttcg gtgacattgg    25380
cgtactttct tttctttctt gacctagccg tgctgtcgac cgcgactcct gccattacct    25440
cgcagtttga ctcgttagtc gatgttggat ggtgcgttat gtccctact gcgctcttcc    25500 ctaggtacat atgtgctgga tgctaaaacc caccttgccg gcaggtatgg aggcgcctac    25560
cagcttggaa gcgcagcgtt ccagcccctg acgggcaaaa tctacagcca gttctcgatc    25620
aaggtagttc tccctcaacc atttgacgca gttggaggct tgggtgctca tgaatagcag    25680
tggacattcc ttgtcttctt cattgtcttt gaactcggct ctgtcctgtg cgccgcagca    25740
cgcaactcgc ccatgttcat cgttggtcgg gtcattgcag gcgtagggtc ggccggcatg    25800
tccaacggcg ccgtaaccac aatctccgcg gtcctgccaa cgcagaaaca ggcgctcttc    25860
atgggcctga acatgggtat gggccagctc ggtcttgcga cgggaccgat tatcggaggc    25920
gcgttcacaa cgaacgtttc gtggcggtgg tgttcgtccc cctgctccct cctttcaaat    25980
cccacctact aggcgaccat gcagagaaga tgcaccagct gatgacgacg caggcttcta    26040
catcaacctc cccctcggcg ccgttgtcgg cggcttcctc ctcttcaaca cgatccccga    26100
gccgaaacca aaggcccctc cgttgcagat cctcggcacc gcaatcaggt ccctcgatct    26160
gccgggattc atgctaatct gccctgccgt ggttatgttc ctcctgggtc tgcaattcgg    26220
gggcaatgag caccctggg acagctccgt cgtgatcggc ctcattgtcg gaggaggtgc    26280
caccttcggt gtcttcctcg tgcaccagtg gtggcgtggc gatgaggcaa tggtcccgtt    26340
tgccctcttg aagcacaagg ttatctggtc tgcggccatg accatgttct tctccctgtc    26400
cagtgtgctc gtcgcggact tctatatcgc gatatacttc caggctatcc gggacgactc    26460
gccactcatg agtggtgtgc acatgttgcc catcacccta ggtctggtct tgtttactgt    26520
tgtttcaggg gcgctgagta tggtcttttc tcctgcgtgc ttgaacaatg gctaaccgtc    26580
cagtctccgt actgggctac tacctgcct tccttcttgc aggcggcgcc atctccgccg    26640
tcggctacgc cctcctctcg acgctgagcc cgaccacctc tgtcgcgaaa tgggtgggat    26700
accagatcct ctacggcgta gccagtggct gcaccaccgc cgctgtatgt cttcagttt   26760 acataccccc ggaacccttt gccttcacct ttaccaggta gaatgccgct gacaaggccg    26820
aatgcagccc tacgtcgcaa tccagaacct cgttcccgcg ccccaaatcc cgcaagcaat    26880
ggcaattatc atcttttggc agaacattgg cgccgccata tctctcattg cggcaaacgc    26940
catcttctcc aactccctcc gcgaccagct agccagcgc gcgagtcaga tcaccgtctc    27000
cccgggcgcg attgttgcgg ccggtgtccg gtccatccgg gacctcgtct ccggctctgc    27060
gcttgcggct gttctggagg cgtatgcgga ggccatcgac agggtcatgt acttgggcat    27120
cgcggttagc gtgatggtta ttgtgttctc gcctggtcta gggtggaaag atattcggaa    27180
```

```
gacaaaagat ctgcaagctc taactagcga tggagcgcag ggtgaagcga cggagaagga    27240
gactgttccg gttgccctgg gttaaggcat cgtctacaag cagatgctag cacacattt    27300 cttcctgccg ctaaaaattg ggtaatgcag agccacctcg cttttttttt ttcgaacatt    27360
ttccatcttg tggtatttct gggttcattt cgctccatat aacgaagatt ggccttggta    27420
cgggctaggg ttcgcgggtg ggatagttat agaatgagaa ataatacttt tatatgtaac    27480
aatttcaact tctcaagatg aatataccat tcggatagag cagcttctga gtatcgacag    27540
acttaggtag gcttatgggt atgctctgtt gaatatcttg tagatgtgac aggcaataga    27600
ttgttagatt atagcctaca atccacagct cagctcagca cgagtttgat tttttcatta    27660
taattggaat aagcactgag ctcagaatga aaccaataga ttactagggc tatgcgtaga    27720
cgttgaacgg gatccatcac caagcgcagt attagggcac cttttgtcgt gggtatatag    27780
caactaaaca cattctcttc ggtcctgttc ggccctcttc ggcctccatt agccagtcaa    27840
aataaacagt aaccagctac aaagtgacaa caagcttctt tcccgaaacc cccttcgct    27900 ggatatccag cgcctcctgg atcttctcga gccccttcc dacaacgagc ggcggcggtg    27960
caggcacaaa ctgccctctc tcgagcgctt ggggcagaaa gtccatgtaa acccggctga    28020
ccacactgtc cgggtccacc agcccgtcaa caaggataaa cttggcgatg acgcctgtgc    28080
ggcgctgccg gatgctcgat ttcaccattc ctcccagcat cccaatgagg taagtcccct    28140
tgccgacgaa ggtggttagc ttctcaggcg ggatgatctc accggcgacg gcgatgaact    28200
ttctcgtcag cgcaggatca tgcttgcgca tcacgagggt gcaggcttcc accgcaccgg    28260
cgccaatggt atatgcgccg acgagctctc tgcccttgag ggcggataag agatccttgg    28320
ccaggaactt gctccggtag tcaaagacgt ggctcgcccc gagccccttg acatagtcga    28380
agttcttggg cgacgaggtc gaaaggacct cgtagcctgc tgcgacagcg agctggatcg    28440
cattgctgcc aacgctgctg gcgccgcccg tgatgatcac cgcgcgcggg gaccccgacc    28500
tgccccgctg cacctctccc ctgcccttt ccgcaagctg cggcatatcg agggccagat    28560
agtccttgtg gaagagacca aatgcggccg tacccagccc gagtccgagc acagatgcct    28620
gcgcatcgct gatcccagcg ggcaccggcg tgagcatatg cactcgcagg acggtataca    28680
gctggaaccc accctcggcc gggtcgttca cctctttcgc aatcgccgtc gcgcttccac    28740
agacgcggtc gcccacggcg aacgggtga cgcccggtcc gacctcgacg acctcgcccg    28800
caacatcagt cccaaagatg aacgggtagt ggatataccc ggccagcgcg ggcccgatga    28860
actgcaagac ccagtcgaac gggttgatag ctacggcgcc gttcttgacg accacctggc    28920
cagggccagg gcgcgtgtag ggggcgtcgc cgactttgaa ggggatcacc ttttttggcgg    28980 ggatccacgc ggcgcggttt ttgggttggg ggtcccgtt gccgttggta gccggcgctg    29040
ctgcggttgc tgcggttgta tcttgagttg ccataacgag gtccaggtga cggtaacgtg    29100
gttcagtgca gttccaatgt atggtagcgt tgtaagctga cacggcgacg gctgcgagag    29160
gggttggggg gacggaacca gctgaaacag gactggcgaa agaaagctgc tgtgttatat    29220
gtaggcagag ctaaagaacc ttgtggagcg acagaaccaa agtcagtctg gccatgggc    29280 tatcttccat aattttggga gctcgaggtc cggattgccc gttaatactc cgccagacta    29340
gggcaagata gggctacgcg gagttttagg tggacggatt tcaaccctcc gaagtccgct    29400
cgaacttttg tcgacgagat taagccacta gcctaaagga atcagacctt taattcctca    29460
ggccgagtcg ggatcattga aggcgagaat gaggtgaggt tgtcagccac atcgtcagct    29520
caatccttta gaccacgttc ttatctcgcg gccgttctcc aatcgacggg cccgctggcc    29580
```

```
cccagcgtgc agattacacc gtctcgctcc gactgcagga tctggcgtct tccatgcgcg   29640
gacgtttcgg acggcgatga ctgtctgagt ggttggcagg gatgcacccc tacctacccc   29700
tgatcgaagc taatggtaat gcagaatacg aggttggtta gactaagcgc ttctgcagct   29760
gcagcgcatg gaagctgttc tgtctggtgg agagactaag cagtgctctg tgctcctctg   29820
tgctgctctg cattgcactg cactgtactg cattgtactg cattgctgtt ctgcacggat   29880
cattcatcca tctaccatgg atccactact aacctcgctt actctagtcg atctggtcaa   29940
gacgaccaag acctcggaga attagatggc aaccaagga tagatgcgag atcaactgat   30000
ccaccgctgg caaacttagt tgtgaatgtc gcgaacgcaa ataccacgga gatggcatgc   30060
agccgcaccc gaaatggaat gctgtaggcc taatcaagct catcgattct cgcccccaaa   30120
tctgggctgc gcggtcctgc aggtgagacg atcctggag gctccatgct ggctggctct   30180
gcctcctcgt ggacgagggt acgatggcag ccagtctgct ggcgtgctgg cgccgctggt   30240
agcacggcca cgagcctatt gattgcacgg gcaaacgttc gtaactcgct cgtaacctat   30300
aattacgata gctaaccaca tcctggttct ctctcataag aatgaatggc attcccgcct   30360
tgatccgtca gcattgtcaa cccggataga ccagtgcctc gtcattcaac atcacagatc   30420
cagagactac aaagaccagc aatcatggcg tgtcccacca gacgaggacg acagcagccc   30480
ggctttgcat gcgaggagtg tcgccgccgc aaagcgcgct gtgatcgcgt gcgtccgaaa   30540
tgcgggttct gcactgagaa tgagctgcag tgtgtgttcg ttgacaagag gcagcagagg   30600
ggtccgatca aagggcagat cacctcgatg cagtcgcagc tgggtaggtg tttgtcttgt   30660
ctcattgtat ctcgtctcgt ctgcgctttt gtgattatgg ggctgccatg tttccggtcc   30720
ggacacaggc atctgcaagg cccgccgctg tgctcccccg atctgcaggg accaatgcag   30780
ctggttctgg agcttgtgct gtgctgcttc cctgtctttc cacatggtcg agtcgagcga   30840
gctagctaac atgggatgcc tcatgctttc agcaacgctt cgatggcagc ttgatcgata   30900
cctgcgacat cgacctcccc cgtccataac catggccggc gagctcgatg agccaccagc   30960
ggatatccag acgatgctgg atgactttga tgtacaggtc gccgcgctga agcaggatgc   31020
cacggcaacc accacaatgt cgacgtcgac agctctcatg cctgccccag ccatctcatc   31080
taaagatgct gctcctgctg gtgctggttt atcgtggcct gacccaacct ggctggatcg   31140
ccagtggcag gatgtcagca gtaccagcct cgtccctcca tcagacctga cagtctcgtc   31200
ggccactacc ctaaccgacc ctctcagctt cgaccttttg aacgagactc ctcctcctcc   31260
ttctacgacg acaacaacgt cgacgacgag gcgagactca tgtactaagg tcatgttaac   31320
tgacctcatc cgggctgaat tgtacactac ctaactgatt tgtctaccat gacacctgac   31380
tgacaatgtg cagagaccaa ctctacttcg accgggtcca cgccttctgc cccatcatcc   31440
accggcgacg gtactttgcg cgggtcgccc gagatagcca taccccagca caggcatgtc   31500
tgcagttcgc catgcgaacg ctcgcagcgg caatgtctgc tcactgccat cttagcgagc   31560
atctctatgc cgagaccaag gccctcttgg agacgcacag ccagacgccc gccacaccgc   31620
gagacaaggt cccgctcgag cacatccagg cctggctgtt gttaagccac tacgagctgc   31680
tgcggatcgg cgtgcaccag gctatgctca cggctggccg ggccttcgt tcgtgcaga   31740 tggcacgact gtcagagctg gatgccgggt cagatcgaca gctctcgccg ccgtcttcgt   31800
cgccgccgtc ttcgctaacc ctatctcctt cggggagaa tgctgagaac ttcgtcgacg   31860
ccgaagaagg ccggcggacg ttctggcttg cttattgctt tgatcgtttg ctttgcttgc   31920
```

```
agaatgagtg gccgttaacg ttacaagaag agatggtacg tcgcgcttct tttattctat    31980
ttacctcaga atttatattc agttattttt tattctaacc ctgctagata ttaacccgcc    32040
tcccctccct cgaacacaac taccagaaca atctccccgc acgcacgccc tttctcactg    32100
aagccatggc ccagaccggg cagagcacaa tgtccccgtt tgccgaatgc attatcatgg    32160
ccacccttca cggccgatgt atgacgcacc gccgcttcta cgcaaacagc aactcgactg    32220
cgtccggctc cgagttcgag tctggcgccg cgacgcgaga cttctgtatc cgccagaatt    32280
ggctgtcgaa tgcagtggac cggcgagtcc agatgctaca gcaggtctcc tcgcccgctg    32340
ttgacagcga cccgatgctg ctcttcacgc agacgctcgg ctaccgcgcg accatgcacc    32400
tgagcgatac cgtccagcaa gtctcctggc gggctctcgc cagctcgccc gttgaccagc    32460
agctactgag cccgggcgcg acgatgtcgc tgtcggccgc cgcgtaccac cagatggcca    32520
gccacgcagc cggcgagatc gtccgcctgg cgaaggccgt cccctcgctg agtccgttca    32580
aggcgcaccc gttcctaccc gatacgttgg cgtgcgccgc cacgttcctc tcgacgggca    32640
gtcccgatcc cacgggcggc gaggggtgc agcatctgct acgagtgtta agcgagctgc    32700
gcgatacaca cagcctggcg cgggattatt tgcaggggtt gtcggtgcag acgcaggacg    32760
aagatcatag acaggatacg aggtggtatt gtacatagag actgattagc tggccgatag    32820
caatgccgcc aataaaactg atagagatgc ggcacgatcc gacagttagt cttggggc     32878
```

<210> SEQ ID NO 8
<211> LENGTH: 8541
<212> TYPE: DNA
<213> ORGANISM: Aspergillus nidulans

<400> SEQUENCE: 8

```
tactcaatac aaccctaccc accaacccgg cacctaccgc ctcaccgtgt gtcccaacac      60
cagcaccacc actactgtgc acagtcaacg aacaatgaca ctcccagtcc tcatcatcgg     120
tgccggcctc tcaggtctca caaccgcgcg tcttctcaca aacgcccaca ttccctgcat     180
cgtcttcgaa gcctcccctc cctcccgcac tcaaggctac gccatctccc tccgcgactg     240
gggcttcaac gccctcctca gggccctggg aaacctcccc ctatccagcc tcacccgggc     300
cgtcgcacct gatcgccaca ttggcggctg gggctggctt gaccagtcat ggcggaataa     360
ccagaccggg gagataatca tgatgccacc caaagagtca aaagagaaac cgaccatact     420
gcgcgctaat cgcaatgcgc ttaggcagtg gattgcggat gcaggtgtgg gggaagacga     480
ggagattgat gtcaggtatg gacatcggct tgtcggcgtg cagctgttga gagagggtgg     540
agatggaaat gtggtaacag ccgagttcgc aaacggcgcc acatacaccg gttcccttct     600
gatcgctgcg gacggggtac actccacagt acggacactg atccttcccg ctgtgaagcc     660
ggagatttta cccgtcctcg tctaccatgg cgacttcaag ctcagtcgcg aggaatacga     720
gtgtgtgatc cggccgcatg caggcgagtc cacgatcgtc gcgggcgtgg gcgacgggtt     780
taacacgccg ctgactgtct gcgacgtcac gtcaacgaca gtgcacatgg actggacgta     840
ctcgcggccc agcattggtg acaacgaccc tctgtataat cccaatatta cgtcggagga     900
agctaaagtc attcccgagg ctttgatcga ggaaatcaat gcgaaaaagc tgggagaacc     960
atggtcgctg ttcctgaatg ggggaggcgat gcgcaggcat cgggtgttca attggctgac    1020
gcgatgtgtt tcgatggaaa ggagtgacgt gaattcctgt acgggcaaag gggtcgtctt    1080
cgtcggagac tcgtggcatg ccatgccaat ctttggaggc gagggtggaa accatgcaat    1140
attcgatggg attgagttgg cgaagatgtt ggaagtggct tggggacgtt ccaaggagga    1200
```

```
tgtgcaggca gcgatcggga agtactatga caagtcttgg agacggtgta atgatgctgt   1260
gcgaaggtca aagcagaggt tctatcagct tcatcgacct attagcgagt ggattgagat   1320
tgcggagaag cagaagatgc gtgcgtaatt tgctcgttca ttaattaggg tttgatcttg   1380
gtacagtagg gacagaatcc ttttctcggt acaaaagaag aattcaatct tcagcgtaaa   1440
taagagcaaa gcaatctaaa tagtttacta catggcgaac aacatctaat cagttaattc   1500
ggccggcgcg acctgacgta ccatcgcctt tttgcagcac tccccggctc aaacccgact   1560
tttcgatcct cagctagctt ccacagaacc tggctcaaga acggcgcaag agctttctca   1620
acctcgtctg taatctcccc atacattgct aggatgattt cgtgtagcgt caagccaccc   1680 cgccccgcc cctgcccagc tgctcggctc tcctcgagta tcgcgtaaac ctgctgcacg   1740
cggaactctc tgtgcttgat gtactctcgc attttatccg gaaggtcatc gatcactgcc   1800
ccgtgcgctg ggtagcccaa tggaaggttc aggttagcca tctgtaccat gctattcatg   1860
tattgtccca agtcttccac caccgagtat ccatggccga gcacattgtc gcctgtgaag   1920
agggcgttct cttcttcaaa gagaaagcac atatggtcgg cagcgtggcc ggggtatga    1980 acggcgcgga gagtggcgcc ttcaacgcga aagacctggc cgtcgagaat atcctttgt    2040 ccggcatcgg gtcggttttt gtatatgcga gaggatagcg ctggattgta cgctatcagg   2100
tccggcacac cacctgtatg atcgccatgc cagtgtgtaa ggagtacata ggagatgtct   2160
atatccctct cttcgaggac tttggcgata tcacggatcc acgagggcat tccctggagc   2220
agacagggag tgtgagccac gtcgccctcc atgcaaggtc ggtaaacagt cacgacgtac   2280
ctgaccagta tcaactagga tacgggatct gcctgttcca acgagatatg tatttgtccc   2340
ctgcagtctc attggtccag catttccgcc caaaactcgg atgacccgtt cagtgatatc   2400
cgtcaccaca ggcagagtag ggatagtgtt ttctctgccg gaaaggtact cattccagaa   2460
gtcctgggca aatggtattc tgaaggccat gttggtgact gaagcgccat ggggatgccg   2520
agcgaaggaa tgtgcgtcga gtctgtaata tcggcagagg ttctgctctt cggccctatc   2580
gccctatgac gggattttaa tcgggcatat tttatgatcc acagtagtat agaaataaga   2640
cccgaacgag ataaaatgca ggtccgggcc agctcatgcc ggaggctcga gcagtcattt   2700
ctccaaaagt ccccgtatgg cattttacac agggtcccat cacaggatgg taattccatc   2760
gcaatttgcg aaacttcccg tgcgggcatt ttgccctcat tgaacaatag catcaaaacc   2820
ccgggtgtat cagtcgattc tgtgtgcgaa tgattgcttg ggaacgctct gctctgattt   2880
gaacgtaatg agcgcttgag ctcgaccagc agagaagtaa caatgaaaga caatacgcat   2940
agcacaaccc taatcttctt tggaaatgag tttcccaacg atgatctcaa agggctgttc   3000
cgctgcctgc tgcggcttag caaggaccgc aggtttcgtc aactggctgc ctttctcgag   3060
gagtcgactt tggtcctcaa gaaagaagtc gctgcacttc cacagcccct gagggatctc   3120
gtaccgcatt tcacacggt attgcccctc gcggagcttg tgactttcg tcaaggtcct    3180 ctaggggctg ctatggagag tgcactcttg actgtgctgg aacttggcat gttcataggg   3240
taaaataccc gttgtttagt tgcggacaaa gagagctgat agaaaccatt aggcattatg   3300
aagctgaagg ccgtgactgg aatttgcttg agcacaacac cacccttgct ggcttgagta   3360 tcggccttt agctgctgct ggtgtggccc tatccaccaa cttagcagag gtcgcccaga    3420
atggagcaga gtgcgttcgc gtgtcttttc gactaggagt atacgtcagc gagatctcgc   3480
ggaaactcga ggcgcctcaa gcagacggta cattactgag ctgggctcat gttgttaccg   3540
```

```
gagagacaaa gtccgccatc caagacgagc tgtcaaaata caactcagaa tcaggcacgc    3600
cagagcttct taaagtcttc attagcgctg ccgataagac ttccgtcagt gtaagcgggc    3660
cgccatcacg catgaaagcc tgcttcagca gttcgcacct cttgcggtat tccaagtctt    3720
tcgccctccc agtatacgac ggtctatgcc atgcgtcgca tctgtataac gaggactcga    3780
tcaacacagt tatcaacagt gcagagtcag tcattcctgt ctctcgtccg gtgcagcttt    3840
cgcttcattc ttccaatact ggccagcctt tcccagcggc tacagctcac gagctgttcc    3900
aagccatcgg caaggagctg ctgactggta ccatctacct tgacaacatc attgacggaa    3960
tcataaaacg cattgaaggg ttcaacccga gtgatcttca agtcgagact tttcgcacgt    4020
caatagtgtt taagagcgta cgagcggctc ttgagggtga gttccctgac ttggagatca    4080
agataaccga cttgatccct tgggctttca gagactatgg tcctcgtctg ccgcgttctt    4140
tcgcccattc gaagctggct gttgtcggta tggcctgtcg tatgccgggt ggtggcaatg    4200
ataccgagct tttctgggag attctggagc agggacgtga cgttcacaca acagtgccgg    4260
cagatcgttt cgacttgtcg actcattacg atcctagtgg caaaacagat aatgctgcaa    4320
cgactcccta cggtaacttt gttgataaac cgggattgtt cgatgctggg tttttcaaca    4380
tgtcgccgaa agaggtacgt cgccccatcc agaccggaac tcgatgcaaa aatacaggta    4440
tgctgacaga tgcaggctga acaaacagac cctatgcagc gactggcgct cgtcactgca    4500
tatgaagctc tggagatggc cggtgtagtc cccggtcgaa ctgcatcgtc gaaccccaaa    4560
cgcattggta cttactacgg gcaggcgagt gacgactggc gagaactgaa tgcctcgcag    4620
aacattggca catacgcagt gacgggtggt gtacgtgcct ttggcaacgg gcgcatcaac    4680
tactatttca gtttcctgg gccctcattc aacgtcgaca cggcctgttc tagcgggctg    4740
gctgccgtcc aggtcgcatg ctcggctctt tgggcggggg aggcggatac agttcttgct    4800
gggggcctga atatcatcac cgaccccgac aactatgcag gtttggggtg tggtcacttc    4860
ctctccaaaa cagggcagtg caaggtttgg gacgaaactg cggacggcta ctgtcgtgct    4920
gatgggatcg gctccgtcgt catcaaacgt ttggaggatg ctgaggcaga taacgataat    4980
atcatcgccg tcgtactctc tgcagctacg aatcactcag ccgaggctat ctcgatcacc    5040
catccccacg cagggaatca gaaagacaat taccgccagg ttatcgatat ggctgccgtt    5100
aacccgttgg atgtgagcta tattgagctt catggaacag ggacccaggc cggtgacgcc    5160
gtggagtctg aatctgtgct cgatgtattc gcgcctcgat cgccgccacg acgtcccgat    5220
cagttgttac agctgggtgc ggtcaaaagc aatatcgggc acggtgaagc ggcagcaggt    5280
attgcgtcgt ttctgaaagt gctgttaatg taccagaaga acatgatccc cgcgcacatt    5340
ggtattcata cagttattaa cccgactatt cccaaagatc ttgaacagcg tcgggtccgg    5400
ttgactcaga cgaacacgcc ttggccgcgt ctaccgggta agaaacggat tgcaatggtc    5460
aactcctttg gagctcatgg tggaaacacg actgttctgt tggaggatgc gcctgagcgt    5520
aacaaggatg ttgcccgaga gaaccgctcg actcataccg tcgtcatatc ggccaaatct    5580
aagaagtctc tccaagccaa tattgcaaac ctagcgctgc atctggagga gaatcctgac    5640
atcgatctgg gcgatttgtc atacacaacc tgcgcacgtc gcatccatta cactctcgc    5700 gttggcttcg cggtctcgag catcgccggg ctaaaggaag ccctacgcaa ggctggcgag    5760
aaagaggctc ttgctgaggt ccgtccaaca ccagggggacg ttcctccggt cgttttcgcc    5820
ttcaccggcc agggagcctt ctaccagggc attgcccggg agctattcga gtcattctct    5880
tacttccgtg acgaagtatt gcaacttgac cacattgtcc aacggcttgg tttccagtcc    5940
```

```
attgtgcccg tgattgacgg aagtattggc gagaatccat cagcaaccgt gtcgcagctt    6000
agcattgtcg tgatcgagat tgcgcttgcg catctctgga ctctactgct cggcatgcaa    6060
cctagcgccg tcatcggcca cagtctaggc gagtatgccg cgctggtcgt tgcgggcgtc    6120
ctatctaccg cggacggtat cttcctcgcc gggcgacgtg cccagttgat tgaaaagtgt    6180
tgtacagctg gcagccacgc gatgttgtcg gttcgtgcat cagtatcgga gatcagcaag    6240
cttctaggca atgccaagta cgagatatcc tgccagaata ctctcaacga tacagttatt    6300
ggcggcacca aggcaaatct ggacgctgcc cgtcaagttc tcgagtctag cagcattaag    6360
tgtgtgccgg tagacgtgcc cttttgcattt cacaccgagc aggtcgaccc agtactagac    6420
caactaaccc gagtcgctga gactgtgcac ttcaaggccc ccagtattcc aatcatatcg    6480
ccattgttga gaagcgtggt gtttgacggc aagactatca attccagtta cttgattaga    6540
gccacacgcg agcccgtcca ctttgctggt gccatagagg ctgcgcagga tctcggcatg    6600
gtgaatgata aaacagtatg ggtcgatgtt ggaccgcatc ctatttgcgc tagctttgtg    6660
cgcagtttga tccccaaggc gcgtgtcgct tcgtcatgcc ggagaaatga ggacaactat    6720
gcaacgatgg cgaagaacct tgtagctctg cacctggctg gttgcactcc tgtctgggac    6780
gagtatttcc gggctaatga aaaggcgtac aacctgctta ctctgcccaa atacgcctgg    6840
aacgatgtca actactggat ccaatatatc ggcacatgga cgttggataa ggctcatctg    6900
aagtatactg gaacaaatgg accaccgcag gttaagccgt cgtcttcggc attgcgcaca    6960
tctctgatcc acgaaatcat cgaagagacc attggcgaag aaacggccac gctcaaaacc    7020
gtctctgact tgcaacaccc ggaattcctc gaggctgttc atggtcatcg gatgaataat    7080
tgtggcgtag caacatcagt aggttcagct gtttttatcct tttagttaag taaactaacg    7140
atagccctca gtcaatctgg accgacatgt cgttgacggt tggcgaatat ctgtataaca    7200
aactagcacc cggatcaaag gtacacatga atgtgggcga gcttgaggtc ttgcacgcaa    7260
ctgtggccaa tcctgccaaa aactgcaccc agaacctgta ccttgacgcc catctagact    7320
tacgcacgca aagatgtca cttgcctggt ttaatgtcga tcctgcaact gggagcaagg    7380
cagccgaatc ttatgctact ggatctgtgc gtttcgaggc tgatgcggag aagtggaagt    7440
ctgaatggga gcgtctgaca cacttggtgc tcggccgaat cgagacatta gagagcatgg    7500
ccaaggacgg acaagcaagc cagttgtcca aggcgttatc ctatgcccta ttcaagaacg    7560
tggttgatta cgctgaccat tatcgcggca tggaacgggt ggtaatgcac gactatgaag    7620
cgttctgcga tatcaagctc acgccagaac gccgaggtat gttccatacg ccgccgcact    7680
ggatcgatag tgtttcccat cttgctggtc ttatcatgaa cgggagcgat gcctccaaca    7740
cccgcgatta cttcttcgtc acaccaggct atgagagttt ccgtttgctg gcaaaactgg    7800
accctgacgt caagtatcag agctatgtgc gcatgttccc actgccagag gccaacatgt    7860
acggaggcga tttgtacatt ttgcaggata atcagatcat tggcatggtt ggtcatttca    7920
agttcagacg agtaccacgc ctgctcatgg atcgattctt ttcggctgaa gcagcctcaa    7980
aacaatcagt ggcggcttct gcgtcttctg cgcctaagac tgcaaccaaa catgccccgc    8040
tgccggcctc caaaccggcc caagcaccag ctgaaccaac ccctcgtcg cttcccacag    8100 ttcaagcaca gaataccagc ccccctcaac aagtaacgcc gtcgaaaccc gcaatgaacg    8160
gcgtgaaaac gcctgaagag gagaagcccg gcaaagcaga tgccgaaggt ccgaacggaa    8220
cgacctctca accagaagcg accggcgtag ttggccaatg cctgcaattg atcgctaacg    8280
```

```
agacaggaca aagcgtgaat gagttgacac cggatgccac ttttgtgcag ctaggagttg    8340
actcgctcat gtcacttgtg ctctcagaga aattccgggc cgagcttggt ttggaggtca    8400
agagctcgct tttcctagag tgcccgacag ttggagatat gatggactgg ttagagcagt    8460
actgttagag aaagatgctt ggaaatcagt atagctttct gtagtttcaa tgaagaatga    8520
gtattagaat gatctccata c                                              8541

<210> SEQ ID NO 9
<211> LENGTH: 20167
<212> TYPE: DNA
<213> ORGANISM: Aspergillus nidulans

<400> SEQUENCE: 9
aaagtcctaa acctcttgta ctttctcctg gaatggtgtt gtccgtatac ttgggtgcca      60
ccaacaacca acaacagcta tgactgtgag ccctaccaca gacgctatgg gcacctctga     120
agaaacacga tccaaacaaa ccaagggtc aaacgacgat attttgagcg cgaagatagc      180
tggaagagtt gctcgccccg tttatcactg cacaagcgca cggctccatg acctagccta     240
cgacccatgg cccattacca ccatcgatac ccacggtctc agttcactga aggctccatc     300
aacgcacacc cggatcttga ttattggcgc aggattcggc ggcctcctct ttgcggtgcg     360
cctcctccaa gccggattct cccgtgacga tctcctcctc gtggattcgg cgggtgggtt     420
tggcgggacg tggtactgga atcgctatcc cggcctaatg tgcgatatag agagttacat     480
ctacatgccc ctacttgaag agacgggcca catgcccagc cggaagtatg tacccggtga     540
agagttgcgt acccacgcgg aggggatagc ggcaaaatgg gagctggagc agcgggcgct     600
attccgtaca actatcagaa ctctcgagtg ggatgaaggt gggaatcaat ggattgctca     660
cgctgagcag ttaggtgtat ttacagacgc aaaacagggg ggaaatggtg gtggtggacc     720
tttaacattt accgcaactt tgccatcat tgcgagtggg acactcagca agcccaaggt     780
ccccaattta catggtgtcg atgacttcca aggacatatc ttccatactg cccgatggga     840
ttacgactat accggcggtt cgccggctaa ccctgccatg caccggttac aagggaaacg     900
ggtaggagta attgggactg gctcaacggc tgttcaggtg attccacagc ttgctcgctg     960
gtccaaggaa ttaatcgtat ttcaacggac accggctgcc gtgggcttgc agaaaaatca    1020
ggttactgat cccgtgtggt ggaagggcaa cattctgaag gctgggtcgg atggcagag     1080 gaaacgatcg gagaatttca acgcgttcat ttccatctcg aacccacccct gcatggagaa    1140 tctagtaaat gatggttgga cgagttcgcc atcattctct gccgcaatcg gtggagcact    1200
gaacatgcag ccgatttcc tggacctagt caaagctatt gatcgaccta ggctggaagc     1260
tgcccaggac catatcagat caactgttcg ggatgatacc accgcagagg cccttatcaa    1320
tttaaaccac ggatggtgca agagaccctg cttccaccag ggatatttg agacatacaa     1380 tctgccgcat gtgaggctga tcaaaaccga cgccgccggc gttacagggc taagtccaaa    1440
gggaatattg gttggggaca ccctctacga agttgatttg gttgttttag ctacaggcta    1500
cgatctgggc agcttgtgtc cggccgatcg ggcgcaaatc caggttctag gctcagaggg    1560
agtggccatg aaggagaaat gggctggcgg tcctacaacg ctgcatgggg taatgactcg    1620
tggatttcca aatcttttt tccccggtac ctcgcaggct ggtgttaccg cgaaccaatc    1680
ttatatgttc gatcgtgccg cagaaacatgt ggcctatatc attcagaact ccacactgga    1740
ggcaggaggc tatattgaca agatccgtat cgagcccacg gcggaaggag aaaagcactg    1800
gacgacgcag tcagtcgcac ggataagtgc attcgcagcc acaacagcgt gtggcactgg    1860
```

```
ggattataca atttcgaacc gttacagaag cagcgatgtt gacacgatgg caaggcatat   1920
gccgtgggga gaaggtatgg caagttatgt gaaaattcta gaggcctgga gagaaagtgg   1980
gactatggaa ggtttggata tcaggtacca ctcatctgag ggttccaggt aggagttatc   2040
agcacgggcg aggagaaggg ggctattgct ctaaaaatat tctctgtatg cccgagttcc   2100
atgtttagca gactcattaa gtcgacaagt aatctagcgc attcattgtg tacatctctc   2160
cagcatttca ctcttctggg gggtagtcta acactttcaa tgaatagtag attcaccttg   2220
gttagcacag gaattggata gactcggtcg tattagcata gtggtgaggt tactaagaac   2280
aactttcaat gctttcatat aattgatact ttctagtaaa ggttttgtat tgaacgaggc   2340
aggaccacaa agcaagtaag ggattgattt cacctcattc tcatatattg gcaatgatga   2400
gtgagaggaa caggaaatag acctacgtag agcgtaatct tatagtaata acgtttgagg   2460
agtgttcact tttattagga ttactatttc cgaacaacag cgcgcctttt tgtttgcaca   2520
cctgactact tcaatctgta tcaagcacag tgtgagaaca tgtaaatcgc ctctgtttcc   2580
tttgcgccca cagcagtgag ctacctgtaa tgacaggtag ctaatcgccc ttcgcctcct   2640
tcccatccct accactttca gtacgacgga aatggaaaaa cacggtaggg tatatcgcgt   2700
cgagagttag ggtaatccca atataaaacc agcataacgg gctatcgagc caagggtcgc   2760
cgccatgctc caataatgat cgtcagtttt atgaacctac tggccattgc tatagtgcgg   2820
aaaaagcagt ttcttgggtg agtaggaagg aggcatgaag ggaatccaga ggacaaaaag   2880
cgcgagtcta cttaccaggt attcagtgac gcccctggag tactgccgcg agagaccaac   2940
tgacagagag atccaagact tgccatagtc tggcacaacg cgccgctcca atggaagccc   3000
agatctgggc caattccatg ggccaatgct agatgacctg ccatgtaccc aactgttacc   3060
gctacatagg ccaagccagc atgtcgcttc atcaacggaa cgtgggccca atcagccggt   3120
gcgtgtcttg caatgatgaa taacatgaca caatgcatca cgaaccaagc acaaatgcca   3180
ccagcccaat gcgagctgga tattgggtag atgaaagcat agacagattc ccatccgaca   3240
tcgcagcaga tagacatgaa cgagctgctg agtaattggt cattcagtgt cgtcctcatg   3300
gtgctaacgc agctcagcga ccagcaaatg aattgtatta gccgcagtac aatttcatag   3360
gctctggggt ccgcgagtat agagtattct ggaagtctcc attacggaga acatggtgag   3420
caaatgaata tagaataagt gcaaaaggta gactattggg aacaaagcct tgcacagctt   3480
cgctttcgta gttgatgcgt cgaaagttaa attcttattt cacaagttga ctaattttga   3540
aacagtacaa tcagaagctc tcagatgcta ctgcgctaga atgtcccaag gggctaggcg   3600
tgttcggact aggagacgag acatatctga gtccagtgat aggacacgtt aagaccggtg   3660
tgctgtgtag gtaggctcag gggcagattc acttcccttg cttttgcaagc ctcgctggtt   3720 atttctagac gtggccgtag cttgcgctga gggttctggt tccttgcggc gcaacactat   3780
tatggcttcg atattccaac cgtccacgtc tatgcattaa gctccaaaat gaaccgcacg   3840
attaatagat aatctgacaa tatatgttgg gagacggccc ggtctattat ggcaactatc   3900
agggctctct gagcagtgta ctggaagaag gaagagcgcg ttatctgcgt ttcaggttgg   3960
actctcgatg cgatgagacg aggccctaaa agagctgcag tttctgattc ctccgcatcg   4020
tcctatctag ggagttcgga ctgggttatt agtcattcac atgcagctca gattgccttt   4080
tacgagataa ggggagatgt ccgatagtga tagcgagctc ctgcaagctc tctataggat   4140
tctcaatcct acgatcgagc aaagtgctgc aggactttcc aatgcgctat gatagacatt   4200
```

```
aagcaatcat atatgaaatg gcacagccaa tatgcaaacc aagagacctg ctgctattca    4260
tcctacactt tcgaactgca atcgcgtgtt tgtagcttat gcaacagatt atgctcgtgg    4320
ctgttaccgc atggtatggc ttctcgctct aattgcagcc aaacgatctt cacatatagt    4380
tagctcacaa ttcgcggagg cttttcacaa ctggcaggct ggtcagcacc ctgtcaggtt    4440
cacgagagag cgggcaagga ggtttcggaa tgaccaatct gccttattgt gctacgctca    4500
aggctcctga agtcaccagt tgctaatgcc ggacatctat tggtacttcg ctcatagatg    4560
ttagaaccgt cggtcatagc gcatgatcac catgtacagc attcggggta gagcatggat    4620
caggagcaac ttttcgccat cagcagggaa agattcgcct ccaccacgca ttcatcacca    4680
accgacattc atagaaaggg gtgactgcaa caacgaagga gttagatcgc gatgccgagt    4740
ctggccaagg atgtcgcagg caaggagctc ggagatacca gtcatgcaag gaggacacgg    4800
gtgcaacctt aaggctcgtt ccgggcccgg caccgaattg tgtgcataat ctggggcctc    4860
actgatgtga tatgttccaa tatgggtcag aagctcgcat cttctcactc gttggcaagg    4920
gctgcaaggg agaaggagaa ccacgcatcc atcattttct ccttacgatg aagcggcagg    4980
agtctaactg ggaagcttag cccgctgatc gcagaatgta tgcatcgaat aagacgtatc    5040
cgtcttctag ggcgctccct tgcctcgttg agaaggtcga ggcacaacac gttgacgggg    5100
cgattagagt aaggatcaca acgctggagc agagtacgcg tcgtaaacca tcccgagcag    5160
attatctata cttttgtgaa gccttttgagc ttttgaacac cttgaggtcg ttctcagtac    5220
ggatttgcca gtatgactat tacacccaac attctagaag actggcgtca agccaaagcc    5280
gccgctgttg aagccaaata cgaagcgaaa cgcgagatcc aacttcgagc tcacggaaac    5340
gtgaaagaca ttgaaatcac ccgcgagtca gcctttgaac actttgcaac agatccctgg    5400
gcccagcatg tgggggtaga catagaagct cagcgcgagc ggttgctagc ggaacctgga    5460
agccgcaaga tcctaatcat cggggccggg tttggaggtc tactgtttgc cgtgcgtttg    5520
atccagactg ggcgatttac cgctgaggat attaccatga tcgacagtgc cgcgggcttc    5580
ggtggcacct ggtattggaa tcgatacccc ggactgatgt gcgatactga gagctatatc    5640
tacatgcccc ttttggagga aactgggtac atgccccgga acaagtatgc gtcgggcaac    5700
gagattaggg agcacgcgga gcggattgca caaacgtacg ggctggcaac tcgagccatg    5760
ttcaggaccg tagtcgaaaa gctggattgg aacgaggcgg aaaaagtctg gacagtagct    5820
ggttctatgc tgggcattgc aaataacggg caaagggata atatgatgtc ttttcagatg    5880
gtttcacaat ttacgatcat ggcctcgggt tcattcgcca gtccgagagt cccggattat    5940
cctaacatat tcgactacaa aggcaaattg ttccacacag ctcgatggga ctacaactac    6000
acgggaggct ccgtggaaaa cccgaagatg ctgggggttag ccgacaagac ggttgccatc    6060
attggaacag gggccagtgc agtccagatt gtgccgcagc tggcaaaata tagcaacaaa    6120
ctcatagtat ttcaacggac cccagctgca gtagacgccc gcaacaattg tcccacagac    6180
ccggtgtggt gggaaaccga gacgcaggcc gagggcactg gatggcagaa cgccgccag    6240
gagaacttca acgctttcac ctgcaacgag aaaccccttc catcagtgaa caaagtggat    6300
gatggctgga ctcgaatgcc gtccttcagc atcctgattg cggcccgca gggactggat    6360
cccgactacg tcgaccggat gcgcgcggtc gatatgaata gacaagagaa gatccgcgcg    6420
cgtgcacaca atattgtaca gtcagaaggt tcagccgatc tcctgacgcc ctggtatcct    6480
gggtggtgca agcggccatg cttccatgac gactatcttt ctgcattcaa cctgcccaac    6540
gtggagctag tcgacattcg ccataatgga atatcccact tcacagccaa tggcctggtc    6600
```

```
gcaaacgata ttgaatatga gctagacgtc atcatcctga gcacggggta cactgtccct    6660
gtcacgcgtg caagcccgtc ttcgcgcgca aacattgccg tctccggccg caacgggacc    6720
accatggagg ccaaatgggc gaatggcctc gcaaccctgc atgggtcat  gacccgcgac    6780 ctgccaaatc tcttttcgc  gggaacctcg caggctggtg cctgtgtcaa tctggtctac    6840
gcactggacc agaacgccac ccatgtagct tatatacttg ccaatgcgtt tgacagacgc    6900
cccagcgaca gcgcgagggt tatcattgag ccgacacccg ggtcagaaga ggcctgggcg    6960
atgcaggtgc tgcagcgggc agctggattc cgcggcatcg ctggctgcac gcctggatat    7020
ctcaatggct acgggatgga tgcctcgtca ttaagtccgg agcagcaaat caacgcggcc    7080
cgtctagctg catggggaga aggaatcgcg agctacgtga gatacctgga ggcatggaga    7140
gcgaagggag acttgaatgg gattgagttg acttttttg cgaagttttg aagcaaaaag    7200
ggaaccttgt gactgaatta tgcgagtatc aatagtcact tggaataagc gtgaaatata    7260
actcacgcat acgcagtaaa agctacccaa aatgaacccc cgagttccat catgagaaaa    7320
caaaaacaag aaaactgaaa actgaataag tgcttctggg attagttctc taactttcac    7380
atgttgccca atttcaaaga aaagcaaaat gtcgtctagt accaggccat caactatttt    7440
accccactag atattccagg aacgaaatgg gtcaccaata gtgcacttat caccactgtc    7500
gaattgcgca cagcccgat  aacaatacga agagagcctc aattcgcctt cagagttcct    7560
gcactcaaac aaggcattcc ggggatccgt taatgcagcg gcattgatgg gtggaaacgg    7620
ggataaatgg gcttcaattg acccgcgaag ttccttgata gaatagcctt taagagacac    7680
gtagaattaa catatatgtc ctgcgtatag gatgacatgt gttactgacc atggatttc    7740 cccagcgtcg aaccacagta atacatggat tgtttgcaat tccctgagag tgcgatggtt    7800
gcgggcagca aactgctcaa gacggcaatt tctaggatga gtttcatctt cctgtcgaga    7860
ttatctgggt aggttcctcc tggaggttgt tataacgtca aaggcagaat ggacatggaa    7920
cgcacggccc ctgcgtgcag cttctacaat gcgtcagcgg catgctatgg ccagcaacgc    7980
cgggttctct aaggagggaa ctatacgcaa ggaatgtatt aataaagaca agctcgacta    8040
cactgtaacc agaaacaaaa agcggtagaa aataaatgaa ttcgccgcaa gtggaatccg    8100
taatgttggc ccaaataaca ttcccattaa ttccccaaca ctatccgata acagcactac    8160
aagcaaagtt agggcacat  cactcccctca catttcaaaa gccacgatcg aaagtcactc    8220
agtaaatact tccgtattcc ctgtaggagt tgaggctcga gatttcccca tgcccggtgc    8280
accatcactc aatctagggc gctgccgtgg gagaaggtac agcggctgct gtagccgcct    8340
gaggtgcatc aatgtgttct atcgtggcgt caatcatctc ggccttgtca ggattatcgg    8400
ccgggcggtc gtctttgggt gttgactgag gagcatccgc ttttgcattt tctggcccgt    8460
cttccaaatc ttcgccttta gtaaggggt  gtggcacagg agtgcaggca ttgtgcgaaa    8520
tgcctccttg ggtagtagtg cttgggttca agctactacc aaagaagttg gggaatccac    8580
cagaacctag gaatccacta aagcctggga atccactgaa gccagaggag ccaccgaaac    8640
cagggaaacc accaaagcca gggaaaccac cgaagccagg ggaactggct gcagcaggtc    8700
ctgccgtgat tgatcccgtt ggtgctccgc caccacctcc aggcatgctg tgagacccgt    8760
cgaagccacc gaagcccggg aatccataga aaccagaatt gccgtatgtg ccagaggagg    8820
gtgcagtgcc cagaacaccg ggccagccac ccatgaagcc tggatagccg gccatgcttg    8880
ggaagactgc agtgcctggg ttgctggaac atgtagtggg cgcatctaaa ttaggcgctt    8940
```

```
ggtcttcagt catatggtta gcttagcggt aagtaattgg ttgttctgct cattctcacc    9000
ctcggttgcc tggggtgtgg gcaaggccat tccatggcta agcatactaa gcagcgcaat    9060
ggtggaggat ttcattttga gctcaaggac ttggtaaatc ttgaaataac aacgatgctg    9120
gtttggataa tggcacaatt cgaagctgaa acgcttcttt taccacttta tatatacgct    9180
ggagagcaac taagatagac aggctggcga aaacagccac cagaagccgc cgtttgcgag    9240
actatggagg cggtgcttta cttttgaggag agctcgcatc cgggctcaca gaacatgctc    9300
ggaatgccct atgattttgc ggacggtgga gacaggatgc tgctcttaca atgatataaa    9360
tctaactcct acgtcagtc agaagaaact actgtacgca atcggcttcc ctacagcaga    9420
ttgagtacgt ttgcggtggt tatattctcc ccatcaatac atggctatac gaagccagcc    9480
atgcagattg caaccagtaa gatggctgct ggatgctgca aacgattcac attaccccga    9540
ttaaagcaga tgagatacat tgctagatca ccattactcg atttagtaaa gaagagtaaa    9600
tcacctatgc taggggcgct attttgacta caatacttgc actagcatga atacaaatag    9660
aaacctctag cggtttgtgg agctccttca gtagaagaca gagccagatg tcggacaaaa    9720
cccagcttca ggcacgatgg gccatttgcc ttgtaatatg gcggacatca acgatactct    9780
tgaacatacg ctatcgaagc ttgagcaagc caaaattcat ataactatct cactgagata    9840
tgtagcgtag tagacataaa aaaaaccgcgt ttgatcacaa atcatgacat agctatgtta    9900
atctgtgcct tatataatgg cttaagattt gcgagaagat aatttccatt accacaacga    9960
ggataggcac taaatactaa ttataagcca acgtgtcttc gcaggaactc gtacccgtcc   10020
acgacagcct ggaacgcatg ctgattgcca gcaaaattgg cctctaggtc aaacaaatgt   10080
agcccatcac gcacgatacg caagtcagag tccacgccac aagcctgcat cttatcatgt   10140
gtccgttgcg cctgttgtac gggaatcaaa tcatccagag taccatgaat caagaaggta   10200
ggggctctgt acgaccccgc agagatctgg gagaacgggc agactttctg aacctcgctt   10260
agaattggtt cgggtaggac gacttcataa tcctgcccag actcagcagc tcgggccctg   10320
tagttgcacc cgtagaacag tactggtaac gtttggccgg tccagttcat gtaaagcgcg   10380
atcctgctac gtggatcact tggtgccatc caacccccca gagctcgctt gctgggtgga   10440
gggttgtacc cggaaatagg cgcatcctgc agcgcatcca aaggattacc tgtctggatg   10500
tcagatgtag agacgtcgac tctatacggg aagttcggtt tgctccagaa cgggtcagtg   10560
taatccgtag ggctgtagaa ggagagaatt gcctcagggg ccgaaacgcc gcgcgcaggt   10620
gctgtccatg ccagcgtcat agctaggtga ccaccagtcg accagcctac ggcaacgaca   10680
ttgtttccgt ctggaagaat gtcacggcgc tgaagctgta gttgaggtaa tttgttccgc   10740
gcccaggcca aagcatcaca ggcatcttgc atggggccgt ctaggagtga tacctccggg   10800
caaagtcggt aatcaatact gacgggcaag aaccccatgt caaacagcat tctgacttgt   10860
tcatggtgta tttccttgcg cgagagcatt atgtggccgc cgccgtggat gagtagggct   10920
atgtgctcaa gttagctcct gagtaccatt gagccaattg cagttatata acctaccgat   10980
tggtcttttt gctccgctac gatccgtctt ttccggatag tagatatccg caaacaactc   11040
caatccgtcc cttgtgttgt agagaaccgt ttgctcctgc acagtgttgc agtcggcttc   11100
gcattcatcg tcaccttcca gggcatagaa aggttgagta gacgacgcaa cgataagacg   11160
cagaatatcc gactcggcag agtcgttgtc tgtccaatct acccagttga atccagcttg   11220
ccgtaggttg tggtcccaga gacgctcgtg agccaaagca tgcgaacgac catcgttaaa   11280
cagccaccag ccctcgagaa gaccaaagac gaggtcaaac cagaacaaat tcctcgtcaa   11340
```

```
ctcaatcagg cacaaaatgc cttcggggcg tagcaacctc cgaatgtttg tgcaggaagt   11400
gatcaaattc cgggtggcgt ggatacagtt tgtggatatt atgatatcgt actgtccctg   11460
taactcaggt gaaggatcat tctcaatatc gagcgttgta tagcgcatga aatcgtaagc   11520
cttgaatcgc ttgcgagcca aggtgaccag ggaagaggag atatctgtga atgtgtactg   11580
gaatcggagg ccaggtactg ctgccagttc ttgaacgagg taattggtcg ttcctcctgt   11640
gccagcgcca atttccaaaa ccttgatctc cctttgggta cctaggttaa aaaggaggtc   11700
tttgagatat tgtgccaact gtatcgtggc tgacttgaac atgggcgcat tggagtatac   11760
gtctgtcatc aatgcacggg cttctgcatt ctggaacagg agggacaaag ggtctgcttt   11820
tccactaaga cactctgcta gtcgcgagcc ggtagtgtgt agtagtttgt gctccgaggc   11880
atgctgagcg tgtttgttga gtatcttctt gtagagaatt agggacggaa cggtgccaac   11940
gggctgttgg cttcgaatta tctctgattc tcttcgctcg atgagatcgg agtattcgag   12000
cacagcgacc agctgattca tgaccttgcc atgttgggga aggattttga caggtggaac   12060
tacctgaccg ggtgtgagcg atgctaggtc ggcacccaat gcgtgaaatg cctccaccac   12120
atagctagtg acaagctcca tctgttgagg gaagacggtg tcgcagaagc ctgcgaaccg   12180
tgtcttgcgg ctgaattcgg cactcgtgcg tgtggtagca aagagtttac tagctttatc   12240
gacaaatgcc gtcggtgatg tatcacatac tggcgcaaga tccaccgaga tactctttgg   12300
ctctcggtct gtgattgtga tttcggtctc gacggccccc tgactgtgag ttttgatgcg   12360
gacaaccgag tgtcccggga agatacgttg taccaatccg ccaacatccg ggatttgtgt   12420
aagctcagcg ttggatatag ccactccaaa ccgtttatta atttcggtta agacttcagt   12480
gctcataagc gagtcgacac cgatatcgcc gagggcagca gctgctgaga gttcgtcggc   12540
agagattccc agtagttcac cgagcatggt ctgcacagct agaagatcac catcgctact   12600
cgaaacgtga gccactgggg tagaggagag agctgtcgcc tcagcagcaa cattaatgga   12660
gacctgctct gcctccgttg gcctggcagt atgattactc agacggttta gggttcgctt   12720
taacgattga atggacacac ccgtgaaggt agcggacagc atgcagacag caagcgcccc   12780
tgtagtatgg tctagtacaa agacatcgca tactattttc ttttttgact ccggctcgta   12840
gttggaatac acagcccagg gaaccgtagc tgctgtgtcc cgtcgcacaa aggattcacc   12900
gatcaataca tccctaccg aactacacac gaaaacctca tcatcatgcg tttcagaaag   12960
acagttaacg tggatgccgg ctacctgaat gaagttgtct atcagaatcg ggtcgcaagg   13020
attgcacttg gtcggcgagg aaggcaggat gactcggcca gtggcttcgt gccctacagc   13080
gtaaacttct tcaacgccgc ggtaatagtc tgcgtagttg acggccctgg caaatgcttg   13140
gtagactgtt gagcgcttaa gcccactgga agaaggagac gtagcaatgg agttccagct   13200
agcaagattc agtagacgtt gtaaggagct taagcgagcg catatcccgg tgttgctacc   13260
ggcagcttgt aacgatactc tgcctgtagc atgtgtcacc gcgtcctgca aaccgtcacg   13320
cgtggacagc acaaatgacc actgtccatg gctctcatcc tgctgcgtca gctgcaggag   13380
aaccgcaccg ggcatcccga ggacaagggg cgagcaaatg ttaaggctct cgatgtgata   13440
cattgttggc tttgtcgctg ttgatgagac aagtaatgct gcctgaacga caagttcaaa   13500
atagagagag gcagggcata aattctggtt ggcgactgca tggccggcgg tgcacattcg   13560
gaagacgttg tccttgttgt tgatggtaaa gagagcttct ttaccatctt gtctcagcag   13620
ccgcacgaga ctcgcttctt gtacattttc ttgatccggt acctgcggag gcgaacggaa   13680
```

```
ggcgtcaggg ttatactcaa tccaatggct ggttttcgcg aattggtatg ggggcaggtt   13740
gatccacctg tacccggtct ccgaaggatg aacggccag aattgaaccg gcacagcttt    13800
tgaccaaagt gtacaggtca cctttgcgag atttgcctgg gcttgggcac cggaaagatc   13860
agtcggaagg tatacatggc ttttgagcgg ccgtgacgct tccacgacac gacgcaccat   13920
attaatgact ggtgaagctg ttcctgcctc gagccaaaca catgggccat cgacacgcga   13980
aagagtccgt tccacggcat catgaaaaaa caccggcttg cgtgagtgtt gcacaatctt   14040
gtcacctgtg acccataacc agtcatcctc ctgttcggca catgcctcga caggaatatc   14100
cagctgtcta aaggtgagcg tattggctac ctcgctcaat cctggcagaa ttgcgtccac   14160
gagacgagag tgaaacgcat gagtattctt caatctcttc agttcaacat gcattccctt   14220
ctcggtggcg atgatttcga tgcggcgaat ggactcctca tcgccggcaa caacaaagtt   14280
atcaggtcca ttcaggcatg caaggtctgc gtgacctgat gcagcgtcta gcagagcttg   14340
gaccttctct ttgctcgctc tcaaagaaag catcactcca gtatgcggtc cccaatgttt   14400
ctggatcagc tgggcgcgag ttgcgacaag tcgcattcca tcaatgagcg ataagccacc   14460
agcaacgcat agggcagtta attgcccaaa gctatgaccg atcattcggg tgacctgcag   14520
tccagaatca agccatgcct ttgcagtggc gtattgaatg gaaaacaata cgcaatggag   14580
gttcacaata tctttgttag ggaaagggct cacaatagcc gggaataggc tagggagatc   14640
taacgcgttg caagcgtttt cacattcatc ctgatgatca gatcagcacg aggccttacg   14700
cgtatccaga atgaaaaaga tagactaacc acgtggaagc gcaggagctc gcaactctca   14760
aataaatttc ttgagatgct cgctgtatct ccggtctgtc cgccgaaaca aataatcaca   14820
ggatgaaagg actgggaccg tctttcgacc tgcgtatgag cggaggcgat agatcctaag   14880
cgtgtcataa gctctgaagg ctccccagcg gcggctggaa atgtgacaaa gtgctccata   14940
tctcggttct gcttccgtgc caaattgtat gcgatatgct gcacggtgtt agtacctgac   15000
tgtgctacct cacggatggt gctctgaaga gcttcacagt acgagcgaag ggactcttcg   15060
gttcgagcag agacgtaaaa aggaacatgc gagggcaggg tctcccgatg ggcactgttt   15120
gaggtagcag tgttgacgc aggttctcgt agaacgatag cagcattgct accggccgcc    15180
ccataattag tcaccatagc cacgcgtttt tcagcttccc agtcaattga ttgagtaggg   15240
atttctatat gattcctctc gtttaatgta attctgggat tcaggcgacg aaagttagct   15300
tgtttgggga ttctgcgctt ctgtatcatc aggatcgtct tcagcatgcc cgcaacacca   15360
gaagacgtct cagtatgccc aatattgtcc ttgatcgacc caacataaag ctttgtggcc   15420
ctattaggcc cggagaatgt tttccggata cttccaaact caattgggtc tccgacttgg   15480
gtgcctgtca atatgttaac gatatctaca gatggttaat gataacaggt agtgggttac   15540
agaccagtgc catgtgcttc aacatagcca acaacgtctg gagtaagtcc agaaagcgac   15600
aaggctttca aatataagct tctttgcgag tttgaatccg ggacagttat cggcgagcag   15660
tttgctccct gattgacgga tgttccagta atcacgcgt gaatgggatc gccatcgcga    15720
agagctgctt ccagggggccg cagcacaagc agcccagcac cttcaccacg acagtatcca  15780
ttggcatctg catcgaatgc cttagatgcc ccggttggcg acagaaacga tgccccagcc   15840
aggttttggg accatcgggg atctgtcatt atattcactc cgccggctac agcgatagcg   15900
caatcattcg ttcgaatggc ctaggtcaag gtacacttta ttagcataat tgtaatagtg   15960
tttgtttggc tagggaacgc acttacctgg cacgcgaggg gaatagcaac agcagctgat   16020
gagcacgccg tgtcaaccgt gacagagggg ccactccaac caaagtaatg gctgatgcgg   16080
```

```
ccactgttaa aagcctggag tgtaccagtt gctgagaagg cagtggcatt acgagatcca   16140
acgttttcac tatagtcgtc gcaaccgact ccaacgtagc agccgatgtc gtcaggaagc   16200
ttcgagcggc gcagcccaca gtaaccagcg gattccatag cttcatacgc aacttgcagt   16260
agtactcttt gctgtggatc cattgactcg gcctcccgcg cggatatccc gaagaatcga   16320
tgatcaaagg catctgggcg cgcgaggtaa tttccaaaga atggccctttt ggctctctc   16380
tgcagactgc cacttttaag ccgactgttg ggcattggac tgacggtgca ctggcccaga   16440
tctaagattc tccacagttc ttccacggaa tcggcttggg gatatcggca tgccatccca   16500
gtaaccgcga taggcactgc ggtggtctcg ggggccgtga catttacccc gacatcaagt   16560
gcagtggcgg actgcatctt gcgtctgcca tttatgtgct cgcctttgtt gaactcaaca   16620
atgttcaaca tacgacatct agcgtgtcgc ggtacgaatt ggcctgcacc tatggggata   16680
atgcttctag catccgattg ccccatgttg tctagagtag cggtgacggt gatcttccaa   16740
tttgcttgcg ttgtcaagat cgactcgact gcaacagtga aaagcgagtc agcttcgcac   16800
actctcccgt tgatattgga tctcggcaga ctgcgcttgt gacacttcga tggcaggcaa   16860
agtcggctat tccgctcaca agattgcaaa atatcctcca cagcttgagt gtggttcgag   16920
tgatggaatc ggcctctaag tgtcgtagtc ttcaccgaga gcccatgttt ctccagctcc   16980
tttgcgaagg aaacggactg agagtcccaa acggtgaccg ttacagcgtt ttcatcagtc   17040
acgcatgaaa tgtatgcctg tcgcgttcat taacaagaag aaaagaagaa tataagcaag   17100
gaacaagcag cactgacacc ttgataacga gttaagactt ccgtcagaag cttatgctcc   17160
tgagcagttc tccacctgac ggcgattgac cttgcaggct gttcacaaag ctcgtccaag   17220
tccactgcag ccccaatgta gacggcgaga cgcaagacgg tgctcacaac tttgccgaat   17280
tcatcctcgt tgtccgacca gcatgcagct gcgatggctg ccaggaatcc gacgcagaat   17340
ccctggatat cgcagacgtc gtagttcttg tcttctttca gctcgaggaa atcgactaaa   17400
tgtcgcaaga ctgtggctgg tactagcaag aaattcatcg gctcggccat atcaggccgt   17460
agcgttccac ccccgagaaa cgctgaaagc tgacggagac gtgcgtcccc atgaagcttc   17520
tcggctgctg gccagagcct caggatatcg tgccagacga aggtaaatc tcggattgcg   17580
tcgtgaagcc agtttgcatt ccgctgattc gaaagatatc tgcgtatgtg cccagctggc   17640
agttcaacct ccgatatttt cggtccgaaa aggaccgaaa cctgctgcaa agtattatca   17700
tcaagggacc ccatctttcg aaataaagtg atcttgacta aaaggaatga gacacagtcg   17760
cttaacaaag tgtgcttatg aaagaaccaa gaaccaacgg cgttgaagca gttgctcaaa   17820
tgactagtcc ccgactctta gaacttgacc gagaatttca agggatatag gcggagccca   17880
ttgaaggaac cctctaatct cagcggacgg tctacttgaa gctcaagagg ggttactgca   17940
gcagcgcctg cactaccgcc catagcggtc caagaatccc caacctattc ctgccagctg   18000
caagtgagga atttttgtcga gatctcgtca ataaagactc agaagacgat atcctgacat   18060
attgttctca aaacaacgcc tgtataggc aaagtgcgca tagcgacagt ccgcccgtgt    18120
cgcacgaaag ggcgcctgct atttcagcgt cgatcaacag ccttctttag gccagatttc   18180
gacttctgca ggagccactg tctggttaca tacgaccaat tcggtccaat tgccagatag   18240
ctcgttatgt atataagcta gggcaaagga tccacaccac tttggaccga accgccgaa    18300
agctagacca gaagaatgtt ggcttctcag tcaatatgcg gccccttgc tccaggctcg    18360
agccaagtgg gcacgcaagg cttagtttgc atttgcattg tcccaagtga ggaaccagat   18420
```

```
cggactcaga tcaaagacat aacccaaagg acggcatttt gtacaaccct aaaaagcgtt    18480
gatcgacata taaaaacagc ctcctttgct gattgccaac cacagctcgt gcttggatcc    18540
gtctttccac tacttgagga atgaacgggc gtatccatca tgcataacac atctacgttc    18600
cttgtagatt atgcccgagt aattccgatc gcagcccttc atgctcaacg tggaatcatc    18660
tcgttgactc cggactgtct agctgcaccg ccattccgtt cgtggctcgt aacagtagct    18720
ggcaaggtat ggcagctctg cagcgtagta tcacatacat atttcacata atatgatact    18780
ctggcgcaag cgatttcctt actgttctta aactcttctt atctttccgt acgtgtccat    18840
cactctacaa ttttggtgct gcggggtctc tccgtgatga gtgctcttaa ttccatacta    18900
ggccatctat ctctgctatt caagtttatt gctcgttatt gtcatcttca tttttactaa    18960
ctatccactc attatagcaa gcacaagccg ttctcaagat tgaacgatga tagcaatgca    19020
acccgaaacc caactaaaaa ccgcccttaa gaacgggttt gacccgaaca tcctctacaa    19080
agacccttta acaatcgtaa aggagcctat gtgtactatt ctcgagaagc acagcaagat    19140
cccagtggac aaagtcgtca gtcatgtcaa caaggtggtg agtaaatcag ccagcccttt    19200
caaatctgct agtctgactt cctttcgcca gagagatcgc gcttttgccg tggttagtac    19260
tctgtatccc tatgcactcc ccaatctgac ccaatgaaag tttccttatg catgcattgg    19320
gcaattctcc tttgtcgagc tgagcatcgc cgcatcgccg tactatcccg agatgctcga    19380
gcgcgtgaag aatggccaca aacttctgga cctaggctgc gcatttggac aggagctccg    19440
tcagctggtg agttccttgt ttcattccag cgatgccttc taccccacca tctgtcctga    19500
ctgatgtccc cagatatatg acggtgctcc tggtgaaagt ttgtacggct cagatatcca    19560
gcaagagttt ctaaacctcg gctacgaact cttcctggac cgtgcaacgc tccctgagtc    19620
ccatcttatc gcttccaaca tcctagacag acagtctcct ctcttcaccc acctcaccgg    19680
aaagctcaac atcgtctaca tttcgctttt cctccacgta tttgacttcg aacagcagat    19740
aactgtggca ggaaacgtgt tggatcttct cgctgccgag cctggctcac tcatcgtatg    19800
ccgggttacc gcctgtcgtg accaaggcgt gcttaacgca acagcggaac gtatgccgta    19860
ctactaccat gaccgggcga gctgggaaca gctctgggag gttgtgcaga aaaggactgg    19920
tgtaaagctt tgtgtagata cctgggaaca gcccgatgag ttggtcaaga agcatccctt    19980
gccagggata tatattttgg ggtctgcgat ccggcgagtt tagcccaccc gccgcctttt    20040
cggtccgagc tgtttatcta caaaggttta gtgtgacagt ctccaaaagt ccacagagta    20100
tactacaaag ataaatttat gaattatctg actttggttg ttaaggagct tgagtaaaat    20160
ggctgat                                                             20167
```